US008389771B2

(12) United States Patent
Scott et al.

(10) Patent No.: US 8,389,771 B2
(45) Date of Patent: Mar. 5, 2013

(54) ALKYNYL PHENYL DERIVATIVE COMPOUNDS FOR TREATING OPHTHALMIC DISEASES AND DISORDERS

(75) Inventors: Ian Leslie Scott, Monroe, WA (US); Vladimir Aleksandrovich Kuksa, Seattle, WA (US); Mark W. Orme, Seattle, WA (US); Thomas Little, Redmond, WA (US); Anna Gall, Woodinville, WA (US); Jennifer Gage, Kenmore, WA (US); Feng Hong, Bellevue, WA (US)

(73) Assignee: Acucela, Inc., Bothell, WA (US)

( * ) Notice: Subject to any disclaimer, the term of this patent is extended or adjusted under 35 U.S.C. 154(b) by 0 days.

(21) Appl. No.: 13/197,659

(22) Filed: Aug. 3, 2011

(65) Prior Publication Data
US 2012/0004269 A1 Jan. 5, 2012

Related U.S. Application Data

(63) Continuation of application No. 12/217,022, filed on Jun. 30, 2008.

(60) Provisional application No. 60/947,321, filed on Jun. 29, 2007.

(51) Int. Cl.
C07C 211/00 (2006.01)
C07C 217/00 (2006.01)
C07C 215/00 (2006.01)

(52) U.S. Cl. .......................... 564/374; 564/354; 564/363

(58) Field of Classification Search .................. 564/374, 564/354, 363
See application file for complete search history.

(56) References Cited

U.S. PATENT DOCUMENTS

| 4,214,001 | A | | 7/1980 | Engelhardt et al. | |
| 4,412,856 | A | * | 11/1983 | Brunner et al. | 504/326 |
| 4,663,334 | A | * | 5/1987 | Carson | 514/357 |
| 5,049,587 | A | | 9/1991 | Okamoto et al. | |
| 6,162,943 | A | | 12/2000 | Lui et al. | |
| 6,313,071 | B1 | * | 11/2001 | Ikegaya et al. | 504/143 |
| 2002/0042116 | A1 | | 4/2002 | Simon et al. | |
| 2002/0058685 | A1 | | 5/2002 | Hamilton | |
| 2003/0032078 | A1 | | 2/2003 | Travis | |
| 2003/0144323 | A1 | * | 7/2003 | Apodaca et al. | 514/317 |
| 2003/0186961 | A1 | | 10/2003 | Hamilton et al. | |
| 2003/0224942 | A1 | | 12/2003 | Ahrens | |
| 2004/0102634 | A1 | | 5/2004 | Matsuura et al. | |
| 2006/0069078 | A1 | | 3/2006 | Rando | |
| 2006/0252107 | A1 | | 11/2006 | Kubota et al. | |
| 2006/0281821 | A1 | | 12/2006 | Palczewski et al. | |
| 2007/0112011 | A1 | | 5/2007 | Kuhnert et al. | |

FOREIGN PATENT DOCUMENTS

| EP | 0805154 | 11/1997 |
| EP | 805154 | 11/1997 |
| JP | 57-38751 | 3/1982 |
| JP | 2000-53503 | 2/2000 |
| JP | 2007-515433 | 6/2007 |
| WO | WO 99-16783 | 4/1999 |
| WO | WO-01-07020 | 2/2001 |
| WO | WO-01-19809 | 3/2001 |
| WO | WO-04-000764 | 12/2003 |
| WO | WO-2005-094822 A1 | 10/2005 |
| WO | WO 2006-031505 A1 | 3/2006 |
| WO | WO-2006-063128 A2 | 6/2006 |
| WO | WO-2006-115895 A2 | 11/2006 |
| WO | WO 2007-089673 | 8/2007 |
| WO | WO-2007-101864 | 9/2007 |
| WO | WO-2009-058216 | 5/2009 |

OTHER PUBLICATIONS

Kotlyarevskii et al. STN Accession No. 1971:53198, Document No. 74:53198 Abstract of Izvestiya Akademii Nauk SSSR, Seriya Khimicheskaya, (1970), (8), 1906-9.*
Radu et al. "Treatment with isotretinoin inhibits lipofuscin accumulation in a mouse model of recessive Stargardt's macular degeneration." PNAS Apr. 15, 2003, 100(8):4742-4747.
Sieving et al. "Inhibition of the visual cycle in vivo by 13-cis retinoic acid protects from light damage and provides a mechanism for night blindness in isotretinoin therapy." PNAS, Feb. 13, 2003, 98(4):1835-1840.
CA2690229 Exam Report mailed Feb. 27, 2012.
Bernstein et al., "Mechanism of action of aromatic amines that short-circuit the visual cycle," Biochem 25(11):3370-3377 (1986).
Golczak et al., "Positively charged retinoids are potent and selective inhibitors of the trans-cis isomerization in the retinoid (visual) cycle," PNAS 102(23):8162-8167 (2005).
Maeda et al., "Evaluation of the role of the retinol G protein-coupled receptor (RGR) in the vertebrate retina in vivo," J. Neurochem. 85(4):944-956 (2003).
Maeda et al., "Redundant and unique roles of retinol dehydrogenase in the mouse retina," Proceedings of the National Academy of Sciences of the United States of America, 104 (49), pp. 19565-19570, 2007.
Maita et al., "Small Molecule RPE65 Antagonists Limit the Visual Cycle and Prevent Lipofuscin Formation," Biochemistry, vol. 45, No. 3, pp. 852-860 (2006).
Mata et al., "Isomerization and Oxidation of Vitamin A in Cone-Cominant Retinas: A Novel Pathway for Visual-Pigment Regeneration in Daylight," Neuron 36:69-80 (2002).
Minami et al., "Enzymatic Approach to Unnatural Glycosides with Diverse Aglycon Scaffolds Using Glycosyltransferase VinC," J. Am. Chem. Soc. 127(17), 6148-6149 (2005).
Patani et al., "Bioisosterism: A Rational Approach in Drug Design," Chem. Rev. 1996, 96, 3147-3176.

(Continued)

Primary Examiner — Nizal Chandrakumar
(74) Attorney, Agent, or Firm — Wilson, Sonsini, Goodrich & Rosati

(57) ABSTRACT

Provided are alkynyl phenyl derivative compounds, pharmaceutical compositions thereof, and methods of treating ophthalmic diseases and disorders, such as age-related macular degeneration and Stargardt's Disease, using said compounds and compositions.

55 Claims, 14 Drawing Sheets

OTHER PUBLICATIONS

Rangisetty et al., "1-(2-methoxy-5-(3-phenylpropyl)-2-aminopropane unexpectedly shows 5-HT2a serotonin receptor affinity and antagonist character," J Med Chem 44(20):3283-3291 (2001).
Remy et al., "Antiarrhythmic agents. 2-,3-, and 4-substituted benzylamines," Eur. J. Med Chem 18(2):142-148 (1975).
West, Anthony R., "Solid State Chemistry and its Applications," Wiley, New York, 1988, pp. 358 & 365.
HCaplus 1992:426103 Abstract, "Lipoxygenase-inhibiting substituted phenylacetylenes, pharmaceuticals containing them, and methods for the preparation of the compounds and pharmaceuticals," Zimmer et al, 1992.
HCaplus 2001:627698, "1-[2-Methoxy-5-(3-phenylpropyl)]-2-aminpropane Unexpectedly shows 5-Ht2A Serotonone Receptor Affinity and Antagonist Character," Rangisety et al, 2001.
EP08779908 Supplementary Search Report mailed May 23, 2011.
Australian 2008271051 Office Action dated Oct. 18, 2010.
Canadian 2,690,229 Office Action dated May 26, 2011.
Korean 2010-7002091 Office Action dated Sep. 20, 2011.
New Zealand 582204 Office Action dated Nov. 2, 2010.
PCT/US08/008169 Search Report dated Feb. 19, 2009.
Russian Federation 2009148137 Office Action dated Jan. 12, 2011.
Ukraine 201000818 Office Action dated Dec. 2, 2010.
JP2010-514855 Office Action mailed Aug. 24, 2012.
Abhigyan et al. "Influence of Lipid Composition on Membrane Activity of Antimicrobial PHenylene Ethynylene Oligomers." *The Journal of Physical Chemistry B*, Mar. 1, 2008, 112(11):3495-3502.
Appeldoorn et al. "Novel multivalent mannose compounds and their inhibition of the adhesion of type 1 fimbriated uropathogenic *E. coli*." *Tetrahedron Asymmetry*, Jan. 24, 2005, 16(2):361-372.
Bonger et al. "Synthesis and evaluation of homodimeric GnRHR antagonists having a rigid bis-propargylated benzene core." *Bioorganic & Medicinal Chemistry*, Apr. 1, 2008, 16(7):3744-3758.
Chukhadzhyan et al. "Behavior of Allylates and Propargylates of $_p$- and m-BIS(3-Dialkylamino-1-Propynyl)Benzenes in Aqueous Alkaline Medium." *Chemistry of Heterocyclic Compounds*, 1997, 33(6):660-664.
Joosten et al. "Inhibition of *Streptococcus suis* Adhesion by Dendritic Galabiose Compounds at Low Naomolar Concentration." *Journal of Medicinal Chemistry*, Dec. 1, 2004, 47(26):6499-6508.
Kotlyarevskii et al. "Physiological Activity of Acetylene Derivatives of 2,5-Dimethyl-4-Hydroxypiperidine." *Izvestia Sibirskogo Otdelenia Akademii Nauk SSSR, Seriabiologiceskih Nauk*, Jan. 1, 1975, No. 3, pp. 146-149.
Kotlyarevskii et al. "Piperidol Derivatives of Some Aromatic Acetylenes." *Izvestia Akademii Nauk SSSR, Seriya Khimicheskaya*, Oct. 1972, 21(10): 2254-2257.
Kumar et al. *Macromolecules*, Jan. 1, 1995, pp. 124-130.
Liao et al. "Optimization study of Sonogashira cross-coupling reaction on high-loading macrobeads using a silyl linker." *Tetrahedron Letters*, Mar. 4, 2001, 42(10) :1815-1818.
Myasnikova et al. "5-Methyl-2, 4-Diethynylphenol and Its Derivatives." *Izvestia Akademii Nauk SSSR, Seriya Khimiceskaa*, Nov. 1970, No. 11, pp. 2637-2639.
Pershin et al. "Bacteriological Properties of Some Aromatic Mono- and Diacetylenic Amines." *Izvestia Akademii Nauk SSSR, Seriya Khimicheskaya*, Aug. 1970, No. 8, pp. 1904-1906.
Rao et al. "Synthesis of Novel Tyrosinyl FRET Cassettes, Terminators, and Their Potential Use in DNA Sequencing." *Nucleosides, Nucleotides and Nucleic Acids*, Oct. 1, 2003, 22(5-8):1443-1445.
Russo et al. "Three-component one-pot process to propargylic amines and related amide and sulfonamide compounds: application to the construction of 2-(aminomethyl)benzofurans and indoles." *Tetrahedron*, Sep. 10, 2007, 63(43):10671-10683.
Russo et al. "Synthesis of Specific Bivalent Probes That Functionally Interact with 5-HT$_4$ Receptor Dimers." *Journal of Medicinal Chemistry*, Sep. 1, 2007, 50(18):4482-4492.
Shishmakova et al. "D1- and Tetraacetylenic Amines of Resorcinal Series." *Izvestia Akademii Nauk SSSR, Seriya Khimicheskaya*, Sep. 1972, 21(9):2029-2032.
Shishmakova et al. "Acetylenic Derviatives of Mesitylene and Phloroglucinal." *Izvestia Akademii Nauk SSSR, Seriya Khimicheskaya*, Sep. 1974, 23(9):1851-2084.
Zybovych et al. "A missense mutation in *Caenorhabditis elegans* prohibitin 2 confers an atypical multidrug resistance." *PNAS*, Oct. 17, 2006, 103(42):15523-15528.
EP08779908 Examination Report mailed May 15, 2012.
CA2690229 Examination Report mailed Feb. 27, 2012.
NZ582204 Examination Report mailed Apr. 27, 2012.
RU2009148137-04 Office Action mailed Mar. 29, 2012.

* cited by examiner

ALKYNYL PHENYL DERIVATIVE COMPOUNDS FOR TREATING OPHTHALMIC DISEASES AND DISORDERS

CROSS-REFERENCE

This application is a continuation application of U.S. patent application Ser. No. 12/217,022, filed on Jun. 30, 2008, and further claims the benefit of U.S. Provisional Application No. 60/947,321, filed on Jun. 29, 2007; the contents all of which are incorporated herein by reference in their entirety.

BACKGROUND OF THE INVENTION

Neurodegenerative diseases, such as glaucoma, macular degeneration, and Alzheimer's disease, affect millions of patients throughout the world. Because the loss of quality of life associated with these diseases is considerable, drug research and development in this area is of great importance.

Macular degeneration affects between ten and fifteen million patients in the United States, and it is the leading cause of blindness in aging populations worldwide. Age-related macular degeneration (AMD) affects central vision and causes the loss of photoreceptor cells in the central part of retina called the macula. Macular degeneration can be classified into two types: dry-type and wet-type. The dry-form is more common than the wet; about 90% of age-related macular degeneration patients are diagnosed with the dry-form. The wet-form of the disease and geographic atrophy, which is the end-stage phenotype of dry AMD, causes the most serious vision loss. All patients who develop wet-form AMD are believed to previously have developed dry-form AMD for a prolonged period of time. The exact causes of age-related macular degeneration are still unknown. The dry-form of AMD may result from the senescence and thinning of macular tissues associated with the deposition of pigment in the macular retinal pigment epithelium. In wet AMD, new blood vessels grow beneath the retina, form scar tissue, bleed, and leak fluid. The overlying retina can be severely damaged, creating "blind" areas in the central vision.

For the vast majority of patients who have the dry-form of macular degeneration, no effective treatment is yet available. Because the dry-form precedes development of the wet-form of macular degeneration, therapeutic intervention to prevent or delay disease progression in the dry-form AMD would benefit patients with dry-form AMD and might reduce the incidence of the wet-form.

Decline of vision noticed by the patient or characteristic features detected by an ophthalmologist during a routine eye exam may be the first indicator of age-related macular degeneration. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Currently available drugs can ameliorate AD symptoms for a relatively period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Glasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277: 19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), is a very rare genetic condition affecting children shortly after birth.

SUMMARY OF THE INVENTION

A need exists in the art for an effective treatment for Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

The present invention relates to alkynyl phenyl derivative compounds, which are inhibitors of an isomerization step of the retinoid cycle and are useful for treating ophthalmic diseases and disorders. Also provided are pharmaceutical compositions comprising the alkynyl phenyl derivative compounds and methods for treating various ophthalmic diseases using these compounds.

In one embodiment is a compound having a structure of Formula (A):

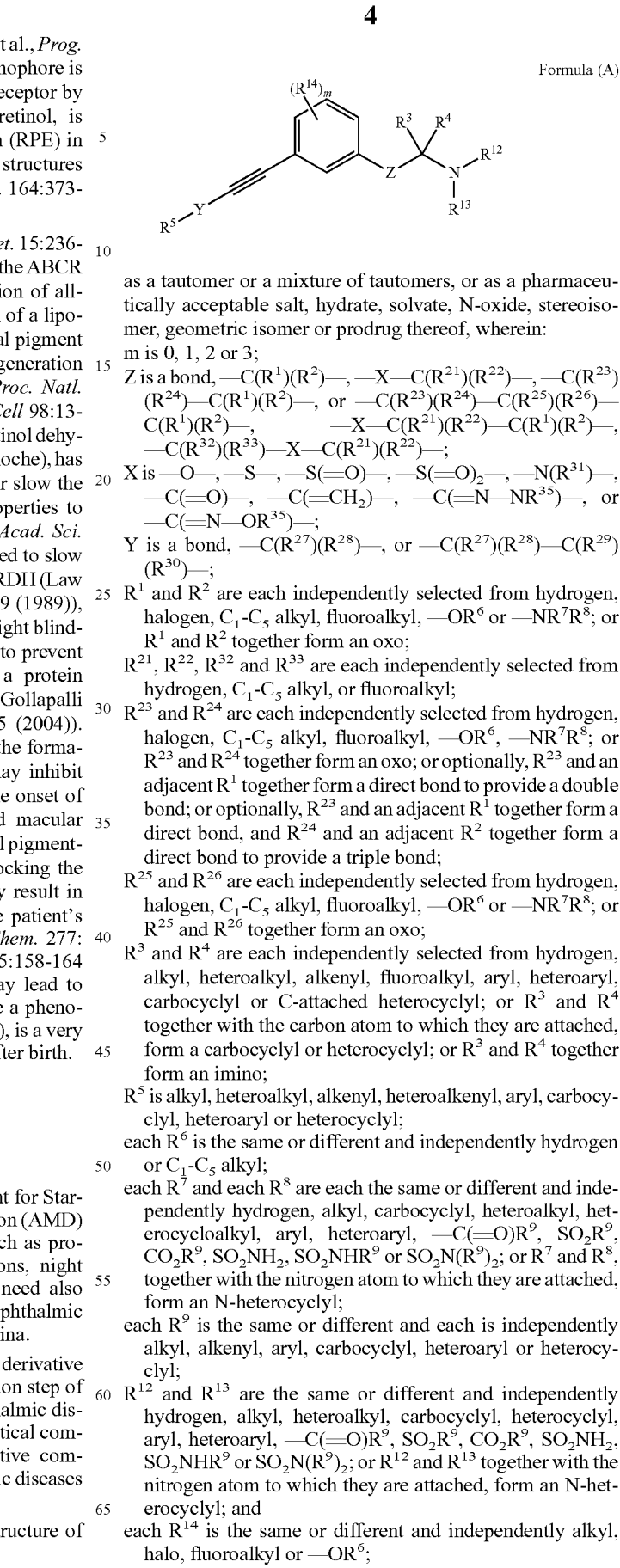

Formula (A)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

Z is a bond, —C($R^1$)($R^2$)—, —X—C($R^{21}$)($R^{22}$)—, —C($R^{23}$)($R^{24}$)—C($R^1$)($R^2$)—, or —C($R^{23}$)($R^{24}$)—C($R^{25}$)($R^{26}$)—C($R^1$)($R^2$)—, —X—C($R^{21}$)($R^{22}$)—C($R^1$)($R^2$)—, —C($R^{32}$)($R^{33}$)—X—C($R^{21}$)($R^{22}$)—;

X is —O—, —S—, —S(=O)—, —S(=O)$_2$—, —N($R^{31}$)—, —C(=O)—, —C(=CH$_2$)—, —C(=N—N$R^{35}$)—, or —C(=N—O$R^{35}$)—;

Y is a bond, —C($R^{27}$)($R^{28}$)—, or —C($R^{27}$)($R^{28}$)—C($R^{29}$)($R^{30}$)—;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{21}$, $R^{22}$, $R^{32}$ and $R^{33}$ are each independently selected from hydrogen, $C_1$-$C_5$ alkyl, or fluoroalkyl;

$R^{23}$ and $R^{24}$ are each independently selected from hydrogen, halogen, $C_1$-$C_5$ alkyl, fluoroalkyl, —O$R^6$, —N$R^7R^8$; or $R^{23}$ and $R^{24}$ together form an oxo; or optionally, $R^{23}$ and an adjacent $R^1$ together form a direct bond to provide a double bond; or optionally, $R^{23}$ and an adjacent $R^1$ together form a direct bond, and $R^{24}$ and an adjacent $R^2$ together form a direct bond to provide a triple bond;

$R^{25}$ and $R^{26}$ are each independently selected from hydrogen, halogen, $C_1$-$C_5$ alkyl, fluoroalkyl, —O$R^6$ or —N$R^7R^8$; or $R^{25}$ and $R^{26}$ together form an oxo;

$R^3$ and $R^4$ are each independently selected from hydrogen, alkyl, heteroalkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is alkyl, heteroalkyl, alkenyl, heteroalkenyl, aryl, carbocyclyl, heteroaryl or heterocyclyl;

each $R^6$ is the same or different and independently hydrogen or $C_1$-$C_5$ alkyl;

each $R^7$ and each $R^8$ are each the same or different and independently hydrogen, alkyl, carbocyclyl, heteroalkyl, heterocycloalkyl, aryl, heteroaryl, —C(=O)$R^9$, SO$_2R^9$, CO$_2R^9$, SO$_2$NH$_2$, SO$_2$NH$R^9$ or SO$_2$N($R^9$)$_2$; or $R^7$ and $R^8$, together with the nitrogen atom to which they are attached, form an N-heterocyclyl;

each $R^9$ is the same or different and each is independently alkyl, alkenyl, aryl, carbocyclyl, heteroaryl or heterocyclyl;

$R^{12}$ and $R^{13}$ are the same or different and independently hydrogen, alkyl, heteroalkyl, carbocyclyl, heterocyclyl, aryl, heteroaryl, —C(=O)$R^9$, SO$_2R^9$, CO$_2R^9$, SO$_2$NH$_2$, SO$_2$NH$R^9$ or SO$_2$N($R^9$)$_2$; or $R^{12}$ and $R^{13}$ together with the nitrogen atom to which they are attached, form an N-heterocyclyl; and each $R^{14}$ is the same or different and independently alkyl, halo, fluoroalkyl or —O$R^6$;

each $R^{27}$, $R^{28}$, $R^{29}$ and $R^{31}$ are the same or different and independently hydrogen, alkyl or —$OR^6$; and $R^{30}$ and $R^{35}$ are each independently hydrogen or $C_1$-$C_5$ alkyl.

In another embodiment is the compound of Formula (A) wherein Z is —C($R^{23}$)($R^{24}$)—C($R^1$)($R^2$)—.

In another embodiment is the compound of Formula (A) wherein $R^5$ is aryl. In another embodiment is the compound of Formula (A) wherein $R^5$ is an unsaturated carbocyclyl. In another embodiment is the compound of Formula (A) wherein $R^5$ is a bicyclic carbocyclyl. In another embodiment is the compound of Formula (A) wherein $R^5$ is norbornyl.

In another embodiment is the compound of Formula (A) wherein $R^5$ is phenyl, Y is a bond and the compound has a structure of Formula (B):

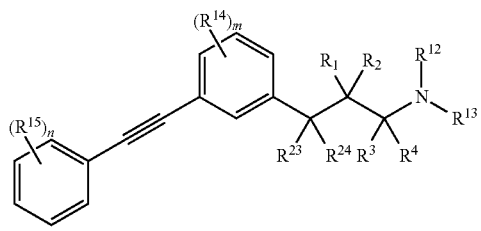

Formula (B)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
n is 0, 1, 2, 3, 4 or 5;
$R^1$ and $R^2$ are each independently selected from hydrogen, halogen, $C_1$-$C_5$ alkyl, fluoroalkyl, —$OR^6$, $NR^7R^8$; or $R^1$ and $R^2$ together form an oxo;
$R^3$ and $R^4$ are each independently selected from hydrogen or alkyl;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently alkyl, alkenyl, aryl, carbocyclyl, heteroaryl or heterocyclyl;
$R^{23}$ and $R^{24}$ are each the same or different and independently hydrogen, halogen, $C_1$-$C_5$ alkyl, fluoroalkyl, —$OR^6$, —$NR^7R^8$ or carbocyclyl; or $R^{23}$ and $R^{24}$ together form an oxo;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{15}$ is the same or different and independently alkyl, —$OR^6$, alkenyl, alkynyl, halo, fluoroalkyl, aryl or aralkyl.

In another embodiment is the compound of Formula (B) wherein each of $R^{12}$ and $R^{13}$ is hydrogen.

In another embodiment is the compound of Formula (B) wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl.

In another embodiment is the compound of Formula (B) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen.

In another embodiment is the compound of Formula (B) wherein m is 0; n is 0, 1 or 2; and each $R^{15}$ is independently alkyl, —$OR^6$ or aryl.

In another embodiment the compound is selected from: 3-(3-((2,6-dimethylphenyl)ethynyl)phenyl)propan-1-amine; 3-(3-((2-methoxyphenyl)ethynyl)phenyl)propan-1-amine; 3-(3-(phenylethynyl)phenyl)propan-1-amine; 3-amino-1-(3-(biphenyl-3-ylethynyl)phenyl)propan-1-ol; and 3-amino-1-(3-((2-methoxyphenyl)ethynyl)phenyl)propan-1-ol.

In another embodiment is the compound of Formula (A) wherein $R^5$ is 1-naphthyl or 2-naphthyl. In another embodiment is the compound wherein each of $R^1$, $R^2$, $R^3$, $R^4$, $R^{23}$ and $R^{24}$ is hydrogen. In another embodiment is the compound of Formula (A) wherein m is 0.

In another embodiment is the compound 3-(3-(naphthalen-2-ylethynyl)phenyl)propan-1-amine.

In another embodiment is the compound of Formula (A) wherein $R^5$ is C($R^{16}$)($R^{17}$)($R^{18}$), Y is a bond and the compound has a structure of Formula (C):

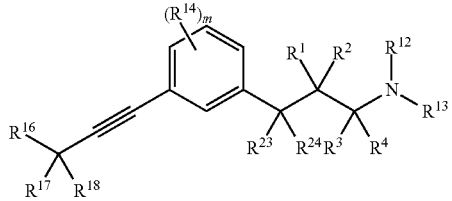

Formula (C)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
$R^1$ and $R^2$ are each the same or different and independently hydrogen, halogen, $C_1$-$C_5$ alkyl, fluoroalkyl, —$OR^6$, —$NR^7R^8$ or carbocyclyl; or $R^1$ and $R^2$ form an oxo;
$R^3$ and $R^4$ are each the same or different and independently hydrogen or alkyl;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently alkyl, alkenyl, aryl, carbocyclyl, heteroaryl or heterocyclyl;
$R^{23}$ and $R^{24}$ are each independently hydrogen, halogen, $C_1$-$C_5$ alkyl, fluoroalkyl, —$OR^6$, —$NR^7R^8$; or $R^{23}$ and $R^{24}$ together form an oxo;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{16}$, $R^{17}$ and $R^{18}$ are the same or different and independently hydrogen, alkyl, —$OR^6$, carbocyclyl or aryl.

In another embodiment is the compound of Formula (C) wherein each of $R^{12}$ and $R^{13}$ is hydrogen. In another embodiment is the compound of Formula (C) wherein $R^1$ and $R^2$ are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound of Formula (C) wherein m is 0, and $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (C) wherein each of $R^{16}$, $R^{17}$ and $R^{18}$ is independently hydrogen, alkyl, carbocyclyl or aryl.

In another embodiment is the compound selected from: 4-(3-(3-aminopropyl)phenyl)but-3-yn-1-ol; 5-(3-(3-aminopropyl)phenyl)pent-4-yn-2-ol; 2-(3-(3-cyclopentylprop-1-ynyl)phenoxy)ethanamine; 3-(3-(3,3-dimethylbut-1-ynyl)phenyl)propan-1-amine; 3-(3-(3-phenylprop-1-ynyl)phenyl)propan-1-amine; 3-(3-(pent-1-ynyl)phenyl)propan-1-amine; 3-(3-(hex-1-ynyl)phenyl)propan-1-amine; 3-amino-1-(3-(3-cyclopentylprop-1-ynyl)phenyl)propan-1-ol; 3-amino-1-(3-(3-phenylprop-1-ynyl)phenyl)propan-1-ol; 6-(3-(3-amino-1-hydroxypropyl)phenyl)hex-5-yn-1-ol; 4-(3-(3-amino-1-hydroxypropyl)phenyl)but-3-yn-1-ol; 3-amino-1-(3-(hept-1-ynyl)phenyl)propan-1-ol; 3-(3-(4-phenylbut-1-ynyl)phenyl)propan-1-amine; 3-amino-1-(3-(4-cyclopentylbut-1-ynyl)phenyl)propan-1-ol; 3-(3-(5-methoxypent-1-ynyl)phenyl)propan-1-amine; 3-amino-1-(3-(4-phenylbut-1-ynyl)phenyl)propan-1-ol; 6-(3-(3-aminopropyl)phenyl)hex-5-yn-1-ol; and 3-(3-(6-methoxyhex-1-ynyl)phenyl)propan-1-amine.

In another embodiment is the compound of Formula (C) wherein $R^{16}$ is —$OR^6$, wherein $R^6$ is hydrogen or $C_1$-$C_5$ alkyl, and each of $R^{17}$ and $R^{18}$ is independently hydrogen, alkyl or aryl.

In another embodiment is the compound selected from: 1-(3-(3-aminopropyl)phenyl)-3-ethylpent-1-yn-3-ol; 4-((3-(3-aminopropyl)phenyl)ethynyl)heptan-4-ol; 5-((3-(3-aminopropyl)phenyl)ethynyl)nonan-5-ol; 3-(3-(3-methoxy-3-propylhex-1-ynyl)phenyl)propan-1-amine; 1-(3-(3-aminopropyl)phenyl)-3-methylhex-1-yn-3-ol; 1-(3-(3-aminopropyl)phenyl)-3,4-dimethylpent-1-yn-3-ol; 4-(3-(3-aminopropyl)phenyl)-2-methylbut-3-yn-2-ol; 1-(3-(3-aminopropyl)phenyl)hex-1-yn-3-ol; 1-(3-(3-aminopropyl)phenyl)-3,4-dimethylhex-1-yn-3-ol; 3-(3-(3-methoxyprop-1-ynyl)phenyl)propan-1-amine; 3-(3-(3-aminopropyl)phenyl)prop-2-yn-1-ol; 1-(3-(3-aminopropyl)phenyl)-3-tert-butyl-4,4-dimethylpent-1-yn-3-ol; (R)-1-(3-(3-aminopropyl)phenyl)oct-1-yn-3-ol; (R)-1-(3-(3-aminopropyl)phenyl)oct-1-yn-3-ol; (R)-3-(3-(3-aminopropyl)phenyl)-1-phenylprop-2-yn-1-ol; 4-((3-(3-amino-1-hydroxypropyl)phenyl)ethynyl)heptan-4-ol; 4-((3-(3-amino-2,2-dimethylpropyl)phenyl)ethynyl)heptan-4-ol; 4-(3-(3-aminopropyl)phenyl)-2-phenylbut-3-yn-2-ol; 1-(3-(3-aminopropyl)phenyl)-4-methylpent-1-yn-3-ol; 1-(3-(3-aminopropyl)phenyl)-3,4,4-trimethylpent-1-yn-3-ol; (R)-3-(3-(3-aminopropyl)phenyl)-1-phenylprop-2-yn-1-ol; 1-(3-(3-aminopropyl)phenyl)-3-isopropyl-4-methylpent-1-yn-3-ol; 4-((3-(3-aminopropyl)phenyl)ethynyl)-2,6-dimethylheptan-4-ol; 1-(3-(3-amino-1-hydroxypropyl)phenyl)-3-ethylpent-1-yn-3-ol; 3-(3-(3-ethylpent-1-ynyl)phenyl)propan-1-amine; 3-(3-(3-propylhex-1-ynyl)phenyl)propan-1-amine; 3-amino-1-(3-(3-ethylpent-1-ynyl)phenyl)propan-1-ol; 3-amino-1-(3-(3-propylhex-1-ynyl)phenyl)propan-1-ol; 3-amino-1-(3-(3-ethylpent-1-ynyl)phenyl)-2-methylpropan-1-ol; 1-(3-(3-amino-1-hydroxy-2-methylpropyl)phenyl)-3-ethylpent-1-yn-3-ol; 1-amino-3-(3-(3-ethylpent-1-ynyl)phenyl)propan-2-ol; 1-(3-(3-amino-2-hydroxypropyl)phenyl)-3-ethylpent-1-yn-3-ol; 3-amino-2-methyl-1-(3-(3-propylhex-1-ynyl)phenyl)propan-1-ol; 4-((3-(3-amino-1-hydroxy-2-methylpropyl)phenyl)ethynyl)heptan-4-ol; 4-((3-(3-amino-2-hydroxypropyl)phenyl)ethynyl)heptan-4-ol; 1-amino-3-(3-(3-propylhex-1-ynyl)phenyl)propan-2-ol.

In another embodiment is the compound of Formula (A) wherein Z is —C($R^{23}$)($R^{24}$)—C($R^1$)($R^2$)— and $R^5$ is carbocyclyl.

In another embodiment is the compound of Formula (A) wherein $R^5$ is cycloalkyl, Y is a bond and the compound has a structure of Formula (D):

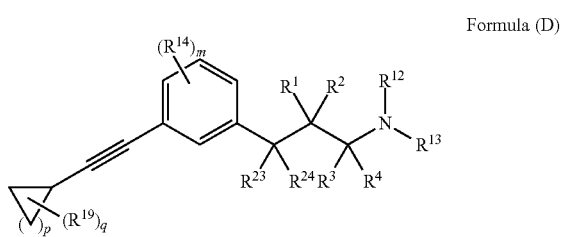

Formula (D)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;
p is 1, 2, 3, 4, 5 or 6;
q is 0, 1, 2, 3, 4, 5, 6, 7, 8 or 9;
$R^1$ and $R^2$ are each the same or different and independently hydrogen, halogen, $C_1$-$C_5$ alkyl, fluoroalkyl, —$OR^6$, —$NR^7R^8$ or carbocyclyl; or $R^1$ and $R^2$ together form an oxo;
$R^3$ and $R^4$ are each the same or different and independently hydrogen or alkyl;
each $R^6$ is the same or different and independently hydrogen or $C_1$-$C_5$ alkyl;
each $R^7$ and each $R^8$ are each the same or different and independently hydrogen, alkyl, carbocyclyl, heteroalkyl, heterocycloalkyl, aryl, heteroaryl, or —C(=O)$R^9$; or $R^7$ and $R^8$, together with the nitrogen atom to which they are attached, form an N-heterocyclyl;
each $R^9$ is the same or different and independently alkyl, alkenyl, aryl, carbocyclyl, heteroaryl or heterocyclyl;
$R^{23}$ and $R^{24}$ are each the same or different and independently hydrogen, halogen, $C_1$-$C_5$ alkyl, fluoroalkyl, —$OR^6$, —$NR^7R^8$ or carbocyclyl; or $R^{23}$ and $R^{24}$ together form an oxo;
$R^{12}$ and $R^{13}$ are each the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{19}$ is the same or different and independently alkyl, —$OR^6$, halo or fluoroalkyl.

In another embodiment is the compound of Formula (D) wherein each of $R^{12}$ and $R^{13}$ is hydrogen. In another embodiment is the compound of Formula (D) wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound of Formula (D) wherein p is 3 and $R^5$ is a substituted or unsubstituted cyclopentyl. In another embodiment is the compound of Formula (D) wherein p is 4, and $R^5$ is a substituted or unsubstituted cyclohexyl. In another embodiment is the compound of Formula (D) wherein p is 5, and $R^5$ is a substituted or unsubstituted cycloheptyl. In another embodiment is the compound of Formula (D) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (D) wherein m is 0. In another embodiment is the compound of Formula (D) wherein q is 0. In another embodiment is the compound of Formula (D) wherein q is 1, 2, 3, 4 or 5, and each $R^{19}$ is independently alkyl or —$OR^6$, wherein $R^6$ is hydrogen or $C_1$-$C_5$ alkyl.

In another embodiment is the compound selected from the following:
3-(3-(cyclopentylethynyl)phenyl)propan-1-amine; 3-(3-(cyclohexylethynyl)phenyl)propan-1-amine; 3-amino-1-(3-(cyclopentylethynyl)phenyl)propan-1-ol; 3-amino-1-(3-(cyclohexylethynyl)phenyl)propan-1-ol; 1-((3-(3-aminopropyl)phenyl)ethynyl)cyclohexanol; 1-((3-(3-aminopropyl)phenyl)ethynyl)-2,2,6,6-tetramethylcyclohexanol; 1-((3-(3-aminopropyl)phenyl)ethynyl)cyclopentanol; 3-(3-(cycloheptylethynyl)phenyl)propan-1-amine; 3-amino-1-(3-(cycloheptylethynyl)phenyl)propan-1-ol; 1-amino-3-(3-(cycloheptylethynyl)phenyl)propan-2-ol; 1-amino-3-(3-(cyclohexylethynyl)phenyl)propan-2-ol; 1-amino-3-(3-(cyclopentylethynyl)phenyl)propan-2-ol; 1-((3-(3-amino-2-hydroxypropyl)phenyl)ethynyl)cyclopentanol; 1-((3-(3-amino-1-hydroxypropyl)phenyl)ethynyl)cyclopentanol; 1-((3-(3-amino-1-hydroxypropyl)phenyl)ethynyl)cyclohexanol; 1-((3-(3-amino-2-hydroxypropyl)phenyl)ethynyl)cycloheptanol; 1-((3-(3-amino-2-hydroxypropyl)phenyl)ethynyl)cyclohexanol; 1-((3-(3-amino-1-hydroxypropyl)phenyl)ethynyl)cycloheptanol; and 1-((3-(3-aminopropyl)phenyl)ethynyl)cycloheptanol.

In another embodiment is the compound of Formula (D) wherein $R^{12}$ is hydrogen, and $R^{13}$ is —C(=O)$R^9$, wherein $R^9$ is alkyl. In another embodiment is the compound of Formula (D) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (D), wherein m is 0. In another embodiment is the compound of claim 36, wherein q is 1, 2, 3, 4 or 5, and each $R^{19}$ is independently alkyl or —$OR^6$, wherein $R^6$ is hydrogen or $C_1$-$C_5$ alkyl. In another embodiment is the compound of Formula (D), wherein p is 4, and $R^5$ is a substituted or unsubstituted cyclohexyl.

In another embodiment is the compound N-(3-hydroxy-3-(3-((1-hydroxycyclohexyl)ethynyl)phenyl)propyl)acetamide.

In another embodiment is the compound of Formula (A) wherein Z is —C($R^{23}$)($R^{24}$)—C($R^1$)($R^2$)—, wherein $R^5$ is heterocyclyl and Y is a bond. In another embodiment is the compound wherein the heterocyclyl can be optionally substituted with —$OR^6$, wherein $R^6$ is hydrogen or $C_1$-$C_5$ alkyl. In another embodiment is the compound wherein each of $R^{12}$ and $R^{13}$ is hydrogen.

In another embodiment is the compound of Formula (A) wherein Z is —C($R^{23}$)($R^{24}$)—C($R^1$)($R^2$)—, wherein Y is a bond, $R^5$ is heterocyclyl and the heterocyclyl can be optionally substituted with —$OR^6$, wherein $R^6$ is hydrogen or $C_1$-$C_5$ alkyl, and each of $R^{12}$ and $R^{13}$ is hydrogen and wherein $R^1$ and $R^2$ are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl.

In another embodiment is the compound of Formula (A) wherein Z is —C($R^{23}$)($R^{24}$)—C($R^1$)($R^2$)—, wherein Y is a bond, $R^5$ is heterocyclyl and the heterocyclyl can be optionally substituted with —$OR^6$, wherein $R^6$ is hydrogen or $C_1$-$C_5$ alkyl, and each of $R^{12}$ and $R^{13}$ is hydrogen and wherein each of $R^1$, $R^2$, $R^3$, $R^4$, $R^{23}$ and $R^{24}$ is hydrogen. In another embodiment is the compound wherein m is 0.

In another embodiment is the compound selected from the following: 4-((3-(3-aminopropyl)phenyl)ethynyl)tetrahydro-2H-thiopyran-4-ol; and 4-((3-(3-aminopropyl)phenyl)ethynyl)tetrahydro-2H-pyran-4-ol.

In another embodiment is the compound of Formula (A) wherein Z is —C($R^{23}$)($R^{24}$)—C($R^1$)($R^2$)—, and $R^5$ is heteroaryl and Y is a bond. In another embodiment is the compound wherein each of $R^{12}$ and $R^{13}$ is hydrogen. In another embodiment is the compound wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound wherein each of $R^1$, $R^2$, $R^3R^4$, $R^{23}$ and $R^{24}$ is hydrogen. In another embodiment is the compound wherein m is 0.

In another embodiment is the compound wherein the compound is selected from:
3-(3-(pyridin-2-ylethynyl)phenyl)propan-1-amine; 3-(3-(pyridin-3-ylethynyl)phenyl)propan-1-amine; 3-(3-(pyridin-4-ylethynyl)phenyl)propan-1-amine; 3-(3-(thiophen-2-ylethynyl)phenyl)propan-1-amine; and 3-(3-(thiophen-3-ylethynyl)phenyl)propan-1-amine.

In another embodiment is the compound of Formula (A) wherein Z is —O—C($R^{21}$)($R^{22}$) Y is a bond and the compound has a structure of Formula (E):

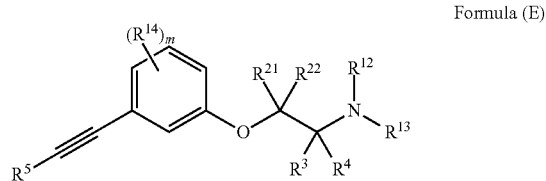

Formula (E)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

$R^{21}$ and $R^{22}$ are each independently hydrogen, $C_1$-$C_5$ alkyl or fluoroalkyl;

$R^3$ and $R^4$ are each the same or different and independently hydrogen or alkyl;

$R^5$ is alkyl, alkenyl, aryl, carbocyclyl, heteroaryl or heterocyclyl;

each $R^6$ is the same or different and independently hydrogen or $C_1$-$C_5$ alkyl;

$R^9$ is alkyl, alkenyl, aryl, carbocyclyl, heteroaryl or heterocyclyl;

$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl; and each $R^{14}$ is the same or different and independently alkyl, halo, fluoroalkyl or —$OR^6$.

In another embodiment is the compound of Formula (E) wherein $R^5$ is an unsaturated carbocyclyl. In another embodiment is the compound of Formula (E) wherein $R^5$ is a bicyclic carbocyclyl. In another embodiment is the compound of Formula (E) wherein $R^5$ is norbornyl.

In another embodiment is the compound of Formula (E) wherein $R^5$ is —$C(R^{16})(R^{17})(R^{18})$, Y is a bond and the compound has a structure of Formula (F):

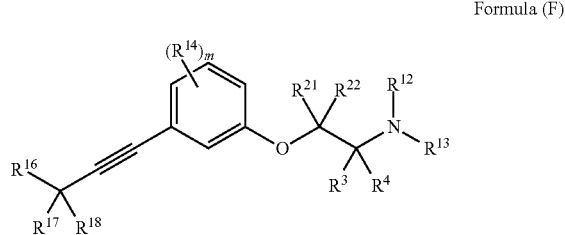

Formula (F)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
$R^{21}$ and $R^{22}$ are each independently hydrogen, $C_1$-$C_5$ alkyl or fluoroalkyl;
$R^3$ and $R^4$ are each the same or different and independently hydrogen or alkyl;
each $R^6$ is the same or different and independently hydrogen or $C_1$-$C_5$ alkyl;
$R^9$ is alkyl, alkenyl, aryl, carbocyclyl, heteroaryl or heterocyclyl;
$R^{12}$ and $R^{13}$ are the same or different and independently hydrogen, alkyl or —$C(=O)R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
$R^{16}$, $R^{17}$ and $R^{18}$ are each the same or different and independently hydrogen, alkyl, —$OR^6$, carbocyclyl or aryl.

In another embodiment is the compound of Formula (F) wherein each of $R^{12}$ and $R^{13}$ is hydrogen. In another embodiment is the compound of Formula (F) wherein each of $R^{21}$, $R^{22}$, $R^3$ and $R^4$ is independently hydrogen or $C_1$-$C_5$ alkyl. In another embodiment is the compound of Formula (F) wherein m is 0. In another embodiment is the compound of Formula (F) wherein each of $R^{16}$, $R^{17}$ and $R^{18}$ is independently hydrogen, alkyl or —$OR^6$, wherein each $R^6$ is independently hydrogen or $C_1$-$C_5$ alkyl. In another embodiment is the compound of Formula (F) wherein each of $R^{16}$, $R^{17}$ and $R^{18}$ is independently hydrogen, alkyl or aryl.

In another embodiment is the compound selected from:
4-((3-(2-aminoethoxy)phenyl)ethynyl)heptan-4-ol; 1-(3-(2-aminoethoxy)phenyl)-3-ethylpent-1-yn-3-ol; 1-(3-(2-aminoethoxy)phenyl)-3-isopropyl-4-methylpent-1-yn-3-ol; 5-((3-(2-aminoethoxy)phenyl)ethynyl)nonan-5-ol; 4-(3-(2-aminoethoxy)phenyl)-2-methylbut-3-yn-2-ol; 2-(3-(hept-1-ynyl)phenoxy)ethanamine; 4-(3-(2-aminoethoxy)phenyl)but-3-yn-1-ol; 2-(3-(3-phenylprop-1-ynyl)phenoxy)ethanamine; 2-(3-(4-methylpent-1-ynyl)phenoxy)ethanamine; 6-(3-(2-aminoethoxy)phenyl)hex-5-yn-1-ol; 2-(3-(3-ethylpent-1-ynyl)phenoxy)propan-1-amine; 2-(3-(3-propylhex-1-ynyl)phenoxy)propan-1-amine; 1-(3-(2-aminoethoxy)phenyl)-3-ethylpent-1-yn-3-ol; 4-((3-(1-aminopropan-2-yloxy)phenyl)ethynyl)heptan-4-ol; 2-(3-(3-ethylpent-1-ynyl)phenoxy)ethanamine; and 2-(3-(3-propylhex-1-ynyl)phenoxy)ethanamine.

In another embodiment is the compound of Formula (E), wherein $R^5$ is carbocyclyl. In another embodiment is the compound of Formula (E) wherein $R^5$ is a cycloalkyl, Y is a bond and the compound has a structure of Formula (G):

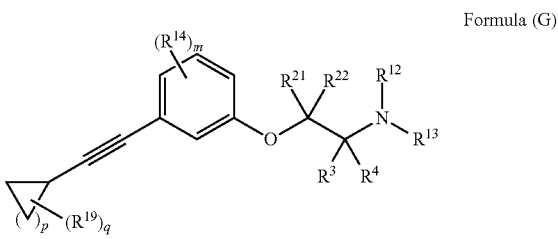

Formula (G)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
p is 1, 2, 3, 4 or 5;
q is 0, 1, 2, 3, 4, 5, 6, 7, 8 or 9;
$R^{21}$ and $R^{22}$ are each the same or different and independently hydrogen, $C_1$-$C_5$ alkyl or fluoroalkyl;
$R^3$ and $R^4$ are each the same or different and independently hydrogen or alkyl;
each $R^6$ is the same or different and independently hydrogen or $C_1$-$C_5$ alkyl;
$R^9$ is alkyl, alkenyl, aryl, carbocyclyl, heteroaryl or heterocyclyl;
$R^{12}$ and $R^{13}$ are the same or different and independently hydrogen, alkyl or —$C(=O)R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{19}$ is the same or different and independently alkyl, —$OR^6$, halo or fluoroalkyl.

In another embodiment is the compound of Formula (G) wherein each of $R^{12}$ and $R^{13}$ is hydrogen. In another embodiment is the compound of Formula (G) wherein m is 0. In another embodiment is the compound of Formula (G) wherein $R^{21}$ and $R^{22}$ are each independently hydrogen or $C_1$-$C_5$ alkyl; and $R^3$ and $R^4$ are each independently hydrogen or alkyl. In another embodiment is the compound of Formula (G) wherein each of $R^{21}$, $R^{22}$, $R^3$ and $R^4$ is hydrogen or $C_1$-$C_5$ alkyl. In another embodiment is the compound of Formula (G) wherein, q is 0 or 1, and each $R^{19}$ is independently alkyl or —$OR^6$, wherein $R^6$ is hydrogen or $C_1$-$C_5$ alkyl.

In another embodiment is the compound is selected from:
1-((3-(2-aminoethoxy)phenyl)ethynyl)cyclopentanol; 1-((3-(2-aminoethoxy)phenyl)ethynyl)cyclohexanol; 2-(3-(cyclohexylethynyl)phenoxy)ethanamine 1-((3-(1-aminopropan-2-yloxy)phenyl)ethynyl)cyclopentanol; 1-((3-(1-aminopropan-2-yloxy)phenyl)ethynyl)cyclohexanol; 1-((3-(1-aminopropan-2-yloxy)phenyl)ethynyl)cycloheptanol; 2-(3-(cycloheptylethynyl)phenoxy)ethanamine; 2-(3-(cycloheptylethynyl)phenoxy)propan-1-amine; 2-(3-(cyclohexylethynyl)phenoxy)propan-1-amine; 2-(3-(cyclopentylethynyl)phenoxy)propan-1-amine; 2-(3-(cyclopentylethynyl)phenoxy)-ethanamine; and 1-((3-(2-aminoethoxy)phenyl)ethynyl)-cycloheptanol.

In another embodiment is the compound of Formula (E) wherein $R^5$ is heterocyclyl. In another embodiment is the compound of Formula (E) wherein m is 0 and each of $R^{12}$ and $R^{13}$ is hydrogen. In another embodiment is the compound of Formula (E) wherein each of $R^{21}$, $R^{22}$, $R^3$ and $R^4$ is independently hydrogen or $C_1$-$C_5$ alkyl.

In another embodiment is the compound 2-(3-(pyridin-3-ylethynyl)phenoxy)ethanamine.

In another embodiment is the compound of Formula (E), wherein $R^5$ is aryl.

In another embodiment is the compound 2-(3-(phenylethynyl)phenoxy)ethanamine.

In another embodiment is a pharmaceutical composition comprising a pharmaceutically acceptable carrier and the compound of any one of Formulas (A)-(G).

In yet another embodiment is a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an IC50 of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an IC50 of about 10 nM or less when assayed in vitro, utilizing extract of cells that express RPE65 and LRAT, wherein the extract further comprises CRALBP, wherein the compound is stable in solution for at least about 1 week, 1 month, 2 months, 4 months, 6 months, 8 months, 10 months, 1 year, 2 years, 5 yeas or longer, at room temperature.

In an additional embodiment is a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment is a non-retinoid compound of wherein the ED50 value is measured after administering a single dose of the compound to said subject for about 2 hours or longer. In an additional embodiment the compound is an alkynyl phenyl-linked amine compound. In a further embodiment the compound is a non-retinoid compound.

In a further embodiment is a pharmaceutical composition comprising a pharmaceutically acceptable carrier and a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In another embodiment, the present invention provides a method of modulating chromophore flux in a retinoid cycle comprising introducing into a subject a compound disclosed herein, including a compound of any one of Formulae (A)-(G) respective substructures thereof. In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject compounds or the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formulae (A)-(G) their respective substructures thereof.

In an additional embodiment is a method of inhibiting regeneration of rhodopsin in a rod photoreceptor cell of the retina comprising contacting the retina with a compound of any one of Formulae (A)-(G) and their respective substructures thereof, a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In a further embodiment is a method of reducing ischemia in an eye of a subject comprising administering to the subject the pharmaceutical composition of a compound of any one of Formulae (A)-(G) and their respective substructures thereof, a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject the pharmaceutical composition of a compound of any one of Formulae (A)-(G), and their respective substructures thereof. In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with the compound of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell In another embodiment, a method is provided for treating an ophthalmic disease or disorder in a subject, comprising administering to the subject the pharmaceutical composition comprising a pharmaceutically acceptable carrier and a compound having a structure of any of Formula (A)-(G) as described above and herein. In one embodiment, the ophthalmic disease or disorder is a retinal disease or disorder. In specific embodiments, the retinal disease or disorder is age-related macular degeneration or Stargardt's macular dystrophy. In another embodiment, the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In yet another embodiment, the ophthalmic disease or disorder is selected from diabetic retinopathy, diabetic maculopathy, retinal blood vessel occlusion, retinopathy of prematurity, or ischemia reperfusion related retinal injury.

Further provided is a method of reducing lipofuscin pigment accumulated in a subject's retina comprising administering to the subject a pharmaceutical composition described here. In one embodiment the lipofuscin pigment is N-retinylidene-N-retinyl-ethanolamine (A2E).

In another embodiment, a method of inhibiting at least one visual cycle trans-cis isomerase in a cell is provided, wherein the method comprises contacting the cell with a compound having a structure of any of Formulae (A)-(G) as described herein, thereby inhibiting the at least one visual cycle trans-cis isomerase. In one certain embodiment, the cell is a retinal pigment epithelial (RPE) cell.

Also provided herein in another embodiment is a method of inhibiting at least one visual cycle trans-cis isomerase in a subject comprising administering to the subject the pharmaceutical composition comprising a pharmaceutically acceptable carrier and a compound having a structure of any of Formulae (A)-(G) as described herein. In certain embodiments, the subject is a human or is a non-human animal.

In particular embodiments of the methods described above and herein, accumulation of lipofuscin pigment is inhibited in an eye of the subject, and in certain particular embodiments, the lipofuscin pigment is N-retinylidene-N-retinyl-ethanolamine (A2E). In other certain embodiments, degeneration of a retinal cell is inhibited. In a specific embodiment, the retinal cell is a retinal neuronal cell, wherein the retinal neuronal cell is a photoreceptor cell, an amacrine cell, a horizontal cell, a ganglion cell, or a bipolar cell. In another specific embodiment, the retinal cell is a retinal pigment epithelial (RPE) cell.

Additionally, in one embodiment, a compound is provided that has a structure of Formula (I):

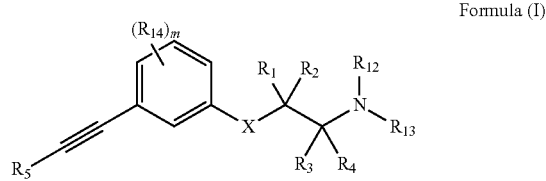

Formula (I)

as a tautomer or a mixture of tautomers, or as a pharmaceutically acceptable salt, hydrate, solvate, N-oxide or prodrug thereof, wherein:

m is 0, 1, 2 or 3;

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_5$ is alkyl, alkenyl, aryl, carbocyclyl, heteroaryl or heterocyclyl;

$R_6$ is hydrogen or alkyl;

$R_7$ and $R_8$ are each the same or different and independently hydrogen, alkyl, carbocyclyl, or —C(=O)$R_9$; or $R_7$ and $R_8$, together with the nitrogen atom to which they are attached, form an N-heterocyclyl;

$R_9$ is alkyl, alkenyl, aryl, carbocyclyl, heteroaryl or heterocyclyl;

X is —C($R_{10}$)($R_{11}$)— or —O—;

$R_{10}$ and $R_{11}$ are each the same or different and independently hydrogen, halogen, alkyl, fluoroalkyl, —$OR_6$, —$NR_7R_8$ or carbocyclyl; or $R_{10}$ and $R_{11}$ form an oxo;

$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl; and each $R_{14}$ is the same or different and independently alkyl, halo, fluoroalkyl or —$OR_6$.

Also provided are compounds having structures of Formulae (II), (IIa), (IIb), (IIc), (III), (IIIa) and (IIIb):

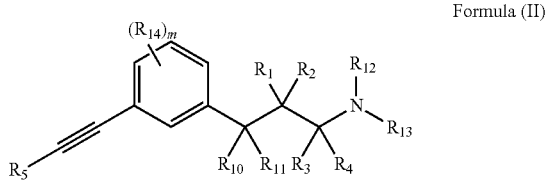

Formula (II)

-continued

Formula (IIa)
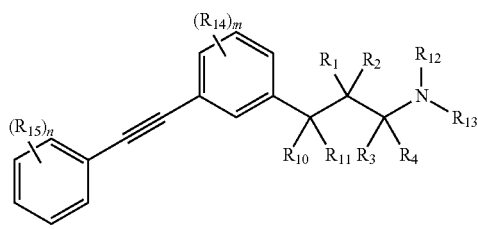

Formula (IIb)
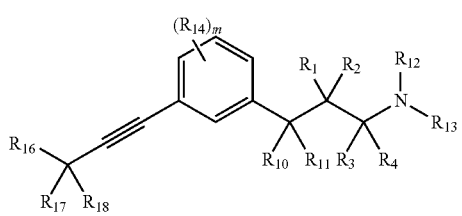

Formula (IIc)
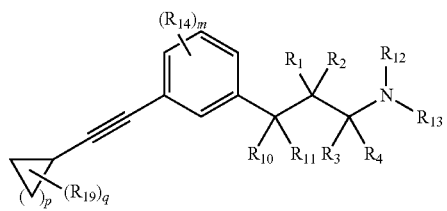

Formula (III)
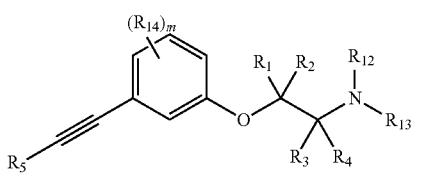

Formula (IIIa)
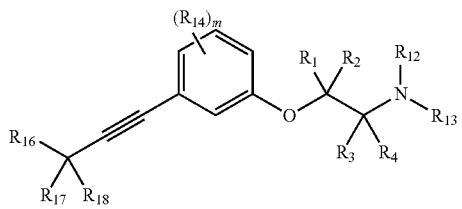

Formula (IIIb)
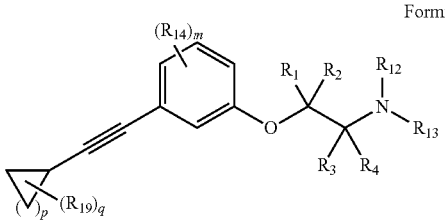

wherein, m, n, p, q, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$ and $R_{19}$, are as defined above and herein (see Detailed Description).

Another embodiment provides a pharmaceutical composition comprising a pharmaceutically acceptable carrier and a compound having a structure of Formula (I):

Formula (I)
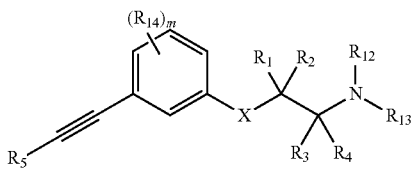

as a tautomer or a mixture of tautomers, or as a pharmaceutically acceptable salt, hydrate, solvate, N-oxide or prodrug thereof, wherein:

wherein, $R_1$, $R_2$, $R_3$, $R_4$, $R_5$, $R_{12}$, $R_{13}$, $R_{14}$ and X are as defined herein.

Also provided are pharmaceutical compositions comprising a compound having a structure of any of Formulae (II), (IIa), (IIb), (IIc), (III), (IIIa) and (IIIb):

Formula (II)
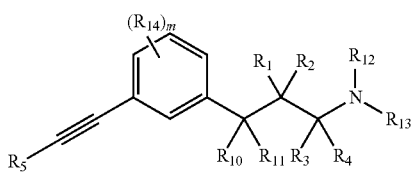

Formula (IIa)
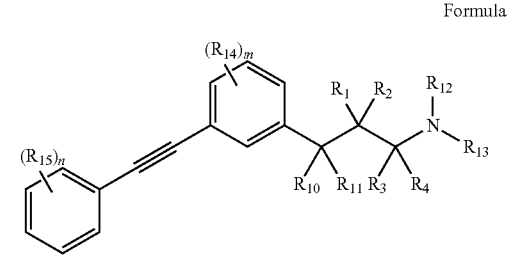

Formula (IIb)
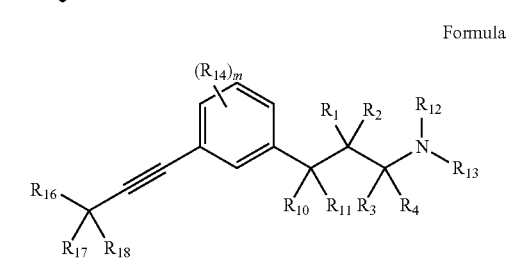

Formula (IIc)
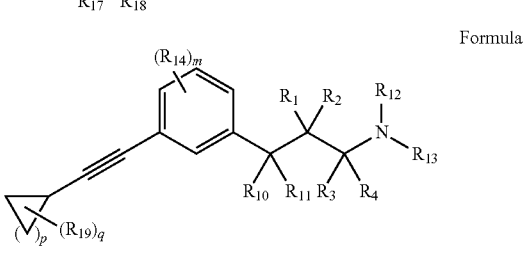

Formula (III)
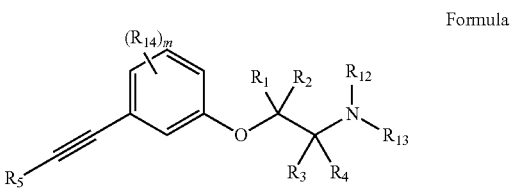

-continued

Formula (IIIa)

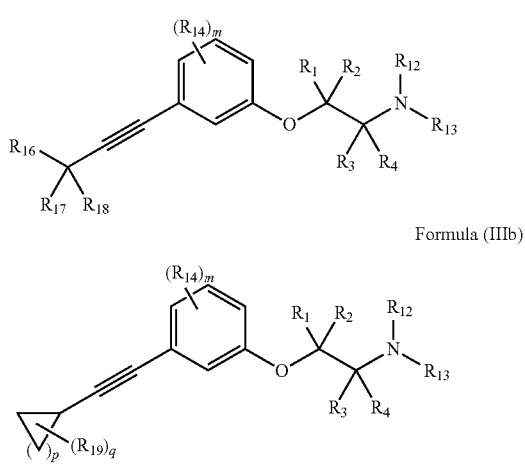

Formula (IIIb)

wherein, m, n, p, q, $R_1$, $R_2$, $R_3$, $R_4$, $R_5$, $R_6$, $R_7$, $R_8$, $R_9$, $R_{10}$, $R_{11}$, $R_{12}$, $R_{13}$, $R^{14}$, $R_{15}$, $R_{16}$, $R^{17}$, $R_{18}$ and $R_{19}$ are as defined above and herein (see Detailed Description).

In an additional embodiment is a pharmaceutical composition comprising a pharmaceutically acceptable carrier and a compound disclosed herein, including without limitation a compound of any one of Formulae (A)-(G) and (I)-(III), and their respective substructures thereof.

In yet another embodiment is a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an $IC_{50}$ of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an $IC_{50}$ of about 10 nM or less when assayed in vitro, utilizing extract of cells that express RPE65 and LRAT, wherein the extract further comprises CRALBP, wherein the compound is stable in solution for at least about 1 week, 1 month, 2 months, 4 months, 6 months, 8 months, 10 months, 1 year, 2 years, 5 years or longer, at room temperature.

In an additional embodiment is a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment is a non-retinoid compound of wherein the $ED_{50}$ value is measured after administering a single dose of the compound to said subject for about 2 hours or longer. In an additional embodiment the compound is an alkynyl phenyl-linked amine compound. In a further embodiment the compound is a non-retinoid compound.

In a further embodiment is a pharmaceutical composition comprising a pharmaceutically acceptable carrier and a compound that inhibits 11-cis-retinol production with an $IC_{50}$ of about 1 uM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject.

In another embodiment, the present invention provides a method of modulating chromophore flux in a retinoid cycle comprising introducing into a subject a compound disclosed herein, including a compound of any one of Formulae (A)-(G) and (I)-(III), and their respective substructures thereof. In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject compounds or the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formulae (A)-(G) and (I)-(III), and their respective substructures thereof.

In an additional embodiment is a method of inhibiting regeneration of rhodopsin in a rod photoreceptor cell of the retina comprising contacting the retina with a compound of any one of Formulae (A)-(G) and (I)-(III), and their respective substructures thereof, a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject.

In a further embodiment is a method of reducing ischemia in an eye of a subject comprising administering to the subject the pharmaceutical composition of a compound of any one of Formulae (A)-(G) and (I)-(III), and their respective substructures thereof, a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject the pharmaceutical composition of a compound of any one of Formulae (A)-(G) and (I)-(III), and their respective substructures thereof. In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with the compound of the compound of Formula (A), a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an $ED_{50}$ value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell In another embodiment, a method is provided for treating an ophthalmic disease or disorder in a subject, comprising administering to the subject the pharmaceutical composition comprising a pharmaceutically acceptable carrier and a compound having a structure of any of Formulae (A)-(G) and (I)-(III) as described above and herein. In one embodiment, the ophthalmic disease or disorder is a retinal disease or disorder. In specific embodiments, the retinal disease or disorder is age-related macular degeneration or Stargardt's macular dystrophy. In another embodiment, the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In yet another embodiment, the ophthalmic disease or disorder is selected from diabetic retinopathy, diabetic maculopathy, retinal blood vessel occlusion, retinopathy of prematurity, or ischemia reperfusion related retinal injury.

Further provided is a method of reducing lipofuscin pigment accumulated in a subject's retina comprising administering to the subject a pharmaceutical composition described here. In one embodiment the lipofuscin pigment is N-retinylidene-N-retinyl-ethanolamine (A2E).

In another embodiment, a method of inhibiting at least one visual cycle trans-cis isomerase in a cell is provided, wherein the method comprises contacting the cell with a compound having a structure of any of Formulae (A)-(G) and (I)-(III) as described herein, thereby inhibiting the at least one visual cycle trans-cis isomerase. In one certain embodiment, the cell is a retinal pigment epithelial (RPE) cell.

Also provided herein in another embodiment is a method of inhibiting at least one visual cycle trans-cis isomerase in a subject comprising administering to the subject the pharmaceutical composition comprising a pharmaceutically acceptable carrier and a compound having a structure of any of Formulae (A)-(G) and (I)-(III) as described herein. In certain embodiments, the subject is a human or is a non-human animal.

In particular embodiments of the methods described above and herein, accumulation of lipofuscin pigment is inhibited in an eye of the subject, and in certain particular embodiments, the lipofuscin pigment is N-retinylidene-N-retinyl-ethanolamine (A2E). In other certain embodiments, degeneration of a retinal cell is inhibited. In a specific embodiment, the retinal cell is a retinal neuronal cell, wherein the retinal neuronal cell is a photoreceptor cell, an amacrine cell, a horizontal cell, a ganglion cell, or a bipolar cell. In another specific embodiment, the retinal cell is a retinal pigment epithelial (RPE) cell.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
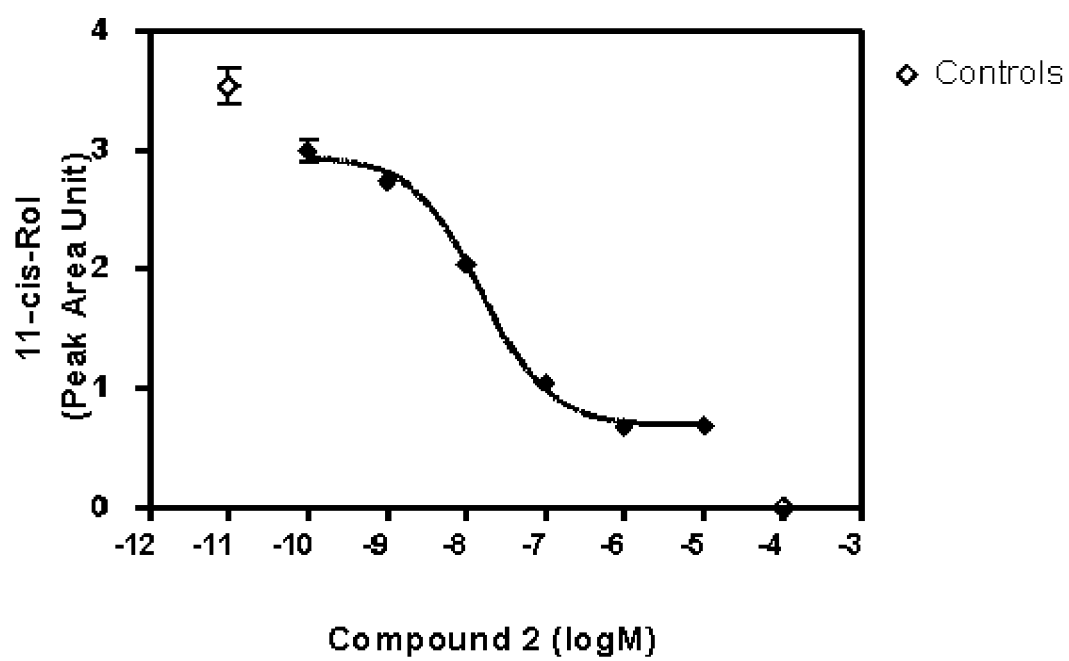
FIG. 1 depicts concentration-dependent inhibition of isomerase activity by Compound 2 in the in vitro recombinatnt RPE65/LRAT system.

Alkynyl phenyl derivative compounds that inhibit an isomerization step of the retinoid cycle are described herein. These compounds and compositions comprising these compounds may be useful for inhibiting degeneration of retinal cells or for enhancing retinal cell survival. The compounds described herein may, therefore, be useful for treating ophthalmic diseases and disorders, such as age-related macular degeneration and Stargardt's disease.

I. ALKYNYL PHENYL DERIVATIVE COMPOUNDS

In certain embodiments, alkynyl phenyl derivative compounds comprising a meta-substituted linkage terminating in a nitrogen-containing moiety are provided. The nitrogen-containing moiety can be, for example, an amine (e.g., primary, secondary and tertiary amine), an amide or an N-heterocyclyl. The linkage atoms form a combination of linearly constructed stable chemical bonds, including carbon-carbon bonds, carbon-oxygen bonds, and the like.

In one embodiment is a compound having a structure of Formula (A):

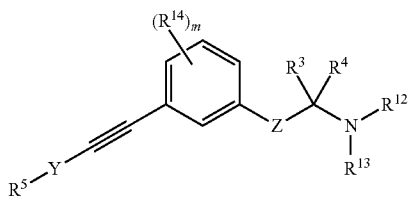

Formula (A)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

Z is a bond, —C($R^1$)($R^2$)—, —X—C($R^{21}$)($R^{22}$)—, —C($R^{23}$)($R^{24}$)—C($R^1$)($R^2$)—, or —C($R^{23}$)($R^{24}$)—C($R^{25}$)($R^{26}$)—C($R^1$)($R^2$)—, —X—C($R^{21}$)($R^{22}$)—C($R^1$)($R^2$)—, —C($R^{32}$)($R^{33}$)—X—C($R^{21}$)($R^{22}$)—;

X is —O—, —S—, —S(=O)—, —S(=O)$_2$—, —N($R^{31}$)—, —C(=O)—, —C(=CH$_2$)—, —C(=N—N$R^{35}$)—, or —C(=N—O$R^{35}$)—;

Y is a bond, —C($R^{27}$)($R^{28}$)—, or —C($R^{27}$)($R^{28}$)—C($R^{29}$)($R^{30}$)—;

$R^1$ and $R^2$ are each independently selected from hydrogen, halogen, $C_1$-$C_5$ alkyl, fluoroalkyl, —OR$^6$ or —NR$^7$R$^8$; or $R^1$ and $R^2$ together form an oxo;

$R^{21}$, $R^{22}$, $R^{32}$ and $R^{33}$ are each independently selected from hydrogen, $C_1$-$C_5$ alkyl, or fluoroalkyl;

$R^{23}$ and $R^{24}$ are each independently selected from hydrogen, halogen, $C_1$-$C_5$ alkyl, fluoroalkyl, —OR$^6$, —NR$^7$R$^8$; or $R^{23}$ and $R^{24}$ together form an oxo; or optionally, $R^{23}$ and an adjacent $R^1$ together form a direct bond to provide a double bond; or optionally, $R^{23}$ and an adjacent $R^1$ together form a direct bond, and $R^{24}$ and an adjacent $R^2$ together form a direct bond to provide a triple bond;

$R^{25}$ and $R^{26}$ are each independently selected from hydrogen, halogen, $C_1$-$C_5$ alkyl, fluoroalkyl, —OR$^6$ or —NR$^7$R$^8$; or $R^{25}$ and $R^{26}$ together form an oxo;

$R^3$ and $R^4$ are each independently selected from hydrogen, alkyl, heteroalkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is alkyl, heteroalkyl, alkenyl, heteroalkenyl, aryl, carbocyclyl, heteroaryl or heterocyclyl;

each $R^6$ is the same or different and independently hydrogen or $C_1$-$C_5$ alkyl;

each $R^7$ and each $R^8$ are each the same or different and independently hydrogen, alkyl, carbocyclyl, heteroalkyl, heterocycloalkyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or $R^7$ and $R^8$, together with the nitrogen atom to which they are attached, form an N-heterocyclyl;

each $R^9$ is the same or different and each is independently alkyl, alkenyl, aryl, carbocyclyl, heteroaryl or heterocyclyl;

$R^{12}$ and $R^{13}$ are the same or different and independently hydrogen, alkyl, heteroalkyl, carbocyclyl, heterocyclyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or $R^{12}$ and $R^{13}$ together with the nitrogen atom to which they are attached, form an N-heterocyclyl; and each $R^{14}$ is the same or different and independently alkyl, halo, fluoroalkyl or —OR$^6$;

each $R^{27}$, $R^{28}$, $R^{29}$ and $R^{31}$ are the same or different and independently hydrogen, alkyl or —OR$^6$; and $R^{30}$ and $R^{35}$ are each independently hydrogen or $C_1$-$C_5$ alkyl.

In another embodiment is the compound of Formula (A) wherein Z is —C($R^{23}$)($R^{24}$)—C($R^1$)($R^2$)—.

In another embodiment is the compound of Formula (A) wherein $R^5$ is aryl. In another embodiment is the compound of Formula (A) wherein $R^5$ is an unsaturated carbocyclyl. In another embodiment is the compound of Formula (A) wherein $R^5$ is a bicyclic carbocyclyl. In another embodiment is the compound of Formula (A) wherein $R^5$ is norbornyl.

In another embodiment is the compound of Formula (A) wherein $R^5$ is phenyl, Y is a bond and the compound has a structure of Formula (B):

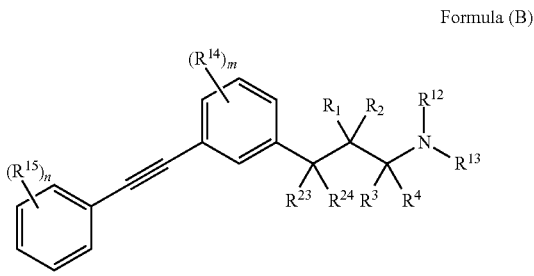

Formula (B)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
n is 0, 1, 2, 3, 4 or 5;
$R^1$ and $R^2$ are each independently selected from hydrogen, halogen, $C_1$-$C_5$ alkyl, fluoroalkyl, —$OR^6$, —$NR^7R^8$; or $R^1$ and $R^2$ together form an oxo;
$R^3$ and $R^4$ are each independently selected from hydrogen or alkyl;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently alkyl, alkenyl, aryl, carbocyclyl, heteroaryl or heterocyclyl;
$R^{23}$ and $R^{24}$ are each the same or different and independently hydrogen, halogen, $C_1$-$C_5$ alkyl, fluoroalkyl, —$OR^6$, —$NR^7R^8$ or carbocyclyl; or $R^{23}$ and $R^{24}$ together form an oxo;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{15}$ is the same or different and independently alkyl, —$OR^6$, alkenyl, alkynyl, halo, fluoroalkyl, aryl or aralkyl.

In another embodiment is the compound of Formula (B) wherein each of $R^{12}$ and $R^{13}$ is hydrogen.

In another embodiment is the compound of Formula (B) wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl.

In another embodiment is the compound of Formula (B) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen.

In another embodiment is the compound of Formula (B) wherein m is 0; n is 0, 1 or 2; and each $R^{15}$ is independently alkyl, —$OR^6$ or aryl.

In another embodiment the compound is selected from:
3-(3-((2,6-dimethylphenyl)ethynyl)phenyl)propan-1-amine;
3-(3-((2-methoxyphenyl)ethynyl)phenyl)propan-1-amine;
3-(3-(phenylethynyl)phenyl)propan-1-amine; 3-amino-1-(3-(biphenyl-3-ylethynyl)phenyl)propan-1-ol; and 3-amino-1-(3-((2-methoxyphenyl)ethynyl)phenyl)propan-1-ol.

In another embodiment is the compound of Formula (A) wherein $R^5$ is 1-naphthyl or 2-naphthyl. In another embodiment is the compound wherein each of $R^1$, $R^2$, $R^3$, $R^4$, $R^{23}$ and $R^{24}$ is hydrogen. In another embodiment is the compound of Formula (A) wherein m is 0.

In another embodiment is the compound 3-(3-(naphthalen-2-ylethynyl)phenyl)propan-1-amine.

In another embodiment is the compound of Formula (A) wherein $R^5$ is $C(R^{16})(R^{17})(R^{18})$, Y is a bond and the compound has a structure of Formula (C):

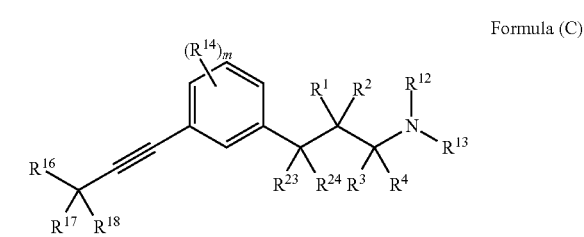

Formula (C)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
$R^1$ and $R^2$ are each the same or different and independently hydrogen, halogen, $C_1$-$C_5$ alkyl, fluoroalkyl, —$OR^6$, —$NR^7R^8$ or carbocyclyl; or $R^1$ and $R^2$ form an oxo;
$R^3$ and $R^4$ are each the same or different and independently hydrogen or alkyl;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently alkyl, alkenyl, aryl, carbocyclyl, heteroaryl or heterocyclyl;
$R^{23}$ and $R^{24}$ are each independently hydrogen, halogen, $C_1$-$C_5$ alkyl, fluoroalkyl, —$OR^6$, —$NR^7R^8$; or $R^{23}$ and $R^{24}$ together form an oxo;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —$OR^6$; and
each $R^{16}$, $R^{17}$ and $R^{18}$ are the same or different and independently hydrogen, alkyl, —$OR^6$, carbocyclyl or aryl.

In another embodiment is the compound of Formula (C) wherein each of $R^{12}$ and $R^{13}$ is hydrogen. In another embodiment is the compound of Formula (C) wherein $R^1$ and $R^2$ are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound of Formula (C) wherein m is 0, and $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (C) wherein each of $R^{16}$, $R^{17}$ and $R^{18}$ is independently hydrogen, alkyl, carbocyclyl or aryl.

In another embodiment is the compound selected from: 4-(3-(3-aminopropyl)phenyl)but-3-yn-1-ol; 5-(3-(3-aminopropyl)phenyl)pent-4-yn-2-ol; 2-(3-(3-cyclopentylprop-1-ynyl)phenoxy)ethanamine; 3-(3-(3,3-dimethylbut-1-ynyl)phenyl)propan-1-amine; 3-(3-(3-phenylprop-1-ynyl)phenyl)propan-1-amine; 3-(3-(pent-1-ynyl)phenyl)propan-1-amine; 3-(3-(hex-1-ynyl)phenyl)propan-1-amine; 3-amino-1-(3-(3-cyclopentylprop-1-ynyl)phenyl)propan-1-ol; 3-amino-1-(3-(3-phenylprop-1-ynyl)phenyl)propan-1-ol; 6-(3-(3-amino-1-hydroxypropyl)phenyl)hex-5-yn-1-ol; 4-(3-(3-amino-1-hydroxypropyl)phenyl)but-3-yn-1-ol; 3-amino-1-(3-(hept-1-ynyl)phenyl)propan-1-ol; 3-(3-(4-phenylbut-1-ynyl)phenyl)propan-1-amine; 3-amino-1-(3-(4-cyclopentylbut-1-ynyl)phenyl)propan-1-ol; 3-(3-(5-methoxypent-1-ynyl)phenyl)propan-1-amine; 3-amino-1-(3-(4-phenylbut-1-ynyl)phenyl)propan-1-ol; 6-(3-(3-aminopropyl)phenyl)hex-5-yn-1-ol; and 3-(3-(6-methoxyhex-1-ynyl)phenyl)propan-1-amine.

In another embodiment is the compound of Formula (C) wherein $R^{16}$ is —$OR^6$, wherein $R^6$ is hydrogen or $C_1$-$C_5$ alkyl, and each of $R^{17}$ and $R^{18}$ is independently hydrogen, alkyl or aryl.

In another embodiment is the compound selected from: 1-(3-(3-aminopropyl)phenyl)-3-ethylpent-1-yn-3-ol; 4-((3-(3-aminopropyl)phenyl)ethynyl)heptan-4-ol; 5-((3-(3-aminopropyl)phenyl)ethynyl)nonan-5-ol; 3-(3-(3-methoxy-3-propylhex-1-ynyl)phenyl)propan-1-amine; 1-(3-(3-aminopropyl)phenyl)-3-methylhex-1-yn-3-ol; 1-(3-(3-aminopropyl)phenyl)-3,4-dimethylpent-1-yn-3-ol; 4-(3-(3-aminopropyl)phenyl)-2-methylbut-3-yn-2-ol; 1-(3-(3-aminopropyl)phenyl)hex-1-yn-3-ol; 1-(3-(3-aminopropyl)phenyl)-3,4-dimethylhex-1-yn-3-ol; 3-(3-(3-methoxyprop-1-ynyl)phenyl)propan-1-amine; 3-(3-(3-aminopropyl)phenyl)prop-2-yn-1-ol; 1-(3-(3-aminopropyl)phenyl)-3-tert-butyl-4,4-dimethylpent-1-yn-3-ol; (R)-1-(3-(3-aminopropyl)phenyl)oct-1-yn-3-ol; (R)-1-(3-(3-aminopropyl)phenyl)oct-1-yn-3-ol; (R)-3-(3-(3-aminopropyl)phenyl)-1-phenylprop-2-yn-1-ol; 4-((3-(3-amino-1-hydroxypropyl)phenyl)ethynyl)heptan-4-ol; 4-((3-(3-amino-2,2-dimethylpropyl)phenyl)ethynyl)heptan-4-ol; 4-(3-(3-aminopropyl)phenyl)-2-phenylbut-3-yn-2-ol; 1-(3-(3-aminopropyl)phenyl)-4-methylpent-1-yn-3-ol; 1-(3-(3-aminopropyl)phenyl)-3,4,4-trimethylpent-1-yn-3-ol; (R)-3-(3-(3-aminopropyl)phenyl)-1-phenylprop-2-yn-1-ol; 1-(3-(3-aminopropyl)phenyl)-3-isopropyl-4-methylpent-1-yn-3-ol; 4-((3-(3-aminopropyl)phenyl)ethynyl)-2,6-dimethylheptan-4-ol; 1-(3-(3-amino-1-hydroxypropyl)phenyl)-3-ethylpent-1-yn-3-ol; 3-(3-(3-ethylpent-1-ynyl)phenyl)propan-1-amine; 3-(3-(3-propylhex-1-ynyl)phenyl)propan-1-amine; 3-amino-1-(3-(3-ethylpent-1-ynyl)phenyl)propan-1-ol; 3-amino-1-(3-(3-propylhex-1-ynyl)phenyl)propan-1-ol; 3-amino-1-(3-(3-ethylpent-1-ynyl)phenyl)-2-methylpropan-1-ol; 1-(3-(3-amino-1-hydroxy-2-methylpropyl)phenyl)-3-ethylpent-1-yn-3-ol; 1-amino-3-(3-(3-ethylpent-1-ynyl)phenyl)propan-2-ol; 1-(3-(3-amino-2-hydroxypropyl)phenyl)-3-ethylpent-1-yn-3-ol; 3-amino-2-methyl-1-(3-(3-propylhex-1-ynyl)phenyl)propan-1-ol; 4-((3-(3-amino-1-hydroxy-2-methylpropyl)phenyl)ethynyl)heptan-4-ol; 4-((3-(3-amino-2-hydroxypropyl)phenyl)ethynyl)heptan-4-ol; 1-amino-3-(3-(3-propylhex-1-ynyl)phenyl)propan-2-ol.

In another embodiment is the compound of Formula (A) wherein Z is —$C(R^{23})(R^{24})$—$C(R^1)(R^2)$— and $R^5$ is carbocyclyl.

In another embodiment is the compound of Formula (A) wherein $R^5$ is cycloalkyl, Y is a bond and the compound has a structure of Formula (D):

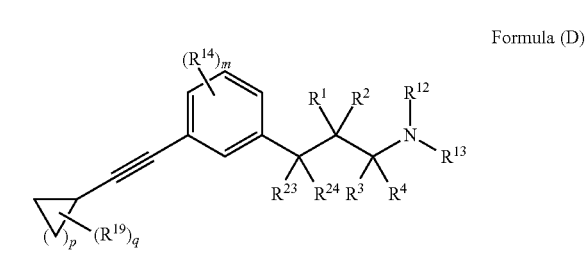

Formula (D)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

p is 1, 2, 3, 4, 5 or 6;

q is 0, 1, 2, 3, 4, 5, 6, 7, 8 or 9;

$R^1$ and $R^2$ are each the same or different and independently hydrogen, halogen, $C_1$-$C_5$ alkyl, fluoroalkyl, —$OR^6$, —$NR^7R^8$ or carbocyclyl; or $R^1$ and $R^2$ together form an oxo;

$R^3$ and $R^4$ are each the same or different and independently hydrogen or alkyl;

each $R^6$ is the same or different and independently hydrogen or $C_1$-$C_5$ alkyl;

each $R^7$ and each $R^8$ are each the same or different and independently hydrogen, alkyl, carbocyclyl, heteroalkyl, heterocycloalkyl, aryl, heteroaryl, or —C(=O)$R^9$; or $R^7$ and $R^8$, together with the nitrogen atom to which they are attached, form an N-heterocyclyl;

each $R^9$ is the same or different and independently alkyl, alkenyl, aryl, carbocyclyl, heteroaryl or heterocyclyl;

$R^{23}$ and $R^{24}$ are each the same or different and independently hydrogen, halogen, $C_1$-$C_5$ alkyl, fluoroalkyl, —$OR^6$, —$NR^7R^8$ or carbocyclyl; or $R^{23}$ and $R^{24}$ together form an oxo;

$R^{12}$ and $R^{13}$ are each the same or different and independently hydrogen, alkyl or —C(=O)$R^9$; or $R^{12}$ and $R^{13}$ together with the nitrogen atom to which they are attached, form an N-heterocyclyl;

each $R^{14}$ is the same or different and independently alkyl, halo, fluoroalkyl or —$OR^6$; and each $R^{19}$ is the same or different and independently alkyl, —$OR^6$, halo or fluoroalkyl.

In another embodiment is the compound of Formula (D) wherein each of $R^{12}$ and $R^{13}$ is hydrogen. In another embodiment is the compound of Formula (D) wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound of Formula (D) wherein p is 3 and $R^5$ is a substituted or unsubstituted cyclopentyl. In another embodiment is the compound of Formula (D) wherein p is 4, and $R^5$ is a substituted or unsubstituted cyclohexyl. In another embodiment is the compound of Formula (D) wherein p is 5, and $R^5$ is a substituted or unsubstituted cycloheptyl. In another embodiment is the compound of Formula (D) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (D) wherein m is 0. In another embodiment is the compound of Formula (D) wherein q is 0. In another embodiment is the compound of Formula (D) wherein q is 1, 2, 3, 4 or 5, and each $R^{19}$ is independently alkyl or —$OR^6$, wherein $R^6$ is hydrogen or $C_1$-$C_5$ alkyl.

In another embodiment is the compound selected from the following:
3-(3-(cyclopentylethynyl)phenyl)propan-1-amine; 3-(3-(cyclohexylethynyl)phenyl)propan-1-amine; 3-amino-1-(3-(cyclopentylethynyl)phenyl)propan-1-ol; 3-amino-1-(3-(cyclohexylethynyl)phenyl)propan-1-ol; 1-((3-(3-aminopropyl) phenyl)ethynyl)cyclohexanol; 1-((3-(3-aminopropyl) phenyl)ethynyl)-2,2,6,6-tetramethylcyclohexanol; 1-((3-(3-aminopropyl)phenyl)ethynyl)cyclopentanol; 3-(3-(cycloheptylethynyl)phenyl)propan-1-amine; 3-amino-1-(3-(cycloheptylethynyl)phenyl)propan-1-ol; 1-amino-3-(3-(cycloheptylethynyl)phenyl)propan-2-ol; 1-amino-3-(3-(cyclohexylethynyl)phenyl)propan-2-ol; 1-amino-3-(3-(cyclopentylethynyl)phenyl)propan-2-ol; 1-((3-(3-amino-2-hydroxypropyl)phenyl)ethynyl)cyclopentanol; 1-((3-(3-amino-1-hydroxypropyl)phenyl)ethynyl)cyclopentanol; 1-((3-(3-amino-1-hydroxypropyl)phenyl)ethynyl)cyclohexanol; 1-((3-(3-amino-2-hydroxypropyl)phenyl)ethynyl)cycloheptanol; 1-((3-(3-amino-2-hydroxypropyl)phenyl)ethynyl)cyclohexanol; 1-((3-(3-amino-1-hydroxypropyl)phenyl) ethynyl)cycloheptanol; and 1-((3-(3-aminopropyl)phenyl) ethynyl)cycloheptanol.

In another embodiment is the compound of Formula (D) wherein $R^{12}$ is hydrogen, and $R^{13}$ is —$C(=O)R^9$, wherein $R^9$ is alkyl. In another embodiment is the compound of Formula (D) wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen. In another embodiment is the compound of Formula (D), wherein m is 0. In another embodiment is the compound of claim 36, wherein q is 1, 2, 3, 4 or 5, and each $R^{19}$ is independently alkyl or —$OR^6$, wherein $R^6$ is hydrogen or $C_1$-$C_5$ alkyl. In another embodiment is the compound of Formula (D), wherein p is 4, and $R^5$ is a substituted or unsubstituted cyclohexyl.

In another embodiment is the compound N-(3-hydroxy-3-(3-((1-hydroxycyclohexyl)ethynyl)phenyl)propyl)acetamide.

In another embodiment is the compound of Formula (A) wherein Z is —$C(R^{23})(R^{24})$—$C(R^1)(R^2)$—, wherein $R^5$ is heterocyclyl and Y is a bond. In another embodiment is the compound wherein the heterocyclyl can be optionally substituted with —$OR^6$, wherein $R^6$ is hydrogen or $C_1$-$C_5$ alkyl. In another embodiment is the compound wherein each of $R^{12}$ and $R^{13}$ is hydrogen.

In another embodiment is the compound of Formula (A) wherein Z is —$C(R^{23})(R^{24})$—$C(R^1)(R^2)$—, wherein Y is a bond, $R^5$ is heterocyclyl and the heterocyclyl can be optionally substituted with —$OR^6$, wherein $R^6$ is hydrogen or $C_1$-$C_5$ alkyl, and each of $R^{12}$ and $R^{13}$ is hydrogen and wherein $R^1$ and $R^2$ are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl.

In another embodiment is the compound of Formula (A) wherein Z is —$C(R^{23})(R^{24})$—$C(R^1)(R^2)$—, wherein Y is a bond, $R^5$ is heterocyclyl and the heterocyclyl can be optionally substituted with —$OR^6$, wherein $R^6$ is hydrogen or $C_1$-$C_5$ alkyl, and each of $R^{12}$ and $R^{13}$ is hydrogen and wherein each of $R^1$, $R^2$, $R^3$, $R^4$, $R^{23}$ and $R^{24}$ is hydrogen. In another embodiment is the compound wherein m is 0.

In another embodiment is the compound selected from the following:
4-((3-(3-aminopropyl)phenyl)ethynyl)tetrahydro-2H-thiopyran-4-ol; and 4-((3-(3-aminopropyl)phenyl)ethynyl)tetrahydro-2H-pyran-4-ol.

In another embodiment is the compound of Formula (A) wherein Z is —$C(R^{23})(R^{24})$—$C(R^1)(R^2)$—, and $R^5$ is heteroaryl and Y is a bond. In another embodiment is the compound wherein each of $R^{12}$ and $R^{13}$ is hydrogen. In another embodiment is the compound wherein $R^1$ and $R^2$, are each independently hydrogen, halogen, $C_1$-$C_5$ alkyl or —$OR^6$, wherein $R^6$ is hydrogen or $C_1$-$C_5$ alkyl; $R^{23}$ and $R^{24}$ are each independently hydrogen, halogen, $C_1$-$C_5$ alkyl or —$OR^6$, wherein $R^6$ is hydrogen or $C_1$-$C_5$ alkyl; and $R^3$ and $R^4$ are each independently hydrogen or alkyl. In another embodiment is the compound wherein each of $R^1$, $R^2$, $R^3$, $R^4$, $R^{23}$ and $R^{24}$ is hydrogen. In another embodiment is the compound wherein m is 0.

In another embodiment is the compound wherein the compound is selected from:
3-(3-(pyridin-2-ylethynyl)phenyl)propan-1-amine; 3-(3-(pyridin-3-ylethynyl)phenyl)propan-1-amine; 3-(3-(pyridin-4-ylethynyl)phenyl)propan-1-amine; 3-(3-(thiophen-2-ylethynyl)phenyl)propan-1-amine; and 3-(3-(thiophen-3-ylethynyl)phenyl)propan-1-amine.

In another embodiment is the compound of Formula (A) wherein Z is —O—$C(R^{21})(R^{22})$—, Y is a bond and the compound has a structure of Formula (E):

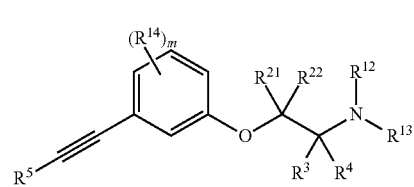

Formula (E)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
$R^{21}$ and $R^{22}$ are each independently hydrogen, $C_1$-$C_5$ alkyl or fluoroalkyl;
$R^3$ and $R^4$ are each the same or different and independently hydrogen or alkyl;
$R^5$ is alkyl, alkenyl, aryl, carbocyclyl, heteroaryl or heterocyclyl;
each $R^6$ is the same or different and independently hydrogen or $C_1$-$C_5$ alkyl;
$R^9$ is alkyl, alkenyl, aryl, carbocyclyl, heteroaryl or heterocyclyl;
$R^{12}$ and $R^{13}$ are the same or different and independently hydrogen, alkyl or —$C(=O)R^9$; or $R^{12}$ and $R^{13}$ together with the nitrogen atom to which they are attached, form an N-heterocyclyl; and
each $R^{14}$ is the same or different and independently alkyl, halo, fluoroalkyl or —$OR^6$.

In another embodiment is the compound of Formula (E) wherein $R^5$ is an unsaturated carbocyclyl. In another embodiment is the compound of Formula (E) wherein $R^5$ is a bicyclic carbocyclyl. In another embodiment is the compound of Formula (E) wherein $R^5$ is norbornyl.

In another embodiment is the compound of Formula (E) wherein $R^5$ is —C($R^{16}$)($R^{17}$)($R^{18}$), Y is a bond and the compound has a structure of Formula (F):

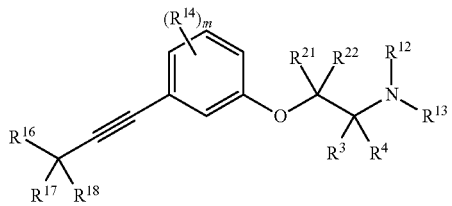

Formula (F)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;
$R^{21}$ and $R^{22}$ are each independently hydrogen, $C_1$-$C_5$ alkyl or fluoroalkyl;
$R^3$ and $R^4$ are each the same or different and independently hydrogen or alkyl;
each $R^6$ is the same or different and independently hydrogen or $C_1$-$C_5$ alkyl;
$R^9$ is alkyl, alkenyl, aryl, carbocyclyl, heteroaryl or heterocyclyl;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —O$R^6$; and
$R^{16}$, $R^{17}$ and $R^{18}$ are each the same or different and independently hydrogen, alkyl, —O$R^6$, carbocyclyl or aryl.

In another embodiment is the compound of Formula (F) wherein each of $R^{12}$ and $R^{13}$ is hydrogen. In another embodiment is the compound of Formula (F) wherein each of $R^{21}$, $R^{22}$, $R^3$ and $R^4$ is independently hydrogen or $C_1$-$C_5$ alkyl. In another embodiment is the compound of Formula (F) wherein m is 0. In another embodiment is the compound of Formula (F) wherein each of $R^{16}$, $R^{17}$ and $R^{18}$ is independently hydrogen, alkyl or —O$R^6$, wherein each $R^6$ is independently hydrogen or $C_1$-$C_5$ alkyl. In another embodiment is the compound of Formula (F) wherein each of $R^{16}$, $R^{17}$ and $R^{18}$ is independently hydrogen, alkyl or aryl.

In another embodiment is the compound selected from:
4-((3-(2-aminoethoxy)phenyl)ethynyl)heptan-4-ol; 1-(3-(2-aminoethoxy)phenyl)-3-ethylpent-1-yn-3-ol; 1-(3-(2-aminoethoxy)phenyl)-3-isopropyl-4-methylpent-1-yn-3-ol; 5-((3-(2-aminoethoxy)phenyl)ethynyl)nonan-5-ol; 4-(3-(2-aminoethoxy)phenyl)-2-methylbut-3-yn-2-ol; 2-(3-(hept-1-ynyl)phenoxy)ethanamine; 4-(3-(2-aminoethoxy)phenyl)but-3-yn-1-ol; 2-(3-(3-phenylprop-1-ynyl)phenoxy)ethanamine; 2-(3-(4-methylpent-1-ynyl)phenoxy)ethanamine; 6-(3-(2-aminoethoxy)phenyl)hex-5-yn-1-ol; 2-(3-(3-ethylpent-1-ynyl)phenoxy)propan-1-amine; 2-(3-(3-propylhex-1-ynyl)phenoxy)propan-1-amine; 1-(3-(2-aminoethoxy)phenyl)-3-ethylpent-1-yn-3-ol; 4-((3-(1-aminopropan-2-yloxy)phenyl)ethynyl)heptan-4-ol; 2-(3-(3-ethylpent-1-ynyl)phenoxy)ethanamine; and 2-(3-(3-propylhex-1-ynyl)phenoxy)ethanamine.

In another embodiment is the compound of Formula (E), wherein $R^5$ is carbocyclyl. In another embodiment is the compound of Formula (E) wherein $R^5$ is a cycloalkyl, Y is a bond and the compound has a structure of Formula (G):

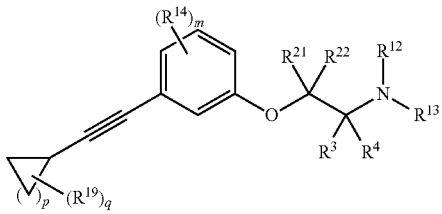

Formula (G)

as a tautomer or a mixture of tautomers, or as a pharmaceutically acceptable salt, hydrate, solvate, N-oxide, stereoisomer, geometric isomer or prodrug thereof, wherein:
m is 0, 1, 2 or 3;
p is 1, 2, 3, 4 or 5;
q is 0, 1, 2, 3, 4, 5, 6, 7, 8 or 9;
$R^{21}$ and $R^{22}$ are each the same or different and independently hydrogen, $C_1$-$C_5$ alkyl or fluoroalkyl;
$R^3$ and $R^4$ are each the same or different and independently hydrogen or alkyl;
each $R^6$ is the same or different and independently hydrogen or $C_1$-$C_5$ alkyl;
$R^9$ is alkyl, alkenyl, aryl, carbocyclyl, heteroaryl or heterocyclyl;
$R^{12}$ and $R^{13}$ are the same or different and independently hydrogen, alkyl or —C(=O)$R^9$; or $R^{12}$ and $R^{13}$ together with the nitrogen atom to which they are attached, form an N-heterocyclyl;
each $R^{14}$ is the same or different and independently alkyl, halo, fluoroalkyl or —O$R^6$; and
each $R^{19}$ is the same or different and independently alkyl, —O$R^6$, halo or fluoroalkyl.

In another embodiment is the compound of Formula (G) wherein each of $R^{12}$ and $R^{13}$ is hydrogen. In another embodiment is the compound of Formula (G) wherein m is 0. In another embodiment is the compound of Formula (G) wherein $R^{21}$ and $R^{22}$ are each independently hydrogen or $C_1$-$C_5$ alkyl; and $R^3$ and $R^4$ are each independently hydrogen or alkyl. In another embodiment is the compound of Formula (G) wherein each of $R^{21}$, $R^{22}$, $R^3$ and $R^4$ is hydrogen or $C_1$-$C_5$ alkyl. In another embodiment is the compound of Formula (G) wherein, q is 0 or 1, and each $R^{19}$ is independently alkyl or —O$R^6$, wherein $R^6$ is hydrogen or $C_1$-$C_5$ alkyl.

In another embodiment is the compound is selected from:
1-((3-(2-aminoethoxy)phenyl)ethynyl)cyclopentanol; 1-((3-(2-aminoethoxy)phenyl)ethynyl)cyclohexanol; 2-(3-(cyclohexylethynyl)phenoxy)ethanamine1-((3-(1-aminopropan-2-yloxy)phenyl)ethynyl)cyclopentanol; 1-((3-(1-aminopropan-2-yloxy)phenyl)ethynyl)cyclohexanol; 1-((3-(1-aminopropan-2-yloxy)phenyl)ethynyl)cycloheptanol; 2-(3-(cycloheptylethynyl)phenoxy)ethanamine; 2-(3-(cycloheptylethynyl)phenoxy)propan-1-amine; 2-(3-(cyclohexylethynyl)phenoxy)propan-1-amine; 2-(3-(cyclopentylethynyl)phenoxy)propan-1-amine; 2-(3-(cyclopentylethynyl)phenoxy)-ethanamine; and 1-((3-(2-aminoethoxy)phenyl)ethynyl)-cycloheptanol.

In another embodiment is the compound of Formula (E) wherein $R^5$ is heterocyclyl. In another embodiment is the compound of Formula (E) wherein m is 0 and each of $R^{12}$ and $R^{13}$ is hydrogen. In another embodiment is the compound of Formula (E) wherein each of $R^{21}$, $R^{22}$, $R^3$ and $R^4$ is independently hydrogen or $C_1$-$C_5$ alkyl.

In another embodiment is the compound 2-(3-(pyridin-3-ylethynyl)phenoxy)ethanamine.

In another embodiment is the compound of Formula (E), wherein $R^5$ is aryl.

In another embodiment is the compound 2-(3-(phenylethynyl)phenoxy)ethanamine.

In another embodiment is a pharmaceutical composition comprising a pharmaceutically acceptable carrier and the compound of any one of Formulas (A)-(G).

In yet another embodiment is a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an IC50 of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an IC50 of about 10 nM or less when assayed in vitro, utilizing extract of cells that express RPE65 and LRAT, wherein the extract further comprises CRALBP, wherein the compound is stable in solution for at least about 1 week, 1 month, 2 months, 4 months, 6 months, 8 months, 10 months, 1 year, 2 years, 5 yeas or longer, at room temperature.

In an additional embodiment is a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment is a non-retinoid compound of wherein the ED50 value is measured after administering a single dose of the compound to said subject for about 2 hours or longer. In an additional embodiment the compound is an alkynyl phenyl-linked amine compound. In a further embodiment the compound is a non-retinoid compound.

In a further embodiment is a pharmaceutical composition comprising a pharmaceutically acceptable carrier and a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In another embodiment, the present invention provides a method of modulating chromophore flux in a retinoid cycle comprising introducing into a subject a compound disclosed herein, including a compound of any one of Formulae (A)-(G) respective substructures thereof. In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject compounds or the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formulae (A)-(G) their respective substructures thereof.

In an additional embodiment is a method of inhibiting regeneration of rhodopsin in a rod photoreceptor cell of the retina comprising contacting the retina with a compound of any one of Formulae (A)-(G) and their respective substructures thereof, a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In a further embodiment is a method of reducing ischemia in an eye of a subject comprising administering to the subject the pharmaceutical composition of a compound of any one of Formulae (A)-(G) and their respective substructures thereof, a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject the pharmaceutical composition of a compound of any one of Formulae (A)-(G), and their respective substructures thereof. In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with the compound of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell In another embodiment, a method is provided for treating an ophthalmic disease or disorder in a subject, comprising administering to the subject the pharmaceutical composition comprising a pharmaceutically acceptable carrier and a compound having a structure of any of Formula (A)-(G) as described above and herein. In one embodiment, the ophthalmic disease or disorder is a retinal disease or disorder. In specific embodiments, the retinal disease or disorder is age-related macular degeneration or Stargardt's macular dystrophy. In another embodiment, the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In yet another embodiment, the ophthalmic disease or disorder is selected from diabetic retinopathy, diabetic maculopathy, retinal blood vessel occlusion, retinopathy of prematurity, or ischemia reperfusion related retinal injury.

Further provided is a method of reducing lipofuscin pigment accumulated in a subject's retina comprising administering to the subject a pharmaceutical composition described here. In one embodiment the lipofuscin pigment is N-retinylidene-N-retinyl-ethanolamine (A2E).

In another embodiment, a method of inhibiting at least one visual cycle trans-cis isomerase in a cell is provided, wherein the method comprises contacting the cell with a compound having a structure of any of Formulae (A)-(G) as described herein, thereby inhibiting the at least one visual cycle trans-cis isomerase. In one certain embodiment, the cell is a retinal pigment epithelial (RPE) cell.

Also provided herein in another embodiment is a method of inhibiting at least one visual cycle trans-cis isomerase in a subject comprising administering to the subject the pharmaceutical composition comprising a pharmaceutically acceptable carrier and a compound having a structure of any of Formulae (A)-(G) as described herein. In certain embodiments, the subject is a human or is a non-human animal.

In particular embodiments of the methods described above and herein, accumulation of lipofuscin pigment is inhibited in an eye of the subject, and in certain particular embodiments, the lipofuscin pigment is N-retinylidene-N-retinyl-ethanolamine (A2E). In other certain embodiments, degeneration of a retinal cell is inhibited. In a specific embodiment, the retinal cell is a retinal neuronal cell, wherein the retinal neuronal cell is a photoreceptor cell, an amacrine cell, a horizontal cell, a ganglion cell, or a bipolar cell. In another specific embodiment, the retinal cell is a retinal pigment epithelial (RPE) cell.

Additionally, the compounds can be represented by Formula (I):

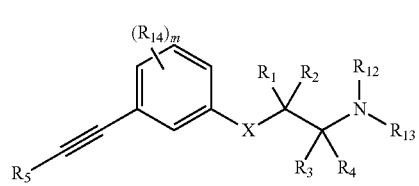

Formula (I)

as a tautomer or a mixture of tautomers, or as a pharmaceutically acceptable salt, hydrate, solvate, N-oxide or prodrug thereof, wherein:

m is 0, 1, 2 or 3;

$R_1$ and $R_2$ are each the same or different and independently hydrogen, halogen, alkyl, fluoroalkyl, —$OR_6$, —$NR_7R_8$ or carbocyclyl; or $R_1$ and $R_2$ form an oxo;

$R_3$ and $R_4$ are each the same or different and independently hydrogen or alkyl;

$R_5$ is alkyl, alkenyl, aryl, carbocyclyl, heteroaryl or heterocyclyl;

$R_6$ is hydrogen or alkyl;

$R_7$ and $R_8$ are each the same or different and independently hydrogen, alkyl, carbocyclyl, or —C(=O)$R_9$; or $R_7$ and $R_8$, together with the nitrogen atom to which they are attached, form an N-heterocyclyl;

$R_9$ is alkyl, alkenyl, aryl, carbocyclyl, heteroaryl or heterocyclyl;

X is —C($R_{10}$)($R_{11}$)— or —O—;

$R_{10}$ and $R_{11}$ are each the same or different and independently hydrogen, halogen, alkyl, fluoroalkyl, —$OR_6$, —$NR_7R_8$ or carbocyclyl; or $R_{10}$ and $R_{11}$ form an oxo;

$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl; and each $R_{14}$ is the same or different and independently alkyl, halo, fluoroalkyl or —$OR_6$.

In certain embodiments, X is —C($R_{10}$)($R_{11}$)— and the compounds of Formula (I) has a propylene linkage. Thus, the compound can be represented by a structure of Formula (II):

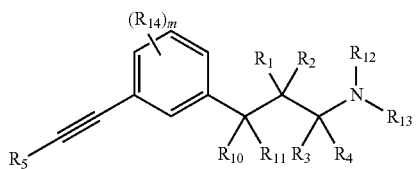

Formula (II)

One embodiment provides a compound having a structure of Formula (II) wherein $R_5$ is aryl, as defined herein.

A further embodiment provides a compound having a structure of Formula (II) wherein $R_5$ is phenyl. The compound can be represented by a structure of Formula (IIa):

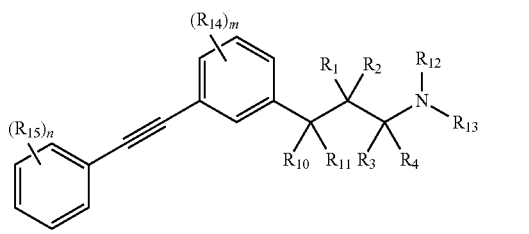

Formula (IIa)

as a tautomer or a mixture of tautomers, or as a pharmaceutically acceptable salt, hydrate, solvate, N-oxide or prodrug thereof, wherein:
m is 0, 1, 2 or 3;
n is 0, 1, 2, 3, 4 or 5;
$R_1$ and $R_2$ are each the same or different and independently hydrogen, halogen, alkyl, fluoroalkyl, —$OR_6$, —$NR_7R_8$ or carbocyclyl; or
$R_1$ and $R_2$ form an oxo;
$R_3$ and $R_4$ are each the same or different and independently hydrogen or alkyl;
$R_6$ is hydrogen or alkyl;
$R_7$ and $R_8$ are each the same or different and independently hydrogen, alkyl, carbocyclyl, or —C(=O)$R_9$; or $R_7$ and $R_8$, together with the nitrogen atom to which they are attached, form an N-heterocyclyl;
$R_9$ is alkyl, alkenyl, aryl, carbocyclyl, heteroaryl or heterocyclyl;
$R_{10}$ and $R_{11}$ are each the same or different and independently hydrogen, halogen, alkyl, fluoroalkyl, —$OR_6$, —$NR_7R_8$ or carbocyclyl; or $R_{10}$ and $R_{11}$ form an oxo;
$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl;
each $R_{14}$ is the same or different and independently alkyl, halo, fluoroalkyl or —$OR_6$; and
each $R_{15}$ is the same or different and independently alkyl, —$OR_6$, alkenyl, alkynyl, halo, fluoroalkyl, aryl or aralkyl.

In certain embodiments, each of $R_{12}$ and $R_{13}$ is hydrogen. In certain embodiments, $R_1$, $R_2$, $R_3$, $R_4$, $R_{10}$ and $R_{11}$ are each independently hydrogen, halogen, alkyl or —$OR_6$, wherein $R_6$ is hydrogen or alkyl. In certain embodiments, each of $R_1$, $R_2$, $R_3$, $R_4$, $R_{10}$ and $R_{11}$ is independently hydrogen or —$OR_6$, wherein $R_6$ is hydrogen or alkyl. In certain embodiments, m is 0, n is 0, 1 or 2, and each $R_{15}$ is independently alkyl, —$OR_6$ or aryl.

In certain specific embodiments, the compounds of Formula (I), (II) or (IIa) have the structures shown in Table 1.

TABLE 1

| Example No. | Structure | Chemical Name |
|---|---|---|
| 17 | 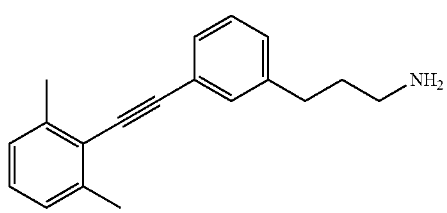 [SMILES: Cc1cccc(C)c1C#Cc1cccc(CCCN)c1] | 3-(3-((2,6-dimethylphenyl)ethynyl)phenyl)-propan-1-amine |
| 36 | 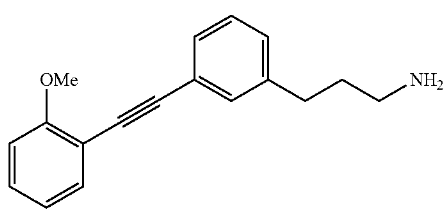 [SMILES: COc1ccccc1C#Cc1cccc(CCCN)c1] | 3-(3-((2-methoxyphenyl)ethynyl)phenyl)-propan-1-amine |
| 37 | 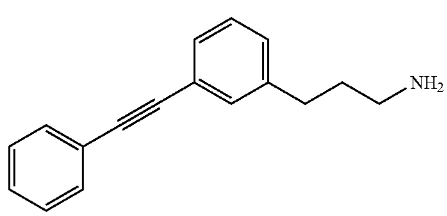 [SMILES: NCCCc1cccc(C#Cc2ccccc2)c1] | 3-(3-(phenylethynyl)phenyl)propan-1-amine |
| 46 | 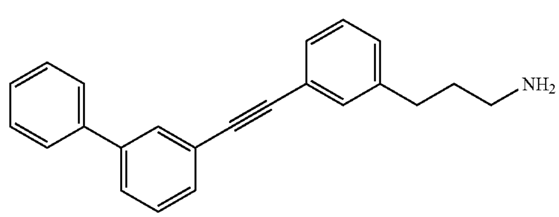 [SMILES: NCCCc1cccc(C#Cc2cccc(-c3ccccc3)c2)c1] | 3-(3-(biphenyl-3-ylethynyl)phenyl)propan-1-amine |

TABLE 1-continued

| Example No. | Structure | Chemical Name |
|---|---|---|
| 54 | 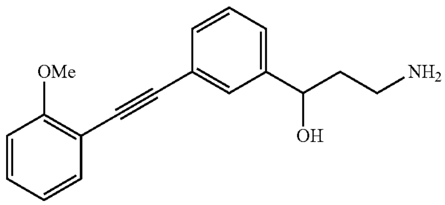 [SMILES: COc1ccccc1C#Cc1cccc(C(O)CCN)c1] | 3-amino-1-(3-((2-methoxyphenyl)ethynyl)phenyl)-propan-1-ol |
| 83 | 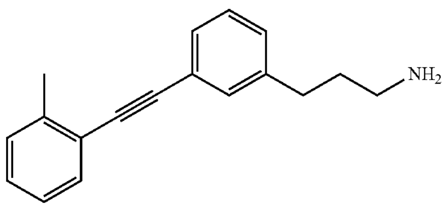 [SMILES: Cc1ccccc1C#Cc1cccc(CCCN)c1] | 3-(3-(o-tolylethynyl)phenyl)propan-1-amine |
| 84 | 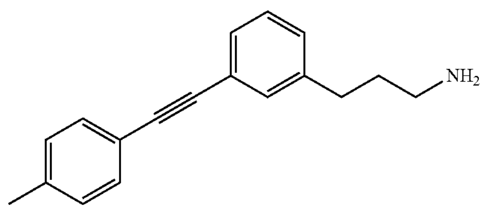 [SMILES: Cc1ccc(C#Cc2cccc(CCCN)c2)cc1] | 3-(3-(p-tolylethynyl)phenyl)propan-1-amine |
| 87 | 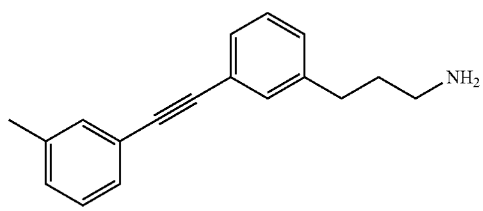 [SMILES: Cc1cccc(C#Cc2cccc(CCCN)c2)c1] | 3-(3-(m-tolylethynyl)phenyl)propan-1-amine |
| 89 | 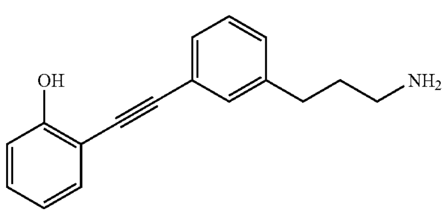 [SMILES: NCCCc1cccc(C#Cc2ccccc2O)c1] | 2-((3-(3-aminopropyl)phenyl)ethynyl)phenol |
| 90 | 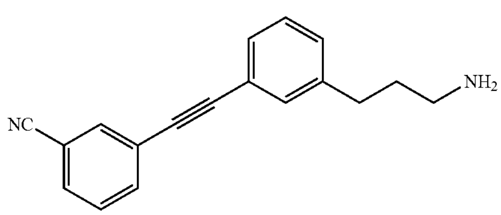 | 3-((3-(3-aminopropyl)phenyl)ethynyl)benzonitrile |
| 92 | 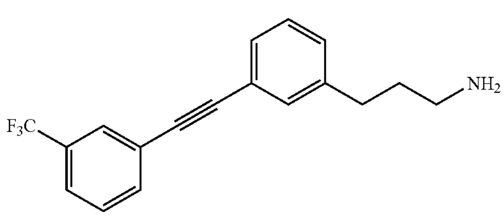 [SMILES: NCCCc1cccc(C#Cc2cccc(C(F)(F)F)c2)c1] | 3-(3-((3-trifluoromethyl)phenyl)ethynyl)phenyl)propan-1-amine |

TABLE 1-continued

| Example No. | Structure | Chemical Name |
|---|---|---|
| 93 | 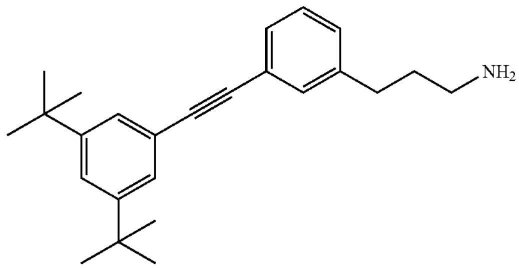 [SMILES: CC(C)(C)c1cc(C#Cc2cccc(CCCN)c2)cc(C(C)(C)C)c1] | 3-(3-((3,5-di-tert-butylphenyl)ethynyl)phenyl)propan-1-amine |
| 94 | 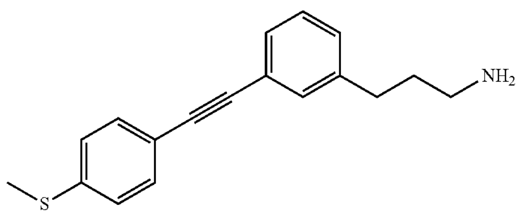 [SMILES: CSc1ccc(C#Cc2cccc(CCCN)c2)cc1] | 3-(3-((4-(methylthio)phenyl)ethynyl)phenyl)propan-1-amine |
| 125 | 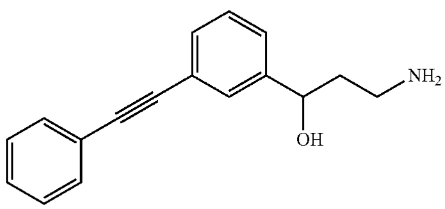 [SMILES: NCCC(O)c1cccc(C#Cc2ccccc2)c1] | 3-amino-1-(3-(phenylethynyl)phenyl)propan-1-ol |
| 139 | 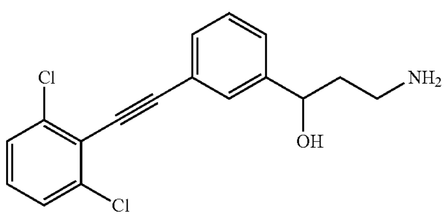 [SMILES: NCCC(O)c1cccc(C#Cc2c(Cl)cccc2Cl)c1] | 3-amino-1-(3-((2,6-dichlorophenyl)ethynyl)-phenyl)propan-1-ol |

Another embodiment provides a compound of Formula (II) wherein $R_5$ is naphthyl. In further embodiments, each of $R_1$, $R_2$, $R_3$, $R_4$, $R_{10}$ and $R_{11}$ is hydrogen.

In a specific embodiment, the compound of Formulae (I) or (II) has the structure shown in Table 2.

TABLE 2

| Example No. | Structure | Chemical Name |
|---|---|---|
| 45 | 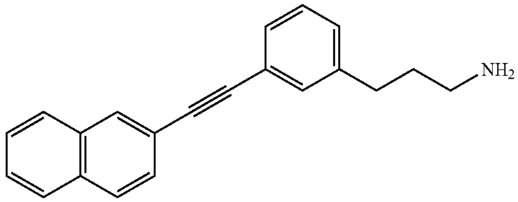 [SMILES: NCCCc1cccc(C#Cc2ccc3ccccc3c2)c1] | 3-(3-(naphthalen-2-ylethynyl)phenyl)propan-1-amine |

TABLE 2-continued

| Example No. | Structure | Chemical Name |
|---|---|---|
| 82 | 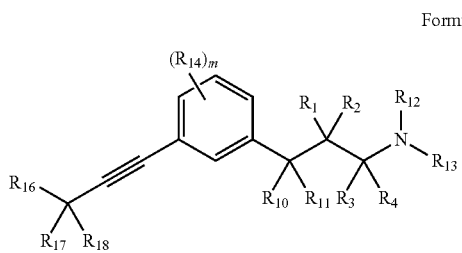 | 3-(3-(naphthalen-1-ylethynyl)phenyl)propan-1-amine |

A further embodiment provides a compound of Formula (II) wherein $R_5$ is alkyl. Thus, the compound can be represented by a structure of Formula (IIb):

Formula (IIb)

as a tautomer or a mixture of tautomers, or as a pharmaceutically acceptable salt, hydrate, solvate, N-oxide or prodrug thereof, wherein:

m is 0, 1, 2 or 3;

$R_1$ and $R_2$ are each the same or different and independently hydrogen, halogen, alkyl, fluoroalkyl, $OR_6$, $NR_7R_8$ or carbocyclyl; or $R_1$ and $R_2$ form an oxo;

$R_3$ and $R_4$ are each the same or different and independently hydrogen or alkyl;

$R_6$ is hydrogen or alkyl;

$R_7$ and $R_8$ are each the same or different and independently hydrogen, alkyl, carbocyclyl, or —C(═O)$R_9$; or $R_7$ and $R_8$, together with the nitrogen atom to which they are attached, form an N-heterocyclyl;

$R_9$ is alkyl, alkenyl, aryl, carbocyclyl, heteroaryl or heterocyclyl;

$R_{10}$ and $R_{11}$ are each the same or different and independently hydrogen, halogen, alkyl, fluoroalkyl, —$OR_6$, —$NR_7R_8$ or carbocyclyl; or $R_{10}$ and $R_{11}$ form an oxo;

$R_{12}$ and $R_{13}$ are the same or different and independently hydrogen, alkyl or —C(═O)$R_9$; or $R_{12}$ and $R_{13}$ together with the nitrogen atom to which they are attached, form an N-heterocyclyl;

each $R_{14}$ is the same or different and independently alkyl, halo, fluoroalkyl or —$OR_6$; and each $R_{16}$, $R_{17}$ and $R_{18}$ are the same or different and independently hydrogen, alkyl, —$OR_6$, carbocyclyl or aryl.

In certain embodiments, each of $R_{12}$ and $R_{13}$ is hydrogen. In certain embodiments, each of $R_1$, $R_2$, $R_3$, $R_4$, $R_{10}$ and $R_{11}$ is independently hydrogen, halogen, alkyl or —$OR_6$, wherein $R_6$ is hydrogen or alkyl. In certain embodiments, m is 0, and each of $R_1$, $R_2$, $R_3$, $R_4$, $R_{10}$ and $R_{11}$ is independently hydrogen or —$OR_6$, wherein $R_6$ is hydrogen or alkyl. In further embodiments, each of $R_{16}$, $R_{17}$ and $R_{18}$ is independently hydrogen, alkyl, carbocyclyl or aryl.

In certain specific embodiments, the compounds of Formula (I), (II) or (IIb) have the structures shown in Table 3.

TABLE 3

| Example No. | Structure | Chemical Name |
|---|---|---|
| 34 | 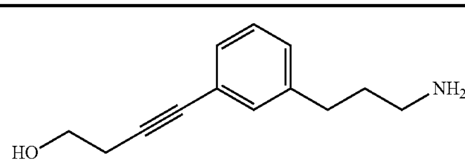 | 4-(3-(3-aminopropyl)phenyl)but-3-yn-1-ol |
| 35 | 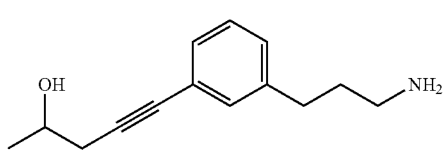 [SMILES: CC(O)CC#Cc1cccc(CCCN)c1] | 5-(3-(3-aminopropyl)phenyl)pent-4-yn-2-ol |
| 39 | 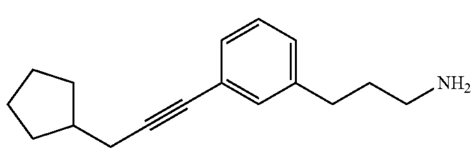 [SMILES: NCCCc1cccc(C#CCC2CCCC2)c1] | 3-(3-(3-cyclopentylprop-1-ynyl)phenyl)propan-1-amine |

TABLE 3-continued

| Example No. | Chemical Name |
|---|---|
| 40 | 3-(3-(3,3-dimethylbut-1-ynyl)phenyl)propan-1-amine |
| 42 | 3-(3-(3-phenylprop-1-ynyl)phenyl)propan-1-amine |
| 43 | 3-(3-(pent-1-ynyl)phenyl)propan-1-amine |
| 44 | 3-(3-(hex-1-ynyl)phenyl)propan-1-amine |
| 48 | 3-amino-1-(3-(3-cyclopentylprop-1-ynyl)phenyl)propan-1-ol |
| 49 | 3-amino-1-(3-(3-phenylprop-1-ynyl)phenyl)propan-1-ol |
| 50 | 6-(3-(3-amino-1-hydroxypropyl)phenyl)hex-5-yn-1-ol |
| 51 | 4-(3-(3-amino-1-hydroxypropyl)phenyl)but-3-yn-1-ol |
| 53 | 3-amino-1-(3-(hept-1-ynyl)phenyl)propan-1-ol |
| 67 | 3-(3-(6-methoxyhex-1-ynyl)phenyl)propan-1-amine |

TABLE 3-continued

| Example No. | Structure | Chemical Name |
|---|---|---|
| 68 | 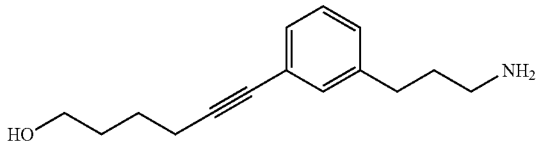 [SMILES: NCCCc1cccc(C#CCCCCO)c1] | 6-(3-(3-aminopropyl)phenyl)hex-5-yn-1-ol |
| 69 | 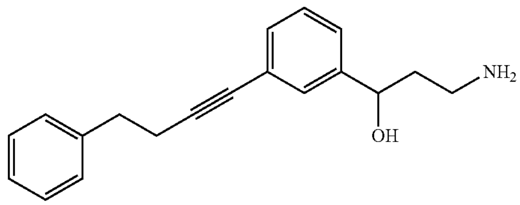 [SMILES: NCCC(O)c1cccc(C#CCCc2ccccc2)c1] | 3-amino-1-(3-(4-phenylbut-1-ynyl)phenyl)propan-1-ol |
| 70 | 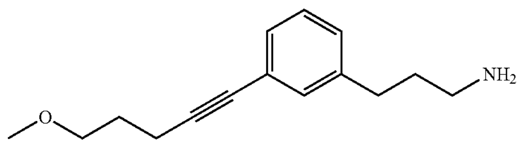 [SMILES: COCCCC#Cc1cccc(CCCN)c1] | 3-(3-(5-methoxypent-1-ynyl)phenyl)propan-1-amine |
| 71 | 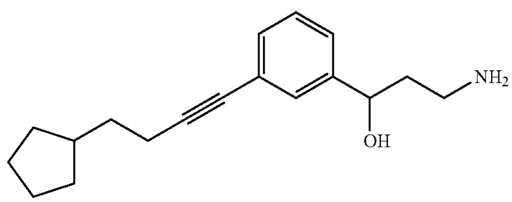 [SMILES: NCCC(O)c1cccc(C#CCCC2CCCC2)c1] | 3-amino-1-(3-(4-cyclopentylbut-1-ynyl)phenyl)propan-1-ol |
| 72 | 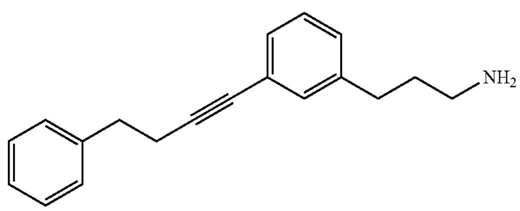 [SMILES: NCCCc1cccc(C#CCCc2ccccc2)c1] | 3-(3-(4-phenylbut-1-ynyl)phenyl)propan-1-amine |
| 102 | 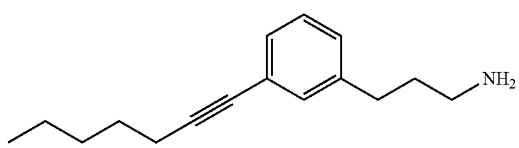 [SMILES: CCCCCC#Cc1cccc(CCCN)c1] | 3-(3-(hept-1-ynyl)phenyl)propan-1-amine |
| 108 | 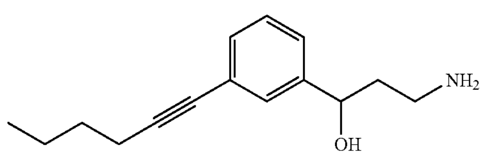 | 3-amino-1-(3-(hex-1-ynyl)phenyl)propan-1-ol |
| 115 | 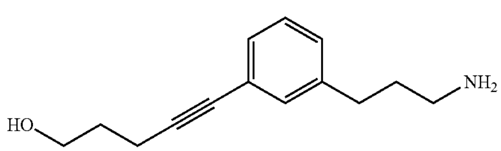 [SMILES: NCCCc1cccc(C#CCCCO)c1] | 5-(3-(3-Aminopropyl)-phenyl)pent-4-yn-1-ol |
| 119 | 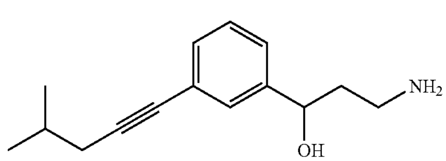 [SMILES: CC(C)CC#Cc1cccc(C(O)CCN)c1] | 3-amino-1-(3-(4-methylpent-1-ynyl)phenyl)propan-1-ol |

TABLE 3-continued

| Example No. | Structure | Chemical Name |
|---|---|---|
| 121 | 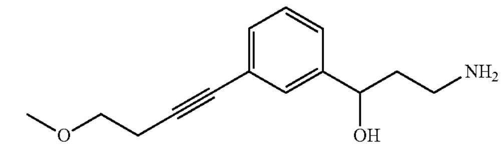 [SMILES: COCCC#Cc1cccc(C(O)CCN)c1] | 3-amino-1-(3-(4-methoxybut-1-ynyl)phenyl)propan-1-ol |
| 126 | 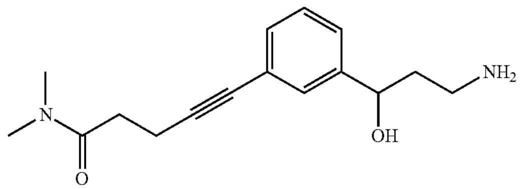 [SMILES: CN(C)C(=O)CCC#Cc1cccc(C(O)CCN)c1] | 5-(3-(3-amino-1-hydroxypropyl)phenyl)-N,N-dimethylpent-4-ynamide |
| 130 | 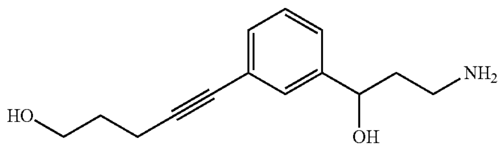 [SMILES: NCCC(O)c1cccc(C#CCCCO)c1] | 5-(3-(3-amino-1-hydroxypropyl)phenyl)pent-4-yn-1-ol |
| 133 | 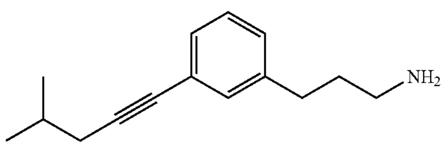 | 3-(3-(4-methylpent-1-ynyl)phenyl)propan-1-amine |
| 138 | 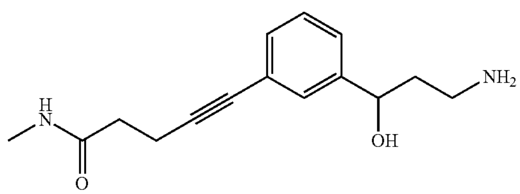 [SMILES: CNC(=O)CCC#Cc1cccc(C(O)CCN)c1] | 5-(3-(3-amino-1-hydroxypropyl)phenyl)-N-methylpent-4-ynamide |
| 150 | 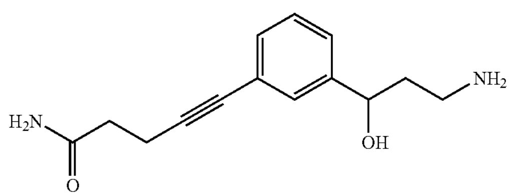 [SMILES: NCCC(O)c1cccc(C#CCCC(N)=O)c1] | 5-(3-(3-Amino-1-hydroxy-propyl)phenyl)-pent-4-ynamide |
| 152 | 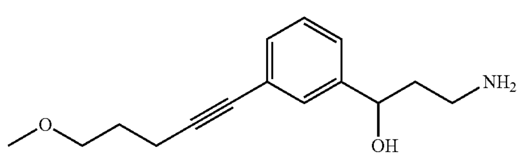 [SMILES: COCCCC#Cc1cccc(C(O)CCN)c1] | 3-amino-1-(3-(5-methoxypent-1-ynyl)phenyl)propan-1-ol |
| 153 | 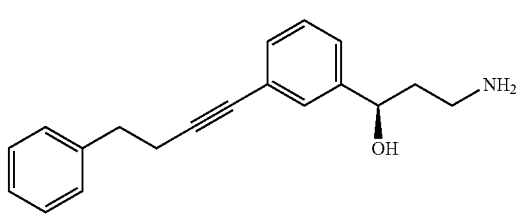 [SMILES: NCC[C@@H](O)c1cccc(C#CCCc2ccccc2)c1] | (R)-3-Amino-1-(3-(4-phenylbut-1-ynyl)phenyl)propan-1-ol |

TABLE 3-continued

| Example No. | Structure | Chemical Name |
|---|---|---|
| 161 | 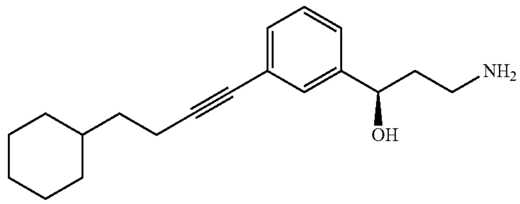 [SMILES: NCC[C@@H](O)c1cccc(C#CCCC2CCCCC2)c1] | (R)-3-Amino-1-(3-(4-cyclohexylbut-1-ynyl)phenyl)propan-1-ol |
| 171 | 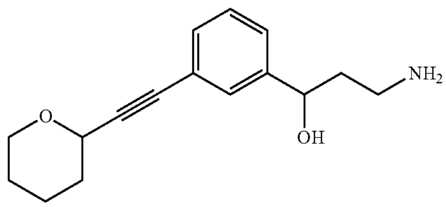 [SMILES: NCCC(O)c1cccc(C#CC2CCCCO2)c1] | 3-amino-1-(3-((tetrahydro-2H-pyran-2-yl)ethynyl)-phenyl)propan-1-ol |
| 172 | 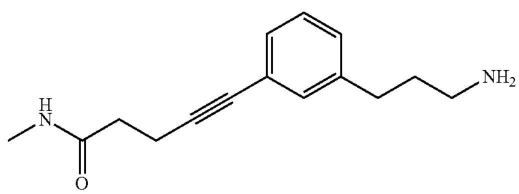 [SMILES: CNC(=O)CCC#Cc1cccc(CCCN)c1] | 5-(3-(3-aminopropyl)-phenyl)-N-methylpent-4-ynamide |
| 173 | 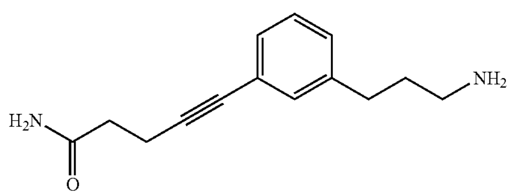 [SMILES: NCCCc1cccc(C#CCCC(N)=O)c1] | 5-(3-(3-aminopropyl)-phenyl)pent-4-ynamide |
| 175 | 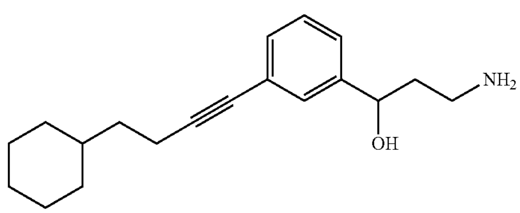 [SMILES: NCCC(O)c1cccc(C#CCCC2CCCCC2)c1] | 3-amino-1-(3-(4-cyclohexylbut-1-ynyl)phenyl)propan-1-ol |
| 179 | 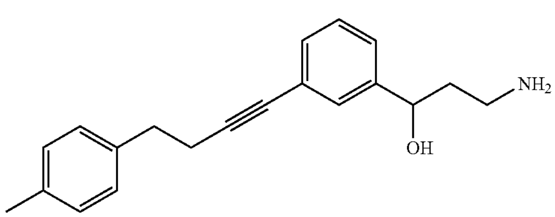 [SMILES: Cc1ccc(CCC#Cc2cccc(C(O)CCN)c2)cc1] | 3-amino-1-(3-(4-p-tolylbut-1-ynyl)phenyl)propan-1-ol |
| 180 | 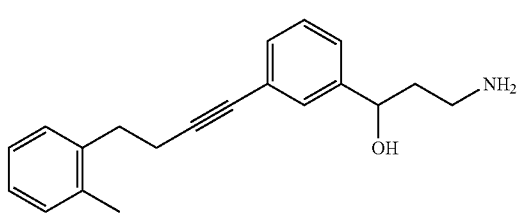 [SMILES: Cc1ccccc1CCC#Cc1cccc(C(O)CCN)c1] | 3-amino-1-(3-(4-o-tolylbut-1-ynyl)phenyl)propan-1-ol |

TABLE 3-continued

| Example No. | Structure | Chemical Name |
|---|---|---|
| 181 | 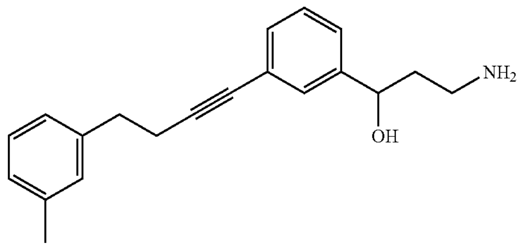 [SMILES: Cc1cccc(CCC#Cc2cccc(C(O)CCN)c2)c1] | 3-amino-1-(3-(4-m-tolylbut-1-ynyl)phenyl)propan-1-ol |
| 183 | 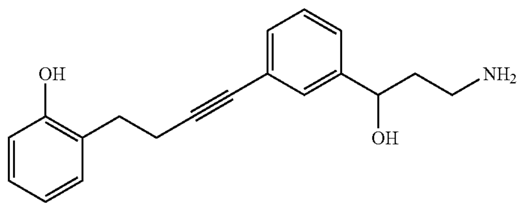 [SMILES: NCCC(O)c1cccc(C#CCCc2ccccc2O)c1] | 2-(4-(3-(3-amino-1-hydroxypropyl)phenyl)but-3-ynyl)phenol |
| 184 | 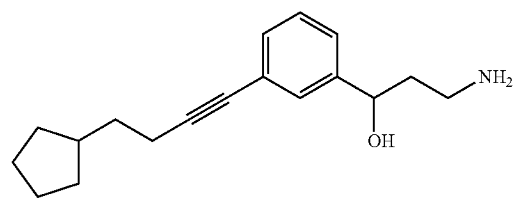 [SMILES: NCCC(O)c1cccc(C#CCCC2CCCC2)c1] | 3-amino-1-(3-(4-cyclopentylbut-1-ynyl)phenyl)propan-1-ol |
| 187 | 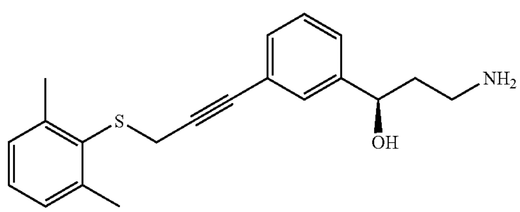 [SMILES: Cc1cccc(C)c1SCC#Cc1cccc([C@H](O)CCN)c1] | (R)-3-amino-1-(3-(3-(2,6-dimethylphenylthio)prop-1-ynyl)phenyl)propan-1-ol |

In other embodiments, $R_{16}$ is $—OR_6$, wherein $R_6$ is hydrogen or alkyl, and each of $R_{17}$ and $R_{18}$ is independently hydrogen, alkyl or aryl.

In further specific embodiments, the compounds of Formula (I), (II) or (IIb) have the structures shown in Table 4.

TABLE 4

| Example No. | Structure | Chemical Name |
|---|---|---|
| 1 | 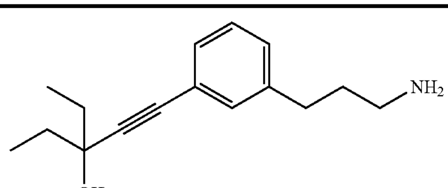 | 1-(3-(3-aminopropyl)phenyl)-3-ethylpent-1-yn-3-ol |
| 2 | 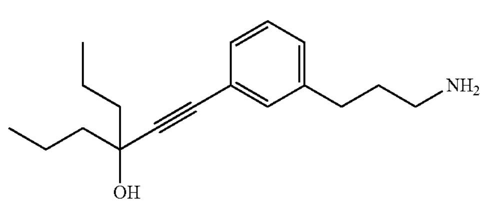 | 4-((3-(3-aminopropyl)phenyl)ethynyl)-heptan-4-ol |

TABLE 4-continued

| Example No. | Structure | Chemical Name |
| --- | --- | --- |
| 3 | 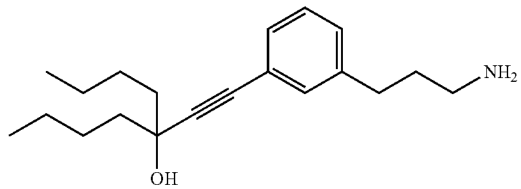 | 5-((3-(3-aminopropyl)phenyl)ethynyl)-nonan-5-ol |
| 4 | 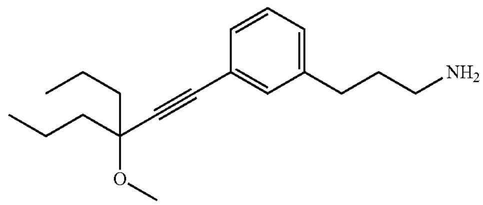 [SMILES: CCCC(C#Cc1cccc(CCCN)c1)(CCC)OC] | 3-(3-(3-methoxy-3-propylhex-1-ynyl)phenyl)propan-1-amine |
| 5 | 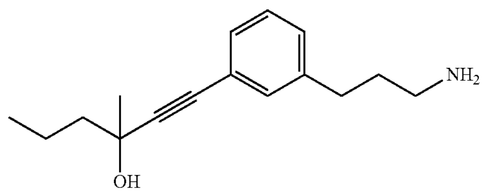 [SMILES: CCCC(C)(O)C#Cc1cccc(CCCN)c1] | 1-(3-(3-aminopropyl)phenyl)-3-methylhex-1-yn-3-ol |
| 6 | 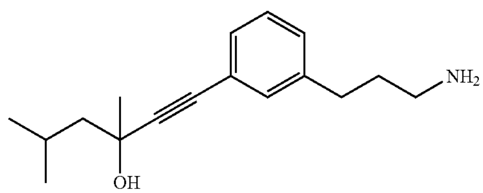 [SMILES: CC(C)CC(C)(O)C#Cc1cccc(CCCN)c1] | 1-(3-(3-aminopropyl)phenyl)-3,4-dimethylhex-1-yn-3-ol |
| 7 | 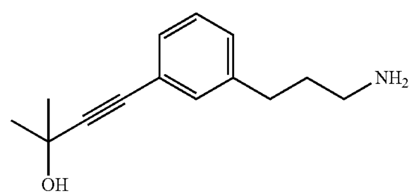 [SMILES: CC(C)(O)C#Cc1cccc(CCCN)c1] | 4-(3-(3-aminopropyl)phenyl)-2-methylbut-3-yn-2-ol |
| 8 | 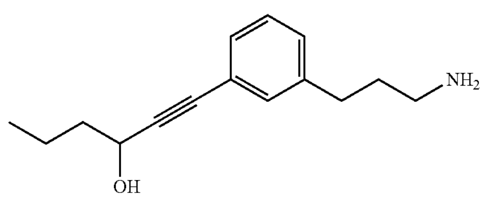 [SMILES: CCCC(O)C#Cc1cccc(CCCN)c1] | 1-(3-(3-aminopropyl)phenyl)hex-1-yn-3-ol |
| 9 | 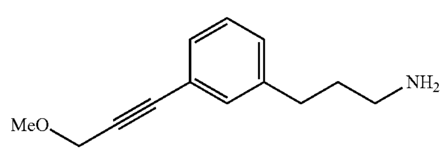 [SMILES: COCC#Cc1cccc(CCCN)c1] | 3-(3-(3-methoxyprop-1-ynyl)phenyl)propan-1-amine |
| 10 | 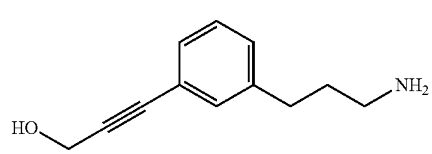 [SMILES: NCCCc1cccc(C#CCO)c1] | 3-(3-(3-aminopropyl)phenyl)prop-2-yn-1-ol |

TABLE 4-continued

| Example No. | Structure | Chemical Name |
| --- | --- | --- |
| 12 | 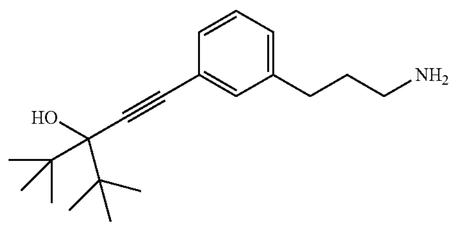 [SMILES: CC(C)(C)C(O)(C#Cc1cccc(CCCN)c1)C(C)(C)C] | 1-(3-(3-aminopropyl)phenyl)-3-tert-butyl-4,4-dimethylpent-1-yn-3-ol |
| 15 | 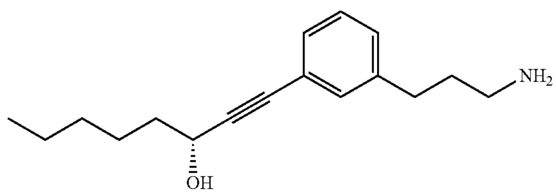 [SMILES: CCCCC[C@@H](O)C#Cc1cccc(CCCN)c1] | (R)-1-(3-(3-aminopropyl)phenyl)oct-1-yn-3-ol |
| 14 | 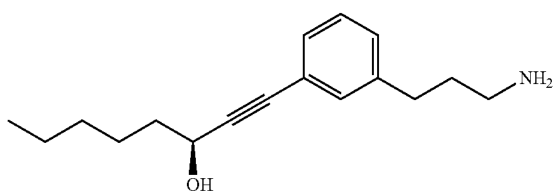 [SMILES: CCCCC[C@H](O)C#Cc1cccc(CCCN)c1] | (S)-1-(3-(3-aminopropyl)phenyl)oct-1-yn-3-ol |
| 16 | 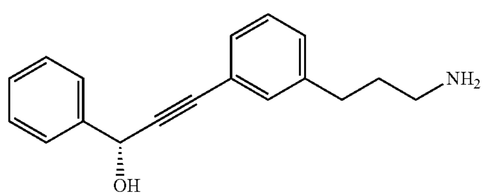 [SMILES: NCCCc1cccc(C#C[C@H](O)c2ccccc2)c1] | (R)-3-(3-(3-aminopropyl)phenyl)-1-phenylprop-2-yn-1-ol |
| 21 | 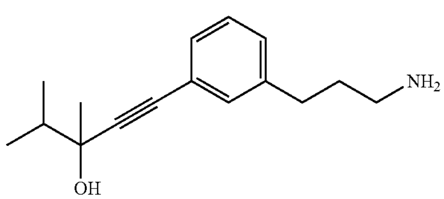 | 1-(3-(3-aminopropyl)phenyl)-3,4-dimethylpent-1-yn-3-ol |
| 19 | 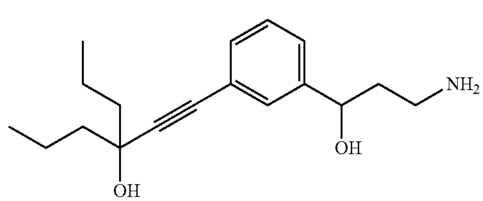 [SMILES: CCCC(O)(C#Cc1cccc(C(O)CCN)c1)CCC] | 4-((3-(3-amino-1-hydroxypropyl)phenyl)ethynyl)heptan-4-ol |
| 100 | 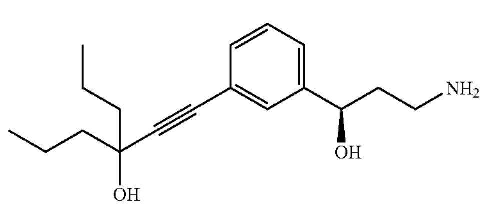 [SMILES: CCCC(O)(C#Cc1cccc([C@H](O)CCN)c1)CCC] | (R)-4-((3-(3-amino-1-hydroxypropyl)phenyl)ethynyl)heptan-4-ol |

TABLE 4-continued
| Example No. | Structure | Chemical Name |
|---|---|---|
| 101 | 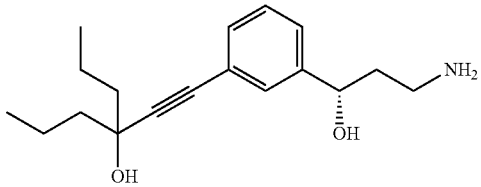 [SMILES: CCCC(O)(C#Cc1cccc([C@@H](O)CCN)c1)CCC] | (S)-4-((3-(3-amino-1-hydroxypropyl)phenyl)ethynyl)heptan-4-ol |
| 20 | 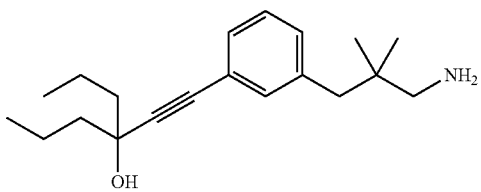 [SMILES: CCCC(O)(C#Cc1cccc(CC(C)(C)CN)c1)CCC] | 4-((3-(3-amino-2,2-dimethylpropyl)phenyl)ethynyl)heptan-4-ol |
| 22 | 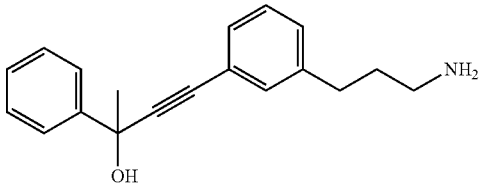 [SMILES: CC(O)(C#Cc1cccc(CCCN)c1)c1ccccc1] | 4-(3-(3-aminopropyl)phenyl)-2-phenylbut-3-yn-2-ol |
| 23 | 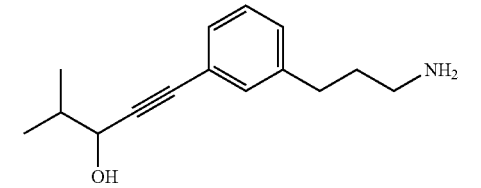 [SMILES: CC(C)C(O)C#Cc1cccc(CCCN)c1] | 1-(3-(3-aminopropyl)phenyl)-4-methylpent-1-yn-3-ol |
| 25 | 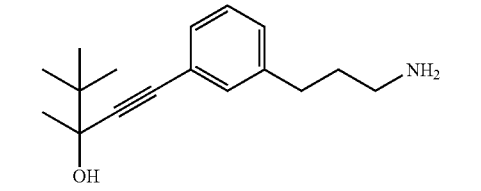 [SMILES: CC(C)(C)C(C)(O)C#Cc1cccc(CCCN)c1] | 1-(3-(3-aminopropyl)phenyl)-3,4,4-trimethylpent-1-yn-3-ol |
| 26 | 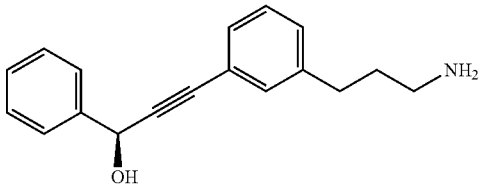 [SMILES: NCCCc1cccc(C#C[C@@H](O)c2ccccc2)c1] | (S)-3-(3-(3-aminopropyl)phenyl)-1-phenylprop-2-yn-1-ol |
| 32 | 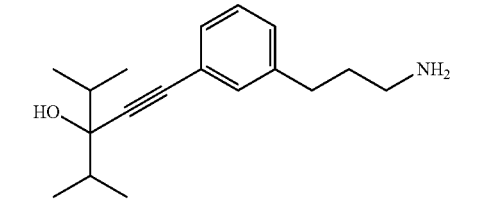 [SMILES: CC(C)C(O)(C#Cc1cccc(CCCN)c1)C(C)C] | 1-(3-(3-aminopropyl)phenyl)-3-isopropyl-4-methylpent-1-yn-3-ol |

TABLE 4-continued

| Example No. | Structure | Chemical Name |
|---|---|---|
| 33 | 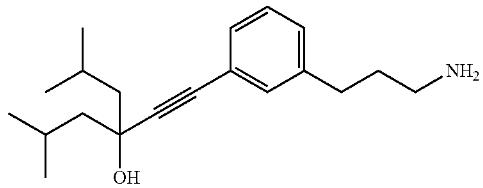 [SMILES: CC(C)CC(O)(C#Cc1cccc(CCCN)c1)CC(C)C] | 4-((3-(3-aminopropyl)phenyl)ethynyl)-2,6-dimethylheptan-4-ol |
| 107 | 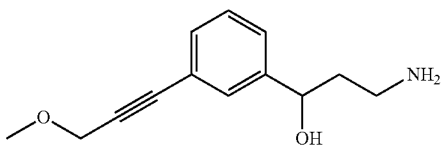 [SMILES: COCC#Cc1cccc(C(O)CCN)c1] | 3-amino-1-(3-(3-methoxyprop-1-ynyl)phenyl)propan-1-ol |
| 109 | 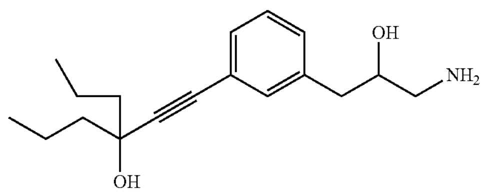 [SMILES: CCCC(O)(C#Cc1cccc(CC(O)CN)c1)CCC] | 4-((3-(3-amino-2-hydroxypropyl)phenyl)ethynyl)heptan-4-ol |
| 111 | 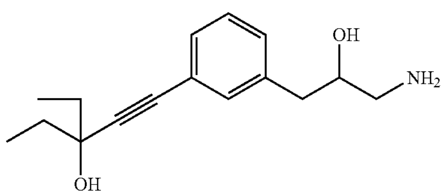 [SMILES: CCC(O)(C#Cc1cccc(CC(O)CN)c1)CC] | 1-(3-(3-amino-2-hydroxypropyl)phenyl)-3-ethylpent-1-yn-3-ol |
| 118 | 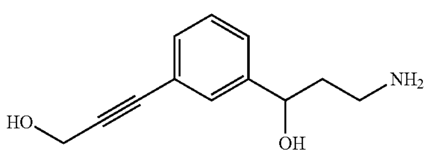 [SMILES: NCCC(O)c1cccc(C#CCO)c1] | 3-(3-(3-amino-1-hydroxypropyl)phenyl)prop-2-yn-1-ol |
| 132 | 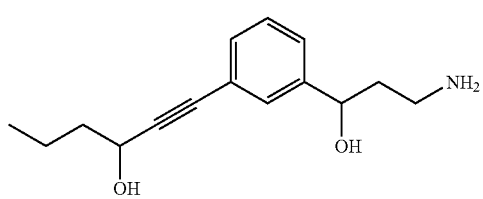 [SMILES: CCCC(O)C#Cc1cccc(C(O)CCN)c1] | 1-(3-(3-amino-1-hydroxypropyl)phenyl)hex-1-yn-3-ol |
| 147 | 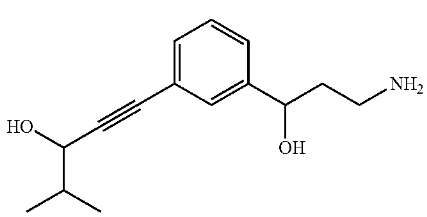 [SMILES: CC(C)C(O)C#Cc1cccc(C(O)CCN)c1] | 1-(3-(3-Amino-1-hydroxypropyl)phenyl)-4-methylpent-1-yn-3-ol |

TABLE 4-continued

| Example No. | Structure | Chemical Name |
|---|---|---|
| 154 | 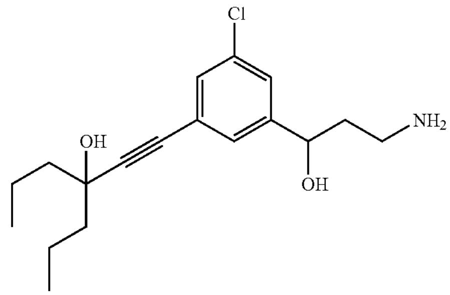 [SMILES: CCCC(O)(C#Cc1cc(Cl)cc(C(O)CCN)c1)CCC] | 4-((3-(3-Amino-1-hydroxy-propyl)-5-chlorophenyl)-ethynyl)heptan-4-ol |
| 155 | 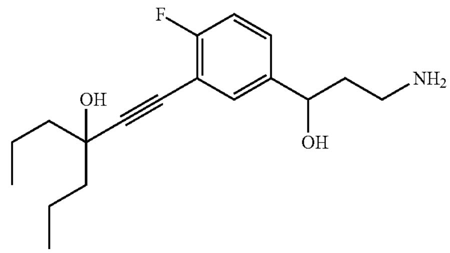 [SMILES: CCCC(O)(C#Cc1cc(C(O)CCN)ccc1F)CCC] | 4-((5-(3-Amino-1-hydroxypropyl)-2-fluorophenyl)ethynyl)heptan-4-ol |
| 156 | 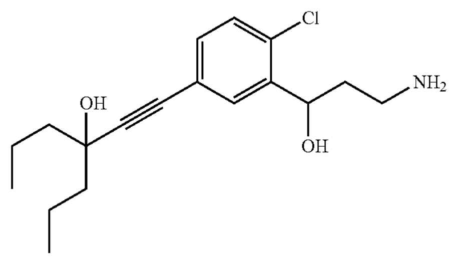 [SMILES: CCCC(O)(C#Cc1ccc(Cl)c(C(O)CCN)c1)CCC] | 4-((3-(3-Amino-1-hydroxypropyl)-4-chlorophenyl)ethynyl)heptan-4-ol |
| 157 | 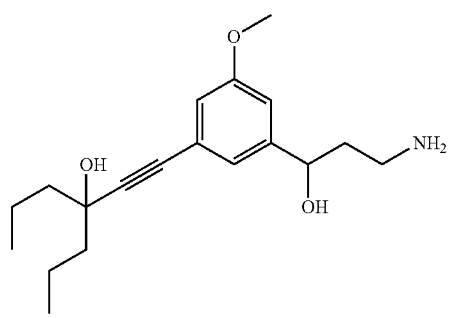 [SMILES: CCCC(O)(C#Cc1cc(OC)cc(C(O)CCN)c1)CCC] | 4-((3-(3-Amino-1-hydroxypropyl)-5-methoxyphenyl)ethynyl)-heptan-4-ol |
| 159 | 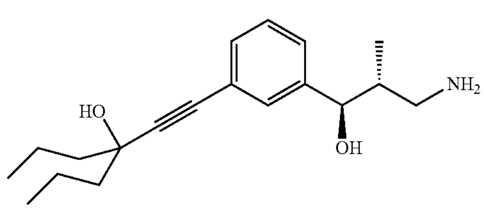 [SMILES: CCCC(O)(C#Cc1cccc([C@H](O)[C@H](C)CN)c1)CCC] | 4-((3-((1R,2R)-3-Amino-1-hydroxy-2-methylpropyl)phenyl)-ethynyl)heptan-4-ol |
| 162 | 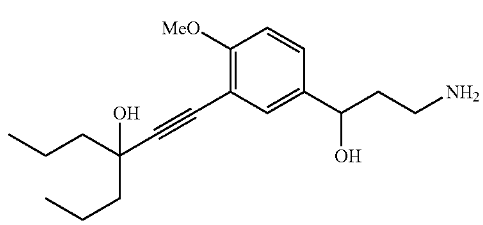 [SMILES: CCCC(O)(C#Cc1cc(C(O)CCN)ccc1OC)CCC] | 4-((5-(3-amino-1-hydroxypropyl)-2-methoxyphenyl)ethynyl)heptan-4-ol |

TABLE 4-continued

| Example No. | Structure | Chemical Name |
|---|---|---|
| 163 | 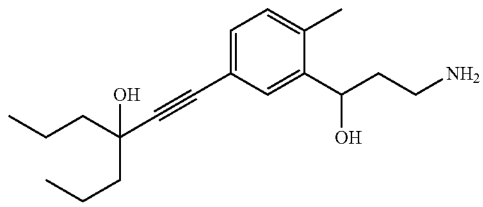 [SMILES: CCCC(O)(C#Cc1ccc(C)c(C(O)CCN)c1)CCC] | 4-((3-(3-amino-1-hydroxypropyl)-4-methylphenyl)ethynyl)heptan-4-ol |
| 170 | 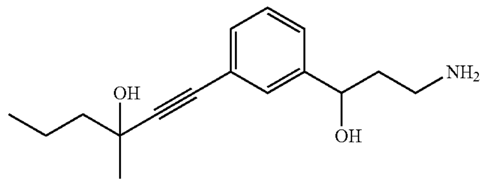 [SMILES: CCCC(C)(O)C#Cc1cccc(C(O)CCN)c1] | 1-(3-(3-amino-1-hydroxypropyl)phenyl)-3-methylhex-1-yn-3-ol |
| 174 | 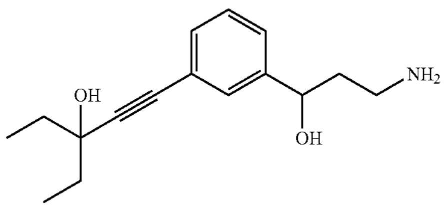 [SMILES: CCC(O)(C#Cc1cccc(C(O)CCN)c1)CC] | 1-(3-(3-amino-1-hydroxypropyl)phenyl)-3-ethylpent-1-yn-3-ol |
| 185 | 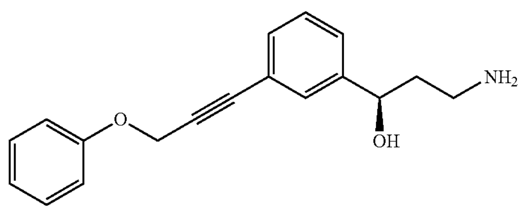 [SMILES: NCC[C@@H](O)c1cccc(C#CCOc2ccccc2)c1] | (R)-3-amino-1-(3-(3-phenoxyprop-1-ynyl)phenyl)propan-1-ol |
| 186 | 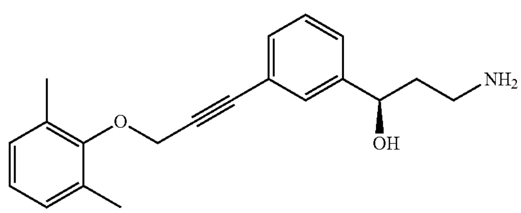 | (R)-3-amino-1-(3-(3-(2,6-dimethylphenoxy)prop-1-ynyl)phenyl)propan-1-ol |

In certain embodiments, $R_{12}$ is hydrogen and $R_{13}$ is —C(=O)$R_9$, wherein $R_9$ is alkyl. One specific embodiment provides the compound: N-(3-3(3-hydroxy-3-propylhex-1-ynyl)phenyl)propyl)acetamide. A further embodiment provides a compound having a structure of Formula (II) wherein $R_5$ is carbocyclyl.

In certain embodiments, $R_5$ is a cycloalkyl and the compound can be represented by a structure of Formula (IIc):

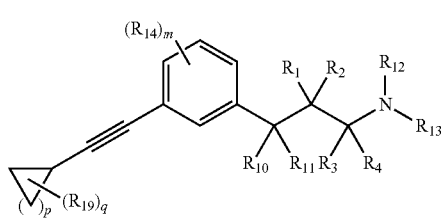

Formula (IIc)

as a tautomer or a mixture of tautomers, or as a pharmaceutically acceptable salt, hydrate, solvate, N-oxide or prodrug thereof, wherein:

m is 0, 1, 2 or 3;

p is 1, 2, 3, 4 or 5;

q is 0, 1, 2, 3, 4, 5, 6, 7, 8 or 9;

$R_1$ and $R_2$ are each the same or different and independently hydrogen, halogen, alkyl, fluoroalkyl, —OR$_6$, —NR$_7$R$_8$ or carbocyclyl; or $R_1$ and $R_2$ form an oxo;

$R_3$ and $R_4$ are each the same or different and independently hydrogen or alkyl;

$R_6$ is hydrogen or alkyl;

$R_7$ and $R_8$ are each the same or different and independently hydrogen, alkyl, carbocyclyl, or —C(=O)R$_9$; or $R_7$ and $R_8$, together with the nitrogen atom to which they are attached, form an N-heterocyclyl;

$R_9$ is alkyl, alkenyl, aryl, carbocyclyl, heteroaryl or heterocyclyl;

R₁₀ and R₁₁ are each the same or different and independently hydrogen, halogen, alkyl, fluoroalkyl, —OR₆, —NR₇R₈ or carbocyclyl; or R₁₀ and R₁₁ form an oxo;

R₁₂ and R₁₃ are the same or different and independently hydrogen, alkyl or —C(=O)R₉; or R₁₂ and R₁₃ together with the nitrogen atom to which they are attached, form an N-heterocyclyl;

each R₁₄ is the same or different and independently alkyl, halo, fluoroalkyl or —OR₆; and each R₁₉ is the same or different and independently alkyl, —OR₆, halo or fluoroalkyl.

In certain embodiments, each of R₁₂ and R₁₃ is hydrogen. In certain embodiments, each of R₁, R₂, R₃, R₄, R₁₀ and R₁₁ is independently hydrogen, halogen, alkyl or —OR₆, wherein R₆ is hydrogen or alkyl. In certain embodiments, each of R₁, R₂, R₃, R₄, R₁₀ and R₁₁ is independently hydrogen or —OR₆, wherein R₆ is hydrogen or alkyl. In certain embodiments, m is 0. In certain embodiments, q is 0. In further embodiments, q is 1, 2, 3, 4 or 5, and each R₁₉ is independently alkyl or —OR₆, wherein R₆ is hydrogen or alkyl. In further embodiments, p is 1 and R₅ is cyclopropyl. In other embodiments, p is 2, and R₅ is cyclobutyl. In other embodiments, p is 3, and R₅ is cyclopentyl. In other embodiments, p is 4, and R₅ is cyclohexyl. In other embodiments, p is 5, and R₅ is cycloheptyl.

In certain specific embodiments, the compounds of Formula (I), (II) or (IIc) have the structures shown in Table 5.

TABLE 5

| Example No. | Structure | Chemical Name |
|---|---|---|
| 38 | 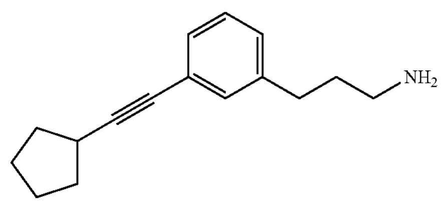 [SMILES: NCCCc1cccc(C#CC2CCCC2)c1] | 3-(3-(cyclopentylethynyl)phenyl)-propan-1-amine |
| 41 | 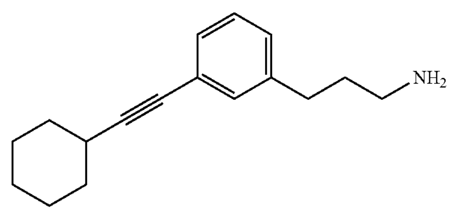 [SMILES: NCCCc1cccc(C#CC2CCCCC2)c1] | 3-(3-(cyclohexylethynyl)phenyl)-propan-1-amine |
| 47 | 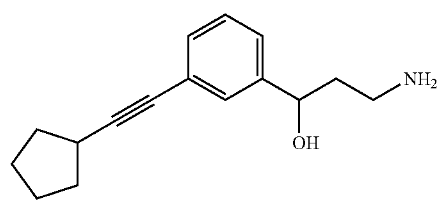 [SMILES: NCCC(O)c1cccc(C#CC2CCCC2)c1] | 3-amino-1-(3-(cyclopentylethynyl)phenyl)-propan-1-ol |
| 52 | 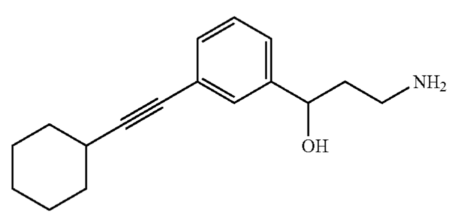 [SMILES: NCCC(O)c1cccc(C#CC2CCCCC2)c1] | 3-amino-1-(3-(cyclohexylethynyl)phenyl)-propan-1-ol |
| 11 | 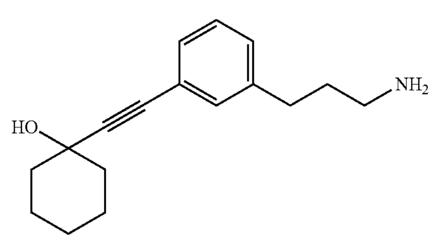 [SMILES: NCCCc1cccc(C#CC2(O)CCCCC2)c1] | 1-((3-(3-aminopropyl)phenyl)ethynyl)-cyclohexanol |

TABLE 5-continued

| Example No. | Structure | Chemical Name |
|---|---|---|
| 13 | 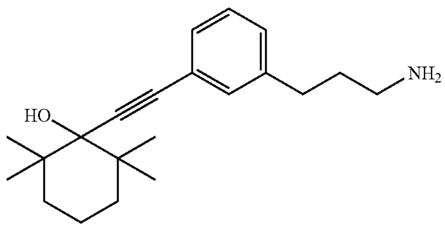 [SMILES: CC1(C)CCCC(C)(C)C1(O)C#Cc1cccc(CCCN)c1] | 1-((3-(3-aminopropyl)phenyl)ethynyl)-2,2,6,6-tetramethylcyclohexanol |
| 24 | 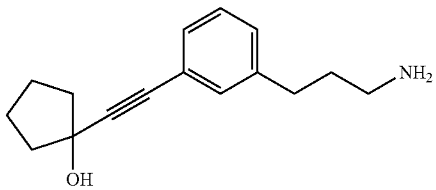 [SMILES: NCCCc1cccc(C#CC2(O)CCCC2)c1] | 1-((3-(3-aminopropyl)phenyl)ethynyl)-cyclopentanol |
| 58 | 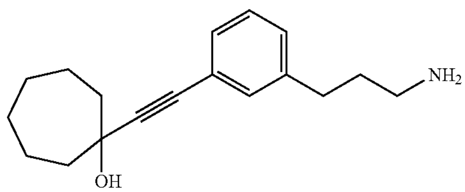 [SMILES: NCCCc1cccc(C#CC2(O)CCCCCC2)c1] | 1-((3-(3-aminopropyl)phenyl)ethynyl)cycloheptanol |
| 59 | 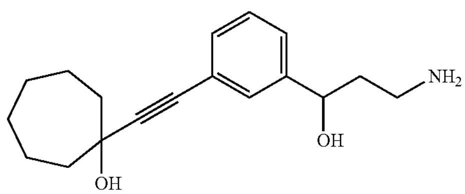 [SMILES: NCCC(O)c1cccc(C#CC2(O)CCCCCC2)c1] | 1-((3-(3-amino-1-hydroxypropyl)phenyl)ethynyl)cycloheptanol |
| 99 | 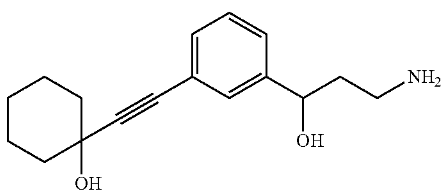 [SMILES: NCCC(O)c1cccc(C#CC2(O)CCCCC2)c1] | 1-((3-(3-amino-1-hydroxypropyl)phenyl)ethynyl)cyclohexanol |
| 105 | 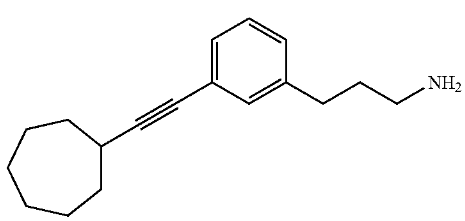 [SMILES: NCCCc1cccc(C#CC2CCCCCC2)c1] | 3-(3-(cycloheptylethynyl)phenyl)propan-1-amine |
| 110 | 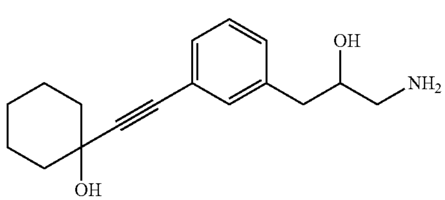 [SMILES: NCC(O)Cc1cccc(C#CC2(O)CCCCC2)c1] | 1-((3-(3-amino-2-hydroxypropyl)phenyl)ethynyl)cyclohexanol |

TABLE 5-continued

| Example No. | Structure | Chemical Name |
| --- | --- | --- |
| 112 | 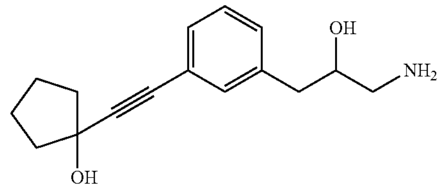 [SMILES: NCC(O)Cc1cccc(C#CC2(O)CCCC2)c1] | 1-((3-(3-amino-2-hydroxypropyl)phenyl)ethynyl)cyclopentanol |
| 127 | 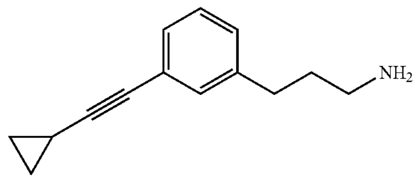 [SMILES: NCCCc1cccc(C#CC2CC2)c1] | 3-(3-(cyclopropylethynyl)phenyl)-propan-1-amine |
| 131 | 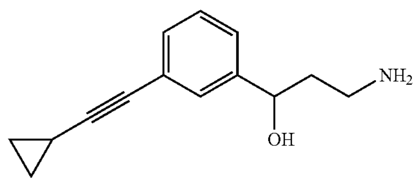 [SMILES: NCCC(O)c1cccc(C#CC2CC2)c1] | 3-amino-1-(3-(cyclopropylethynyl)phenyl)propan-1-ol |
| 136 | 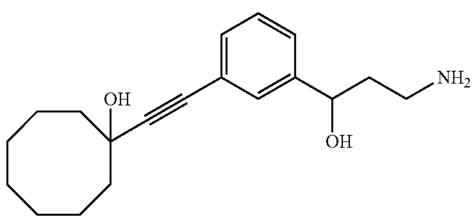 [SMILES: NCCC(O)c1cccc(C#CC2(O)CCCCCCC2)c1] | 1-((3-(3-amino-1-hydroxypropyl)phenyl)ethynyl)cyclooctanol |
| 140 | 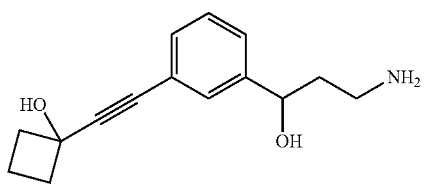 [SMILES: NCCC(O)c1cccc(C#CC2(O)CCC2)c1] | 1-((3-(3-amino-1-hydroxypropyl)phenyl)-ethynyl)cyclobutanol |
| 143 | 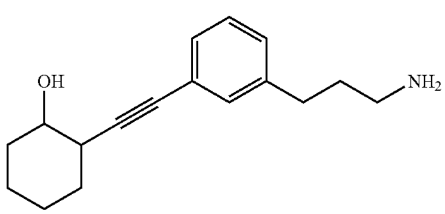 [SMILES: NCCCc1cccc(C#CC2CCCCC2O)c1] | 2-((3-(3-Aminopropyl)-phenyl)ethynyl)cyclohexanol |
| 145 | 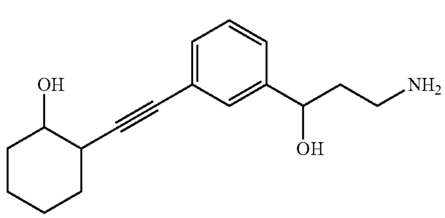 [SMILES: NCCC(O)c1cccc(C#CC2CCCCC2O)c1] | 2-((3-(3-Amino-1-hydroxy-propyl)phenyl)ethynyl)cyclohexanol |

TABLE 5-continued

| Example No. | Structure | Chemical Name |
|---|---|---|
| 148 | 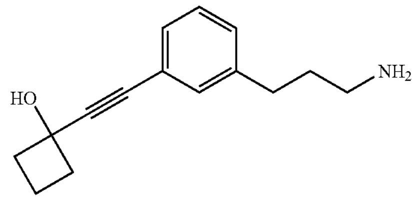 [SMILES: NCCCc1cccc(C#CC2(O)CCC2)c1] | 1-(2-(3-(3-Aminopropyl)-phenyl)ethynyl)cyclobutanol |
| 149 | 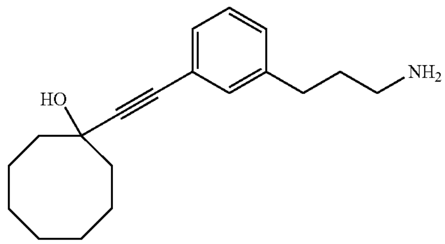 [SMILES: NCCCc1cccc(C#CC2(O)CCCCCCC2)c1] | 1-(2-(3-(3-Aminopropyl)-phenyl)ethynyl)cyclooctanol |
| 151 | 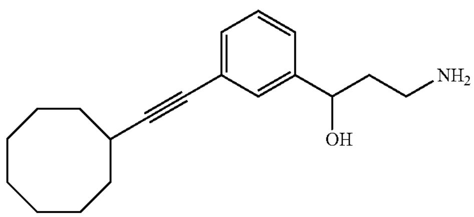 [SMILES: NCCC(O)c1cccc(C#CC2CCCCCCC2)c1] | 3-Amino-1-(3-(2-cyclooctylethynyl)phenyl)-propan-1-ol |
| 160 | 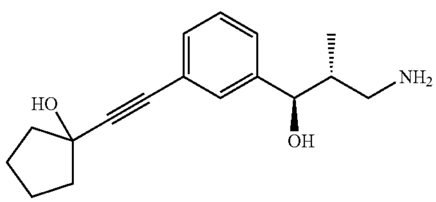 [SMILES: C[C@H](CN)[C@@H](O)c1cccc(C#CC2(O)CCCC2)c1] | 1-((3-((1R,2R)-3-Amino-1-hydroxy-2-methylpropyl)phenyl)-ethynyl)cyclopentanol |
| 176 | 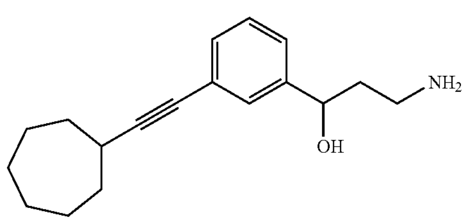 [SMILES: NCCC(O)c1cccc(C#CC2CCCCCC2)c1] | 3-amino-1-(3-(cycloheptylethynyl)phenyl)-propan-1-ol |
| 182 | 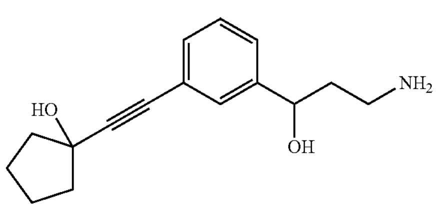 [SMILES: NCCC(O)c1cccc(C#CC2(O)CCCC2)c1] | 1-((3-(3-amino-1-hydroxypropyl)phenyl)-ethynyl)cyclopentanol |

In certain embodiments, $R_{12}$ is hydrogen and $R_{13}$ is —C(=O)$R_9$, wherein $R_9$ is alkyl. In certain embodiments, each of $R_1$, $R_2$, $R_3$, $R_4$, $R_{10}$ and $R_{11}$ is independently hydrogen or —O$R_6$, wherein $R_6$ is hydrogen or alkyl. In certain embodiments, m is 0. In certain embodiments, q is 0. In further embodiments, q is 1, 2, 3, 4 or 5, and each $R_{19}$ is independently alkyl or —O$R_6$, wherein $R_6$ is hydrogen or alkyl. In further embodiments, p is 1 and $R_5$ is cyclopropyl. In other embodiments, p is 2, and $R_5$ is cyclobutyl. In other embodiments, p is 3, and $R_5$ is cyclopentyl. In other embodiments, p is 4, and $R_5$ is cyclohexyl. In other embodiments, p is 5, and $R_5$ is cycloheptyl.

In a specific embodiment, the compound of Formula (I), (II) or (IIc) has the structures shown in Table 6.

TABLE 6

| Example No. | Structure | Chemical Name |
|---|---|---|
| 60 | 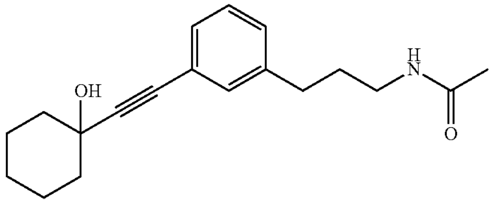 [SMILES: CC(=O)NCCCc1cccc(C#CC2(O)CCCCC2)c1] | N-(3-(3-((1-hydroxycyclohexyl)ethynyl)phenyl)propyl)acetamide |
| 103 | 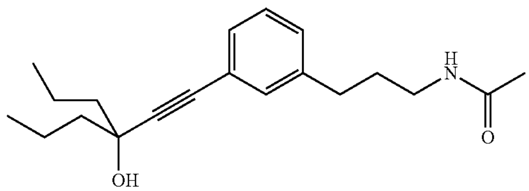 [SMILES: CCCC(O)(C#Cc1cccc(CCCNC(C)=O)c1)CCC] | N-(3-(3-(3-hydroxy-3-propylhex-1-ynyl)phenyl)propyl)acetamide |
| 104 | 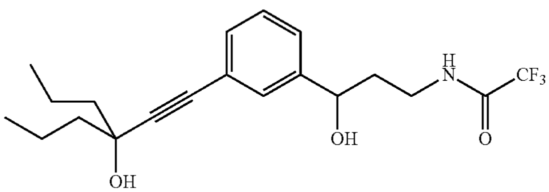 [SMILES: CCCC(O)(C#Cc1cccc(C(O)CCNC(=O)C(F)(F)F)c1)CCC] | 2,2,2-trifluoro-N-(3-hydroxy-3-(3-(3-hydroxy-3-propylhex-1-ynyl)phenyl)propyl)acetamide |
| 177 | 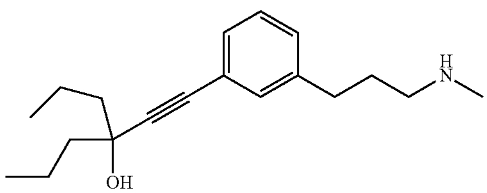 [SMILES: CCCC(O)(C#Cc1cccc(CCCNC)c1)CCC] | 4-((3-(3-(methylamino)propyl)phenyl)ethynyl)heptan-4-ol |

A further embodiment provides a compound having a structure of Formula (II) wherein $R_5$ is heterocyclyl, as defined herein. In certain embodiments, the heterocyclyl can be optionally substituted with —$OR_6$, wherein $R_6$ is hydrogen or alkyl. In certain embodiments, each of $R_{12}$ and $R_{13}$ is hydrogen. In certain embodiments, m is 0. In certain embodiments, each of $R_1$, $R_2$, $R_3$, $R_4$, $R_{10}$ and $R_{11}$ is independently hydrogen, halogen, alkyl or —$OR_6$, wherein $R_6$ is hydrogen or alkyl. In certain embodiments, each of $R_1$, $R_2$, $R_3$, $R_4$, $R_{10}$ and $R_{11}$ is hydrogen.

In certain specific embodiments, the compounds of Formula (I) or (II) have the structures shown in Table 7.

TABLE 7

| Example No. | Structure | Chemical Name |
|---|---|---|
| 55 | 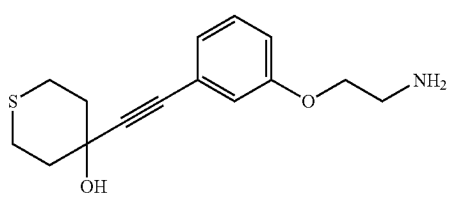 [SMILES: NCCOc1cccc(C#CC2(O)CCSCC2)c1] | 4-((3-(2-aminoethoxy)phenyl)ethynyl)tetrahydro-2H-thiopyran-4-ol |
| 56 | 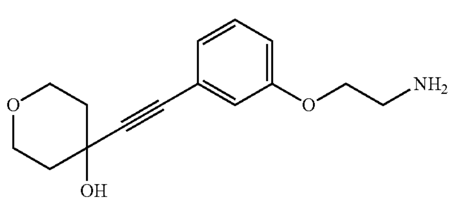 [SMILES: NCCOc1cccc(C#CC2(O)CCOCC2)c1] | 4-((3-(2-aminoethoxy)phenyl)ethynyl)tetrahydro-2H-pyran-4-ol |

A further embodiment provides a compound having a structure of Formula (II) wherein $R_5$ is heteroaryl, as defined herein. In certain embodiments, each of $R_{12}$ and $R_{13}$ is hydrogen. In certain embodiments, m is 0. In certain embodiments, each of $R_1$, $R_2$, $R_3$, $R_4$, $R_{10}$ and $R_{11}$ is independently hydrogen, halogen, alkyl or —$OR_6$, wherein $R_6$ is hydrogen or alkyl. In certain embodiments, each of $R_1$, $R_2$, $R_3$, $R_4$, $R_{10}$ and $R_{11}$ is hydrogen.

In certain specific embodiments, the compounds of Formula (I) or (II) have the structures shown in Table 8.

TABLE 8

| Example No. | Structure | Chemical Name |
|---|---|---|
| 61 | 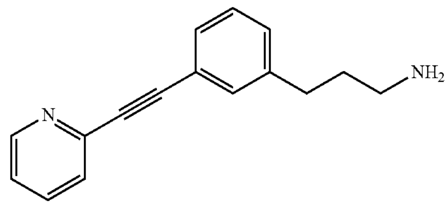 [SMILES: NCCCc1cccc(C#Cc2ccccn2)c1] | 3-(3-(pyridin-2-ylethynyl)phenyl)propan-1-amine |
| 64 | 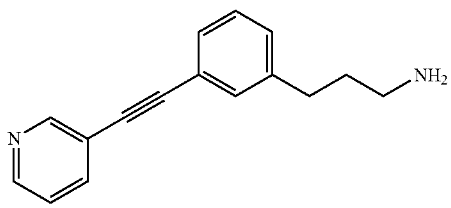 [SMILES: NCCCc1cccc(C#Cc2cccnc2)c1] | 3-(3-(pyridin-3-ylethynyl)phenyl)propan-1-amine |
| 63 | 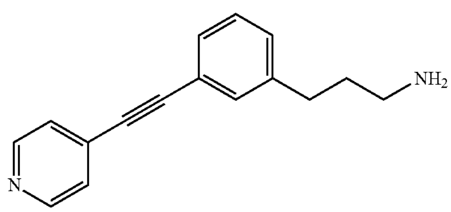 [SMILES: NCCCc1cccc(C#Cc2ccncc2)c1] | 3-(3-(pyridin-4-ylethynyl)phenyl)propan-1-amine |
| 65 | 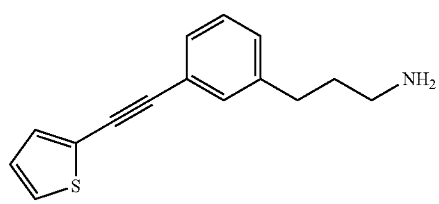 [SMILES: NCCCc1cccc(C#Cc2cccs2)c1] | 3-(3-(thiophen-2-ylethynyl)phenyl)propan-1-amine |
| 66 | 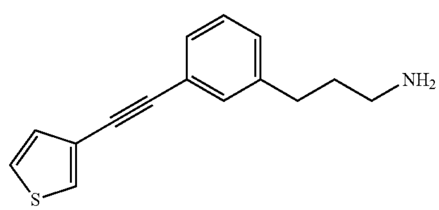 [SMILES: NCCCc1cccc(C#Cc2ccsc2)c1] | 3-(3-(thiophen-3-ylethynyl)phenyl)propan-1-amine |

A further embodiment provides a compound of Formula (I) wherein X is —O—, and the compound has an ethylene oxide linkage. Thus, the compound can be represented by a structure of Formula (III):

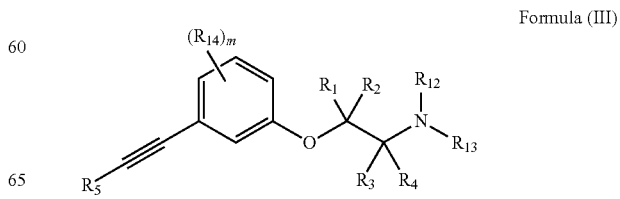

Formula (III)

as a tautomer or a mixture of tautomers, or as a pharmaceutically acceptable salt, hydrate, solvate, N-oxide or prodrug thereof, wherein:

m is 0, 1, 2 or 3;

$R_1$ and $R_2$ are each the same or different and independently hydrogen, alkyl or fluoroalkyl; or $R_1$ and $R_2$ form an oxo;

$R_3$ and $R_4$ are each the same or different and independently hydrogen or alkyl;

$R_5$ is alkyl, alkenyl, aryl, carbocyclyl, heteroaryl or heterocyclyl;

$R_6$ is hydrogen or alkyl;

$R_9$ is alkyl, alkenyl, aryl, carbocyclyl, heteroaryl or heterocyclyl;

$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl; and each $R_{14}$ is the same or different and independently alkyl, halo, fluoroalkyl or —O$R_6$.

In one embodiment, $R_5$ is alkyl and the compound has a structure of Formula (Ma):

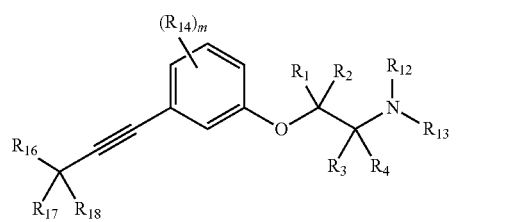

Formula (IIIa)

as a tautomer or a mixture of tautomers, or as a pharmaceutically acceptable salt, hydrate, solvate, N-oxide or prodrug thereof, wherein:

m is 0, 1, 2 or 3;

$R_1$ and $R_2$ are each the same or different and independently hydrogen, alkyl or fluoroalkyl; or $R_1$ and $R_2$ form an oxo;

$R_3$ and $R_4$ are each the same or different and independently hydrogen or alkyl;

$R_6$ is hydrogen or alkyl;

$R_9$ is alkyl, alkenyl, aryl, carbocyclyl, heteroaryl or heterocyclyl;

$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl;

each $R_{14}$ is the same or different and independently alkyl, halo, fluoroalkyl or —O$R_6$; and $R_{16}$, $R_{17}$ and $R_{18}$ are each the same or different and independently hydrogen, alkyl, —O$R_6$, carbocyclyl or aryl.

In certain embodiments, each of $R_{12}$ and $R_{13}$ is hydrogen. In certain embodiments, m is 0. In certain embodiments, each of $R_1$, $R_2$, $R_3$ and $R_4$ is independently hydrogen or alkyl. In further embodiments, each of $R_{16}$, $R_{17}$ and $R_{18}$ is independently hydrogen, alkyl or —O$R_6$, wherein $R_6$ is hydrogen or alkyl. In further embodiments, $R_{16}$ is —O$R_6$, wherein $R_6$ is hydrogen or alkyl, and each of $R_{17}$ and $R_{18}$ is independently alkyl. In other embodiments, each of $R_{16}$, $R_{17}$ and $R_{18}$ is independently hydrogen or aryl. In other embodiments, each of $R_{16}$, $R_{17}$ and $R_{18}$ is independently hydrogen or alkyl.

In further specific embodiments, the compounds of Formula (I), (III) or (IIIa) have the structures shown in Table 9.

TABLE 9

| Example No. | Structure | Chemical Name |
| --- | --- | --- |
| 18 | ![structure] | 4-((3-(2-aminoethoxy)phenyl)ethynyl)-heptan-4-ol |
| 27 | ![structure] | 1-(3-(2-aminoethoxy)phenyl)-3-ethylpent-1-yn-3-ol |
| 28 | ![structure] | 1-(3-(2-aminoethoxy)phenyl)-3-isopropyl-4-methylpent-1-yn-3-ol |

TABLE 9-continued

| Example No. | Structure | Chemical Name |
| --- | --- | --- |
| 29 | 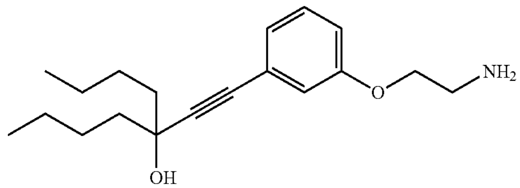 [SMILES: CCCCC(O)(C#Cc1cccc(OCCN)c1)CCCC] | 5-((3-(2-aminoethoxy)phenyl)ethynyl)-nonan-5-ol |
| 30 | 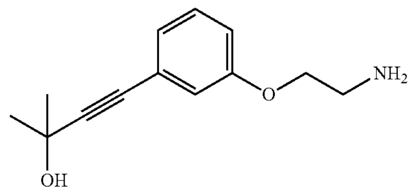 [SMILES: CC(C)(O)C#Cc1cccc(OCCN)c1] | 4-(3-(2-aminoethoxy)phenyl)-2-methylbut-3-yn-2-ol |
| 73 | 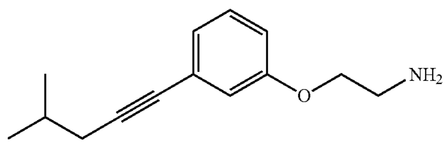 [SMILES: CC(C)CC#Cc1cccc(OCCN)c1] | 2-(3-(4-methylpent-1-ynyl)phenoxy)ethanamine |
| 74 | 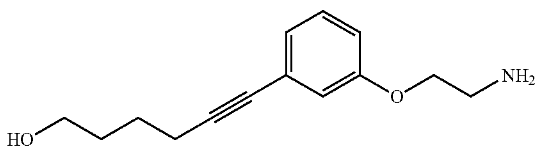 [SMILES: NCCOc1cccc(C#CCCCCO)c1] | 6-(3-(2-aminoethoxy)phenyl)hex-5-yn-1-ol |
| 75 | 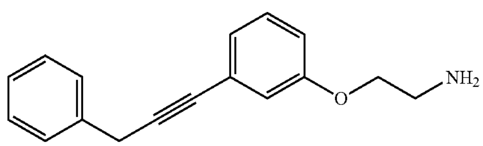 [SMILES: NCCOc1cccc(C#CCc2ccccc2)c1] | 2-(3-(3-phenylprop-1-ynyl)phenoxy)ethanamine |
| 76 | 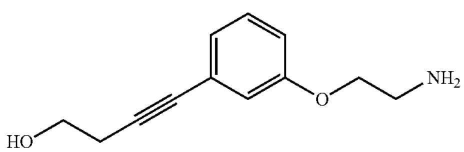 [SMILES: NCCOc1cccc(C#CCCO)c1] | 4-(3-(2-aminoethoxy)phenyl)but-3-yn-1-ol |
| 77 | 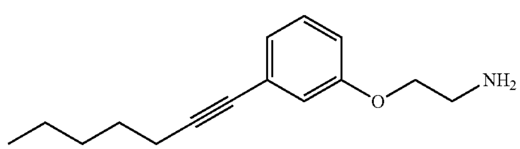 [SMILES: CCCCCC#Cc1cccc(OCCN)c1] | 2-(3-(hept-1-ynyl)phenoxy)ethanamine |
| 85 | 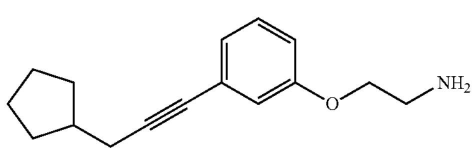 [SMILES: NCCOc1cccc(C#CCC2CCCC2)c1] | 2-(3-(3-cyclopentylprop-1-ynyl)phenoxy)ethanamine |
| 86 | 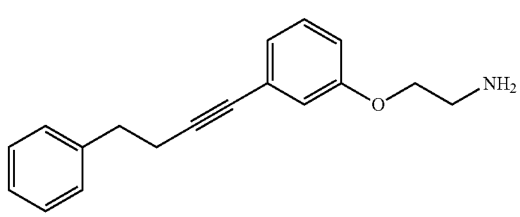 [SMILES: NCCOc1cccc(C#CCCc2ccccc2)c1] | 2-(3-(4-phenylbut-1-ynyl)phenoxy)ethanamine |

TABLE 9-continued

| Example No. | Structure | Chemical Name |
| --- | --- | --- |
| 114 | 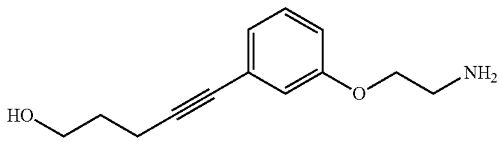 [SMILES: NCCOc1cccc(C#CCCCO)c1] | 5-(3-(2-aminoethoxy)phenyl)pent-4-yn-1-ol |
| 116 | 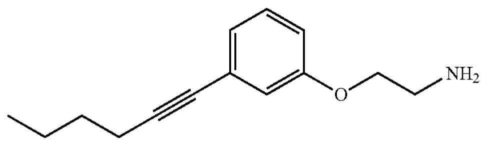 [SMILES: CCCCC#Cc1cccc(OCCN)c1] | 2-(3-(hex-1-ynyl)phenoxy)ethanamine |
| 117 | 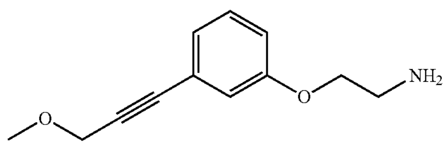 | 2-(3-(3-methoxyprop-1-ynyl)phenoxy)ethanamine |
| 120 | 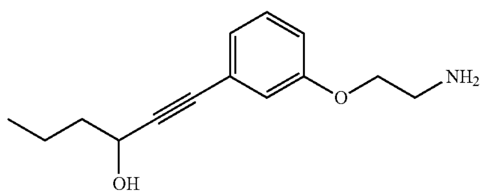 [SMILES: CCCC(O)C#Cc1cccc(OCCN)c1] | 1-(3-(2-aminoethoxy)phenyl)hex-1-yn-3-ol |
| 122 | 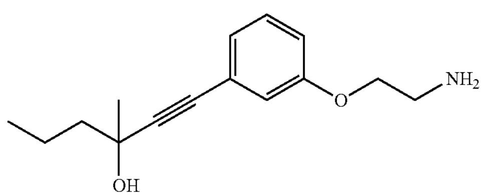 [SMILES: CCCC(C)(O)C#Cc1cccc(OCCN)c1] | 1-(3-(2-aminoethoxy)phenyl)-3-methylhex-1-yn-3-ol |
| 124 | 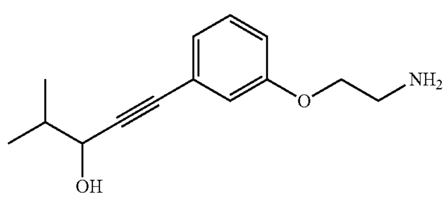 [SMILES: CC(C)C(O)C#Cc1cccc(OCCN)c1] | 1-(3-(2-aminoethoxy)phenyl)-4-methylpent-1-yn-3-ol |
| 128 | 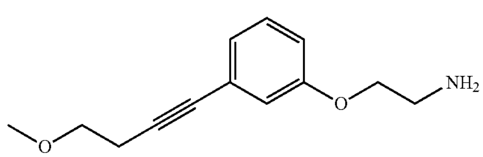 [SMILES: COCCC#Cc1cccc(OCCN)c1] | 2-(3-(4-methoxybut-1-ynyl)phenoxy)ethanamine |
| 134 | 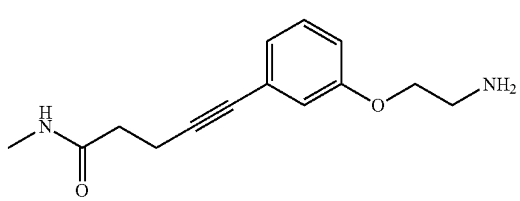 [SMILES: CNC(=O)CCC#Cc1cccc(OCCN)c1] | 5-(3-(2-aminoethoxy)-phenyl)-N-methylpent-4-ynamide |
| 135 | 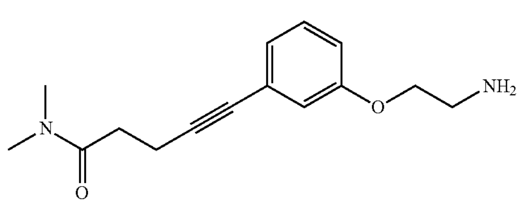 [SMILES: CN(C)C(=O)CCC#Cc1cccc(OCCN)c1] | 5-(3-(2-aminoethoxy)phenyl)-N,N-dimethylpent-4-ynamide |

TABLE 9-continued

| Example No. | Structure | Chemical Name |
|---|---|---|
| 137 | 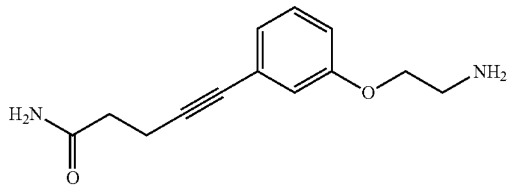 | 5-(3-(2-aminoethoxy)phenyl)pent-4-ynamide |
| 158 | 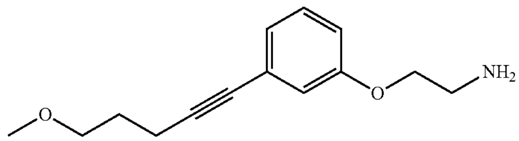 | 2-(3-(5-methoxypent-1-ynyl)phenoxy)ethanamine |

A further embodiment provides a compound having a structure of Formula (III) wherein $R_5$ is carbocyclyl.

In certain embodiments, $R_5$ is a cycloalkyl and the compound can be represented by a structure of Formula (IIIb):

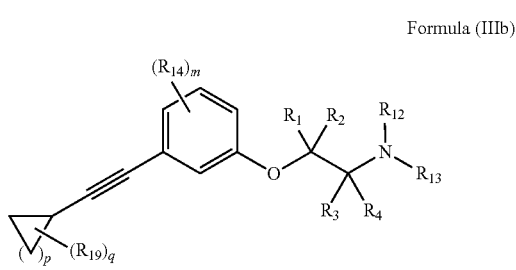

Formula (IIIb)

as a tautomer or a mixture of tautomers, or as a pharmaceutically acceptable salt, hydrate, solvate, N-oxide or prodrug thereof, wherein:

m is 0, 1, 2 or 3;
p is 1, 2, 3, 4 or 5;
q is 0, 1, 2, 3, 4, 5, 6, 7, 8 or 9;
$R_1$ and $R_2$ are each the same or different and independently hydrogen, alkyl or fluoroalkyl; or $R_1$ and $R_2$ form an oxo;
$R_3$ and $R_4$ are each the same or different and independently hydrogen or alkyl;
$R_6$ is hydrogen or alkyl;
$R_9$ is alkyl, alkenyl, aryl, carbocyclyl, heteroaryl or heterocyclyl;
$R_{12}$ and $R_{13}$ are the same or different and independently hydrogen, alkyl or —C(=O)$R_9$; or $R_{12}$ and $R_{13}$ together with the nitrogen atom to which they are attached, form an N-heterocyclyl;
each $R_{14}$ is the same or different and independently alkyl, halo, fluoroalkyl or —OR$_6$; and
each $R_{19}$ is the same or different and independently alkyl, —OR$_6$, halo or fluoroalkyl.

In certain embodiments, each of $R_{12}$ and $R_{13}$ is hydrogen. In certain embodiments, m is 0. In certain embodiments, each of $R_1$, $R_2$, $R_3$, $R_4$, $R_{10}$ and $R_{11}$ is independently hydrogen, halogen, alkyl or —OR$_6$, wherein $R_6$ is hydrogen or alkyl. In certain embodiments, each of $R_1$, $R_2$, $R_3$ and $R_4$ is independently hydrogen or alkyl. In further embodiments, q is 1, 2, 3, 4 or 5, and each $R_{19}$ is independently alkyl or —OR$_6$, wherein $R_6$ is hydrogen or alkyl. In further embodiments, q is 0. In further embodiments, q is 1 and $R_{19}$ is —OR$_6$, wherein $R_6$ is hydrogen or alkyl. In further embodiments, p is 1 and $R_5$ is cyclopropyl. In other embodiments, p is 2, and $R_5$ is cyclobutyl. In other embodiments, p is 3, and $R_5$ is cyclopentyl. In other embodiments, p is 4, and $R_5$ is cyclohexyl. In other embodiments, p is 5, and $R_5$ is cycloheptyl.

In certain specific embodiments, the compounds of Formula (I), (III) or (IIIb) have the structures shown in Table 10.

TABLE 10

| Example No. | Structure | Name |
|---|---|---|
| 31 | 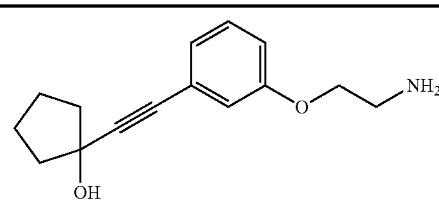 | 1-((3-(2-aminoethoxy)phenyl)ethynyl)-cyclopentanol |
| 57 | 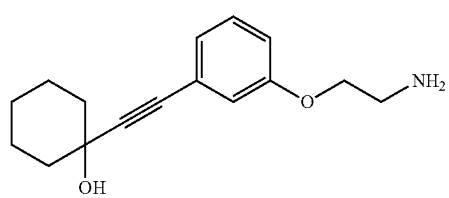 [SMILES: NCCOc1cccc(C#CC2(O)CCCCC2)c1] | 1-((3-(2-aminoethoxy)phenyl)ethynyl)-cyclohexanol |

TABLE 10-continued

| Example No. | Structure | Name |
|---|---|---|
| 78 | 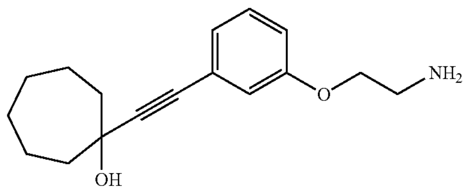 [SMILES: NCCOc1cccc(C#CC2(O)CCCCCC2)c1] | 1-((3-(2-aminoethoxy)phenyl)ethynyl)-cycloheptanol |
| 79 | 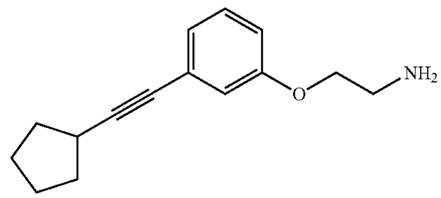 [SMILES: NCCOc1cccc(C#CC2CCCC2)c1] | 2-(3-(cyclopentylethynyl)phenoxy)-ethanamine |
| 80 | 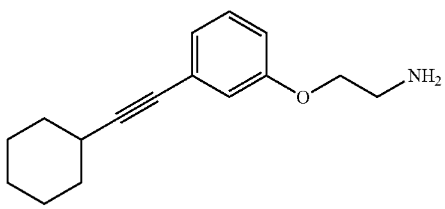 [SMILES: NCCOc1cccc(C#CC2CCCCC2)c1] | 2-(3-(cyclohexylethynyl)phenoxy)ethanamine |
| 106 | 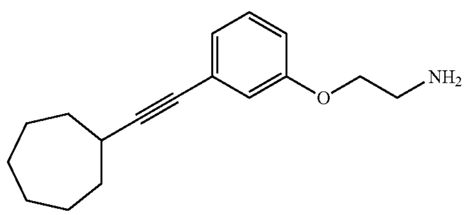 [SMILES: NCCOc1cccc(C#CC2CCCCCC2)c1] | 2-(3-(cycloheptylethynyl)phenoxy)ethanamine |
| 113 | 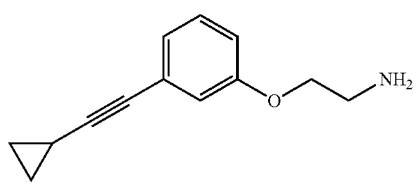 [SMILES: NCCOc1cccc(C#CC2CC2)c1] | 2-(3-(cyclopropylethynyl)-phenoxy)ethanamine |
| 123 | 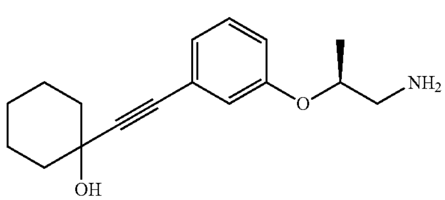 [SMILES: C[C@@H](CN)Oc1cccc(C#CC2(O)CCCCC2)c1] | (S)-1-((3-(1-aminopropan-2-yloxy)phenyl)ethynyl)cyclohexanol |
| 129 | 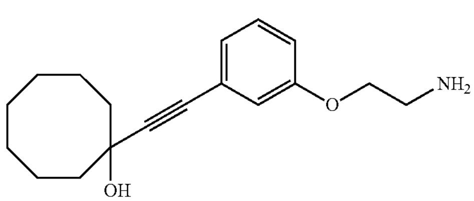 [SMILES: NCCOc1cccc(C#CC2(O)CCCCCCC2)c1] | 1-((3-(2-aminoethoxy)phenyl)ethynyl)cyclooctanol |

TABLE 10-continued

| Example No. | Structure | Name |
|---|---|---|
| 144 | 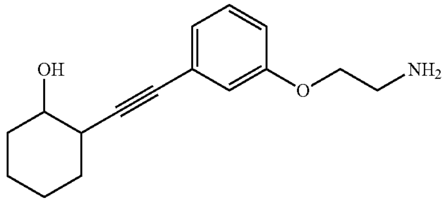 [SMILES: NCCOc1cccc(C#CC2CCCCC2O)c1] | 2-((3-(2-Aminoethoxy)-phenyl)ethynyl)cyclohexanol |
| 146 | 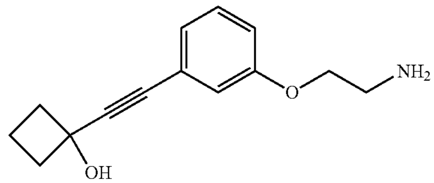 [SMILES: NCCOc1cccc(C#CC2(O)CCC2)c1] | 1-(2-(3-(2-Aminoethoxy)-phenyl)ethynyl)cyclobutanol |
| 168 | 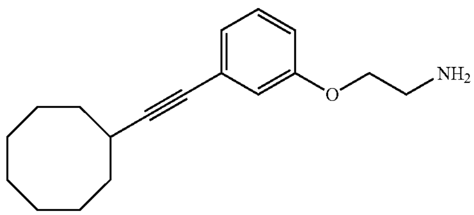 [SMILES: NCCOc1cccc(C#CC2CCCCCCC2)c1] | 2-(3-(cyclooctylethynyl)-phenoxy)ethanamine |

A further embodiment provides a compound having a structure of Formula (III) wherein $R_5$ is heteroaryl. In certain embodiments, each of $R_{12}$ and $R_{13}$ is hydrogen. In certain embodiments, m is 0. In certain embodiments, each of $R_1$, $R_2$, $R_3$ and $R_4$ is independently hydrogen or alkyl.

In further specific embodiments, the compound of Formula (I) or (III) has the structure shown in Table 11.

TABLE 11

| Example No. | Chemical Formula | Chemical Name |
|---|---|---|
| 62 | | 2-(3-(pyridin-3-ylethynyl)phenoxy)ethanamine |
| 95 | | 2-(3-(thiophen-2-ylethynyl)phenoxy)ethanamine |
| 96 | | 2-(3-(thiophen-3-ylethynyl)phenoxy)ethanamine |

TABLE 11-continued

| Example No. | Chemical Formula | Chemical Name |
|---|---|---|
| 97 | | 2-(3-(pyridin-4-ylethynyl)phenoxy)ethanamine |
| 98 | | 2-(3-(pyridin-2-ylethynyl)phenoxy)ethanamine |

A further embodiment provides a compound having a structure of Formula (III) wherein $R_5$ is aryl. In certain embodiments, each of $R_{12}$ and $R_{13}$ is hydrogen. In certain embodiments, m is 0. In certain embodiments, each of $R_1$, $R_2$, $R_3$ and $R_4$ is independently hydrogen or alkyl.

In further specific embodiments, the compound of Formula (I) or (III) has the structure shown in Table 12.

TABLE 12

| Example No. | Chemical Formula | Chemical Name |
|---|---|---|
| 81 | | 2-(3-(phenylethynyl)phenoxy)-ethanamine |
| 88 | | 3-((3-(2-aminoethoxy)phenyl)ethynyl)benzonitrile |
| 91 | | 2-(3-((2-methoxyphenyl)ethynyl)phenoxy)ethanamine |

In further specific embodiments, the compound of Formula (A)-(G) and (I)-(III) has the structure shown in Table 13.

TABLE 13

| Example No. | Structure | Chemical Name |
| --- | --- | --- |
| 141 | 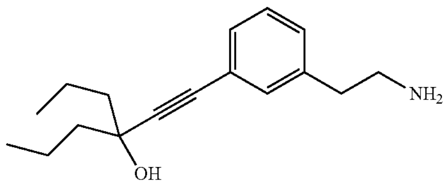 [SMILES: CCCC(O)(C#Cc1cccc(CCN)c1)CCC] | 4-((3-(2-Aminoethyl)-phenyl)ethynyl)heptan-4-ol |
| 142 | 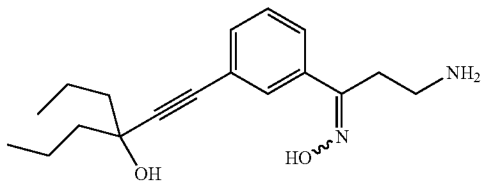 [SMILES: CCCC(O)(C#Cc1cccc(C(CCN)=NO)c1)CCC] | 3-Amino-1-(3-(3-hydroxy-3-propylhex-1-ynyl)phenyl)propan-1-one oxime |
| 164 | 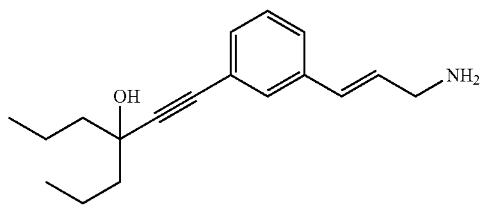 [SMILES: CCCC(O)(C#Cc1cccc(/C=C/CN)c1)CCC] | (E)-4-((3-(3-aminoprop-1-enyl)phenyl)ethynyl)heptan-4-ol |
| 165 | 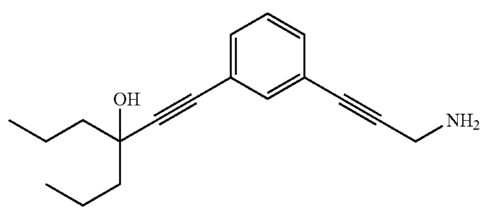 [SMILES: CCCC(O)(C#Cc1cccc(C#CCN)c1)CCC] | 4-((3-(3-aminoprop-1-ynyl)phenyl)ethynyl)heptan-4-ol |
| 166 | 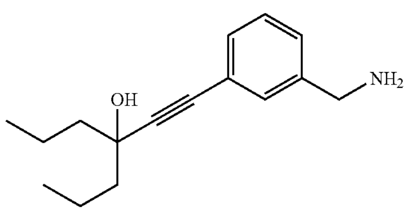 [SMILES: CCCC(O)(C#Cc1cccc(CN)c1)CCC] | 4-((3-(aminomethyl)phenyl)ethynyl)heptan-4-ol |
| 167 | 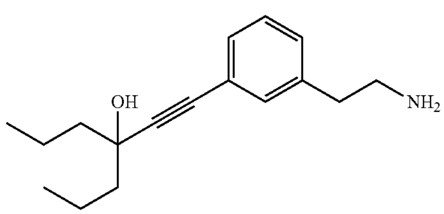 [SMILES: CCCC(O)(C#Cc1cccc(CCN)c1)CCC] | 4-((3-(2-aminoethyl)phenyl)ethynyl)heptan-4-ol |
| 169 | 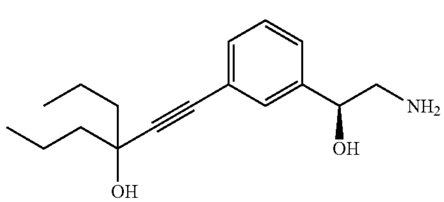 [SMILES: CCCC(O)(C#Cc1cccc([C@H](O)CN)c1)CCC] | (S)-4-((3-(2-amino-1-hydroxyethyl)phenyl)ethynyl)heptan-4-ol |

TABLE 13-continued

| Example No. | Structure | Chemical Name |
| --- | --- | --- |
| 178 | 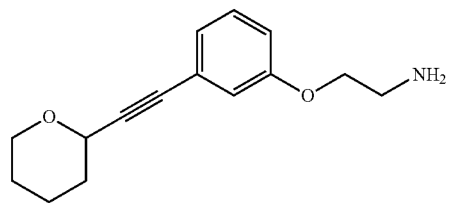 [SMILES: NCCOc1cccc(C#CC2CCCCO2)c1] | 2-(3-((tetrahydro-2H-pyran-2-yl)ethynyl)phenoxy)-ethanamine |
| 188 | 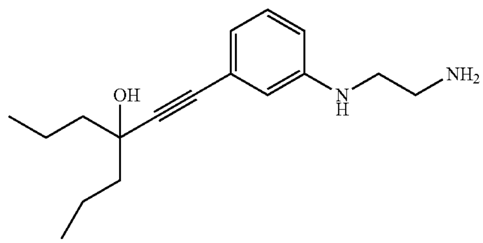 [SMILES: CCCC(O)(C#Cc1cccc(NCCN)c1)CCC] | 4-((3-(2-aminoethylamino)-phenyl)ethynyl)heptan-4-ol |
| 189 | 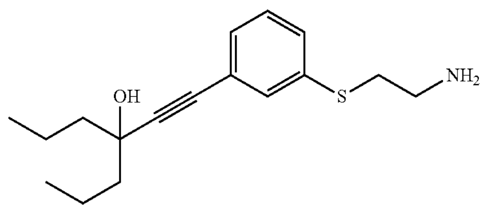 [SMILES: CCCC(O)(C#Cc1cccc(SCCN)c1)CCC] | 4-((3-(2-aminoethylthio)phenyl)ethynyl)heptan-4-ol |
| 190 | 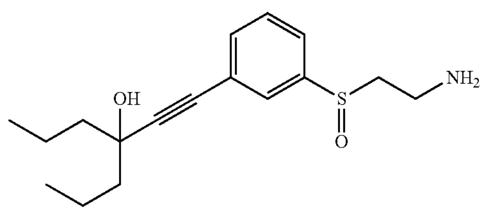 [SMILES: CCCC(O)(C#Cc1cccc(S(=O)CCN)c1)CCC] | 4-((3-(2-aminoethylsulfinyl)phenyl)ethynyl)heptan-4-ol |
| 191 | 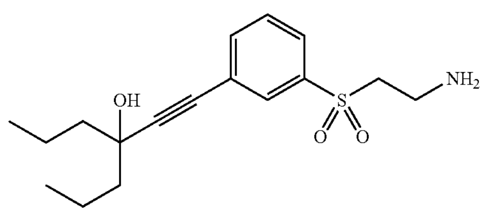 [SMILES: CCCC(O)(C#Cc1cccc(S(=O)(=O)CCN)c1)CCC] | 4-((3-(2-aminoethylsulfonyl)phenyl)ethynyl)heptan-4-ol |
| 192 | 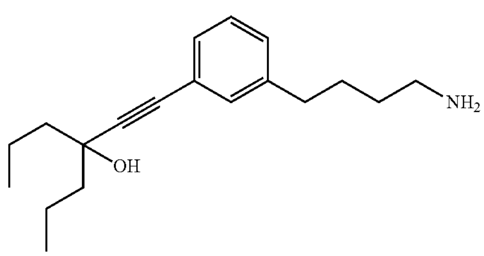 [SMILES: CCCC(O)(C#Cc1cccc(CCCCN)c1)CCC] | 4-((3-(4-aminobutyl)phenyl)ethynyl)heptan-4-ol |

II. DEFINITIONS

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Imino" refers to the =NH radical.
"Thioxo" refers to the =S radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t$$R^a$ (where t is 1 or 2), —S(O)$_t$$OR^a$ (where t is 1 or 2) and —S(O)$_t$$N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t$$R^a$ (where t is 1 or 2), —S(O)$_t$$OR^a$ (where t is 1 or 2) and —S(O)$_t$$N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t$$R^a$ (where t is 1 or 2), —S(O)$_t$$OR^a$ (where t is 1 or 2) and —S(O)$_t$$N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t$$R^a$ (where t is 1 or 2), —S(O)$_t$$OR^a$ (where t is 1 or 2) and —S(O)$_t$$N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —$N(R^a)$C(O)$R^a$, —$N(R^a)$S(O)$_t$$R^a$ (where t is 1 or 2), —S(O)$_t$$OR^a$ (where t is 1 or 2) and —S(O)$_t$$N(R^a)_2$ (where t is 1 or 2) where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R \%$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, and includes fused or bridged ring systems. The heteroatoms in the heterocyclyl radical is optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R \%$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocylyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposeable mirror images of one another.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

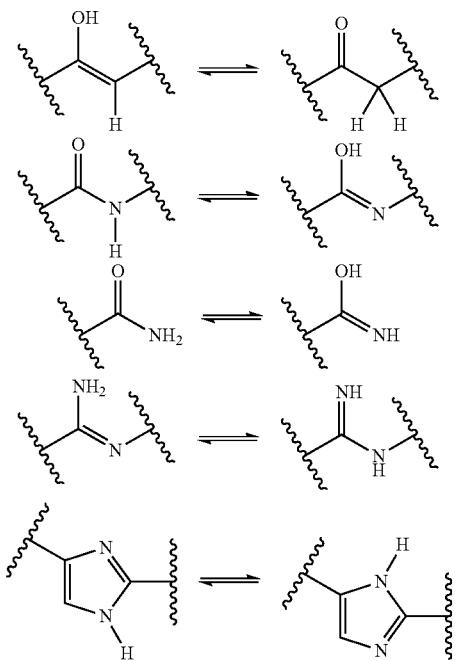

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the alkynyl phenyl-linked amine derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinyl amine and any derived amide, retinoic acid and any derived ester or amide. A non-retinoid compound can comprise though not require an internal cyclic group (e.g., aromatic group). A non-retinoid compound can contain though not require an alkynyl phenyl-linked amine group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

III. PREPARATION OF THE ALKYNYL PHENYL DERIVATIVE COMPOUNDS

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the alkynyl phenyl derivative compounds described herein is P. H. Stahl & C. G. Wermuth "Handbook of Pharmaceutical Salts", Verlag Helvetica Chimica Acta, Zurich, 2002.

Generally speaking, compounds disclosed herein can be prepared in a stepwise manner involving an acetylene formation and a side chain formation of a phenyl ring. Typically, the acetylene formation can take place by attaching an acetylene precursor to a phenyl. For example, in certain embodiments, an acetylene intermediate can be first constructed, which forms the precursor to the alkynyl phenyl core structure. A side chain moiety, which is a precursor to the linkage (i.e., propylene or ethylene oxide) and the nitrogen-containing moiety of the compounds disclosed herein, can then be attached to the acetylene intermediate.

In other embodiments, the compounds disclosed herein can be prepared by first preparing a phenyl intermediate having an appropriate side chain, followed by an acetylene formation to provide the alkynyl core structure.

The following Methods illustrate various synthetic pathways for preparing acetylene intermediates and the side chain moieties. One skilled in the art will recognize that a method for acetylene formation can be combined with a method for side chain formation to provide the compounds disclosed herein. For example, any one of Methods A-D can be combined with any of Methods E-H, or any of Methods I-J. They can be further combined with any of Methods K-S to modify the linkage and/or the terminal nitrogen-containing moiety.

1. Acetylene Formation:

Methods A-D below describe various approaches to acetylene formation.

More specifically, Method A illustrates the construction of an acetylene intermediate (A-3) in a Sonogashira or Castro-Stephens reaction. Depending on the sequence of the reactions, Ar can be a phenyl derivative compound that is already attached to a side chain moiety, or Ar may comprise a reactive group (appropriately protected), which will be coupled to a side chain moiety after the acetylene formation step.

According to Method A, an alkyne (A-1) can be coupled to an aryl halide or a reactive equivalent (A-2) to provide the acetylene intermediate (A-3) in the presence of a copper (I) catalyst (Castro-Stephens) or a mixture of $Pd^0$ and $Cu^I$ catalysts (Sonogashira).

The alkyne (A-1) has a terminal acetylene structure that is capable of coupling to A-2. Alkynes comprising diverse $R_5$ groups can be prepared according to known methods in the art. For example, organic halides (e.g., $R_5Br$) can be converted to the corresponding alkyne (A-1) by coupling to an ethyne. The halobenzene or its reactive equivalent (A-2) may be commercially available or can be prepared by known methods in the art.

Palladium catalysts suitable for coupling reactions are known to one skilled in the art. Exemplary palladium(0) catalysts include, for example, tetrakis(triphenylphosphine)palladium(0) [Pd(PPh$_3$)$_4$] and tetrakis(tri(o-tolylphosphine)palladium(0), tetrakis(dimethylphenylphosphine)palladium(0), tetrakis(tris-p-methoxyphenylphosphine)palladium(0) and the like. It is understood that a palladium (II) salt can also be used, which generates the palladium (0) catalyst in situ. Suitable palladium (II) salts include, for example, palladium diacetate [Pd(OAc)$_2$], bis(triphenylphosphine)-palladium diacetate and the like.

Copper catalysts suitable for coupling reactions are known to one skilled in the art. Typically, the copper (I) catalyst can be copper (I) iodide.

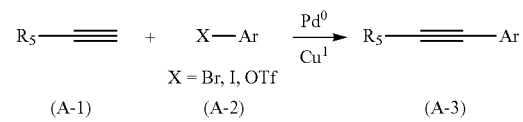

Method B shows an alternative construction of the acetylene intermediate (A-3) by coupling an organic halide (i.e., $R_5X$) with a phenyl comprising a terminal acetylene (A-5).

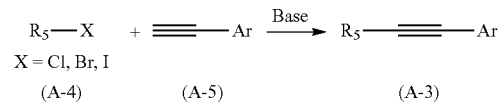

Method C shows the construction of an acetylene intermediate (A-7) through the addition of a terminal acetylene (A-5) to an aldehyde or ketone (A-6).

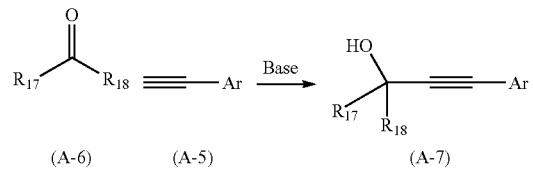

Method D shows the construction of an acetylene intermediate (A-8) through the addition of a terminal acetylene (A-5) to an epoxide (A-9).

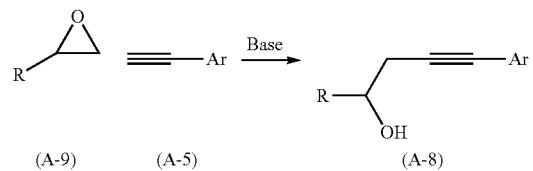

2. Side Chain Formation and Modification

Methods E-S below describe various approaches to side chain formation and modifications.

Generally speaking, a suitably substituted phenyl derivative can be coupled to a diverse range of side chains, which may be further modified to provide the final linkages and the nitrogen-containing moieties of the compounds disclosed herein.

Methods E-H illustrate pathways to form propylene linkages of the compounds disclosed herein.

Method E illustrates an aryl halide coupled with an allyl alcohol in the presence of a palladium(0) catalyst. The terminal alcohol group of allyl alcohol has been simultaneously oxidized to an aldehyde group, which can be further reductively aminated to an amine (—NR$_{12}$R$_{13}$).

Method E

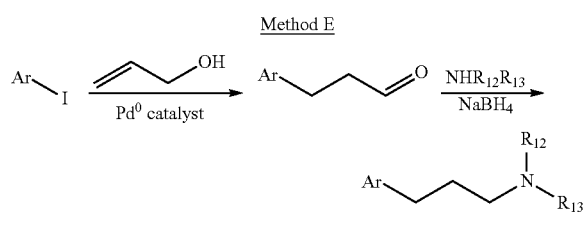

Method F illustrates an aldol condensation between an aryl aldehyde or aryl ketone with a nitrile reagent comprising at least one α-hydrogen. The resulting condensation intermediate can be further reduced to an amine (—$NR_{12}R_{13}$).

Method F

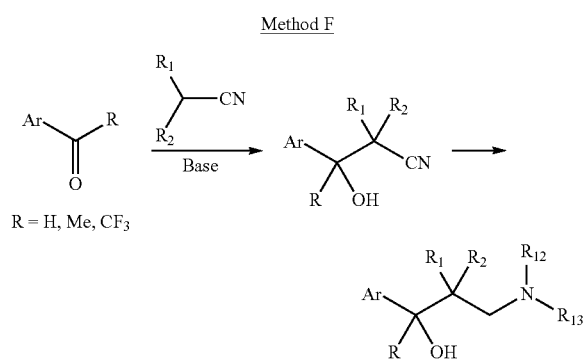

R = H, Me, $CF_3$

Method G shows an acylation reaction to form a ketone-based linkage (i.e., $R_{10}$ and $R_{11}$ of Formula (I) form an oxo). One skilled in the art will recognize that the R' group may comprise functional groups that can be further modified.

Method G

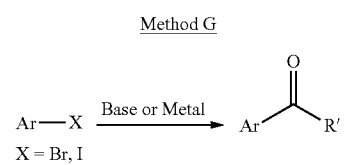

X = Br, I

Method H shows a ring-opening reaction of an epoxide reagent to form a hydroxy-substituted propylene side chain linkage.

Method H

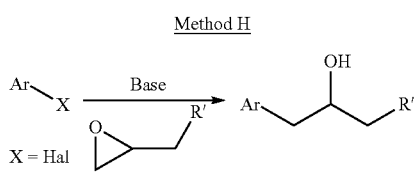

X = Hal

Method I illustrates an attachment of side chain moieties by an oxygen, which can be a precursor to an ethylene oxide linkage. More specifically, a side chain precursor (R'OH) can be condensed with an aryl derivative by eliminating a molecule of $H_2O$. R' may comprise functional groups that can be further modified to prepare linkages and nitrogen-containing moieties of compounds of Formula (III) and its substructures, including Formulae (IIIa) and (IIIb).

Method I

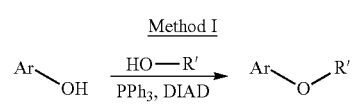

Method J shows a condensation reaction that provides an oxygen linking atom. Here, a molecule of HX is eliminated as the result of the condensation.

Method J $$Ar\diagdown X \xrightarrow{HO-R'} Ar\diagdown O\diagdown R'$$

X is Halo

After attachment, the side chain moiety can be further modified to provide the final linkage and the terminal nitrogen-containing moiety for the compounds disclosed herein. The following methods illustrate a variety of synthetic pathways to manipulate or modify the side chain moiety by reduction, oxidation, nucleophilic or electrophilic substitution, fluorination, acylation and the like. As a result, a diverse group of linkages can be synthesized.

Method K illustrates an amination process in which carboxylic acid is converted to an amine. Typically, the carboxylic acid (or ester) can be first reduced to primary alcohol, which can then be converted to an amine via mesylate, halide, azide, phthalimide, or Mitsunobu reaction and the like. Suitable reducing agents include, for example, sodium borohydride ($NaBH_4$), sodium cyanoborohydride ($NaBH_3CN$), sodium triacetoxyborohydride ($NaBH(OCOCH_3)_3$), lithium aluminum hydride ($LiAlH_4$) and the like. As shown, the resulting amine can be further functionalized, by known methods in the art.

Method K

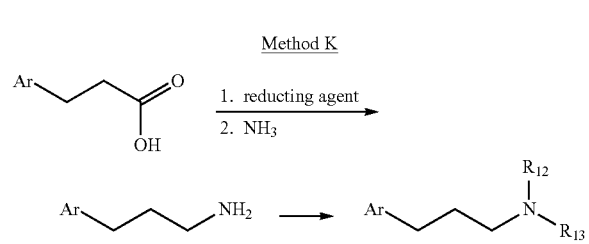

Additional or alternative modifications can be carried out according to the methods illustrated below.

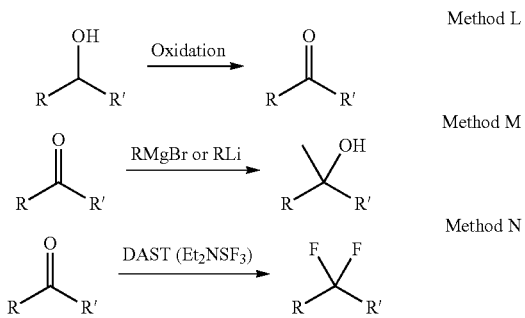

Method L

Method M

Method N

Method O
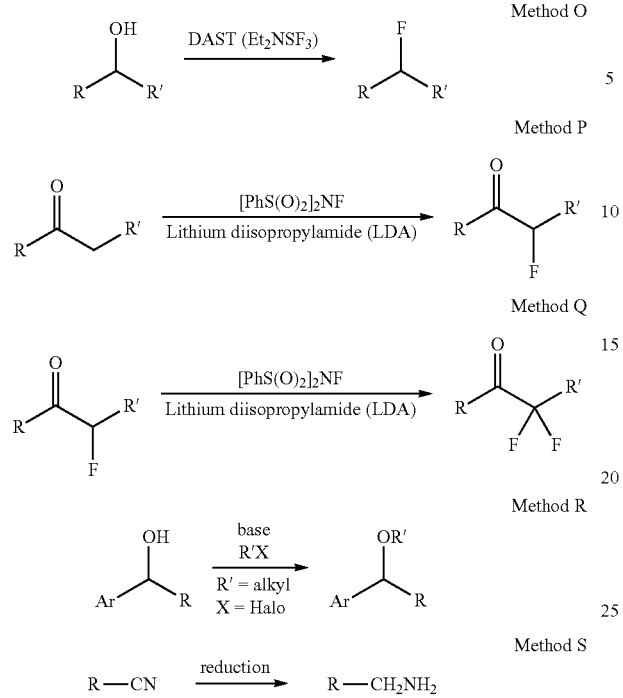

Method P

Method Q

Method R

Method S

Scheme I illustrates a complete synthetic sequence for preparing a compound disclosed herein.

Scheme I
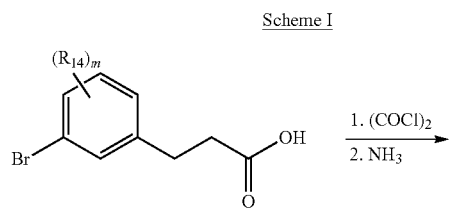

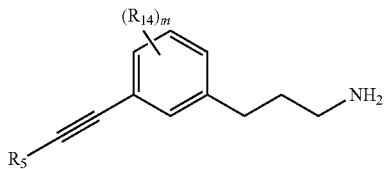

In Scheme I, the side chain moiety is first constructed and the amine protected. The acetylene moiety is then formed through coupling with a terminal acetylene according to Method A. The coupling product is then deprotected to give rise to the final alkynyl phenyl derivative compound comprising a propylene linkage terminating in a primary amine. Other nitrogen-containing moieties ($-NR_{12}R_{13}$) can be further derived from the terminal amine, according to known methods in the art.

One skilled in the art should recognize, however, that the order of the reactions may vary. Thus, in other embodiments, acetylene formation may precede the side chain attachment.

Scheme II illustrates a complete synthetic sequence for preparing a compound disclosed herein.

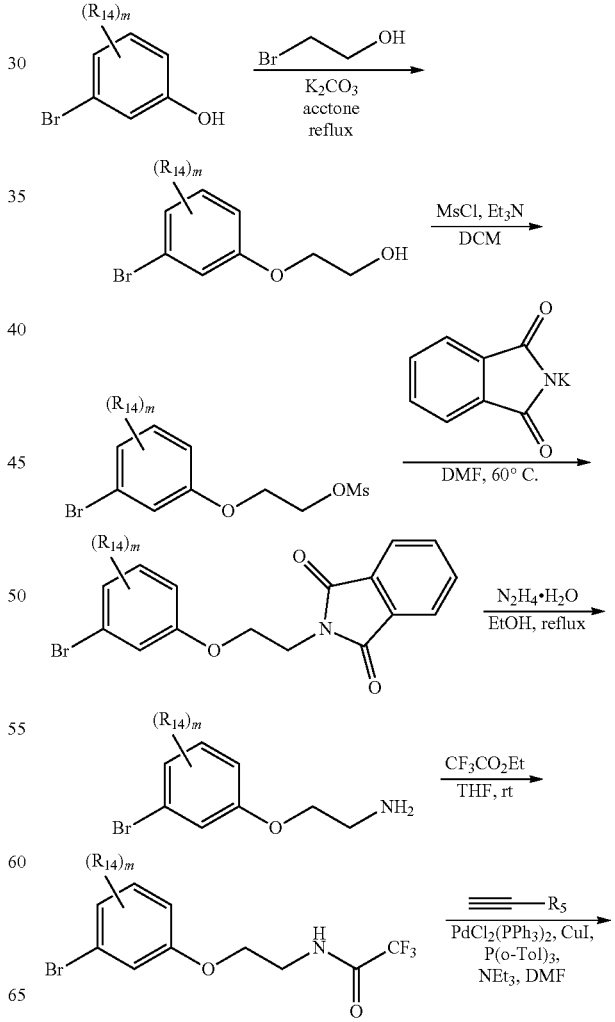

-continued

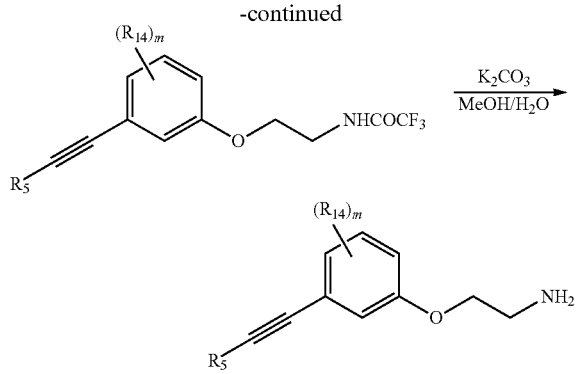

In addition to the generic reaction schemes and methods discussed above, other exemplary reaction schemes are also provided to illustrate methods for preparing any of the compounds disclosed herein.

IV. TREATMENT OF OPHTHALMIC DISEASES AND DISORDERS

Alkynyl phenyl-linked amine derivative compounds as described in detail herein, including compounds having the structure as set forth in any one of Formulae (A)-(G) and (I)-(III), and substructures thereof, and the specific alkynyl pheny-linked amine compounds described herein that may be useful for treating an ophthalmic disease or disorder may inhibit one or more steps in the visual cycle, for example, by inhibiting or blocking a functional activity of a visual cycle trans-cis isomerase (also including a visual cycle trans-cis isomerase). The compounds described herein, may inhibit, block, or in some manner interfere with the isomerization step in the visual cycle. In a particular embodiment, the compound inhibits isomerization of an all-trans-retinyl ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerase, which may also be referred to herein and in the art as a retinal isomerase or an isomerohydrolase. The compound may block or inhibit binding of an all-trans-retinyl ester substrate to an isomerase. Alternatively, or in addition, the compound may bind to the catalytic site or region of the isomerase, thereby inhibiting the capability of the enzyme to catalyze isomerization of an all-trans-retinyl ester substrate. On the basis of scientific data to date, an at least one isomerase that catalyzes the isomerization of all-trans-retinyl esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102:12413-18 (2004); Chen et al., *Invest. Ophthalmol. Vis. Sci.* 47:1177-84 (2006); Lamb et al. supra).

A method for determining the effect of a compound on isomerase activity may be performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the alkynyl pheny-linked amine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science*, 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 µM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When administered into a subject, one or more compounds of the present invention exhibits an $ED_{50}$ value of about 5 mg/kg, 5 mg/kg or less as ascertained by inhibition of an isomerase reaction that results in production of 11-cis retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering a subject compound or a pharmaceutical composition thereof.

The compounds described herein may be useful for treating a subject who has an ophthalmic disease or disorder, particularly a retinal disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinylethanolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and an alkynyl phenyl-linked amine derivative compound as described in detail herein, including a compound having the structure as set forth in any one of Formulae (A)-(G) and (I)-(III), and substructures thereof, and the specific alkynyl phenyl-linked amine compounds described herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The alkynyl phenyl-linked amine derivative compounds described herein may be useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to or interact with A2E A2E-related and/or derived molecules or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein may be used for treating other ophthalmic diseases or disorders, for example, glaucoma, cone-rod dystrophy, retinal detachment, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle", refractive errors including but not limited to myopia (see, e.g., Quinn G E et al. Nature 1999; 399:113-114; Zadnik K et al. Nature 2000; 404:143-144; Gwiazda J et al. Nature 2000; 404: 144), etc.

In other embodiments, methods are provided herein for inhibiting neovascularization (including but not limited to neovascular glycoma) in the retina using any one or more of the alkynyl phenyl-linked amine derivative compound as described in detail herein, including a compound having the structure as set forth in any one of Formulae (A)-(G) and (I)-(III), and substructures thereof, and the specific alkynyl phenyl-linked amine compounds described herein. In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and a alkynyl phenyl-linked amine derivative compound as described in detail herein, including a compound having the structure as set forth in any one of Formulae (A)-(G) and (I)-(III), and substructures thereof, and the specific alkynyl phenyl-linked amine compounds described herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. The alkynyl phenyl derivative compounds described herein that modulate the visual cycle can be administered to prevent, inhibit, and/or delay dark adaptation of rod photoreceptor cells, and may therefore reduce metabolic demand, thereby reducing hypoxia and inhibiting neovascularization.

By way of background, oxygen is a critical molecule for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Ophthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., *Br. J. Ophthalmol.* 89:764 (2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Ophthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the alkynyl phenyl-linked amine derivative compounds described herein that inhibits at least one visual cycle trans-cis isomerase (which may include inhibition of isomerization of an all-trans-retinyl ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinyl ester is inhibited or reduced. The at least one alkynyl phenyl-linked derivative compound (or composition comprising at least one compound) may be administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinol/retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin. Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans retinoid is then hydrolyzed and the visual pigment is in the form of the apoprotein, opsin, which is also called apo-rhodopsin in the art and herein. This all-trans retinoid is transported or chaperoned out of the photoreceptor cell and across the extracellular space to the RPE cells, where the retinoid is converted to the 11-cis isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form (i.e., bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis retinal bound) may be reduced or depleted, preventing or inhibiting dark adaptation of rod photoreceptors. This in turn may reduce retinal metabolic demand, attenuating the nighttime risk of retinal ischemia and neovascularization, and thereby inhibiting or slowing retinal degeneration.

In one embodiment, at least one of the compounds described herein (i.e., an alkynyl phenyl-linked amine derivative compound as described in detail herein, including a compound having the structure as set forth in any one of Formulae (A)-(G) and (I)-(III), and substructures thereof, and the specific alkynyl phenyl-linked amine compounds described herein) that, for example, blocks, reduces, inhibits, or in some manner attenuates the catalytic activity of a visual cycle isomerase in a statistically or biologically significant manner, may prevent, inhibit, or delay dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the alkynyl phenyl-linked amine derivative compounds may prevent or inhibit dark adaptation of a rod photoreceptor cell, thereby reducing ischemia (i.e., decreasing, preventing, inhibiting, slowing the progression of ischemia in a statistically or biologically significant manner). In yet another embodiment, any one of the alkynyl phenyl-linked amine derivative compounds described herein may prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one alkynyl phenyl-linked amine derivative compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The alkynyl phenyl-linked amine derivative compounds described herein (i.e., an alkynyl phenyl-linked amine derivative compound as described in detail herein, including a compound having the structure as set forth in any one of Formulae (A)-(G) and (I)-(III), and substructures thereof, and the specific alkynyl phenyl-linked amine compounds described herein) may prevent (i.e., delay, slow, inhibit, or decrease) recovery of the visual pigment chromophore, which may prevent or inhibit or retard the formation of retinals and may increase the level of retinyl esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other certain embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells may be delayed 30 minutes, one hour, two hours, three hours, or four hours compared to dark adaptation of rod photoreceptors in the absence of the compound. By contrast, when an alkynyl phenyl-linked amine derivative compound is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one alkynyl phenyl-linked amine derivative compound, regeneration of rhodopsin in a rod photoreceptor cell may be inhibited or the rate of regeneration may be reduced (i.e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) may be determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) may be determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, may have a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of an alkynyl phenyl-linked amine derivative compound described herein, the effect of the compound may also be characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the alkynyl phenyl-linked amine derivative compounds described herein (i.e., a compound as described in detail herein, including a compound having the structure as set forth in any one of Formulae (A)-(G) and (I)-(III), and substructures thereof, and the specific alkynyl phenyl-linked amine compounds described herein), under conditions and at a time sufficient to permit interaction between the agent and an isomerase present in a retinal cell (such as an RPE cell). A first level of 11-cis-retinal in a rod photoreceptor cell in the presence of the compound may be determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin may also include increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique may be used to view and analyze retinosome structures in the RPE, which structures are believed to store retinyl esters (see, e.g., Imanishi et al., $J.$ $Cell$ $Biol.$ 164:373-83 (2004), Epub 2004 Jan. 26). A first level of retinyl esters may be determined prior to administration of the compound, and a second level of retinyl esters may be determined after administration of a first dose or any subsequent dose, wherein an increase in the second level compared to the first level indicates that the compound inhibits regeneration of rhodopsin.

Retinyl esters may be analyzed by gradient HPLC according to methods practiced in the art (see, for example, Mata et al., $Neuron$ 36:69-80 (2002); Trevino et al. $J.$ $Exp.$ $Biol.$ 208: 4151-57 (2005)). To measure 11-cis and all-trans retinals, retinoids may be extracted by a formaldehyde method (see, e.g., Suzuki et al., $Vis.$ $Res.$ 28:1061-70 (1988); Okajima and Pepperberg, $Exp.$ $Eye$ $Res.$ 65:331-40 (1997)) or by a hydroxylamine method (see, e.g., Groenendijk et al., $Biochim.$ $Biophys.$ $Acta.$ 617:430-38 (1980)) before being analyzed on isocratic HPLC (see, e.g., Trevino et al., supra). The retinoids may be monitored spectrophotometrically (see, e.g., Maeda et al., $J.$ $Neurochem.$ 85:944-956 (2003); Van Hooser et al., $J.$ $Biol.$ $Chem.$ 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering an alkynyl phenyl-linked amine derivative compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Yan et al. $J.$ $Biol.$ $Chem.$ 279:48189-96 (2004)).

A subject in need of such treatment may be a human or may be a non-human primate or other animal (i.e., veterinary use)

who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and an alkynyl phenyl-linked amine derivative compound described in detail herein, including a compound having any one of the structures set forth in Formulae (A)-(G) and (I)-(III) substructures thereof, and specific alkynyl phenyl-linked amine compounds recited herein. Retinal neuronal cells include photoreceptor cells, bipolar cells, horizontal cells, ganglion cells, and amacrine cells. In another embodiment, methods are provided for enhancing survival or inhibiting degeneration of a mature retinal cell such as a RPE cell or a Miller glial cell. In other embodiments, a method for preventing or inhibiting photoreceptor degeneration in an eye of a subject are provided. A method that prevents or inhibits photoreceptor degeneration may include a method for restoring photoreceptor function in an eye of a subject. Such methods comprise administering to the subject a composition comprising an alkynyl phenyl-linked amine derivative compound as described herein and a pharmaceutically or acceptable carrier (i.e., excipient or vehicle). More specifically, these methods comprise administering to a subject a pharmaceutically acceptable excipient and an alkynyl phenyl-linked amine derivative compound described herein, including a compound having any one of the structures set forth in Formulae (A)-(G) and (I)-(III) or substructures thereof described herein. Without wishing to be bound by theory, the compounds described herein may inhibit an isomerization step of the retinoid cycle (i.e., visual cycle) and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and an alkynyl phenyl-linked amine compound as described in detail herein, including a compound having the structure as set forth in any one of Formulae (A)-(G) and (I)-(III) or substructures thereof.

An alkynyl phenyl-linked amine compound can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an alkynyl phenyl-linked amine derivative compound and reduce or eliminate the requirement for endogenous retinoid. In certain embodiments, the level of endogenous retinoid may be compared before and after any one or more doses of an alkynyl phenyl-linked amine compound is administered to a subject to determine the effect of the compound on the level of endogenous retinoids in the subject.

In another embodiment, the methods described herein for treating an ophthalmic disease or disorder, for inhibiting neovascularization, and for reducing ischemia in the retina comprise administering at least one of the alkynyl phenyl-linked amine compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the compounds in the methods described herein may reduce the consumption of ATP in the rod photoreceptor cells that are prevented, inhibited, or delayed from dark adaptation compared with rod photoreceptor cells that are dark-adapted (such as the cells prior to administration or contact with the compound or cells that are never exposed to the compound).

The methods described herein that may prevent or inhibit dark adaptation of a rod photoreceptor cell may therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A biological sample may be a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like. Mature retinal cells, including retinal neuronal cells, RPE cells, and Müller glial cells, may be present in or isolated from a biological sample as described herein. For example, the mature retinal cell may be obtained from a primary or long-term cell culture or may be present in or isolated from a biological sample obtained from a subject (human or non-human animal).

3. Retinal Cells

The retina is a thin layer of nervous tissue located between the vitreous body and choroid in the eye. Major landmarks in the retina are the fovea, the macula, and the optic disc. The retina is thickest near the posterior sections and becomes thinner near the periphery. The macula is located in the posterior retina and contains the fovea and foveola. The foveola contains the area of maximal cone density and, thus, imparts the highest visual acuity in the retina. The foveola is contained within the fovea, which is contained within the macula.

The peripheral portion of the retina increases the field of vision. The peripheral retina extends anterior to the ciliary body and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e., fully differentiated cells) display several specific antigenic markers. Neurons may be classified functionally into three groups: (1) afferent neurons (or sensory neurons) that transmit information into the brain for conscious perception and motor coordination; (2) motor neurons that transmit commands to muscles and glands; and (3) interneurons that are responsible for local circuitry; and (4) projection interneurons that relay information from one region of the brain to anther region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones. Many neurodegenerative diseases, such as AMD, that result in blindness affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). WB Saunders; Philadelphia, Pa. (1971)); Eye and Orbit, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Miller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. Similar process occurs with the disc of the cones. RPE cells also produce, store, and transport a variety of factors that contribute to the normal function and survival of photoreceptors. Another function of RPE cells is to recycle vitamine A as it moves between photoreceptors and the RPE during light and dark adaptation in the process known as the visual cycle.

Described herein is an exemplary long-term in vitro cell culture system permits and promotes the survival in culture of mature retinal cells, including retinal neurons, for at least 2-4 weeks, over 2 months, or for as long as 6 months. The cell culture system may be used for identifying and characterizing the alkynyl phenyl-linked amine derivative compounds that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system comprises all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of an alkynyl phenyl-linked amine derivative compound and reduce or eliminate the requirement for endogenous retinoid.

4. In Vivo and In Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Miller glial cells using the compounds described herein. Such methods comprise, in certain embodiments, administration of an alkynyl phenyl-linked amine derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of an alkynyl phenyl-linked amine derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. No. 6,117,675; U.S. Pat. No. 5,736,516; WO 99/29279; WO 01/83714; WO 01/42784; U.S. Pat. No. 6,183,735; U.S. Pat. No. 6,090,624; WO 01/09327; U.S. Pat. No. 5,641,750; U.S. Patent Application Publication No. 2004/0147019; and U.S. Patent Application Publication No. 2005/0059148.

Compounds described herein that may be useful for treating an ophthalmic disease or disorder (including a retinal disease or disorder) may inhibit, block, impair, or in some manner interfere with one or more steps in the visual cycle (also called the retinoid cycle herein and in the art). Without wishing to be bound by a particular theory, an alkynyl phenyl-linked amine derivative may inhibit or block an isomerization step in the visual cycle, for example, by inhibiting or blocking a functional activity of a visual cycle trans-cis isomerase. The compounds described herein may inhibit, directly or indirectly, isomerization of all-trans-retinol to 11-cis-retinol. The compounds may bind to, or in some manner interact with, and inhibit the isomerase activity of at least one isomerase in a retinal cell. Any one of the compounds described herein may also directly or indirectly inhibit or reduce the activity of an isomerase that is involved in the visual cycle. The compound may block or inhibit the capability of the isomerase to bind to one or more substrates, including but not limited to, an all-trans-retinyl ester substrate or all-trans-retinol. Alternatively, or in addition, the compound may bind to the catalytic site or region of the isomerase, thereby inhibiting the capability of the enzyme to catalyze isomerization of at least one substrate. On the basis of scientific data to date, an at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Ophthalmol. Vis. Sci.* 47:1177-84 (2006)), other persons skilled in the art believe that the RPE65 acts primarily as a chaperone for all-trans-retinyl esters (see, e.g., Lamb et al. supra).

Exemplary methods are described herein and practiced by persons skilled in the art for determining the level of enzymatic activity of a visual cycle isomerase in the presence of any one of the compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and an alkynyl phenyl-linked amine derivative compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease. A decrease in the level of isomerase activity in the presence of the compound compared to the level of isomerase activity in the absence of the compound indicates that the compound may also be useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of an alkynyl phenyl-linked amine compound described herein to inhibit or to prevent dark adaptation of a rod photoreceptor cell by inhibiting regeneration of rhodopsin may be determined by in vitro assays and/or in vivo animal models. By way of example, inhibition of regeneration may be determined in a mouse model in which a diabetes-like condition is induced chemically or in a diabetic mouse model (see, e.g., Phipps et al., *Invest. Ophthalmol. Vis. Sci.* 47:3187-94 (2006); Ramsey et al., *Invest. Ophthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Ophthalmologica* 79:125-39 (1992).

Inhibiting regeneration of rhodopsin by an alkynyl phenyl-linked amine compound described herein comprises reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of an alkynyl phenyl-linked amine compound to reduce retinal hypoxia includes measuring the level of retinal oxygenation, for example, by Magnetic Resonance Imaging (MRI) to measure changes in oxygen pressure (see, e.g., Luan et al., *Invest. Ophthalmol. Vis. Sci.* 47:320-28 (2006)). Methods are also available and routinely practiced in the art to determine or characterize the capability of compounds described herein to inhibit degeneration of a retinal cell (see, e.g., Wenzel et al., *Prog. Retin. Eye Res.* 24:275-306 (2005)).

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the alkynyl phenyl-linked amine compounds described herein. (See, e.g., Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Ophthalmol. Vis. Sci.* 47:5553-60 (2006)). Such a technique may be performed in an animal model using Rho⁻/Rho⁻ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Ophthalmol. Vis. Sci.* 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006); Dembinska et al., *Invest. Ophthalmol. Vis. Sci.* 43:2481-90 (2002); Penn et al., *Invest. Ophthalmol. Vis. Sci.* 35:3429-35 (1994); Hancock et al., *Invest. Ophthalmol. Vis. Sci.* 45:1002-1008 (2004)).

A method for determining the effect of a compound on isomerase activity may be performed in vitro as described herein and in the art (Stecher et al., *J. Biol. Chem.* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the alkynyl phenyl-linked amine derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Ophthalmologica* 100:77-92 (2000)). See also Deigner et al., *Science*, 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

Cell culture methods, such as the method described herein, are also useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of an alkynyl phenyl-linked amine derivative compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of an alkynyl phenyl-linked amine derivative compound that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing an alkynyl phenyl-linked amine derivative compound that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system comprises all the major retinal neuronal cell types (photoreceptors, bipolar cells, horizontal cells, amacrine cells, and ganglion cells), and may also include other mature retinal cells such as RPE and Müller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of an alkynyl phenyl-linked amine derivative compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the alkynyl phenyl-linked amine derivative compounds described herein to alter (preferably increase, prolong, enhance, improve) retinal cell or retinal pigment epithelial cell viability or retinal cell survival.

The addition of a cell stressor to the cell culture system is useful for determining the capability of an alkynyl phenyl-linked amine derivative compound to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, Zn++, or Fe++); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitroproprionic acid; rotenone, cyanide); MPTP (1-methyl-4-phenyl-1,2,3,6,-tetrahydropyridine), which metabolizes to its active, toxic metabolite MPP+ (1-methyl-4-phenylpryidine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Müller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of an alkynyl phenyl-linked amine derivative compound) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. An alkynyl phenyl-linked amine compound may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as an alkynyl phenyl-linked amine derivative compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, an alkynyl phenyl-linked amine derivative compound is incorporated into screening assays comprising the retinal cell culture stress model system described herein to determine whether and/or to what level or degree the compound increases or prolongs viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether an alkynyl phenyl-linked amine derivative compound, enhances survival of photoreceptor cells. One method comprises contacting a retinal cell culture system as described herein with an alkynyl phenyl-linked amine compound under conditions and for a time sufficient to permit interaction between the retinal neuronal cells and the compound. Enhanced survival (prolonged survival) may be measured according to methods described herein and known in the art, including detecting expression of rhodopsin.

The capability of an alkynyl phenyl-linked amine derivative compound to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or nonviable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of an alkynyl phenyl-linked amine derivative compound on cell integrity, morphology, and/or survival may also be determined by measuring the phosphorylation state of neuronal cell polypeptides, for example, cytoskeletal polypeptides (see, e.g., Sharma et al., *J. Biol. Chem.* 274: 9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases, and retinal diseases and disorders as described herein. A subject in need of such treatment may be a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and an alkynyl phenyl-linked amine derivative compound (e.g., a compound having the structure of any one of Formulae (A)-(G) and (I)-(III), and substructures thereof.) As described herein, a method is provided for enhancing survival of neuronal cells such as retinal neuronal cells, including photoreceptor cells, and/or inhibiting degeneration of retinal neuronal cells by administering the pharmaceutical compositions described herein comprising an alkynyl phenyl-linked amine derivative compound.

Enhanced survival (or prolonged or extended survival) of one or more retinal cell types in the presence of an alkynyl phenyl-linked amine derivative compound indicates that the compound may be an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD).

In various embodiments, AMD can be wet- or dry-form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., *Am. J. Hum. Genet.* 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Ophthalmol. Clin. North Am.* 15:93-100, viii (2002); Weng et al., Cell 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Ophthalmology* 108:2060-67 (2001); Yates et al., *J. Med. Genet.* 37:83-7 (2000); Jaakson et al., *Hum. Mutat.* 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11 cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with alkynyl phenyl-linked amine derivative compounds may inhibit lipofuscin accumulation and thus delay the onset of visual loss in Stargardt's and AMD patients without toxic effects that would preclude treatment with an alkynyl phenyl-linked amine derivative compound. The compounds described herein may be used for effective treatment of other forms of retinal or macular degeneration associated with lipofuscin accumulation.

Administration of an alkynyl phenyl-linked amine derivative compound to a subject can prevent formation of the lipofuscin pigment, A2E (and A2E related molecules), that is toxic towards retinal cells and causes retinal degeneration. In certain embodiments, administration of an alkynyl phenyl-linked amine derivative compound can lessen the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, an alkynyl phenyl-linked amine derivative compound is administered to a subject such as a human with a mutation in the ABCA4 transporter in the eye. The alkynyl phenyl-linked amine derivative compound can also be administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, an alkynyl phenyl-linked amine derivative compound described herein may be a strong inhibitor of an isomerase involved in the visual cycle. Treating patients with an alkynyl phenyl-linked amine derivative compound as described herein may prevent or slow the formation of A2E (and A2E related molecules) and can have protective properties for normal vision.

In other certain embodiments, one or more of the compounds described herein may be used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, at least one of the compounds described herein may be used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Diabetic retinopathy occurs when diabetes damages blood vessels inside the retina. Non-proliferative retinopathy is a common, usually mild form that generally does not interfere with vision. Abnormalities are limited to the retina, and vision is impaired only if the macula is involved. If left untreated retinopathy can progress to proliferative retinopathy, the more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the methods and compositions described herein include diseases, disorders, and conditions that are associated with, exacerbated by, or caused by ischemia in the retina. Retinal ischemia includes ischemia of the inner retina and the outer retina. Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Retinal ischemia may be associated with retinal blood vessel occlusion. In the United States, both branch and central retinal vein occlusions are the second most common retinal vascular diseases after diabetic retinopathy. About 7% to 10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic ophthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) may be any mammal, including a human, that may have or be afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. Accordingly, the term "treating" includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders. The term "therapeutic effect" refers to the reduction, elimination, or prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of an alkynyl phenyl-linked amine derivative compound to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and ophthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein can be administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

V. PHARMACEUTICAL COMPOSITIONS

In certain embodiments, an alkynyl phenyl-linked amine derivative compound may be administered as a pure chemical. In other embodiments, the alkynyl phenyl-linked amine derivative compound can be combined with a pharmaceutical carrier (also referred to herein as a pharmaceutically acceptable excipient (i.e., a pharmaceutically suitable and acceptable carrier, diluent, etc., which is a non-toxic, inert material that does not interfere with the activity of the active ingredient)) selected on the basis of a chosen route of administration and standard pharmaceutical practice as described, for example, in $Remington: The Science and Practice of Pharmacy$ (Gennaro, $21^{st}$ Ed. Mack Pub. Co., Easton, Pa. (2005)), the disclosure of which is hereby incorporated herein by reference, in its entirety.

Accordingly, provided herein is a pharmaceutical composition comprising one or more alkynyl phenyl-linked amine derivative compounds, or a stereoisomer, tautomer, prodrug, pharmaceutically acceptable salt, hydrate, solvate, acid salt hydrate, N-oxide or isomorphic crystalline form thereof, of a compound described herein, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an ophthalmologically suitable or acceptable composition.

Thus, another embodiment provides a pharmaceutical composition comprising a pharmaceutically acceptable excipient and a compound having a structure of Formula (A):

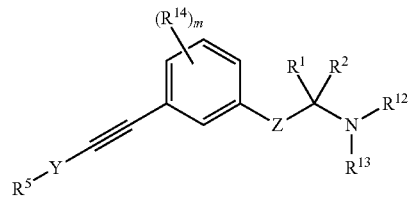

Formula (A)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

Z is a bond, —C(R$^1$)(R$^2$)—, —X—C(R$^{21}$)(R$^{22}$)—, —C(R$^{23}$)(R$^{24}$)—C(R$^1$)(R$^2$)—, or —C(R$^{23}$)(R$^{24}$)—C(R$^{25}$)(R$^{26}$)—C(R$^1$)(R$^2$)—, —X—C(R$^{21}$)(R$^{22}$)—C(R$^1$)(R$^2$)—, —C(R$^{32}$)(R$^{33}$)—X—C(R$^{21}$)(R$^{22}$)—;

X is —O—, —S—, —S(=O)—, —S(=O)$_2$—, —N(R$^{31}$)—, —C(=O)—, —C(=CH$_2$)—, —C(=N—NR$^{35}$)—, or —C(=N—OR$^{35}$)—;

Y is a bond, —C(R$^{27}$)(R$^{28}$)—, or —C(R$^{27}$)(R$^{28}$)—C(R$^{29}$)(R$^{30}$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{21}$, R$^{22}$, R$^{32}$ and R$^{33}$ are each independently selected from hydrogen, C$_1$-C$_5$ alkyl, or fluoroalkyl;

R$^{23}$ and R$^{24}$ are each independently selected from hydrogen, halogen, C$_1$-C$_5$ alkyl, fluoroalkyl, —OR$^6$, —NR$^7$R$^8$; or R$^{23}$ and R$^{24}$ together form an oxo; or optionally, R$^{23}$ and an adjacent R$^1$ together form a direct bond to provide a double bond; or optionally, R$^{23}$ and an adjacent R$^1$ together form a direct bond, and R$^{24}$ and an adjacent R$^2$ together form a direct bond to provide a triple bond;

R$^{25}$ and R$^{26}$ are each independently selected from hydrogen, halogen, C$_1$-C$_5$ alkyl, fluoroalkyl, —OR$^6$ or —NR$^7$R$^8$; or R$^{25}$ and R$^{26}$ together form an oxo;

R$^3$ and R$^4$ are each independently selected from hydrogen, alkyl, heteroalkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is alkyl, heteroalkyl, alkenyl, heteroalkenyl, aryl, carbocyclyl, heteroaryl or heterocyclyl;

each R$^6$ is the same or different and independently hydrogen or C$_1$-C$_5$ alkyl;

each R$^7$ and each R$^8$ are each the same or different and independently hydrogen, alkyl, carbocyclyl, heteroalkyl, heterocycloalkyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or R$^7$ and R$^8$, together with the nitrogen atom to which they are attached, form an N-heterocyclyl;

each R$^9$ is the same or different and each is independently alkyl, alkenyl, aryl, carbocyclyl, heteroaryl or heterocyclyl;

R$^{12}$ and R$^{13}$ are the same or different and independently hydrogen, alkyl, heteroalkyl, carbocyclyl, heterocyclyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or R$^{12}$ and R$^{13}$ together with the nitrogen atom to which they are attached, form an N-heterocyclyl; and each R$^{14}$ is the same or different and independently alkyl, halo, fluoroalkyl or —OR$^6$; each R$^{27}$, R$^{28}$, R$^{29}$ and R$^{31}$ are the same or different and independently hydrogen, alkyl or —OR$^6$; and R$^{30}$ and R$^{35}$ are each independently hydrogen or C$_1$-C$_5$ alkyl.

Various embodiments further provide pharmaceutical compositions comprising a pharmaceutically acceptable excipient and a compound of any one of Formulae (B)-(G) and (I)-(III):

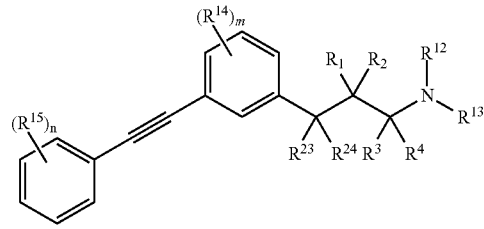
Formula (B)

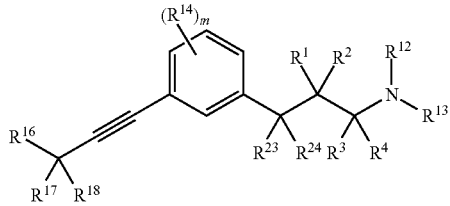
Formula (C)

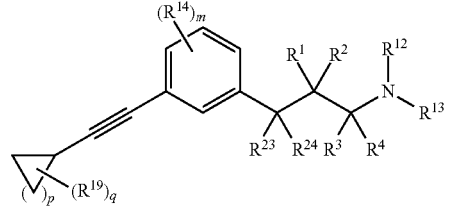
Formula (D)

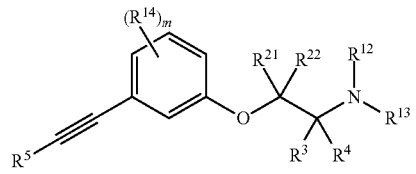
Formula (E)

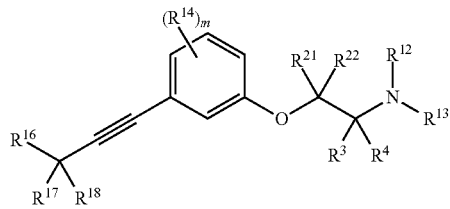
Formula (F)

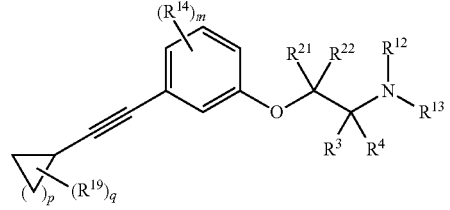
Formula (G)

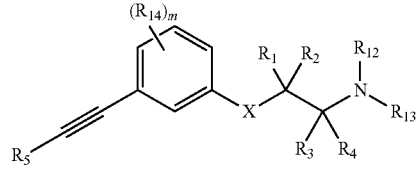
Formula (I)

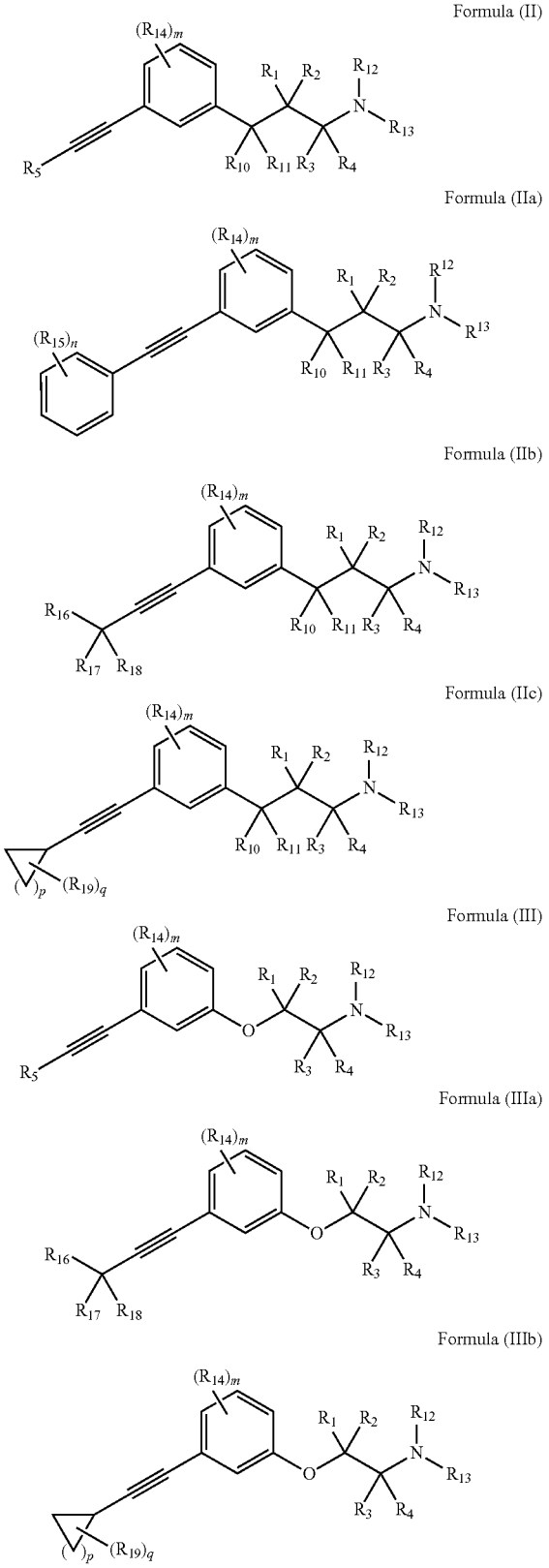

wherein, the structures are as defined above and herein.

A pharmaceutical composition (e.g., for oral administration or delivery by injection, or combined devices, or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampules, disposable syringes or multiple dose vials made of glass or plastic. Physiological saline is commonly used as an excipient, and an injectable pharmaceutical composition or a composition that is delivered ocularly is preferably sterile.

At least one alkynyl phenyl-linked amine derivative compound can be administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more alkynyl phenyl-linked amine derivative compounds can be administered.

An alkynyl phenyl-linked amine derivative compound can be delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, eye drops, intraocular injection or periocular injection. Periocular injection typically involves injection of the synthetic isomerization inhibitor, i.e., alkynyl phenyl-linked amine derivative compound under the conjunctiva or into the Tennon's space (beneath the fibrous tissue overlying the eye). Intraocular injection typically involves injection of the alkynyl phenyl-linked amine derivative compound into the vitreous. In certain embodiments, the administration is non-invasive, such as by eye drops or oral dosage form, or as a combined device.

An alkynyl phenyl-linked amine derivative compound can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the alkynyl phenyl-linked amine derivative compound. Suitable ophthalmological compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8, or pH 5 to 7, or pH 6 to 7, or pH 4 to 7, or pH 5 to 8, or pH 6 to 8, or pH 4 to 6, or pH 5 to 6, or pH 7 to 8.

For injection, the alkynyl phenyl-linked amine derivative compound can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The alkynyl phenyl-linked amine derivative compounds described herein may be formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, an alkynyl phenyl-linked amine derivative compound is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the alkynyl phenyl-linked amine derivative compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses may generally be determined using experimental models and/or clinical trials. The optimal dose may depend upon the body mass, weight, or blood volume of the patient.

The doses of the alkynyl phenyl-linked amine derivative compounds can be suitably selected depending on the clinical status, condition and age of the subject, dosage form and the like. In the case of eye drops, an alkynyl phenyl-linked amine derivative compound can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the alkynyl phenyl-linked amine derivative compound, one to seven times per week. In other embodiments, about 1.0 to about 30 mg of the alkynyl phenyl-linked amine derivative compound can be administered one to seven times per week.

Oral doses can typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2% to about 60%.

In certain embodiments, at least one alkynyl phenyl-linked amine compound described herein may be administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound may be administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that may be administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound can be administered one to seven times per week. Oral doses can typically range from about 1.0 to about 1000 mg, administered any number of days between one to seven days per week. An exemplary dosing range for oral administration is from about 10 to about 800 mg once per day prior to sleeping. In other embodiments, the composition may be delivered by intravitreal administration.

Also provided are methods of manufacturing the compounds and pharmaceutical compositions described herein. A composition comprising a pharmaceutically acceptable excipient or carrier and at least one of the alkynyl phenyl-linked amine derivative compounds described herein may be prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Unless otherwise noted, reagents and solvents were used as received from commercial suppliers. Anhydrous solvents and oven-dried glassware were used for synthetic transformations generally considered sensitive to moisture and/or oxygen. Flash column chromatography and thin layer chromatography (TLC) were performed on silica gel unless otherwise noted. Proton and carbon nuclear magnetic resonance spectra were obtained on a either a Varian VnmrS 400 at 400 MHz for proton and 100 MHz for carbon, or on Bruker AMX 500 or 300 spectrometers at 500 or 300 MHz for proton and 125 or 75 MHz for carbon, as noted. Spectra are given in ppm (δ) and coupling constants, J, are reported in Hertz. For proton spectra either tetramethylsilane was used as an internal standard or the solvent peak was used as the reference peak. For carbon spectra the solvent peak was used as the reference. Chiral HPLC Analyses were obtained using a Chiralpak IA column (4.6 mm×250 mm, 5μ) with diode array detection. The flow rate was 1 mL/min.

ANALYTICAL HPLC METHODS

Method 001A
Column: YMC ODA-A (150 mm×4.6 mm×5μ)
Flow Rate: 1.2 mL/min
Injection Volume: 10 μL
Column Oven temp: 30° C.
Cell Temp: 40° C.
Wavelength: Dual 220 nm & 254 nm
Bandwidth: 4 nm
Mobile Phase:
A: 0.05% TFA In water.
B: 0.05% TFA in Acetonitrile.
Run Time: 10 min.
Gradient program.

| Time (min) | Flow | % A | % B |
|---|---|---|---|
| 0.0 | 1.2 | 90 | 10 |
| 5.0 | 1.2 | 20 | 80 |
| 7.0 | 1.2 | 20 | 80 |
| 7.01 | 1.2 | 90 | 10 |
| 10.0 | 1.2 | 90 | 10 |

Diluent: Acetonitrile:Water (1:1) 0.05% TFA
Method 002A
Column: YMC ODA-A (150 mm×4.6 mm×5μ)
Flow Rate: 1.2 mL/min
Injection Volume: 10 μL
Column Oven temp: 30° C.
Cell Temp: 40° C.
Wavelength: Dual 220 nm & 254 nm
Bandwidth: 4 nm
Mobile Phase:
A: 0.05% TFA In water.
B: 0.05% TFA in Acetonitrile.
Run Time: 10 min.
Gradient program.

| Time (min) | Flow | % A | % B |
|---|---|---|---|
| 0.0 | 1.2 | 100 | 0 |
| 5.0 | 1.2 | 50 | 50 |
| 7.0 | 1.2 | 50 | 50 |
| 7.01 | 1.2 | 100 | 0 |
| 10.0 | 1.2 | 100 | 0 |

Diluent: Acetonitrile:Water (1:1) 0.05% TFA
Method 003A
Column: YMC ODA-A (150 mm×4.6 mm×5μ)
Flow Rate: 1.2 mL/min
Injection Volume: 10 μL
Column Oven temp: 30° C.
Cell Temp: 40° C.
Wavelength: Dual 220 nm & 254 nm
Bandwidth: 4 nm
Mobile Phase:
A: 0.05% TFA In water.
B: 0.05% TFA in Acetonitrile.
Run Time: 10 min.
Gradient program.

| Time (min) | Flow | % A | % B |
|---|---|---|---|
| 0.0 | 1.2 | 50 | 50 |
| 5.0 | 1.2 | 0 | 100 |
| 7.0 | 1.2 | 0 | 100 |
| 7.01 | 1.2 | 50 | 50 |
| 10.0 | 1.2 | 50 | 50 |

Diluent: Acetonitrile:Water (1:1) 0.05% TFA
Preparative Methods
Method 001P
Column: YMC ODA-A (500 mm×30 mm×10μ)
Flow Rate: 30 mL/min
Injection Volume: 5 mL
Column Oven temp: Ambient
Wavelength: Dual 220 nm
Mobile Phase:
A: 0.05% TFA in water.
B: 0.05% TFA in acetonitrile
Run Time: 10 min.
Gradient program.

| Time (min) | Flow | % A | % B |
|---|---|---|---|
| 0.0 | 30 | 90 | 10 |
| 5.0 | 30 | 90 | 10 |
| 25 | 30 | 20 | 80 |
| 35 | 30 | 80 | 80 |

Solvents for sample preparation: Methanol, Acetonitrile, Acetonitrile:Methanol (1:1)
Method 003P
Column: YMC ODA-A (500 mm×30 mm×10μ)
Flow Rate: 30 mL/min
Injection Volume: 5 mL
Column Oven temp: Ambient
Wavelength: Dual 220 nm
Mobile Phase:
A: 0.05% TFA In water.
B: 0.05% TFA in Acetonitrile
Run Time: 10 min.
Gradient program.

| Time (min) | Flow | % A | % B |
|---|---|---|---|
| 0.0 | 30 | 50 | 50 |
| 5.0 | 30 | 50 | 50 |
| 25 | 30 | 100 | 100 |
| 35 | 30 | 100 | 100 |

Solvents for sample preparation: Methanol, Acetonitrile, Acetonitrile:Methanol (1:1)
Method 004P
Column: YMC ODA-A (500 mm×30 mm×10μ)
Flow Rate: 30 mL/min
Injection Volume: 5 mL
Column Oven temp: Ambient
Wavelength: Dual 220 nm
Mobile Phase:
A: water.
B: Acetonitrile
Run Time: 10 min.
Gradient program.

| Time (min) | Flow | % A | % B |
|---|---|---|---|
| 0.0 | 30 | 90 | 10 |
| 5.0 | 30 | 90 | 10 |
| 25 | 30 | 20 | 80 |
| 35 | 30 | 80 | 80 |

Solvents for sample preparation: Methanol, Acetonitrile, Acetonitrile:Methanol (1:1)

Example 1

PREPARATION OF 1-(3-(3-AMINOPROPYL)PHENYL)-3-ETHYLPENT-1-YN-3-OL

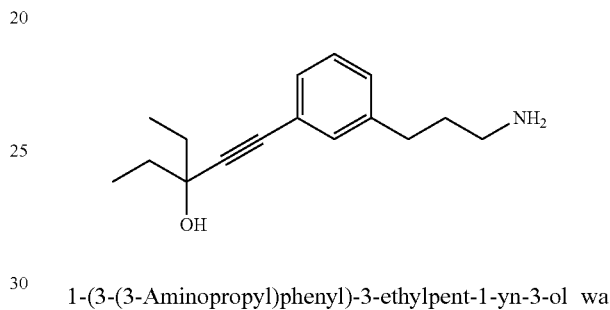

1-(3-(3-Aminopropyl)phenyl)-3-ethylpent-1-yn-3-ol was prepared following the method shown in Scheme 1:

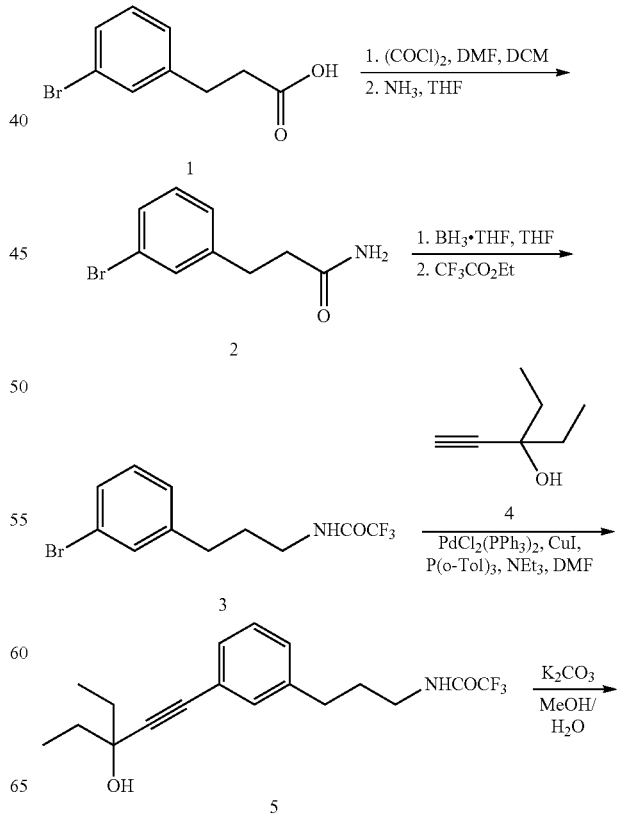

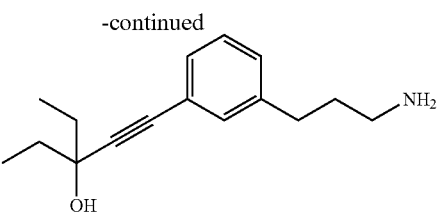

Step 1: To a stirred solution of 3-(3-bromophenyl)propanoic acid (1) (25.0 g, 109.1 mmole) in CH$_2$Cl$_2$ (150 ml) was added oxalyl chloride (27.7 g, 218.3 mmol) followed by DMF (2 drops). The solution was stirred at room temperature overnight. The resulting mixture was concentrated under reduced pressure to give the crude acid chloride which was used immediately in the next reaction.

Step 2: The crude material was dissolved in anhydrous THF (150 ml) and cooled in an ice bath. Ammonia gas was bubbled into the solution for 3-4 minutes and the mixture was warmed to room temperature and stirred overnight. The mixture was concentrated under reduced pressure. Saturated NaHCO$_3$ (100 ml) was added to the residue and the mixture was extracted with EtOAc (2×200 ml). The combined organics were dried over Na$_2$SO$_4$ and concentrated under reduced pressure to give amide 2 as a white solid. Yield (23.9 g, 96%): $^1$H NMR (400 MHz, DMSO-d$_6$) δ 7.40 (s, 1H), 7.35 (dt, J=6.4, 2.4 Hz, 1H), 7.26 (br s, 1H), 7.18-7.24 (m, 2H), 6.75 (br s, 1H), 2.78 (t, J=7.6 Hz, 2H), 2.34 (t, J=7.6 Hz, 2H).

Step 3: To an ice-cold solution of amide 2 (23.85 g, 104.6 mmol) in anhydrous THF (250 ml) was added BH$_3$.THF (209 ml of a 1.0 M solution in THF, 209 mmol). The solution was warmed to room temperature and stirred for 18 h. The reaction was quenched by the slow addition of 6 N HCl until pH 1 was achieved. The solution was then stirred at room temperature for 4 h. at which time the pH was adjusted to >10 with the addition of 50% aqueous NaOH. The solution was extracted with EtOAc (2×250 ml). The combined organic layers were washed with brine, dried over Na$_2$SO$_4$ and concentrated under reduced pressure to give the crude amine which was used immediately in the next reaction.

Step 4: Crude 3-(3-bromophenyl)propan-1-amine (ca. 104.6 mmol) was stirred with ethyl trifluoroacetate (30 ml) overnight. The mixture was concentrated under reduced pressure. Purification by flash chromatography (20% EtOAc-hexanes) gave trifluoroacetamide 3. Yield (21.1 g, 62%): $^1$H NMR (400 MHz, DMSO-d$_6$) δ 9.40 (br s, 1H), 7.43 (s, 1H), 7.36 (dt, J=7.2, 2.0 Hz, 1H), 7.19-7.25 (m, 2H), 3.16 (q, J=6.8 Hz, 2H), 2.57 (t, J=7.6 Hz, 2H), 1.77 (quint., J=7.2 Hz, 2H).

Step 5: To a degassed solution of N-(3-(3-bromophenyl)propyl)-2,2,2-trifluoroacetamide (3) (0.930 g, 3 mmol) and 3-ethylpent-1-yn-3-ol (4) (0.670 g, 6 mmol) in triethylamine (4 mL) and DMF (12 mL) was added PdCl$_2$(PPh$_3$)$_2$ (0.053 g, 0.075 mmol), tri-o-tolylphosphine (0.046 g, 0.15 mmol), and CuI (0.014 g, 0.075 mmol). The resulting mixture was degassed and stirred under argon at 90° C. for 6 h. The mixture was cooled to room temperature then concentrated under reduced pressure and diluted with EtOAc (100 mL) and water (70 mL). After vigorous shaking, the layers were separated. The organic layer was treated with charcoal, dried over MgSO$_4$, filtered, and concentrated under reduced pressure. Purification by flash column chromatography (7 to 60% EtOAc-hexanes gradient) gave N-(3-(3-(3-ethyl-3-hydroxypentyl)phenyl)propyl)-2,2,2-trifluoroacetamide (5) as a yellow oil. Yield (0.663 g, 65%): $^1$H NMR (400 MHz, DMSO-d$_6$) δ 9.40 (s, 1H), 7.17-7.28 (m, 4H), 5.11 (s, 1H), 3.16 (q, J=7.2 Hz, 2H), 2.56 (t, J=7.2 Hz, 2H), 1.76 (quint, J=7.2 Hz, 2H), 1.53-1.67 (m, 4H), 0.97 (t, J=7.2 Hz, 6H).

Step 6: N-(3-(3-(3-ethyl-3-hydroxypentyl)phenyl)propyl)-2,2,2-trifluoroacetamide (5) (0.660 g, 1.93 mmol) was dissolved in MeOH (15 mL), and an aqueous solution of K$_2$CO$_3$ (0.42 g in 3 mL water, 3.0 mmol) was added. The resulting mixture was stirred at 45° C. for 4 h. After cooling, the reaction mixture was concentrated under reduced pressure and diluted with EtOAc (50 mL) and water (50 mL). After vigorous shaking, the layers were separated. The organic layer was dried over Na$_2$SO$_4$, filtered, and concentrated under reduced pressure. Purification by flash column chromatography (72:8:20 to 90:10:0 EtOAc/7 M NH$_3$ in MeOH/hexanes) gave Example 1 as a clear oil. Yield (0.421 g, 89%): $^1$H NMR (400 MHz, DMSO-d$_6$) δ 7.15-7.26 (m, 4H), 5.11 (s, 1H), 2.56 (t, J=7.6 Hz, 2H), 2.47 (t, J=5.2 Hz, 2H), 1.55-1.65 (m, 6H), 1.39 (br s, 2H), 0.97 (t, J=7.6 Hz, 6H).

Example 2

PREPARATION OF 4-((3-(3-AMINOPROPYL)PHENYL)ETHYNYL)HEPTAN-4-OL

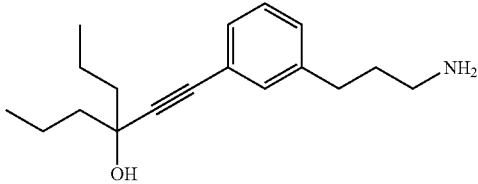 [SMILES: CCCC(O)(C#Cc1cccc(CCCN)c1)CCC]

4-((3-(3-Aminopropyl)phenyl)ethynyl)heptan-4-ol was prepared following the method described in Example 1.

Step 1: Coupling of 4-ethynylheptan-4-ol with bromide 3 gave 2,2,2-trifluoro-N-(3-(3-(3-hydroxy-3-propylhex-1-ynyl)phenyl)propyl)acetamide as a clear oil. Yield (0.103 g, 31%): $^1$H NMR (400 MHz, DMSO-d$_6$) δ 9.40 (s, 1H), 7.18-7.29 (m, 4H), 3.16 (q, J=7.2 Hz, 2H), 2.56 (t, J=7.2 Hz, 2H), 1.76 (quint, J=7.2 Hz, 2H), 1.53-1.67 (m, 8H), 0.97 (t, J=7.2 Hz, 6H).

Step 2: To a solution of 2,2,2-trifluoro-N-(3-(3-(3-hydroxy-3-propylhex-1-ynyl)phenyl)propyl)acetamide (0.1 g, 0.27 mmol) in MeOH (3 mL) was added concentrated NH$_4$OH (7 mL) and the solution was stirred at room temperature overnight. The solvent was removed under reduced pressure and the residue was extracted twice with EtOAc. The combined organics were washed with water and brine, dried over Na$_2$SO$_4$ and concentrated under reduced pressure to give Example 2 as a clear oil. Yield (0.079 g, 100%): $^1$H NMR (400 MHz, DMSO-d$_6$) δ 7.14-7.26 (m, 4H), 5.12 (s, 1H), 5.11 (s, 1H), 2.56 (t, J=7.2 Hz, 2H), 2.47 (t, J=7.2 Hz, 2H), 1.42-1.63 (m, 12H), 0.90 (t, J=7.2 Hz, 6H).

Example 3

PREPARATION OF 5-((3-(3-AMINOPROPYL) PHENYL)ETHYNYL)NONAN-5-OL

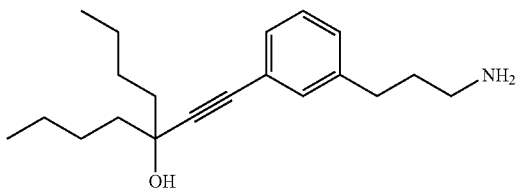 [SMILES: CCCCC(O)(C#Cc1cccc(CCCN)c1)CCCC]

5-((3-(3-Aminopropyl)phenyl)ethynyl)nonan-5-ol was prepared following the method described in Example 1.

Step 1: Coupling of 3-ethynylnonan-5-ol with bromide 3 gave N-(3-(3-(3-butyl-3-hydroxyhept-1-ynyl)phenyl)propyl)-2,2,2-trifluoroacetamide as a brown oil. Yield (0.346 g, 22%): $^1$H NMR (400 MHz, DMSO-$d_6$) δ 9.40 (br s, 1H), 7.14-7.26 (m, 4H), 5.11 (s, 1H), 2.56 (t, J=7.6 Hz, 2H), 2.47 (m, 2H), 1.43-1.62 (m, 14H), 0.88 (t, J=7.2 Hz, 6H).

Step 2: Deprotection of N-(3-(3-(3-butyl-3-hydroxyhept-1-ynyl)phenyl)propyl)-2,2,2-trifluoroacetamide gave Example 3 as a light yellow oil. Yield (0.219 g, 84%): $^1$H NMR (400 MHz, DMSO-$d_6$) δ 7.22-7.26 (m, 1H), 7.14-7.17 (m, 3H), 5.11 (s, 1H), 2.56 (t, J=7.6 Hz, 2H), 2.49 (t, J=6.8 Hz, 2H), 1.25-1.62 (m, 14H), 0.88 (t, J=7.2 Hz, 6H).

Example 4

PREPARATION OF 3-(3-(3-METHOXY-3-PROPYLHEX-1-YNYL)PHENYL)PROPAN-1-AMINE

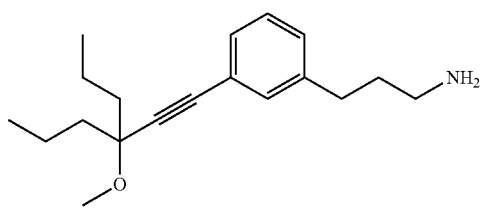 [SMILES: CCCC(C#Cc1cccc(CCCN)c1)(CCC)OC]

3-(3-(3-Methoxy-3-propylhex-1-ynyl)phenyl)propan-1-amine was prepared following the method used in Example 1.

Step 1: Coupling of 4-ethynyl-4-methoxyheptane with bromide 3 gave 2,2,2-trifluoro-N-(3-(3-(3-methoxy-3-propylhex-1-ynyl)phenyl)propyl)acetamide as a light yellow oil. Yield (0.596 g, 93%): $^1$H NMR (400 MHz, DMSO-$d_6$) δ 9.40 (br s, 1H), 7.18-7.29 (m, 4H), 3.25 (s, 3H), 3.14-3.20 (m, 2H), 2.56 (t, J=7.6 Hz, 2H), 1.73-1.80 (m, 2H), 1.64 (t, J=8.4 Hz, 4H), 1.34-1.44 (m, 4H), 0.88 (t, J=7.2 Hz, 6H).

Step 2: Deprotection of 2,2,2-trifluoro-N-(3-(3-(3-methoxy-3-propylhex-1-ynyl)phenyl)propyl)acetamide gave Example 4 as a clear oil. Yield (0.341 g, 93%): $^1$H NMR (400 MHz, DMSO-$d_6$) δ 7.27-7.18 (m, 4H), 3.25 (s, 3H), 2.56 (t, J=7.6 Hz, 2H), 2.47 (t, J=6.8 Hz, 2H), 1.56-1.66 (m, 6H), 1.32-1.44 (m, 6H), 0.88 (t, J=7.2 Hz, 6H).

Example 5

PREPARATION OF 1-(3-(3-AMINOPROPYL) PHENYL)-3-METHYLHEX-1-YN-3-OL

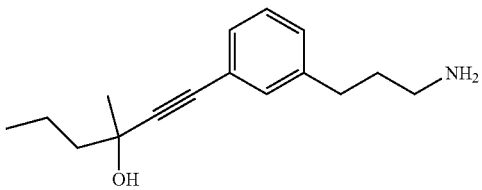 [SMILES: CCCC(C)(O)C#Cc1cccc(CCCN)c1]

1-(3-(3-Aminopropyl)phenyl)-3-methylhex-1-yn-3-ol was prepared following the method used in Example 1.

Step 1: Coupling of 3-methylhex-1-yn-3-ol with bromide 3 gave 2,2,2-trifluoro-N-(3-(3-(3-hydroxy-3-methylhex-1-ynyl)phenyl)propyl)acetamide contaminated with alkyne dimer. Yield (0.699 g, >100%): $^1$H NMR (400 MHz, DMSO-$d_6$) δ 9.40 (br s, 1H), 7.25 (dd, J=8.8, 7.2 Hz, 1H), 7.17-7.21 (m, 3H), 5.29 (s, 1H), 3.17 (q, J=6.8 Hz, 2H), 2.56 (t, J=7.6 Hz, 2H), 1.76 (quint, J=7.2 Hz, 2H), 1.48-1.61 (m, 4H), 1.39 (s, 3H), 0.90 (t, J=7.6 Hz, 3H).

Step 2: Deprotection of 2,2,2-trifluoro-N-(3-(3-(3-hydroxy-3-methylhex-1-ynyl)phenyl)propyl)acetamide followed by purification by flash chromatography chromatography (72:8:20 to 90:10:0 EtOAc/7 M $NH_3$ in MeOH/hexanes) gave Example 5 as a yellow oil. Yield (0.371 g, 76%, two steps): $^1$H NMR (400 MHz, DMSO-$d_6$) δ 7.24 (t, J=8 Hz, 1H), 7.14-7.18 (m, 3H), 5.29 (br s, 1H), 2.56 (t, J=7.6 Hz, 2H), 2.47 (t, J=7.2 Hz, 2H), 1.41-1.62 (m, 6H), 1.39 (s, 3H), 1.34 (br s, 2H), 0.90 (t, J=7.6 Hz, 3H).

Example 6

PREPARATION OF 1-(3-(3-AMINOPROPYL) PHENYL)-3,5-DIMETHYLHEX-1-YN-3-OL

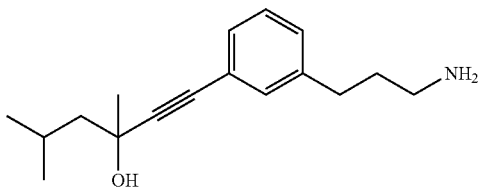 [SMILES: CC(C)CC(C)(O)C#Cc1cccc(CCCN)c1]

1-(3-(3-Aminopropyl)phenyl)-3,5-dimethylhex-1-yn-3-ol was prepared following the described used in Example 2.

Step 1: Coupling of 3,5-dimethylhex-1-yn-3-ol with bromide 3 following the method described in Example 2 (except that the alkynol was added after degassing) gave 2,2,2-trifluoro-N-(3-(3-(3-hydroxy-3,5-dimethylhex-1-ynyl)phenyl)propyl)acetamide as a brown oil. Yield (0.287 g, 40%): $^1$H NMR (400 MHz, DMSO-$d_6$) δ 9.41 (br s, 1H), 7.26 (t, J=7.6 Hz, 1H), 7.16-7.20 (m, 3H), 5.25 (s, 1H), 3.16 (q, J=6.8 Hz, 2H), 2.56 (t, J=7.2 Hz, 2H), 1.90-1.96 (m, 1H), 1.76 (quint, J=7.6 Hz, 2H), 1.53 (m, 2H), 1.42 (s, 3H), 0.96 (d, J=6.8 Hz, 6H).

Step 2: Deprotection of 2,2,2-trifluoro-N-(3-(3-(3-hydroxy-3,5-dimethylhex-1-ynyl)phenyl)propyl)acetamide following the method of Example 2 except that the reaction mixture was stirred at room temperature overnight gave Example 6 as a clear oil. Yield (0.141 g, 72%): $^1$H NMR (400 MHz, DMSO-$d_6$) δ 7.14-7.27 (m, 4H), 5.25 (s, 1H), 2.56 (t, J=7.2 Hz, 2H), 2.47 (t, J=6.0 Hz, 2H), 1.93 (quint, J=6.4 Hz, 1H), 1.60 (q, J=6.8 Hz, 2H), 1.54 (t, J=6.0 Hz, 2H), 1.42 (s, 3H), 1.35 (br s, 2H), 0.97 (d, J=6.4 Hz, 6H).

Example 7

PREPARATION OF 4-(3-(3-AMINOPROPYL)PHENYL)-2-METHYLBUT-3-YN-2-OL

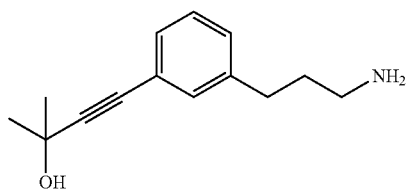 [SMILES: CC(C)(O)C#Cc1cccc(CCCN)c1]

4-(3-(3-Aminopropyl)phenyl)-2-methylbut-3-yn-2-ol was prepared following the method described in Example 2.

Step 1: Coupling of 2-methylbut-3-yn-2-ol with bromide 3 in THF without the use of tri-o-tolylphosphine gave 2,2,2-trifluoro-N-(3-(3-(3-hydroxy-3-methylbut-1-ynyl)phenyl)propyl)acetamide. Yield (0.5 g, 81%): $^1$H NMR (400 MHz, DMSO-$d_6$) δ 9.40 (br s, 1H), 7.17-7.28 (m, 4H), 3.16 (q, J=7.2 Hz, 2H), 2.56 (t, J=7.2 Hz, 2H), 1.76 (quint, J=7.6 Hz, 2H), 1.44 (s, 3H), 1.35 (s, 3H).

Step 2: Deprotection of 2,2,2-trifluoro-N-(3-(3-(3-hydroxy-3-methylbut-1-ynyl)phenyl)propyl)acetamide followed by purification by flash chromatography (72:8:20 to 90:10:0 EtOAc/7 M NH$_3$ in MeOH/hexanes gradient) gave Example 7 as a light yellow oil. Yield (0.212 g, 62%): $^1$H NMR (400 MHz, DMSO-$d_6$) δ 7.14-7.26 (m, 4H), 5.41 (br s, 1H), 2.56 (t, J=7.2 Hz, 2H), 2.47-2.50 (m, 2H), 1.55-1.63 (m, 2H), 1.44 (s, 6H), 1.36 (br s, 2H).

Example 8

PREPARATION OF 1-(3-(3-AMINOPROPYL)PHENYL)HEX-1-YN-3-OL

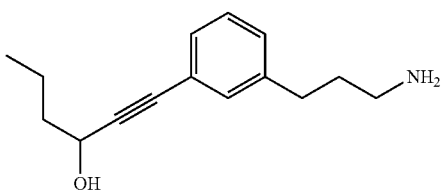 [SMILES: CCCC(O)C#Cc1cccc(CCCN)c1]

1-(3-(3-Aminopropyl)phenyl)hex-1-yn-3-ol was prepared following the method described in Example 7.

Step 1: Coupling of hex-1-yn-3-ol with bromide 3 gave 2,2,2-trifluoro-N-(3-(3-(3-hydroxyhex-1-ynyl)phenyl)propyl)acetamide as a brown oil. Yield (0.271 g, 26%).

Step 2: Deprotection of 2,2,2-trifluoro-N-(3-(3-(3-hydroxyhex-1-ynyl)phenyl)propyl)acetamide gave Example 8 as a tan solid. Yield (0.086 g, 45%): $^1$H NMR (400 MHz, DMSO-$d_6$) δ 7.16-7.26 (m, 4H), 5.36 (d, J=5.2 Hz, 1H), 4.41 (dt, J=6.4, 5.2 Hz, 1H), 2.56 (t, J=7.2 Hz, 2H), 2.47-2.49 (m, 2H), 1.38-1.64 (m, 8H), 0.90 (t, J=7.2 Hz, 3H).

Example 9

PREPARATION OF 3-(3-(3-METHOXYPROP-1-YNYL)PHENYL)PROPAN-1-AMINE

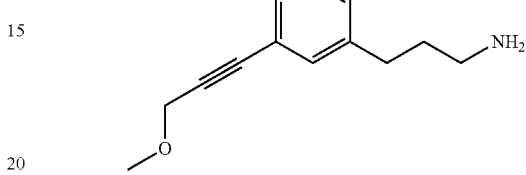

3-(3-(3-Methoxyprop-1-ynyl)phenyl)propan-1-amine was prepared following the method described in Example 7.

Step 1: Coupling of 3-methoxyprop-1-yne with bromide 3 gave 2,2,2-trifluoro-N-(3-(3-(3-methoxyprop-1-ynyl)phenyl)-propyl)acetamide as a light yellow oil. Yield (0.193 g, 32%): $^1$H NMR (400 MHz, DMSO-$d_6$) δ 9.40 (br s, 1H), 7.21-7.31 (m, 4H), 4.30 (s, 2H), 3.31 (s, 3H), 3.16 (q, J=7.2 Hz, 2H), 2.56 (t, J=7.6 Hz, 2H), 1.77 (quint, J=7.2 Hz, 2H).

Step 2: Deprotection of 2,2,2-trifluoro-N-(3-(3-(3-methoxyprop-1-ynyl)phenyl)propyl)acetamide gave Example 9 as a clear oil. Yield (0.069 g, 54%): $^1$H NMR (400 MHz, DMSO-$d_6$) δ 7.19-7.28 (m, 4H), 4.29 (s, 2H), 3.31 (s, 3H), 2.57 (t, J=7.6 Hz, 2H), 2.47 (m, 2H), 1.56-1.63 (m, 2H), 1.36 (br s, 2H).

Example 10

PREPARATION OF 3-(3-(3-AMINOPROPYL)PHENYL)PROP-2-YN-1-OL

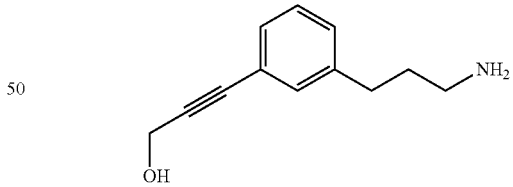

3-(3-(3-Aminopropyl)phenyl)prop-2-yn-1-ol was prepared following the method described in Example 7.

Step 1: Coupling of prop-2-yn-1-ol with bromide 3 gave 2,2,2-trifluoro-N-(3-(3-(3-hydroxyprop-1-ynyl)phenyl)propyl)acetamide as a light yellow oil. Yield (0.148 g, 26%): $^1$H NMR (400 MHz, DMSO-$d_6$) δ 9.41 (br s, 1H), 7.19-7.29 (m, 4H), 5.28 (t, J=5.6 Hz, 1H), 4.27 (d, J=6.4 Hz, 2H), 3.16 (t, J=7.2 Hz, 2H), 2.56 (t, J=7.6 Hz, 2H), 1.76 (q, J=7.6 Hz, 2H).

Step 2: Deprotection of 2,2,2-trifluoro-N-(3-(3-(3-hydroxyprop-1-ynyl)phenyl)propyl)acetamide gave Example 10 as a clear oil. Yield (0.073 g, 76%): $^1$H NMR (400 MHz, DMSO-d$_6$) δ 7.17-7.27 (m, 4H), 5.28 (br s, 1H), 4.27 (d, J=3.6 Hz, 2H), 2.59 (t, J=7.6 Hz, 2H), 2.47 (m, 2H), 1.52-1.63 (m, 4H).

Example 11

PREPARATION OF 1-((3-(3-AMINOPROPYL)PHENYL)ETHYNYL)CYCLOHEXANOL

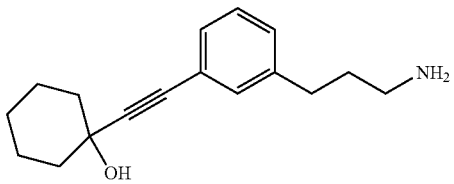 [SMILES: NCCCc1cccc(C#CC2(O)CCCCC2)c1]

1-((3-(3-Aminopropyl)phenyl)ethynyl)cyclohexanol was prepared following the method described in Example 7.

Step 1: Coupling of 1-ethynylcyclohexanol with bromide 3 gave 2,2,2-trifluoro-N-(3-(3-((1-hydroxycyclohexyl)ethynyl)phenyl)propyl)acetamide as a brown oil. Yield (0.205 g, >100%): $^1$H NMR (400 MHz, DMSO-d$_6$) δ 9.40 (br s, 1H), 7.26 (t, J=7.6 Hz, 1H), 7.17-7.24 (m, 3H), 5.37 (s, 1H), 3.16 (q, J=6.8 Hz, 2H), 2.56 (t, J=7.2 Hz, 2H), 1.15-1.83 (m, 12H).

Step 2: Deprotection of 2,2,2-trifluoro-N-(3-(3-((1-hydroxycyclohexyl)ethynyl)phenyl)propyl)acetamide gave Example 11 as a light yellow solid. Yield (0.13 g, 87%): $^1$H NMR (400 MHz, DMSO-d$_6$) δ 7.14-7.26 (m, 4H), 5.37 (s, 1H), 2.56 (t, J=7.6 Hz, 2H), 2.47 (m, 2H), 1.15-1.83 (m, 14H).

Example 12

PREPARATION OF 1-(3-(3-AMINOPROPYL)PHENYL)-3-TERT-BUTYL-4,4-DIMETHYLPENT-1-YN-3-OL

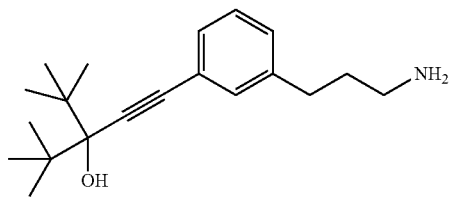 [SMILES: CC(C)(C)C(O)(C#Cc1cccc(CCCN)c1)C(C)(C)C]

1-(3-(3-Aminopropyl)phenyl)-3-tert-butyl-4,4-dimethylpent-1-yn-3-ol was prepared following the method described in Example 7.

Step 1: Coupling of 3-tert-butyl-4,4-dimethylpent-1-yn-3-ol with bromide 3 gave N-(3-(3-(3-tert-butyl-3-hydroxy-4,4-dimethylpent-1-ynyl)phenyl)propyl)-2,2,2-trifluoroacetamide as a brown oil. Yield (0.15 g, 67%): $^1$H NMR (400 MHz, DMSO-d$_6$) δ 9.40 (br s, 1H), 7.27 (t, 7.6 Hz, 1H), 7.18-7.21 (m, 3H), 4.92 (s, 1H), 3.18 (q, J=6.4 Hz, 2H), 2.57 (t, J=7.2 Hz, 2H), 1.76 (quint, J=7.6 Hz, 2H), 1.15 (br s, 18H).

Step 2: Deprotection of N-(3-(3-(3-tert-butyl-3-hydroxy-4,4-dimethylpent-1-ynyl)phenyl)propyl)-2,2,2-trifluoroacetamide following the procedure described in Example 7, except that the product was purified by flash chromatography (10% 7 M NH$_3$ in MeOH-EtOAc), gave Example 12 as a yellow oil. Yield (0.102 g, 90%): $^1$H NMR (400 MHz, DMSO-d$_6$) δ 7.16-7.27 (m, 4H), 4.92 (s, 1H), 2.57 (t, J=7.2 Hz, 2H), 2.47 (t, J=6.8 Hz, 2H), 1.56 (q, J=7.2 Hz, 2H), 1.52 (br s, 2H), 1.14 (s, 18H).

Example 13

PREPARATION OF 1-((3-(3-AMINOPROPYL)PHENYL)ETHYNYL)-2,2,6,6-TETRAMETHYL-CYCLOHEXANOL

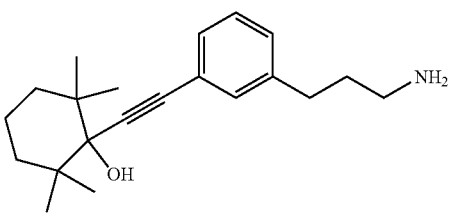 [SMILES: CC1(C)CCCC(C)(C)C1(O)C#Cc1cccc(CCCN)c1]

1-((3-(3-Aminopropyl)phenyl)ethynyl)-2,2,6,6-tetramethylcyclohexanol was prepared following the method described in Example 7.

Step 1: Coupling of 1-ethynyl-2,2,6,6-tetramethylcyclohexanol with bromide 3 gave 2,2,2-trifluoro-N-(3-(3-((1-hydroxy-2,2,6,6-tetramethylcyclohexyl)ethynyl)phenyl)propyl)acetamide as a light brown foam. Yield (0.192 g, 84%): $^1$H NMR (400 MHz, DMSO-d$_6$) δ 9.40 (br s, 1H), 7.27 (t, J=7.6 Hz, 1H), 7.18-7.23 (m, 3H), 4.92 (s, 1H), 3.18 (q, J=6.8 Hz, 2H), 2.57 (t, J=7.2 Hz, 2H), 1.76 (quint, J=7.6 Hz, 2H), 1.22-1.50 (m, 6H), 1.14 (s, 6H), 1.04 (s, 6H).

Step 2: Deprotection of 2,2,2-trifluoro-N-(3-(3-((1-hydroxy-2,2,6,6-tetramethylcyclohexyl)ethynyl)phenyl)propyl)acetamide was conducted following the procedure described in Example 7, except that the product was purified by flash chromatography (10% 7 M NH$_3$ in MeOH-EtOAc). Example 13 was isolated as a white solid. Yield (0.016 g, 73%): $^1$H NMR (400 MHz, DMSO-d$_6$) δ 7.15-7.27 (m, 4H), 4.92 (s, 1H), 2.57 (t, J=7.2 Hz, 2H), 2.47 (t, J=7.2 Hz, 2H), 1.26-1.66 (m, 10H), 1.14 (s, 6H), 1.04 (s, 6H).

Example 14

PREPARATION OF (S)-1-(3-(3-AMINOPROPYL)PHENYL)OCT-1-YN-3-OL

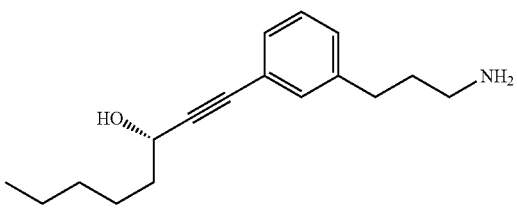 [SMILES: CCCCC[C@H](O)C#Cc1cccc(CCCN)c1]

(S)-1-(3-(3-Aminopropyl)phenyl)oct-1-yn-3-ol 1 was prepared following the method shown in Scheme 2

SCHEME 2

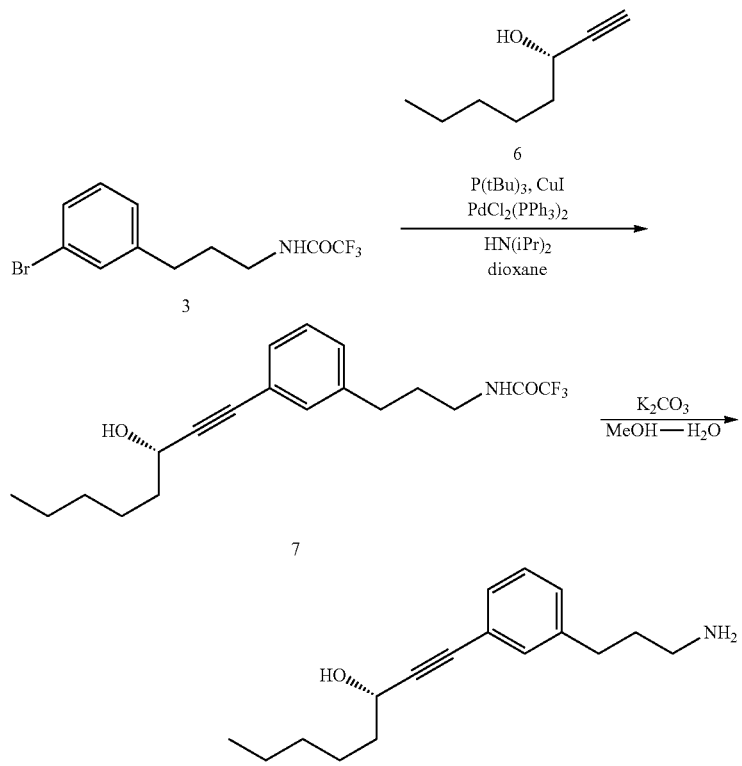

Step 1: An oven-dried flask was charged with N-(3-(3-bromophenyl)propyl)-2,2,2-trifluoroacetamide (3) (0.507 g, 1.63 mmol), (R)-octyn-3-ol (6) (0.33 mL, 2.26 mmol), CuI (0.0090 g, 0.047 mmol), PdCl$_2$(PPh$_3$)$_2$ (0.0430 g, 0.06 mmol), diisopropylamine (0.34 mL, 2.4 mmol) and anhydrous dioxane (2 mL). The flask was alternately placed under vacuum then argon three times. P($^t$Bu)$_3$ (0.1 mL, 1.0 M solution in dioxane, 0.1 mmol) was added, and the flask placed under vacuum then argon again. The mixture was heated at 45° C. under argon for 17 h. The reaction mixture was diluted with EtOAc, filtered through a small pad of Celite and silica gel, and concentrated under reduced pressure. Purification by flash column chromatography (20 to 80% EtOAc-hexanes gradient) gave alkyne 7 as a brown oil (0.215 g, 37%): $^1$H NMR (400 MHz, DMSO-d$_6$) δ 9.40 (br s, 1H), 7.18-7.28 (m, 4H), 5.37 (d, J=5.7, 1H), 4.39 (dt, J=6.4, 5.7 Hz, 1H), 3.16 (q, J=6.7 Hz, 2H), 2.56 (t, J=7.4 Hz, 2H), 1.76 (quint, J=7.3 Hz, 2H), 1.58-1.65 (m, 2H), 1.37-1.45 (m, 2H), 1.24-1.30 (m, 4H), 0.85 (t, J=7.0 Hz, 3H).

Step 2: Alkyne 7 (0.206 g, 0.58 mmol) was dissolved in MeOH (15 mL). H$_2$O (1.5 mL) and K$_2$CO$_3$ (0.200 g, 1.45 mmol) were added and the mixture was stirred at room temperature for 30 h. The reaction mixture was concentrated under reduced pressure and the residue was dissolved in ~10% MeOH-EtOAc, dried over Na$_2$SO$_4$, filtered through a cotton plug then concentrated under reduced pressure. Purification by flash chromatography (90 to 100% EtOAc-hexanes; then 10% 7 M NH$_3$ in MeOH-EtOAc) gave Example 14 as a light yellow oil (0.154 g, quant.). $^1$H NMR (400 MHz, CD$_3$OD) δ 7.16-7.26 (m, 4H), 4.49 (t, J=6.8 Hz, 1H), 2.61-2.67 (m, 4H), 1.70-1.80 (m, 4H), 1.50-1.53 (m, 2H), 1.34-1.39 (m, 4H), 0.93 (t, J=7.0 Hz, 3H). ESI MS m/z 242.27 [M+H–H$_2$O]$^+$.

Example 15

PREPARATION OF (R)-1-(3-(3-AMINOPROPYL)PHENYL)OCT-1-YN-3-OL

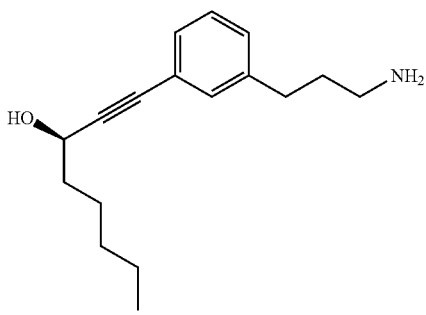 [SMILES: CCCCC[C@@H](O)C#Cc1cccc(CCCN)c1]

(R)-1-(3-(3-Aminopropyl)phenyl)oct-1-yn-3-ol was prepared following the method used in Example 14.

Step 1: Coupling of (R)-oct-1-yn-3-ol with bromide 3 gave (R)-2,2,2-trifluoro-N-(3-(3-(3-hydroxyoct-1-ynyl)phenyl)propyl)acetamide as a brown oil. Yield (0.292 g, 41%): $^1$H NMR (400 MHz, DMSO-d$_6$) δ 9.40 (br s, 1H), 7.27 (t, J=7.6 Hz, 1H), 7.28-7.18 (m, 3H), 5.36 (d, J=5.6 Hz, 1H), 4.40 (q, J=5.6 Hz, 1H), 3.16 (q, J=6.8 Hz, 2H), 2.56 (t, J=7.2 Hz, 2H), 1.76 (q, J=7.6 Hz, 2H), 1.16-1.65 (m, 8H), 0.86 (m, 3H).

Step 2: Deprotection of (R)-2,2,2-trifluoro-N-(3-(3-(3-hydroxyoct-1-ynyl)phenyl)propyl)acetamide following the procedure described in Example 2 except the product was purified by flash chromatography (72:8:20 to 90:10:0 EtOAc/7 M NH$_3$ in MeOH/hexanes gradient) gave Example 15 as a light yellow oil. Yield (0.119 g, 56%): $^1$H NMR (400 MHz, DMSO-d$_6$) δ 7.16-7.27 (m, 4H), 5.36 (d, J=5.2 Hz, 1H), 4.39 (dt, J=5.2, 6.4 Hz, 1H), 2.56 (t, J=7.2 Hz, 2H), 2.47 (t obs, J=6.8 Hz, 2H), 1.55-1.65 (m, 4H), 1.25-1.43 (m, 8H), 0.86 (t, J=6.8 Hz, 3H).

Example 16

PREPARATION OF (R)-3-(3-(3-AMINOPROPYL)PHENYL)-1-PHENYLPROP-2-YNOL

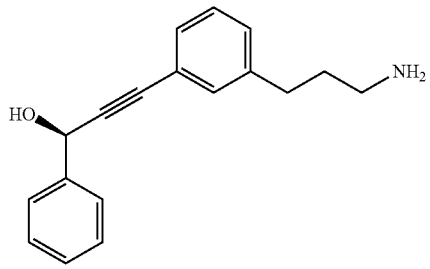 [SMILES: NCCCc1cccc(C#C[C@H](O)c2ccccc2)c1]

(R)-3-(3-(3-Aminopropyl)phenyl)-1-phenylprop-2-ynol was prepared following the method described in Example 15.

Step 1: Coupling of N-(3-(3-bromophenyl)propyl)-2,2,2-trifluoroacetamide (3) with (S)-3-phenylpropyn-3-ol gave (R)-2,2,2-trifluoro-N-(3-(3-(3-hydroxy-3-phenylprop-1-ynyl)phenyl)propyl)acetamide as a brown oil (0.202 g; contaminated with alkyne dimer). The product was used in the next synthetic step without purification.

Step 2: Deprotection of (R)-2,2,2-trifluoro-N-(3-(3-(3-hydroxy-3-phenylprop-1-ynyl)phenyl)propyl)acetamide and purification by flash chromatography gave Example 16 as a yellow oil. Yield (0.079 g, 53%): $^1$H NMR (400 MHz, CD$_3$OD) δ 7.56-7.59 (m, 2H), 7.37 (m, 2H), 7.25-7.32 (m, 3H), 7.22 (d, J=7.6 Hz, 1H), 7.18 (dt, J=7.2, 2.0 Hz, 1H), 5.61 (s, 1H), 2.59-2.65 (m, 4H), 1.75 (quint, J=7.6 Hz, 2H). ESI MS m/z 266.27 [M+H]$^+$.

Example 17

PREPARATION OF 3-(3-((2,6-DIMETHYLPHENYL)ETHYNYL)PHENYL)PROPAN-1-AMINE

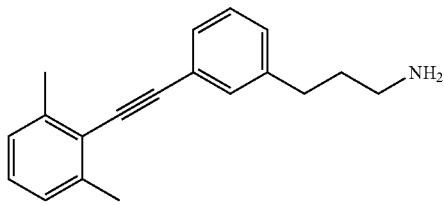 [SMILES: Cc1cccc(C)c1C#Cc1cccc(CCCN)c1]

3-(3-((2,6-Dimethylphenyl)ethynyl)phenyl)propan-1-amine was prepared following the method shown in Scheme 3:

SCHEME 3

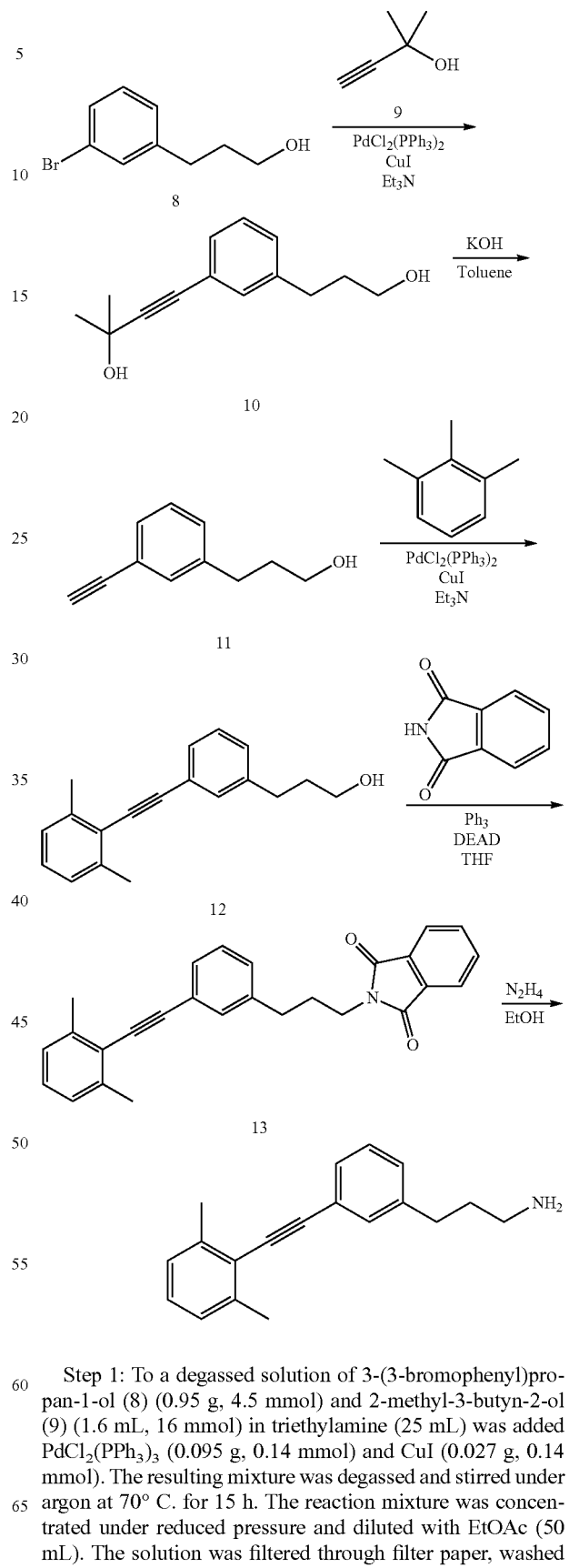

Step 1: To a degassed solution of 3-(3-bromophenyl)propan-1-ol (8) (0.95 g, 4.5 mmol) and 2-methyl-3-butyn-2-ol (9) (1.6 mL, 16 mmol) in triethylamine (25 mL) was added PdCl$_2$(PPh$_3$)$_3$ (0.095 g, 0.14 mmol) and CuI (0.027 g, 0.14 mmol). The resulting mixture was degassed and stirred under argon at 70° C. for 15 h. The reaction mixture was concentrated under reduced pressure and diluted with EtOAc (50 mL). The solution was filtered through filter paper, washed with water (50 mL) and brine (50 mL), dried over Na₂SO₄ and concentrated under reduced pressure. Purification by flash chromatography (10 to 100% EtOAc-hexanes gradient) gave 4-(3-(3-hydroxypropyl)phenyl)-2-methylbut-3-yn-2-ol (10) as a light brown oil: Yield (0.78 g, 80%): ¹H NMR (400 MHz, DMSO-d₆) δ 7.29-7.18 (m, 4H), 5.46 (s, 1H), 4.48 (t, J=5.2 Hz, 1H), 3.38 (q, J=6.0 Hz, 2H), 2.59 (t, J=7.2 Hz, 2H), 1.66-1.73 (m, 2H), 1.46 (s, 6H).

Step 2: To a solution of 4-(3-(3-hydroxypropyl)phenyl)-2-methylbut-3-yn-2-ol (10) (0.750 g, 3.4 mmol) in toluene (50 mL) was added powdered KOH (0.390 g, 7 mmol). The resulting mixture was heated to reflux for 45 min, concentrated under reduced pressure to 10-15 mL and diluted with EtOAc (100 mL). The solution was washed with water (2×100 mL) and brine (50 mL), dried over MgSO₄ and concentrated under reduced pressure. Purification by flash chromatography gave 3-(3-ethynylphenyl)propan-1-ol (11) as a light brown oil. Yield (0.272 g, 49%): ¹H NMR (400 MHz, DMSO-d₆) δ 7.24-7.32 (m, 4H), 4.49 (t, J=5.2 Hz, 1H), 4.15 (s, 1H), 3.39 (dt, J=6.4, 5.6 Hz, 2H), 2.60 (t, J=7.6 Hz, 2H), 1.66-1.73 (m, 2H).

Step 3: To a degassed solution of 3-(3-ethynylphenyl)propan-1-ol (11) (0.270 g, 1.7 mmol) and 2-iodo-1,3-dimethylbenzene (0.392 g, 1.7 mmol) in triethylamine (10 mL) was added PdCl₂(PPh₃)₃ (0.036 g, 0.05 mmol) and CuI (0.010 g, 0.05 mmol). The resulting mixture was degassed and stirred under argon at 70° C. for 1.5 h. The reaction mixture was concentrated under reduced pressure and diluted with EtOAc (30 mL). The solution was filtered through filter paper, washed with water (2×20 mL), dried over Na₂SO₄ and concentrated under reduced pressure. Purification by flash chromatography (7 to 60% EtOAc-hexanes gradient) gave (3-((2,6-dimethylphenyl)ethynyl)phenyl)propan-1-ol (12) as a light brown oil. Yield (0.085 g, 19%). This material was taken on to the next synthetic step without further purification.

Step 4: Triphenylphosphine (0.087 g, 0.33 mmol), phthalimide (0.049 g, 0.33 mmol) and (3-((2,6-dimethylphenyl)ethynyl)phenyl)propan-1-ol (12) (0.085 g, 0.32 mmol) were dissolved in anhydrous THF (3 mL) under argon, and the solution was cooled over an ice bath. Diethyl azodicarboxylate (0.052 mL, 0.33 mmol) was added dropwise with rapid stirring, and the resulting mixture was stirred at room temperature for 2.5 h. The reaction mixture was concentrated under reduced pressure and purified by flash chromatography (6 to 60% EtOAc-hexanes gradient) to yield 2-(3-(3-((2,6-dimethylphenyl)ethynyl)phenyl)propyl)isoindoline-1,3-dione (13) as a white solid. Yield (0.095 g, 75%): ¹H NMR (400 MHz, DMSO-d₆) δ 7.82-7.89 (m, 4H), 7.42 (s, 1H), 7.13-7.35 (m, 6H), 3.63 (t, J=7.2 Hz, 2H), 2.67 (t, J=7.6 Hz, 2H), 2.51 (s, 6H), 1.90-1.97 (m, 2H).

Step 5: A solution of 2-(3-(3-((2,6-dimethylphenyl)ethynyl)phenyl)propyl)isoindoline-1,3-dione (13) (0.094 g, 0.24 mmol) and hydrazine hydrate (0.038 g, 0.75 mmol) in dry EtOH (5 mL) was heated under reflux for 3 h. Additional hydrazine hydrate (0.038 g, 0.75 mmol) was added and heating continued for a further 4 h. The solvent was removed under reduced pressure and the residue was sonicated in a mixture of hexanes and aqueous Na₂SO₄. The mixture was filtered through Celite and washed with hexanes. The organic layer was concentrated under reduced pressure. Purification by flash chromatography (10:1:9 EtOAc/7 M NH₃ in MeOH/hexanes) gave 3-(3-((2,6-dimethylphenyl)ethynyl)phenyl)propan-1-amine as a colorless oil. Yield (0.015 g, 25%): ¹H NMR (400 MHz, DMSO-d₆) δ 7.32-7.39 (m, 3H), 7.25 (m, 1H), 7.13-7.22 (m, 3H), 2.65 (t, J=7.6 Hz, 2H), 2.54 (t, J=7.2 Hz, 2H), 2.46 (s, 6H), 1.61-1.69 (m, 2H), 1.40 (br s, 2H).

Example 18

PREPARATION OF 4-((3-(2-AMINOETHOXY)PHENYL)ETHYNYL)HEPTAN-4-OL

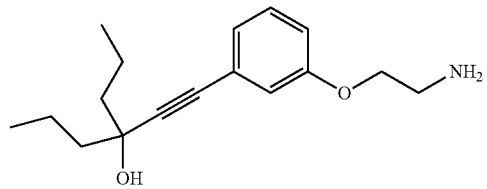 [SMILES: CCCC(O)(C#Cc1cccc(OCCN)c1)CCC]

4-((3-(2-Aminoethoxy)phenyl)ethynyl)heptan-4-ol was prepared following the method shown in Scheme 4:

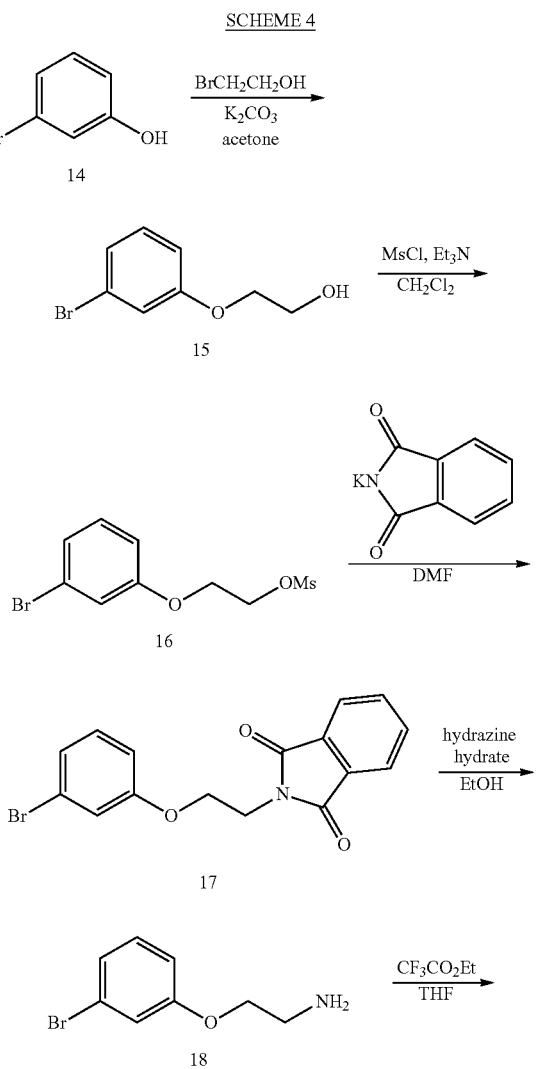

-continued

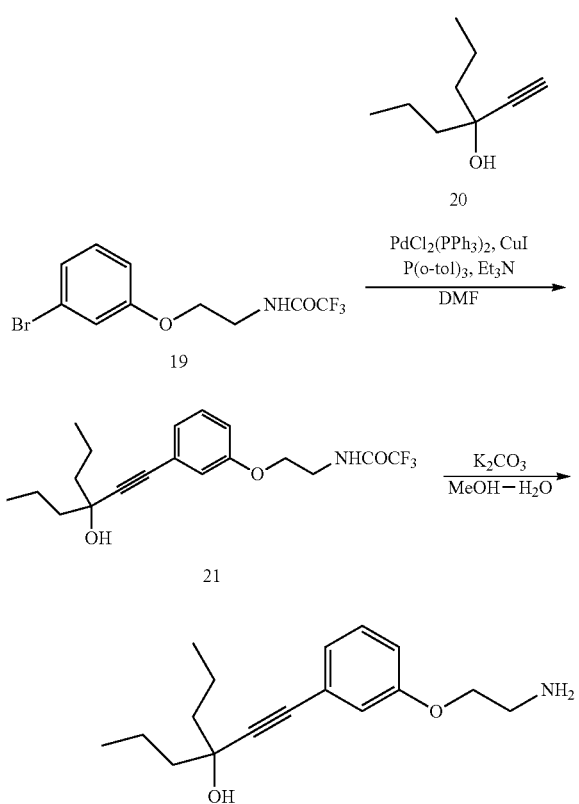

Step 1: To a solution of 3-bromophenol (14) (36.38 g, 210.3 mmol) in acetone (175 ml) was added $K_2CO_3$ (0.033 g, 237 mmol) and 2-bromoethanol (20 ml, 283.3 mmol). The mixture was heated to reflux for 4 d under argon then cooled to room temperature. The solids were removed by filtration and the filtrate concentrated under reduced pressure. The residue was dissolved in diethyl ether (150 ml) and washed with water (100 ml), aqueous NaOH (10%, 100 ml, 3×50 mL, 5%, 200 ml), water (100 ml), and brine, dried over $MgSO_4$ and concentrated under reduced pressure to give 2-(3-bromophenoxy)ethanol (15) as light brown oil. Yield (21.07 g, 46%): $^1$H NMR (400 MHz, $CDCl_3$) δ 7.14 (t, J=7.8 Hz, 1H), 7.07-7.12 (m, 2H), 6.85 (ddd, J=7.8, 2.4, 1.3 Hz, 1H), 4.06 (m, 2H), 3.95 (m, 2H), 2.11 (t, J=12.3 Hz, 1H).

Step 2: To an ice-cold mixture of 2-(3-bromophenoxy)ethanol (15) (16.06 g, 74.0 mmol) and triethylamine (9.12 g, 90.13 ml) in anhydrous $CH_2Cl_2$ (120 ml) under argon was slowly added neat methanesulfonyl chloride (6 ml, 77.2 mmol) and the reaction mixture stirred at 0° C. for 15 min. A precipitate formed after the addition was complete. The mixture was concentrated under reduced pressure and the residue was dissolved in EtOAc, washed twice with water, once with brine, dried over $MgSO_4$ and concentrated under reduced pressure. 2-(3-Bromophenoxy)ethyl methanesulfonate (16) was isolated as a brown oil and used in the next synthetic step without further purification. Yield (21.32 g, 98%): $^1$H NMR (400 MHz, $CDCl_3$) δ 7.16 (t, J=7.8 Hz, 1H), 7.11-7.14 (m, 1H), 7.07 (m, 1H), 6.39 (ddd, J=7.6, 2.5, 1.8 Hz, 1H), 4.56 (m, 2H), 4.22 (m, 2H), 3.08 (s, 3H).

Step 3: To a solution of mesylate 16 (24.05 g, 81.5 mmol) in anhydrous DMF (160 ml) was added potassium phthalimide (15.53 g, 83.8 mmol) and the reaction mixture stirred at 60° C. for 14 h. After cooling to room temperature, the mixture was concentrated under reduced pressure. The residue was diluted with hexanes-EtOAc (7:1, 150 ml) and water (150 ml) and the mixture shaken in separating funnel. A precipitate formed which was removed by filtration, washed excessively with water and hexane, then dried under vacuum to give N-(2-(3-bromophenoxy)ethyl)phthalimide (17) as white fluffy crystals (22.05 g, 78%). The organic layer of the filtrate was concentrated under reduced pressure and the residue was suspended in 10% EtOAc-hexanes. The solution was washed with water and the precipitate collected by filtration, washed with water then hexanes and dried under vacuum to give additional phthalimide 17 (5.65 g). Combined yield (21.18 g, 98%): $^1$H NMR (400 MHz, $CDCl_3$) δ 7.86 (m, 2H), 7.73 (m, 2H), 7.03-7.12 (m, 3H), 6.80 (ddd, J=8.0, 2.5 and 1.4 Hz, 1H), 4.21 (t, J=6.9 Hz, 2H), 4.10 (t, J=6.0 Hz, 2H).

Step 4: To a suspension of phthalimide 17 (22.82 g, 65.9 mmol) in absolute EtOH (200 ml) was added hydrazine hydrate (6 ml, 123.7 mmol) and the reaction mixture heated to reflux under argon for 1.5 h. After cooling to room temperature, solids were removed by filtration and the filtrate concentrated under reduced pressure. The residue was re-suspended in hexane (100 ml) and the mixture was filtered. The filtrate was concentrated under reduced pressure then dried by concentration from EtOH and then toluene to give amine 18 as a thick yellow oil. Yield (10.63 g, 75%): $^1$H NMR (400 MHz, $CDCl_3$) δ 7.06-7.15 (m, 3H), 6.84 (ddd, J=8.0, 2.5, 1.2 Hz, 1H), 3.96 (t, J=5.3 Hz, 2H), 3.07 (t, J=5.1 Hz, 2H), 1.43 (s, 2H).

Step 5: To a solution of amine 18 (10.63 g, 49.2 mmol) in anhydrous THF (80 ml) was added ethyl trifluoroacetate (12 ml, 100.6 mmol) and the reaction mixture stirred at room temperature overnight. The solution was concentrated under reduced pressure and the residue dissolved in 50% EtOAc-hexanes. The solution was filtered through a layer of a silica gel and eluted with 50% EtOAc-hexanes. Concentration under reduced pressure gave bromide 19 as a pale yellow oil which crystallized upon standing to a light yellow solid. Yield (13.69 g, 89%): $^1$H NMR (400 MHz, $CDCl_3$) δ 7.16 (t, J=8.0 Hz, 1H), 7.12-7.14 (m, 1H), 7.05-7.07 (m, 1H), 6.83 (ddd, J=7.6, 2.5, 1.8 Hz, 1H), 6.75 (br s, 1H), 4.09 (t, J=4.9 Hz, 2H), 3.78 (dt, J=5.5 Hz, 2H).

Step 6: Bromide 19 was coupled with alkynol 20 following the procedure described in Example 1 except that the reaction was run for 20 h to give alkyne 21 as a yellow oil. Yield (0.89 g, 73%): $^1$H NMR (400 MHz, $CDCl_3$) δ 7.22 (t, J=8.0 Hz, 1H), 7.06 (dt, J=7.6, 1.0 Hz, 1H), 6.93 (dd, J=2.5, 1.4 Hz, 1H), 6.85 (ddd, J=8.4, 2.7, 1.0 Hz, 1H), 6.77 (br s, 1H), 4.09 (t, J=5.1 Hz, 2H), 3.78 (dt, J=5.5 Hz, 2H), 2.00 (s, 1H), 1.67-1.73 (m, 4H), 1.57-1.61 (m, 4H), 0.98 (t, J=7.4 Hz, 6H)

Step 7: Alkyne 21 was deprotected according to the procedure described in Example 1, except that the reaction was run with 5 equivalents of $K_2CO_3$ at room temperature for 7 h, followed by purification by flash chromatography (9:1 EtOAc: (7 M ammonia in MeOH) to give Example 18 trifluoroacetate as a cream-colored solid. Yield (5 g, 76%): $^1$H NMR (400 MHz, DMSO-$d_6$) δ 7.23 (t, J=7.8 Hz, 1H), 6.92-6.93 (m, 1H), 6.90-6.91 (m, 1H), 6.85-6.86 (m, 1H), 5.13 (br s, 1H), 3.89 (t, J=5.9 Hz, 2H), 2.83 (t, J=5.7 Hz, 2H), 1.42-1.60 (m, 10H), 0.89 (t, J=7.2 Hz, 6H); $^{13}$C NMR (100 MHz, DMSO-$d_6$) δ 159.28, 130.47, 124.49, 124.26, 117.34, 115.80, 94.78, 83, 15, 71.03, 70.26, 44.86, 41.60, 17.96, 15.01. ESI MS m/z 276.39 [M+H]⁺, 258.38 [M+H−H₂O]⁺.

Example 19

PREPARATION OF 4-((3-(3-AMINO-1-HYDROXYPROPYL)PHENYL)ETHYNYL)HEPTAN-4-OL

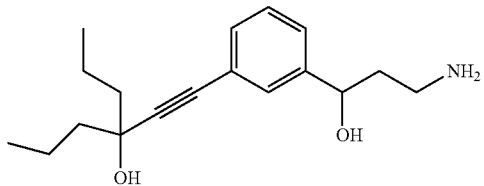 [SMILES: CCCC(O)(C#Cc1cccc(C(O)CCN)c1)CCC]

4-((3-(3-Amino-1-hydroxypropyl)phenyl)ethynyl)heptan-4-ol was prepared following the method shown in Scheme 5:

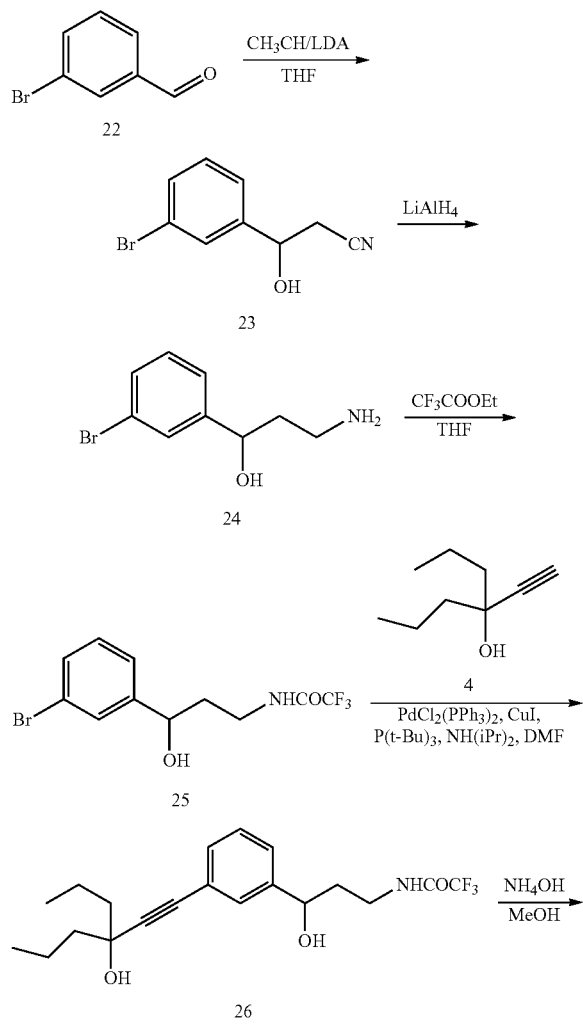

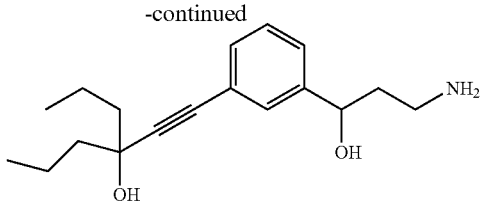

Step 1: To a −78° C. solution of acetonitrile (1.05 mL, 20 mmol) in anhydrous THF (25 mL) under argon, was added lithium diisopropylamide (11 mL of a 2 M solution in THF, 22 mmol) dropwise. The resulting mixture was stirred at −78° C. for 15 min. A solution of 3-bromobenzaldehyde (22) (2.78 g, 15 mmol) in anhydrous THF (10 mL) was added dropwise. The reaction mixture was allowed to warm to room temperature, then concentrated under reduced pressure and diluted with EtOAc (75 mL). The solution was washed with water (50 mL) and brine (50 mL), dried over Na₂SO₄ and concentrated under reduced pressure. Purification by flash chromatography (20 to 100% EtOAc-hexanes gradient) gave 3-(3-bromophenyl)-3-hydroxypropanenitrile (23) as a light yellow oil. Yield (2.75 g, 81%): ¹H NMR (400 MHz, DMSO-d₆) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 4.87-4.92 (m, 1H), 2.94-2.80 (m, 2H).

Step 2: To an ice cold solution of 3-(3-bromophenyl)-3-hydroxypropanenitrile (23) (2.70 g, 11.9 mmol) in anhydrous THF (20 mL) under argon was added a solution of LiAlH₄ in THF (11.9 mL of a 2 M solution in THF, 23.8 mmol). The mixture was stirred at 0° C. for 45 min, diluted with ether (50 mL), and quenched with the dropwise addition of saturated aqueous Na₂SO₄ (approximately 2 mL). After drying over MgSO₄, the solution was filtered and concentrated under reduced pressure to give amine 24 as a light green oil. Yield (2.30 g, 84%.) This material was used in the next step without further purification. ¹H NMR (400 MHz, DMSO-d₆) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 3: To a solution of 3-amino-1-(3-bromophenyl)propan-1-ol (24) (2.30 g, 10 mmol) in anhydrous THF (20 mL) was added ethyl trifluoroacetate (4.0 mL, 33.5 mmol). The reaction mixture was stirred at room temperature for 3 h, then concentrated under reduced pressure. Purification by column chromatography (10 to 70% EtOAc-hexanes gradient) gave N-(3-(3-bromophenyl)-3-hydroxypropyl)-2,2,2-trifluoroacetamide (25) as an oil containing ~15% of 2,2,2-trifluoro-N-(3-hydroxy-3-phenylpropyl)acetamide. Yield (1.96 g, 60%): ¹H NMR (400 MHz, DMSO-d₆) δ 9.33 (s, 1H), 7.51 (t, J=2.0 Hz, 1H), 7.41 (dt, J=7.6, 2.0 Hz, 1H), 7.25-7.32 (m, 2H), 5.46 (d, J=6.4 Hz, 1H), 4.55-4.60 (m, 1H), 3.20-3.23 (m, 2H), 1.75-1.82 (m, 2H).

Step 4: Coupling of N-(3-(3-bromophenyl)-3-hydroxypropyl)-2,2,2-trifluoroacetamide (25) (1.95 g, 6 mmol) with 4-ethynylheptan-4-ol (20) following the method described in Example 15 gave 2,2,2-trifluoro-N-(3-hydroxy-3-(3-(3-hydroxy-3-propylhex-1-ynyl)phenyl)propyl)acetamide (26) as a light brown oil. Yield (0.87 g, 37%): ¹H NMR (400 MHz, DMSO-d₆) δ 9.35 (m, 1H), 7.29-7.34 (m, 3H), 7.22-7.26 (m, 1H), 5.39 (d, J=4.4 Hz, 1H), 5.12 (s, 1H), 4.59 (dt, J=8.4, 4.8 Hz, 1H), 3.25 (quint, J=7.6 Hz, 2H), 1.80 (quint, J=8.0 Hz, 2H), 1.44-1.63 (m, 8H), 0.92 (t, J=7.2 Hz, 6H).

Step 5: Deprotection of 2,2,2-trifluoro-N-(3-hydroxy-3-(3-(3-hydroxy-3-propylhex-1-ynyl)phenyl)propyl)acetamide (26) following the method described in Example 2 gave Example 19. Yield (0.303 g, 47%): ¹H NMR (400 MHz, DMSO-$d_6$) δ 7.16-7.32 (m, 4H), 5.13 (s, 1H), 4.65 (t, J=6.0 Hz, 1H), 2.56-2.64 (m, 2H), 1.44-1.63 (m, 12H), 0.90 (t, J=7.6 Hz, 6H).

Alternatively, the following reagents and conditions can be used to prepare Example 19.

Step 1: To a cold (−50° C.) stirred solution of potassium tert-butoxide (1M/THF, 703 mL, 703 mmol) under argon was added $CH_3CN$ (27.73 g, 675.6 mmol) via syringe over 5 min and the reaction mixture was stirred at −50° C. for 30 min. Then a solution of 3-bromobenzaldehyde (22) (100 g, 540.5 mmol) was added over 5 min. The reaction mixture was stirred for 30 min at −50° C. and allowed to warm to room temperature. Aqueous $NH_4Cl$ (25%, 250 mL) was added, the mixture was stirred and layers were separated. Organic layer was washed with saturated brine (200 mL), dried over anhydrous $Na_2SO_4$, filtered, the filtrate was concentrated under reduced pressure and the residue was dried in vacuum overnight to give hydroxynitrile 23 as a pale yellow oil. Yield (117.6 g, 96%); $^1$H NMR (400 MHz, DMSO-$d_6$) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 2.94-2.80 (m, 2H).

Step 2: To a solution of 3-(3-bromophenyl)-3-hydroxypropanenitrile (23) (117.5 g, 519.8 mmol) in anhydrous THF (300 mL) under argon borane-methylsulfide (68 mL, 675.7 mmol) was slowly added over 30 min via a dropping funnel. The reaction mixture was boiled under reflux for 2.5 hr and cooled to room temperature. HCl solution (1.25M in EtOH, 350 mL) was slowly added for 30 min and the mixture was concentrated under reduced pressure. Water (400 mL) was added and the pH of the mixture was then adjusted to 12 with aqueous NaOH (50% wt). The product was extracted with $CH_2Cl_2$ (500 mL), the extract was dried over anhydrous $Na_2SO_4$ and concentrated under reduced pressure to give hydroxyamine 24 as a colorless oil. Yield (104 g, 87%). $^1$H NMR (400 MHz, DMSO-$d_6$) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 3: To a cooled (0° C.) solution of 3-amino-1-(3-bromophenyl)propan-1-ol (24) (40 g, 173.8 mmol) in MTBE (250 mL) was added ethyl trifluoroacetate (28 mL, 234.7 mmol) over 7 min and the reaction mixture was stirred at room temperature for 50 min. Concentration under reduced pressure gave trifluoroacetamide 25 as a colorless oil. Yield (55.35 g, 98%): $^1$H NMR (400 MHz, DMSO-$d_6$) δ 9.33 (s, 1H), 7.51 (t, J=2.0 Hz, 1H), 7.41 (dt, J=7.6, 2.0 Hz, 1H), 7.25-7.32 (m, 2H), 5.46 (d, J=6.4 Hz, 1H), 4.55-4.60 (m, 1H), 3.20-3.23 (m, 2H), 1.75-1.82 (m, 2H).

Step 4: Coupling of N-(3-(3-bromophenyl)-3-hydroxypropyl)-2,2,2-trifluoroacetamide (25) (55.35 g, 169.7 mmol) with 4-ethynylheptan-4-ol (20) (30.13 g, 214.9 mmol) following the method described in Example 1 gave crude 2,2,2-trifluoro-N-(3-hydroxy-3-(3-(3-hydroxy-3-propylhex-1-ynyl)phenyl)propyl)acetamide (26) as a brown oil which was used in the next step without additional purification. Yield (90.32 g, quant.): $^1$H NMR (400 MHz, DMSO-$d_6$) δ 9.35 (m, 1H), 7.29-7.34 (m, 3H), 7.22-7.26 (m, 1H), 5.39 (d, J=4.4 Hz, 1H), 5.12 (s, 1H), 4.59 (dt, J=8.4, 4.8 Hz, 1H), 3.25 (quint, J=7.6 Hz, 2H), 1.80 (quint, J=8.0 Hz, 2H), 1.44-1.63 (m, 8H), 0.92 (t, J=7.2 Hz, 6H).

Step 5: Deprotection of 2,2,2-trifluoro-N-(3-hydroxy-3-(3-(3-hydroxy-3-propylhex-1-ynyl)phenyl)propyl)acetamide (26) following the method described in Example 14 gave Example 19 after purification by column chromatography on a silica gel twice (first chromatography: EtOAc, then 10% 7N $NH_3$/MeOH in $CH_2Cl_2$; second: 8% 7N $NH_3$/MeOH in $CH_2Cl_2$). Yield (29.97 g, 60%): $^1$H NMR (400 MHz, DMSO-$d_6$) δ 7.16-7.32 (m, 4H), 5.13 (s, 1H), 4.65 (t, J=6.0 Hz, 1H), 2.56-2.64 (m, 2H), 1.44-1.63 (m, 12H), 0.90 (t, J=7.6 Hz, 6H).

Example 20

PREPARATION OF 4-((3-(3-AMINO-2,2-DIMETHYLPROPYL)PHENYL)ETHYNYL)HEPTAN-4-OL

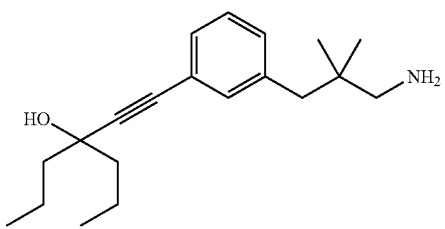 [SMILES: CCCC(O)(C#Cc1cccc(CC(C)(C)CN)c1)CCC]

4-((3-(3-Amino-2,2-dimethylpropyl)phenyl)ethynyl)heptan-4-ol was prepared following the method shown in Scheme 6:

SCHEME 6

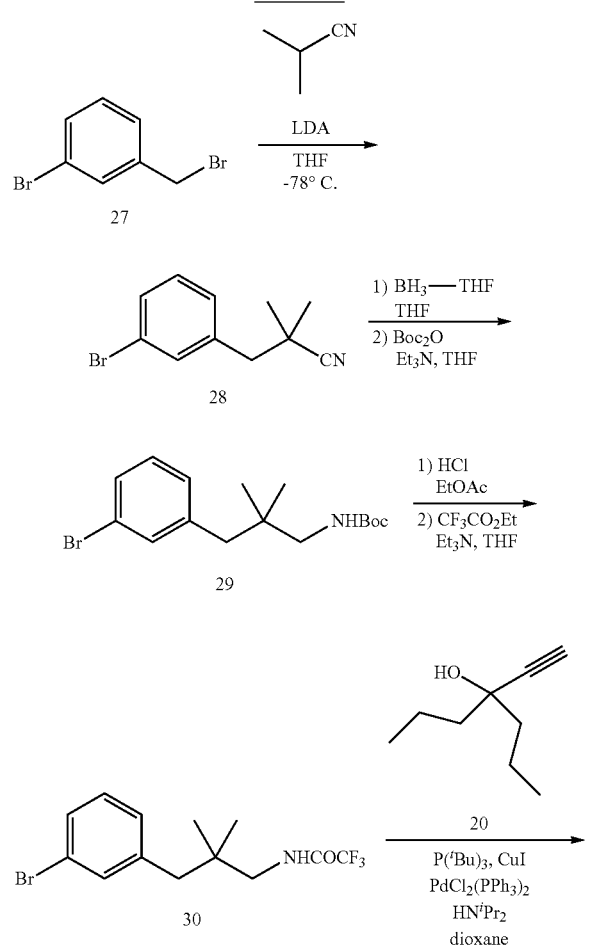

-continued

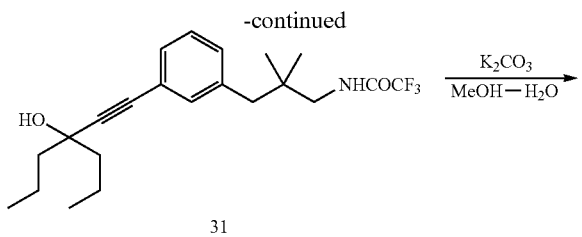

31

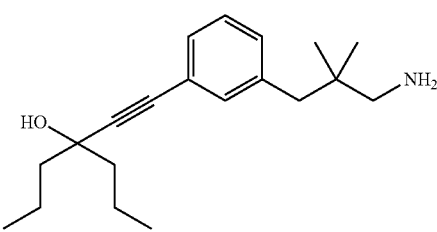

Step 1: An oven-dried flask under argon was charged with isobutyronitrile (2.15 mL, 24.0 mmol) and anhydrous THF (60 mL) and cooled to −78° C. A solution of lithium diisopropylamide (12 mL of a 2.0 M solution in heptane/THF/ethylbenzene, 24 mmol) was added in aliquots over 20 min then the reaction was stirred for 25 min. 3-Bromobenzyl bromide (27) (3.98 g, 15.92 mmol) was added and the cold bath was removed. After stirring for an additional 2 h, the reaction was quenched with the slow addition of water, then EtOAc was added. The aqueous layer was partly saturated with sodium chloride. The layers were separated, and the aqueous layer was extracted with EtOAc twice. The combined organics were washed with water and brine, dried over $Na_2SO_4$ and concentrated under reduced pressure to give nitrile 28 as an orange oil which later solidified (4.16 g, quant. yield). This material was used in the next synthetic step without further purification. $^1$H NMR (400 MHz, $CDCl_3$) δ 7.40-7.45 (m, 2H), 7.20-7.25 (m, 2H), 2.78 (s, 2H), 1.36 (s, 6H).

Step 2: To an ice-cold mixture of crude 3-(3-bromophenyl)-2,2-dimethylpropanenitrile (28) (3.0 g, 12.6 mmol) in anhydrous THF (20 mL) was added $BH_3$-THF (20 mL of a 1M solution in THF, 20 mmol) slowly. The reaction was allowed to warm slowly and stirred for 19 h. The reaction was quenched with the dropwise addition of 6 M HCl then stirred for 1.5 h. Volatiles were removed under reduced pressure. The aqueous layer was extracted with diethyl ether twice then EtOAc was added and the mixture was made basic with 5 M aqueous KOH. The layers were separated and the aqueous layer was extracted with EtOAc twice. The combined organics were washed with brine, dried over $Na_2SO_4$ and concentrated under reduced pressure to give 3-(3-bromophenyl)-2,2-dimethylpropan-1-amine as a light yellow oil (2.3 g). This material was taken on to the next step without further purification. $^1$H NMR (400 MHz, $CDCl_3$) δ 7.32-7.35 (m, 1H), 7.30 (t, J=1.7 Hz, 1H), 7.13 (t, J=7.7 Hz, 1H), 7.06 (dd, J=7.6, 1.2 Hz, 1H), 2.50 (s, 2H), 2.47 (s, 2H), 0.84 (s, 6H).

Step 3: Crude 3-(3-bromophenyl)-2,2-dimethylpropan-1-amine (2.3 g) was dissolved in THF (40 mL). Di-tert-butyl dicarbonate (2.3 g, 10.5 mmol), then triethylamine (2.8 mL, 20.1 mmol) were added and the mixture was stirred for 1.5 h. The reaction mixture was concentrated under reduced pressure and the product was purified by flash chromatography (0-35% EtOAc-hexanes gradient) to give aryl bromide 29 as a colorless oil. Yield (3.3 g, 77%): $^1$H NMR (400 MHz, $CDCl_3$) δ 7.34 (d, J=7.6 Hz, 1H), 7.27 (t, J=1.6 Hz, 1H), 7.14 (t, J=7.7 Hz, 1H), 7.05 (d, J=7.8 Hz, 1H), 4.58 (br s, 1H), 2.98 (d, J=6.5 Hz, 2H), 2.48 (s, 2H), 1.45 (s, 9H), 0.85 (s, 6H).

Step 4: tert-Butyl 3-(3-bromophenyl)-2,2-dimethylpropylcarbamate (29) (3.2 g, 9.35 mmol) was dissolved in EtOAc (55 mL), and a solution of HCl-EtOAc (~4.2 M, 20 mL, 84 mmol) was added. The reaction was vented with a needle and stirred at room temperature for 2.5 h. The reaction was then diluted with hexanes and the white solid was collected on a fritted glass funnel. The mother liquor was concentrated under reduced pressure, suspended in ~5-10% EtOAc-hexanes, and the white solid was collected and combined with the first batch. The solid was dried in a vacuum oven at room temperature overnight to give pure 3-(3-bromophenyl)-2,2-dimethylpropan-1-amine hydrochloride as a white solid. Yield (1.52 g): $^1$H NMR (400 MHz, $CDCl_3$) δ 8.53 (br s, 2H), 7.37 (dq, J=1.2 and 8.0 Hz, 1H), 7.31 (t, J=1.6 Hz, 1H), 7.13 (t, J=7.7 Hz, 1H), 7.08 (dt, J=8.0, 1.6 Hz, 1H), 2.83-2.84 (m, 2H), 2.67 (s, 2H), 1.09 (s, 6H).

Step 5: 3-(3-Bromophenyl)-2,2-dimethylpropan-1-amine hydrochloride (1.52 g, 5.45 mmol) was dissolved in anhydrous THF (50 mL). $Et_3N$ (1.5 mL, 10.76 mmol) was added slowly to produce a white slurry. Ethyl trifluoroacetate (2 mL, 16.8 mmol) was added and the mixture was stirred at room temp for 15.5 h. Additional ethyl trifluoroacetate (~0.75 mL, 6.2 mmol) and triethylamine (0.75 mL, 5.4 mmol) were added and the mixture was stirred for 4 h. The reaction mixture was concentrated under reduced pressure. The product was taken up in EtOAc and the solution was washed with saturated aqueous $NaHCO_3$ (2×) and brine, dried over $Na_2SO_4$ and concentrated under reduced pressure to give N-(3-(3-bromophenyl)-2,2-dimethylpropyl)-2,2,2-trifluoroacetamide (30) as a yellow oil. Yield (1.84 g, 58% yield for two steps): $^1$H NMR (400 MHz, $CDCl_3$) δ 7.39 (ddd, J=8.0, 2.0, 0.8 Hz, 1H), 7.29 (t, J=1.6 Hz, 1H), 7.17 (t, J=7.6 Hz, 1H), 7.05 (dt, J=7.6, 1.6 Hz, 1H), 6.16 (br s, 1H), 3.24 (d, J=6.8 Hz, 2H), 2.53 (s, 2H), 0.93 (s, 6H).

Step 6: N-(3-(3-bromophenyl)-2,2-dimethylpropyl)-2,2,2-trifluoroacetamide (30) (0.489 g, 1.45 mmol) was coupled with 4-ethynylheptan-4-ol (20) (0.28 g, 2.0 mmol) following the method described in Example 15 and the product was purified by flash chromatography (0 to 50% EtOAc-hexanes gradient) to give 2,2,2-trifluoro-N-(3-(3-(3-hydroxy-3-propylhex-1-ynyl)phenyl)-2,2-dimethylpropyl)acetamide (31) as a yellow oil. Yield (0.350 g, 61%): $^1$H NMR (400 MHz, $CD_3OD$) δ 7.20-7.25 (m, 3H), 7.12-7.15 (m, 1H), 3.19 (s, 2H), 2.54 (s, 2H), 1.58-1.71 (m, 8H), 0.98 (t, J=7.2 Hz, 6H), 0.85 (s, 6H).

Step 7: Deprotection of 2,2,2-trifluoro-N-(3-(3-(3-hydroxy-3-propylhex-1-ynyl)phenyl)-2,2-dimethylpropyl)acetamide (31) (0.345 g, 0.87 mmol) was conducted following the method described in Example 1 and the product was purified by flash chromatography (90 to 100% EtOAc-hexanes then 10% 3.5 M $NH_3$ in MeOH-EtOAc) to give Example 20 as an oil along with recovered starting material. Yield (0.0847 g, 32% yield): $^1$H NMR (400 MHz, $CD_3OD$) δ 7.19-

7.24 (m, 3H), 7.11-7.13 (m, 1H), 2.53 (s, 2H), 2.44 (s, 2H), 1.56-1.72 (m, 8H), 0.98 (t, J=7.2 Hz, 6H), 0.85 (s, 6H).

Example 21

PREPARATION OF 1-(3-(3-AMINOPROPYL) PHENYL)-3,4-DIMETHYLPENT-1-YN-3-OL

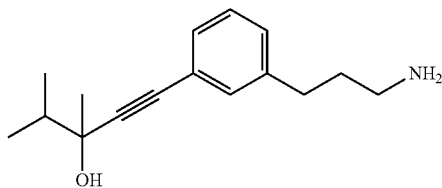

1-(3-(3-Aminopropyl)phenyl)-3,4-dimethylpent-1-yn-3-ol was prepared following the method used in Example 1.

Step 1: Coupling of 3,4-dimethylpent-1-yn-3-ol with bromide 3 gave 2,2,2-trifluoro-N-(3-(3-(3-hydroxy-3,4-dimethylpent-1-ynyl)phenyl)propyl)acetamide as an amber oil. Yield (0.98 g, 89%): $^1$H NMR (400 MHz, CD$_3$OD) δ 7.15-7.25 (m, 4H), 3.27-3.31 (m, 2H), 2.62 (t, J=7.6 Hz, 2H), 1.82-1.90 (m, 3H), 1.50 (s, 3H), 1.09 (d, J=6.4 Hz, 3H), 1.05 (d, J=6.8 Hz, 3H).

Step 2: Deprotection of 2,2,2-trifluoro-N-(3-(3-(3-hydroxy-3,4-dimethylpent-1-ynyl)phenyl)propyl)acetamide gave Example 21 as a yellow oil. Yield (0.456 g, 65%): $^1$H NMR (400 MHz, CD$_3$OD) δ 7.15-7.25 (m, 4H), 2.60-2.65 (m, 4H), 1.85 (quint, J=6.8 Hz, 1H), 1.72-1.79 (m, 2H), 1.47 (s, 3H), 1.09 (d, J=6.8 Hz, 3H), 1.05 (d, J=6.8 Hz, 3H).

Example 22

PREPARATION OF 4-(3-(3-AMINOPROPYL) PHENYL)-2-PHENYLBUT-3-YN-2-OL

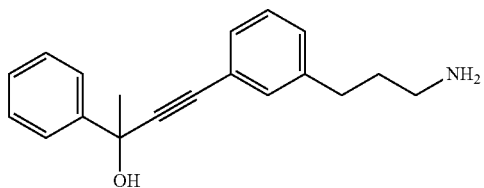 [SMILES: CC(O)(C#Cc1cccc(CCCN)c1)c1ccccc1]

1-((4-(3-(3-Aminopropyl)phenyl)-2-phenylbut-3-yn-2-ol was prepared following the method described in Example 7.

Step 1: Coupling of 2-phenylbut-3-yn-2-ol with bromide 3 gave 2,2,2-trifluoro-N-(3-(3-(3-hydroxy-3-phenylbut-1-ynyl)phenyl)propyl)acetamide as a yellow oil. $^1$H NMR (400 MHz, DMSO-d$_6$) δ 9.41 (br s, 1H), 7.62 (m, 2H), 7.51 (m, 1H), 7.36 (m, 2H), 7.26 (m, 4H), 6.15 (s, 1H), 3.16 (m, 2H), 2.57 (m, 2H), 1.78 (m, 2H), 1.69 (s, 3H).

Step 2: Deprotection of 2,2,2-trifluoro-N-(3-(3-(3-hydroxy-3-phenylbut-1-ynyl)phenyl)propyl)acetamide gave Example 22 as a yellow oil. Yield (0.122 g, 27% for two steps): $^1$H NMR (400 MHz, DMSO-d$_6$) δ 7.60-7.63 (m, 1H), 7.33-7.38 (m, 1H), 7.18-7.28 (m, 7H), 6.16 (br s, 1H), 2.57 (m, 2H), 2.51 (m, 2H), 1.69 (s, 3H), 1.56-1.63 (m, 2H), 1.34 (br s, 2H).

Example 23

PREPARATION OF 1-(3-(3-AMINOPROPYL) PHENYL)-4-METHYLPENT-1-YN-3-OL

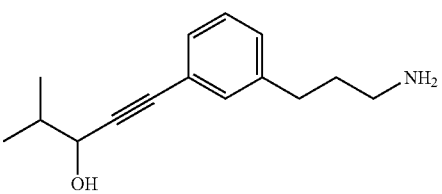 [SMILES: CC(C)C(O)C#Cc1cccc(CCCN)c1]

1-(3-(3-Aminopropyl)phenyl)-4-methylpent-1-yn-3-ol was prepared following the method described in Example 7.

Step 1: Coupling of 4-methylpent-1-yn-3-ol with bromide 3 gave 2,2,2-trifluoro-N-(3-(3-(3-hydroxy-4-methylpent-1-ynyl)phenyl)propyl)acetamide as a yellow oil contaminated with alkyne dimer which was used without purification in the next step. $^1$H NMR (400 MHz, DMSO-d$_6$) δ 9.40 (br s, 1H), 7.18-7.29 (m, 4H), 5.37 (d, J=5.6 Hz, 1H), 4.20 (t, J=5.6 Hz, 1H), 3.16 (dt, J=6.8, 6.0 Hz, 2H), 2.56 (t, J=7.6 Hz, 2H), 1.70-1.81 (m, 3H), 0.96 (d, J=6.8 Hz, 3H), 0.94 (d, J=6.8 Hz, 3H).

Step 2: Deprotection of 2,2,2-trifluoro-N-(3-(3-(3-hydroxy-4-methylpent-1-ynyl)phenyl)propyl)acetamide gave Example 23 as a yellow oil. Yield (10.174 g, 47%, two steps): $^1$H NMR (400 MHz, DMSO-d$_6$) δ 7.15-7.27 (m, 4H), 4.29 (d, J=5.6 Hz, 1H), 2.63 (m, 4H), 1.88 (m, 1H), 1.76 (m, 2H), 0.96 (d, J=6.8 Hz, 3H), 0.94 (d, J=6.4 Hz, 3H).

Example 24

PREPARATION OF 1-((3-(3-AMINOPROPYL)PHENYL)ETHYNYL) CYCLOPENTANOL

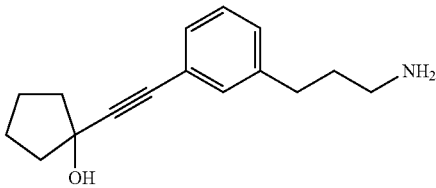 [SMILES: NCCCc1cccc(C#CC2(O)CCCC2)c1]

1-((3-(3-Aminopropyl)phenyl)ethynyl)cyclopentanol was prepared following the method used in Example 7.

Step 1: Coupling of 1-ethynylcyclopentanol with bromide 3 gave 2,2,2-trifluoro-N-(3-(3-((1-hydroxycyclopentyl)ethynyl)phenyl)propyl)acetamide as a yellow oil which was used without purification in the next step: $^1$H NMR (400 MHz, CD$_3$OD) δ 7.15-7.25 (m, 4H), 3.28 (t, J=7.2 Hz, 2H), 2.62 (t, J=7.2 Hz, 2H), 1.97-2.00 (m, 2H), 1.73-1.91 (m, 8H).

Step 2: Deprotection of 2,2,2-trifluoro-N-(3-(3-((1-hydroxycyclopentyl)ethynyl)phenyl)propyl)acetamide gave Example 24 as a yellow oil. Yield (0.478 g, 62% for two steps): ¹H NMR (400 MHz, DMSO-d₆) δ 7.14-7.34 (m, 4H), 2.59-2.64 (m, 4H), 1.97-2.00 (m, 4H), 1.71-1.87 (m, 6H).

Example 25

PREPARATION OF 1-(3-(3-AMINOPROPYL) PHENYL)-3,4,4-TRIMETHYLPENT-1-YN-3-OL

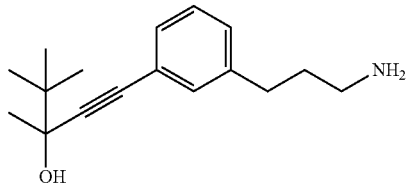 [SMILES: CC(C)(C)C(C)(O)C#Cc1cccc(CCCN)c1]

1-(3-(3-Aminopropyl)phenyl)-3,4,4-trimethylpent-1-yn-3-ol was prepared following the method described in Example 1.

Step 1: Coupling of 3,4,4-trimethylpent-1-yn-3-ol with bromide 3 in a 1:1 mixture of DMF and triethylamine gave 2,2,2-trifluoro-N-(3-(3-(3-hydroxy-3,4,4-trimethylpent-1-ynyl)phenyl)propyl)acetamide as an orange oil. Yield (0.84 g, 73%): ¹H NMR (400 MHz, CD₃OD) δ 7.15-7.25 (m, 4H), 3.29 (t, J=7.2 Hz, 2H), 2.61 (t, J=8.0 Hz, 2H), 1.86 (quint, J=7.6 Hz, 2H), 1.49 (s, 3H), 1.09 (br s, 9H).

Step 2: Deprotection of 2,2,2-trifluoro-N-(3-(3-(3-hydroxy-3,4,4-trimethylpent-1-ynyl)phenyl)propyl)acetamide gave Example 25 as a yellow oil. Yield (0.493 g, 83%): ¹H NMR (400 MHz, DMSO-d₆) δ 7.15-7.24 (m, 4H), 2.60-2.65 (m, 4H), 1.72-1.79 (m, 2H), 1.49 (s, 3H), 1.09 (s, 9H).

Example 26

PREPARATION OF (S)-3-(3-(3-AMINOPROPYL) PHENYL)-1-PHENYLPROP-2-YN-1-OL

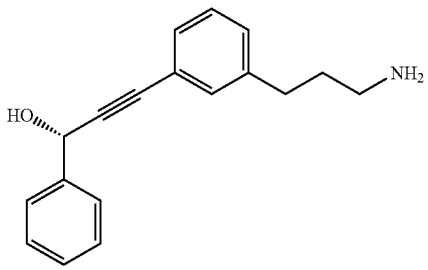 [SMILES: NCCCc1cccc(C#C[C@@H](O)c2ccccc2)c1]

(S)-3-(3-(3-Aminopropyl)phenyl)-1-phenylprop-2-yn-1-ol was prepared following the method described in Example 1.

Step 1: Coupling of (R)-1-phenylprop-2-yn-1-ol with bromide 3 gave (S)-2,2,2-trifluoro-N-(3-(3-(3-hydroxy-3-phenylprop-1-ynyl)phenyl)propyl)acetamide as an amber oil. Yield (0.73 g, 62%): ¹H NMR (400 MHz, DMSO-d₆) δ 7.57-7.59 (m, 2H), 7.17-7.40 (m, 7H), 5.60 (s, 1H), 3.26-3.29 (m, 2H), 2.62 (t, J=7.6 Hz, 2H), 1.86 (quint, J=6.8 Hz, 2H)

Step 2: Deprotection of (S)-2,2,2-trifluoro-N-(3-(3-(3-hydroxy-3-phenylprop-1-ynyl)phenyl)propyl)acetamide gave Example 26 as a pale yellow oil. Yield (0.239 g, 30%): ¹H NMR (400 MHz, CD₃OD) δ 7.56-7.59 (m, 1H), 7.16-7.39 (m, 8H), 5.60 (s, 1H), 2.58-2.62 (m, 4H), 1.69-1.77 (m, 2H).

Example 27

PREPARATION OF 1-(3-(2-AMINOETHOXY) PHENYL)-3-ETHYLPENT-1-YN-3-OL

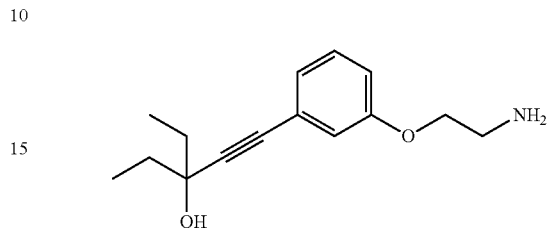

1-(3-(2-Aminoethoxy)phenyl)-3-ethylpent-1-yn-3-ol was prepared following the method described in Example 18.

Step 1: Coupling of 3-ethylpent-1-yn-3-ol with bromide 19 following the method described in Example 18 except that the reaction was run for 20 h, gave N-(2-(3-(3-ethyl-3-hydroxypent-1-ynyl)phenoxy)ethyl)-2,2,2-trifluoroacetamide as a brown oil. Yield (0.52 g, 60%): ¹H NMR (400 MHz, CDCl₃) δ 7.22 (t, J=8.0 Hz, 1H), 7.06 (dt, J=7.8, 1.2 Hz, 1H), 6.94 (dd, J=2.5, 1.4 Hz, 1H), 6.89 (br s, 1H), 6.85 (ddd, J=8.2, 2.5, 1.0 Hz, 1H), 4.08 (t, J=5.1 Hz, 2H), 3.76 (dt, J=5.1 Hz, 2H), 2.11 (s, 1H), 1.76 (m, 4H), 1.09 (t, J=7.4 Hz, 6H).

Step 2: Deprotection of N-(2-(3-(3-ethyl-3-hydroxypent-1-ynyl)phenoxy)ethyl)-2,2,2-trifluoroacetamide gave Example 27 as an oil which solidified upon standing. Yield (0.243 g, 65%): ¹H NMR (400 MHz, DMSO-d₆) δ 7.24 (t, J=8.0 Hz, 1H), 6.90-6.94 (m, 2H), 6.86-6.88 (m, 1H), 5.13 (br s, 1H), 3.89 (t, J=5.9 Hz, 2H), 2.83 (t, J=5.8 Hz, 2H), 1.54-1.65 (m, 4H), 1.47 (br s, 2H), 0.97 (t, J=7.4 Hz, 6H). ¹³C NMR (100 MHz, DMSO-d₆) δ 159.28, 130.47, 124.48, 124.29, 117.37, 115.86, 94.28, 83.34, 71.22, 71.04, 41.60, 34.71, 9.40. ESI MS m/z 248.35 [M+H]⁺, 230.32 [M+H−H₂O]⁺.

Example 28

PREPARATION OF 1-(3-(2-AMINOETHOXY) PHENYL)-3-ISOPROPYL-4-METHYLPENT-1-YN-3-OL

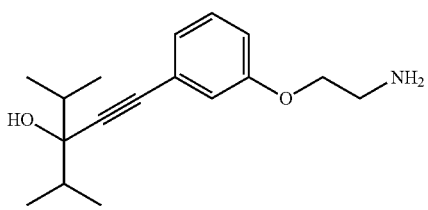 [SMILES: CC(C)C(O)(C#Cc1cccc(OCCN)c1)C(C)C]

1-(3-(2-Aminoethoxy)phenyl)-3-isopropyl-4-methylpent-1-yn-3-ol was prepared following the method used in Example 18.

Step 1: Coupling of 3-isopropyl-4-methylpent-1-yn-3-ol with bromide 19 following the method described in Example 18 except that the reaction was run for 20 h, gave 2,2,2-trifluoro-N-(2-(3-(3-hydroxy-3-isopropyl-4-methylpent-1- ynyl)phenoxy)ethyl)acetamide as an oil which solidified upon standing. Yield (0.94 g, 46%): ¹H NMR (400 MHz, CDCl₃) δ 7.23 (t, J=8.0 Hz, 1H), 7.07 (dt, J=7.6, 1.0 Hz, 1H), 6.95 (dd, J=2.5, 1.4 Hz, 1H), 6.85 (ddd, J=8.4, 2.7, 1.0 Hz, 1H), 6.70 (br s, 1H), 4.10 (t, J=5.1 Hz, 2H), 3.79 (dt, J=5.1 Hz, 2H), 2.04 (m, 2H), 1.80 (s, 1H), 1.09 (d, J=6.7 Hz, 6H), 1.05 (d, J=6.7 Hz, 6H).

Step 2: Deprotection of 2,2,2-trifluoro-N-(2-(3-(3-hydroxy-3-isopropyl-4-methylpent-1-ynyl)phenoxy)ethyl)acetamide gave Example 28 as a white solid. Yield (0.529 g, 76%): ¹H NMR (400 MHz, DMSO-d₆) δ 7.24 (t, J=7.8 Hz, 1H), 6.90-6.95 (m, 2H), 6.87-6.88 (m, 1H), 4.83 (br s, 1H), 3.89 (t, J=5.7 Hz, 2H), 2.83 (t, J=5.7 Hz, 2H), 1.86 (m, 2H), 1.47 (br s, 2H), 0.98 (d, J=6.8 Hz, 6H), 0.93 (d, J=6.7 Hz, 6H). ¹³C NMR (100 MHz, DMSO-d₆) δ 159.29, 130.48, 124.58, 124.32, 117.46, 115.72, 92.60, 84.54, 76.74, 71.04, 41.62, 34.95, 18.98, 17.21. ESI MS m/z 276.39 [M+H]⁺, 258.37 [M+H–H₂O]⁺.

Example 29

PREPARATION OF 5-((3-(2-AMINOETHOXY)PHENYL)ETHYNYL)NONAN-5-OL

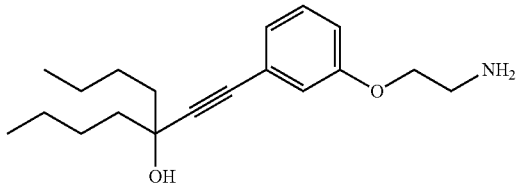

5-((3-(2-Aminoethoxy)phenyl)ethynyl)nonan-5-ol was prepared following the method described in Example 18.

Step 1: Coupling of 5-ethynylnonan-5-ol with bromide 19 following the method described in Example 18 except that the reaction was run for 18 h, gave N-(2-(3-(3-butyl-3-hydroxyhept-1-ynyl)phenoxy)ethyl)-2,2,2-trifluoroacetamide. Yield (1.06 g, 75%): ¹H NMR (400 MHz, CDCl₃) δ 7.23 (t, J=8.0 Hz, 1H), 7.06 (dt, J=7.6 and 1.2 Hz, 1H), 6.94 (dd, J=2.5, 1.4 Hz, 1H), 6.86 (ddd, J=8.4, 2.7, 1.0 Hz, 1H), 6.72 (br s, 1H), 4.10 (t, J=5.3 Hz, 2H), 3.79 (dt, J=5.3 Hz, 2H), 1.96 (s, 1H), 1.70-1.75 (m, 4H), 1.50-1.58 (m, 4H), 1.34-1.43 (m, 4H), 0.94 (t, J=7.2 Hz, 6H).

Step 2: Deprotection of N-(2-(3-(3-butyl-3-hydroxyhept-1-ynyl)phenoxy)ethyl)-2,2,2-trifluoroacetamide gave Example 29 as an oil which solidified upon standing. Yield (0.695 g, 92%): ¹H NMR (400 MHz, DMSO-d₆) δ 7.24 (t, J=7.8 Hz, 1H), 6.92-6.93 (m, 1H), 6.90-6.91 (m, 1H), 6.85-6.86 (m, 1H), 5.13 (br s, 1H), 3.89 (t, J=5.7 Hz, 2H), 2.83 (t, J=5.7 Hz, 2H), 1.52-1.60 (m, 6H), 1.40-1.49 (m, 4H), 1.25-1.34 (m, 4H), 0.88 (t, J=7.2 Hz, 6H). ¹³C NMR (100 MHz, DMSO-d₆) δ 159.28, 130.49, 124.50, 124.26, 117.35, 115.76, 94.87, 83.08, 71.03, 70.27, 42.19, 41.60, 26.85, 23.15, 14.74. ESI MS m/z 304.42 [M+H]⁺, 286.42 [M+H–H₂O]⁺.

Example 30

PREPARATION OF 4-(3-(2-AMINOETHOXY)PHENYL)-2-METHYLBUT-3-YN-2-OL

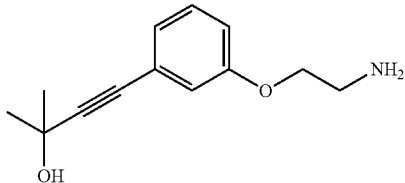 [SMILES: CC(C)(O)C#Cc1cccc(OCCN)c1]

4-(3-(2-Aminoethoxy)phenyl)-2-methylbut-3-yn-2-ol was prepared following the method described in Example 18.

Step 1: Coupling of 2-methylbut-3-yn-2-ol with bromide 3 following the method described in Example 18 except that the reaction was run for 19 h, gave 2,2,2-trifluoro-N-(2-(3-(3-hydroxy-3-methylbut-1-ynyl)phenoxy)ethyl)acetamide. Yield (0.667 g, 70%): ¹H NMR (400 MHz, CDCl₃) δ 7.23 (t, J=7.8 Hz, 1H), 7.06 (dt, J=7.6 and 1.2 Hz, 1H), 6.94 (dd, J=2.5, 1.4 Hz, 1H), 6.86 (ddd, J=8.2, 2.5, 1.0 Hz, 1H), 6.74 (br s, 1H), 4.09 (t, J=4.9 Hz, 2H), 3.80 (dt, J=5.5 Hz, 2H), 2.04 (s, 1H), 1.61 (s, 6H).

Step 2: Deprotection of 2,2,2-trifluoro-N-(2-(3-(3-hydroxy-3-methylbut-1-ynyl)phenoxy)ethyl)acetamide gave Example 30 as a white solid. Yield (0.240 g, 52%): ¹H NMR (400 MHz, DMSO-d₆) δ 7.23 (t, J=8.0 Hz, 1H), 6.89-6.93 (m, 2H), 6.86-6.88 (m, 1H), 5.43 (br s, 1H), 3.89 (t, J=5.9 Hz, 2H), 2.83 (t, J=5.9 Hz, 2H), 1.45 (br s, 2H), 1.44 (s, 6H). ¹³C NMR (100 MHz, DMSO-d₆) δ 159.27, 130.45, 124.38, 124.20, 117.21, 116.00, 96.57, 80.99, 71.03, 64.27, 41.59, 32.28. ESI MS m/z 220.31 [M+H]⁺, 202.28 [M+H–H₂O]⁺; HPLC (Method A) t_R=2.79 min.

Example 31

PREPARATION OF 1-((3-(2-AMINOETHOXY)PHENYL)ETHYNYL)CYCLOPENTANOL

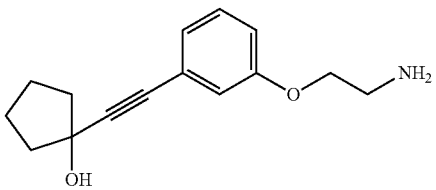 [SMILES: NCCOc1cccc(C#CC2(O)CCCC2)c1]

1-((3-(2-Aminoethoxy)phenyl)ethynyl)cyclopentanol was prepared following the method described in Example 18.

Step 1: Coupling of 1-ethynylcyclopentanol with bromide 19 following the method described in Example 18 except that the reaction was run for 19.5 h, gave 2,2,2-trifluoro-N-(2-(3-((1-hydroxycyclopentyl)ethynyl)phenoxy)ethyl)acetamide as a brown oil. Yield (1.055 g, 92%): ¹H NMR (400 MHz, CDCl₃) δ 7.23 (t, J=8.0 Hz, 1H), 7.06 (dt, J=7.6, 1.2 Hz, 1H), 6.95 (dd, J=2.5, 1.4 Hz, 1H), 6.85 (ddd, J=8.4, 2.7, 1.0 Hz, 1H), 6.72 (br s, 1H), 4.09 (t, J=5.3 Hz, 2H), 3.78 (dt, J=5.1 Hz, 2H), 2.00-2.09 (m, 4H), 1.76-1.93 (m, 5H).

Step 2: Deprotection of 2,2,2-trifluoro-N-(2-(3-((1-hydroxycyclopentyl)ethynyl)phenoxy)ethyl)acetamide gave Example 31 as an oil which solidified upon standing. Yield (0.502 g, 66%): $^1$H NMR (400 MHz, DMSO-$d_6$) δ 7.23 (t, J=8.0 Hz, 1H), 6.88-6.94 (m, 3H), 5.28 (br s, 1H), 3.89 (t, J=5.7 Hz, 2H), 2.83 (t, J=5.7 Hz, 2H), 1.82-1.89 (m, 4H), 1.63-1.74 (m, 4H), 1.48 (br s, 2H). $^{13}$C NMR (100 MHz, DMSO-$d_6$) δ 159.27, 130.45, 124.50, 124.18, 117.20, 115.93, 95.65, 81.97, 73.44, 71.01, 42.66, 41.58, 23.75. ESI MS m/z 246.33 [M+H]$^+$, 228.30 [M+H–H$_2$O]$^+$; HPLC (Method A) $t_R$=4.19 min.

Example 32

PREPARATION OF 1-(3-(3-AMINOPROPYL)PHENYL)-3-ISOPROPYL-4-METHYLPENT-1-YN-3-OL

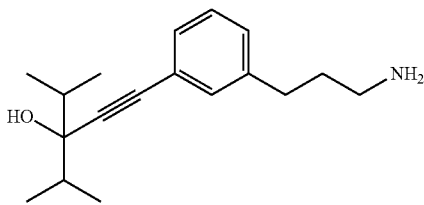 [SMILES: CC(C)C(O)(C#Cc1cccc(CCCN)c1)C(C)C]

1-(3-(3-Aminopropyl)phenyl)-3-isopropyl-4-methylpent-1-yn-3-ol was prepared following the method used in Example 1.

Step 1: Coupling of 3-isopropyl-4-methylpent-1-yn-3-ol with bromide 3 following the coupling method described in Example 17 gave 2,2,2-trifluoro-N-(3-(3-(3-hydroxy-3-isopropyl-4-methylpent-1-ynyl)phenyl)propyl)acetamide as a pale yellow oil. Yield (1.375 g, 66%): $^1$H NMR (400 MHz, DMSO-$d_6$) δ 9.40 (br s, 1H), 7.26 (t, J=7.6 Hz, 1H), 7.17-7.22 (m, 3H), 4.81 (s, 1H), 3.17 (q, J=6.8 Hz, 2H), 2.56 (t, J=8.0 Hz, 2H), 1.86 (quint, J=6.8 Hz, 2H), 1.76 (quint, J=7.6 Hz, 2H), 0.99 (d, J=6.8 Hz, 6H), 0.94 (d, J=6.8 Hz, 6H).

Step 2: Deprotection of 2,2,2-trifluoro-N-(3-(3-(3-hydroxy-3-isopropyl-4-methylpent-1-ynyl)phenyl)propyl)acetamide followed by flash chromatography (9:1 CH$_2$Cl$_2$: 7 M NH$_3$ in MeOH) gave Example 32 as a clear oil. Yield (0.835 g, 82%): $^1$H NMR (400 MHz, DMSO-$d_6$) δ 7.15-7.26 (m, 4H), 4.82 (br s, 1H), 2.56 (t, J=7.6 Hz, 2H), 2.47-2.52 (m, 2H), 1.86 (quint, J=6.8 Hz, 2H), 1.59 (quint, J=6.8 Hz, 2H), 1.56 (br.s, 2H), 1.05 (d, J=6.8 Hz, 6H), 1.03 (d, J=6.8 Hz, 6H).

Example 33

PREPARATION OF 4-((3-(3-AMINOPROPYL)PHENYL)ETHYNYL)-2,6-DIMETHYLHEPTAN-4-OL

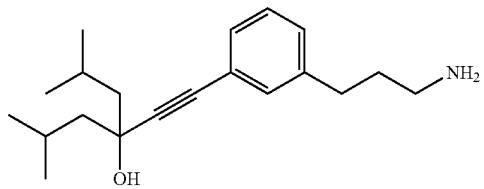 [SMILES: CC(C)CC(O)(C#Cc1cccc(CCCN)c1)CC(C)C]

4-((3-(3-Aminopropyl)phenyl)ethynyl)-2,6-dimethylheptan-4-ol was prepared following the method described in Example 32.

Step 1: Coupling of 4-ethynyl-2,6-dimethylheptan-4-ol with bromide 3 gave 2,2,2-trifluoro-N-(3-(3-(3-hydroxy-3-isobutyl-5-methylhex-1-ynyl)phenyl)propyl)acetamide as a pale yellow oil. Yield (1.25 g, 63%): $^1$H NMR (400 MHz, DMSO-$d_6$) δ 9.40 (br s, 1H), 7.14-7.28 (m, 4H), 5.02 (s, 1H), 3.17 (q, J=6.8 Hz, 2H), 2.56 (t, J=7.6 Hz, 2H), 1.93-1.99 (m, 2H), 1.75 (quint, J=7.6 Hz, 2H), 1.47-1.56 (m, 4H), 0.86-0.98 (m, 12H).

Step 2: Deprotection of 2,2,2-trifluoro-N-(3-(3-(3-hydroxy-3-isobutyl-5-methylhex-1-ynyl)phenyl)propyl)acetamide gave Example 33 as a clear oil. Yield (0.73 g, 77%): $^1$H NMR (400 MHz, DMSO-$d_6$) 7.22-7.26 (m, 1H), 7.12-7.18 (m, 3H), 5.04 (br s, 1H), 2.56 (t, J=7.2 Hz, 2H), 2.50 (t, J=6.8 Hz, 2H), 1.91-2.01 (m, 2H), 1.47-1.62 (m, 6H), 0.98 (m, 6H), 0.96 (m, 6H).

Example 34

PREPARATION OF 4-(3-(3-AMINOPROPYL)PHENYL)BUT-3-YN-1-OL

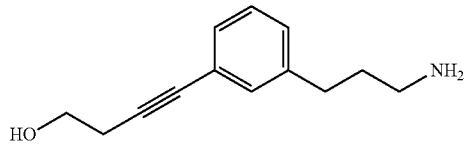 [SMILES: NCCCc1cccc(C#CCCO)c1]

4-(3-(3-Aminopropyl)phenyl)but-3-yn-1-ol was prepared following the method described in Example 14.

Step 1: Coupling of but-3-yn-1-ol with bromide 3 at room temperature gave 2,2,2-trifluoro-N-(3-(3-(4-hydroxybut-1-ynyl)phenyl)propyl)acetamide as a pale yellow oil. Yield (0.9 g, 62%): $^1$H NMR (400 MHz, DMSO-$d_6$) δ 9.40 (br s, 1H), 7.15-7.26 (m, 4H), 4.86 (br s, 1H), 3.56 (t app, J=6.8 Hz, 2H), 3.16 (q, J=6.8 Hz, 2H), 2.47-2.56 (m, 4H), 1.76 (quint, J=7.6 Hz, 2H).

Step 2: Deprotection of 2,2,2-trifluoro-N-(3-(3-(4-hydroxybut-1-ynyl)phenyl)propyl)acetamide following the method used in Example 2 except that the product was purified by flash chromatography (CH$_2$Cl$_2$/EtOH/NH$_4$OH 85:14:1) gave Example 34 as a clear oil. Yield (0.236 g, 65%): $^1$H NMR (400 MHz, DMSO-$d_6$) δ 7.12-7.24 (m, 4H), 3.56 (t, J=6.9 Hz, 2H), 2.47-2.57 (m, 6H), 1.59 (quint, J=6.9 Hz, 2H).

Example 35

PREPARATION OF 5-(3-(3-AMINOPROPYL)PHENYL)PENT-4-YN-2-OL

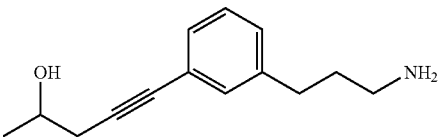 [SMILES: CC(O)CC#Cc1cccc(CCCN)c1]

5-(3-(3-Aminopropyl)phenyl)pent-4-yn-2-ol was prepared following the methods described in Examples 14 and 34.

Step 1: Coupling of pent-4-yn-2-ol with bromide 3 at room temperature gave 2,2,2-trifluoro-N-(3-(3-(4-hydroxypent-1-ynyl)phenyl)propyl)acetamide as a pale yellow oil. Yield (0.95 g, 63%): ¹H NMR (400 MHz, DMSO-d₆) δ 9.40 (br s, 1H), 7.14-7.26 (m, 4H), 4.80 (s, 1H), 3.81 (q, J=5.6 Hz, 1H), 3.16 (q, J=6.8 Hz, 2H), 2.54 (t, J=5.6 Hz, 2H), 2.39 (dd, J=16.8, 6.8 Hz, 2H), 1.76 (quint, J=7.2 Hz, 2H), 1.17 (d, J=5.6 Hz, 3H).

Step 2: Deprotection of 2,2,2-trifluoro-N-(3-(3-(4-hydroxypent-1-ynyl)phenyl)propyl)acetamide following the method described in Example 34 gave Example 35 as a clear oil Yield (0.34 g, 94%): ¹H NMR (400 MHz, CDCl₃) δ 7.24-7.25 (m, 1H), 7.23 (t, J=1.6 Hz, 1H), 7.20 (ddd, J=7.4, 7.4, 0.6 Hz, 1H), 7.11 (dt, J=7.2, 1.6 Hz, 1H), 4.04 (dq, J=12.5, 6.3 Hz, 1H), 2.72 (t, J=6.9 Hz, 2H), 2.51-2.64 (m, 4H), 1.72-1.79 (m, 2H), 1.65 (br s, 3H), 1.32 (d, J=6.3 Hz, 3H).

Example 36

PREPARATION OF 3-(3-((2-METHOXYPHENYL)ETHYNYL)PHENYL)PROPAN-1-AMINE

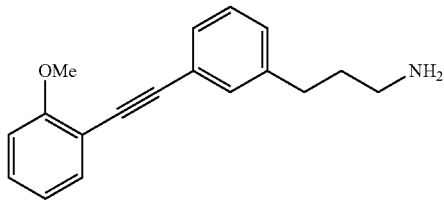 [SMILES: COc1ccccc1C#Cc1cccc(CCCN)c1]

3-(3-((2-Methoxyphenyl)ethynyl)phenyl)propan-1-amine was prepared following the method shown in Scheme 7.

SCHEME 7

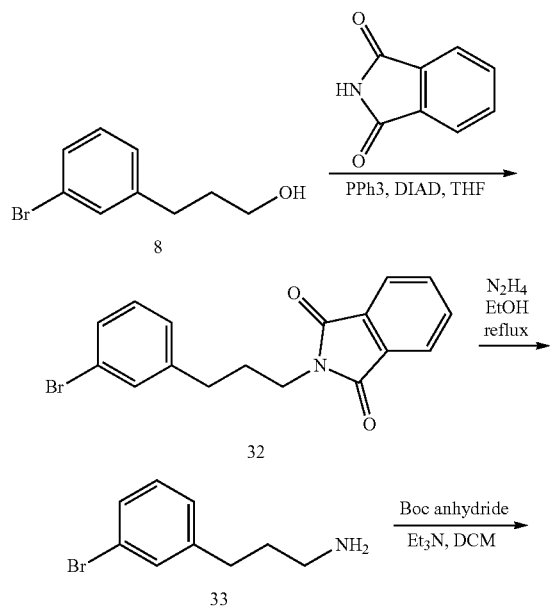

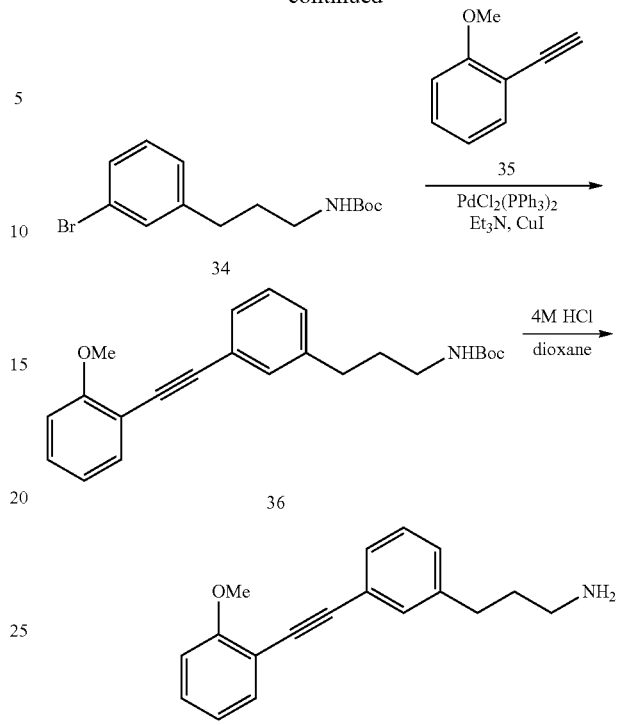

Step 1: Coupling of alcohol 8 with phthalimide following the procedure described in Example 17 except using diisopropyl azodicarboxylate instead of diethyl azodicarboxylate gave phthalimide 32. Yield (6.9 g, 50%): ¹H NMR (400 MHz, DMSO-d₆) δ 7.78-7.86 (m, 4H), 7.40-7.43 (m, 1H), 7.29 (dt, J=2.0, 6.8 Hz, 1H), 7.16-7.22 (m, 2H), 3.58 (t, J=6.8 Hz, 2H), 2.61 (t, J=7.2 Hz, 2H), 1.84-1.93 (m, 2H).

Step 2: Deprotection of phthalimide 32 following the procedure described in Example 17 gave amine 33. Yield (4.2 g, 97%).

Step 3: Protection of amine 33 with Boc anhydride following the procedure described in Example 20 gave carbamate 34. Yield (5.57 g, 86%): ¹H NMR (400 MHz, DMSO-d₆) δ 7.33 (s, 1H), 7.26-7.34 (m, 1H), 7.08-7.20 (m, 2H), 4.55 (br s, 1H), 3.15 (q, J=6 Hz, 2H), 2.61 (t, J=8.0 Hz, 2H), 1.79 (quint, J=7.6 Hz, 2H), 1.44 (s, 9H).

Step 4: Coupling of carbamate 34 with alkyne 35 following the method described in Example 1 gave alkyne 36 as a brown oil. Yield (0.201 g, 36%): ¹H NMR (400 MHz, CDCl₃) δ 7.53 (dd, J=7.2, 2 Hz, 2H), 7.42-7.47 (m, 1H), 7.36-7.38 (m, 1H), 7.20-7.26 (m, 2H), 7.11 (d, J=8.0 Hz, 1H), 6.98 (t, J=7.6 Hz, 1H), 6.86 (m, 1H), 3.87 (s, 3H), 2.91 (q, J=6.4 Hz, 2H), 2.55 (t obs, J=7.6 Hz, 2H), 1.65 (quint, J=7.2 Hz, 2H), 1.38 (s, 9H).

Step 5: Alkyne 36 (0.200 gm, 0.54 mmol) was dissolved in CH₂Cl₂, (5 mL) and HCl in dioxane (15 mL, saturated soln) was added. The mixture was stirred at room temperature for 18 h. The mixture was concentrated under reduced pressure then triturated with hexanes (25 mL×2) to give a solid which was washed with diethyl ether to give Example 36 hydrochloride salt as a cream solid. Yield (0.127 gm, 76%): ¹H NMR (400 MHz, CDCl₃) δ 8.38 (br s, 3H), 7.48 (dd, J=7.6, 1.6 Hz, 1H), 7.38 (m, 2H), 7.29 (t obs, J=7.2 Hz, 1H), 7.22 (t, J=8.0 Hz, 1H), 7.14 (d, J=7.6 Hz, 1H), 6.92 (t, J=7.6 Hz, 1H), 6.88

(d, J=8.4 Hz, 1H), 3.89 (s, 3H), 3.00 (t, J=7.6 Hz, 2H), 2.72 (t, J=7.6 Hz, 2H), 2.10 (quint, J=7.6 Hz, 2H).

Example 37

PREPARATION OF 3-(3-(PHENYLETHYNYL)PHENYL)PROPAN-1-AMINE

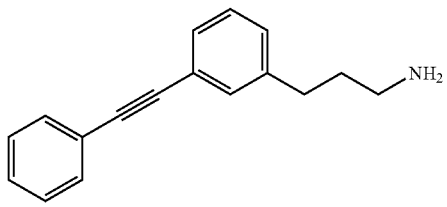 [SMILES: NCCCc1cccc(C#Cc2ccccc2)c1]

3-(3-(Phenylethynyl)phenyl)propan-1-amine was prepared following the method described in Example 36.

Step 1: Coupling of phenylacetylene with bromide 34 gave tert-butyl 3-(3-(phenylethynyl)phenyl)propylcarbamate as a brown oil. Yield (0.32 g, 50%): $^1$H NMR (400 MHz, CDCl$_3$) δ 7.53 (dd, J=7.2, 2 Hz, 2H), 7.42-7.47 (m, 1H), 7.36-7.38 (m, 1H), 7.20-7.26 (m, 2H), 7.11 (d, J=8.0 Hz, 1H), 6.98 (t, J=7.6 Hz, 1H), 6.86 (m, 1H), 4.54 (br s, 1H), 3.14-3.17 (m, 2H), 2.63 (quint, J=7.6 Hz, 2H), 1.76-1.86 (m, 2H), 1.38 (s, 9H).

Step 2: Deprotection of tert-butyl 3-(3-(phenylethynyl)phenyl)propylcarbamate gave Example 37 hydrochloride as an off white solid. Yield (0.19 g, 73%): $^1$H NMR (400 MHz, DMSO-d$_6$) δ 8.08 (br s, 2H), 7.55-7.57 (m, 1H), 7.21-7.46 (m, 6H), 7.21-7.30 (m, 2H), 2.77 (q, J=7.6 Hz, 2H), 2.66 (q, J=7.6 Hz, 2H), 1.82-1.93 (m, 2H).

Example 38

PREPARATION OF 3-(3-(CYCLOPENTYLETHYNYL)PHENYL)PROPAN-1-AMINE

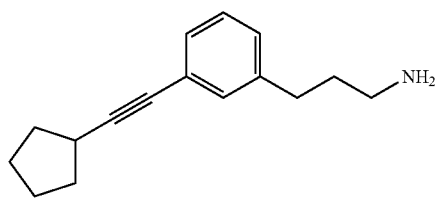 [SMILES: NCCCc1cccc(C#CC2CCCC2)c1]

3-(3-(Cyclopentylethynyl)phenyl)propan-1-amine was prepared following the method described in Example 36.

Step 1: Coupling of ethynylcyclopentane with bromide 34 gave tert-butyl 3-(3-(cyclopentylethynyl)phenyl)propylcarbamate as a brown oil. Yield (0.70 g, 84%): $^1$H NMR (400 MHz, DMSO-d$_6$) δ 7.06-7.33 (m, 4H), 2.85 (quint, J=7.4 Hz, 1H), 2.57-2.66 (m, 2H), 2.62 (t, J=8.0 Hz, 2H), 1.93-2.01 (m, 2H), 1.82 (quint, J=7.6 Hz, 2H), 1.66-1.75 (m, 2H), 1.55-1.64 (m, 4H), 1.45 (m, 9H).

Step 2: Deprotection of tert-butyl 3-(3-(cyclopentylethynyl)phenyl)propylcarbamate following purification by preparative HPLC (Method 001P) gave Example 38 trifluoroacetate as a white solid. Yield (0.22 g, 30%): $^1$H NMR (400 MHz, DMSO-d$_6$) δ 7.68 (br s, 3H), 7.27 (t, J=7.6 Hz, 1H), 7.16-7.24 (m, 3H), 2.85 (quint, J=7.6 Hz, 1H), 2.75 (br s, 2H), 2.62 (t, J=7.2 Hz, 2H), 1.93-2.01 (m, 2H), 1.82 (quint, J=7.6 Hz, 2H), 1.67-1.71 (m, 2H), 1.56-1.66 (m, 4H).

Example 39

PREPARATION OF 3-(3-(3-CYCLOPENTYL-PROP-1-YNYL)PHENYL)PROPAN-1-AMINE

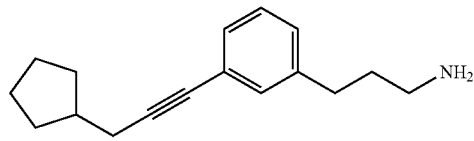 [SMILES: NCCCc1cccc(C#CCC2CCCC2)c1]

3-(3-(3-Cyclopentylprop-1-ynyl)phenyl)propan-1-amine was prepared following the method described in Example 36.

Step 1: Coupling of prop-2-ynylcyclopentane with bromide 34 was conducted following the method used in Example 36. Purification by flash chromatography (6% EtOAc-hexanes) gave tert-butyl 3-(3-(cyclopentylethynyl)phenyl)propylcarbamate as a brown oil. Yield (0.70 g, 84%): $^1$H NMR (400 MHz, DMSO-d$_6$) δ 7.06-7.33 (m, 4H), 2.85 (quint, J=7.4 Hz, 1H), 2.57-2.66 (m, 2H), 2.62 (t, J=8.0 Hz, 2H), 1.93-2.01 (m, 2H), 1.82 (quint, J=7.6 Hz, 2H), 1.71 (m, 2H), 1.59 (m, 4H), 1.45 (m, 9H).

Step 2: Deprotection of tert-butyl 3-(3-(3-cyclopentylprop-1-ynyl)phenyl)propylcarbamate followed by purification by preparative HPLC (Method 001P) gave Example 39 trifluoroacetamide as a white solid. Yield (0.4 g, 10%): $^1$H NMR (400 MHz, DMSO-D$_6$) δ 7.69 (br s, 2H), 7.14-7.34 (m, 4H), 2.76 (t, J=6.4 Hz, 2H), 2.62 (t, J=7.6 Hz, 2H), 2.42 (d, J=6.8 Hz, 2H), 2.08 (m, 1H), 1.80 (m, 4H), 1.48-1.70 (m, 4H), 1.22-1.40 (m, 2H).

Example 40

PREPARATION OF 3-(3-(3,3-DIMETHYLBUT-1-YNYL)PHENYL)PROPAN-1-AMINE

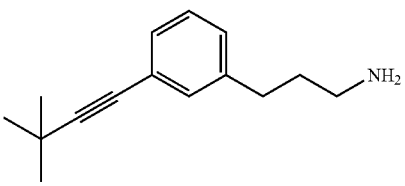 [SMILES: CC(C)(C)C#Cc1cccc(CCCN)c1]

3-(3-(3,3-Dimethylbut-1-ynyl)phenyl)propan-1-amine was prepared following the method described in Example 36.

Step 1: Coupling of 3,3-dimethylbut-1-yne with bromide 34 gave tert-butyl 3-(3-(3,3-dimethylbut-1-ynyl)phenyl)propylcarbamate as a brown oil. Yield (0.43 g, 54%).

Step 2: Deprotection of tert-butyl 3-(3-(3,3-dimethylbut-1-ynyl)phenyl)propylcarbamate following purification by preparative HPLC (Method 001P) gave Example 40 trifluoroacetate as a pale yellow solid. Yield (0.08 g, 18%): $^1$H NMR (400 MHz, DMSO-d$_6$) δ 7.79 (br s, 3H), 7.27 (t, J=7.6 Hz, 1H), 7.16-7.22 (m, 3H), 2.77 (m, 2H), 2.61 (t, J=7.6 Hz, 2H), 1.82 (quint, J=7.2 Hz, 2H), 1.29 (s, 9H).

Example 41

PREPARATION OF 3-(3-(CYCLOHEXYLETHYNYL)PHENYL)PROPAN-1-AMINE

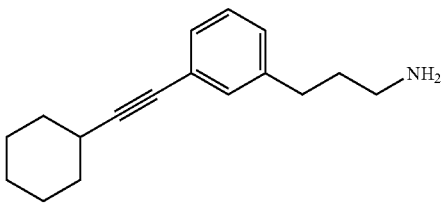 [SMILES: NCCCc1cccc(C#CC2CCCCC2)c1]

3-(3-(Cyclohexylethynyl)phenyl)propan-1-amine was prepared following the method described in Example 36.

Step 1: Coupling of ethynylcyclohexane with bromide 34 was conducted following the method used in Example 36. Purification by flash chromatography (5% EtOAc-hexanes) gave tert-butyl 3-(3-(cyclohexylethynyl)phenyl)propylcarbamate as a brown oil. Yield (0.50 g, 57%).

Step 2: Deprotection of tert-butyl 3-(3-(cyclohexylethynyl)phenyl)propylcarbamate followed by purification by preparative HPLC (Method 001P) gave Example 41 trifluoroacetate as a cream solid. Yield (0.21 g, 40%): $^1$H NMR (400 MHz, DMSO-$d_6$) δ 7.67 (br s, 3H), 7.28 (t, J=7.6 Hz, 1H), 7.17-7.24 (m, 3H), 2.74-2.79 (m, 1H), 2.64 (t, J=7.6 Hz, 4H), 1.82 (quint, J=7.2 Hz, 4H), 1.67-1.68 (m, 2H), 1.32-1.52 (m, 6H).

Example 42

PREPARATION OF 3-(3-(3-PHENYLPROP-1-YNYL)PHENYL)PROPAN-1-AMINE

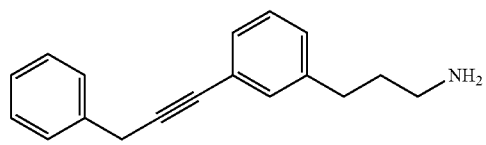 [SMILES: NCCCc1cccc(C#CCc2ccccc2)c1]

3-(3-(3-Phenylprop-1-ynyl)phenyl)propan-1-amine was prepared following the method described in Example 36.

Step 1: Coupling of prop-2-ynylbenzene with bromide 34 gave tert-butyl 3-(3-(3-phenylprop-1-ynyl)phenyl)propylcarbamate as a brown oil. Yield (0.85 g, 73%): $^1$H NMR (400 MHz, CDCl$_3$) δ 7.41-7.43 (m, 2H), 7.35 (t, J=8.0 Hz, 2H), 7.10-7.28 (m, 5H), 4.52 (br s, 1H), 3.84 (s, 2H), 3.14-3.16 (m, 2H), 2.61 (t, J=7.6 Hz, 2H), 1.80 (quint, J=7.6 Hz, 2H), 1.48 (s, 9H).

Step 2: Deprotection of tert-butyl 3-(3-(3-phenylprop-1-ynyl)phenyl)propylcarbamate followed by purification by preparative HPLC (Method-001P) gave Example 42 trifluoroacetate as a white solid. Yield (0.45 g, 51%): $^1$H NMR (400 MHz, DMSO-$d_6$) δ 7.69 (br s, 3H), 7.35-7.42 (m, 4H), 7.25-7.31 (m, 4H), 7.20-7.22 (m, 1H), 3.89 (s, 2H), 2.76 (t, J=7.2 Hz, 2H), 2.63 (t, J=7.6 Hz, 2H), 1.82 (quint, J=7.6 Hz, 2H).

Example 43

PREPARATION OF 3-(3-(PENT-1-YNYL)PHENYL)PROPAN-1-AMINE

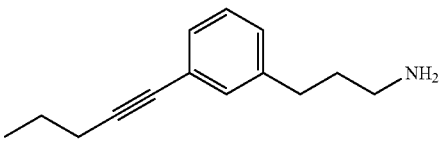

3-(3-(Pent-1-ynyl)phenyl)propan-1-amine was prepared following the method described in Example 36.

Step 1: Coupling of 1 pent-1-yne with bromide 34 gave tert-butyl 3-(3-(pent-1-ynyl)phenyl)propylcarbamate as a brown oil. Yield (0.35 g, 58%): $^1$H NMR (400 MHz, CDCl$_3$) δ 7.07-7.33 (m, 4H), 4.52 (br s, 1H), 3.14-3.15 (m, 2H), 2.58-2.66 (m, 2H), 2.38 (t, J=7.2 Hz, 2H), 1.79 (quint, J=7.6 Hz, 2H), 1.64 (q, J=7.2 Hz, 2H), 1.45 (s, 9H), 1.05 (t, J=6.8 Hz, 3H).

Step 2: Deprotection of tert-butyl 3-(3-(pent-1-ynyl)phenyl)propylcarbamate followed by purification by preparative HPLC (Method 001P) gave Example 43 trifluoroacetate as a white solid. Yield (0.17 g, 32%): $^1$H NMR (400 MHz, DMSO-$d_6$) δ 7.71 (br s, 3H), 7.28 (t, J=7.6 Hz, 1H), 7.17-7.25 (m, 3H), 2.76 (t, J=7.2 Hz, 2H), 2.62 (t, J=7.2 Hz, 2H), 2.39 (t, J=6.8 Hz, 2H), 1.82 (quint, J=7.6 Hz, 2H), 1.51-1.60 (m, 2H), 1.00 (t, J=7.6 Hz, 3H).

Example 44

PREPARATION OF 3-(3-(HEX-1-YNYL)PHENYL)PROPAN-1-AMINE

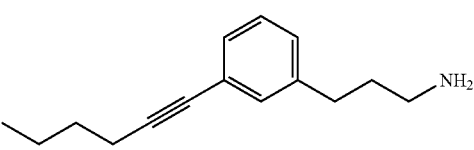 [SMILES: CCCCC#Cc1cccc(CCCN)c1]

3-(3-(Hex-1-ynyl)phenyl)propan-1-amine was prepared following the method described in Example 36.

Step 1: Coupling of hex-1-yne with bromide 34 gave tert-butyl 3-(3-(hex-1-ynyl)phenyl)propylcarbamate as a brown oil. Yield (0.64 g, 64%).

Step 2: Deprotection of tert-butyl 3-(3-(hex-1-ynyl)phenyl)propylcarbamate followed by purification by preparative HPLC (Method 004P) gave Example 44 hydrochloride as a white solid. Yield (0.17 g, 33%): $^1$H NMR (400 MHz, DMSO-$d_6$) δ 7.71 (br s, 3H), 7.28 (t, J=7.2 Hz, 1H), 7.17-7.25 (m, 3H), 2.76 (t, J=7.6 Hz, 2H), 2.62 (t, J=7.2 Hz, 2H), 2.42 (t, J=7.0 Hz, 2H), 1.82 (quint, J=7.6 Hz, 2H), 1.52 (quint, J=7.0 Hz, 2H), 1.44 (quint, J=7.0 Hz, 2H), 0.92 (t, J=7.6 Hz, 3H).

Example 45

PREPARATION OF 3-(3-(NAPHTHALEN-2-YLETHYNYL)PHENYL)PROPAN-1-AMINE

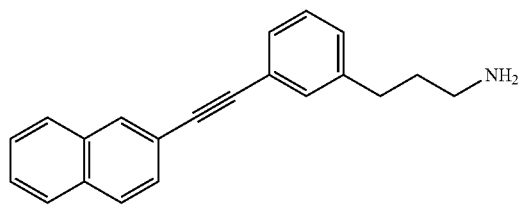 [SMILES: NCCCc1cccc(C#Cc2ccc3ccccc3c2)c1]

3-(3-(Naphthalen-2-ylethynyl)phenyl)propan-1-amine was prepared following the method described in Scheme 8.

SCHEME 8

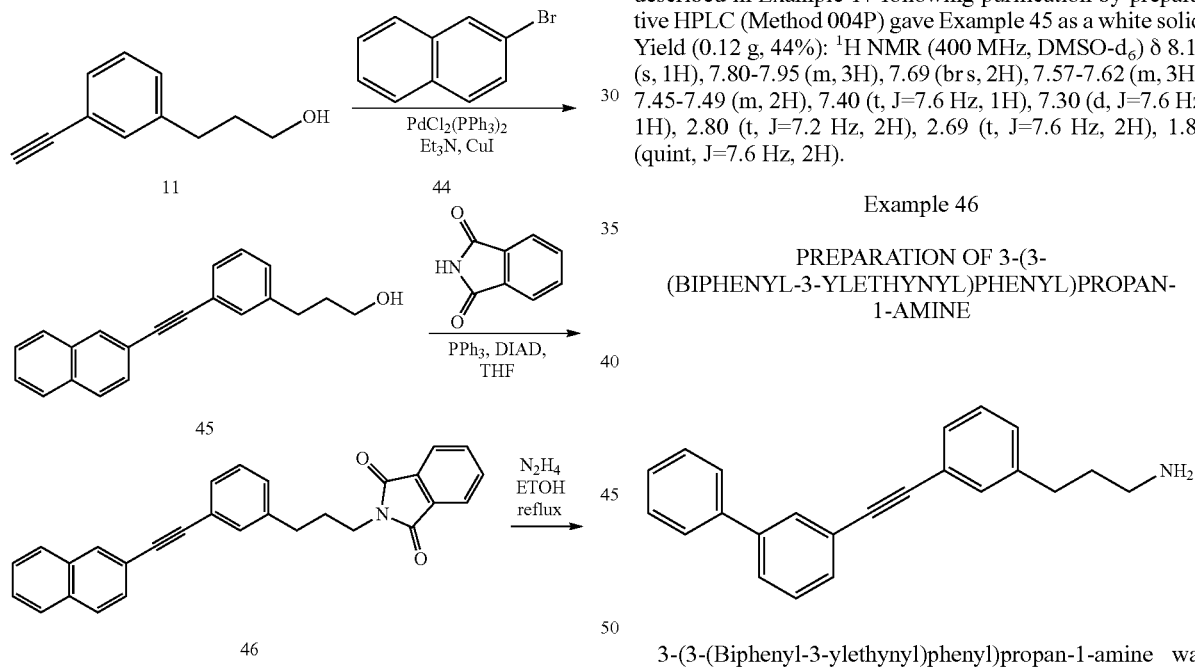

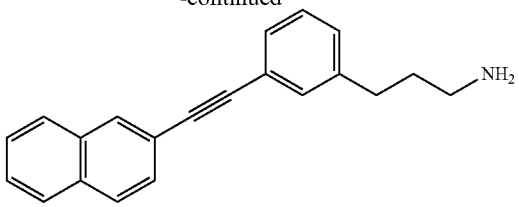

Step 1: Coupling of alcohol 11 with 2-bromonaphthalene (44) following the method described in Example 17 gave alcohol 45. Yield (0.40 g, 45%): $^1$H NMR (400 MHz, CDCl$_3$) δ 8.06 (br s, 1H), 7.80-7.83 (m, 2H), 7.58 (dd, J=8.8, 2.0 Hz, 1H), 7.47-7.51 (m, 2H), 7.41-7.43 (m, 2H), 7.26-7.31 (m, 2H), 7.18 (d, J=7.6 Hz, 1H), 4.77 (br s, 1H), 4.11 (t, J=6.4 Hz, 2H), 2.71 (t, J=7.6 Hz, 2H), 1.99 (quint, J=6.8 Hz, 2H).

Step 2: Coupling of alcohol 45 with phthalimide following the method described in Example 17 gave alkyne 46. Yield (0.40 g, 80%): $^1$H NMR (400 MHz, CDCl$_3$) δ 8.44 (d, J=8.0 Hz, 1H), 7.82-7.88 (m, 4H), 7.76 (dd, J=7.2, 1.2 Hz, 1H), 7.70 (dd, J=5.2, 3.2 Hz, 2H), 7.59-7.64 (m, 1H), 7.52-7.56 (m, 1H), 7.42-7.49 (m, 3H), 7.29 (d, J=7.6 Hz, 1H), 7.22 (d, J=8.0 Hz, 1H), 3.79 (t, J=7.2 Hz, 2H), 2.73 (t, J=7.2 Hz, 2H), 2.09 (quint, J=7.2 Hz, 2H).

Step 3: Deprotection of alkyne 46 following the method described in Example 17 following purification by preparative HPLC (Method 004P) gave Example 45 as a white solid. Yield (0.12 g, 44%): $^1$H NMR (400 MHz, DMSO-d$_6$) δ 8.18 (s, 1H), 7.80-7.95 (m, 3H), 7.69 (br s, 2H), 7.57-7.62 (m, 3H), 7.45-7.49 (m, 2H), 7.40 (t, J=7.6 Hz, 1H), 7.30 (d, J=7.6 Hz, 1H), 2.80 (t, J=7.2 Hz, 2H), 2.69 (t, J=7.6 Hz, 2H), 1.87 (quint, J=7.6 Hz, 2H).

Example 46

PREPARATION OF 3-(3-(BIPHENYL-3-YLETHYNYL)PHENYL)PROPAN-1-AMINE

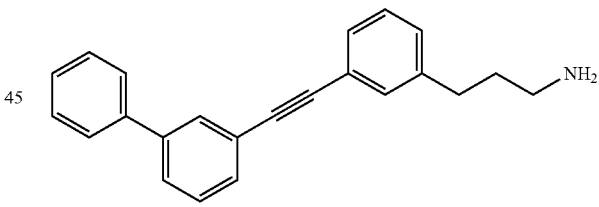

3-(3-(Biphenyl-3-ylethynyl)phenyl)propan-1-amine was prepared following the method described in Scheme 9.

SCHEME 9

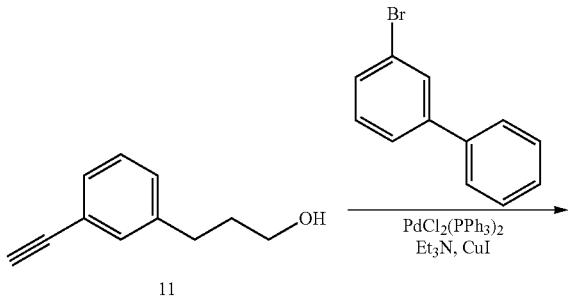

-continued

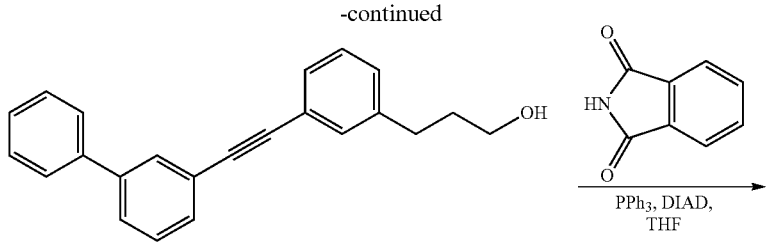

47

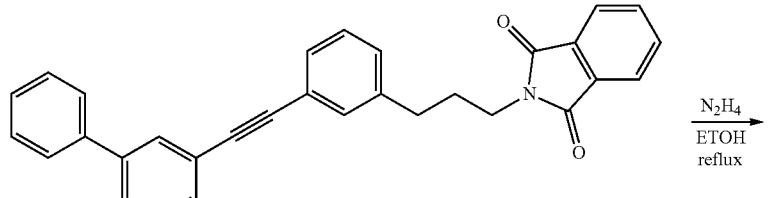

48

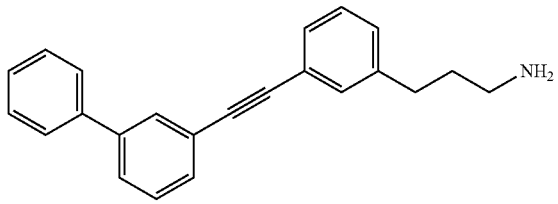 [SMILES: NCCCc1cccc(C#Cc2cccc(-c3ccccc3)c2)c1]

Step 1: Coupling of alcohol 11 with 3-biphenylacetylene was conducted following the method described in Example 1. Purification by flash chromatography (5% EtOAc-hexanes) gave alcohol 47 as a brown oil. Yield (0.560 g, 67%): $^1$H NMR (400 MHz, CDCl$_3$) δ 7.78 (br s, 1H), 7.61 (d, J=7.2 Hz, 2H), 7.56 (d, J=7.6 Hz, 1H), 7.51 (d, J=8.0 Hz, 1H), 7.37-7.48 (m, 6H), 7.29 (d, J=7.6 Hz, 1H), 7.19 (d, J=7.6 Hz, 1H), 3.70 (dt, J=6.2, 5.2 Hz, 2H), 2.73 (t, J=7.6 Hz, 2H), 1.92 (quint., J=6.8 Hz, 2H), 1.27 (t, J=5.2 Hz, 1H).

Step 2: Coupling of alcohol 47 with phthalimide was conducted following the method described in Example 17. Purification by flash chromatography (6% EtOAc-hexanes) gave alkyne 48. Yield (0.320 g, 42%): $^1$H NMR (400 MHz, CDCl$_3$) δ 7.84 (dd, J=5.6, 3.2 Hz, 2H), 7.77 (m, 1H), 7.71 (dd, J=5.6, 3.2 Hz, 2H), 7.61-7.63 (m, 2H), 7.32-7.57 (m, 8H), 7.18-7.25 (m, 2H), 3.77 (t, J=7.2 Hz, 2H), 2.70 (t, J=7.2 Hz, 2H), 2.02-2.09 (m, 2H).

Step 3: Deprotection of alkyne 48 following the method described in Example 17 followed by purification by preparative HPLC (Method 001P) gave Example 46 trifluoroacetate as a white sticky solid. Yield (0.16 g, 52%): $^1$H NMR (400 MHz, DMSO-d$_6$) δ 7.83 (br s, 1H), 7.71-7.15 (m, 3H), 7.67 (br s, 2H), 7.38-7.55 (m, 8H), 7.28-7.30 (m, 1H), 2.77-2.82 (m, 2H), 2.68 (t, J=7.2 Hz, 2H), 1.86 (quint, J=7.6 Hz, 2H).

Example 47

PREPARATION OF 3-AMINO-1-(3-(CYCLOPENTYLETHYNYL)PHENYL)PROPAN-1-OL

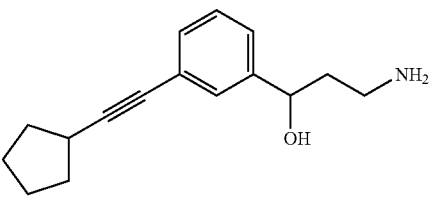 [SMILES: NCCC(O)c1cccc(C#CC2CCCC2)c1]

3-Amino-1-(3-(cyclopentylethynyl)phenyl)propan-1-ol was prepared following the method shown Scheme 10.

SCHEME 10

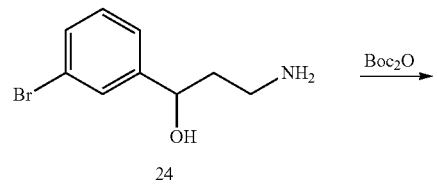

24

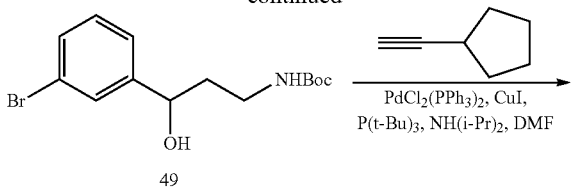

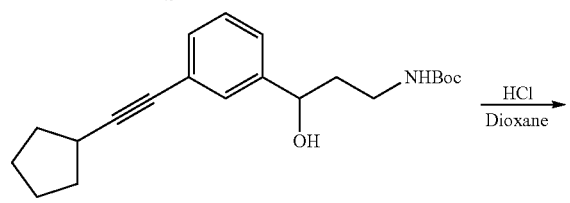

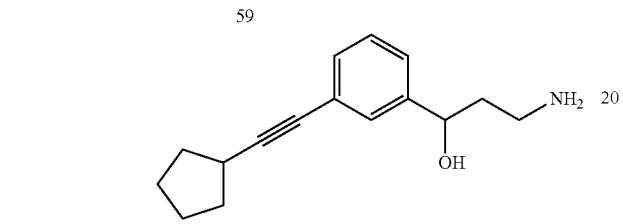

Step 1: Coupling of bromide 24 with di-tert-butyl dicarbonate was conducted following the method used in Example 20. Purification by flash chromatography (13% EtOAc-hexanes) provided tert-butyl 3-(3-bromophenyl)-3-hydroxypropylcarbamate (49) as a thick brown oil. Yield (4.0 g, 48%): $^1$H NMR (400 MHz, CDCl$_3$) δ 7.53 (s, 1H), 7.39 (d, J=8.0 Hz, 1H), 7.29 (d, J=7.6 Hz, 1H), 7.20 (t, J=7.6 Hz, 1H), 4.87 (br s, 1H), 4.71 (d, J=6.4 Hz, 1H), 3.64 (br s, 1H), 3.50-3.59 (m, 1H), 3.12-3.19 (m, 1H), 1.77-1.87 (m, 2H), 1.46 (s, 9H).

Step 2: Coupling of ethynylcyclopentane with tert-butyl 3-(3-bromophenyl)-3-hydroxypropylcarbamate (49) gave tert-butyl 3-(3-(cyclopentylethynyl)phenyl)-3-hydroxypropylcarbamate (50) as a brown oil. Yield (0.386 g, 92%).

Step 3: Deprotection of tert-butyl 3-(3-(cyclopentylethynyl)phenyl)-3-hydroxypropylcarbamate (50) followed by purification by preparative HPLC (Method 001P) gave Example 47 trifluoroacetate as a white solid. Yield (0.15 g, 37%): $^1$H NMR (400 MHz, CDCl$_3$) δ 7.88 (br s, 3H), 7.17-7.31 (m, 4H), 4.85 (dd, J=7.6, 4.0 Hz, 1H), 3.11-3.17 (m, 2H), 2.69 (quint, J=7.2 Hz, 2H), 1.56-2.02 (m, 10H).

Example 48

PREPARATION OF 3-AMINO-1-(3-(3-CYCLOPENTYLPROP-1-YNYL)PHENYL)PROPAN-1-OL

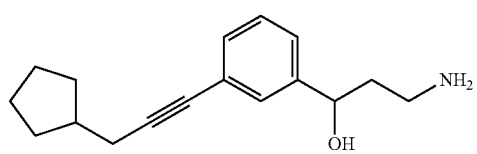 [SMILES: NCCC(O)c1cccc(C#CCC2CCCC2)c1]

3-Amino-1-(3-(3-cyclopentylprop-1-ynyl)phenyl)propan-1-ol was prepared following the method described in Example 47.

Step 1: Coupling of prop-2-ynylcyclopentane with tert-butyl 3-(3-bromophenyl)-3-hydroxypropylcarbamate (49) gave tert-butyl 3-(3-(3-cyclopentylprop-1-ynyl)phenyl)-3-hydroxypropylcarbamate as a brown oil. Yield (0.11 g, 26%).

Step 2: Deprotection of tert-butyl 3-(3-(3-cyclopentylprop-1-ynyl)phenyl)-3-hydroxypropylcarbamate followed by purification by preparative HPLC (Method 001P) gave Example 48 trifluoroacetate as a white solid. Yield (0.05 g, 44%): $^1$H NMR (400 MHz, DMSO-d$_6$) δ 7.57 (br s, 3H), 7.26-7.35 (m, 4H), 4.67 (dd, J=7.6, 4.8 Hz, 1H), 2.81-2.86 (m, 2H), 2.09 (quint, J=8.8 Hz, 2H), 1.74-1.88 (m, 5H), 1.52-1.65 (m, 4H), 1.27-1.35 (m, 2H).

Example 49

PREPARATION OF 3-AMINO-1-(3-(3-PHENYL-PROP-1-YNYL)PHENYL)PROPAN-1-OL

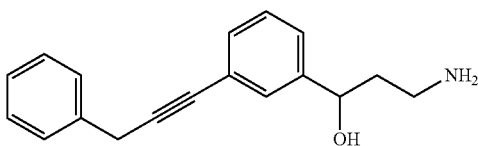 [SMILES: NCCC(O)c1cccc(C#CCc2ccccc2)c1]

3-Amino-1-(3-(3-phenylprop-1-ynyl)phenyl)propan-1-ol was prepared following the method described in Example 47.

Step 1: Coupling of prop-2-ynylbenzene with bromide 49 gave tert-butyl 3-hydroxy-3-(3-(3-phenylprop-1-ynyl)phenyl)propylcarbamate as a brown oil. Yield (0.404 g, 91%): $^1$H NMR (400 MHz, CDCl$_3$) δ 7.40-7.45 (m, 3H), 7.32-7.36 (m, 3H), 7.20-7.29 (m, 3H), 4.87 (br s, 1H), 4.72 (br s, 1H), 3.83 (s, 2H), 3.51-3.54 (m, 1H), 3.35 (br s, 1H), 3.12-3.19 (m, 1H), 1.81-1.84 (m, 2H), 1.45 (s, 9H).

Step 2: Deprotection of tert-butyl 3-hydroxy-3-(3-(3-phenylprop-1-ynyl)phenyl)propylcarbamate followed by purification by preparative HPLC (Method 001P) gave Example 49 trifluoroacetate as a white solid. Yield (0.114 g, 27%): $^1$H NMR (400 MHz, CDCl$_3$) δ 7.92 (br s, 3H), 7.26-7.37 (m, 5H), 7.16-7.23 (m, 4H), 4.79 (dd, J=8.4, 3.6 Hz, 1H), 3.75 (s, 2H), 3.02-3.16 (m, 2H), 1.93-1.98 (m, 2H).

Example 50

PREPARATION OF 6-(3-(3-AMINO-1-HYDROXYPROPYL)PHENYL)HEX-5-YN-1-OL

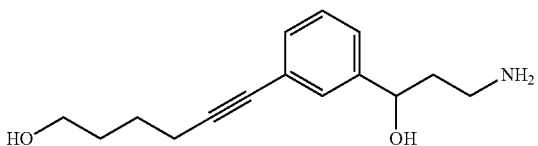 [SMILES: NCCC(O)c1cccc(C#CCCCCO)c1]

6-(3-(3-Amino-1-hydroxypropyl)phenyl)hex-5-yn-1-ol was prepared following the method described in Example 47.

Step 1: Coupling of hex-5-yn-1-ol with bromide 49 gave tert-butyl 3-hydroxy-3-(3-(6-hydroxyhex-1-ynyl)phenyl)propylcarbamate as a brown oil. Yield (0.405 g, 77%).

Step 2: Deprotection of tert-butyl 3-hydroxy-3-(3-(6-hydroxyhex-1-ynyl)phenyl)propylcarbamate followed by purification by preparative HPLC (Method 004P) gave Example 50 hydrochloride as a white solid. Yield (0.12 g, 32%): $^1$H NMR (400 MHz, DMSO-d$_6$) δ 7.87 (br s, 3H), 7.25-7.35 (m, 4H), 5.51 (br s, 1H), 4.68 (dd, J=7.8, 4.4 Hz, 1H), 4.46 (t, J=6.4 Hz, 1H), 3.40-3.44 (m, 2H), 2.77-2.88 (m, 2H), 2.41-2.44 (m, 2H), 1.80-1.93 (m, 2H), 1.56-1.62 (m, 4H).

Example 51

PREPARATION OF 4-(3-(3-AMINO-1-HYDROXYPROPYL)PHENYL)BUT-3-YN-1-OL

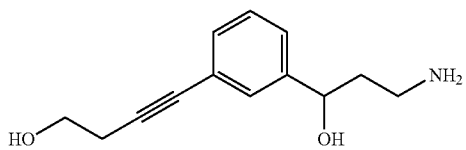 [SMILES: NCCC(O)c1cccc(C#CCCO)c1]

4-(3-(3-Amino-1-hydroxypropyl)phenyl)but-3-yn-1-ol was prepared following the method described in Example 47.

Step 1: Coupling of but-3-yn-1-ol with bromide 49 gave tert-butyl 3-hydroxy-3-(3-(4-hydroxybut-1-ynyl)phenyl)propylcarbamate as a brown oil. Yield (0.27 g, 56%): $^1$H NMR (400 MHz, DMSO-d$_6$) δ 7.42 (s, 1H), 7.31 (m, 3H), 5.60 (s, 1H), 3.89 (q, J=8.8 Hz, 2H), 3.80 (q, J=5.8 Hz, 2H), 2.70 (t, J=6.2 Hz, 2H), 2.54 (t, J=6.2 Hz, 2H), 1.81 (m, 2H), 1.49 (s, 9H).

Step 2: Deprotection of tert-butyl 3-hydroxy-3-(3-(4-hydroxybut-1-ynyl)phenyl)propylcarbamate followed by purification by preparative HPLC (Method 004P) gave Example 51 hydrochloride as a clear oil. Yield (0.03 g, 8%): $^1$H NMR (400 MHz, DMSO-D$_6$) δ 7.64 (br s, 3H), 7.26-7.36 (m, 4H), 4.90 (t, J=5.4 Hz, 1H), 4.68 (dd, J=7.7, 4.6 Hz, 1H), 3.58 (dt, J=6.4, 5.9 Hz, 2H), 2.80-2.85 (m, 2H), 2.57 (m, 2H), 1.81-1.88 (m, 2H).

Example 52

PREPARATION OF 3-AMINO-1-(3-(CYCLOHEXYLETHYNYL)PHENYL)PROPAN-1-OL

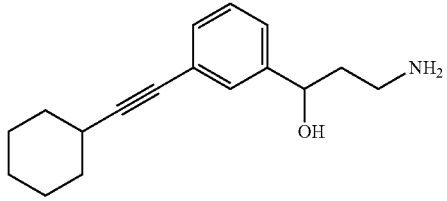 [SMILES: NCCC(O)c1cccc(C#CC2CCCCC2)c1]

3-Amino-1-(3-(cyclohexylethynyl)phenyl)propan-1-ol was prepared following the method described in Example 47.

Step 1: Coupling of ethynylcyclohexane with bromide 49 gave tert-butyl 343-(cyclohexylethynyl)phenyl)-3-hydroxypropylcarbamate as a brown oil. Yield (0.3 g, 75%).

Step 2: Deprotection of tert-butyl 3-(3-(cyclohexylethynyl)phenyl)-3-hydroxypropylcarbamate followed by purification by preparative HPLC (Method 004P) gave Example 52 hydrochloride as a white solid. Yield (0.05 g, 16%): $^1$H NMR (400 MHz, DMSO-d$_6$) δ 8.01 (br s, 3H), 7.23-7.34 (m, 4H), 5.61 (br s, 1H), 4.68 (dd, J=8.0, 4.4 Hz, 1H), 2.77-2.87 (m, 2H), 2.61-2.65 (m, 1H), 1.78-1.93 (m, 4H), 1.67-1.69 (m, 2H), 1.42-1.51 (m, 3H), 1.32-1.39 (m, 3H).

Example 53

PREPARATION OF 3-AMINO-1-(3-(HEPT-1-YNYL)PHENYL)PROPAN-1-OL

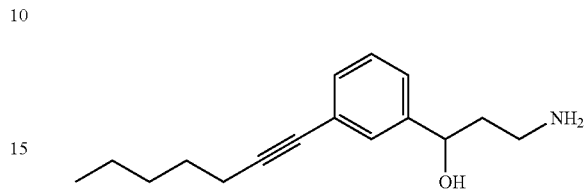

3-Amino-1-(3-(hept-1-ynyl)phenyl)propan-1-ol was prepared following the method described in Example 47.

Step 1: Coupling of hept-1-yne with bromide 49 gave tert-butyl 3-(3-(hept-1-ynyl)phenyl)-3-hydroxypropylcarbamate as a clear oil. Yield 0.32 g, 60%).

Step 2: Deprotection of tert-butyl 3-(3-(hept-1-ynyl)phenyl)-3-hydroxypropylcarbamate followed by purification by preparative HPLC (Method 004P) gave Example 53 hydrochloride as a white solid. Yield (0.03 g, 11%): $^1$H NMR (400 MHz, DMSO-d$_6$) δ 7.63 (br s, 3H), 7.24-7.33 (m, 4H), 5.59 (d, J=4.4 Hz, 1H), 4.65-4.67 (m, 1H), 2.82 (br s, 2H), 2.40 (t, J=7.2 Hz, 2H), 1.78-1.85 (m, 2H), 1.49-1.55 (m, 2H), 1.28-1.40 (m, 4H), 0.88 (t, J=7.2 Hz, 3H).

Example 54

PREPARATION OF 3-AMINO-1-(3-((2-METHOXYPHENYL)ETHYNYL)PHENYL)PROPAN-1-OL

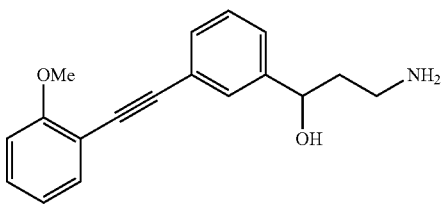

3-Amino-1-(3-((2-methoxyphenyl)ethynyl)phenyl)propan-1-ol was prepared following the method described in Example 47.

Step 1: Coupling of 1-ethynyl-2-methoxybenzene with bromide 49 gave tert-butyl 3-hydroxy-3-(3-((2-methoxyphenyl)ethynyl)phenyl)propylcarbamate as a brown oil. Yield (0.23 g, 50%): $^1$H NMR (400 MHz, CDCl$_3$) δ 7.58 (s, 1H), 7.51 (dd, J=7.6, 6.0 Hz, 1H), 7.46-7.49 (m, 1H), 7.30-7.34 (m, 3H), 6.97 (dd, J=7.6, 1.2 Hz, 1H), 6.92 (d, J=8.4, 1H), 4.88 (br s, 1H), 4.76 (quint\, J=4.4 Hz, 1H), 3.93 (s, 3H), 3.54 (br s, 1H), 3.32 (s, 1H), 3.18 (ddd, J=14.4, 10.8, 5.2 Hz, 1H), 1.84-1.88 (m, 2H), 1.51 (s, 9H).

Step 2: Deprotection of tert-butyl 3-hydroxy-3-(3-((2-methoxyphenyl)ethynyl)phenyl)propylcarbamate followed by purification by preparative HPLC (Method 001P) gave Example 54 trifluoroacetate as a white solid. Yield (0.15 g, 63%): $^1$H NMR (400 MHz, DMSO-d$_6$) δ 7.65 (br s, 3H), 7.35-7.49 (m, 6H), 7.10 (d, J=8.0 Hz, 1H), 6.98 (t, J=7.6 Hz, 1H), 5.67 (m, 1H), 4.73 (m, 1H), 3.86 (s, 3H), 2.85 (m, 2H), 1.83-1.91 (m, 2H).

Example 55

PREPARATION OF 4-((3-(2-AMINOETHOXY)PHENYL)ETHYNYL)TETRAHYDRO-2H-THIOPYRAN-4-OL

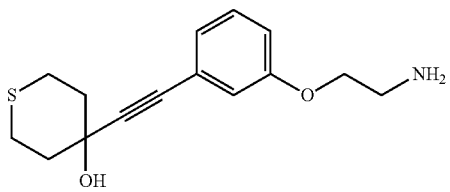 [SMILES: NCCOc1cccc(C#CC2(O)CCSCC2)c1]

4-((3-(3-Aminopropyl)phenyl)ethynyl)tetrahydro-2H-thiopyran-4-ol was prepared following the method described in Example 18.

Step 1: Coupling of 4-ethynyltetrahydro-2H-thiopyran-4-ol with bromide 19 in THF at 60° C. overnight followed by purification by flash chromatography (EtOAc/heptane (2:1)) gave 2,2,2-trifluoro-N-(3-(3-((4-hydroxytetrahydro-2H-thiopyran-4-yl)ethynyl)phenyl)propyl)acetamide as a pale yellow oil. Yield (0.822 g, 72%): $^1$H NMR (400 MHz, CDCl$_3$) δ 7.26 (t, J=4.5 Hz, 1H), 7.07 (dt, J=7.6, 1.2 Hz, 1H), 6.95 (dd, J=2.5, 1.4 Hz, 1H), 6.87 (ddd, J=8.2, 2.5, 0.8 Hz, 1H), 4.10 (m, 3H), 3.79 (q, J=5.5 Hz, 2H), 2.73-2.92 (m, 4H), 2.26-2.31 (m, 2H), 2.01-2.04 (m, 2H).

Step 2: Deprotection of 2,2,2-trifluoro-N-(3-(3-((4-hydroxytetrahydro-2H-thiopyran-4-yl)ethynyl)phenyl)propyl)acetamide followed by purification by flash chromatography (CH$_2$Cl$_2$/EtOH/NH$_4$OH 85:14:1) gave Example 55 as a white amorphous solid. Yield (0.41 g, 68%): $^1$H NMR (400 MHz, DMSO-d$_6$) δ7.23-7.28 (m, 1H), 6.93-6.98 (m, 3H), 6.72 (br s, 1H), 5.69 (br s, 1H), 3.90 (t, J=5.8 Hz, 2H), 2.83 (t, J=5.8 Hz, 2H), 2.69 (t, J=5.6 Hz, 4H), 2.09 (dt, J=13.0 and 4.6 Hz, 2H), 1.80 (quint, J=6.6 Hz, 2H), 1.60 (br s, 2H).

Example 56

PREPARATION OF 4-((3-(2-AMINOETHOXY)PHENYL)ETHYNYL)TETRAHYDRO-2H-PYRAN-4-OL,

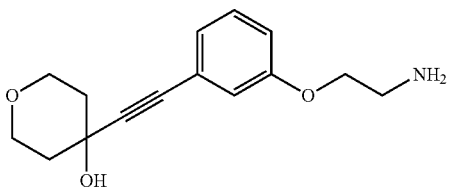 [SMILES: NCCOc1cccc(C#CC2(O)CCOCC2)c1]

4-((3-(2-Aminoethoxy)phenyl)ethynyl)tetrahydro-2H-pyran-4-ol was prepared following the method described in Example 55.

Step 1: Coupling of 4-ethynyltetrahydro-2H-pyran-4-ol with bromide 19 gave 2,2,2-trifluoro-N-(3-(3-((4-hydroxytetrahydro-2H-pyran-4-yl)ethynyl)phenyl)propyl)acetamide as a pale yellow oil. Yield (0.12 g, 22%).

Step 2: Deprotection of 2,2,2-trifluoro-N-(3-(3-((4-hydroxytetrahydro-2H-pyran-4-yl)ethynyl)phenyl)propyl)acetamide gave Example 56 as a white amorphous solid. Yield (0.050 g, 57%): $^1$H NMR (400 MHz, DMSO-d$_6$) δ7.23-7.27 (m, 1H), 6.93-6.98 (m, 3H), 5.70 (br s, 1H), 3.90 (t, J=5.8 Hz, 2H), 3.72-3.78 (m, 2H), 3.51-3.57 (m, 2H), 2.83 (t, J=5.8 Hz, 2H), 1.82-1.97 (m, 2H), 1.64-1.70 (m, 2H), 1.52 (br s, 2H).

Example 57

PREPARATION OF 1-((3-(2-AMINOETHOXY)PHENYL)ETHYNYL)CYCLOHEXANOL

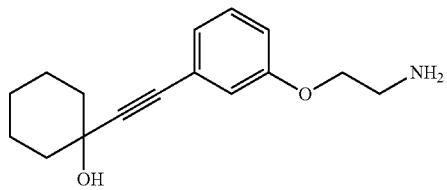 [SMILES: NCCOc1cccc(C#CC2(O)CCCCC2)c1]

1-((3-(2-Aminoethoxy)phenyl)ethynyl)cyclohexanol was prepared following the methods used in Example 32.

Step 1: Coupling of 1-ethynylcyclohexanol with bromide 17 gave 2-(2-(3-((1-hydroxycyclohexyl)ethynyl)phenoxy)ethyl)isoindoline-1,3-dione as a pale yellow oil. Yield (1.22 g, 57%): $^1$H NMR (400 MHz, DMSO-d$_6$) δ 7.82-7.88 (m, 4H), 7.21 (t, J=8.0 Hz, 1H), 6.92 (dt, J=8.0, 0.8 Hz, 1H), 6.84-6.88 (m, 2H), 5.38 (bs, 1H), 4.20 (t, J=5.6 Hz, 2H), 3.95 (t, J=5.6 Hz, 2H), 1.78-1.82 (m, 2H), 1.59-1.62 (m, 2H), 1.41-1.53 (m, 5H), 1.22-1.94 (m, 1H).

Step 2: Deprotection of 2-(2-(3-((1-hydroxycyclohexyl)ethynyl)phenoxy)ethyl)isoindoline-1,3-dione following the method described in Example 17 except that the reaction temperature was 70° C., gave Example 57 as a white amorphous solid. Yield (0.47 g, 67%): $^1$H NMR (400 MHz, DMSO-d$_6$) δ 7.24 (t, J=8.0 Hz, 1H), 6.93 (dt, J=8.0, 1.2 Hz, 1H), 6.88-6.91 (m, 2H), 5.35 (bs, 1H), 3.89 (t, J=6.0 Hz, 2H), 2.83 (t, J=6.0 Hz, 2H), 1.77-1.84 (m, 2H), 1.45-1.63 (m, 9H), 1.20-1.23 (m, 1H).

Example 58

PREPARATION OF 1-((3-(3-AMINOPROPYL)PHENYL)ETHYNYL)CYCLOHEPTANOL

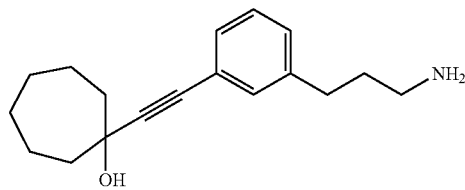 [SMILES: NCCCc1cccc(C#CC2(O)CCCCCC2)c1]

1-((3-(3-Aminopropyl)phenyl)ethynyl)cycloheptanol was prepared following the methods described in Example 32.

Step 1: Coupling of 1-ethynylcycloheptanol with bromide 3, following the method used to prepare Example 17 gave 2,2,2-trifluoro-N-(3-(3-((1-hydroxycycloheptyl)ethynyl)phenyl)propyl)acetamide as a pale yellow oil. Yield (1.78 g, 60%): ¹H NMR (400 MHz, DMSO-d₆) δ 9.40 (s, 1H), 7.26 (t, J=7.6, 1H), 7.17-7.22 (m, 3H), 5.26 (s, 1H), 3.16 (q, J=6.0 Hz, 2H), 2.56 (t, J=7.2 Hz, 2H), 1.91-1.97 (m, 2H), 1.73-1.79 (m, 4H), 1.45-1.63 (m, 8H).

Step 2: Deprotection of 2,2,2-trifluoro-N-(3-(3-((1-hydroxycycloheptyl)ethynyl)phenyl)propyl)acetamide following the method used to prepare Example 1 gave Example 58 as a clear oil. Yield (0.635 g, 86%): ¹H NMR (400 MHz, DMSO-d₆) δ 7.24 (t, J=8.0 Hz, 1H), 7.15-7.19 (m, 3H), 5.28 (br s, 1H), 2.56 (t, J=7.2 Hz, 2H), 2.44 (m, 2H), 1.91-1.97 (m, 2H), 1.73-1.79 (m, 2H), 1.44-1.63 (m, 10H), 1.32 (br s, 2H).

Example 59

PREPARATION OF 1-((3-(3-AMINO-1-HYDROXYPROPYL)PHENYL)ETHYNYL)CYCLOHEPTANOL

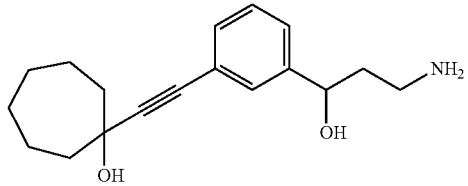 [SMILES: NCCC(O)c1cccc(C#CC2(O)CCCCCC2)c1]

1-((3-(3-Amino-1-hydroxypropyl)phenyl)ethynyl)cycloheptanol was prepared following the method described in Example 32.

Step 1: Coupling of 1-ethynylcycloheptanol with bromide 25 followed by purification by flash chromatography (2:1 to 3:2 to 1:1 hexanes/EtOAc) gave 2,2,2-trifluoro-N-(3-hydroxy-3-(3-((1hydroxycycloheptyl)ethynyl)phenyl)propyl)acetamide as a brown oil. Yield (0.97 g, 57%): ¹H NMR (400 MHz, CDCl₃) δ 7.40 (t, J=1.6 Hz, 1H), 7.38 (m, 1H), 7.28 (dt, J=6.8, 1.6 Hz, 1H), 7.24-7.34 (m, 2H), 4.84 (ddd, J=6.4, 5.2, 3.2 Hz, 1H), 3.66 (dddd, J=12.0, 7.2, 6.8, 6.8 Hz, 1H), 3.64 (dddd, J=12.4, 8.0, 5.6, 4.8 Hz, 1H), 2.56 (d, J=2.4 Hz, 1H), 2.10 (dd, J=14.0, 7.6 Hz, 2H), 2.04 (s, 1H), 1.86-2.00 (m, 4H), 1.56-1.76 (m, 8H).

Step 2: Deprotection of 2,2,2-trifluoro-N-(3-hydroxy-3-(3-((1-hydroxycycloheptyl)ethynyl)phenyl)propyl)acetamide followed by flash chromatography (9:1 CH₂Cl₂/MeOH to 9:1 to 8:2 CH₂Cl₂/10% concentrated NH₄OH in MeOH) gave Example 59. The resulting wet oil was dissolved in CH₂Cl₂ and dried over MgSO₄ and concentrated under reduced pressure to give Example 59 as a clear oil which solidified to a white solid on standing. Yield (0.41 g, 36%): ¹H NMR (400 MHz, DMSO-d₆) δ 7.32 (br s, 1H), 7.24-7.29 (m, 2H), 7.19-7.22 (m, 1H), 5.27 (s, 1H), 4.65 (t, J=6.4 Hz, 1H), 2.55-2.65 (m, 2H), 1.94 (dd, J=13.6, 7.6 Hz, 2H), 1.74-1.79 (m, 2H), 1.42-1.66 (m, 10H).

Example 60

PREPARATION OF N-(3-(3-((1-HYDROXYCYCLOHEXYL)ETHYNYL)PHENYL)PROPYL)ACETAMIDE

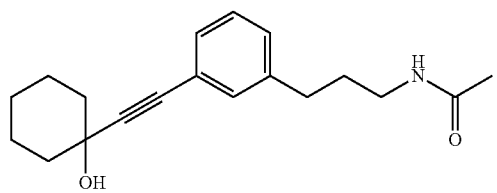 [SMILES: CC(=O)NCCCc1cccc(C#CC2(O)CCCCC2)c1]

N-(3-(3-((1-Hydroxycyclohexyl)ethynyl)phenyl)propyl)acetamide was prepared following the method shown in Scheme 11.

SCHEME 11

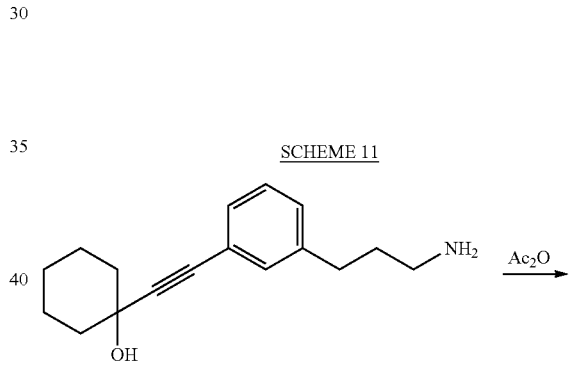

Example 11

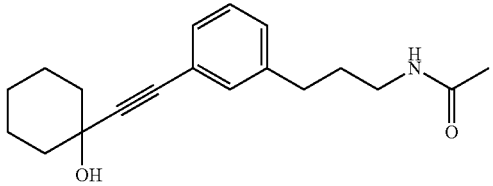

1-((3-(3-Aminopropyl)phenyl)ethynyl)cyclohexanol (Example 11) (0.057 g, 0.19 mmole) was stirred in acetic anhydride (2.0 ml) for 2 h at room temperature. Water (10 ml) was added with swirling and sonication. The product was collected by filtration and washed with water (2×5 ml) and dried under vacuum overnight giving Example 60 as a white solid. Yield (0.050 g, 76%): ¹H NMR (400 MHz, DMSO-d₆) δ 7.81 (bs, 1H), 7.25 (t, J=8.0 Hz, 1H), 7.22 (s, 1H), 7.16-7.19 (m, 2H), 5.38 (s, 1H), 2.99 (q, J=5.6 Hz, 2H), 2.54 (t, J=7.2 Hz, 2H), 1.80-1.84 (m, 2H), 1.78 (s, 3H), 1.43-1.68 (m, 9H), 1.20-1.23 (m, 1H).

Example 61

PREPARATION OF 3-(3-(PYRIDIN-2-YLETHYNYL)PHENYL)PROPAN-1-AMINE

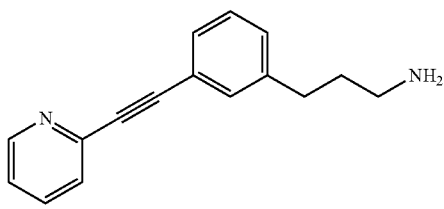 [SMILES: NCCCc1cccc(C#Cc2ccccn2)c1]

3-(3-(Pyridin-2-ylethynyl)phenyl)propan-1-amine was prepared following the method shown in Scheme 12.

SCHEME 12

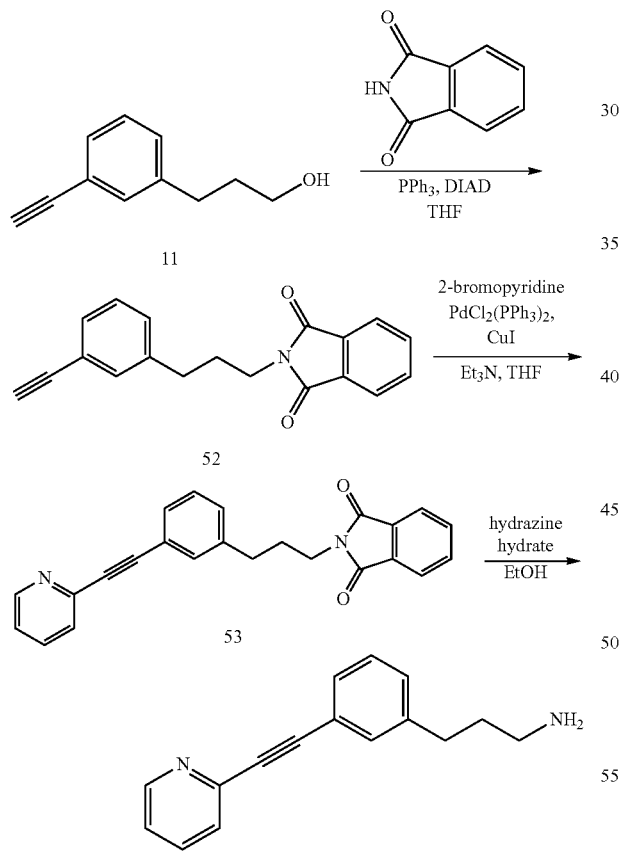

Step 1: Coupling of alcohol 11 with phthalimide following the procedure described in Example 17 except that diisopropyl azodicarboxylate was used in place of diethyl azodicarboxylate gave alkyne 52. Yield (6 g, 76%): $^1$H NMR (400 MHz, CDCl$_3$) δ 7.83 (dd, J=5.2, 2.8 Hz, 2H), 7.70 (dd, J=5.6, 3.2 Hz, 2H), 7.33 (s, 1H), 7.24-7.29 (m, 1H), 7.16-7.22 (m, 2H), 3.74 (t, J=7.2 Hz, 2H), 3.04 (s, 1H), 2.66 (t, J=8.0 Hz, 2H), 2.02 (quint, J=7.2 Hz, 2H).

Step 2: Coupling of 2-bromopyridine with alkyne 52 following the method described in Example 17 gave 2-(3-(3-(pyridin-2-ylethynyl)phenyl)propyl)isoindoline-1,3-dione (53) as a brown oil. Yield (0.6 g, 80%): $^1$H NMR (400 MHz, CDCl$_3$): δ 8.62 (d, J=4.1 Hz, 1H), 7.84 (dd, J=5.6, 3.2 Hz, 2H), 7.71 (dd, J=5.6, 3.2 Hz, 2H), 7.66-7.69 (m, 1H), 7.52 (d, J=8.0 Hz, 1H), 7.44 (s, 1H), 7.38 (dt, J=7.2, 1.6 Hz, 1H), 7.20-7.28 (m, 3H), 3.76 (t, J=7.2 Hz, 2H), 2.69 (t, J=8.4 Hz, 2H), 2.04 (quint, J=7.6 Hz, 2H).

Step 3: Deprotection of 2-(3-(3-(pyridin-2-ylethynyl)phenyl)propyl)isoindoline-1,3-dione (53) was conducted following the method described in Example 17 except that the reaction was run at room temperature overnight. Purification by preparative HPLC (Method 001P) gave Example 61 trifluoroacetate as a brown oil. The trifluoroacetate was suspended in CH$_2$Cl$_2$ (15 ml) and shaken with aqueous ammonia (12.5%, 20 mL). The organic layer was washed with water followed by brine, dried over anhydrous Na$_2$SO$_4$ and concentrated under reduced pressure to give Example 61 as a brown oil. Yield (0.20 g, 35%): $^1$H NMR (400 MHz, DMSO-d$_6$) δ 8.65 (d, J=4.8 Hz, 1H), 7.81 (dt, J=7.6, 1.6 Hz, 1H), 7.60 (d, J=7.6 Hz, 1H), 7.24-7.44 (m, 4H), 2.68 (t, J=7.6 Hz, 2H), 2.57 (t, J=6.8 Hz, 2H), 1.70 (quint, J=6.8 Hz, 2H).

Example 62

PREPARATION OF 2-(3-(PYRIDIN-3-YLETHYNYL)PHENOXY)ETHANAMINE

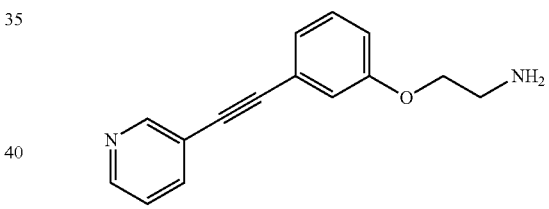

2-(3-(Pyridin-3-ylethynyl)phenoxy)ethanamine was prepared following the method shown in Scheme 13.

SCHEME 13

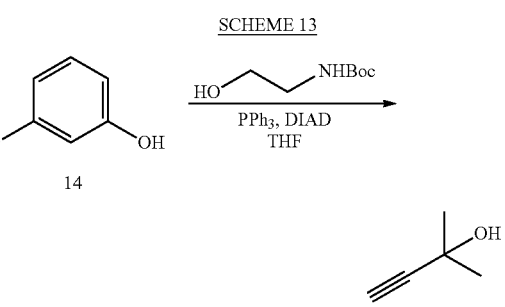

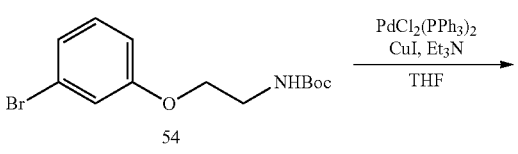

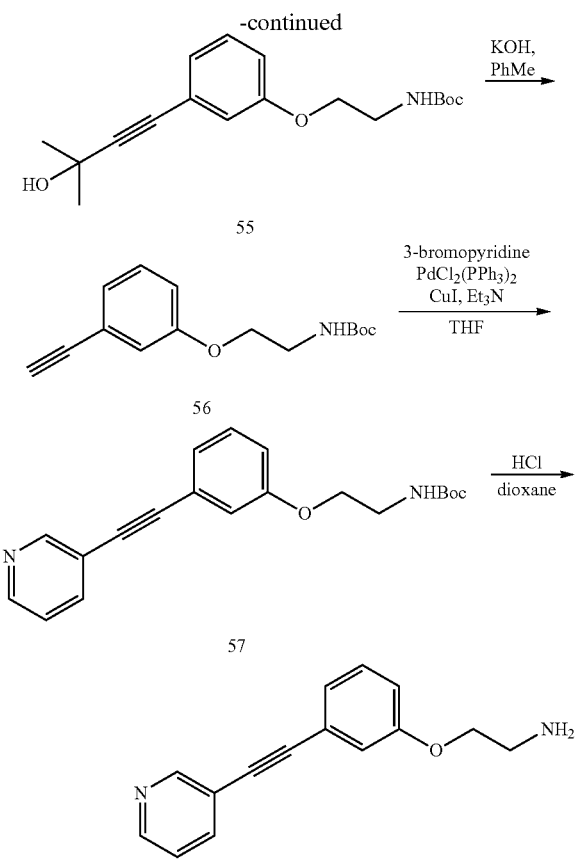

Step 1: Coupling of 3-bromophenol (14) with N-Boc-ethanolamine following the method used in Example 17 gave bromide 54 as a pale yellow oil. Yield (8.34 g, 91%): $^1$H NMR (400 MHz, CDCl$_3$) δ 7.14 (t, J=8.0 Hz, 1H), 7.09 (dd, J=8.0, 1.6 Hz, 1H), 7.05 (t, J=1.6 Hz, 1H), 6.82 (ddd, J=8.0, 2.4, 1.6 Hz, 1H), 4.95 (bs, 1H), 4.00 (t, J=5.2 Hz, 2H), 3.53 (quint, J=5.2 Hz, 2H), 1.45 (s, 9H).

Step 2: Coupling of bromide 54 with alkyne 9 following the method used in Example 17 gave alkyne 55 as a tan solid. Yield (0.90 g, 90%): $^1$H NMR (400 MHz, CDCl$_3$): δ 7.21 (t, J=8.0 Hz, 1H), 7.02 (d, J=7.6 Hz, 1H), 6.93-6.95 (m, 1H), 6.85 (ddd, J=8.4, 2.8, 0.8 Hz, 1H), 4.97 (br s, 1H), 4.01 (t, J=5.2 Hz, 2H), 3.51-3.52 (m, 2H), 1.62, (s, 6H), 1.56 (s, 9H).

Step 3: Treatment of alkyne 55 with KOH following the method used in Example 17 gave alkyne 56 as a brown oil Yield (0.2 g, 80%): $^1$H NMR (400 MHz, CDCl$_3$) δ 7.23 (d, J=8.0 Hz, 1H), 7.10 (dt, J=7.6, 1.2 Hz, 1H), 7.00-7.02 (m, 1H), 6.90 (ddd, J=8.4, 2.8, 0.8 Hz, 1H), 4.97 (br s, 1H), 4.01 (t, J=5.2 Hz, 2H), 3.49-3.54 (m, 2H), 3.06 (s, 1H), 1.45 (s, 9H).

Step 4: Coupling of alkyne 56 with 3-bromopyridine following the method used in Example 17 gave alkyne 57 as a brown oil. Yield (0.340 g, 44%): $^1$H NMR (400 MHz, CDCl$_3$): δ 8.76 (d, J=1.4 Hz, 1H), 8.55 (dd, J=4.8, 1.2 Hz, 1H), 7.81 (dt, J=8.0, 1.6 Hz, 1H), 7.29 (t, J=4.4 Hz, 1H), 7.28 (s, 1H), 7.16 (d, J=8.0 Hz, 1H), 7.06 (br s, 1H), 6.92 (dd, J=8.4, 2.8 Hz, 1H), 4.05 (t, J=5.2 Hz, 2H), 3.54 (q, J=5.2 Hz, 2H), 1.46 (s, 9H)

Step 5: Deprotection of alkyne 57 with HCl/dioxane following the method used in Example 36 gave Example 62 hydrochloride as an off-white solid. Yield (0.230 g, 83%): $^1$H NMR (400 MHz, DMSO-d$_6$) δ 8.78 (br s, 1H), 8.60 (dd, J=4.8, 1.6 Hz, 1H), 8.11 (br s, 3H), 8.02-8.04 (m, 1H), 7.51 (dd, J=8.0, 5.2 Hz, 1H), 7.37 (t, J=8.0 Hz, 1H), 7.20 (d, J=8.0 Hz, 1H), 7.18 (d, J=1.6 Hz, 1H), 7.06 (dd, J=8.4, 2.4 Hz, 1H), 4.20 (t, J=4.8 Hz, 2H), 3.19 (dd, J=10.4, 5.6 Hz, 2H).

Example 63

PREPARATION OF 3-(3-(PYRIDIN-4-YLETHYNYL)PHENYL)PROPAN-1-AMINE

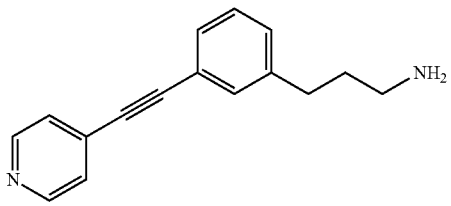 [SMILES: NCCCc1cccc(C#Cc2ccncc2)c1]

3-(3-(Pyridin-4-ylethynyl)phenyl)propan-1-amine was prepared following the method used in Example 61.

Step 1: Coupling of 4-bromopyridine with alkyne 52 and purification by flash chromatography (15% EtOAc-hexanes) gave 2-(3-(3-(pyridin-4-ylethynyl)phenyl)propyl)isoindoline-1,3-dione as a yellow solid. Yield (0.271 g, 53%): $^1$H NMR (400 MHz, DMSO-d$_6$): δ 8.58 (dd, J=4.4, 1.6 Hz, 2H), 7.48 (dd, J=4.4, 1.6 Hz, 2H), 7.41 (s, 1H), 7.38 (d, J=7.6 Hz, 1H), 7.33 (t, J=7.6 Hz, 1H), 7.27 (d, J=7.6 Hz, 1H), 2.59 (t, J=7.6 Hz, 2H), 2.49 (t, J=6.4 Hz, 2H), 1.60 (quint, J=7.2 Hz, 2H).

Step 2: Deprotection of 2-(3-(3-(pyridin-4-ylethynyl)phenyl)propyl)isoindoline-1,3-dione gave, after conversion to the free base, Example 63 as a yellow oil. Yield (0.023 g, 13%): $^1$H NMR (400 MHz, DMSO-d$_6$) δ 8.58 (d, J=4.0 Hz, 2H), 7.85-7.52, (m, 4H), 7.48 (d, J=5.2 Hz, 2H), 7.44 (s, 1H), 7.34 (m, 1H), 7.30 (d, J=5.2 Hz, 2H), 3.57 (t, J=6.9 Hz, 2H), 2.63 (t, J=7.4 Hz, 2H), 1.89 (quint, J=8.0 Hz, 2H).

Example 64

PREPARATION OF 3-(3-(PYRIDIN-3-YLETHYNYL)PHENYL)PROPAN-1-AMINE

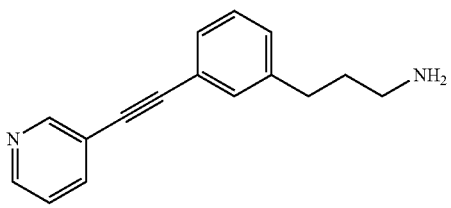

3-(3-(Pyridin-3-ylethynyl)phenyl)propan-1-amine was prepared following the method described in Example 61.

Step 1: Coupling of 3-bromopyridine with alkyne 52 gave 2-(3-(3-(pyridin-4-ylethynyl)phenyl)propyl)isoindoline-1,3-dione as a brown oil. Yield (0.032 g, 42%): $^1$H NMR (400 MHz, CDCl$_3$): δ 8.76 (d, J=1.6 Hz, 1H), 8.55 (dd, J=5.2, 1.6 Hz, 1H), 7.83 (dd, J=5.2, 2.8 Hz, 2H), 7.80 (dt, J=8.0, 1.6 Hz, 1H), 7.71 (dd, J=5.2, 2.8 Hz, 2H), 7.39 (s, 1H), 7.16-7.24 (m, 4H), 3.76 (t, J=7.2 Hz, 2H), 2.70 (t, J=8.0 Hz, 2H), 2.05 (quint, J=7.2 Hz, 2H).

Step 2: Deprotection of 2-(3-(3-(pyridin-4-ylethynyl)phenyl)propyl)isoindoline-1,3-dione gave, after conversion to the free base, Example 64 as a yellow oil. Yield (0.135 g, 65%): $^1$H NMR (400 MHz, DMSO-$d_6$) δ 8.71 (d, J=2.0 Hz, 1H), 8.55 (dd, J=5.2, 2.0 Hz, 1H), 8.55 (dt, J=8.0, 1.6 Hz, 1H), 7.43 (dd, J=8.0, 4.8 Hz, 1H), 7.39 (s, 1H), 7.38 (d, J=7.6 Hz, 1H), 7.31 (t, J=7.2 Hz, 1H), 7.25 (d, J=7.6 Hz, 1H), 3.30 (obs m, 2H), 2.59 (t, J=7.6 Hz, 2H), 1.60 (quint, J=8.4 Hz, 2H).

Example 65

PREPARATION OF 3-(3-(THIOPHEN-2-YLETHYNYL)PHENYL)PROPAN-1-AMINE

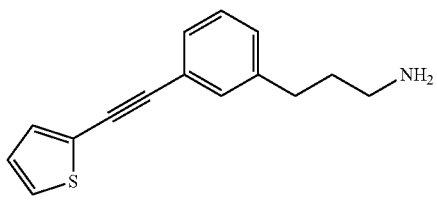 [SMILES: NCCCc1cccc(C#Cc2cccs2)c1]

3-(3-(Thiophen-2-ylethynyl)phenyl)propan-1-amine was prepared following the method described in Example 61.

Step 1: Alkyne 52 was coupled with 2-bromothiophene and purified by flash chromatography (15% EtOAc-hexanes) to give 2-(3-(3-(thiophen-2-ylethynyl)phenyl)propyl)isoindoline-1,3-dione as a yellow solid. Yield (0.490 g, 50%): $^1$H NMR (400 MHz, CDCl$_3$) δ 7.84 (dd, J=5.6, 3.2 Hz, 2H), 7.71 (dd, J=5.2, 3.2 Hz, 2H), 7.35 (s, 1H), 7.26-7.30 (m, 3H), 7.23 (t, J=7.6 Hz, 1H), 7.18 (d, J=7.6 Hz, 1H), 7.01 (dd, J=5.2, 3.6 Hz, 1H), 3.76 (t, J=7.2 Hz, 2H), 2.69 (t, J=7.6 Hz, 2H), 2.05 (quint., J=7.6 Hz, 2H).

Step 2: 2-(3-(3-(Thiophen-2-ylethynyl)phenyl)propyl) isoindoline-1,3-dione was deprotected following the method in Example 61. The reaction mixture was diluted with diethyl ether and the precipitate was removed by filtration. The filtrate was concentrated under reduced pressure and the diethyl ether precipitation step was repeated. Purification by prep HPLC (method 001) gave Example 65 trifluoroacetate as a cream-colored solid. Yield (0.210 g, 65%): $^1$H NMR (400 MHz, CDCl$_3$) δ 7.94 (br s, 3H), 7.33 (d, J=7.6 Hz, 1H), 7.25-7.28 (m, 2H), 7.22 (d, J=7.6 Hz, 1H), 7.09 (d, J=7.6 Hz, 1H), 6.99 (dd, J=5.2, 3.6 Hz, 1H), 2.89 (t, J=7.2 Hz, 2H), 2.63 (t, J=7.6 Hz, 2H), 1.92-1.99 (m, 2H).

Example 66

PREPARATION OF 3-(3-(THIOPHEN-3-YLETHYNYL)PHENYL)PROPAN-1-AMINE

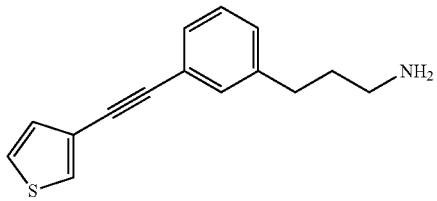 [SMILES: NCCCc1cccc(C#Cc2ccsc2)c1]

3-(3-(Thiophen-3-ylethynyl)phenyl)propan-1-amine was prepared following the method described in Example 61.

Step 1: Coupling of alkyne 52 with 3-bromothiophene and purification by flash chromatography (17% EtOAc-hexanes) gave 2-(3-(3-(thiophen-3-ylethynyl)phenyl)propyl)isoindoline-1,3-dione as an off-white solid. Yield (0.441 g, 43%): $^1$H NMR (400 MHz, CDCl$_3$) δ 7.84 (dd, J=5.2, 3.2 Hz, 2H), 7.71 (dd, J=5.2, 3.2 Hz, 2H), 7.51 (dd, J=2.8, 1.2 Hz, 1H), 7.36 (s, 1H), 7.23 (t, J=7.6 Hz, 1H), 7.19 (dd, J=4.8, 1.2 Hz, 1H), 7.17 (d, J=7.6 Hz, 1H), 3.76 (t, J=6.8 Hz, 2H), 2.68 (t, J=7.6 Hz, 2H), 2.04 (quint., J=7.6 Hz, 2H).

Step 2: Deprotection of 2-(3-(3-(thiophen-3-ylethynyl) phenyl)propyl)isoindoline-1,3-dione according to the method used in Example 65, except that HPLC purification was not necessary, gave Example 66 as a brown oil. Yield (0.190 g, 66%): $^1$H NMR (400 MHz, CDCl$_3$) δ 7.51-7.52 (m, 1H), 7.15-7.36 (m, 6H), 2.74 (t, J=7.2 Hz, 2H), 2.66 (t, J=7.9 Hz, 2H), 1.75-1.83 (m, 2H), 1.54 (br s, 2H).

Example 67

PREPARATION OF 3-(3-(6-METHOXYHEX-1-YNYL)PHENYL)PROPAN-1-AMINE

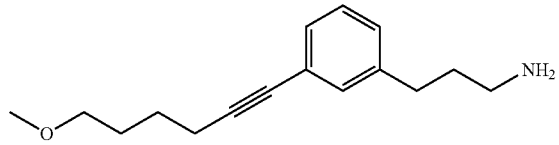 [SMILES: COCCCCC#Cc1cccc(CCCN)c1]

3-(3-(6-Methoxyhex-1-ynyl)phenyl)propan-1-amine was prepared following the method in Example 36.

Step 1: Coupling of aryl bromide 34 with 6-methoxyhex-1-yne following the method used for the preparation of Example 36 and purification by flash chromatography (10% EtOAc-hexanes) gave tert-butyl 3-(3-(6-methoxyhex-1-ynyl) phenyl)propylcarbamate as a brown oil. Yield (0.20 g, 36%).

Step 2: Deprotection of tert-butyl 3-(3-(6-methoxyhex-1-ynyl)phenyl)propylcarbamate following the method used in Example 36, except that CH$_2$Cl$_2$ was used as a cosolvent in the reaction (HCl-dioxanesolution: CH$_2$Cl$_2$ 7:5), and purification by prep HPLC (Method 004P) gave Example 67 hydrochloride as an off white solid. Yield (0.050 g, 30%): $^1$H NMR (400 MHz, CDCl$_3$) δ 8.37 (br s, 3H), 7.10-7.24 (m, 4H), 4.02 (t, J=6.4 Hz, 2H), 3.78 (s, 3H), 2.98 (t, J=7.6 Hz, 2H), 2.69 (t, J=7.6 Hz, 2H), 2.44 (t, J=7.6 Hz, 2H), 2.04-2.12 (m, 2H), 1.82-1.89 (m, 2H), 1.63-1.73 (m, 2H).

Example 68

PREPARATION OF 6-(3-(3-AMINOPROPYL) PHENYL)HEX-5-YN-1-OL

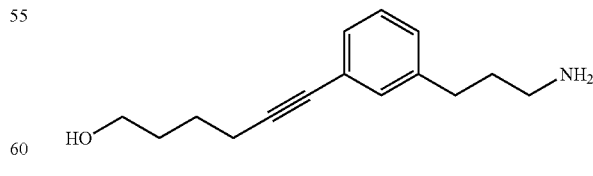

6-(3-(3-Aminopropyl)phenyl)hex-5-yn-1-ol was prepared following the method used in Example 36.

Step 1: Coupling of hex-5-yn-1-ol with bromide 34 was conducted following the method used in Example 36. Purification by flash chromatography (30% EtOAc-hexanes) gave tert-butyl 3-(3-(6-hydroxyhex-1-ynyl)phenyl)propylcarbamate as a white solid. Yield (0.350 g, 66%): $^1$H NMR (400 MHz, CDCl$_3$) δ 7.17-7.23 (m, 3H), 7.07-7.10 (m, 1H), 6.81-6.84 (m, 1H), 4.53 (br s, 1H), 3.72 (q, J=6.0 Hz, 2H), 3.10-3.18 (m, 2H), 2.60 (t, J=8.0 Hz, 2H), 2.46 (t, J=6.8 Hz, 2H), 1.63-1.83 (m, 6H), 1.44 (s, 9H).

Step 2: Deprotection of tert-butyl 3-(3-(6-hydroxyhex-1-ynyl)phenyl)propylcarbamate following purification by prep HPLC using Method 001P gave Example 68 as a white solid. Yield (0.140 g, 34%): $^1$H NMR (400 MHz, CDCl$_3$) δ 7.21 (d, J=7.6 Hz, 2H), 7.17 (t, J=7.6 Hz, 1H), 7.07 (dm, J=7.2 Hz, 1H), 3.68 (t, J=6.4 Hz, 2H), 2.95 (t, J=7.6 Hz, 2H), 2.67 (t, J=7.6, 2H), 2.43 (t, J=6.4 Hz, 2H), 2.06 (quint., J=7.6 Hz, 2H), 1.71-1.79 (m, 2H), 1.61-1.68 (m, 2H).

Example 69

PREPARATION OF 3-AMINO-1-(3-(4-PHENYL-BUT-1-YNYL)PHENYL)PROPAN-1-OL

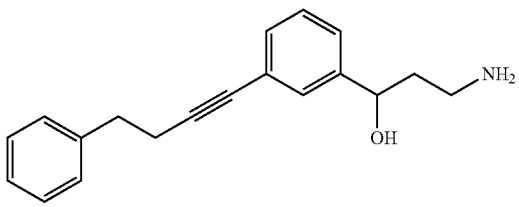 [SMILES: NCCC(O)c1cccc(C#CCCc2ccccc2)c1]

3-Amino-1-(3-(4-phenylbut-1-ynyl)phenyl)propan-1-ol was prepared following the general scheme used in Example 19 with modifications.

Step 1: Coupling of aryl bromide 25 with but-3-ynylbenzene following the method used in Example 1 and purification by flash chromatography (20% EtOAc-hexanes) gave 2,2,2-trifluoro-N-(3-hydroxy-3-(3-(4-phenylbut-1-ynyl)phenyl)propyl)acetamide as a brown oil. Yield (0.340 g, 52%): $^1$H NMR (400 MHz, CDCl$_3$) δ 7.28-7.36 (m, 7H), 7.24-7.27 (m, 2H), 4.84-4.88 (m, 1H), 3.66-3.74 (m, 1H), 3.41 (ddd, J=17.6, 8.0, 4.4 Hz, 1H), 2.93 (t, J=7.6 Hz, 2H), 2.70 (t, J=7.6 Hz, 2H), 2.27 (d, J=1.6 Hz, 1H), 1.90-2.03 (m, 2H).

Step 2: Deprotection of 2,2,2-trifluoro-N-(3-hydroxy-3-(3-(4-phenylbut-1-ynyl)phenyl)propyl)acetamide was conducted following the method used in Example 1, except that the reaction was heated overnight. Purification by prep HPLC (method 004P) gave Example 69 as a brown solid. Yield (0.085 g, 33%): $^1$H NMR (400 MHz, DMSO-d$_6$) δ 7.21-7.34 (m, 9H), 4.67 (t, J=6.0 Hz, 1H), 2.88 (t, J=7.2 Hz, 2H), 2.68-2.74 (m, 4H), 1.68 (q, J=6.4 Hz, 2H), 0.86-0.92 (m, 1H).

Example 70

PREPARATION OF 3-(3-(5-METHOXYPENT-1-YNYL)PHENYL)PROPAN-1-AMINE

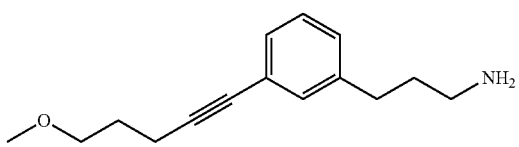 [SMILES: COCCCC#Cc1cccc(CCCN)c1]

3-(3-(5-Methoxypent-1-ynyl)phenyl)propan-1-amine was prepared following the method used in Example 36.

Step 1: Coupling of aryl bromide 34 with 5-methoxypent-1-yne and purification by flash chromatography (10% EtOAc-hexanes) gave tert-butyl 3-(3-(5-methoxypent-1-ynyl)phenyl)propylcarbamate as a yellow oil. Yield (0.170 g, 32%): $^1$H NMR (400 MHz, CDCl$_3$) δ 7.17-7.23 (m, 3H), 7.08-7.10 (m, 1H), 4.52 (br s, 1H), 4.31 (t, J=6.4 Hz, 2H), 3.79 (s, 3H), 3.08-3.17 (m, 2H), 2.60 (t, J=7.6 Hz, 2H), 2.53 (t, J=7.2 Hz, 2H), 1.94-2.01 (m, 2H), 1.76-1.83 (m, 2H), 1.44 (s, 9H).

Step 2: Deprotection of tert-butyl 3-(3-(5-methoxypent-1-ynyl)phenyl)propylcarbamate and purification by prep HPLC (method 001P) gave Example 70 trifluoroacetate as a white solid. Yield (0.110 g, 92%): $^1$H NMR (400 MHz, CDCl$_3$) δ 7.11-7.24 (m, 4H), 4.30 (t, J=6.4 Hz, 2H), 3.78 (s, 3H), 2.97 (t, J=7.2 Hz, 2H), 2.70 (t, J=7.6 Hz, 2H), 2.52 (t, J=7.2 Hz, 2H), 2.02-2.11 (m, 2H), 1.94-2.00 (m, 2H).

Example 71

PREPARATION OF 3-AMINO-1-(3-(4-CYCLO-PENTYLBUT-1-YNYL)PHENYL)PROPAN-1-OL

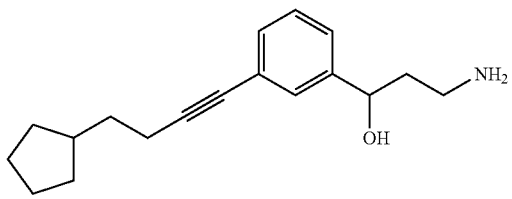 [SMILES: NCCC(O)c1cccc(C#CCCC2CCCC2)c1]

3-Amino-1-(3-(4-cyclopentylbut-1-ynyl)phenyl)propan-1-ol is prepared following the method used in Example 69.

Example 72

PREPARATION OF 3-(3-(4-PHENYLBUT-1-YNYL)PHENYL)PROPAN-1-AMINE

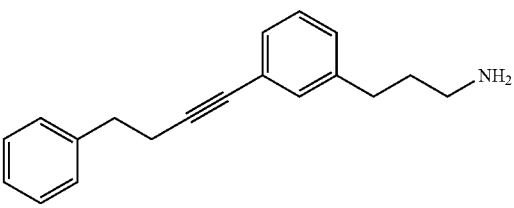 [SMILES: NCCCc1cccc(C#CCCc2ccccc2)c1]

3-(3-(4-Phenylbut-1-ynyl)phenyl)propan-1-amine was prepared following the method used in Example 36.

Step 1: Coupling of aryl bromide 34 with but-3-ynylbenzene was conducted following the method used in Example 36. Purification by flash chromatography (10% EtOAc-hexanes) gave tert-butyl 3-(3-(4-phenylbut-1-ynyl)phenyl)propylcarbamate as a brown oil. Yield (0.40 g, 82%).

Step 2: Deprotection of tert-butyl 3-(3-(4-phenylbut-1-ynyl)phenyl)propylcarbamate gave Example 72 hydrochloride as a white solid. $^1$H NMR (400 MHz, DMSO-d$_6$) δ 7.74

(br s, 3H), 7.14-7.28 (m, 9H), 2.82 (t, J=7.2 Hz, 2H), 2.71 (t, J=7.6 Hz, 2H), 2.67 (t, J=7.2 Hz, 2H), 2.58 (t, J=7.6 Hz, 2H), 1.78 (quint., J=7.6 Hz, 2H).

Example 73

PREPARATION OF 2-(3-(4-METHYLPENT-1-YNYL)PHENOXY)ETHANAMINE

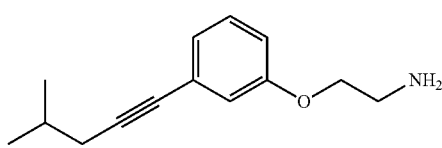 [SMILES: CC(C)CC#Cc1cccc(OCCN)c1]

2-(3-(4-Methylpent-1-ynyl)phenoxy)ethanamine was prepared following the method described in Scheme 14.

Scheme 14

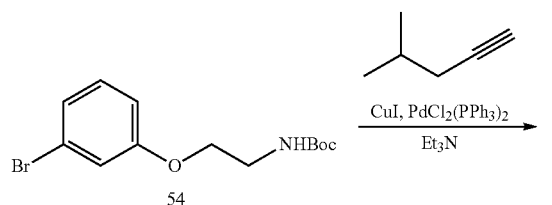

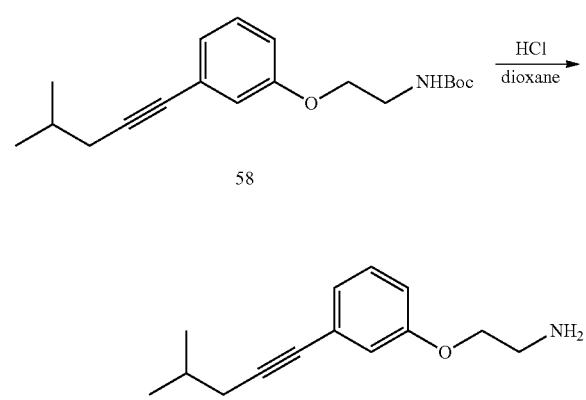

Step 1: Coupling of aryl bromide 54 with 4-methylpent-1-yne following the method used in Example 1 and purification by flash chromatography (20% EtOAc-hexanes) gave alkyne 58 as a brown oil. Yield (0.289 g, 48%).

Step 2: Deprotection of alkyne 58 following the method used in Example 36 and purification by prep HPLC (method 004P) gave Example 73 hydrochloride as a white solid. Yield (0.040 g, 20%): $^1$H NMR (400 MHz, DMSO-d$_6$) δ 8.11 (br s, 3H), 7.25 (t, J=8.4 Hz, 1H), 6.92-6.98 (m, 3H), 4.14 (t, J=4.8 Hz, 2H), 3.15 (t, J=4.8 Hz, 2H), 2.28 (d, J=6.4 Hz, 2H), 1.78-1.84 (m, 1H), 0.96 (d, J=6.8 Hz, 6H).

Example 74

PREPARATION OF 6-(3-(2-AMINOETHOXY)PHENYL)HEX-5-YN-1-OL

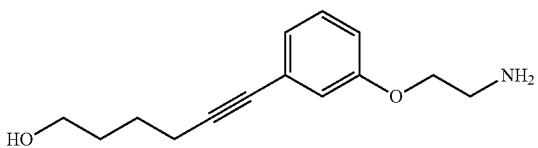 [SMILES: NCCOc1cccc(C#CCCCCO)c1]

6-(3-(2-Aminoethoxy)phenyl)hex-5-yn-1-ol was prepared following the method used in Example 73.

Step 1: Coupling of aryl bromide 54 with hex-5-yn-1-ol and purification by flash chromatography (15% EtOAc-hexanes) provided tert-butyl 2-(3-(6-hydroxyhex-1-ynyl)phenoxy)ethylcarbamate as a brown oil. Yield (0.500 g, 79%): $^1$H NMR (400 MHz, CDCl$_3$) δ 7.17 (t, J=7.6 Hz, 1H), 6.99 (d, J=7.6 Hz, 1H), 6.91 (s, 1H), 6.81 (d, J=8.4 Hz, 1H), 4.72 (br s, 1H), 4.00 (t, J=4.8 Hz, 2H), 3.72 (m, 2H), 3.48-3.55 (m, 2H), 2.46 (d, J=6.8 Hz, 2H), 1.66-1.79 (m, 4H), 1.58 (s, 1H), 1.45 (s, 9H).

Step 2: Deprotection of tert-butyl 2-(3-(6-hydroxyhex-1-ynyl)phenoxy)ethylcarbamate and purification as described in Example 73 gave Example 74 hydrochloride as a brown solid. Yield (0.161 g, 40%): $^1$H NMR (400 MHz, DMSO-d$_6$) δ 8.15 (br s, 3H), 7.22-7.27 (m, 1H), 6.92-6.97 (m, 3H), 4.14 (t, J=5.0 Hz, 2H), 3.40 (t, J=5.8 Hz, 2H), 3.14-3.15 (m, 2H), 2.39 (t, J=6.6 Hz, 2H), 1.51-1.53 (m, 4H).

Example 75

PREPARATION OF 2-(3-(3-PHENYLPROP-1-YNYL)PHENOXY)ETHANAMINE

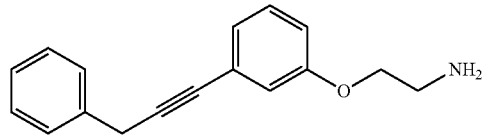 [SMILES: NCCOc1cccc(C#CCc2ccccc2)c1]

2-(3-(3-phenylprop-1-ynyl)phenoxy)ethanamine was prepared following the method used in Example 73.

Step 1: Coupling of aryl bromide 54 with prop-2-ynylbenzene and purification by flash chromatography (5% EtOAc-hexanes) gave tert-butyl 2-(3-(3-phenylprop-1-ynyl)phenoxy)ethylcarbamate as a brown oil. Yield (0.530 g, 79%): $^1$H NMR (400 MHz, CDCl$_3$) δ 7.33-7.42 (m, 3H), 7.05-7.23 (m, 4H), 6.97 (s, 1H), 6.81-6.85 (m, 1H), 4.97 (br s, 1H), 4.01 (t, J=4.8 Hz, 2H), 3.83 (s, 2H), 3.52 (q, J=4.8 Hz, 2H), 1.45 (s, 9H).

Step 2: Deprotection of tert-butyl 2-(3-(3-phenylprop-1-ynyl)phenoxy)ethylcarbamate and purification as described in Example 73 gave Example 75 hydrochloride as a cream-colored solid. Yield (0.208 g, 54%): $^1$H NMR (400 MHz, DMSO-$d_6$) δ 8.29 (br s, 2H), 7.20-7.38 (m, 6H), 6.95-7.04 (m, 3H), 4.17 (t, J=5.2 Hz, 2H), 3.85 (s, 3H), 3.14 (t, J=5.2 Hz, 2H).

Example 76

PREPARATION OF 4-(3-(2-AMINOETHOXY)PHENYL)BUT-3-YN-1-OL

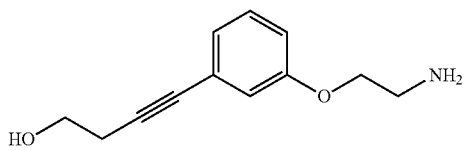 [SMILES: NCCOc1cccc(C#CCCO)c1]

4-(3-(2-Aminoethoxy)phenyl)but-3-yn-1-ol was prepared following the method used in Example 73.

Step 1: Coupling of aryl bromide 54 with but-3-yn-1-ol and purification by flash chromatography (35% EtOAc-hexanes) provided tert-butyl 2-(3-(4-hydroxybut-1-ynyl)phenoxy)ethylcarbamate as a brown oil contaminated with alkyne dimer. Yield (0.296 g, 51%): $^1$H NMR (400 MHz, CDCl$_3$) δ 7.20 (t, J=8.0 Hz, 1H), 7.02 (d, J=7.6 Hz, 1H), 6.94 (s, 1H), 6.84 (ddd, J=8.4, 2.8, 0.8 Hz, 1H), 4.98 (br s, 1H), 4.00 (t, J=5.2 Hz, 2H), 3.83 (q, J=6.4 Hz, 2H), 3.53 (q, J=5.2 Hz, 2H), 2.69 (t, J=6.4 Hz, 2H), 1.83 (t, J=6.0 Hz, 1H), 1.45 (s, 9H).

Step 2: Deprotection of tert-butyl 2-(3-(4-hydroxybut-1-ynyl)phenoxy)ethylcarbamate and purification as described in Example 73 gave Example 76 hydrochloride as an off-white solid. Yield (0.064 g, 32%): $^1$H NMR (400 MHz, DMSO-$d_6$) δ 8.07 (br s, 3H), 7.25 (t, J=8.0 Hz, 1H), 6.92-6.99 (m, 3H), 4.87-4.90 (m, 1H), 4.14 (t, J=5.2 Hz, 2H), 3.54 (q, J=6.4 Hz, 2H), 3.16 (s, 2H), 2.51 (t, J=6.4 Hz, 2H).

Example 77

PREPARATION OF 2-(3-(HEPT-1-YNYL)PHENOXY)ETHANAMINE

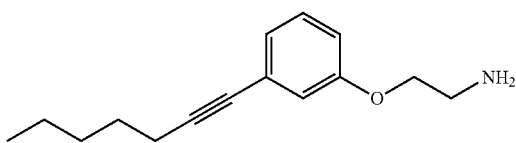 [SMILES: CCCCCC#Cc1cccc(OCCN)c1]

2-(3-(hept-1-ynyl)phenoxy)ethanamine was prepared following the method used in Example 73.

Step 1: Coupling of aryl bromide 54 with 1-heptyne and purification by flash chromatography (15% EtOAc-hexanes) gave tert-butyl 2-(3-(hept-1-ynyl)phenoxy)ethylcarbamate as a brown oil. Yield (0.238 g, 37%).

Step 2: Deprotection of tert-butyl 2-(3-(hept-1-ynyl)phenoxy)ethylcarbamate and purification as described in Example 73 gave Example 77 hydrochloride as a white solid. Yield (0.018 g, 11%): $^1$H NMR (400 MHz, DMSO-$d_6$) δ 7.95 (br s, 3H), 7.25 (t, J=8.4 Hz, 1H), 6.92-6.97 (m, 3H), 4.13 (t, J=4.8 Hz, 2H), 3.17 (t, J=4.8 Hz, 2H), 2.37 (t, J=7.2 Hz, 2H), 1.47-1.54 (m, 2H), 1.24-1.39 (m, 4H), 0.85 (t, J=6.8 Hz, 3H).

Example 78

PREPARATION OF 1-((3-(2-AMINOETHOXY)PHENYL)ETHYNYL)-CYCLOHEPTANOL

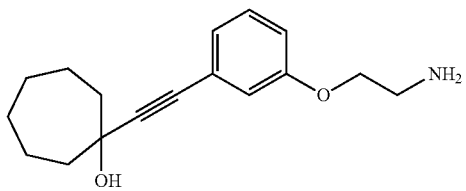 [SMILES: NCCOc1cccc(C#CC2(O)CCCCCC2)c1]

1-((3-(2-aminoethoxy)phenyl)ethynyl)-cycloheptanol was prepared following the method used in Example 18.

Step 1: Coupling of bromide 19 with 1-ethynylcycloheptanol was conducted following the procedure described in Example 18, except that the reaction was heated for 2 h. After the reaction mixture was cooled to room temperature, it was diluted with EtOAc and washed with water. The combined organics were filtered through Celite. The filtrate was dried over Na$_2$SO$_4$ and treated with activated charcoal. Following filtration, the solution was concentrated under reduced pressure. Purification by flash chromatography (10 to 50% EtOAc-hexanes gradient) gave 2,2,2-trifluoro-N-(2-(3-((1-hydroxycycloheptyl)ethynyl)phenoxy)ethyl)acetamide as an orange oil. Yield (1.078 g, 60%): $^1$H NMR (400 MHz, CDCl$_3$) δ 7.20 (br s, 1H), 7.18 (t, J=8.0 Hz, 1H), 7.02 (dt, J=7.2, 0.8 Hz, 1H), 6.90 (dd, J=2.4, 1.6 Hz, 1H), 6.81 (ddd, J=8.4, 2.4, 0.8 Hz, 1H), 4.05 (t, J=5.2 Hz, 2H), 3.72 (q, J=5.3 Hz, 2H), 2.43 (br s, 1H), 2.05-2.11 (m, 2H), 1.84-1.91 (m, 2H), 1.53-1.70 (m, 8H).

Step 2: To a solution of 2,2,2-trifluoro-N-(2-(3-((1-hydroxycycloheptyl)ethynyl)phenoxy)ethyl)acetamide (1.07 g, 2.9 mmol) in MeOH (20 mL) was added saturated aqueous K$_2$CO$_3$ (~10 mL). The reaction mixture was stirred vigorously and heated at 50° C. for 2 h. After removal of the volatiles by concentration under reduced pressure, the mixture was partitioned into EtOAc and water. The organic layer was dried over Na$_2$SO$_4$ and concentrated under reduced pressure. Purification by flash chromatography (10% 7M NH$_3$ in MeOH-EtOAc) gave Example 78 as a pale yellow solid. (Yield 0.70 g, 88%): $^1$H NMR (400 MHz, CDCl$_3$) δ 7.19 (t, J=8.0 Hz, 1H), 7.01 (dt, J=8.0, 0.8 Hz, 1H), 6.95 (dd, J=2.8, 1.6 Hz, 1H), 6.85 (ddd, J=8.4, 2.4, 1.2 Hz, 1H), 3.97 (t, J=4.8 Hz, 2H), 3.07 (br s, 2H), 2.08-2.13 (m, 2H), 1.87-1.94 (m, 2H), 1.59-1.74 (m, 11H).

Example 79

PREPARATION OF 2-(3-(CYCLOPENTYLETHYNYL)PHENOXY)-ETHANAMINE

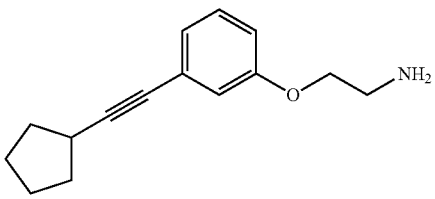 [SMILES: NCCOc1cccc(C#CC2CCCC2)c1]

2-(3-(Cyclopentylethynyl)phenoxy)-ethanamine was prepared following the method used in Example 73.

Step 1: Coupling of aryl bromide 54 with ethynylcyclopentane and purification by flash chromatography (20% EtOAc-hexanes) gave tert-butyl 2-(3-(cyclopentylethynyl)phenoxy)ethylcarbamate as a yellow oil. Yield (0.290 g, 46%).

Step 2: Deprotection of tert-butyl 2-(3-(cyclopentylethynyl)phenoxy)ethylcarbamate and purification as described in Example 73 gave Example 79 hydrochloride as a white solid. Yield (0.100 g, 49%): $^1$H NMR (400 MHz, DMSO-$d_6$) δ 8.24 (br s, 3H), 7.23 (dd, J=9.2, 7.6 Hz, 1H), 6.91-6.95 (m, 3H), 4.15 (t, J=5.2 Hz, 2H), 3.13 (t, J=5.2 Hz, 2H), 2.77-2.85 (m, 1H), 1.89-1.97 (m, 2H), 1.52-1.71 (m, 6H).

Example 80

PREPARATION OF 2-(3-(CYCLOHEXYLETHYNYL)PHENOXY)ETHANAMINE

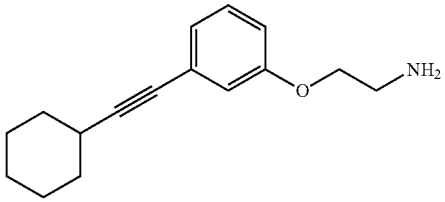

2-(3-(Cyclohexylethynyl)phenoxy)ethanamine was prepared following the method used in Example 73.

Step 1: Coupling of aryl bromide 54 with ethynylcyclohexane and purification by flash chromatography (5-10% EtOAc-hexanes) gave tert-butyl 2-(3-(cyclohexylethynyl)phenoxy)ethylcarbamate as a brown oil. Yield (0.170 g, 26%).

Step 2: Deprotection of tert-butyl 2-(3-(cyclohexylethynyl)phenoxy)ethylcarbamate and purification as described in Example 73 gave Example 80 hydrochloride as a white solid. Yield (0.023 g, 16%): $^1$H NMR (400 MHz, DMSO-$d_6$) δ 7.93 (br s, 3H), 7.23-7.27 (m, 1H), 6.92-6.97 (m, 3H), 4.13 (t, J=4.8 Hz, 2H), 3.16 (t, J=5.2 Hz, 2H), 1.74-1.82 (m, 2H), 1.60-1.68 (m, 2H), 1.36-1.50 (m, 3H), 1.28-1.48 (m, 4H).

Example 81

PREPARATION OF 2-(3-(PHENYLETHYNYL)PHENOXY)-ETHANAMINE

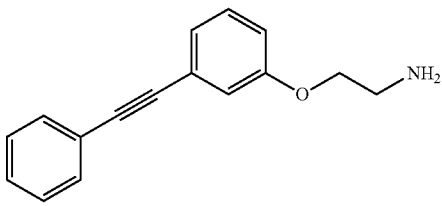 [SMILES: NCCOc1cccc(C#Cc2ccccc2)c1]

2-(3-(Phenylethynyl)phenoxy)-ethanamine was prepared following the method used in Example 73.

Step 1: Coupling of aryl bromide 54 with ethynylbenzene and purification by flash chromatography (22% EtOAc-hexanes) gave tert-butyl 2-(3-(phenylethynyl)phenoxy)ethylcarbamate as a yellow oil. Yield (0.200 g, 31%).

Step 2: Deprotection of tert-butyl 2-(3-(phenylethynyl)phenoxy)ethylcarbamate and purification as described in Example 73 gave Example 81 hydrochloride as a white solid. Yield (0.150 g, 71%): $^1$H NMR (400 MHz, DMSO-$d_6$) δ 8.12 (br s, 3H), 7.52-7.54 (m, 2H), 7.40-7.41 (m, 3H), 7.34 (t, J=8.0 Hz, 1H), 7.12-7.16 (m, 2H), 7.02 (dd, J=8.4, 2.0 Hz, 1H), 4.19 (t, J=4.8 Hz, 2H), 3.18 (t, J=4.8 Hz, 2H).

Example 82

PREPARATION OF 3-(3-(NAPHTHALEN-1-YLETHYNYL)PHENYL)PROPAN-1-AMINE

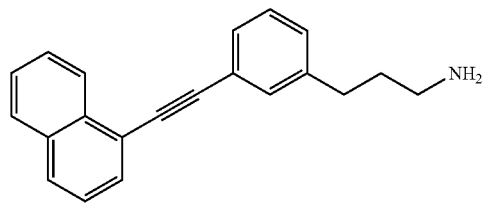 [SMILES: NCCCc1cccc(C#Cc2cccc3ccccc23)c1]

3-(3-(Naphthalen-1-ylethynyl)phenyl)propan-1-amine was prepared following the method used in Example 61.

Step 1: Coupling of alkyne 52 with 2-bromonaphthalene and purification by flash chromatography (3-5% EtOAc-hexanes) gave 2-(3-(3-(naphthalen-1-ylethynyl)phenyl)propyl)isoindoline-1,3-dione as a brown oil. Yield (0.300 g, 41%): $^1$H NMR (400 MHz, CDCl$_3$) δ 8.44 (d, J=8.0 Hz, 1H), 7.82-7.88 (m, 4H), 7.76 (dd, J=7.2, 1.2 Hz, 1H), 7.70 (dd, J=5.2, 3.2 Hz, 2H), 7.59-7.64 (m, 1H), 7.52-7.56 (m, 1H), 7.42-7.49 (m, 3H), 7.29 (d, J=7.6 Hz, 1H), 7.22 (d, J=8.0 Hz, 1H), 3.79 (t, J=7.2 Hz, 2H), 2.73 (t, J=7.2 Hz, 2H), 2.09 (quint., J=7.2 Hz, 2H).

Step 2: Deprotection of 2-(3-(3-(naphthalen-1-ylethynyl)phenyl)propyl)isoindoline-1,3-dione and purification following the method used in Example 61 gave Example 82 as a semi-solid. Yield (0.040 g, 25%): $^1$H NMR (400 MHz, DMSO-$d_6$) δ 8.18 (s, 1H), 7.80-7.95 (m, 3H), 7.69 (br s, 2H), 7.57-7.62 (m, 3H), 7.45-7.49 (m, 2H), 7.40 (t, J=7.6 Hz, 1H), 7.30 (d, J=7.6 Hz, 1H), 2.80 (t, J=7.2 Hz, 2H), 2.69 (t, J=7.6 Hz, 2H), 1.87 (quint, J=7.6 Hz, 2H).

Example 83

PREPARATION OF 3-(3-(o-TOLYLETHYNYL)PHENYL)PROPAN-1-AMINE

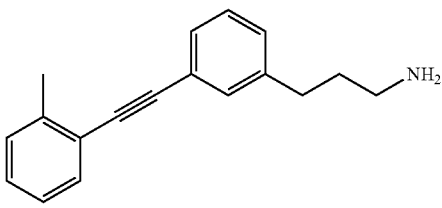 [SMILES: Cc1ccccc1C#Cc1cccc(CCCN)c1]

3-(3-(o-Tolylethynyl)phenyl)propan-1-amine was prepared following the method used in Example 61.

Step 1: Coupling of alkyne 52 with 1-ethynyl-2-methylbenzene and purification by flash chromatography (15% EtOAc-hexanes) gave 2-(3-(3-(o-tolylethynyl)phenyl)propyl)isoindoline-1,3-dione as a brown oil. Yield (0.480 g, 61%): $^1$H NMR (400 MHz, CDCl$_3$) δ 7.83 (dd, J=5.6, 3.2 Hz, 2H), 7.76 (dd, J=5.6, 3.2 Hz, 2H), 7.48 (d, J=7.2 Hz, 1H), 7.37 (m, 1H), 7.31-7.32 (m, 1H), 7.15-7.24 (m, 5H), 3.77 (t, J=7.2 Hz, 2H), 2.70 (t, J=7.2 Hz, 2H), 2.50 (s, 3H), 2.02-2.09 (m, 2H).

Step 2: Deprotection of 2-(3-(3-(o-tolylethynyl)phenyl)propyl)isoindoline-1,3-dione and purification by prep HPLC (method 004P) gave Example 83 as a brown solid. Yield (0.080 g, 25%): $^1$H NMR (400 MHz, DMSO-d$_6$) δ 7.24-7.53 (m, 8H), 2.65 (t, J=8.0 Hz, 2H), 2.57 (t, J=6.8 Hz, 2H), 2.49 (s, 3H), 1.65-1.72 (m, 2H).

Example 84

PREPARATION OF 3-(3-(p-TOLYLETHYNYL)PHENYL)PROPAN-1-AMINE

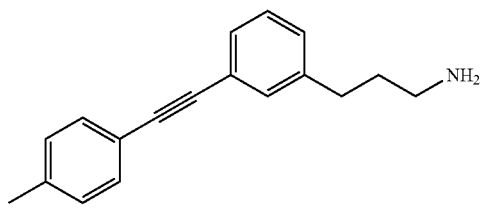 [SMILES: Cc1ccc(C#Cc2cccc(CCCN)c2)cc1]

3-(3-(p-Tolylethynyl)phenyl)propan-1-amine was prepared following the method used in Example 61.

Step 1: Coupling of alkyne 52 with 1-ethynyl-4-methylbenzene and purification by flash chromatography (10% EtOAc-hexanes) gave 2-(3-(3-(p-tolylethynyl)phenyl)propyl)isoindoline-1,3-dione as a brown oil. Yield (0.487 g, 61%): $^1$H NMR (400 MHz, CDCl$_3$) δ 7.83 (dd, J=5.2, 2.8 Hz, 2H), 7.70 (dd, J=5.2, 2.8 Hz, 2H), 7.41 (d, J=8.0 Hz, 1H), 7.14-7.36 (m, 7H), 3.76 (t, J=7.2 Hz, 2H), 2.69 (t, J=7.6 Hz, 2H), 2.37 (s, 3H), 2.01-2.09 (m, 2H).

Step 2: Deprotection of 2-(3-(3-(p-tolylethynyl)phenyl)propyl)isoindoline-1,3-dione and purification according to the method used in Example 61 gave Example 84 trifluoroacetate as a white solid. Yield (0.060 g, 18%): $^1$H NMR (400 MHz, DMSO-d$_6$) δ 7.53 (br s, 3H), 7.31-7.41 (m, 5H), 7.20-7.24 (m, 3H), 2.74 (t, J=7.6 Hz, 1H), 2.63 (t, J=7.2 Hz, 2H), 2.31 (s, 3H), 1.77-1.85 (m, 2H).

Example 85

PREPARATION OF 2-(3-(3-CYCLOPENTYLPROP-1-YNYL)PHENOXY)ETHANAMINE

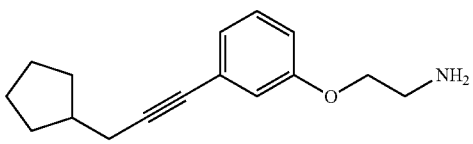 [SMILES: NCCOc1cccc(C#CCC2CCCC2)c1]

2-(3-(3-Cyclopentylprop-1-ynyl)phenoxy)ethanamine was prepared following the method used in Example 73.

Step 1: Coupling of prop-2-ynylcyclopentane with bromide 54 and purification by flash chromatography (15% EtOAc-hexanes) gave tert-butyl 2-(3-(3-cyclopentylprop-1-ynyl)phenoxy)ethylcarbamate as a white solid. Yield (0.500 g, 76%): $^1$H NMR (400 MHz, CDCl$_3$) δ 6.91-7.21 (m, 3H), 6.80-6.84 (m, 1H), 4.97 (br s, 1H), 4.00 (t, J=4.8 Hz, 2H), 3.52 (q, J=4.4 Hz, 2H), 2.40 (d, J=6.8 Hz, 2H), 2.07-2.17 (m, 1H), 1.80-1.87 (m, 2H), 1.48-1.70 (m, 4H), 1.45 (s, 9H), 1.29-1.40 (m, 2H).

Step 2: Deprotection of tert-butyl 2-(3-(3-cyclopentylprop-1-ynyl)phenoxy)ethylcarbamate and purification by flash chromatography (7% MeOH—CH$_2$Cl$_2$) gave Example 85 hydrochloride as a white solid. Yield (0.160 g, 45%): $^1$H NMR (400 MHz, DMSO-d$_6$) δ 7.20-7.24 (m, 1H), 6.89-6.94 (m, 3H), 4.00 (t, J=5.0 Hz, 2H), 3.00 (br s, 2H), 2.04 (quint., J=7.2, 2H), 1.71-1.78 (m, 2H), 1.44-1.62 (m, 4H), 1.20-1.31 (m, 3H).

Example 86

PREPARATION OF 2-(3-(4-PHENYLBUT-1-YNYL)PHENOXY)ETHANAMINE

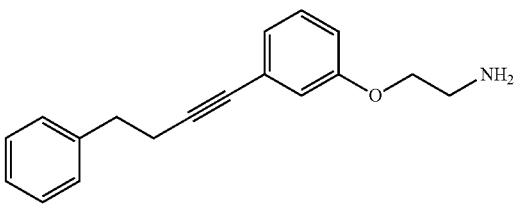

2-(3-(4-Phenylbut-1-ynyl)phenoxy)ethanamine was prepared following the method used in Example 73.

Step 1: Coupling of but-3-ynylbenzene with bromide 54 and purification by flash chromatography (5-10% EtOAc-hexanes) gave tert-butyl 2-(3-(4-phenylbut-1-ynyl)phenoxy)ethylcarbamate as a brown oil. Yield (0.503 g, 72%).

Step 2: Deprotection of tert-butyl 2-(3-(4-phenylbut-1-ynyl)phenoxy)ethylcarbamate and purification by flash chromatography (1-10% MeOH—CH$_2$Cl$_2$ containing trace triethylamine) gave Example 86 as a yellow solid. Yield (0.127 g, 33%): $^1$H NMR (400 MHz, CDCl$_3$) δ 7.27-7.28 (m, 4H), 7.17-7.22 (m, 2H), 6.82-6.89 (m, 3H), 3.88 (t, J=5.6 Hz, 2H), 2.80-2.86 (m, 4H), 2.66 (t, J=7.2 Hz, 2H).

Example 87

PREPARATION OF 3-(3-(m-TOLYLETHYNYL)PHENYL)PROPAN-1-AMINE

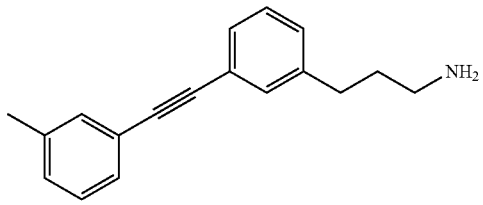 [SMILES: Cc1cccc(C#Cc2cccc(CCCN)c2)c1]

3-(3-(m-Tolylethynyl)phenyl)propan-1-amine was prepared following the method used in Example 61.

Step 1: Coupling of alkyne 52 with 3-iodotoluene and purification by flash chromatography (10% EtOAc-hexanes) gave 2-(3-(3-(m-tolylethynyl)phenyl)propyl)isoindoline-1,3-dione as a brown oil. Yield (0.396 g, 50%): $^1$H NMR (400 MHz, CDCl$_3$) δ 8.40 (dd, J=5.6, 3.2 Hz, 2H), 7.71 (dd, J=5.2, 3.2 Hz, 2H), 7.13-7.36 (m, 8H), 3.76 (t, J=7.2 Hz, 2H), 2.69 (t, J=7.6 Hz, 2H), 2.36 (s, 3H), 2.01-2.09 (m, 2H).

Step 2: Deprotection of 2-(3-(3-(m-tolylethynyl)phenyl)propyl)isoindoline-1,3-dione and purification according to the method used in Example 61 gave Example 87 trifluoroacetate as an off-white solid. Yield (0.030 g, 12%): $^1$H NMR (400 MHz, DMSO-d$_6$) δ 7.60 (br s, 3H), 7.21-7.39 (m, 8H), 2.75 (t, J=8.0 Hz, 1H), 2.63 (t, J=7.6 Hz, 2H), 2.29 (s, 3H), 1.77-1.85 (m, 2H).

Example 88

PREPARATION OF 3-((3-(2-AMINOETHOXY)PHENYL)ETHYNYL)BENZONITRILE

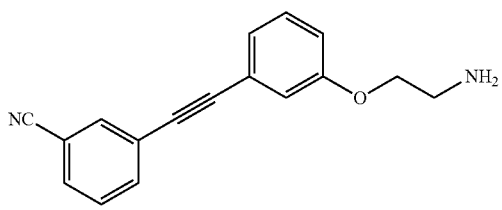 [SMILES: N#Cc1cccc(C#Cc2cccc(OCCN)c2)c1]

3-((3-(2-Aminoethoxy)phenyl)ethynyl)benzonitrile was prepared following the method used in Example 62.

Step 1: Coupling of alkyne 56 with 3-bromobenzonitrile and purification by flash chromatography (15% EtOAc-hexanes) gave tert-butyl 2-(3-((3-cyanophenyl)ethynyl)phenoxy)ethylcarbamate as a brown oil. Yield (0.275 g, 39%): $^1$H NMR (400 MHz, CDCl$_3$) δ 7.81 (s, 1H), 7.73 (dt, J=8.0, 1.2 Hz, 1H), 7.61 (dt, J=7.6, 1.2 Hz, 1H), 7.47 (t, J=8.0 Hz, 1H), 7.28-7.31 (m, 1H), 7.15 (d, J=7.6 Hz, 1H), 7.05 (s, 1H), 6.93 (dd, J=8.0, 2.0 Hz, 1H), 4.98 (br s, 1H), 4.05 (t, J=5.2 Hz, 2H), 3.55 (q, J=5.2 Hz, 2H), 1.46 (s, 9H).

Step 2: Deprotection of tert-butyl 2-(3-((3-cyanophenyl)ethynyl)phenoxy)ethylcarbamate afforded Example 88 hydrochloride as a white solid. Yield (0.195 g, 97%): $^1$H NMR (400 MHz, DMSO-d$_6$) δ 8.03 (s, 4H), 7.85-7.88 (m, 2H), 7.62 (t, J=8.0 Hz, 1H), 7.37 (t, J=8.0 Hz, 1H), 7.16-7.20 (m, 2H), 7.06 (dd, J=8.4, 2.4 Hz, 1H), 4.19 (t, J=4.8 Hz, 2H), 3.20 (q, J=4.8 Hz, 2H).

Example 89

PREPARATION OF 2-((3-(3-AMINOPROPYL)PHENYL)ETHYNYL)PHENOL

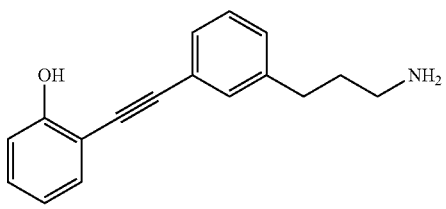 [SMILES: NCCCc1cccc(C#Cc2ccccc2O)c1]

2-((3-(3-Aminopropyl)phenyl)ethynyl)phenol was prepared following the method used in Example 61.

Step 1: Coupling of alkyne 52 with 2-iodophenol and purification by flash chromatography (8% EtOAc-hexanes) gave 2-(3-(3-((2-hydroxyphenyl)ethynyl)phenyl)propyl)isoindoline-1,3-dione as a yellow oil. Yield (0.550 g, 69%).

Step 2: 2-(3-(3-(m-Tolylethynyl)phenyl)propyl)isoindoline-1,3-dione was deprotected and purified according to the method used in Example 61 to give Example 89 trifluoroacetate as an off-white solid. Yield (0.195 g, 53%): $^1$H NMR (400 MHz, CD$_3$OD) δ 7.75 (s, 1H), 7.69-7.71 (m, 1H), 7.58 (d, J=7.6 Hz, 1H), 7.48-7.51 (m, 1H), 7.33-7.38 (m, 1H), 7.19-7.29 (m, 3H), 7.14-7.15 (m, 1H), 2.67-2.74 (m, 4H), 1.80-1.88 (m, 2H).

Example 90

PREPARATION OF 3-((3-(3-AMINOPROPYL)PHENYL)ETHYNYL)BENZONITRILE

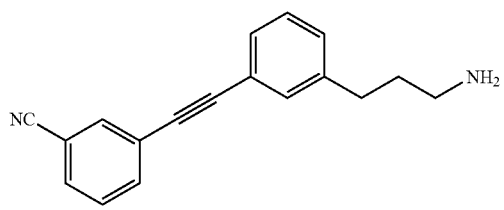 [SMILES: N#Cc1cccc(C#Cc2cccc(CCCN)c2)c1]

3-((3-(3-Aminopropyl)phenyl)ethynyl)benzonitrile was prepared following the method used in Example 61.

Step 1: Coupling of alkyne 52 with 3-bromobenzonitrile and purification by flash chromatography (20% EtOAc-hexanes) gave 3-((3-(3-(1,3-dioxoisoindolin-2-yl)propyl)phenyl)ethynyl)benzonitrile as a yellow oil. Yield (0.456 g, 56%): $^1$H NMR (400 MHz, CDCl$_3$) δ 7.84 (dd, J=5.6, 2.8 Hz, 2H), 7.80 (t, J=1.2 Hz, 1H), 7.70-7.74 (m, 3H), 7.60 (dt, J=7.6, 1.2 Hz, 1H), 7.47 (t, J=8.0 Hz, 1H), 7.39 (s, 1H), 7.21-7.33 (m, 3H), 3.76 (t, J=7.2 Hz, 2H), 2.70 (t, J=7.6 Hz, 2H), 2.02-2.09 (m, 2H).

Step 2: Deprotection of 3-((3-(3-(1,3-dioxoisoindolin-2-yl)propyl)phenyl)ethynyl)benzonitrile purification and conversion to the free base according to the method used in Example 61 gave Example 90 as a yellow oil. Yield (0.085 g, 28%): $^1$H NMR (400 MHz, DMSO-d$_6$) δ 8.02 (t, J=1.2 Hz, 1H), 7.85 (dd, J=8.0, 1.6 Hz, 2H), 7.60 (t, J=8.0 Hz, 1H), 7.39 (s, 1H), 7.36 (dt, J=7.6, 1.2 Hz, 1H), 7.32 (t, J=7.6 Hz, 1H), 7.26 (dt, J=7.2, 1.2 Hz, 1H), 2.59 (t, J=7.6 Hz, 2H), 2.49 (t, J=7.2 Hz, 2H), 1.57-1.64 (m, 2H).

Example 91

PREPARATION OF 2-(3-((2-METHOXYPHENYL)ETHYNYL)PHENOXY)ETHANAMINE

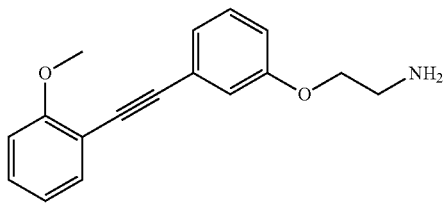 [SMILES: COc1ccccc1C#Cc1cccc(OCCN)c1]

2-(3-((2-Methoxyphenyl)ethynyl)phenoxy)ethanamine was prepared following the method used in Example 73.

Step 1: Coupling of 1-ethynyl-2-methoxybenzene with bromide 54 and purification by flash chromatography (12% EtOAc-hexanes) gave tert-butyl 2-(3-((2-methoxyphenyl)ethynyl)phenoxy)ethylcarbamate as a brown oil. Yield (0.500 g, 44%): $^1$H NMR (400 MHz, CDCl$_3$) δ 7.49 (dd, J=7.6, 1.6 Hz, 1H), 7.23-7.34 (m, 2H), 7.18 (dt, J=7.6, 1.2 Hz, 1H), 7.06-7.08 (m, 1H), 6.86-6.96 (m, 3H), 4.99 (br s, 1H), 4.04 (t, J=5.2 Hz, 2H), 3.97 (s, 3H), 3.54 (q, J=5.2 Hz, 2H), 1.46 (s, 9H).

Step 2: Deprotection of tert-butyl 2-(3-((2-methoxyphenyl)ethynyl)phenoxy)ethylcarbamate and purification by flash chromatography (6% MeOH—CH$_2$Cl$_2$) gave Example 91 hydrochloride as a white solid. Yield (0.160 g, 43%): $^1$H NMR (400 MHz, DMSO-d$_6$) δ 7.44 (dd, J=7.6, 1.6 Hz, 1H), 7.30-7.39 (m, 2H), 7.06-7.11 (m, 3H), 6.93-7.01 (m, 2H), 4.13 (t, J=5.2 Hz, 2H), 3.82 (s, 3H), 3.12 (t, J=5.2 Hz, 2H).

Example 92

PREPARATION OF 3-(3-((3-(TRIFLUOROMETHYL)PHENYL)ETHYNYL)PHENYLPROPAN-1-AMINE

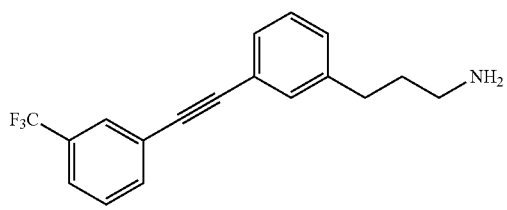

3-(3-((3-(Trifluoromethyl)phenyl)ethynyl)phenyl)propan-1-amine was prepared following the method used in Example 61.

Step 1: Coupling of alkyne 52 with 3-bromobenzotrifluoride and purification by flash chromatography (5% EtOAc-hexanes) gave 2-(3-(3-((3-(trifluoromethyl)phenyl)ethynyl)phenyl)propyl)isoindoline-1,3-dione as a brown oil. Yield (0.477 g, 53%): $^1$H NMR (400 MHz, CDCl$_3$) δ 7.84 (dd, J=5.2, 3.2 Hz, 2H), 7.79 (s, 1H), 7.68-7.72 (m, 3H), 7.57 (d, J=8.0 Hz, 1H), 7.48 (t, J=7.6 Hz, 1H), 7.39 (s, 1H), 7.32 (dt, J=7.2, 1.2 Hz, 1H), 7.26 (t, J=7.6 Hz, 1H), 7.21 (d, J=7.6 Hz, 1H), 3.77 (t, J=7.2 Hz, 2H), 2.70 (t, J=7.2 Hz, 2H), 2.02-2.09 (m, 2H).

Step 2: Deprotection of 2-(3-(3-((3-(trifluoromethyl)phenyl)ethynyl)phenyl)propyl)isoindoline-1,3-dione, purification and conversion to the free base according to the method used in Example 61 gave Example 92 as a semi-solid. Yield (0.240 g, 71%): $^1$H NMR (400 MHz, DMSO-d$_6$) δ 7.88 (s, 1H), 7.82 (d, J=8.0 Hz, 1H), 7.74 (d, J=8.0 Hz, 1H), 7.64 (t, J=7.6 Hz, 1H), 7.41 (s, 1H), 7.37 (d, J=7.6 Hz, 1H), 7.32 (t, J=7.6 Hz, 1H), 7.25 (d, J=7.2 Hz, 1H), 2.59 (t, J=7.6 Hz, 2H), 2.50 (t, J=6.8 Hz, 2H), 1.58-1.65 (m, 2H).

Example 93

PREPARATION OF 3-(3-((3,5-DI-TERT-BUTYLPHENYL)ETHYNYL)PHENYL)PROPAN-1-AMINE

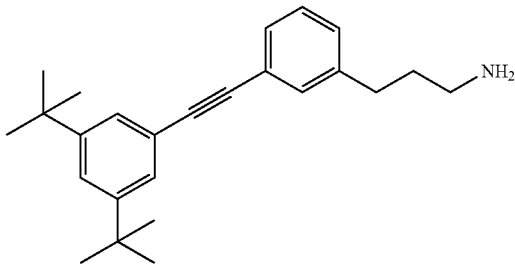 [SMILES: CC(C)(C)c1cc(C#Cc2cccc(CCCN)c2)cc(C(C)(C)C)c1]

3-(3-((3,5-Di-tert-butylphenyl)ethynyl)phenyl)propan-1-amine was prepared following the method used in Example 61.

Step 1: Coupling of alkyne 52 with 1-bromo-3,5-di-tert-butylbenzene and purification by flash chromatography (12% EtOAc-hexanes) gave 2-(3-(3-((3,5-di-tert-butylphenyl)ethynyl)phenyl)propyl)isoindoline-1,3-dione as a colorless oil. Yield (0.410 g, 41%): $^1$H NMR (400 MHz, CDCl$_3$) δ 7.84 (dd, J=5.2, 3.2 Hz, 2H), 7.71 (dd, J=5.6, 3.2 Hz, 2H), 7.15-7.40 (m, 7H), 3.77 (t, J=7.2 Hz, 2H), 2.69 (t, J=7.6 Hz, 2H), 2.01-2.09 (m, 2H), 1.34 (s, 18H).

Step 2: Deprotection of 2-(3-(3-((3,5-di-tert-butylphenyl)ethynyl)phenyl)propyl)isoindoline-1,3-dione, purification and conversion to the free base according to the method used in Example 61 gave Example 93 as a colorless oil. Yield (0.150 g, 50%): $^1$H NMR (400 MHz, DMSO-d$_6$) δ 7.41 (t, J=1.6 Hz, 1H), 7.37 (s, 1H), 7.32-7.34 (m, 3H), 7.29 (t, J=7.6

Hz, 1H), 7.20 (d, J=7.2 Hz, 1H), 2.58 (t, J=7.6 Hz, 2H), 2.49 (t, J=6.8 Hz, 2H), 1.57-1.65 (m, 2H), 1.27 (s, 18H).

Example 94

PREPARATION OF 3-(3-((4-(METHYLTHIO)PHENYL)ETHYNYL)PHENYLPROPAN-1-AMINE

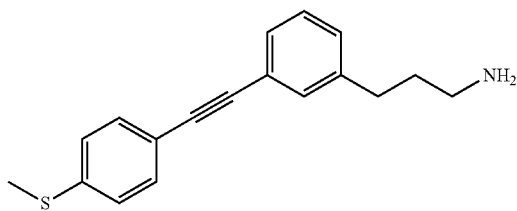 [SMILES: CSc1ccc(C#Cc2cccc(CCCN)c2)cc1]

3-(3-((4-(Methylthio)phenyl)ethynyl)phenyl)propan-1-amine was prepared following the method used in Example 61.

Step 1: Coupling of alkyne 52 with 4-bromothioanisole and purification by flash chromatography (16% EtOAc-hexanes) gave 2-(3-(3-((4-(methylthio)phenyl)ethynyl)phenyl)propyl)isoindoline-1,3-dione as a brown oil. Yield (0.160 g, 32%): $^1$H NMR (400 MHz, CDCl$_3$) δ 7.83 (dd, J=5.6, 3.2 Hz, 2H), 7.71 (dd, J=5.2, 2.8 Hz, 2H), 7.43 (dt, J=8.8, 2.0 Hz, 2H), 7.36 (s, 1H), 7.30 (d, J=7.6 Hz, 1H), 7.20-7.25 (m, 3H), 7.17 (d, J=7.6 Hz, 1H), 3.76 (t, J=7.2 Hz, 2H), 2.69 (t, J=7.6 Hz, 2H), 2.50 (s, 3H), 2.01-2.08 (m, 2H).

Step 2: Deprotection of 2-(3-(3-((4-(methylthio)phenyl)ethynyl)phenyl)propyl)isoindoline-1,3-dione, purification and conversion to the free base according to the method used in Example 61 gave Example 94 as a light yellow solid. Yield (0.050 g, 45%): $^1$H NMR (400 MHz, CDCl$_3$) δ 7.44 (d, J=8.4 Hz, 2H), 7.34-7.36 (m, 2H), 7.15-7.28 (m, 4H), 2.74 (t, J=7.2 Hz, 2H), 2.66 (t, J=7.6 Hz, 2H), 2.50 (s, 3H), 1.75-1.83 (m, 2H).

Example 95

PREPARATION OF 2-(3-(THIOPHEN-2-YLETHYNYL)PHENOXY)ETHANAMINE

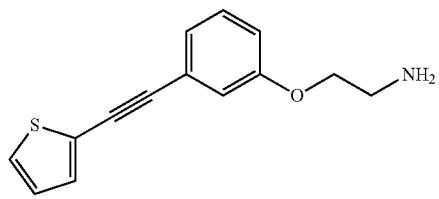 [SMILES: NCCOc1cccc(C#Cc2cccs2)c1]

2-(3-(Thiophen-2-ylethynyl)phenoxy)ethanamine was prepared following the method used in Example 62.

Step 1: Coupling of alkyne 56 with 2-bromothiophene and purification by flash chromatography (5-20% EtOAc-hexanes) gave tert-butyl 2-(3-(thiophen-2-ylethynyl)phenoxy)ethylcarbamate as a yellow oil. Yield (0.605 g, 57%): $^1$H NMR (400 MHz, CDCl$_3$) δ 7.30 (dd, J=5.2, 1.2 Hz, 1H), 7.28-7.29 (m, 1H), 7.25 (d, J=8.4 Hz, 1H), 7.12 (dt, J=7.6, 1.2 Hz, 1H), 7.03-7.04 (m, 1H), 7.02 (dd, J=5.2, 3.6 Hz, 1H), 6.89 (ddd, J=8.0, 2.4, 0.8 Hz, 1H), 4.99 (br s, 1H), 4.04 (t, J=4.8 Hz, 2H), 3.55 (dt, J=5.2, 4.8 Hz, 2H), 1.46 (s, 9H).

Step 2: Deprotection of tert-butyl 2-(3-(thiophen-2-ylethynyl)phenoxy)ethylcarbamate was conducted according to the method used in Example 62. After completion of the reaction, diethyl ether was added and the solids were collected by filtration and dried under vacuum to afford Example 95 hydrochloride as a white solid. Yield (0.436 g, 88%): $^1$H NMR (400 MHz, DMSO-d$_6$) δ 8.14 (br s, 3H), 7.66 (dd, J=5.2, 1.2 Hz, 1H), 7.40 (dd, J=3.6, 1.2 Hz, 1H), 7.14 (dd, J=7.6, 1.2 Hz, 1H), 7.10-7.12 (m, 3H), 7.03 (ddd, J=8.4, 2.4, 1.2 Hz, 1H), 4.19 (t, J=5.2 Hz, 2H), 3.17 (t, J=5.2, 2H).

Example 96

PREPARATION OF 2-(3-(THIOPHEN-3-YLETHYNYL)PHENOXY)ETHANAMINE

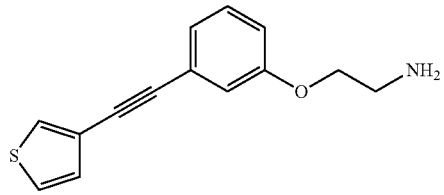 [SMILES: NCCOc1cccc(C#Cc2ccsc2)c1]

2-(3-(Thiophen-3-ylethynyl)phenoxy)ethanamine was prepared following the method used in Example 62.

Step 1: Coupling of alkyne 56 with 3-bromothiophene and purification by flash chromatography (13% EtOAc-hexanes) gave tert-butyl 2-(3-(thiophen-3-ylethynyl)phenoxy)ethylcarbamate as a brown oil. Yield (0.630 g, 60%).

Step 2: Deprotection of tert-butyl 2-(3-(thiophen-3-ylethynyl)phenoxy)ethylcarbamate was conducted according to the method used in Example 62, except that trituration was done with diethyl ether instead of hexanes. Example 96 hydrochloride was isolated as an off-white solid. Yield (0.430 g, 83%): $^1$H NMR (400 MHz, CDCl$_3$) δ 8.18 (br s, 3H), 7.87 (dd, J=2.8, 1.2 Hz, 1H), 7.63 (dd, J=4.8, 2.8 Hz, 1H), 7.33 (t, J=8.0 Hz, 1H), 7.23 (dd, J=5.2, 1.2 Hz, 1H), 7.08-7.13 (m, 2H), 6.99-7.02 (m, 1H), 4.19 (t, J=4.8 Hz, 2H), 3.17 (t, J=4.8 Hz, 2H).

Example 97

PREPARATION OF 2-(3-(PYRIDIN-4-YLETHYNYL)PHENOXY)ETHANAMINE

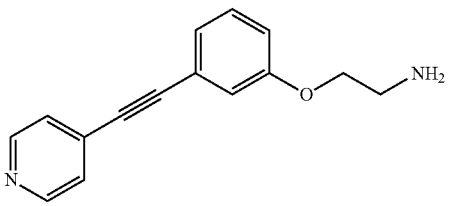 [SMILES: NCCOc1cccc(C#Cc2ccncc2)c1]

2-(3-(Pyridin-4-ylethynyl)phenoxy)ethanamine was prepared following the method used in Example 96.

Step 1: Coupling of alkyne 56 with 4-bromopyridine and purification by flash chromatography (12% EtOAc-hexanes) gave tert-butyl 2-(3-(pyridin-4-ylethynyl)phenoxy)ethylcarbamate as a brown oil. Yield (0.298 g, 38%): $^1$H NMR (400 MHz, CDCl$_3$) δ 8.61 (d, J=6.0 Hz, 2H), 7.38 (d, J=6.0 Hz, 2H), 7.29 (t, J=8.0 Hz, 1H), 7.17 (d, J=8.0 Hz, 1H), 7.07 (br s, 1H), 6.94 (ddd, J=8.4, 2.4, 0.8 Hz, 1H), 4.99 (br s, 1H), 4.05 (t, J=5.2, 2H), 3.55-3.57 (m, 2H), 1.46 (s, 9H).

Step 2: Deprotection of tert-butyl 2-(3-(thiophen-3-ylethynyl)phenoxy)ethylcarbamate gave Example 97 hydrochloride as a white solid. Yield (0.298 g, 38%): $^1$H NMR (400 MHz, DMSO-d$_6$) δ 8.78 (d, J=1.0 Hz, 2H), 8.23 (br s, 3H), 7.85 (s, 2H), 7.41 (t, J=8.0 Hz, 1H), 7.25-7.27 (m, 2H), 7.13 (dd, J=8.0, 2.8 Hz, 1H), 4.22 (t, J=5.2 Hz, 2H), 3.18 (q, J=5.2 Hz, 2H).

Example 98

PREPARATION OF 2-(3-(PYRIDIN-2-YLETHYNYL)PHENOXY)ETHANAMINE

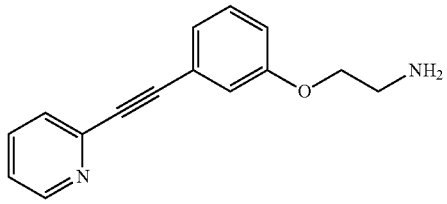 [SMILES: NCCOc1cccc(C#Cc2ccccn2)c1]

2-(3-(Pyridin-2-ylethynyl)phenoxy)ethanamine was prepared following the method used in Example 96.

Step 1: Coupling of alkyne 56 with 4-bromopyridine and purification by flash chromatography (17% EtOAc-hexanes) gave tert-butyl 2-(3-(pyridin-2-ylethynyl)phenoxy)ethylcarbamate as a yellow oil. Yield (0.50 g, 64%): $^1$H NMR (400 MHz, CDCl$_3$): δ 8.63 (d, J=4.0 Hz, 1H), 7.69 (dt, J=7.6, 1.6 Hz, 1H), 7.53 (d, J=7.6 Hz, 1H), 7.24-7.26 (m, 2H), 7.21 (dt, J=8.0, 1.2 Hz, 1H), 7.12-7.13 (m, 1H), 6.93 (ddd, J=8.0, 2.4, 1.2 Hz, 1H), 4.98 (br s, 1H), 4.03 (t, J=5.2, 2H), 3.54-3.56 (m, 2H), 1.46 (s, 9H).

Step 2: Deprotection of tert-butyl 2-(3-(pyridin-2-ylethynyl)phenoxy)ethylcarbamate gave Example 98 hydrochloride as a white solid. Yield (0.300 g, 85%): $^1$H NMR (400 MHz, DMSO-d$_6$) δ 8.61 (dt, J=5.2, 0.8 Hz, 1H), 8.20 (br s, 3H), 7.92 (dt, J=8.0, 2.0 Hz, 1H), 7.69 (d, J=8.0 Hz, 1H), 7.47 (ddd, J=7.6, 5.2, 1.2 Hz, 1H), 7.39 (t, J=8.0 Hz, 1H), 7.22 (d, J=7.6 Hz, 1H), 7.19-7.20 (m, 1H), 7.08 (ddd, J=8.0, 2.4, 0.8 Hz, 1H), 4.21 (t, J=5.2 Hz, 2H), 3.18 (dt, J=5.6, 5.2 Hz, 2H).

Example 99

PREPARATION OF 1-((3-(3-AMINO-1-HYDROXYPROPYL)PHENYL)ETHYNYL)CYCLOHEXANOL

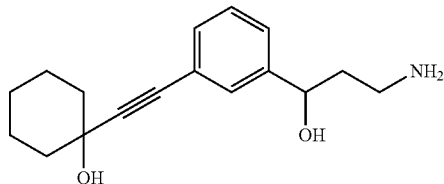 [SMILES: NCCC(O)c1cccc(C#CC2(O)CCCCC2)c1]

1-((3-(3-Amino-1-hydroxypropyl)phenyl)ethynyl)cyclohexanol was prepared following the method used in Example 19 with modifications.

Step 1: Coupling of aryl bromide 25 with 1-ethynylcyclohexanol following the coupling conditions used in Example 17 and purification by flash chromatography (40% EtOAc-hexanes) gave 2,2,2-trifluoro-N-(3-hydroxy-3-(3-((1-hydroxycyclohexyl)ethynyl)phenyl)propyl)acetamide as a pale yellow oil. Yield (0.621 g, 55%): $^1$H NMR (400 MHz, DMSO-d$_6$) δ 9.32 (t, J=4.8 Hz, 1H), 7.34 (s, 1H), 7.27-7.30 (m, 2H), 7.22-7.25 (m, 1H), 5.36-5.37 (m, 2H), 4.54-4.58 (m, 1H), 3.19-3.26 (m, 2H), 1.70-1.83 (m, 4H), 1.60-1.63 (m, 2H), 1.45-1.54 (m, 5H), 1.20-1.22 (m, 1H).

Step 2: Deprotection of 2,2,2-trifluoro-N-(3-hydroxy-3-(3-((1-hydroxycyclohexyl)ethynyl)phenyl)propyl)acetamide was conducted following the method used in Example 18, except that the solvent was 90% MeOH-water and the reaction was stirred overnight. The reaction mixture was concentrated under reduced pressure and partitioned into EtOAc and water. The combined organics were dried over Na$_2$SO$_4$ and concentrated under reduced pressure. The crude material was crystallized from hot EtOAc. After cooling, the product was collected by filtration, washed with EtOAc and hexanes, and dried. Example 99 was isolated as a white solid. Yield (0.210 g, 47%): $^1$H NMR (400 MHz, DMSO-d$_6$) δ 7.23-7.26 (m, 4H), 5.45 (br s, 1H), 4.68 (t, J=8.4 Hz, 1H), 2.62 (br s, 2H), 1.83-1.88 (m, 2H), 1.48-1.67 (m, 9H), 1.15-1.34 (m, 1H).

Example 100

PREPARATION OF (R)-4-((3-(3-AMINO-1-HYDROXYPROPYL)PHENYL)ETHYNYL)HEPTAN-4-OL

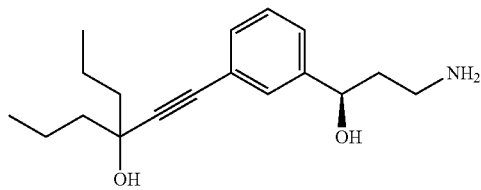 [SMILES: CCCC(O)(C#Cc1cccc([C@H](O)CCN)c1)CCC]

(R)-4-((3-(3-amino-1-hydroxypropyl)phenyl)ethynyl)heptan-4-ol was prepared following the method shown in Scheme 15.

Scheme 15

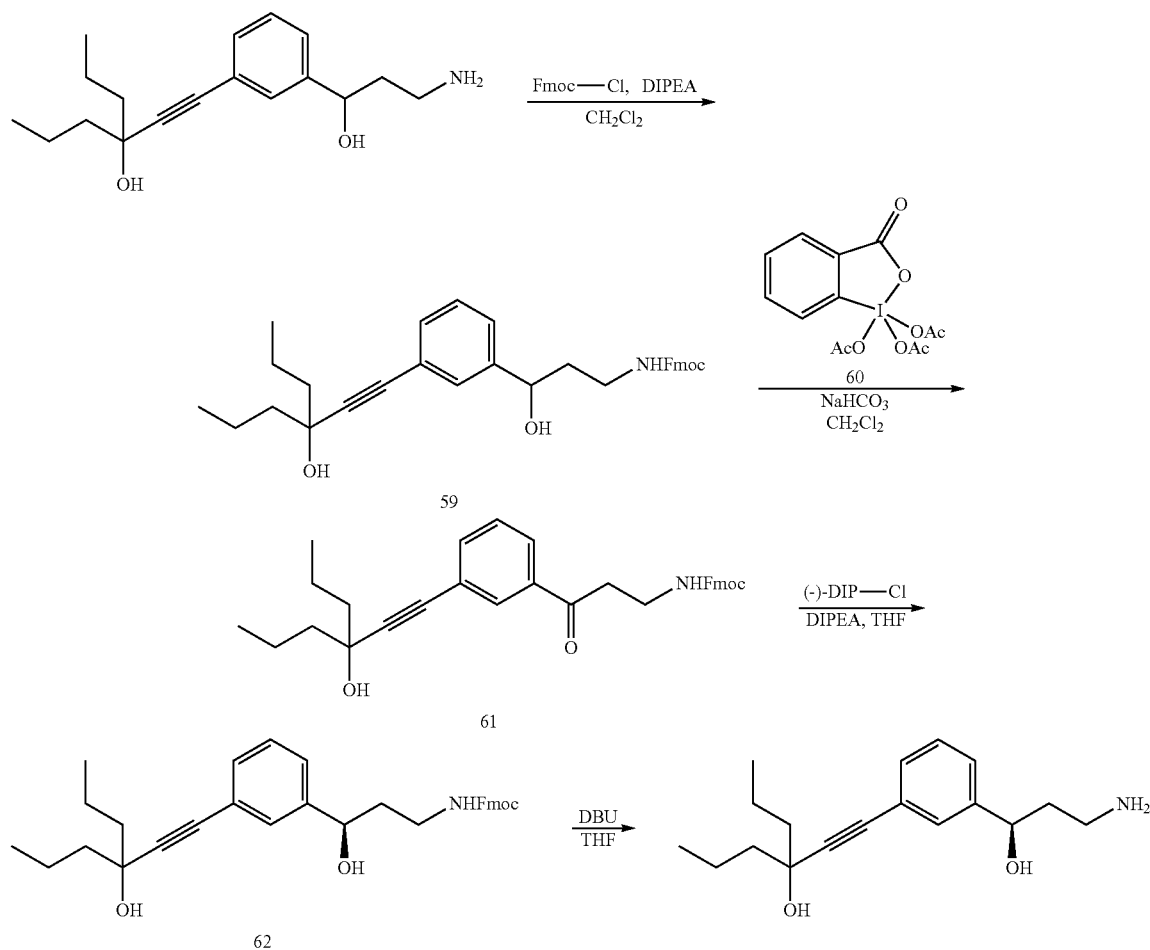

Step 1: To a solution of 4-((3-(3-amino-1-hydroxypropyl)phenyl)ethynyl)heptan-4-ol (Example 19) (1.39 g, 4.80 mmol) in CH$_2$Cl$_2$ (25 mL) was added diisopropylethylamine (1.2 mL) and a solution of 9-fluorenylmethoxycarbonyl chloride (Fmoc-Cl, 1.35 g, 5.2 mmol) in CH$_2$Cl$_2$ (10 mL). The reaction was stirred at room temperature for 20 min then concentrated under reduced pressure and purified by flash chromatography (30 to 70% EtOAc-hexanes gradient) to give alcohol 59. Yield (1.81 g, 74%): $^1$H NMR (400 MHz, DMSO-d$_6$) δ 7.91 (d, J=7.0 Hz, 2H), 7.67 (d, J=7.5 Hz, 2H), 7.28-7.43 (m, 8H), 5.19 (s, 1H), 4.80 (dd, J=9.1, 5.0 Hz, 1H), 4.54 (d, J=4.6 Hz, 2H), 4.31 (t, J=5.1 Hz, 1H), 3.42-3.53 (m, 2H), 1.99-2.06 (m, 1H), 1.45-1.63 (m, 4H), 1.30-1.32 (m, 10H), 0.92 (t, J=7.0 Hz, 6H).

Step 2: To a solution of alcohol 59 (1.81 g, 3.54 mmol) in CH$_2$Cl$_2$ (25 mL) was added NaHCO$_3$ (0.890 g, 10.6 mmol) and Dess-Martin periodinane (60, 1.65 g, 3.9 mmol). The reaction mixture was stirred at room temperature for 10 min, then the solids were removed by filtration through Celite. The filtrate was concentrated under reduced pressure and the residue was purified by flash chromatography (20 to 70% EtOAc-hexanes gradient) to give ketone 61. Yield (1.36 g, 75%).

Step 3: Preparation of (−)-B-chlorodiisopinocampheylborane solution ((−)-DIP-Cl): To an ice-cold solution of (−)-α-pinene (7.42 g, 54.56 mmol) in hexanes (5 mL) under argon was added chloroborane-methyl sulfide complex (2.55 mL, 24.46 mmol) over 1.5 min. The mixture was stirred for 2.5 min then allowed to warm to room temperature over 3 min. The reaction mixture was heated at 30° C. for 2.5 h. The resulting solution was approximately 1.5 M.

To a −25° C. solution of ketone 61 (0.6472 g, 1.27 mmol) in THF (5 mL) was added diisopropylethylamine (0.0408 g, 0.32 mmol) and (−)-DIP-Cl solution (1.5 mL of a 1.5 M solution in hexane, 2.25 mmol). The reaction mixture was stirred at −25° C. for 12 min then allowed to warm to 0° C. and stirred for 1 h, 15 min. The mixture was allowed to warm to room temperature over 20 min then additional (−)-DIP-Cl solution (1.5 mL of a 1.5 M solution in hexane, 2.25 mmol) was added. Stirring at room temperature was continued for 35 min then diisopropylethylamine (1 mL, 5.74 mmol) and saturated aqueous NaHCO$_3$ were added. The layers were separated and the aqueous layer was extracted with EtOAc. The combined organics were washed with brine, dried over MgSO$_4$ and concentrated under reduced pressure. Purification by flash chromatography (10 to 70% EtOAc-hexanes gradient) provided alcohol 62. (Yield 0.3295 g, 51%).

Step 4: To a solution of alcohol 62 (0.3295 g, 0.644 mmol) in THF (6 mL) was added 1,8-diazabicyclo[5.4.0]undec-7-ene (DBU, 0.11 mL, 0.74 mmol). The mixture was stirred at room temperature 20 min then concentrated under reduced pressure. Purification by flash chromatography (10:40:50 to 20:80:0.7 M NH3 in MeOH/EtOAc/hexanes) gave Example 100 as an oil. Yield (0.1383 g, 74%): ¹H NMR data was consistent with that reported for Example 19. Chiral HPLC (25° C.; eluent 90% heptane-EtOH containing 0.1% ethanesulfonic acid): 95.5% major enantiomer (AUC), $t_R$=17.622 min (minor enantiomer: 4.4%, $t_R$=21.756 min). $[\alpha]_D$=+20.09 (26.6° C., c=0.980 g/100 mL in EtOH).

Determination of the Absolute Stereochemistry of Example 100

The absolute stereochemistry of Example 100 was determined by the method shown in Scheme 16 where Example 100 and (R)-3-amino-1-phenylpropan-1-ol were synthesized from a common intermediate (bromide 64). The optical rotation of (R)-3-amino-1-phenylpropan-1-ol was consistent with the value reported in the literature (Kamal, Ahmed et al. Tetrahedron: Asymmetry 2002, 13(18), 2039-52); $[\alpha]_D$=+41.8 (30° C., c=1.0 g/100 mL in MeOH).

Step 2: To an ice-cold solution of ketone 63 (0.6465 g, 1.99 mmol) in THF (10 mL) was added diisopropylethylamine (0.1 mL, 0.57 mmol) and freshly prepared (+DIP-Cl (2.5 mL of a 1.67 M solution in hexane, 4.2 mmol). The reaction was allowed to warm to room temperature and stirred for 2.5 h. Additional (+DIP-Cl solution was added (1 mL, 1.67 mmol) and the mixture was stirred for 2.5 h. The reaction was partitioned into saturated aqueous NaHCO₃ and EtOAc. The combined organics were washed with brine, dried over Na₂SO₄ and concentrated under reduced pressure. Purification by flash chromatography (10 to 100% EtOAc-hexanes gradient) afforded aryl bromide 64. Yield (0.62 g, 95%): ¹H NMR (400 MHz, CDCl₃) δ 7.50 (t, J=1.6 Hz, 1H), 7.43 (dt, J=7.2, 2.0 Hz, 1H), 7.21-7.27 (m, 2H), 4.84 (dt, J=8.8, 3.2 Hz, 1H), 3.65-3.73 (m, 1H), 3.36-3.43 (m, 1H), 2.47 (dd, J=2.9, 1.0 Hz, 1H), 1.80-2.00 (m, 2H).

Scheme 16

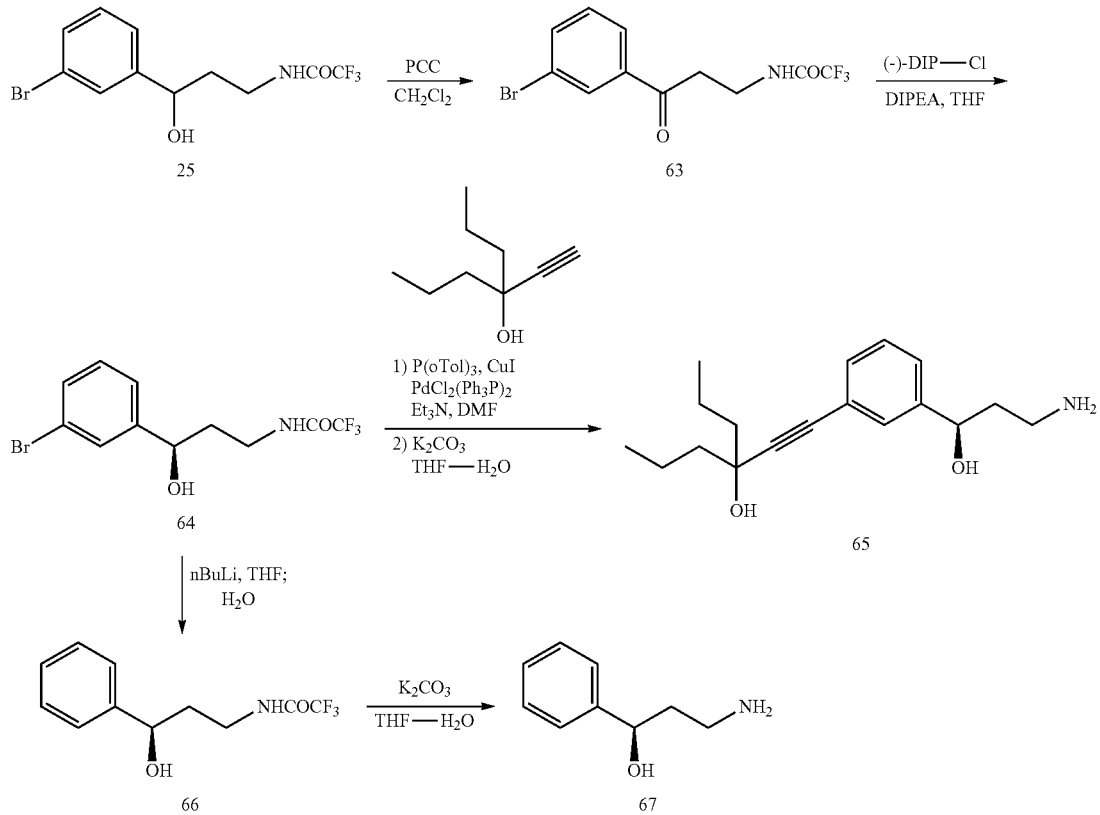

Step 1: To a solution of aryl bromide 25 (1.0552 g, 3.23 mmol) in CH₂Cl₂ (25 mL) was added pyridinium chlorochromate (0.9152 g, 4.2 mmol) and Celite (1.96 g). The reaction mixture was stirred at room temperature for 1 h, 50 min then a second portion of pyridinium chlorochromate (0.4936 g, 2.3 mmol) was added. Stirring was continued for 1 h then solids were removed by filtration through Celite. The filtrate was concentrated under reduced pressure and purified by flash chromatography (10 to 50% EtOAc-hexanes gradient) to give ketone 63 as a white solid. Yield (0.6465 g, 62%): ¹H NMR (400 MHz, DMSO-d₆) δ 9.40 (br s, 1H), 8.06 (t, J=2.0 Hz, 1H), 7.93 (d, J=7.6 Hz, 1H), 7.83 (ddd, J=7.6, 2.0, 0.8 Hz, 1H), 7.48 (t, J=8.0 Hz, 1H), 3.50 (t, J=6.8 Hz, 2H), 3.30 (t, J=6.8 Hz, 2H).

Step 3: To a solution of aryl bromide 64 (0.2732 g, 0.84 mmol) in triethylamine (1 mL) and DMF (5 mL) was added 4-ethynylheptan-4-ol (0.35 g, 2.5 mmol), tri(o-tolyl)phosphine (0.0164 g, 0.05 mmol), CuI (0.0110 g, 0.058 mmol), and PdCl₂(Ph₃P)₂ (0.0208 g, 0.03 mmol) and the mixture was degassed (vacuum/argon purge three times). The mixture was heated at 60° C. for 15 h then cooled to room temperature. The mixture was concentrated under reduced pressure and triturated with EtOAc. The solids were removed by filtration and the filtrate was concentrated under reduced pressure. Purification by flash chromatography (10 to 70% EtOAc-hexanes gradient) afforded (R)-2,2,2-trifluoro-N-(3-hydroxy-3-(3-(3-hydroxy-3-propylhex-1-ynyl)phenyl)propyl)acetamide.

Yield (0.2551 g, 79%): the ¹H NMR data was consistent with that of (R/S)-2,2,2-trifluoro-N-(3-hydroxy-3-(3-(3-hydroxy- 3-propylhex-1-ynyl)phenyl)propyl)acetamide (an intermediate in Example 19 synthesis) reported above.

Step 4: To a solution of (R)-2,2,2-trifluoro-N-(3-hydroxy-3-(3-(3-hydroxy-3-propylhex-1-ynyl)phenyl)propyl)acetamide (0.2551 g, 0.66 mmol) in MeOH—H$_2$O (2:1, 12 mL) was added K$_2$CO$_3$ (0.4967 g, 3.6 mmol) and the mixture was heated at 60° C. for 1 h. After cooling to room temperature, the mixture was partitioned into EtOAc and brine. The combined organics were dried over Na$_2$SO$_4$ and concentrated under reduced pressure. Purification by flash chromatography (50:40:10 to 0:80:20 hexanes:EtOAc: 7 M NH$_3$ in MeOH gradient) gave alkyne 65 as an oil. Yield (0.1421 g, 74%): the $^1$H NMR data was consistent with that of Example 100 reported above. Chiral HPLC (25° C.; eluent 90% heptane-EtOH containing 0.1% ethanesulfonic acid): 93.6% major enantiomer (AUC), $t_R$=15.880 min (minor enantiomer: 6.4%, $t_R$=20.068 min). $[\alpha]_D$=+20.77 (24.1° C., c=1.920 g/100 mL in EtOH).

Preparation of (R)-3-amino-1-phenylpropan-1-ol (67) from aryl bromide 64

Step 1: To a –78° C. solution of aryl bromide 64 (1.3155 g, 4.03 mmol) in THF (13 mL) was added a solution of n-butyl lithium (13 mL of a 1.6 M solution in hexanes, 20.8 mmol). The mixture was stirred at –78° C. for 10 min then quenched with 30% aqueous NH$_4$Cl. After warming to room temperature, the mixture was extracted with EtOAc. The combined organics were washed with brine, dried over MgSO$_4$ and concentrated under reduced pressure. Purification by flash chromatography (10 to 70% EtOAc-hexanes) afforded alcohol 66 contaminated with ~3% of the bromide starting material. Yield (0.3730 g, 37%): $^1$H NMR (400 MHz, CDCl$_3$) δ 9.33 (br s, 1H), 7.51 (t, J=7.6 Hz, 1H), 7.44 (d, J=8.0 Hz, 1H), 7.39 (s, 1H), 7.33 (ddd, J=8.4, 2.8, 0.8 Hz, 1H), 5.59 (d, J=4.8 Hz, 1H), 4.66 (dt, J=8.0, 4.4 Hz, 1H), 3.19-3.28 (m, 2H), 1.71-1.86 (m, 2H).

Step 2: Deprotection of alcohol 66 and purification as described for alkyne 65 gave (R)-3-amino-1-phenylpropan-1-ol (67) as an oil. Yield (0.1749 g, 77%): $^1$H NMR (400 MHz, CDCl$_3$) δ 7.31-7.38 (m, 4H), 7.21-7.25 (m, 1H), 4.94 (dd, J=8.8, 3.2 Hz, 1H), 3.05-3.10 (m, 1H), 2.91-2.97 (m, 1H), 2.62 (br s, 3H), 1.82-1.89 (m, 1H), 1.70-1.79 (m, 1H). $[\alpha]_D$=+34.84 (25.7° C., c=2.05 g/100 mL in MeOH).

Example 101

PREPARATION OF (S)-4-((3-(3-AMINO-1-HYDROXYPROPYL)PHENYL)ETHYNYL)HEPTAN-4-OL

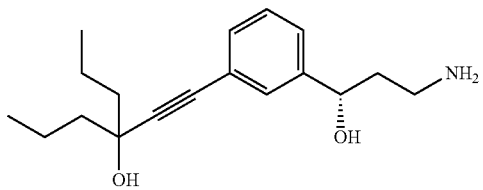 [SMILES: CCCC(O)(C#Cc1cccc([C@@H](O)CCN)c1)CCC]

(S)-4-(3-(3-amino-1-hydroxypropyl)phenyl)ethynyl)heptan-4-ol was prepared following the method used in Example 100.

Step 1: Ketone 61 was reduced with (+)-DIP-Cl and purified by flash chromatography (10 to 70% EtOAc-hexanes gradient) to afford (S)-(9H-fluoren-9-yl)methyl 3-hydroxy-3-(3-(3-hydroxy-3-propylhex-1-ynyl)phenyl)propylcarbamate. Yield (0.50 g, 70%): the $^1$H NMR data was consistent with that reported above.

Step 2: (S)-(9H-Fluoren-9-yl)methyl 3-hydroxy-3-(3-(3-hydroxy-3-propylhex-1-ynyl)phenyl)propylcarbamate was deprotected and purified according to the method used in Example 100 to give Example 101 as an oil. Yield (0.1845, 65%): $^1$H NMR data was consistent with that reported for Example 19. Chiral HPLC (25° C.; eluent 90% heptane-EtOH containing 0.1% ethanesulfonic acid): 95.7% major enantiomer (AUC), $t_R$=21.562 min (minor enantiomer: 4.2%, $t_R$=17.572 min). $[\alpha]_D$=–24.93 (26.6° C., c=0.955 g/100 mL in EtOH).

Example 102

PREPARATION OF 3-(3-(HEPT-1-YNYL)PHENYL)PROPAN-1-AMINE

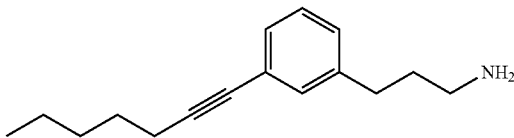 [SMILES: CCCCCC#Cc1cccc(CCCN)c1]

3-(3-(Hept-1-ynyl)phenyl)propan-1-amine was prepared following the method used in Example 36.

Step 1: Coupling of aryl bromide 34 with hept-1-yne and purification by flash chromatography (30% EtOAc-hexanes) gave tert-butyl 3-(3-(hept-1-ynyl)phenyl)propylcarbamate as a yellow oil. Yield (0.300 g, 57%).

Step 2: Deprotection of tert-butyl 3-(3-(hept-1-ynyl)phenyl)propylcarbamate was conducted following the method used in Example 36. Purification by prep HPLC (Method 004P) gave Example 102 hydrochloride as a white solid. Yield (0.200 g, 15%): $^1$H NMR (400 MHz, DMSO-d$_6$) δ 7.98 (br s, 2H), 7.28 (t, J=7.6 Hz, 1H), 7.24-7.18 (m, 3H), 2.74 (t, J=7.2 Hz, 2H), 2.63 (t, J=7.6 Hz, 2H), 2.41 (t, J=6.8 Hz, 2H), 1.84 (quint, J=7.6 Hz, 2H), 1.54 (quint, J=7.6 Hz, 2H), 1.43-1.28 (m, 4H), 0.89 (t, J=7.2 Hz, 3H).

Example 103

PREPARATION OF N-(3-(3-(3-HYDROXY-3-PROPYLHEX-1-YNYL)PHENYL)PROPYL)ACETAMIDE

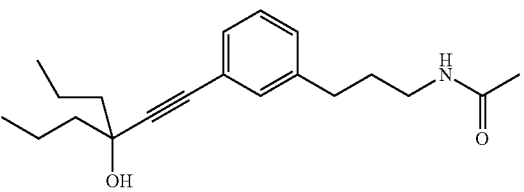 [SMILES: CCCC(O)(C#Cc1cccc(CCCNC(C)=O)c1)CCC]

N-(3-(3-(3-Hydroxy-3-propylhex-1-ynyl)phenyl)propyl)acetamide was prepared following the method used in Example 60.

4-((3-(3-Aminopropyl)phenyl)ethynyl)heptan-4-ol (Example 2) was acylated to give Example 103 as a clear oil. Yield (0.087 g, 80%): $^1$H NMR (400 MHz, DMSO-d$_6$) δ 7.81

(bs, 1H), 7.24 (t, J=7.6 Hz, 1H), 7.12-7.15 (m, 3H), 5.11 (s, 1H), 2.99 (q, J=12.8, 7.8 Hz, 2H), 2.54 (t, J=7.2, 2H), 1.77 (s, 3H), 1.68-1.42 (m, 10H), 0.89 (t, J=6.8 Hz, 6H).

Example 104

PREPARATION OF 2,2,2-TRIFLUORO-N-(3-HYDROXY-3-(3-(3-HYDROXY-3-PROPYLHEX-1-YNYL)PHENYL)PROPYL)ACETAMIDE

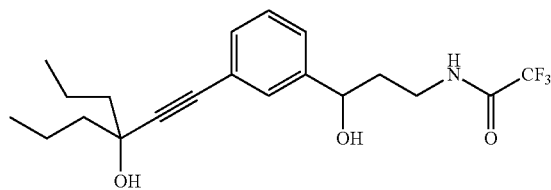 [SMILES: CCCC(O)(C#Cc1cccc(C(O)CCNC(=O)C(F)(F)F)c1)CCC]

2,2,2-trifluoro-N-(3-Hydroxy-3-(3-(3-hydroxy-3-propylhex-1-ynyl)phenyl)propyl)acetamide (Compound 26) was prepared as described in Example 19, Scheme 5.

Example 105

PREPARATION OF 3-(3-(CYCLOHEPTYLETHYNYL)PHENYL)PROPAN-1-AMINE

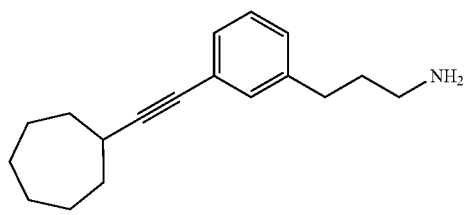 [SMILES: NCCCc1cccc(C#CC2CCCCCC2)c1]

3-(3-(Cycloheptylethynyl)phenyl)propan-1-amine was prepared following the method shown in shown in Scheme 17.

SCHEME 17

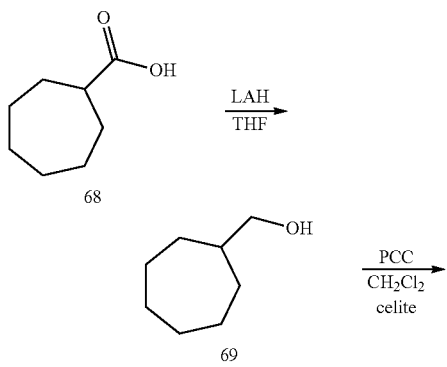

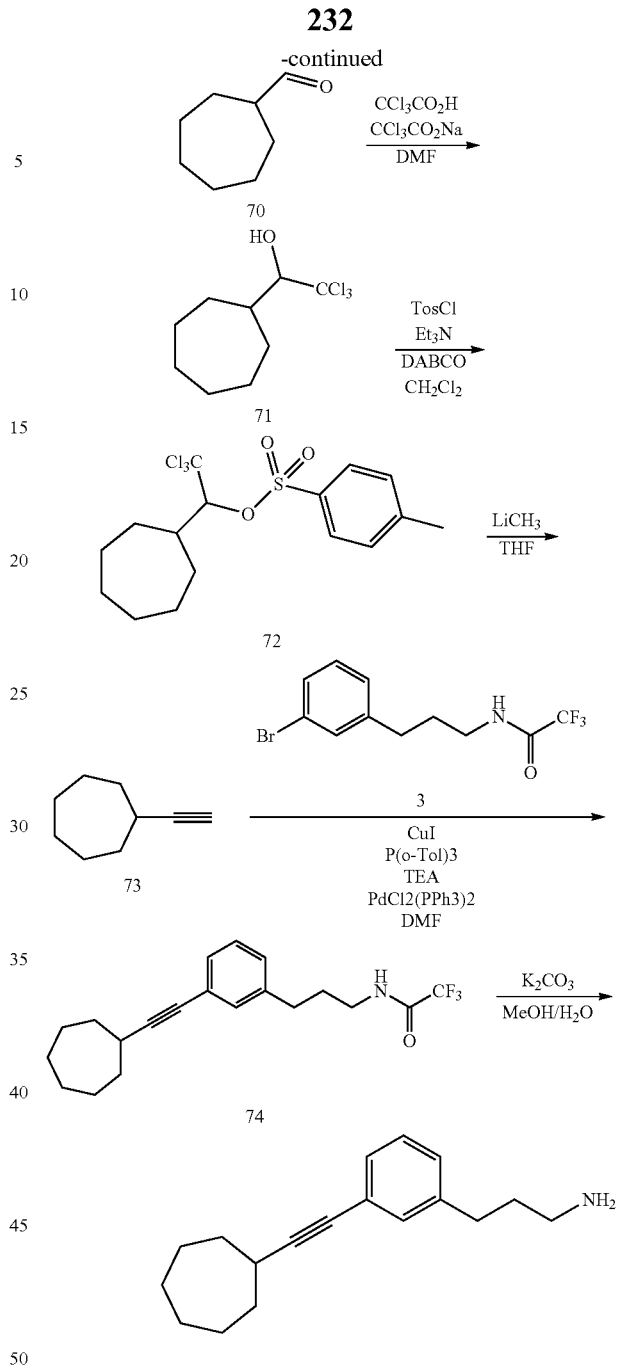

Step 1: LAH (180 mL of a 1M solution, 176 mmol) was added slowly to a solution of acid 68 (25 g, 176 mmol), in anhydrous THF (500 mL) under argon at 5° C. The reaction was allowed to warm to room temperature, stirred 1 h, cooled again to 5° C., then quenched by slow addition of saturated aqueous $Na_2SO_4$. The resultant precipitate was removed by filtration, then the filtrate was extracted with EtOAc, washed with water and brine, dried over $Na_2SO_4$, filtered and concentrated to give the alcohol 69 as colorless oil. Yield (21 g, 98%). $^1$H NMR (400 MHz, CDCl$_3$) δ 3.38 (d, J=6.4 Hz, 2H), 1.38-1.80 (m, 12H), 1.10-1.20 (m, 2H).

Step 2: A solution of alcohol 69 (4.5 g, 35 mmol) in dichloromethane (10 mL) was added to a stirring mixture of pyridinium chlorochromate (9.4 g, 43.8 mmol) and celite (10 g) in dichloromethane (100 mL) and the reaction stirred 16 hr. The mixture was filtered through a pad of silica gel and the pad rinsed with diethyl ether. The combined filtrate was concentrated, giving impure aldehyde 70 as a green oil, which was taken on to the next step without purification. Yield (4.1 g, 93%). $^1$H NMR (400 MHz, CDCl$_3$) δ 9.58 (d, J=0.8 Hz, 1H), 2.28-2.36 (m, 1H), 1.88-1.95 (m, 2H), 1.40-1.70 (m, 10H).

Step 3: Sodium trichloroacetate was added in 3 aliquots over 10 min to a stirred solution of aldehyde 70 (14.9 g, 118 mmole) and trichloroacetic acid (19.3 g, 177 mmol) in DMF (150 mL). The reaction was stirred at room temperature for 2 h, cooled in an ice bath, then quenched and diluted with water. The solution was extracted with hexanes and washed with saturated aqueous NH$_4$Cl, water, and brine. The combined organics were dried over Na$_2$SO$_4$, filtered, and concentrated under reduced pressure, giving impure alcohol 71 as a yellow oil, which was taken on to the next step without purification. Yield (23.4 g, 80%). $^1$H NMR (400 MHz, CDCl$_3$) δ 3.95 (d, J=2.0 Hz, 1H), 2.85 (br s, 1H), 2.20-2.30 (m, 1H), 1.88-2.08 (m, 1H), 1.36-1.84 (m, 11H).

Step 4: p-toluenesulfonyl chloride (3.34 g, 17.5 mmol) was added to a solution of alcohol 71 (4.3 g, 17.5 mmol), triethylamine (3.6 mL, 26.3 mmol), and diazabicyclooctane (0.586 g, 5.2 mmol) in 40 mL dichloromethane and stirred at room temperature for 90 min. The reaction was quenched by washing with water (40 mL), then washed with 5N HCl. The combined aqueous was extracted with dichloromethane (40 mL) and the combined organics further washed with 2N HCl, water, and brine, then dried over Na$_2$SO$_4$, filtered, and concentrated under reduced pressure. Purification by flash chromatography (0-10% EtOAc/hexanes gradient) gave the sulfonate 72 as pale yellow crystals. Yield (2.65 g, 38%): $^1$H NMR (400 MHz, CDCl$_3$) δ 7.81 (d, J=8.8 Hz, 2H), 7.32 (d, J=8 Hz, 2H), 2.43 (s, 3H), 2.24-2.32 (m, 1H), 1.98-2.06 (s, 1H), 1.78-1.88 (m, 1H), 1.60-1.73 (m, 3H), 1.28-1.60 (m, 8H).

Step 5: Methyllithium (7.0 mL of a 1.6 M solution in diethyl ether, 11.25 mmol) was added dropwise to a stirring solution of sulfonate 72 (1 g, 2.5 mmol) in anhydrous THF (15 mL) under argon at 5° C. The reaction was allowed to warm to room temperature, stirred 16 hr, then quenched by the slow addition of saturated aqueous NH$_4$Cl. The mixture was extracted with hexanes, and the combined organics washed with brine, dried over Na$_2$SO$_4$, filtered, and concentrated under reduced pressure, giving the alkyne 73 as yellow oil. Yield (0.270 g, 88%) $^1$H NMR (400 MHz, CDCl$_3$) δ 2.51 (s, 1H), 1.99 (d, J=2.8 Hz, 1H), 1.73-1.83 (m, 2H), 1.55-1.70 (m, 4H), 1.35-1.55 (m, 6H).

Step 6: The sonogashira coupling was conducted following the method used in Example 1. Purification by flash chromatography (0-25% EtOAc/hexanes gradient), gave the alkyne 74 as an amber oil. Yield (0.556 g, 59%): $^1$H NMR (400 MHz, CDCl$_3$) δ 7.16-7.26 (m, 3H), 7.03-7.08 (m, 1H), 6.28 (br s, 1H), 3.36 (dt, J=6.8, 6.8 Hz, 2H), 2.75-2.83 (m, 1H), 2.63 (t, J=7.2 Hz, 2H), 1.85-1.95 (m, 4H), 1.69-1.80 (m, 4H), 1.48-1.65 (m, 6H).

Step 7: Deprotection of the alkyne 74 was conducted following the method used in Example 1. Purification by flash chromatography (5% (7N NH3/MeOH)/dichloromethane) gave Example 106 as a colorless oil. Yield (0.226 g, 56%): $^1$H NMR (400 MHz, CDCl$_3$) δ 7.13-7.25 (m, 3H), 7.03-7.08 (m, 1H), 2.74-2.82 (m, 1H), 2.69 (t, J=7.2 Hz, 2H), 2.59 (t, J=7.2 Hz, 2H), 1.84-1.94 (m, 2H), 1.68-1.80 (m, 6H), 1.46-1.64 (m, 6H), 1.30 (br s, 2H).

Example 106

PREPARATION OF 2-(3-(CYCLOHEPTYLETHYNYL)PHENOXY) ETHANAMINE

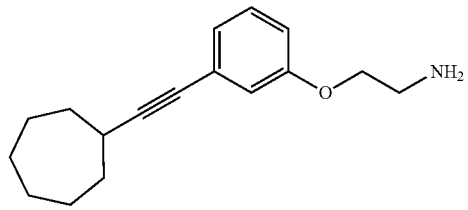 [SMILES: NCCOc1cccc(C#CC2CCCCCC2)c1]

2-(3-(Cycloheptylethynyl)phenoxy)ethanamine was prepared following the method used in Example 18.

Step 1: Sonogashira coupling of alkyne 73 with phenyl bromide 19 followed by flash chromatography (0-25% EtOAc/hexanes gradient), gave N-(2-(3-(cycloheptylethynyl)phenoxy)ethyl)-2,2,2-trifluoroacetamide as an amber oil. Yield (0.154 g, 27%): $^1$H NMR (400 MHz, CDCl$_3$) δ 7.12 (t, J=8 Hz, 1H), 6.98-6.98 (m, 1H), 6.83-6.86 (m, 1H), 6.65-6.80 (m, 2H), 4.01 (t, J=4.8 Hz, 2H), 3.66-3.73 (m, 2H), 2.68-2.77 (m, 1H), 1.79-1.88 (m, 2H), 1.63-1.73 (m, 4H), 1.40-1.57 (m, 6H).

Step 2: Deprotection of N-(2-(3-(cycloheptylethynyl)phenoxy)ethyl)-2,2,2-trifluoroacetamide followed by flash chromatography (5% (7N NH3/MeOH)/dichloromethane) gave Example 106 as a pale brown oil. Yield (0.064 g, 53%): $^1$H NMR (400 MHz, CDCl$_3$) δ 7.16 (t, J=8 Hz, 1H), 6.95-6.99 (m, 1H), 6.90-6.94 (m, 1H), 6.78-6.83 (m, 1H), 3.95 (t, J=5.2 Hz, 2H), 3.05 (t, J=4.8 Hz, 2H), 2.74-2.82 (m, 1H), 1.84-1.94 (m, 2H), 1.68-1.80 (m, 4H), 1.44-1.64 (m, 8H).

Example 107

PREPARATION OF 3-AMINO-1-(3-(3-METHOXYPROP-1-YNYL)PHENYL)PROPAN-1-OL

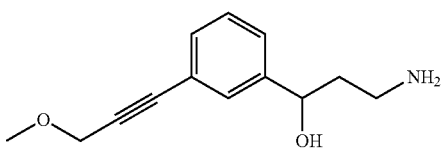 [SMILES: COCC#Cc1cccc(C(O)CCN)c1]

3-Amino-1-(3-(3-methoxyprop-1-ynyl)phenyl)propan-1-ol was prepared following the method shown in Scheme 18.

SCHEME 18

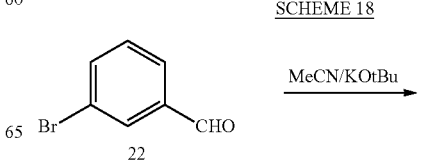

-continued

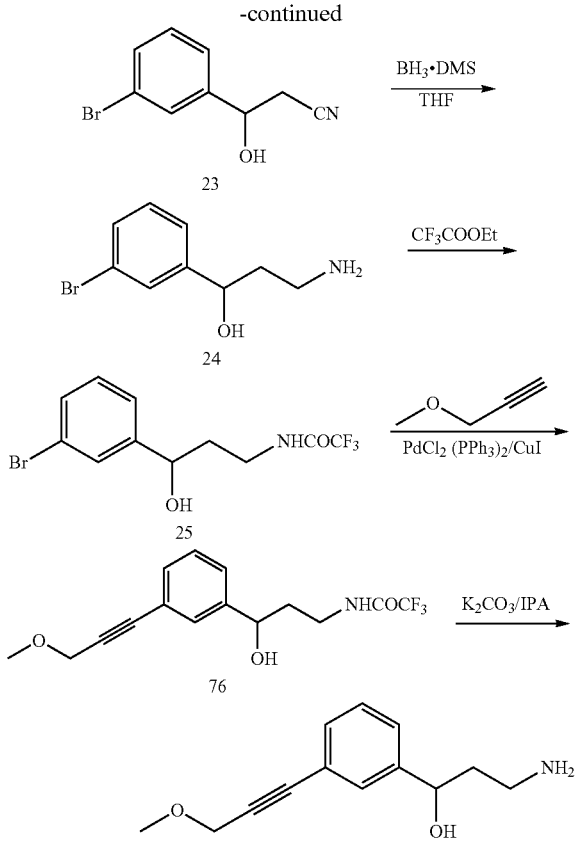

Step 1: To a stirred mixture of THF (200 mL) and CH₃CN (7.8 mL, 148 mmol) cooled to −50° C., was added KOtBu (18.16 g, 162 mmol) in portions by maintaining the temperature at −50° C. After stirring for 30 min, 3-bromobenzaldehyde (25 g, 135 mmol) was charged maintaining the same internal temperature. After stirring for 30 min, the reaction mixture was warmed to 0° C. and stirred for additional 3 h. This was recooled to −10° C. and quenched with excess water. Extraction with ethyl acetate yielded the crude product, which was purified by flash chromatography (0 to 20% EtOAc-hexanes gradient) to give 23 as light yellow oil. Yield (21 g, 69%): ¹H NMR (400 MHz, DMSO-d₆) δ 7.61 (s, 1H), 7.49 (bd, J=7.8 Hz, 1H), 7.47 (bd, J=7.6 Hz, 1H), 7.34 (t, J=7.6 Hz, 1H), 6.09 (d, J=4.4 Hz, 1H), 4.92 (m, 1H), 2.81-2.95 (m, 2H).

Step 2: To a solution of nitrile 23 (22.4 g, 99 mmol) in anhydrous THF (200 mL) under nitrogen was added BH₃·SMe₂ (28.4 mL, 297 mmol) via addition funnel over a period of 1 h. The mixture was then refluxed for 14 h. After cooling to 0° C., the excess borane was quenched by slow addition of methanol. This was concentrated to dryness under reduced pressure. The process was repeated six times. This was followed by the dissolution of the crude product in 6N HCl and extraction with DCM. Aqueous layer was basified to pH 10 with conc. NH₄OH and extracted with DCM. Combined organics were dried over Na₂SO₄. The solution was filtered and concentrated under reduced pressure to give 24 as clear oil. Yield (15.94 g, 70%): ¹H NMR (400 MHz, DMSO-d₆) δ 7.51 (s, 1H), 7.42 (bd, J=7.6 Hz, 1H), 7.22-7.34 (m, 2H), 4.69 (m, 1H), 2.67-2.74 (m, 2H), 1.65-1.77 (m, 2H).

Step 3: To a solution of 24 (15.9 g, 69 mmol) in anhydrous THF (200 mL) was added ethyl trifluoroacetate (10 mL, 83 mmol). The resulting mixture was stirred at room temperature for 3 h during which the transformation was found to be complete. The reaction mixture was then concentrated to dryness under reduced pressure. The product was pure enough to be utilized as such for the next transformation. Yield (19 g, crude): ¹H NMR (400 MHz, DMSO-d₆) δ 9.35 (bs, 1H), 7.53 (s, 1H), 7.44 (bd, J=7.6 Hz, 1H), 7.22-7.34 (m, 2H), 5.48 (d, J=4.8 Hz, 1H), 4.57-45.61 (m, 1H), 3.18-3.30 (m, 2H), 1.73-1.87 (m, 2H).

Step 4: A mixture of 25, methyl propargyl ether (0.2 mL, 2.25 mmol), PdCl₂ (PPh₃)₂ (108 mg, 0.075 mmol), tri-o-tolylphosphine (47 mg, 0.075 mmol), copper (I) iodide (29 mg, 0.075 mmol), in diisopropylamine (10 mL) was heated under reflux overnight. The mixture was cooled to room temperature and then concentrated under reduced pressure. Purification by flash chromatography (0 to 30% EtOAc-hexanes gradient) gave ether 76 as yellow oil. Yield (0.4 g, 82%): ¹H NMR (400 MHz, CDCl₃) δ 7.44 (s, 1H), 7.38-7.40 (m, 1H), 7.31-7.34 (m, 2H), 4.88 (m, 1H), 4.12 (s, 2H), 3.66-3.70 (m, 1H), 3.43 (s, 3H), 3.38-3.41 (m, 1H), 2.37 (d, J=2Hz, 1H) 1.93-1.97 (m, 2H).

Step 5: A mixture of 76, potassium carbonate (438 mg, 3.26 mmol) and water (2 mL) in 2-PrOH (10 mL) was heated under reflux overnight. Reaction mass was concentrated to dryness under reduced pressure and diluted with water (10 mL). This mass was acidified to pH 2 and extracted with DCM. The aqueous layer was basified with saturated NaHCO₃ solution to pH 10 and extracted with DCM. The combined organics were dried over Na₂SO₄. The solution was concentrated under reduced pressure to give Example 107 as brown oil. Yield (0.138 g, 77%): ¹H NMR (400 MHz, DMSO-d₆) δ 7.40 (s, 1H), 7.25-7.35 (m, 3H), 4.67 (t, J=6.4 Hz, 1H), 4.34 (s, 2H), 2.59-2.64 (m, 2H), 2.50 (s, 3H), 1.74-1.80 (m, 2H). ¹³C NMR (100 MHz, DMSO-d₆) δ 147.1, 129.5, 128.7, 128.4, 126.2, 121.5, 86.1, 85.5, 70.8, 59.5, 57.0, 42.2. ESI MS m/z 220 [M+l]⁺.

Example 108

PREPARATION OF 3-AMINO-1-(3-(HEX-1-YNYL)PHENYL)PROPAN-1-OL

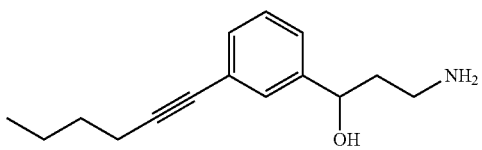 [SMILES: CCCCC#Cc1cccc(C(O)CCN)c1]

3-Amino-1-(3-(hex-1-ynyl)phenyl)propan-1-ol was prepared following the method used in Example 107.

Step 1: Sonogashira reaction of 25 with 1-hexyne resulted in 2,2,2-trifluoro-N-(3-(3-(hex-1-ynyl)phenyl)-3-hydroxypropyl)acetamide as yellow oil. Yield (1.53 g, 76%): ¹H NMR (400 MHz, CDCl₃) δ 7.38 (s, 1H), 7.25-7.34 (m, 3H), 4.88 (m, 1H), 3.65-3.73 (m, 1H), 3.38-3.42 (m, 1H), 2.40 (t, J=7.2 Hz, 2H), 2.25 (d, J=2.0, 1H) 1.93-1.99 (m, 2H), 1.45-1.61 (m, 4H), 0.94 (t, J=7.2 Hz, 3H).

Step 2: Deprotection of 2,2,2-trifluoro-N-(3-(3-(hex-1-ynyl)phenyl)-3-hydroxypropyl)acetamide gave yellow oil. Crude product was dissolved in methanol (5 ml) and stirred for 30 min with HCl in Dioxane (1 mL, 4M). The mixture was concentrated to dryness under reduced pressure. Purification by flash chromatography gave Example 108, as a pale yellow semi-solid, as the hydrochloride. Yield (0.17 g, 41%): ¹H NMR (400 MHz, DMSO-d₆) δ 7.23-7.32 (m, 4H), 4.62-4.65

(m, 1H), 2.78-2.86 (m, 2H), 2.38 (t, J=6.8 Hz, 2H), 1.74-1.85 (m, 2H), 1.35-1.52 (m, 4H), 0.87 (t, J=7.2 Hz, 3H). $^{13}$C NMR (100 MHz, DMSO-d$_6$) δ 145.7, 129.7, 128.5, 128.4, 125.2, 123.1, 90.5, 80.7, 69.2, 36.5, 36.3, 30.3, 21.5, 18.3, 13.5. ESI MS m/z 232 [M+1]$^+$.

Example 109

PREPARATION OF 4-((3-(3-AMINO-2-HYDROXYPROPYL)PHENYL)ETHYNYL)HEPTAN-4-OL

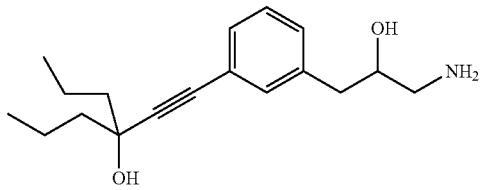 [SMILES: CCCC(O)(C#Cc1cccc(CC(O)CN)c1)CCC]

4-((3-(3-Amino-2-hydroxypropyl)phenyl)ethynyl)heptan-4-ol was prepared following the method shown in Scheme 19.

SCHEME 19

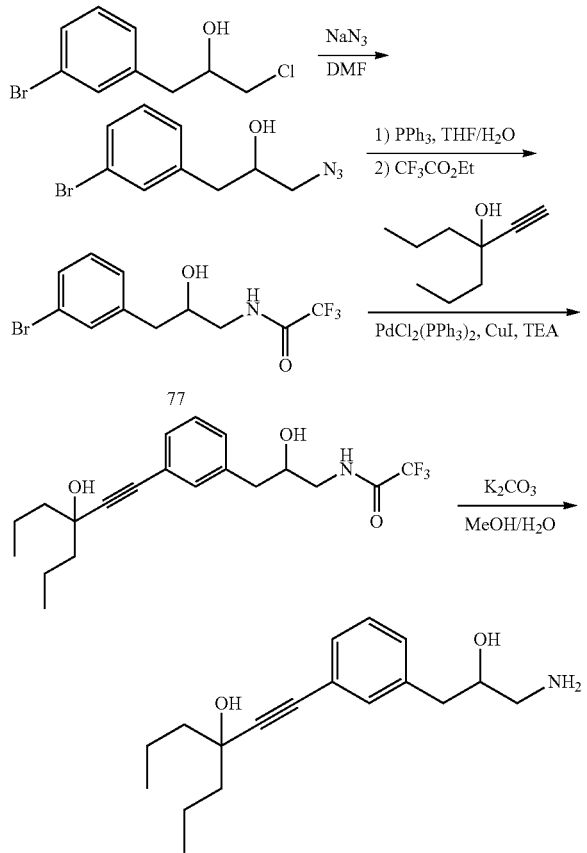

Step 1: To a solution of 1-(3-bromophenyl)-3-chloropropan-2-ol (8.49 g, 34.0 mmol) in anhydrous DMF (100 mL) under N$_2$ was added NaN$_3$ (11.05 g, 170.0 mmol) and NaI (cat., 0.75 g, 5.0 mmol). The mixture was heated at 75° C. overnight. After cooling to room temperature, the mixture was diluted with ether and washed with water and brine. The solution was dried over Na$_2$SO$_4$ and concentrated under reduced pressure. The product was dried in a vacuum oven at 40° C. for 2 h to give 1-azido-3-(3-bromophenyl)propan-2-ol as a yellow oil which was used without purification. Yield (8.6 g, 98% crude).

Step 2: To a solution of 1-azido-3-(3-bromophenyl)propan-2-ol (8.59 g, 33.28 mmol) in THF (60 mL) under N$_2$ was added PPh$_3$ (8.73 g, 33.28 mmol) and water (20 mL). The reaction mixture was heated at 50° C. for 24 h. After cooling to room temperature, the mixture was diluted with brine and extracted with EtOAc. The organic layer was dried over Na$_2$SO$_4$ and concentrated under reduced pressure. The crude amine was dissolved in THF (20 ml) and ethyl trifluoroacetate (20 ml) and stirred overnight at room temperature. Evaporation under reduced pressure followed by purification by flash chromatography (5% EtOAc/CH$_2$Cl$_2$) gave bromide 77 as a white solid. Yield (3.72 g, 35%): $^1$H NMR (400 MHz, DMSO-d$_6$) δ 9.33 (t, J=5.2 Hz, 1H), 7.42 (d, J=1.2 Hz, 1H), 7.38-7.35 (m, 1H), 7.24-7.20 (m, 2H), 5.00 (d, J=6.0 Hz, 1H), 3.83-3.75 (m, 1H), 3.21-3.07 (m, 2H), 2.70 (dd, J=13.6 Hz, 4.8, 1H), 2.55 (dd, J=14.0, 6.0 Hz, 1H).

Step 3: Coupling of bromide 77 with 4-ethynylheptan-4-ol following the procedure described in Example 17 gave 2,2,2-trifluoro-N-(2-hydroxy-3-(3-(3-hydroxy-3-propylhex-1-ynyl)phenyl)propyl)acetamide as a clear oil. Yield (0.455 g, 59%): $^1$H NMR (400 MHz, DMSO-d$_6$) δ 9.32 (t, J=5.4 Hz, 1H), 7.25-7.22 (m, 2H), 7.18-7.16 (m, 2H), 5.11 (s, 1H), 4.96 (d, J=5.6 Hz, 1H), 3.81-3.74 (m, 1H), 3.21-3.07 (m, 2H), 2.68 (dd, J=14.0, 4.6 Hz, 1H), 2.54 (dd, J=14.0, 7.8 Hz, 1H), 1.61-1.40 (m, 8H), 0.89 (t, J=7.2 Hz, 6H).

Step 4: Deprotection of 2,2,2-trifluoro-N-(2-hydroxy-3-(3-(3-hydroxy-3-propylhex-1-ynyl)phenyl)propyl)acetamide following the procedure described in Example 1 gave Example 109 as a pale yellow oil. Yield (0.273 g, 82%): $^1$H NMR (400 MHz, DMSO-d$_6$) δ 7.24-7.20 (m, 2H), 7.17-7.13 (m, 2H), 5.11 (bs, 1H), 4.55 (bs, 1H), 3.51-3.46 (m, 1H), 2.67 (dd, J=13.6, 5.2 Hz, 1H), 2.50 (dd, J=13.6, 7.6 Hz, 1H), 2.45 (dd, obs., 1H), 2.37 (dd, J=12.8, 6.8 Hz, 1H), 1.61-1.40 (m, 8H), 0.89 (t, J=7.6 Hz, 6H).

Example 110

PREPARATION OF 1-((3-(3-AMINO-2-HYDROXYPROPYL)PHENYL)ETHYNYL)CYCLOHEXANOL

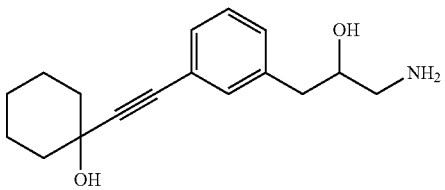 [SMILES: NCC(O)Cc1cccc(C#CC2(O)CCCCC2)c1]

1-((3-(3-Amino-2-hydroxypropyl)phenyl)ethynyl)cyclohexanol was prepared following the method used in Example 109.

Step 1: Coupling of bromide 77 with 1-ethynylcyclohexanol gave 2,2,2-trifluoro-N-(2-hydroxy-3-(3-((1-hydroxycyclohexyl)ethynyl)phenyl)propyl)acetamide as a clear oil. Yield (0.48 g, 65%): $^1$H NMR (400 MHz, DMSO-d$_6$) δ 9.32 (t, J=5.6 Hz, 1H), 7.26-7.22 (m, 2H), 7.20-7.16 (m, 2H), 5.37 (s, 1H), 4.97 (d, J=5.6 Hz, 1H), 3.82-3.75 (m, 1H), 3.21-3.07

(m, 2H), 2.66 (dd, J=14.0, 4.8 Hz, 1H), 2.55 (dd, J=13.6, 7.8 Hz, 1H), 1.83-1.79 (m, 2H), 1.63-1.60 (m, 2H), 1.54-1.44 (m, 5H), 1.23-1.18 (m, 1H).

Step 2: Deprotection of 2,2,2-trifluoro-N-(2-hydroxy-3-(3-((1-hydroxycyclohexyl)ethynyl)phenyl)propyl)acetamide gave Example 110 as a pale yellow solid. Yield (0.227 g, 65%): ¹H NMR (400 MHz, DMSO-d₆) δ 7.25-7.21 (m, 2H), 7.18-7.15 (m, 2H), 5.37 (bs, 1H), 4.59 (bs, 1H), 3.53-3.47 (m, 1H), 2.67 (dd, J=13.6, 5.2 Hz, 1H), 2.51 (dd, J=13.6, 7.6 Hz, 1H), 2.48 (obs m, 1H), 2.38 (dd, J=12.8, 6.8 Hz, 1H), 1.83-1.77 (m, 2H), 1.63-1.60 (m, 2H), 1.54-1.45 (m, 5H), 1.23-1.18 (m, 1H).

Example 111

PREPARATION OF 1-(3-(3-AMINO-2-HYDROXYPROPYL)PHENYL)-3-ETHYLPENT-1-YN-3-OL

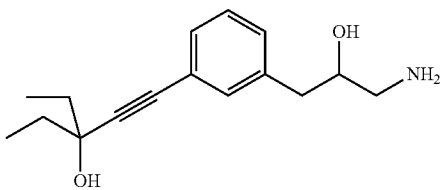 [SMILES: CCC(O)(C#Cc1cccc(CC(O)CN)c1)CC]

1-(3-(3-Amino-2-hydroxypropyl)phenyl)-3-ethylpent-1-yn-3-ol was prepared following the general method used in Example 109.

Step 1: Coupling of bromide 77 with 3-ethylpent-1-yn-3-ol gave N-(3-(3-(3-ethyl-3-hydroxypent-1-ynyl)phenyl)-2-hydroxypropyl)-2,2,2-trifluoroacetamide as a clear oil. Yield (0.472 g, 66%): ¹H NMR (400 MHz, DMSO-d₆) δ 9.32 (t, J=5.6 Hz, 1H), 7.26-7.22 (m, 2H), 7.20-7.16 (m, 2H), 5.11 (s, 1H), 4.96 (d, J=5.6 Hz, 1H), 3.80-3.74 (m, 1H), 3.21-3.07 (m, 2H), 2.68 (dd, J=14.0, 4.8 Hz, 1H), 2.53 (dd, J=13.6, 7.6 Hz, 1H), 1.66-1.52 (m, 4H), 0.96 (t, J=7.2 Hz, 6H).

Step 2: Deprotection of N-(3-(3-(3-ethyl-3-hydroxypent-1-ynyl)phenyl)-2-hydroxypropyl)-2,2,2-trifluoroacetamide gave Example 111 as a pale yellow oil. Yield (0.232 g, 69%): ¹H NMR (400 MHz, DMSO-d₆) δ 7.24-7.20 (m, 2H), 7.17-7.15 (m, 2H), 5.11 (bs, 1H), 4.55 (bs, 1H), 3.51-3.45 (m, 1H), 2.67 (dd, J=13.6, 5.2 Hz, 1H), 2.51 (dd, J=13.6, 7.6 Hz, 1H), 2.45 (obs dm, J=44 Hz, 1H), 2.37 (dd, J=12.8, 6.8 Hz, 1H), 1.66-1.52 (m, 4H), 0.96 (t, J=7.2 Hz, 6H).

Example 112

PREPARATION OF 1-((3-(3-AMINO-2-HYDROXYPROPYL)PHENYL)ETHYNYL)CYCLOPENTANOL

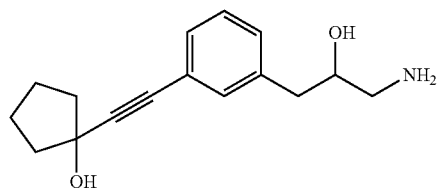 [SMILES: NCC(O)Cc1cccc(C#CC2(O)CCCC2)c1]

1-((3-(3-Amino-2-hydroxypropyl)phenyl)ethynyl)cyclopentanol was prepared following the general method used in Example 109.

Step 1: Coupling of bromide 77 with 1-ethynylcyclopentanol gave 2,2,2-trifluoro-N-(2-hydroxy-3-(3-((1-hydroxycyclopentyl)ethynyl)phenyl)propyl)acetamide as a clear oil. Yield (0.441 g, 62%): ¹H NMR (400 MHz, DMSO-d₆) δ 9.32 (t, J=5.6 Hz, 1H), 7.26-7.22 (m, 2H), 7.19-7.16 (m, 2H), 5.26 (bs, 1H), 4.97 (bs, 1H), 3.78 (bs, 1H), 3.20-3.06 (m, 2H), 2.67 (dd, J=14.0, 4.8 Hz, 1H), 2.53 (dd, J=13.6, 7.6 Hz, 1H), 1.91-1.79 (m, 4H), 1.76-1.60 (m, 4H).

Step 2: Deprotection of 2,2,2-trifluoro-N-(2-hydroxy-3-(3-((1-hydroxycyclopentyl)ethynyl)phenyl)propyl)acetamide gave Example 112 as a pale yellow solid. Yield (0.217 g, 69%): ¹H NMR (400 MHz, DMSO-d₆) δ 7.24-7.20 (m, 2H), 7.17-7.15 (m, 2H), 5.26 (bs, 1H), 4.55 (bs, 1H), 3.51-3.45 (m, 1H), 2.66 (dd, J=13.6, 5.2 Hz, 1H), 2.51 (dd, J=13.6, 8.0 Hz, 1H), 2.45 (obs dm, J=44 Hz, 1H), 2.36 (dd, J=12.8, 6.8 Hz, 1H), 1.91-1.80 (m, 4H), 1.76-1.60 (m, 4H).

Example 113

PREPARATION OF 2-(3-(CYCLOPROPYLETHYNYL)PHENOXY)ETHANAMINE

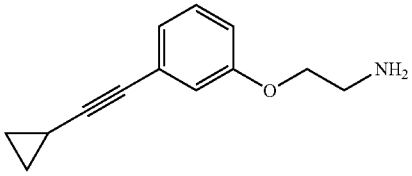 [SMILES: NCCOc1cccc(C#CC2CC2)c1]

2-(3-(Cyclopropylethynyl)phenoxy)ethanamine was prepared following the method used in Example 18.

Step 1: Sonogashira reaction of bromide 19 with cyclopropyl acetylene gave N-(2-(3-(2-cyclopropylethynyl)phenoxy)ethyl)-2,2,2-trifluoroacetamide as a clear oil. Yield (2.0 g, 71%): The crude material was directly utilized for further deprotection reaction.

Step 2: Deprotection of N-(2-(3-(2-cyclopropylethynyl)phenoxy)ethyl)-2,2,2-trifluoroacetamide gave Example 113 as pale yellow oil. Yield (0.350 g, 52%): ¹H NMR (400 MHz, DMSO-d₆) δ 7.19-7.24 (m, 1H), 6.87-6.93 (m, 3H), 3.90 (t, J=5.6 Hz, 2H), 2.86 (t, J=5.6 Hz, 2H), 1.49-1.56 (m, 1H), 0.85-0.90 (m, 2H), 0.72-0.77 (m, 2H): ¹³C NMR (100 MHz, DMSO-d₆) δ 158.4, 129.6, 124.2, 123.6, 116.7, 114.9, 93.6, 75.5, 69.9, 40.7, 8.3, −0.3. ESI MS m/z 202 [M+1]⁺.

Example 114

PREPARATION OF 5-(3-(2-AMINOETHOXY)PHENYL)PENT-4-YN-1-OL

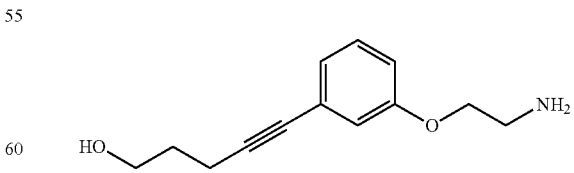

5-(3-(2-Aminoethoxy)phenyl)pent-4-yn-1-ol was prepared following the method used in Example 18.

Step 1: A mixture of bromide (19) (2.5 g, 8 mmol), pentyn-1-ol (1.34 g, 16 mmol) in triethylamine (6 mL, 60 mmol) and DMF (18 mL) was purged with nitrogen for 10 minutes. This was followed by the addition of PdCl$_2$(PPh$_3$)$_2$ (0.28 g, 0.4 mmol), P(o-Tol)$_3$ (0.122 g, 0.4 mmol) and CuI (0.076 g, 0.4 mmol) and the flask was purged once again with nitrogen and the resulting mixture was heated at 90° C. overnight. This was then poured into water, extracted with ethyl acetate. The organic layer was washed with water, dried over anhydrous Na$_2$SO$_4$, filtered and concentrated under reduced pressure. Purification by flash chromatography (0 to 30% EtOAc-hexanes gradient) gave 2,2,2-trifluoro-N-(2-(3-(5-hydroxypent-1-ynyl)phenoxy)ethyl)acetamide as yellow oil. Yield (1.61 g, 63%): $^1$H NMR (400 MHz, CDCl$_3$) δ 7.18-7.24 (m, 1H), 7.03 (d, J=7.6 Hz, 1H), 6.91 (dd, J=0.8, 1.2 Hz, 1H), 6.83 (dd, J=5.6, 2.0 Hz, 1H), 6.76 (bs, 1H), 4.06-4.10 (m, 2H), 3.76-3.84 (m, 4H), 2.53 (t, J=7.2 Hz, 2H), 1.82-1.90 (m, 2H).

Step 2: To the stirred solution of the alkyne (1.6 g, 5 mmol) in MeOH-water (25 mL: 5 mL) was added K$_2$CO$_3$ (3.5 g, 25 mmol) and the resulting mixture was stirred over night. The solvent was removed under reduced pressure. The residue was partitioned between EtOAc and water and the combined organics were washed with water and dried over Na$_2$SO$_4$. The filtered solution was concentrated under reduced pressure to give Example 114 as a yellow oil. Yield (0.360 g, 33%): $^1$H NMR (400 MHz, DMSO-d$_6$) δ 7.21-7.26 (m, 1H), 6.94 (s, 1H), 6.88-6.93 (m, 2H), 4.55 (bs, 2H), 3.90 (t, J=6.4 Hz, 2H), 3.50 (t, J=6.4 Hz, 2H), 2.84 (t, J=5.6 Hz, 2H), 2.44 (t, J=7.2 Hz, 2H), 1.63-1.71 (m, 2H). $^{13}$C NMR (100 MHz, DMSO-d$_6$) δ 159.0, 130.1, 124.8, 124.0, 117.1, 115.3, 90.8, 80.8, 70.7, 59.9, 41.3, 32.0, 15.7. ESI MS m/z 220 [M+1]$^+$.

Example 115

PREPARATION OF 5-(3-(3-AMINOPROPYL)PHENYL)PENT-4-YN-1-OL

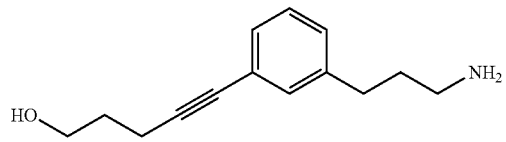 [SMILES: NCCCc1cccc(C#CCCCO)c1]

5-(3-(3-Aminopropyl)phenyl)pent-4-yn-1-ol was prepared following the method used in Example 127.

Step 1: Sonogashira coupling of bromide 87 (0.5 g, 1.5 mmol) with 4-pentyn-1-ol gave tert-butyl (3-(5-hydroxypent-1-ynyl)phenyl ethylcarbamate. (0.35 g, 69%): $^1$H NMR (400 MHz, CDCl$_3$) δ 7.17-7.24 (m, 3H), 7.07-7.11 (m, 1H), 3.83 (t, J=6.0 Hz, 2H), 3.13-3.15 (m, 2H), 2.50-2.61 (m, 4H), 2.05 (s, 1H), 1.77-1.89 (m, 4H), 1.44 (s, 9H).

Step 2: Deprotection of tert-butyl (3-(5-hydroxypent-1-ynyl)phenyl)ethyl carbamate with HCl/dioxane in THF gave Example 115 hydrochloride. Yield (0.14 g, 63%): $^1$H NMR (400 MHz, DMSO-d$_6$) δ 7.22-7.27 (m, 1H), 7.14-7.21 (m, 3H), 3.48 (t, J=6.0 Hz, 2H), 2.75 (t, J=7.6 Hz, 2H), 2.57 (t, J=7.6 Hz, 2H), 2.40 (t, J=6.8 Hz, 2H), 1.74-1.82 (m, 2H), 1.61-1.68 (m, 2H).

Example 116

PREPARATION OF 2-(3-(HEX-1-YNYL)PHENOXY)ETHANAMINE

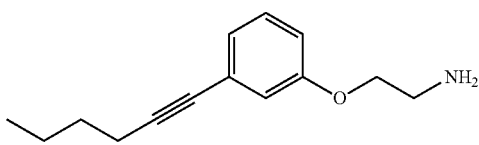 [SMILES: CCCCC#Cc1cccc(OCCN)c1]

2-(3-(Hex-1-ynyl)phenoxy)ethanamine was prepared following the method used in Example 18.

Step 1: Sonogashira reaction of bromide 19 with 1-hexyne gave 2,2,2-trifluoro-N-(2-(3-(hex-1-ynyl)phenoxy)ethyl)acetamide as a clear oil. Yield (1.8 g, 72%): $^1$H NMR (400 MHz, CDCl$_3$) δ 7.19-7.23 (m, 1H), 7.05 (d, J=7.6 Hz, 1H), 6.84 (s, 1H), 6.80 (dd, J=8.0, 2.4 Hz, 1H), 4.10 (t, J=5.2 Hz, 2H), 3.77-3.80 (m, 2H), 2.40 (t, J=7.2 Hz, 2H), 1.53-1.61 (m, 2H), 1.43-1.50 (m, 2H), 0.95 (t, J=7.2 Hz, 3H).

Step 2: Deprotection of 2,2,2-trifluoro-N-(2-(3-(hex-1-ynyl)phenoxy)-ethyl)acetamide gave Example 116 as yellow oil. Yield (0.620 g, 90%): $^1$H NMR (400 MHz, DMSO-d$_6$) δ 7.20-7.25 (m, 1H), 6.87-6.93 (m, 3H), 3.91 (t, J=5.2 Hz, 2H), 2.79-2.87 (m, 2H), 2.38 (t, J=6.4 Hz, 2H), 1.42-1.53 (m, 2H), 1.30-1.40 (m, 2H), 0.88 (t, J=7.2 Hz, 3H). $^{13}$C NMR (100 MHz, DMSO-d$_6$) δ 158.9, 130.1, 124.8, 124.1, 117.2, 115.3, 90.9, 80.9, 70.3, 41.1, 30.7, 21.9, 18.7, 13.9. ESI MS m/z 218 [M+1]$^+$.

Example 117

PREPARATION OF 2-(3-(3-METHOXYPROP-1-YNYL)PHENOXY)ETHANAMINE

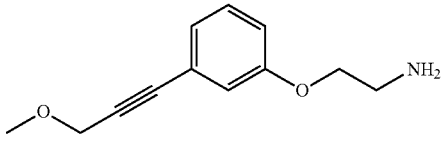

2-(3-(3-Methoxyprop-1-ynyl)phenoxy)ethanamine was prepared following the method used in Example 18.

Step 1: Sonogashira reaction of bromide 19 with 3-methoxy-propyne gave 2,2,2-trifluoro-N-(2-(3-(3-methoxyprop-1-ynyl)phenoxy)ethyl)acetamide as a clear oil. Yield (0.51 g, 21%): $^1$H NMR (400 MHz, CDCl$_3$) δ 7.22-7.27 (m, 1H), 7.10 (d, J=7.6 Hz, 1H), 6.98 (s, 1H), 6.88 (dd, J=6.8, 1.6 Hz, 1H), 6.71 (bs, 1H), 4.32 (s, 2H), 4.10 (t, J=5.2 Hz, 2H), 3.77-3.82 (m, 2H), 3.45 (s, 3H).

Step 2: Deprotection of 2,2,2-trifluoro-N-(2-(3-(3-methoxyprop-1-ynyl)phenoxy)ethyl)acetamide gave Example 117 as an off white oil. Yield (0.160 g, 47%): $^1$H NMR (400 MHz, DMSO-d$_6$) δ 7.27-7.32 (m, 1H), 6.96-7.05 (m, 3H), 4.32 (s, 2H), 3.97 (t, J=5.6 Hz, 2H), 3.33 (s, 3H), 2.92 (t, J=5.6 Hz, 2H). $^{13}$C NMR (100 MHz, DMSO-d$_6$) δ 158.9, 130.4, 124.3, 123.7, 123.4, 117.3, 116.2, 86.2, 86.1, 69.6, 59.9, 57.5, 40.8. ESI MS m/z 206 [M+1]$_+$.

Example 118

PREPARATION OF 3-(3-(3-AMINO-1-HYDROXYPROPYL)PHENYL)PROP-2-YN-1-OL

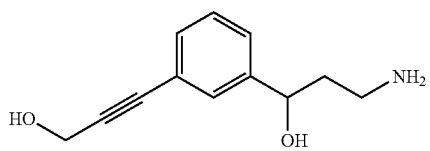 [SMILES: NCCC(O)c1cccc(C#CCO)c1]

3-(3-(3-Amino-1-hydroxypropyl)phenyl)prop-2-yn-1-ol was prepared following the method used in Example 108.

Step 1: Sonogashira reaction of 25 with propargyl alcohol resulted in 2,2,2-trifluoro-N-(3-hydroxy-3-(3-(3-hydroxyprop-1-ynyl)phenyl)propyl)acetamide as dark yellow oil. Yield (0.37 g, 80%): $^1$H NMR (400 MHz, CDCl$_3$) δ 7.44 (s, 1H), 7.30-7.37 (m, 3H), 4.87 (m, 1H), 4.50 (d, J=5.6 Hz, 2H), 3.66-3.69 (m, 1H), 3.40-3.43 (m, 1H), 2.45 (bs, 1H) 1.93-2.04 (m, 2H).

Step 2: Deprotection of 2,2,2-trifluoro-N-(3-hydroxy-3-(3-(3-hydroxyprop-1-ynyl)phenyl)propyl)acetamide (0.48 g, 1.59 mmol) gave Example 118 as a pale yellow semi-solid hydrochloride. Yield (0.14 g, 42%): $^1$H NMR (400 MHz, DMSO-d$_6$) δ 8.17 (bs, 3H), 7.29-7.35 (m, 4H), 5.5.59-5.65 (bs, 1H), 5.39 (t, J=6.0 Hz, 1H), 4.30 (d, J=5.6 Hz, 2H), 2.83 (m, 2H), 1.89 (m, 2H). $^{13}$C NMR (100 MHz, DMSO-d$_6$) δ 145.9, 130.2, 129.8, 128.7, 126.1, 122.5, 89.9, 84.0, 69.5, 49.6, 36.5, 36.4. Mass: 206 [M+1]$^+$.

Example 119

PREPARATION OF 3-AMINO-1-(3-(4-METHYLPENT-1-YNYL)PHENYL)PROPAN-1-OL

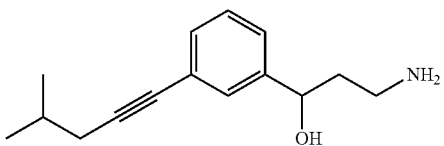 [SMILES: CC(C)CC#Cc1cccc(C(O)CCN)c1]

3-Amino-1-(3-(4-methylpent-1-ynyl)phenyl)propan-1-ol ol was prepared following the method used in Example 132.

Step 1: Sonogashira reaction of 25 with 4-methyl-pent-1-yne yielded 2,2,2-trifluoro-N-(3-hydroxy-3-(3-(4-methylpent-1-ynyl)phenyl)propyl)acetamide as dark brown oil. Yield (0.94 g, 94%): $^1$H NMR (400 MHz, CDCl$_3$) δ 7.38 (s, 1H), 7.25-7.35 (m, 3H), 4.86 (m, 1H), 3.67-3.72 (m, 1H), 3.38-3.44 (m, 1H), 2.30 (d, J=6.4 Hz, 2H), 2.28 (bs, 1H), 1.87-1.99 (m, 3H), 1.05 (d, J=6.8 Hz, 6H).

Step 2: Deprotection of 2,2,2-trifluoro-N-(3-hydroxy-3-(3-(4-methylpent-1-ynyl)phenyl)propyl)acetamide gave Example 119 as yellow oil. Yield (0.508 g, 76%): $^1$H NMR (400 MHz, DMSO-d$_6$) δ 7.33 (s, 1H), 7.23-7.29 (m, 3H), 5.12 (bs, 2H), 4.66 (t, J=6.4 Hz, 1H), 2.68 (t, J=6.8 Hz, 2H), 2.32 (d, J=6.4 Hz, 2H), 1.82-1.86 (m, 1H), 1.67-1.72 (m, 2H), 0.95 (d, J=6.8 Hz, 6H). $^{13}$C NMR (100 MHz, DMSO-d$_6$) δ 146.8, 130.0, 128.9, 128.8, 125.7, 123.4, 89.6, 82.1, 70.7, 40.6, 38.3, 28.1, 28.0, 22.3. ESI MS m/z 232 [M+1]$_+$.

Example 120

PREPARATION OF 1-(3-(2-AMINOETHOXY)PHENYL)HEX-1-YN-3-OL

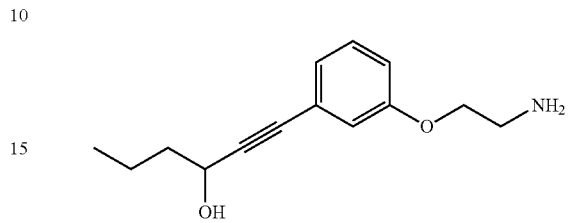

1-(3-(2-Aminoethoxy)phenyl)hex-1-yn-3-ol was prepared following the method used in Example 18.

Step 1: Sonogashira reaction of bromide 19 with 4-methyl-pent-1-yn-3-ol gave 2,2,2-trifluoro-N-(2-(3-(3-hydroxyhex-1-ynyl)phenoxy)ethyl)acetamide as a clear oil. Yield (3 g, crude): The crude material was directly utilized for further deprotection reaction.

Step 2: Deprotection of 2,2,2-trifluoro-N-(2-(3-(3-hydroxyhex-1-ynyl)phenoxy)ethyl)acetamide gave Example 120 as a yellow oil. Yield (1.858 g, 88%): $^1$H NMR (400 MHz, DMSO-d$_6$) δ 7.23-7.29 (m, 1H), 6.90-6.98 (m, 3H), 4.42 (t, J=6.4 Hz, 2H), 3.92 (t, J=4.8 Hz, 2H), 2.86 (bs, 2H), 1.56-1.68 (m, 2H), 1.40-1.49 (m, 2H), 0.91 (t, J=7.6 Hz, 3H). $^{13}$C NMR (100 MHz, DMSO-d$_6$) δ 159.0, 130.3, 124.0, 117.1, 115.8, 92.8, 833, 70.4, 61.0, 41.2, 40.1, 18.6, 14.2. ESI MS m/z 234 [M+1]$^+$.

Example 121

PREPARATION OF 3-AMINO-1-(3-(4-METHOXYBUT-1-YNYL)PHENYL)PROPAN-1-OL

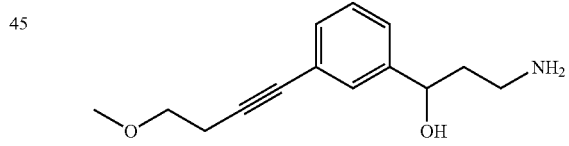

3-Amino-1-(3-(4-methoxybut-1-ynyl)phenyl)propan-1-ol was prepared following the method used in Example 132.

Step 1: Sonogashira reaction of 25 with 4-methoxy-but-1-yne yielded 2,2,2-trifluoro-N-(3-hydroxy-3-(3-(4-methoxybut-1-ynyl)phenyl)propyl)acetamide as a dark yellow oil. Yield (0.51 g, 51%). Compound could not be purified completely and was forwarded as such into the next step.

Step 2: Deprotection of 2,2,2-trifluoro-N-(3-hydroxy-3-(3-(4-methoxybut-1-ynyl)phenyl)propyl)acetamide following the method used in Example 132 except that the reaction mixture was stirred at room temperature for 16 h. Example 121 was obtained as a yellow oil. Yield (0.22 g, 60%): $^1$H NMR (400 MHz, DMSO-d$_6$) δ 7.33 (s, 1H), 7.28-7.29 (m, 2H), 7.21-7.24 (m, 1H), 4.66 (t, J=6.4 Hz, 1H), 3.50 (t, J=6.4 Hz, 2H), 3.28 (s, 3H), 2.63-2.69 (m, 4H) 1.65-1.77 (m, 2H). $^{13}$C NMR (100 MHz, DMSO-d$_6$) δ 146.5, 129.4, 128.5, 128.2, 125.4, 122.6, 87.7, 81.1, 70.4, 70.1, 57.8, 40.6, 40.1, 19.8. ESI MS m/z 234 [M+1]$_+$.

Example 122

PREPARATION OF 1-(3-(2-AMINOETHOXY)PHENYL)-3-METHYLHEX-1-YN-3-OL

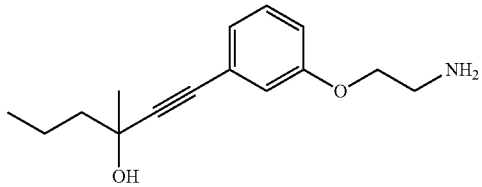 [SMILES: CCCC(C)(O)C#Cc1cccc(OCCN)c1]

1-(3-(2-Aminoethoxy)phenyl)-3-methylhex-1-yn-3-ol was prepared following the method used in Example 18.

Step 1: Sonogashira reaction of bromide 19 with but-3-ynyl-benzene gave 2,2,2-trifluoro-N-(2-(3-(3-hydroxy-3-methylhex-1-ynyl)phenoxy)ethyl)acetamide as a clear oil. Yield (2.0 g, 71%): The crude material was directly utilized for further deprotection reaction.

Step 2: Deprotection of 2,2,2-trifluoro-N-(2-(3-(3-hydroxy-3-methylhex-1-ynyl)phenoxy)ethyl)acetamide gave Example 122 as pale yellow oil. Yield (0.700 g, 35%): $^1$H NMR (400 MHz, DMSO-d$_6$) δ 7.23-7.28 (m, 1H), 6.91-6.95 (m, 2H), 6.87-6.89 (m, 1H), 5.34 (s, 1H), 3.91 (t, J=6.0 Hz, 2H), 2.85 (t, J=5.6 Hz, 2H), 1.45-1.70 (m, 5H), 1.41 (s, 3H), 0.89-0.94 (m, 3H). $^{13}$C NMR (100 MHz, DMSO-d$_6$) δ 158.6, 129.8, 123.7, 123.6, 116.6, 115.2, 81.4, 70.3, 66.6, 45.9, 40.9, 29.9, 17.7, 14.3. ESI MS m/z 248 [M+1]$^+$.

Example 123

PREPARATION OF (S)-1-((3-(1-AMINOPROPAN-2-YLOXY)PHENYL)ETHYNYL)CYCLOHEXANOL

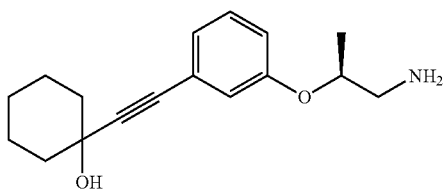 [SMILES: C[C@@H](CN)Oc1cccc(C#CC2(O)CCCCC2)c1]

(S)-1-(3-(1-Aminopropan-2-yloxy)phenyl)ethynyl)cyclohexanol was prepared following the method shown in Scheme 20.

SCHEME 20

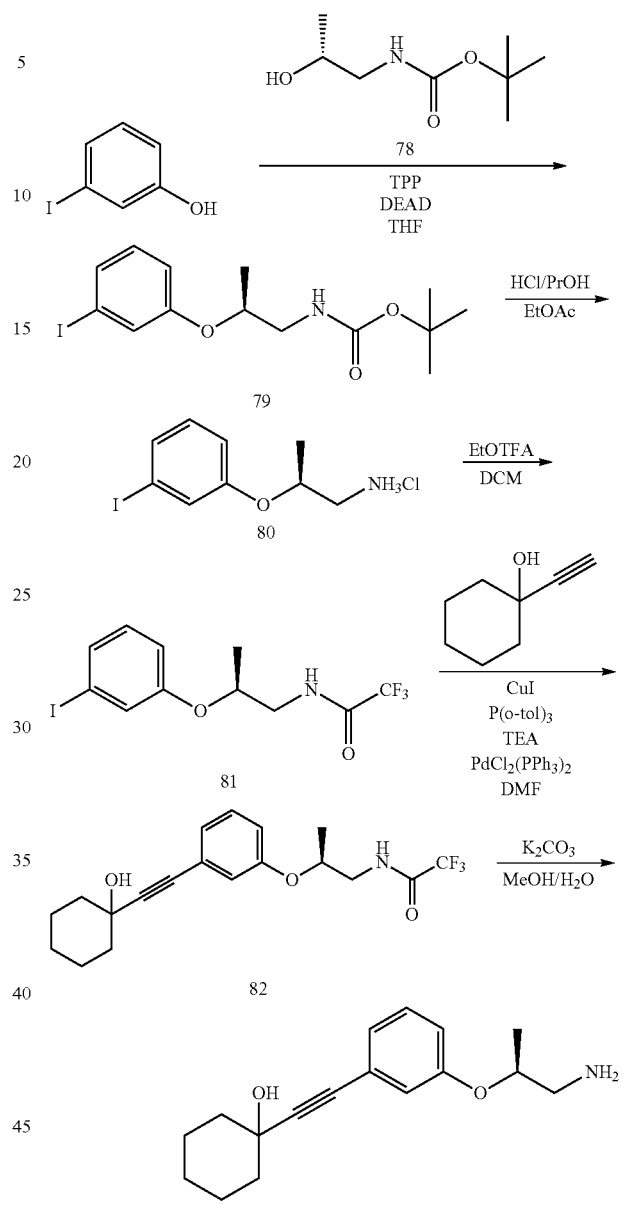

Step 1: Diethylazodicarboxylate (17.4 g, 100 mmol) was added slowly to a solution of 3-iodophenol (18.5 g, 84 mmol), alcohol (78) 14.73 g, 84 mmol), and triphenyl phosphine (26.2 g, 100 mmol) in THF (200 mL) at 0° C. under argon. The reaction was allowed to warm and stirred at room temperature for 2 hours, heated to 80° C. for 6 hours, then concentrated under reduced pressure. The residue was triturated with diethyl ether and the resulting white solids removed by filtration. The filtrate was concentrated under reduce pressure and the residue partitioned in ethyl acetate and 1 N NaOH. The organics were combined, washed with brine, and concentrated under reduced pressure. The residue was purified by flash chromatography (5-20% ethyl acetate/hexanes gradient) on silica gel, giving the carbamate (79) as an impure yellow oil which was carried on to the next step without further purification. Yield (17.3 g, 54%).

Step 2: HCl (12 mL of a 4.8 M solution in iPrOH, 56 mmol) was added to a solution of carbamate (79) (10 g, 28 mmol) in ethyl acetate (25 mL). After stirring 1 h, the reaction mixture was filtered and the solids dried under reduced pressure, giving the hydrochloride salt (80) as a white solid which was carried on to the next step without purification or analysis. Yield (2.9 g, 30%).

Step 3: Protection of amine hydrochloride (80) with ethyltrifluoroacetate according the method used in Example 18, except that 1 equivalent of TEA was used and the reaction was carried out in dichloromethane, gave trifluoroamide (81) as a yellow oil. Yield (3.4 g, quantitative). $^1$H NMR (400 MHz, CDCl$_3$) δ 7.29-7.33 (m, 1H), 7.24-7.26 (m, 1H), 6.99 (t, J=8.0 Hz, 1H), 6.83-6.87 (m, 1H), 6.75 (brs, 1H), 4.45-4.55 (m, 1H), 3.52-3.53 (m, 1H), 3.40-3.50 (m, 1H), 1.29 (d, J=6.4 Hz, 3H).

Step 4: A mixture of trifluoroamide 81 (500 mg, 1.34 mmol), 1-ethynylcyclohexanol (250 mg, 2.01 mmol), copper iodide (25 mg, 0.13 mmol), tri-o-tolylphosphine (40 mg, 0.13 mmol), TEA (0.279 mL, 2.01 mL), and bis-chloro-triphenylphosphine palladium (91 mg, 0.13 mmol) in DMF (13 mL) was degassed, placed under argon atmosphere, and stirred overnight at 90° C. The reaction mixture was filtered and the filtrate partitioned in EtOAc/water. The organic layers were combined and washed with brine, dried over sodium sulfate, filtered, and concentrated under reduced pressure. The residue was purified by flash chromatography (10-30% EtOAc/hexanes gradient) giving alkyne 82 as a yellow glassy oil. Yield (0.322 g, 65%). %). $^1$H NMR (400 MHz, CDCl$_3$) δ 7.21 (t, J=8.0 Hz, 1H), 7.04-7.08 (m, 1H), 6.94-6.96 (m, 1H), 6.83-6.87 (m, 1H), 6.81 (brs, 1H), 4.48-4.57 (m, 1H), 3.72-3.80 (m, 1H), 3.39-3.49 (m, 1H), 1.85-2.04 (m, 3H), 1.50-1.80 (m, 8H), 1.29 (d, J=6.4 Hz, 3H).

Step 5: Deprotection of alkyne 82 according to the method used in Example 1 gave Example 123 as a yellow oil. Yield (0.200 g, 85%). $^1$H NMR (400 MHz, CDCl$_3$) δ 7.18 (t, J=8.0 Hz, 1H), 6.96-7.02 (m, 2H), 6.84-6.88 (m, 1H), 4.30-4.38 (m, 1H), 2.87 (d, J=5.2 Hz, 2H), 1.85-2.02 (m, 2H), 1.50-1.80 (m, 11H), 1.25 (d, J=6.4 Hz, 3H). ESI MS m/z 274.3 [m+H]$^+$.

Example 124

PREPARATION OF 1-(3-(2-AMINOETHOXY) PHENYL)-4-METHYLPENT-1-YN-3-OL

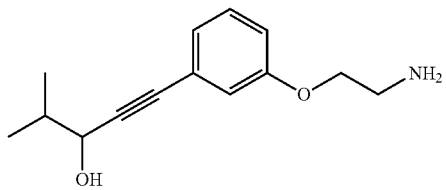 [SMILES: CC(C)C(O)C#Cc1cccc(OCCN)c1]

1-(3-(2-Aminoethoxy)phenyl)-4-methylpent-1-yn-3-ol was prepared following the method used in Example 18.

Step 1: Sonogashira reaction of bromide 19 with 4-methylpent-1-yn-3-ol gave 2,2,2-trifluoro-N-(2-(3-(3-hydroxy-4-methylpent-1-ynyl)phenoxy)ethyl)acetamide as yellow oil. Yield (0.51 g, 21%): $^1$H NMR (400 MHz, CDCl$_3$) δ 7.22-7.27 (m, 1H), 7.08-7.12 (d, J=7.6 Hz, 1H), 6.98 (s, 1H), 6.88 (dd, 1H, J=6.8 Hz, 1.6, 1H), 6.71 (bs, 1H), 4.32 (s, 2H), 4.09 (t, J=5.2 Hz, 2H), 3.77-3.82 (m, 2H), 1.77-1.83 (m, 1H), 0.94-0.99 (m, 6H).

Step 2: Deprotection of 2,2,2-trifluoro-N-(2-(3-(3-hydroxy-4-methylpent-1-ynyl)phenoxy)ethyl)acetamide gave Example 124 as yellow oil. Yield (0.160 g, 47%): $^1$H NMR (400 MHz, DMSO-d$_6$) δ 7.22-7.30 (m, 1H), 6.90-7.00 (m, 3H), 4.21 (d, J=5.6 Hz, 1H), 3.93 (t, J=5.2 Hz, 2H), 2.87 (bs, 2H), 1.77-1.83 (m, 1H), 0.94-0.99 (m, 6H). $^{13}$C NMR (100 MHz, DMSO-d$_6$) δ 158.5, 129.8, 123.7, 116.7, 115.2, 91.0, 83.6, 69.9, 66.3, 40.7, 34.3, 18.3, 17.7. ESI MS m/z 234 [M+1]$^+$.

Example 125

PREPARATION OF 3-AMINO-1-(3-(PHENYLETHYNYL) PHENYL)PROPAN-1-OL

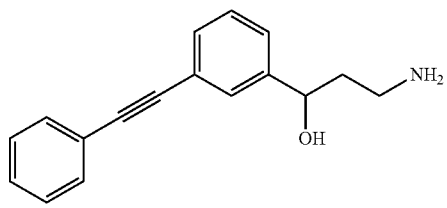 [SMILES: NCCC(O)c1cccc(C#Cc2ccccc2)c1]

3-Amino-1-(3-(phenylethynyl)phenyl)propan-1-ol was prepared following the method used in Example 121.

Step 4: Sonogashira reaction of 25 with ethynyl-benzene yielded 2,2,2-trifluoro-N-(3-hydroxy-3-(3-(2-phenylethynyl)phenyl)propyl)acetamide as yellow oil. Yield (0.78 g, 73%).

Step 5: Deprotection of 2,2,2-trifluoro-N-(3-hydroxy-3-(3-(2-phenylethynyl)phenyl)propyl)acetamide gave Example 125 as white semi-solid. Yield (0.3 g, 53%): $^1$H NMR (400 MHz, DMSO-d$_6$) δ 7.51-7.53 (m, 2H), 7.48 (s, 1H), 7.34-7.42 (m, 6H), 5.52 (bs, 2H), 4.66 (t, J=6.4 Hz, 1H), 2.70 (t, J=7.2 Hz, 2H), 1.76 (t, J=7.2 Hz, 2H). $^{13}$C NMR (100 MHz, DMSO-d$_6$) δ 146.9, 131.8, 130.2, 129.3, 129.0, 126.6, 122.7, 122.4, 89.9, 89.5, 70.5, 40.6, 38.0. ESI MS m/z 252 [M+1]$^+$.

Example 126

PREPARATION OF 5-(3-(3-AMINO-1-HYDROXYPROPYL)PHENYL)-N,N-DIMETHYLPENT-4-YNAMIDE

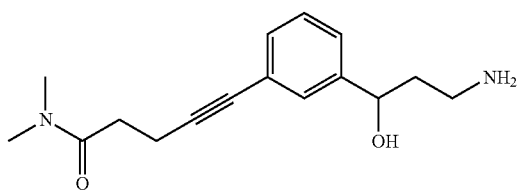 [SMILES: CN(C)C(=O)CCC#Cc1cccc(C(O)CCN)c1]

5-(3-(3-Amino-1-hydroxypropyl)phenyl)-N,N-dimethylpent-4-ynamide was prepared following the method used in Example 121.

Step 1: Sonogashira reaction of 4 with pent-4-ynoic acid dimethylamide yielded 5-(3-(1-hydroxy-3-(2,2,2-trifluoroacetamido)propyl)phenyl)-N,N-dimethylpent-4-ynamide as dark yellow oil. Yield (0.33 g, 48%). This compound had some traces of the starting material and was used without further purification.

Step 2: Deprotection of 5-(3-(1-hydroxy-3-(2,2,2-trifluoroacetamido)-propyl)phenyl)-N,N-dimethylpent-4-ynamide gave example 126 as pale yellow oil. Yield (0.147 g, 60%): $^1$H NMR (400 MHz, DMSO-d$_6$) δ 7.64 (bs, 2H), 7.34 (s, 1H), 7.24-7.32 (m, 3H), 5.59 (bs, 1H), 4.66 (t, J=5.2 Hz, 1H), 2.97 (s, 3H), 2.83 (s, 3H), 2.80 (m, 2H), 2.60 (s, 4H), 1.75-1.88 (m, 2H). $^{13}$C NMR (100 MHz, DMSO-d$_6$) δ 170.2, 145.6, 129.7, 128.5, 125.2, 123.0, 90.2, 80.3, 69.3, 40.1, 36.4, 36.3, 34.9, 31.7, 14.8. ESI MS m/z 275 [M+1]$^+$.

Example 127

PREPARATION OF 3-(3-(CYCLOPROPYLETHYNYL)PHENYL)PROPAN-1-AMINE

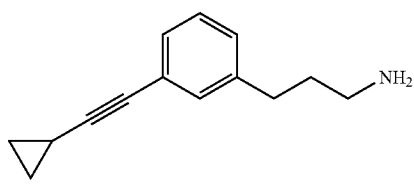

3-(3-(Cyclopropylethynyl)phenyl)propan-1-amine was prepared following the method shown in Scheme 21.

SCHEME 21

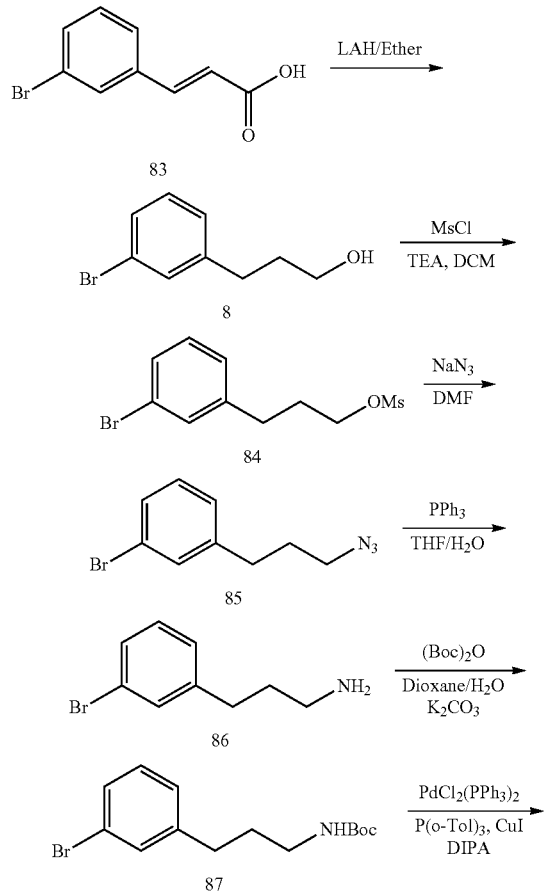

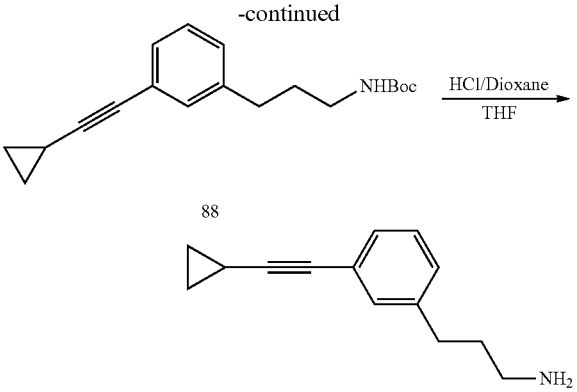

Step 1: To suspension of LiAlH$_4$ (0.5 g, 1.3 mmol) in diethyl ether (25 mL) was added 3-bromocinnamic acid (83, 1.0 g, 4 mmol), in portions, at RT. The resulting suspension was stirred for 3 hours. The reaction was quenched by the successive addition of 15% aq. NaOH solution (1 mL) and water. The resulting white suspension was filtered through a pad of Celite. The filter cake was washed with ether and then ethyl acetate. The filtrate was concentrated to afford crude 8 as yellow oil. Yield (0.7 g, 74%). $^1$H NMR (400 MHz, CDCl$_3$) δ 7.10-7.35 (m, 4H), 3.65 (t, J=6.5 Hz, 2H), 2.68 (t, J=7.8 Hz, 2H), 1.82-1.91 (m, 2H).

Step 2: To a stirred solution of alcohol 8 (1.0 g, 4.6 mmol) and triethylamine (1.0 mL, 99 mmol) in DCM (15 mL) was added MsCl (0.7 mL, 66 mmol) over a period of 5 min at 0° C. The resulting mixture was stirred at 0° C. for 30 min, brought up to room temp and stirred for 30 min during which the conversion was complete. The mixture poured into water and extracted with ethyl acetate. The combined organic layer was washed with water and brine, and dried over anhydrous Na$_2$SO$_4$. This was filtered and concentrated to afford the mesylate 84 as a yellow oil (1.0 g, 73%). This crude product was utilized immediately for the next transformation.

Step 3: To a solution of crude mesylate 84 (1.0 g, 3.4 mmol) in DMF (8 mL) was added NaN$_3$ (0.44 g, 6.8 mmol). The resulting mixture was stirred at 80° C. for 1 h. This was cooled, poured into water and extracted with ethyl acetate. The combined organics were washed with water and brine, dried over anhydrous Na$_2$SO$_4$. Filtration, followed by concentration under reduced pressure afforded 85 as a colorless oil. Yield (0.7 g, 85%). $^1$H NMR (400 MHz, CDCl$_3$) δ 7.32-7.38 (m, 2H), 7.09-7.20 (m, 2H), 3.29 (t, J=6.4 Hz, 2H), 2.68 (t, J=7.2 Hz, 2H), 1.84-1.94 (m, 2H).

Step 4: To a solution of azide 85 (15 g, 62.7 mmol) in a mixture of THF (133 mL) and water (13 mL) was added Ph$_3$P (16 g, 62.7 mmol) at room temperature. The mixture was stirred for 48 hr during which the conversion was found to be complete. The solvent was removed under reduced pressure and the resulting residue was carried forward to the next step.

Step 5: The amine 86 was dissolved in 1,4-dioxane (300 mL) and water (180 mL). K$_2$CO$_3$ (17.2 g, 120 mmol), (Boc)$_2$O (14 mL, 60 mmol) were successively added and the mixture was stirred for 2 hour. After removal of 1,4-dioxane under reduced pressure, the aqueous phase was extracted with ethyl acetate. The organic phase was washed with water and brine, dried over anhydrous Na$_2$SO$_4$. This was concentrated to afford crude yellow oil. Purification by flash chromatography (0-9% ethyl acetate:Hexane gradient) gave a 87 as pale yellow oil. Yield (15 g, 79%). $^1$H NMR (400 MHz, CDCl$_3$) δ 7.30-7.35 (m, 2H), 7.09-7.2 (m, 2H), 4.53 (bs, 1H), 3.14 (m, 2H), 2.61 (t, J=7.6 Hz, 2H), 1.74-1.84 (m, 2H), 1.45 (s, 9H).

Step 6: To a degassed solution of bromide 87 (1.0 g, 3.1 mmol) and cyclopropyl acetylene (2.9 mL, 3.4 mmol, 70% soln in toluene) in diisopropylamine (4 mL) was added PdCl$_2$(PPh$_3$)$_2$ (0.120 g, 0.17 mmol), tri-o-tolylphosphine (0.048 g, 0.16 mmol) and CuI (0.026 g, 0.16 mmol). The resulting mixture was degassed and stirred under nitrogen at 90° C. for overnight. The mixture was cooled to room temperature and concentrated under reduced pressure. The residue was partitioned between water and ethyl acetate. The organic layer was dried over anhydrous Na$_2$SO$_4$, filtered, and concentrated under reduced pressure. Purification by flash chromatography (10-40% ethyl acetate-hexane gradient) gave tert-butyl-[3-(3-cyclopropylethynyl-phenyl)-propyl carbamate (88). Yield (0.756 g, 79%). This alkyne was used for deprotection without further purification.

Step 7: Alkyne 88 was dissolved in THF (4.0 mL) and HCl in dioxane (5 mL, 4M) was added. The mixture was stirred at room temperature for 18 h. Concentration under reduced pressure followed by triturated with hexane gave Example 127 hydrochloride as a yellow semi-solid. Yield (0.2 g, 85%): $^1$H NMR (400 MHz, DMSO-d$_6$) δ 7.22-7.27 (m, 1H), 7.13-7.19 (m, 3H), 2.74 (t, J=7.2 Hz, 2H), 2.55 (t, J=7.6 Hz, 2H), 1.74-1.82 (m, 2H), 1.44-1.51 (m, 1H), 0.84-0.89 (m, 2H), 0.64-0.68 (m, 2H) $^{13}$C NMR (100 MHz, DMSO-d$_6$): 141.2, 131.1, 128.9, 127.9, 123.2, 93.6, 75.6, 8.1, 31.4, 28.4, 8.3, −0.3. ESI MS m/z 200 [M+1]$^+$ Example 128

PREPARATION OF 2-(3-(4-METHOXYBUT-1-YNYL)PHENOXY) ETHANAMINE

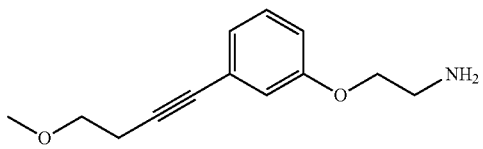 [SMILES: COCCC#Cc1cccc(OCCN)c1]

2-(3-(4-Methoxybut-1-ynyl)phenoxy)ethanamine was prepared following the method used in Example 18.

Step 1: Sonogashira reaction of bromide 19 with 4-methoxybut-1-yne gave 2,2,2-trifluoro-N-(2-(3-(4-methoxybut-1-ynyl)phenoxy)ethyl)acetamide as yellow oil. Yield (0.45 g, 45%): This material was directly utilized for the deprotection reaction.

Step 2: Deprotection of 2,2,2-trifluoro-N-(2-(3-(4-methoxybut-1-ynyl)phenoxy)ethyl)acetamide gave Example 128 as a yellow oil. Yield (0.120 g, 50%): $^1$H NMR (400 MHz, DMSO-d$_6$) δ 7.21-7.26 (m, 1H), 6.89-6.96 (m, 3H), 3.90 (t, J=5.6 Hz, 2H), 3.49 (t, J=6.4 Hz, 2H), 3.29 (s, 3H), 2.84 (t, J=5.6 Hz, 2H), 2.65 (t, J=6.4 Hz, 2H). $^{13}$C NMR (100 MHz, DMSO-d$_6$) δ 158.6, 129.7, 124.1, 123.6, 116.7, 115.0, 87.9, 80.9, 70.3, 70.0, 57.9, 40.9, 19.9. ESI MS m/z 220 [M+1]$^+$.

Example 129

PREPARATION OF 1-(2-(3-(2-AMINOETHOXY)PHENYL) ETHYNYL)CYCLOOCTANOL

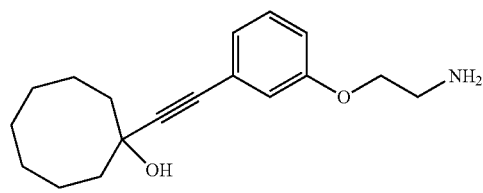 [SMILES: NCCOc1cccc(C#CC2(O)CCCCCCC2)c1]

1-(2-(3-(2-aminoethoxy)phenyl)ethynyl)cyclooctanol was prepared following the method used in Example 18.

Step 1: Sonogashira reaction of bromide 19 with 1-ethynyl-cyclooctanol gave 2,2,2-trifluoro-N-(2-(3-(2-(1-hydroxycyclooctyl)ethynyl)phenoxy)ethyl)acetamide as a clear oil. Yield (1.3 g, 72%): $^1$H NMR (400 MHz, DMSO-d$_6$) δ 7.22 (d, J=8.0 Hz, 1H), 7.07 (d, J=7.6 Hz, 1H), 6.91-6.96 (m, 2H), 4.09-4.13 (m, 2H), 2.00-2.06 (m, 6H), 1.48-1.72 (m, 11H).

Step 2: Deprotection of 2,2,2-trifluoro-N-(2-(3-(2-(1-hydroxycyclooctyl)-ethynyl)phenoxy)ethyl)acetamide gave Example 129 as a yellow oil. Yield (1.858 g, 88%): $^1$H NMR (400 MHz, DMSO-d$_6$) δ 7.24-7.29 (m, 1H), 6.91-6.96 (m, 2H), 6.89 (s, 1H), 3.94 (t, J=5.6 Hz, 2H), 2.88 (t, J=5.6 Hz, 2H), 1.80-1.92 (m, 5H), 1.50-1.60 (m, 7H), 1.42-1.44 (m, 3H). $^{13}$C NMR (100 MHz, DMSO-d$_6$) δ 158.5, 129.8, 123.8, 123.6, 116.7, 115.1, 95.7, 81.6, 69.7, 40.6, 37.7, 27.6, 24.1, 21.7. ESI MS m/z 234 [M+1]$_+$.

Example 130

PREPARATION OF 5-(3-(3-AMINO-1-HYDROXYPROPYL)PHENYL)PENT-4-YN-1-OL

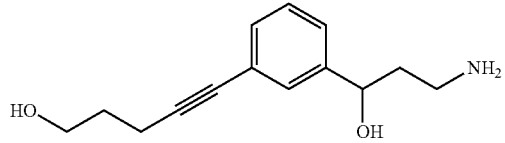 [SMILES: NCCC(O)c1cccc(C#CCCCO)c1]

5-(3-(3-Amino-1-hydroxypropyl)phenyl)pent-4-yn-1-ol was prepared following the method used in Example 132.

Step 1: Sonogashira reaction of 25 with pent-4-yn-1-ol gave 2,2,2-trifluoro-N-(3-hydroxy-3-(3-(5-hydroxypent-1-ynyl)phenyl)propyl)acetamide as brown oil. Yield (1.46 g, 69%): $^1$H NMR (400 MHz, CDCl$_3$) δ 7.38 (s, 1H), 7.22-7.34 (m, 3H), 4.86 (d, J=8.0 Hz, 1H), 3.83 (t, J=5.2 Hz, 2H), 3.65-3.69 (m, 1H), 3.38-3.42 (m, 1H), 2.56 (t, J=7.2 Hz, 2H), 2.38 (bs, 1H) 1.93-1.99 (m, 2H), 1.83-1.88 (m, 2H).

Step 2: Deprotection of 2,2,2-trifluoro-N-(3-hydroxy-3-(3-(5-hydroxypent-1-ynyl)phenyl)propyl)acetamide gave example 130 as yellow oil. Yield (0.64 g, 65%): $^1$H NMR (400 MHz, DMSO-d$_6$) δ 7.32 (s, 1H), 7.25-7.28 (m, 2H), 7.20-7.22 (m, 1H) 4.66 (t, J=6.4 Hz, 1H), 4.55 (bs, 1H), 3.52 (t, J=6.4 Hz, 2H), 2.57-2.66 (m, 2H), 2.44 (t, J=7.2 Hz, 2H), 1.60-1.70 (m, 4H). $^{13}$C NMR (100 MHz, DMSO-d$_6$) δ 147.2, 129.8, 129.0, 128.7, 125.7, 123.3, 90.6, 81.1, 71.1, 59.9, 41.8, 38.9, 32.0, 15.7. ESI MS m/z 234 [M+1]+.

Example 131

PREPARATION OF 3-AMINO-1-(3-(CYCLOPROPYLETHYNYL)PHENYL)PROPAN-1-OL

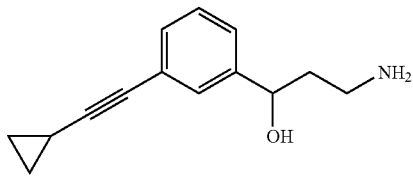 [SMILES: NCCC(O)c1cccc(C#CC2CC2)c1]

3-Amino-1-(3-(2-cyclopropylethynyl)phenyl)propan-1-ol was prepared following the method used in Example 132 except that the deprotection was carried out at RT for 16 h.

Step 1: Sonogashira reaction of 25 with ethynylcyclopropane yielded N-(3-(3-(2-cyclopropylethynyl)phenyl)-3-hydroxypropyl)-2,2,2-trifluoroacetamide as dark brown oil. Yield (0.8 g, 83%). This used without further purification in the next transformation.

Step 2: Deprotection of N-(3-(3-(2-cyclopropylethynyl)phenyl)-3-hydroxypropyl)-2,2,2-trifluoroacetamide gave Example 131 as yellow oil. Yield (0.13 g, 24%): $^1$H NMR (400 MHz, DMSO-d$_6$) δ 7.23-7.33 (m, 4H), 4.64 (t, J=6.4 Hz, 1H), 2.71 (t, J=7.2 Hz, 2H), 1.65-1.73 (m, 2H), 1.50-1.56 (m, 1H), 0.86-0.91 (m, 2H), 0.69-0.73 (m, 2H). $^{13}$C NMR (100 MHz, DMSO-d$_6$) δ 146.2, 129.5, 128.5, 128.3, 125.1, 122.8, 93.5, 75.7, 70.1, 40.1, 37.6, 8.34, −0.3. ESI MS m/z 216 [M+1]+.

Example 132

1-(3-(3-AMINO-1-HYDROXYPROPYL)PHENYL)HEX-1-YN-3-OL

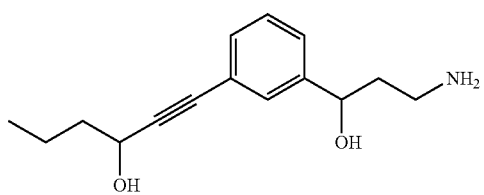 [SMILES: CCCC(O)C#Cc1cccc(C(O)CCN)c1]

1-(3-(3-amino-1-hydroxypropyl)phenyl)hex-1-yn-3-ol was prepared following the method used in Example 107.

Step 1: Sonogashira reaction of 25 (3 g, 9.2 mmol) with hex-1-yn-3-ol yielded 2,2,2-trifluoro-N-(3-hydroxy-3-(3-(3-hydroxyhex-1-ynyl)phenyl)propyl)acetamide as yellow oil. Yield (2.31 g, 73%): $^1$H NMR (400 MHz, CDCl$_3$) δ 7.42 (s, 1H), 7.26-7.38 (m, 3H), 4.86 (m, 1H), 4.61 (dd, J=2.0, 5.6 Hz, 1H), 3.67-3.71 (m, 1H), 3.37-3.46 (m, 1H), 2.38 (d, J=2.0 Hz, 1H), 1.95-1.99 (m, 2H), 1.75-1.88 (m, 2H), 1.53-1.57 (m, 2H), 0.97 (t, J=7.2 Hz, 3H).

Step 2: A mixture of 2,2,2-trifluoro-N-(3-hydroxy-3-(3-(3-hydroxyhex-1-ynyl)phenyl)propyl)acetamide, potassium carbonate (0.438 g, 3.26 mmol) and water (2 mL) in 2-PrOH (10 mL) was heated under reflux overnight. The reaction mixture was concentrated to dryness under reduced pressure. Purification by flash chromatography, eluent 10% (9.5:0.5 MeOH—NH$_3$)-DCM gave Example 132 as a yellow oil. Yield (0.42 g, 49%): $^1$H NMR (400 MHz, DMSO-d$_6$) δ 7.23-7.36 (m, 4H), 6.90 (bs, 2H), 5.44 (d, J=4.8 Hz, 1H), 4.67 (t, J=7.6 Hz, 1H), 4.44 (d, J=5.2 Hz, 1H), 2.82 (t, J=7.6 Hz, 2H), 1.79-1.83 (m, 2H), 1.60-1.64 (m, 2H), 1.41-1.47 (m, 2H), 0.93 (t, J=7.2 Hz, 3H). $^{13}$C NMR (100 MHz, DMSO-d$_6$) δ 145.8, 129.7, 128.5, 128.4, 125.6, 122.3, 92.4, 83.0, 69.5, 60.5, 37.0, 36.6, 18.2, 13.7. ESI MS m/z 248 [M+1]+.

Example 133

PREPARATION OF 3-(3-(4-METHYLPENT-1-YNYL)PHENYL)PROPAN-1-AMINE

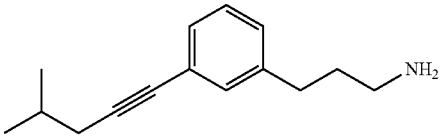 [SMILES: CC(C)CC#Cc1cccc(CCCN)c1]

3-(3-(4-Methylpent-1-ynyl)phenyl)propan-1-amine was prepared following the method used in Example 127.

Step 1: Sonogashira coupling of bromide 87 (0.5 g, 1.5 mmol) with 4-methyl-1-pentyne (0.2 mL, 2.4 mmol) gave tert-butyl 3-(4-methylpent-1-ynyl)phenylcarbamate. Yield (0.35 g, 69%). $^1$H NMR (400 MHz, CDCl$_3$) δ 7.16-7.28 (m, 3H), 7.07 (d, J=7.2 Hz, 1H), 4.50 (bs, 1H), 3.12-3.15 (m, 2H), 2.60 (d, J=7.6 Hz, 2H), 2.29 (d, J=6.8 Hz, 2H), 1.84-1.94 (m, 2H), 1.74-1.82 (m, 1H), 1.44 (s, 9H), 1.04 (d, J=6.8 Hz, 6H).

Step 2: Deprotection of tert-butyl 3-(4-methylpent-1-ynyl)phenyl carbamate with HCl/dioxane in THF gave Example 133 hydrochloride as a pale yellow solid. Yield (0.2 g, 64%): $^1$H NMR (400 MHz, DMSO-d$_6$) δ 7.23-7.29 (m, 1H), 7.13-7.21 (m, 3H), 2.76 (t, J=7.6 Hz, 2H), 2.56 (t, J=7.6 Hz, 2H), 2.25 (d, J=6.4 Hz, 2H), 1.75-1.83 (m, 3H), 0.94 (d, J=6.8 Hz, 6H). $^{13}$C NMR (100 MHz, DMSO-d$_6$): 141.2, 131.0, 128.9, 128.6, 127.9, 123.3, 38.1, 31.4, 28.4, 27.6, 27.5, 21.7. ESI MS m/z 216 [M+1]+.

Example 134

PREPARATION OF 5-(3-(2-AMINOETHOXY)-PHENYL)-N-METHYLPENT-4-YNAMIDE

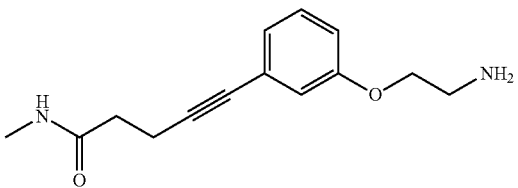 [SMILES: CNC(=O)CCC#Cc1cccc(OCCN)c1]

5-(3-(2-Aminoethoxy)-phenyl)-N-methylpent-4-ynamide was prepared following the method used in Example 18.

Step 1: Sonogashira reaction of bromide 19 with pent-4-ynoic acid methylamide gave N-methyl-5-(3-(2-(2,2,2-trifluoroacetamido)ethoxy)phenyl)pent-4-ynamide as a clear oil. Yield (1.4 g, crude). The crude material was used without further purification in the next step.

Step 2: Deprotection of N-methyl-5-(3-(2-(2,2,2-trifluoroacetamido)ethoxy)phenyl)pent-4-ynamide gave Example 134 as a brown solid. Yield (0.110 g, 10%): $^1$H NMR (400 MHz, DMSO-$d_6$) δ 7.27-7.31 (m, 1H), 6.95-7.00 (m, 3H), 4.14-4.17 (m, 2H), 3.18 (t, J=5.2 Hz, 2H), 2.58-2.62 (m, 2H), 2.58 (s, 3H), 2.32 (t, J=7.2 Hz, 2H). $^{13}$C NMR (100 MHz, DMSO-$d_6$) δ 170.6, 157.7, 129.8, 124.3, 124.2, 117.0, 115.1, 90.0, 80.2, 64.4, 38.2, 34.2, 25.4, 15.2. ESI MS m/z 266 [M+1]$^+$.

Example 135

PREPARATION OF 5-(3-(2-AMINOETHOXY) PHENYL)-N,N-DIMETHYLPENT-4-YNAMIDE

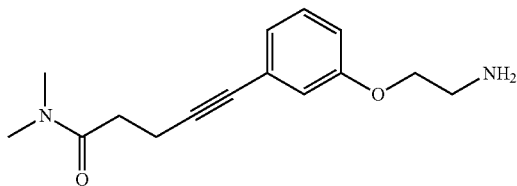

5-(3-(2-Aminoethoxy)phenyl)-N,N-dimethylpent-4-ynamide was prepared following the method us Step 1: Sonogashira reaction of bromide 19 with pent-4-ynoic acid N,N-dimethyl amide gave N,N-dimethyl-5-(3-(2-(2,2,2-trifluoroacetamido)ethoxy)phenyl)pent-4-ynamide as a brown oil. Yield (0.9 g, 50%): The crude material was used without further purification in the next step.

Step 2: Deprotection of N,N-dimethyl-5-(3-(2-(2,2,2-trifluoroacetamido)-ethoxy)phenyl)pent-4-ynamide gave Example 135 as a brown oil. Yield (0.14 g, 55%): $^1$H NMR (400 MHz, DMSO-$d_6$) δ 7.22-7.28 (m, 1H), 6.90-6.97 (m, 3H), 4.0 (t, J=5.6 Hz, 2H), 2.94-3.0 (m, 2H), 2.83 (s, 6H), 2.57-2.62 (m, 4H). $^{13}$C NMR (100 MHz, DMSO-$d_6$) δ 170.2, 158.2, 158.0, 157.7, 129.8, 124.3, 123.9, 116.8, 115.0, 90.3, 80.2, 36.6, 34.9, 31.6, 14.8. ESI MS m/z 261 [M+1]$^+$.

Example 136

PREPARATION OF 1-((3-(3-AMINO-1-HYDROXYPROPYL)PHENYL)ETHYNYL)CYCLOOCTANOL

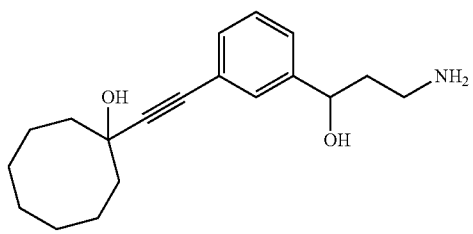 [SMILES: NCCC(O)c1cccc(C#CC2(O)CCCCCCC2)c1]

1-(2-(3-(3-amino-1-hydroxypropyl)phenyl)ethynyl)cyclooctanol was prepared following the method used in Example 131.

Step 1: Sonogashira reaction of 25 with 1-ethynyl-cyclooctanol yielded 2,2,2-trifluoro-N-(3-hydroxy-3-(3-(2-(1-hydroxycyclooctyl)ethynyl)phenyl)propyl)acetamide as yellow oil. Yield (0.54 g, 44%). This compound was used without further purification in the next step.

Step 2: Deprotection of 2,2,2-trifluoro-N-(3-hydroxy-3-(3-(2-(1-hydroxycyclooctyl)ethynyl)phenyl)propyl)acetamide gave Example 136 as a white solid. Yield (0.26 g, 64%): $^1$H NMR (400 MHz, DMSO-$d_6$) δ 7.20-7.29 (m, 4H), 5.23 (s, 1H), 4.66 (t, J=6.4 Hz, 1H), 2.55-2.62 (m, 2H), 1.79-1.90 (m, 4H), 1.62-1.66 (m, 2H), 1.55-1.60 (m, 8H), 1.40-1.42 (m, 2H). $^{13}$C NMR (100 MHz, DMSO-$d_6$) δ 147.0, 129.2, 128.5, 128.2, 125.6, 122.3, 95.4, 81.9, 70.8, 69.7, 42.4, 40.1, 39.9, 37.7, 27.5, 24.0, 21.7. ESI MS m/z 302 [M+1]$^+$.

Example 137

PREPARATION OF 543-(2-AMINOETHOXY)PHENYLPENT-4-YNAMIDE

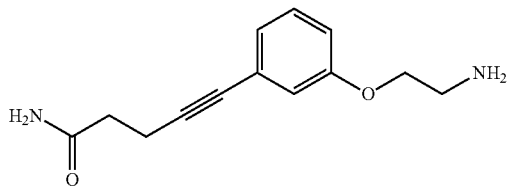 [SMILES: NCCOc1cccc(C#CCCC(N)=O)c1]

5-(3-(2-Aminoethoxy)phenyl)pent-4-ynamide was prepared following the method used in Example 18.

Step 1: Sonogashira reaction of bromide 6 with pent-4-ynoic acid amide gave 5-(3-(2-(2,2,2-trifluoroacetamido)ethoxy)phenyl)pent-4-ynamide as a clear oil. Yield (0.8 g, 50%): This compound was used without further purification in the next step.

Step 2: Deprotection of 5-(3-(2-(2,2,2-trifluoroacetamido)ethoxy)phenyl)pent-4-ynamide gave Example 137 as pale yellow oil. Yield (0.093 g, 16%): $^1$H NMR (400 MHz, DMSO-$d_6$) δ 7.21-7.26 (m, 1H), 6.88-6.94 (m, 3H), 3.92 (t, J=5.6 Hz, 2H), 2.88 (t, J=5.6 Hz, 2H), 2.59 (t, J=7.2 Hz, 2H), 2.34 (t, J=7.2 Hz, 2H). $^{13}$C NMR (100 MHz, DMSO-$d_6$) δ 172.4, 158.5, 129.7, 124.2, 123.7, 116.8, 114.9, 89.9, 80.3, 69.6, 40.6, 34.1, 15.0. ESI MS m/z 233 [M+1]$^+$.

Example 138

5-(3-(3-AMINO-1-HYDROXYPROPYL)PHENYL)-N-METHYLPENT-4-YNAMIDEOCTANOL

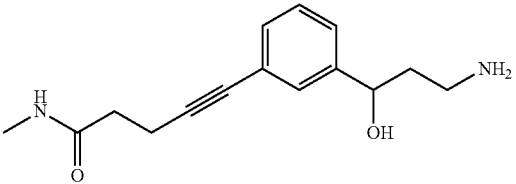

5-(3-(3-amino-1-hydroxypropyl)phenyl)-N-methylpent-4-ynamide was prepared following the method shown in Scheme 22.

SCHEME 22

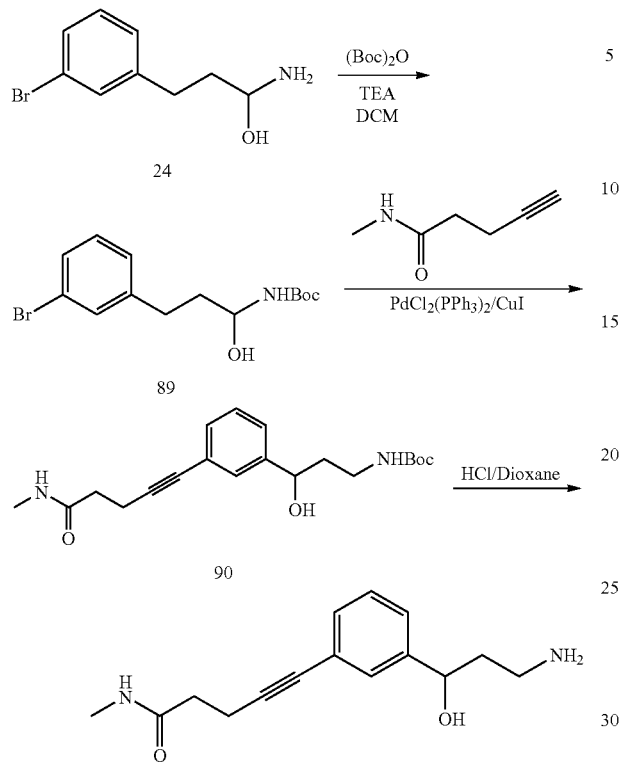

Step 1: To a solution of 24 (17 g, 74 mmol) in DCM (250 mL) was added (Boc)₂O (21.5 mL, 89 mmol) and triethylamine (15.5 mL, 111 mmol). The reaction mixture was stirred at room temperature for 15 h, then diluted with DCM (250 mL) and washed with satd. NaHCO₃ solution. The organic layer was dried over sodium sulfate and concentrated under reduced pressure. Purification by flash chromatography (0 to 30% EtOAc-hexanes gradient) gave 89 as a yellow oil. Yield (15.2 g, 61%): $^1$H NMR (400 MHz, DMSO-$d_6$) δ 7.53 (s, 1H), 7.39 (d, J=7.6 Hz, 1H), 7.29 (d, J=7.6 Hz, 1H), 7.20 (t, J=7.2 Hz, 1H), 4.85 (bs, 1H), 4.69-4.71 (m, 1H), 3.60 (bs, 1H), 3.53-3.55 (m, 1H), 3.11-3.18 (m, 1H), 1.76-1.84 (m, 2H), 1.47 (s, 9H).

Step 2: Sonogashira reaction of 89 with pent-4-ynoic acid methyl amide gave tert-butyl 3-hydroxy-3-(3-(5-(methyl amino)-5-oxopent-1-ynyl)phenyl)propylcarbamate as dark brown oil. Yield (0.27 g, 36%): $^1$H NMR (400 MHz, DMSO-$d_6$) δ 7.39 (s, 1H), 7.26-7.30 (m, 3H), 5.64 (bs, 1H), 4.85 (bs, 1H), 4.69-4.71 (m, 1H), 3.46-3.51 (m, 1H), 3.35 (bs, 1H), 3.11-3.18 (m, 1H), 2.85 (d, J=4.8 Hz, 3H), 2.73 (t, J=6.4 Hz, 2H), 2.46 (t, J=6.4 Hz, 2H), 1.55-1.84 (m, 2H), 1.46 (s, 9H).

Step 3: To a solution of tert-butyl 3-hydroxy-3-(3-(5-(methyl amino)-5-oxopent-1-ynyl)phenyl)propylcarbamate (0.7 g, 2.1 mmol) in MeOH-THF (1:1, 10 mL) was added HCl in Dioxane (0.7 mL, 4M) and the resulting reaction mixture was stirred for 24 h at RT. The mixture was evaporated to dryness under reduced pressure. Purification by flash chromatography (0-15% MeOH-DCM gradient) gave Example 14 hydrochloride as yellow solid. Yield (0.17 g, 76%): $^1$H NMR (400 MHz, DMSO-$d_6$) δ 7.27-7.33 (m, 3H), 7.23-7.27 (m, 1H), 4.64-4.66 (m, 1H), 2.75-2.82 (m, 2H), 2.60-2.62 (m, 2H), 2.58 (s, 3H), 2.33-2.35 (m, 2H), 1.78-1.90 (m, 2H). $^{13}$C NMR (100 MHz, DMSO-$d_6$) δ 171.1, 146.1, 130.3, 128.9, 128.8, 125.7, 123.4, 90.3, 81.0, 69.7, 36.9, 36.8, 34.8, 25.9, 15.6. ESI MS m/z 261 [M+1]⁺.

Example 139

3-AMINO-1-(3-((2,6-DICHLOROPHENYL)ETHYNYL)PHENYL)PROPAN-1-OL

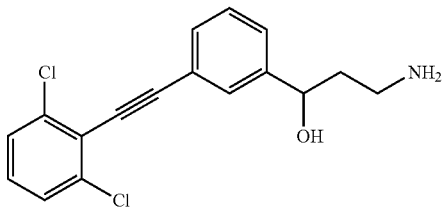 [SMILES: NCCC(O)c1cccc(C#Cc2c(Cl)cccc2Cl)c1]

3-Amino-1-(3-(2-(2,6-dichlorophenyl)ethynyl)phenyl) propan-1-ol was prepared following the method used in Example 132.

Step 1: Sonogashira reaction of 25 with 1,3-dichloro-2-ethynyl-benzene gave N-(3-(3-(2-(2,6-dichlorophenyl)ethynyl)phenyl)-3-hydroxypropyl)-2,2,2-trifluoroacetamide as dark brown oil. Yield (0.32 g, 37%). This compound could not be separated completely from the starting bromide and was used directly in the step.

Step 2: Deprotection of N-(3-(3-(2-(2,6-dichlorophenyl)ethynyl)phenyl)-3-hydroxypropyl)-2,2,2-trifluoroacetamide gave example 139 as a yellow solid. Yield (0.149 g, 60%): $^1$H NMR (400 MHz, DMSO-$d_6$) δ 7.69 (bs, 2H), 7.63 (d, J=8.4 Hz, 2H), 7.51 (s, 1H), 7.43-7.53 (m, 4H), 5.71 (bs, 1H), 4.66 (m, 1H), 2.82-2.90 (m, 2H), 1.82-1.95 (m, 2H). $^{13}$C NMR (100 MHz, DMSO-$d_6$) δ 146.2, 136.0, 130.8, 128.9, 128.5, 128.2, 127.0, 121.8, 121.2, 118.8, 115.8, 99.6, 83.0, 69.3, 36.5, 36.4. ESI MS m/z 320 [M+1]₊.

Example 140

5-(3-(3-AMINO-1-HYDROXYPROPYL)PHENYL)-N-METHYLPENT-4-YNAMIDEOCTANOL

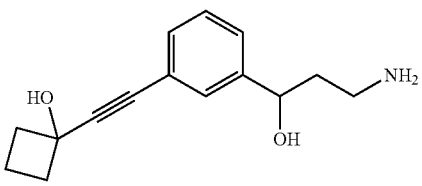 [SMILES: NCCC(O)c1cccc(C#CC2(O)CCC2)c1]

5-(3-(3-amino-1-hydroxypropyl)phenyl)-N-methylpent-4-ynamide was prepared following the method used in Example 138.

Step 1: Sonogashira reaction of 24 with 1-ethynyl-cyclobutanol yielded tert-butyl 3-hydroxy-3-(3-(2-(1-hydroxycyclobutyl)ethynyl)phenyl)propylcarbamate as yellow oil. Yield (1.5 g, 70%): $^1$H NMR (400 MHz, DMSO-$d_6$) δ 7.45 (s, 1H), 7.27-7.34 (m, 3H), 4.85 (bs, 1H), 4.71 (m, 1H), 3.48-3.51 (m, 2H), 3.14-3.16 (m, 1H), 2.50-2.52 (m, 2H), 2.30-2.49 (m, 3H), 1.80-1.90 (m, 4H), 1.45 (s, 9H).

Step 2: Deprotection of tert-butyl 3-hydroxy-3-(3-(2-(1-hydroxy cyclobutyl)ethynyl)phenyl)propyl carbamate gave example 140 hydrochloride as a pale yellow semi-solid. Yield (0.161 g, 30%): $^1$H NMR (400 MHz, DMSO-$d_6$) δ 7.28-7.36 (m, 4H), 4.64-4.67 (m, 1H), 2.77-2.86 (m, 2H), 2.30-2.39 (m, 2H), 2.16-2.24 (m, 2H), 1.70-1.90 (m, 4H). $^{13}$C NMR (100 MHz, DMSO-$d_6$) δ 145.8, 129.7, 128.5, 128.4, 125.6, 122.3, 94.6, 81.6, 69.1, 66.2, 40.1, 36.5, 36.2, 12.8. ESI MS m/z 246 [M+1]$^+$.

Example 141

PREPARATION OF 4-((3-(2-AMINOETHYL)PHENYL)ETHYNYL)HEPTAN-4-OL

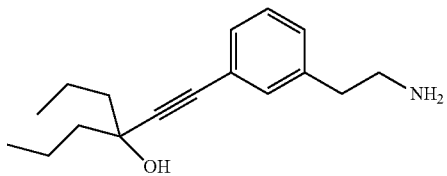 [SMILES: CCCC(O)(C#Cc1cccc(CCN)c1)CCC]

4-((3-(2-Aminoethyl)phenyl)ethynyl)heptan-4-ol was prepared following the method used in Example 18.

Step 1. Condensation of 3-bromophenethylamine with ethyl trifluoroacetate gave N-(3-bromophenethyl)-2,2,2-trifluoroacetamide as a colorless oil. Yield (3.30 g, quant.). $^1$H NMR (400 MHz, CDCl$_3$) δ 7.40 (ddd, J=7.8, 1.8, 1.0 Hz, 1H), 7.53 (t, J=1.8 Hz, 1H), 7.21 (t, J=7.6 Hz, 1H), 7.10-7.13 (m, 1H), 6.32 (br s, 1H), 3.61 (q, J=6.7 Hz, 2H), 2.87 (t, J=7.2 Hz, 2H).

Step 2. N-(3-Bromophenethyl)-2,2,2-trifluoroacetamide was coupled with alkynol 20 following the procedure described in Example 18 except that the reaction was run for 17 h to give 2,2,2-trifluoro-N-(3-(3-hydroxy-3-propylhex-1-ynyl)phenethyl)-acetamide as a brown oil after purification by flash chromatography (10% to 50% EtOAc in hexanes gradient). Yield (0.975 g, 66%). $^1$H NMR (400 MHz, CDCl$_3$) δ 7.32 (dt, J=7.8, 1.2 Hz, 1H), 7.24-7.29 (m, 2H), 7.10-7.15 (m, 1H), 6.27 (br.s, 1H), 3.61 (q, J=6.7 Hz, 2H), 2.86 (t, J=7.0 Hz, 2H), 1.95 (s, 1H), 1.66-1.74 (m, 4H), 1.52-1.64 (m, 4H), 0.99 (t, J=7.2 Hz, 6H).

Step 3. Deprotection of 2,2,2-trifluoro-N-(3-(3-hydroxy-3-propylhex-1-ynyl)phenethyl)acetamide was done following the procedure described in Example 1 except that the reaction was stirred at 40° C. for 18. Purification by flash chromatography (75% to 100% of 20% 7N NH$_3$/MeOH in EtOAc—hexanes gradient) gave Example 141 as a colorless oil. Yield (0.385 g, 54%). $^1$H NMR (400 MHz, DMSO-$d_6$) δ 7.21-7.26 (m, 1H), 7.14-7.29 (m, 3H), 5.12 (s, 1H), 2.72 (t, J=7.0 Hz, 2H), 2.59 (t, J=7.2 Hz, 2H), 1.40-1.60 (m, 8H), 0.89 (t, J=7.0 Hz, 6H). $^{13}$C NMR (100 MHz, DMSO-$d_6$) δ 141.7, 132.2, 129.4, 129.2, 123.2, 94.6, 83.4, 70.3, 44.9, 44.2, 40.1, 18.0, 15.0; ESI MS m/z 260.4 [M+H]$^+$; RP-HPLC 100.0% (AUC, 220 nm).

Example 142

PREPARATION OF 3-AMINO-1-(3-(3-HYDROXY-3-PROPYLHEX-1-YNYL)PHENYL)PROPAN-1-ONE OXIME

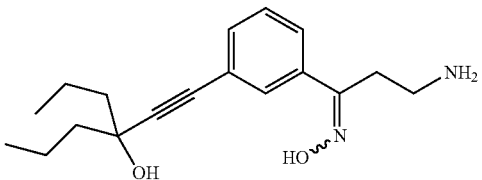 [SMILES: CCCC(O)(C#Cc1cccc(C(CCN)=NO)c1)CCC]

3-Amino-1-(3-(3-hydroxy-3-propylhex-1-ynyl)phenyl)propan-1-one oxime was prepared following the methods used in Example 18 and 11.

Step 1. N-(3-(3-Bromophenyl)-3-oxopropyl)-2,2,2-trifluoroacetamide (63) was coupled with alkynol 20 following the procedure described in Example 18 except that the reaction was run at 80° C. for 3 h to give 3-amino-1-(3-(3-hydroxy-3-propylhex-1-ynyl)phenyl)propan-1-one as a dark amber oil after purification by flash chromatography (20% EtOAc in hexanes). Yield (28.1 g, 99.6%). $^1$H NMR (400 MHz, DMSO-$d_6$) δ 9.40 (br. t, 1H), 7.84-7.92 (m, 2H), 7.58-7.63 (m, 1H), 7.50 (t, J=7.6 Hz, 1H), 5.19 (s, 1H), 3.51 (q, J=5.7 Hz, 2H), 3.30 (t, J=6.7 Hz, 2H), 1.40-1.63 (m, 8H), 0.90 (t, J=7.2 Hz, 6H).

Step 2. To a solution of 3-amino-1-(3-(3-hydroxy-3-propylhex-1-ynyl)phenyl)propan-1-one (0.236 g, 0.62 mmol) and hydroxylamine hydrochloride (0.109 g, 1.56 mmol) in EtOH (abs, 10 mL) was added diisopropylethylamine (0.3 mL, 1.72 mmol) and the reaction mixture was stirred at room temperature for 3 days. Concentration under reduced pressure followed by the flash chromatography of the residue (10% to 100% EtOAc in hexanes gradient) afforded 2,2,2-trifluoro-N-(3-(3-(3-hydroxy-3-propylhex-1-ynyl)phenyl)-3-(hydroxyimino)propy)acetamide as a colorless oil. Yield (0.225 g, 91%). $^1$H NMR (400 MHz, DMSO-$d_6$) δ 11.5 (s, 1H), 9.50 (t, J=5.5 Hz, 1H), 7.55-7.62 (m, 2H), 7.30-7.40 (m, 2H), 5.14 (s, 1H), 3.34 (q, J=6.8 Hz, 2H), 2.92 (t, J=7.8 Hz, 2H), 1.39-1.62 (m, 8H), 0.89 (t, J=7.2 Hz, 6H).

Step 3. Deprotection of 2,2,2-trifluoro-N-(3-(3-(3-hydroxy-3-propylhex-1-ynyl)phenyl)-3-(hydroxyimino)propy) acetamide was done following the procedure described in Example 1 except that the reaction was stirred at 40° C. for 18 hrs. Purification by flash chromatography (50% to 100% of 20% 7N NH$_3$/MeOH in EtOAc-hexanes gradient) gave Example 142 as a colorless oil. Yield (0.056 g, 33%). $^1$H NMR (400 MHz, DMSO-$d_6$) δ 7.59-7.62 (m, 2H), 7.30-7.37 (m, 2H), 5.15 (s, 1H), 2.74-2.80 (m, 2H), 2.60-2.66 (m, 2H), 1.39-1.63 (m, 8H), 0.89 (t, J=7.4 Hz, 6H); $^{13}$C NMR (100 MHz, DMSO-$d_6$) δ 155.4, 137.4, 131.8, 129.5, 129.0, 126.5, 123.5, 95.1, 83.1, 70.3, 44.9, 39.5, 30.8, 18.0, 15.0; ESI MS m/z 260.4 [M+H]⁺; RP-HPLC 100.0% (AUC, 220 nm).

Example 143

PREPARATION OF 2-((3-(3-AMINOPROPYL)PHENYL)ETHYNYL)CYCLOHEXANOL

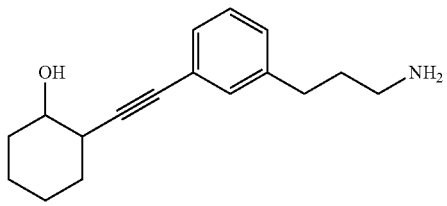 [SMILES: NCCCc1cccc(C#CC2CCCCC2O)c1]

2-((3-(3-aminopropyl)phenyl)ethynyl)cyclohexanol was prepared following the method shown in Example 1:

Step 1: Sonogashira coupling of bromide 3 with 2-ethynylcyclohexanol followed by flash chromatography (5-50% EtOAc/hexanes gradient), gave 2,2,2-trifluoro-N-(3-(3-((2-hydroxycyclohexyl)ethynyl)phenyl)propyl)acetamide as a yellow oil. Yield (1.2 g, 43%): ¹H NMR (400 MHz, CDCl₃) δ 7.18-7.28 (m, 3H), 7.06-7.30 (m, 3H), 6.33 (brs, 1H), 3.48-3.57 (m, 1H), 3.36 (app q, J=6.8 Hz, 2H), 2.63 (t, J=7.2 Hz, 2H), 2.38-2.46 (m, 1H), 2.32 (brs, 1H), 2.02-2.10 (m, 2H), 1.91 (quint, J=7.2 Hz, 2H), 1.74-1.82 (m, 1H), 1.66-1.74 (m, 1H), 1.40-1.52 (m, 1H), 1.16-1.40 (m, 4H).

Step 2: Deprotection of 2,2,2-trifluoro-N-(3-(3-((2-hydroxycyclohexyl)-ethynyl)phenyl)propyl)acetamide followed by flash chromatography (10% (7N NH₃/MeOH)/dichloromethane) gave Example 143 as an orange oil. Yield (0.606 g, 69%): ¹H NMR (400 MHz, CDCl₃) δ 7.16-7.26 (m, 3H), 7.08-7.12 (m, 1H), 3.48-3.56 (m, 1H), 2.71 (t, J=7.2 Hz, 2H), 2.61 (t, J=7.2 Hz, 2H), 2.38-2.46 (m, 1H), 2.01-2.10 (m, 2H), 1.64-1.82 (m, 7H), 1.40-1.52 (m, 1H), 1.16-1.40 (m, 3H).

Example 144

PREPARATION OF 2-((3-(2-AMINOETHOXY)PHENYL)ETHYNYL)CYCLOHEXANOL

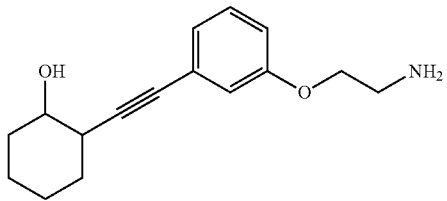 [SMILES: NCCOc1cccc(C#CC2CCCCC2O)c1]

2-((3-(2-aminoethoxy)phenyl)ethynyl)cyclohexanol was prepared following the method shown in Example 18:

Step 1: Sonogashira coupling of bromide 19 with 2-ethynylcyclohexanol followed by flash chromatography (5-50% EtOAc/hexanes gradient), gave 2,2,2-trifluoro-N-(2-(3-((2-hydroxycyclohexyl)ethynyl)phenoxy)ethyl)acetamide as a yellow oil. Yield (0.88 g, 31%): ¹H NMR (400 MHz, CDCl₃) δ 7.18 (t, J=8.0 Hz, 1H), 7.01-7.04 (m, 1H), 6.90-6.98 (brs, 1H), 6.91-6.92 (m, 1H), 6.79-6.83 (m, 1H), 4.05-4.07 (m, 2H), 3.74 (app q, J=5.2 Hz, 2H), 3.48-3.56 (m, 1H), 2.35-2.46 (m, 2H), 2.00-2.08 (m, 1H), 1.64-1.80 (m, 2H), 1.40-1.52 (m, 1H), 1.14-1.40 (m, 4H).

Step 2: Deprotection of 2,2,2-trifluoro-N-(2-(3-((2-hydroxycyclohexyl)-ethynyl)phenoxy)ethyl)acetamide followed by purification by flash chromatography (10% (7N NH₃/MeOH)/dichloromethane) gave Example 144 as a white solid. Yield (0.29 g, 45%): ¹H NMR (400 MHz, CDCl₃) δ 7.18 (t, J=7.6 Hz, 1H), 6.98-7.03 (m, 1H), 6.93-6.95 (m, 1H), 6.83-6.86 (m, 1H), 3.96 (t, J=5.2 Hz, 2H), 3.49-3.57 (m, 1H), 3.08 (brs, 2H), 2.38-2.46 (m, 1H), 2.01-2.10 (m, 2H), 1.55-2.00 (brs, 1H), 1.74-1.82 (m, 2H), 1.65-1.74 (m, 2H), 1.40-1.52 (m, 1H), 1.16-1.40 (m, 3H).

Example 145

PREPARATION OF 2-((3-(3-AMINO-1-HYDROXYPROPYL)PHENYL)ETHYNYL)CYCLOHEXANOL

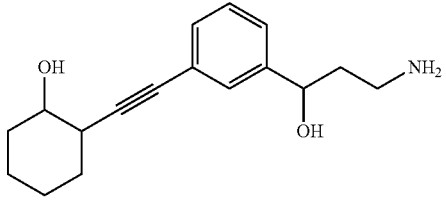 [SMILES: NCCC(O)c1cccc(C#CC2CCCCC2O)c1]

2-((3-(3-amino-1-hydroxypropyl)phenyl)ethynyl)cyclohexanol was prepared following the method shown in Example 19:

Step 1: Sonogashira coupling of bromide 25 with 2-ethynylcyclohexanol followed by flash chromatography (5-50% EtOAc/hexanes gradient), gave 2,2,2-trifluoro-N-(3-hydroxy-3-(3-((2-hydroxycyclohexyl)ethynyl)phenyl)propyl)acetamide as a yellow oil. Yield (1.9 g, 63%): ¹H NMR (400 MHz, CDCl₃) δ 7.39-7.41 (m, 1H), 7.23-7.36 (m, 4H), 4.84 (q, J=4.0 Hz, 1H), 3.62-3.72 (m, 1H), 3.50-3.57 (m, 1H), 3.34-3.44 (m, 1H), 2.38-2.46 (m 1H), 2.18 (brs, 2H), 1.90-2.10 (m, 4H), 1.66-1.84 (m, 2H), 1.40-1.53 (m, 1H), 1.16-1.40 (m, 3H).

Step 2: Deprotection of 2,2,2-trifluoro-N-(3-hydroxy-3-(3-((2-hydroxycyclohexyl)ethynyl)phenyl)propyl)acetamide followed by flash chromatography (10% (7N NH₃/MeOH)/dichloromethane) gave Example 145 as a light yellow glassy solid. Yield (0.402 g, 29%): ¹H NMR (400 MHz, CDCl₃) δ 7.44-7.46 (m, 1H), 7.21-7.31 (m, 3H), 4.92 (dd, J=8.8, 3.2 Hz, 1H), 3.47-3.56 (m, 1H), 3.05-3.12 (m, 1H), 3.01 (brs, 4H), 2.90-2.99 (m, 1H), 2.37-2.44 (m, 1H), 2.00-2.09 (m, 2H), 1.81-1.90 (m, 1H), 1.64-1.81 (m, 3H), 1.40-1.52 (m, 1H), 1.14-1.40 (m, 3H).

Example 146

PREPARATION OF 14243-(2-AMINOETHOXY)PHENYL)ETHYNYL)CYCLOBUTANOL

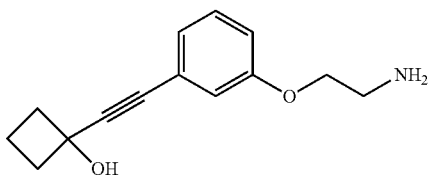 [SMILES: NCCOc1cccc(C#CC2(O)CCC2)c1]

1-(2-(3-(2-Aminoethoxy)phenyl)ethynyl)cyclobutanol was prepared following the method used in Example 18.

Step 7: Sonogashira reaction of bromide 19 with 1-ethynyl-cyclobutanol gave 2,2,2-trifluoro-N-(2-(3-(2-(1-hydroxycyclobutyl)ethynyl)phenoxy)ethyl)acetamide as a brown oil. Yield (0.85 g, 39%): $^1$H NMR (400 MHz, DMSO-$d_6$) δ 7.27-7.30 (m, 1H), 6.92-7.03 (m, 3H), 4.09-4.13 (m, 4H), 3.54-3.58 (m, 2H), 2.33-2.37 (m, 2H), 2.16-2.24 (m, 2H), 1.74-1.81 (m, 2H).

Step 8: Deprotection of 2,2,2-trifluoro-N-(2-(3-(2-(1-hydroxycyclobutyl)ethynyl)phenoxy)ethyl)acetamide gave Example 146 as brown oil. Yield (0.09 g, 31%): $^1$H NMR (400 MHz, DMSO-$d_6$) δ 7.25-7.29 (m, 1H), 6.98 (d, J=8.0 Hz, 1H), 6.93-6.96 (m, 2H), 3.95 (t, J=5.4 Hz, 2H), 2.88 (t, J=5.4 Hz, 2H), 2.33-2.35 (m, 2H), 2.16-2.24 (m, 2H), 1.71-1.78 (m, 2H). $^{13}$C NMR (100 MHz, DMSO-$d_6$) δ 158.5, 129.8, 123.7, 123.6, 116.7, 115.4, 94.6, 81.5, 69.5, 66.6, 38.6, 12.8. ESI MS m/z 232 [M+1]$^+$.

Example 147

PREPARATION OF 1-(3-(3-AMINO-1-HYDROXYPROPYL)PHENYL)-4-METHYLPENT-1-YN-3-OL

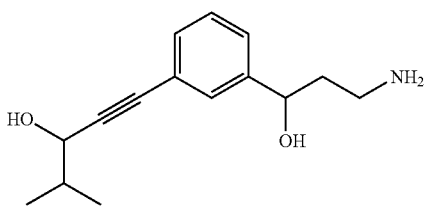 [SMILES: CC(C)C(O)C#Cc1cccc(C(O)CCN)c1]

1-(3-(3-Amino-1-hydroxypropyl)phenyl)-4-methylpent-1-yn-3-ol was prepared following the method used in Example 138.

Step 1: Sonogashira reaction of 24 with 4-methyl-pent-1-yn-3-ol yielded tert-butyl 3-hydroxy-3-(3-(3-hydroxy-4-methylpent-1-ynyl)phenyl)propylcarbamate as dark brown oil. Yield (1.73 g, 81%): $^1$H NMR (400 MHz, CDCl$_3$) δ 7.44 (s, 1H), 7.28-7.34 (m, 3H), 4.86 (bs, 1H), 4.72 (bs, 1H), 4.39 (t, J=6.0 Hz, 1H), 3.46-3.51 (m, 2H), 3.11-3.19 (m, 1H), 1.78-2.04 (m, 4H), 1.45 (s, 9H), 1.02 (d, J=7.2 Hz, 3H), 1.06 (d, J=7.2 Hz, 3H).

Step 2: Deprotection of tert-butyl 3-hydroxy-3-(3-(3-hydroxy-4-methylpent-1-ynyl)phenyl)propylcarbamate following the method used in Example 138 except that EtOAc was used as solvent gave Example 147 hydrochloride as a pale yellow semi-solid. Yield (0.31 g, 56%): $^1$H NMR (400 MHz, DMSO-$d_6$) δ 7.80-7.98 (bs, 2H), 7.30-7.37 (m, 4H), 5.44 (d, J=4.8 Hz, 1H), 4.68 (bs, 1H), 4.13 (m, 1H), 2.82 (m, 2H), 1.80-1.83 (m, 3H), 0.95 (d, J=7.2 Hz, 3H), 0.93 (d, J=7.2 Hz, 3H). $^{13}$C NMR (100 MHz, DMSO-$d_6$) δ 146.3, 130.2, 129.0, 128.9, 126.1, 122.8, 91.5, 84.2, 69.5, 66.7, 36.9, 36.7, 34.8, 18.8, 18.2. ESI MS m/z 248 [M+1]$_+$.

Example 148

PREPARATION OF 1-(2-(3-(3-AMINOPROPYL)PHENYL)ETHYNYL)CYCLOBUTANOL

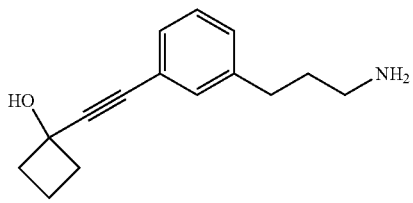 [SMILES: NCCCc1cccc(C#CC2(O)CCC2)c1]

1-(2-(3-(3-Aminopropyl)phenyl)ethynyl)cyclobutanol was prepared following the method used in Example 127:

Step 1: Sonogashira coupling of bromide 87 with 1-ethynyl-cyclobutanol gave tert-butyl 3-(3-(2-(1-hydroxycyclobutyl)ethynyl)phenyl)propylcarbamate as a brown oil. Yield (0.32 g, 61%). $^1$H NMR (400 MHz, CDCl$_3$) δ 7.11-7.30 (m, 4H), 4.52 (bs, 1H), 3.10-3.16 (m, 2H), 2.62 (t, J=7.6 Hz, 2H), 2.42-2.56 (m, 2H), 2.22-2.40 (m, 2H), 1.78-1.91 (m, 4H), 1.44 (s, 9H).

Step 2: Deprotection of tert-butyl 3-(3-(2-(1-hydroxycyclobutyl)ethynyl)phenyl)propylcarbamate with HCl/dioxane in THF afforded a yellow oil after work-up. The crude product was dissolved in a small quantity of methanolic NH$_3$ (2 M) and applied onto a silica column. Purification by flash chromatography (0-(9.5-0.5) MeOH—NH$_3$)-DCM gradient) gave Example 148 as a yellow oil. Yield (0.09 g, 43%): $^1$H NMR (400 MHz, DMSO-$d_6$) δ 7.21-7.33 (m, 4H), 2.74 (t, J=7.4 Hz, 2H), 2.64 (t, J=7.6 Hz, 2H), 2.33-2.40 (m, 2H), 2.18-2.26 (m, 2H), 1.72-1.86 (m, 4H). $^{13}$C NMR (100 MHz, DMSO-$d_6$): 141.5, 131.1, 128.9, 128.7, 128.5, 122.6, 94.6, 81.6, 66.6, 38.6, 38.3, 31.5, 28.9, 12.8. ESI MS m/z 230 [M+1]$^+$.

Example 149

PREPARATION OF 1-(2-(3-(3-AMINOPROPYL)PHENYL)ETHYNYL)CYCLOOCTANOL

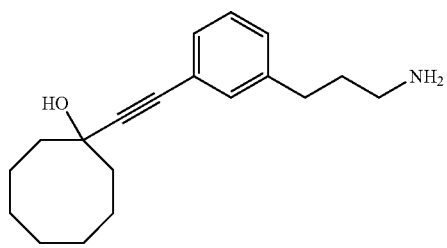 [SMILES: NCCCc1cccc(C#CC2(O)CCCCCCC2)c1]

1-(2-(3-(3-Aminopropyl)phenyl)ethynyl)cyclooctanol was prepared following the method shown in Scheme 23:

SCHEME 23

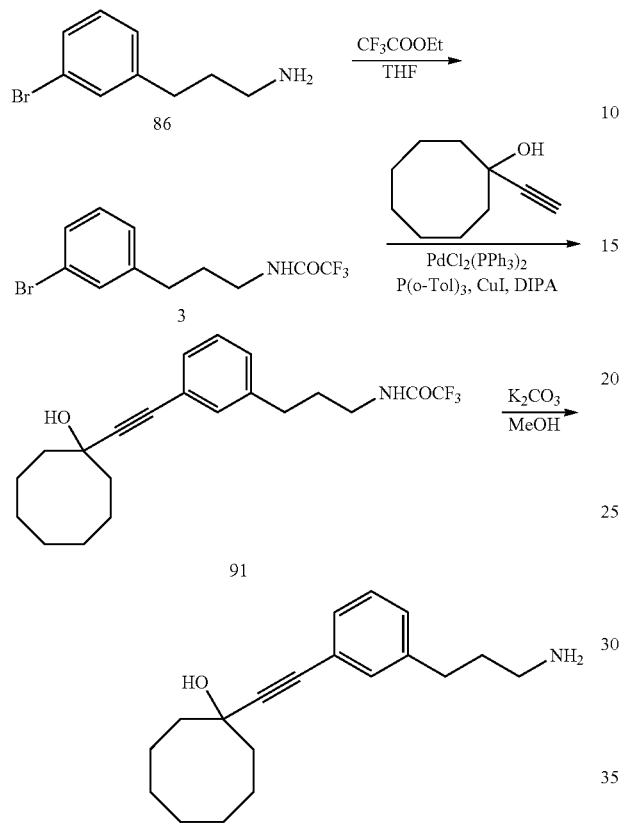

Step 1: To a solution of amine 86 (0.68 g, 2.9 mmol) in THF (5 mL) was added ethyl trifluoroacetate (0.9 mL, 6 mmol) at room temperature. The mixture was stirred at room temperature under inert atmosphere overnight. Upon removal of solvent under reduced pressure, the reaction mixture was extracted with ethyl acetate. The organic phase was washed with water and brine, dried over anhydrous $Na_2SO_4$ and concentrated under reduced pressure to give a yellow oil. Purification by flash chromatography (0-10% ethyl acetate:hexane gradient) gave 3 as a pale yellow oil. Yield (0.61 g, 62%). $^1$H NMR (400 MHz, $CDCl_3$) δ 7.33-7.37 (m, 2H), 7.15-7.19 (m, 1H), 7.09-7.12 (m, 1H), 6.24 (bs, 1H), 3.37-3.42 (m, 2H), 2.66 (t, J=7.6 Hz, 2H), 1.88-1.96 (m, 2H).

Step 2: Sonogashira coupling of bromide 3 with 1-ethynyl-cyclooctanol gave 2,2,2-trifluoro-N-(3-(3-(2-(1-hydroxycyclooctyl)ethynyl)phenyl)propyl)acetamide. Yield (0.344 g, 47%). $^1$H NMR (400 MHz, $CDCl_3$) δ 7.22-7.29 (m, 2H), 7.15-7.19 (m, 1H), 7.11-7.13 (m, 1H), 6.23 (bs, 1H), 3.36-3.42 (m, 2H), 1.48-2.07 (m, 18H).

Step 3: To a solution of alkyne 91 (0.34 g, 0.8 mmol) in methanol (5.0 mL) was added $K_2CO_3$ (0.25 g, 1.7 mmol). The resulting mixture was stirred at room temperature for overnight. The mixture was concentrated under reduced pressure and the residue was partitioned between water and ethyl acetate. The organic layer was washed with water, dried over anhydrous $Na_2SO_4$ and concentrated under reduced pressure. Purification by flash chromatography (0-10% (9.5-0.5 MeOH—$NH_3$)-DCM gradient) afforded Example 149 as yellow oil. Yield (0.12 g, 47%): $^1$H NMR (400 MHz, DMSO-$d_6$) δ 7.24-7.28 (m, 1H), 7.14-7.19 (m, 3H), 2.56-2.62 (m, 4H), 1.83-1.94 (m, 4H), 1.54-1.70 (m, 9H), 1.42-1.50 (m, 3H). $^{13}$C NMR (100 MHz, DMSO-$d_6$): 142.9, 131.5, 129.1, 129.0, 128.8, 123.1, 100.0, 96.0, 82.2, 70.2, 38.2, 33.6, 32.4, 28.0, 24.5, 22.2. ESI MS m/z 286 [M+1]$^+$.

Example 150

PREPARATION OF 54343-AMINO-1-HYDROXYPROPYL)PHENYL)-PENT-4-YNAMIDE

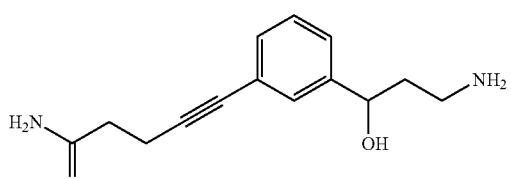

5-(3-(3-Amino-1-hydroxypropyl)phenyl)-pent-4-ynamide was prepared following the method used in Example 138.

Step 1: Sonogashira reaction of 24 with pent-4-ynoic acid amide yielded tert-butyl 3-hydroxy-3-(3-(5-amino-5-oxopent-1-ynyl)phenyl)propylcarbamate as yellow oil which is used directly in the next reaction. Yield (580 mg, 78%).

Step 2: Deprotection of tert-butyl 3-hydroxy-3-(3-(5-amino-5-oxopent-1-ynyl)phenyl)propylcarbamate gave Example 150 hydrochloride as pale yellow semi-solid. Yield (110 mg, 51%): $^1$H NMR (400 MHz, DMSO-$d_6$) δ 7.22-7.29 (m, 4H), 4.63-4.66 (m, 1H), 2.77-2.82 (m, 2H), 2.59 (t, J=7.2 Hz, 2H), 2.33 (t, J=7.2 Hz, 2H), 1.75-1.84 (m, 2H), $^{13}$C NMR (100 MHz, DMSO-$d_6$) δ 172.9, 146.2, 130.2, 128.9, 100.0, 125.7, 123.4, 90.3, 81.0, 69.8, 37.5, 36.9, 34.6, 15.5, ESI MS m/z 247 [M+1]$^+$.

Example 151

PREPARATION OF 3-AMINO-1-(3-(2-CYCLOOCTYLETHYNYL)PHENYL)PROPAN-1-OL

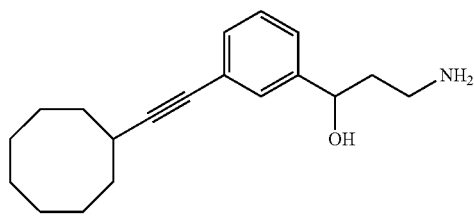 [SMILES: NCCC(O)c1cccc(C#CC2CCCCCCC2)c1]

3-Amino-1-(3-(2-cyclooctylethynyl)phenyl)propan-1-ol was prepared following the method used in Example 138.

Step 1: Sonogashira reaction of 24 with ethynyl cyclooctane yielded tert-butyl 3-(3-(2-cyclooctylethynyl)phenyl)-3-hydroxypropylcarbamate as light yellow oil. Yield (470 mg, 91%): $^1$H NMR (400 MHz, $CDCl_3$) δ 7.39 (s, 1H), 7.22-7.29 (m, 3H), 4.86 (bs, 1H), 4.72 (m, 1H), 3.23 (bs, 1H), 3.11-3.19 (m, 1H), 2.76-2.79 (m, 2H), 1.92-1.96 (m, 2H), 1.74-1.81 (m, 6H), 1.53-1.60 (m, 6H), 1.45 (s, 9H), 1.27 (m, 2H).

Step 5: Deprotection of tert-butyl 3-(3-(2-cyclooctylethynyl)phenyl)-3-hydroxypropylcarbamate gave Example 151 hydrochloride as pale yellow semi-solid. Yield (86 mg, 34%):

¹H NMR (400 MHz, DMSO-d₆) δ 7.77-7.94 (bs, 3H), 7.23-7.33 (m, 4H), 5.60 (bs, 1H), 4.65-4.69 (m, 1H), 2.80-2.84 (m, 3H), 1.77-1.89 (m, 8H), 1.12-1.24 (m, 8H), ¹³C NMR (100 MHz, DMSO-d₆) δ 146.1, 130.2, 128.9, 125.6, 123.6, 95.6, 81.0, 69.6, 37.0, 36.7, 31.5, 30.4, 27.4, 25.3, 24.4, ESI MS m/z 286 [M+1]⁺.

Example 152

PREPARATION OF 3-AMINO-1-(3-(5-METHOXYPENT-1-YNYL)PHENYL)PROPAN-1-OL

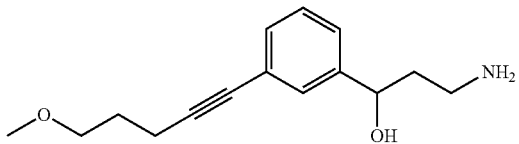 [SMILES: COCCCC#Cc1cccc(C(O)CCN)c1]

3-Amino-1-(3-(5-methoxypent-1-ynyl)phenyl)propan-1-ol was prepared following the method used in Example 138.

Step 1: Sonogashira reaction of 24 with 5-methoxy-pent-1-yne gave tert-butyl-3-(3-(5-methoxypent-1-ynyl)phenyl) propylcarbamate as a yellow oil. Yield (280 mg, 27%): ¹H NMR (400 MHz, CDCl₃) δ 7.40 (s, 1H), 7.22-7.29 (m, 3H), 4.86 (bs, 1H), 4.71 (m, 1H), 3.52 (t, J=6.0 Hz, 2H), 3.45-3.50 (m, 1H), 3.37 (s, 3H), 3.13-3.18 (m, 1H), 2.49 (t, J=7.2 Hz, 2H), 1.82-1.89 (m, 4H), 1.45 (s, 9H).

Step 2: Deprotection of tert-butyl-3-(3-(5-methoxypent-1-ynyl)phenyl)propylcarbamate gave Example 152 hydrochloride as a pale yellow semi-solid. Yield (151 mg, 68%): ¹H NMR (400 MHz, DMSO-d₆) δ 7.67 (bs, 2H), 7.26-7.35 (m, 4H), 5.60 (bs, 1H), 4.65-4.69 (m, 1H), 3.44 (t, J=6.4, 2H), 3.25 (s, 3H), 2.80-2.85 (m, 2H), 2.46 (t, J=7.2 Hz, 2H), 1.72-1.87 (m, 4H). ¹³C NMR (100 MHz, DMSO-d₆) δ 146.1, 130.2, 128.9, 125.7, 123.4, 90.4, 81.2, 70.9, 69.7, 58.4, 36.9, 36.7, 28.7, 15.9. MS: 248 [M+1]⁺.

Example 153

PREPARATION OF (R)-3-AMINO-1-(3-(4-PHENYLBUT-1-YNYL)PHENYL)PROPAN-1-OL

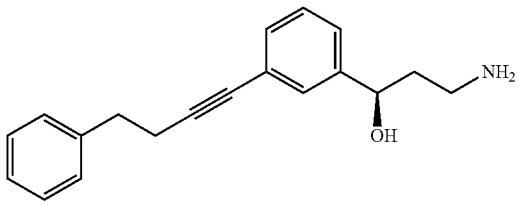 [SMILES: NCC[C@@H](O)c1cccc(C#CCCc2ccccc2)c1]

(R)-3-Amino-1-(3-(4-phenylbut-1-ynyl)phenyl)propan-1-ol was prepared following the method described in Scheme 16 for the absolute stereochemistry determination of Example 100.

Step 1. Sonogashira coupling between aryl bromide (64) and 4-phenylbutyne following the method used in Example 1 except that the reaction mixture was stirred at 70° C. for 4 h, and then at 60° C. for 17 h, afforded crude (R)-2,2,2-trifluoro-N-(3-hydroxy-3-(3-(4-phenylbut-1-ynyl)phenyl)propyl)acetamide as a light yellow oil which was used in the next step without purification. Yield (0.49 g, 77%).

Step 2. Deprotection of (R)-2,2,2-trifluoro-N-(3-hydroxy-3-(3-(4-phenylbut-1-ynyl)phenyl)propyl)acetamide following the method used in Example 100 (Determination of the Absolute Stereochemistry) gave Example 153 as a colorless oil. Yield (0.195 g, 60%); ¹H NMR (400 MHz, CD₃OD) δ 7.31-7.33 (m, 1H), 7.15-7.29 (m, 8H), 4.67 (dd, J=8.0, 5.3 Hz, 1H), 2.87 (t, J=7.2 Hz, 2H), 2.64-2.74 (m, 4H), 1.72-1.85 (m, 2H); ¹³C NMR (100 MHz, CD₃OD) δ 145.6, 140.9, 130.1, 128.8, 128.7, 128.4, 128.2, 126.1, 125.1, 124.1, 89.0, 81.1, 72.0, 71.9, 41.5, 38.4, 35.0, 21.2; RP-HPLC, 96.4% (AUC); LCMS m/z=280.2.

Example 154

PREPARATION OF 4-((3-(3-AMINO-1-HYDROXYPROPYL)-5-CHLOROPHENYL)ETHYNYL)HEPTAN-4-OL

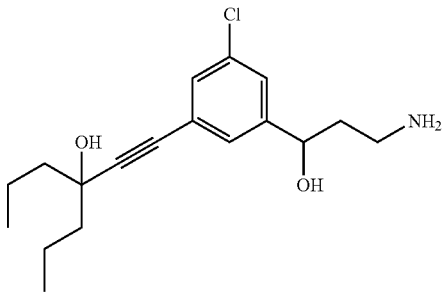 [SMILES: CCCC(O)(C#Cc1cc(Cl)cc(C(O)CCN)c1)CCC]

4-((3-(3-Amino-1-hydroxypropyl)-5-chlorophenyl)ethynyl)heptan-4-ol was prepared following the method used in Examples 107, 10 and 1.

Step 1: Alkylation of 5-bromo-3-chlorobenzaldehyde with acetonitrile gave 3-(5-bromo-3-chlorophenyl)-3-hydroxypropanenitrile as a clear oil. Yield (3.21 g, 54%): ¹H NMR (400 MHz, DMSO-d₆) δ 7.62 (t, J=2.0 Hz, 1H), 7.58-7.57 (m, 1H), 7.49-4.48 (m, 1H), 6.18 (d, J=4.8 Hz, 1H), 4.93-4.90 (m, 1H), 2.93 (ABd, J=16.8, 5.2 Hz, 1H), 2.86 (ABd, J=17.2, 6.8 Hz, 1H).

Step 2: Reduction of 3-(5-bromo-3-chlorophenyl)-3-hydroxypropanenitrile with BH₃-THF followed by protection of the amine gave N-(3-(5-bromo-3-chlorophenyl)-3-hydroxypropyl)-2,2,2-trifluoroacetamide as a clear oil. Yield (3.15 g, 71%): ¹H NMR (400 MHz, DMSO-d₆) δ 9.30 (bs, 1H), 7.55 (t, J=2.0 Hz, 1H), 7.49-7.48 (m, 1H), 7.394-7.387 (m, 1H), 5.57 (d, J=4.8 Hz, 1H), 3.30-3.15 (m, 2H), 1.86-1.70 (m, 2H).

Step 3: N-(3-(5-bromo-3-chlorophenyl)-3-hydroxypropyl)-2,2,2-trifluoroacetamide was coupled with alkynol 20 following the procedure described in Example 10 to give N-(3-(3-chloro-5-(3-hydroxy-3-propylhex-1-ynyl)phenyl)-3-hydroxypropyl)-2,2,2-trifluoroacetamide as a pale yellow oil. Yield (1.02 g, 66%):

¹H NMR (400 MHz, DMSO-d₆) δ 9.30 (bs, 1H), 7.35 (t, J=1.6 Hz, 1H), 7.30 (s, 1H), 7.25 (t, J=1.6 Hz, 1H), 5.51 (d, J=4.8, 1H), 5.17 (s, 1H), 3.30-3.14 (m, 2H), 1.85-1.69 (m, 2H), 1.62-1.39 (m, 8H), 0.89 (t, J=7.2 Hz, 6H).

Step 4: N-(3-(3-chloro-5-(3-hydroxy-3-propylhex-1-ynyl)phenyl)-3-hydroxypropyl)-2,2,2-trifluoroacetamide was deprotected following the procedure in Example 1 to give Example 154 as a pale yellow oil. Yield (0.68 g, 87%): ¹H NMR (400 MHz, DMSO-d₆) δ 7.33 (t, J=1.6 Hz, 1H), 7.26 (s, 1H), 7.22 (t, J=1.6 Hz, 1H), 5.17 (bs, 1H), 4.68-4.65 (m, 1H), 2.63-2.53 (m, 2H), 1.62-1.40 (m, 10H), 0.89 (t, J=7.2 Hz, 6H).

Example 155

PREPARATION OF 4-((5-(3-AMINO-1-HYDROXYPROPYL)-2-FLUOROPHENYL)ETHYNYL)HEPTAN-4-OL

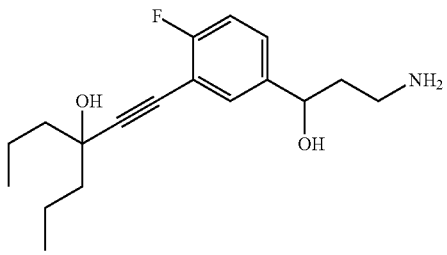 [SMILES: CCCC(O)(C#Cc1cc(C(O)CCN)ccc1F)CCC]

4-((5-(3-Amino-1-hydroxypropyl)-2-fluorophenyl)ethynyl)heptan-4-ol was prepared following the method used in Example 154.

Step 1: Alkylation of 3-bromo-4-fluorobenzaldehyde with acetonitrile gave 3-(3-bromo-4-fluorophenyl)-3-hydroxypropanenitrile as a pale yellow oil. Yield (4.2 g, 70%): $^1$H NMR (400 MHz, DMSO-d$_6$) δ 7.71 (dd, J=6.8, 2.0 Hz, 1H), 7.44 (ddd, J=8.4, 5.2, 2.4 Hz, 1H), 7.35 (t, J=8.8 Hz, 1H), 6.08 (bs, 1H), 4.90 (s, 1H), 2.90 (ABd, J=16.8, 5.2 Hz, 1H), 2.83 (ABd, J=16.8, 6.4 Hz, 1H).

Step 2: Reduction of 3-(3-bromo-4-fluorophenyl)-3-hydroxypropanenitrile with BH$_3$-THF followed by protection of the amine gave N-(3-(3-bromo-4-fluorophenyl)-3-hydroxypropyl)-2,2,2-trifluoroacetamide as a clear oil. Yield (4.3 g, 73%): $^1$H NMR (400 MHz, DMSO-d$_6$) δ 9.31 (bs, 1H), 7.62 (dd, J=6.8, 2.0 Hz, 1H), 7.37-7.33 (m, 1H), 7.30 (t, J=8.8 Hz, 1H), 5.48 (d, J=4.4 Hz, 1H), 4.60-4.56 (m, 1H), 3.28-3.15 (m, 2H), 1.84-1.71 (m, 2H).

Step 3: N-(3-(3-bromo-4-fluorophenyl)-3-hydroxypropyl)-2,2,2-trifluoroacetamide was coupled with alkynol 20 to give 2,2,2-trifluoro-N-(3-(4-fluoro-3-(3-hydroxy-3-propylhex-1-ynyl)phenyl)-3-hydroxypropyl)acetamide as a pale yellow oil. Yield (1.37 g, 78%): $^1$H NMR (400 MHz, DMSO-d$_6$) δ 9.31 (t, J=5.0 Hz, 1H), 7.37 (dd, J=6.8, 2.0 Hz, 1H), 7.34-7.30 (m, 1H), 7.18 (t, J=9.0 Hz, 1H), 5.41 (d, J=4.8 Hz, 1H), 5.19 (s, 1H), 4.58-4.54 (m, 1H), 3.28-3.16 (m, 2H), 1.82-1.69 (m, 2H), 1.63-1.41 (m, 8H), 0.89 (t, J=7.2 Hz, 6H).

Step 4: 2,2,2-trifluoro-N-(3-(4-fluoro-3-(3-hydroxy-3-propylhex-1-ynyl)phenyl)-3-hydroxypropyl)acetamide was deprotected to give Example 155) as a pale yellow oil. Yield (0.85 g, 82%): $^1$H NMR (400 MHz, DMSO-d$_6$) δ 7.35 (dd, J=6.8, 2.0 Hz, 1H), 7.31-7.27 (m, 1H), 7.16 (t, J=9.0 Hz, 1H), 5.19 (bs, 1H), 4.64 (t, J=6.4 Hz, 1H), 2.64-2.52 (m, 2H), 1.63-1.42 (m, 10H), 0.89 (t, J=7.2 Hz, 6H).

Example 156

PREPARATION OF 4-((3-(3-AMINO-1-HYDROXYPROPYL)-4-CHLOROPHENYL)ETHYNYL)HEPTAN-4-OL

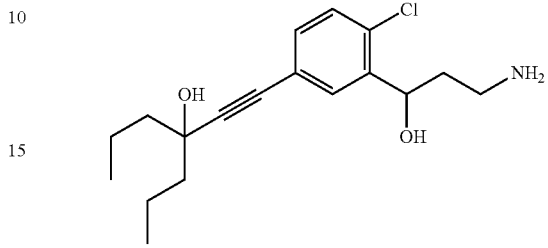

4-((3-(3-Amino-1-hydroxypropyl)-4-chlorophenyl)ethynyl)heptan-4-ol was prepared following the method used in Example 154.

Step 1: Alkylation of 5-bromo-2-chlorobenzaldehyde with acetonitrile gave 3-(5-bromo-2-chlorophenyl)-3-hydroxypropanenitrile as a pale yellow liquid. Yield (4.42 g, 75%): $^1$H NMR (400 MHz, DMSO-d$_6$) δ 7.74 (d, J=2.8 Hz, 1H), 7.53 (dd, J=8.8, 2.8 Hz, 1H), 7.39 (d, J=8.8 Hz, 1H), 6.30 (d, J=4.8 Hz, 1H), 5.13-5.09 (m, 1H), 2.96 (ABd, J=16.8, 4.8 Hz, 1H), 2.83 (ABd, J=17.0, 6.0 Hz, 1H).

Step 2: Reduction of 3-(5-bromo-2-chlorophenyl)-3-hydroxypropanenitrile with BH$_3$-THF followed by protection of the amine gave N-(3-(5-bromo-2-chlorophenyl)-3-hydroxypropyl)-2,2,2-trifluoroacetamide as an orange oil. Yield (2.6 g, 43%): $^1$H NMR (400 MHz, DMSO-d$_6$) δ 9.42 (bs, 1H), 7.67 (d, J=2.4 Hz, 1H), 7.45 (dd, J=8.8, 2.4 Hz, 1H), 7.33 (d, J=8.8 Hz, 1H), 5.64 (d, J=4.4 Hz, 1H), 3.33-3.29 (m, 2H), 1.96-1.80 (m, 1H), 1.68-1.59 (m, 1H).

Step 3: N-(3-(5-bromo-2-chlorophenyl)-3-hydroxypropyl)-2,2,2-trifluoroacetamide was coupled with alkynol 20 to give N-(3-(2-chloro-5-(3-hydroxy-3-propylhex-1-ynyl)phenyl)-3-hydroxypropyl)-2,2,2-trifluoroacetamide as a pale yellow oil. Yield (1.03 g, 68%): $^1$H NMR (400 MHz, DMSO-d$_6$) δ 9.42 (t, J=5.6 Hz, 1H), 7.53 (d, J=2.0 Hz, 1H), 7.34 (d, J=8.0 Hz, 1H), 7.23 (dd, J=8.0 Hz, 2.0, 1H), 5.57 (d, J=4.0 Hz, 1H), 5.17 (s, 1H), 4.87-4.82 (m, 1H), 3.33-3.28 (m, 2H), 1.87-1.79 (m, 1H), 1.66-1.39 (m, 9H), 0.89 (t, J=7.2 Hz, 6H).

Step 4: N-(3-(2-chloro-5-(3-hydroxy-3-propylhex-1-ynyl)phenyl)-3-hydroxypropyl)-2,2,2-trifluoroacetamide was deprotected to give Example 156 as a pale yellow oil. Yield (0.77 g, 98%): $^1$H NMR (400 MHz, DMSO-d$_6$) δ 7.53 (d, J=2.4 Hz, 1H), 7.34 (d, J=8.0 Hz, 1H), 7.23 (dd, J J=8.0, 2.4 Hz, 1H), 5.17 (bs, 1H), 4.93 (dd, J=8.8, 2.4 Hz, 1H), 2.72-2.63 (m, 2H), 1.70-1.62 (m, 1H), 1.59-1.39 (m, 9H), 0.89 (t, J=7.2 Hz, 6H).

Example 157

PREPARATION OF 4-((3-(3-AMINO-1-HYDROXYPROPYL)-5-METHOXYPHENYL)ETHYNYL)HEPTAN-4-OL

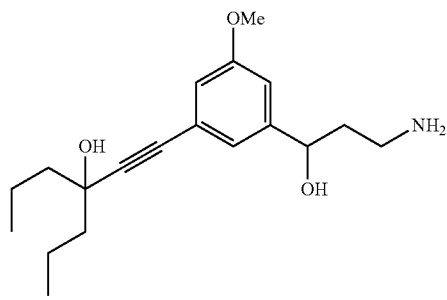 [SMILES: CCCC(O)(C#Cc1cc(OC)cc(C(O)CCN)c1)CCC]

4-((3-(3-Amino-1-hydroxypropyl)-5-methoxyphenyl)ethynyl)heptan-4-ol was prepared following the method used in Example 107.

Step 1: Alkylation of 3-bromo-5-methoxybenzaldehyde with acetonitrile gave 3-(3-bromo-5-methoxyphenyl)-3-hydroxypropanenitrile as a pale yellow oil. Yield (4.1 g, 70%): $^1$H NMR (400 MHz, DMSO-$d_6$) δ 7.16-7.15 (m, 1H), 7.04-7.03 (m, 1H), 6.97-6.96 (m, 1H), 6.04 (d, J=4.8 Hz, 1H), 4.87-4.83 (m, 1H), 3.74 (s, 3H), 2.89 (ABd, J=16.4, 5.2 Hz, 1H), 2.81 (ABd, J=16.8, 6.8 Hz, 1H). h

Example 158

PREPARATION OF 2-(3-(5-METHOXYPENT-1-YNYL)PHENOXY)ETHANAMINE

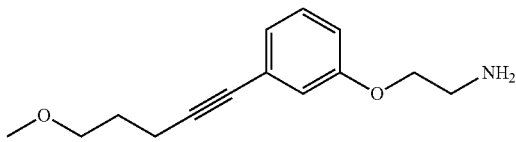

2-(3-(5-Methoxypent-1-ynyl)phenoxy)ethanamine was prepared following the method used in Example 18.

Step 1: Sonogashira reaction of bromide 19 with 5-methoxy-pent-1-yne gave 2,2,2-trifluoro-N-(2-(3-(5-methoxypent-1-ynyl)phenoxy)ethyl)acetamide as a brown oil. Yield (1.2 g, 57%): $^1$H NMR (400 MHz, DMSO-$d_6$) δ 7.19-7.23 (m, 1H), 7.04 (d, J=7.2 Hz, 1H), 6.92 (s, 1H), 6.82 (dd, J=8.0, 2.4 Hz, 1H), 4.09 (t, J=5.0 Hz, 2H), 3.76-3.80 (m, 2H), 3.52 (t, J=6.2 Hz, 2H), 3.36 (s, 3H), 2.50 (t, J=7.2 Hz, 2H), 1.83-1.90 (m, 2H).

Step 2: Deprotection of 2,2,2-trifluoro-N-(2-(3-(5-methoxypent-1-ynyl)phenoxy)ethyl)acetamide gave Example 158 as brown oil. Yield (0.125 g, 31%): $^1$H NMR (400 MHz, DMSO-$d_6$) δ 7.22-7.26 (m, 1H), 6.91-6.96 (m, 3H), 3.94 (t, J=7.2 Hz, 2H), 3.43 (t, J=6.2 Hz, 2H), 3.25 (s, 3H), 2.89 (t, J=5.6 Hz, 2H), 2.45 (t, J=7.2 Hz, 2H), 1.72-1.79 (m, 2H). $^{13}$C NMR (100 MHz, DMSO-$d_6$) δ 158.4, 129.7, 124.2, 123.4, 116.8, 114.9, 89.9, 80.6, 70.4, 69.4, 57.9, 40.5, 28.2, 15.5. ESI MS m/z 234 [M+1]$^+$.

Example 159

PREPARATION OF 4-((3-((1R,2R)-3-AMINO-1-HYDROXY-2-METHYLPROPYL)-PHENYL)ETHYNYL)HEPTAN-4-OL

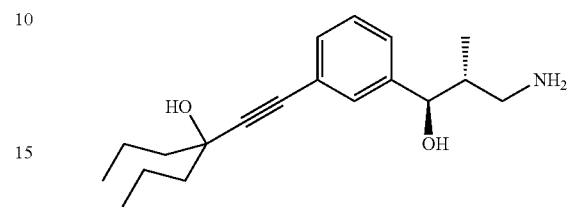

4-((3-((1R,2R)-3-Amino-1-hydroxy-2-methylpropyl)phenyl)ethynyl)heptan-4-ol was prepared following the method shown in Scheme 24.

SCHEME 24

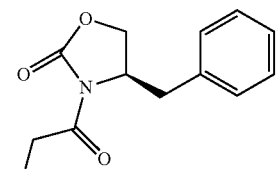

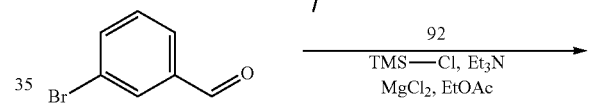

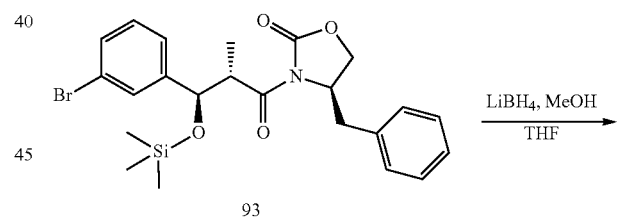

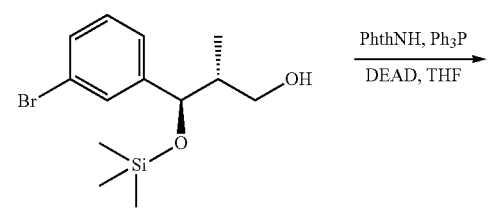

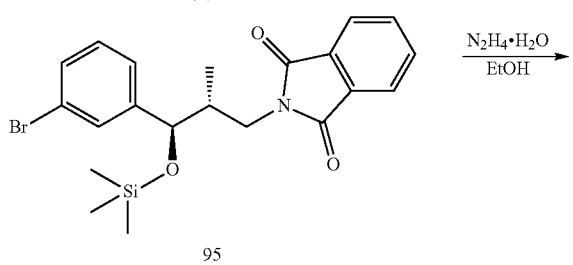

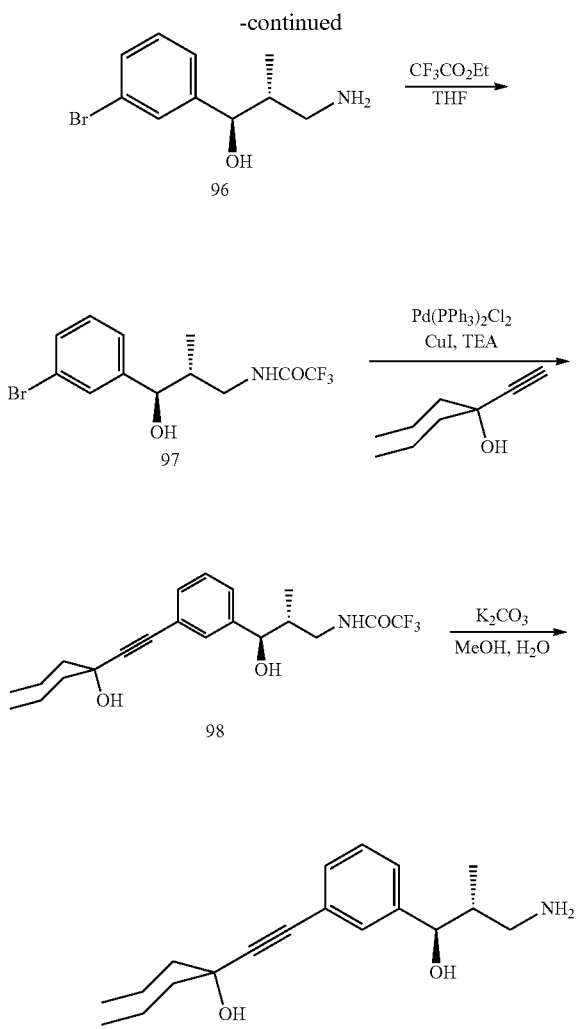

Step 1. To a mixture of 3-bromobenzaldehyde (22) (4.16 g, 22.5 mmol), (R)-4-benzyl-3-propionyloxazolidin-2-one (92) (5.111 g, 21.9 mmol) and anhydrous MgCl$_2$ (0.21 g, 2.23 mmol) in ethyl acetate (40 mL) was added Et$_3$N (6.3 mL, 45.2 mmol) and chlorotrimethylsilane (4.3 mL, 34.0 mmol) under argon. The reaction mixture was stirred for 22 hrs at room temperature, then filtered through a layer of a silica gel, washing with EtOAc. The filtrate was concentrated under reduced pressure and the residue was purified by flash chromatography (2 to 25% EtOAc/hexane gradient) to give oxazolidinone 93 as a colorless oil. Yield (9.79 g, 91%); $^1$H NMR (400 MHz, DMSO-d$_6$) δ 7.56 (t, J=1.8 Hz, 1H), 7.49 (ddd, J=1.2, 2.0, 7.8 Hz, 1H), 7.40 (dt, J=1.2, 7.6 Hz, 1H), 7.23-7.35 (m, 6H), 4.94 (d, J=9.4 Hz, 1H), 4.67-4.75 (m, 1H), 4.30 (t, J=8.6 Hz, 1H), 4.12 (dd, J=2.9, 8.8 Hz, 1H), 4.00-4.08 (m, 1H), 3.02 (dd, J=3.1, 13.5 Hz, 1H), 2.91 (dd, J=7.4, 13.5 Hz, 1H), 0.78 (d, J=7.0 Hz, 3H), −0.09 (s, 9H).

Step 2. To an ice-cold solution of LiBH$_4$ (2M in THF, 65 mL, 130 mmol) was added MeOH (2.6 mL, 64.2 mmol) and the mixture was stirred at 0° C. for 5 mins. A solution of oxazolidinone 93 (9.59 g, 19.6 mmol) in anhydrous THF (170 mL) was added and reaction mixture was stirred at 0° C. for 1.5 hrs and then at room temperature for 1.5 hrs. An aqueous solution of NH$_4$Cl (25%, 75 mL) was added slowly to reaction mixture for over 1 hr followed by addition of EtOAc and stirring was continued at room temperature until the mixture became clear. The layers were separated and the aqueous layer was extracted with EtOAc. The combined organic layers were washed with saturated brine, dried with anhydrous MgSO$_4$, filtered and concentrated under reduced pressure. The residue was purified by flash chromatography (5 to 30% EtOAc/hexane gradient) to give alcohol 94 as colorless oil. Yield (2.97 g, 48%); $^1$H NMR (400 MHz, DMSO-d$_6$) δ 7.38-7.43 (m, 2H), 7.24-7.27 (m. 2H), 4.58 (d, J=6.85 Hz, 1H), 4.38 (t, J=5.3 Hz, 1H), 3.32-3.38 (m, 1H), 3.22-3.29 (m, 1H), 1.73-1.80 (m, 1H), 0.61 (d, J=6.85 Hz, 3H), −0.05 (s, 9H).

Step 3. DEAD (1.9 mL, 11.4 mmol) was added to a solution of alcohol 94 (2.97 g, 9.36 mmol), phthalimide (1.52 g, 10.3 mmol) and Ph$_3$P (3.02 g, 11.5 mmol) in anhydrous THF (40 mL) and the mixture was stirred at room temperature for 1 hr. The solvent was concentrated under reduced pressure to give an orange residue which was vigorously stirred with 10% EtOAc in hexanes. The triphenylphosphine oxide precipitated and was removed by filtration, washing with 5% EtOAc in hexanes. The filtrate was concentrated under reduced pressure and the residue was purified by flash chromatography (5 to 30% EtOAc/hexane gradient) to give bromide 95 as colorless oil. Yield (3.97 g, 95%): $^1$H NMR (400 MHz, DMSO-d$_6$) δ 7.76-7.80 (m, 4H), 7.47 (t, J=1.8 Hz, 1H), 7.27-7.35 (m, 2H), 7.22 (t, J=7.8 Hz, 1H), 4.66 (d, J=5.7 Hz, 1H), 3.63 (dd, J=5.7, 13.7 Hz, 1H), 3.38 (dd, J=8.8, 13.5 Hz, 1H), 2.24-2.32 (m, 1H), 0.68 (d, J=6.8 Hz, 3H), −0.03 (s, 9H).

Step 4: Deprotection of 2-((2R,3R)-3-(3-bromophenyl)-2-methyl-3-(trimethylsilyloxy)propyl)isoindoline-1,3-dione (95) following method used in Example 17 gave (1R,2R)-3-amino-1-(3-bromophenyl)-2-methylpropan-1-ol (96) as a colorless oil that is directly used in next step reaction without further purification.

Step 5: Protection of (1R,2R)-3-amino-1-(3-bromophenyl)-2-methylpropan-1-ol (96) was performed following the method used in Example 1. Purification by flash column chromatography (silica gel, 5% to 30% of 20% EtOAc/hexanes gradient) gave N-((2R,3R)-3-(3-bromophenyl)-3-hydroxy-2-methylpropyl)-2,2,2-trifluoroacetamide (97) as a colorless oil. Yield (1.38 g, 81%): $^1$H NMR (400 MHz, DMSO-d$_6$) δ 9.21 (m, 1H), 7.49 (t, J=1.6 Hz, 1H), 7.41 (dt, J=7.2, 1.6 Hz, 1H), 7.25-7.29 (m, 2H), 5.49 (d, J=4.4 Hz, 1H), 4.40 (dd, J=6.4, 4.8 Hz, 1H), 3.23-3.29 (m, 1H), 3.01-3.08 (m, 1H), 1.92-2.08 (m, 1H), 0.68 (d, J=6.8 Hz, 3H).

Step 6: Coupling of bromide 97 and 4-ethynylheptan-4-ol was performed following the method used in Example 1 (silica gel, 40% to 60% of EtOAc/hexanes gradient) gave 2,2,2-trifluoro-N-((2R,3R)-3-hydroxy-3-(3-(3-hydroxy-3-propylhex-1-ynyl)phenyl)-2-methylpropyl)acetamide (98) as a light yellow oil. Yield (0.01 g, 25%): $^1$H NMR (400 MHz, MeOH-d$_4$) δ 7.38 (s, 1H), 7.27-7.30 (m, 3H), 4.40 (d, J=7.2 Hz, 1H), 3.45 (dd, J=13.6, 4.2 Hz, 1H), 3.26 (dd, J=13.6, 8.0 Hz, 1H), 2.03-2.12 (m, 1H), 1.52-1.99 (m, 8H), 0.97 (t, J=7.2 Hz, 6H), 0.76 (d, J=7.2 Hz, 3H).

Step 7: Deprotection of 98 was performed following the method used in Example 1 gave Example 159 as a light yellow oil. Yield (0.04 g, 45%): $^1$H NMR (400 MHz, MeOH-d$_4$) δ 7.37 (s, 1H), 7.28-7.30 (m, 3H), 4.39 (d, J=8.0 Hz, 1H), 2.82 (dd, J=12.8, 6.4 Hz, 1H), 2.67 (dd, J=12.8, 6.0 Hz, 1H), 1.79-1.88 (m, 1H), 1.54-1.72 (m, 8H), 0.97 (t, J=7.2 Hz, 6H), 0.76 (d, J=7.2 Hz, 3H).

Example 160

PREPARATION OF 1-((3-((1R,2R)-3-AMINO-1-HYDROXY-2-METHYLPROPYL)PHENYL) ETHYNYL)CYCLOPENTANOL

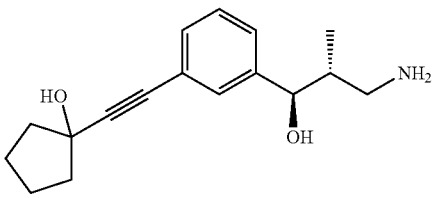 [SMILES: C[C@H](CN)[C@@H](O)c1cccc(C#CC2(O)CCCC2)c1]

1-((3-((1R,2R)-3-Amino-1-hydroxy-2-methylpropyl)phenyl)ethynyl)-cyclopentanol was prepared following the method used in Example 159.

Step 1: Coupling of bromide 97 and 1-ethynylcyclopentanol was performed following the method used in Example 18 except using triethyl amine as solvent and no phosphine (silica gel, 50% to 65% of EtOAc/hexanes gradient) gave 2,2,2-trifluoro-N-((2R,3R)-3-hydroxy-3-(3-((1-hydroxycyclopentyl)ethynyl)phenyl)-2-methylpropyl)acetamide as a light yellow oil. Yield (0.33 g, 89%): $^1$H NMR (400 MHz, MeOH-$d_4$) δ 7.38 (s, 1H), 7.25-7.33 (m, 3H), 4.40 (d, J=7.2 Hz, 1H), 3.45 (dd, J=13.2, 4.2 Hz, 1H), 3.26 (dd, J=13.2, 8.0 Hz, 1H), 1.95-2.10 (m, 5H), 1.73-1.88 (m, 4H), 0.76 (d, J=6.8 Hz, 3H).

Step 2: Deprotection of 2,2,2-trifluoro-N-((2R,3R)-3-hydroxy-3-(3-((1-hydroxycyclopentyl)ethynyl)phenyl)-2-methylpropyl)acetamide was performed following the method used in Example 11 to give Example 160 as a light yellow solid. Yield (0.07 g, 41%): $^1$H NMR (400 MHz, MeOH-$d_4$) δ 7.87 (s, 1H), 7.77-7.80 (m, 3H), 4.99 (d, J=8.0 Hz, 1H), 3.32 (dd, J=12.8, 6.0 Hz, 1H), 3.17 (dd, J=12.8, 6.0 Hz, 1H), 2.22-2.54 (m, 9H), 1.22 (d, J=6.8 Hz, 3H).

Example 161

PREPARATION OF (R)-3-AMINO-1-(3-(4-CYCLOHEXYLBUT-1-YNYL)PHENYL)PROPAN-1-OL

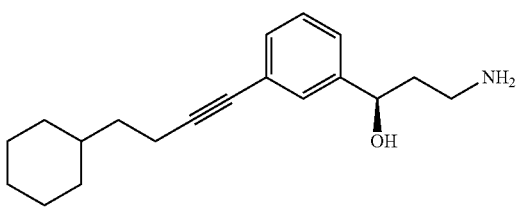 [SMILES: NCC[C@@H](O)c1cccc(C#CCCC2CCCCC2)c1]

(R)-3-amino-1-(3-(4-cyclohexylbut-1-ynyl)phenyl)propan-1-ol was prepared following the method shown in Scheme 16.

Step 1. Sonogashira coupling between aryl bromide 64 and 4-cyclohexanebutyne following the method used in Example 153 afforded (R)—N-(3-(3-(4-cyclohexylbut-1-ynyl)phenyl)-3-hydroxypropyl)-2,2,2-trifluoroacetamide as a brownish oil. Yield (0.672 g, 88%). $^1$H NMR (400 MHz, DMSO-$d_6$) δ 9.32 (br. t, 1H), 7.28-7.32 (m, 1H), 7.23-7.28 (m, 2H), 7.18-7.23 (m, 1H), 5.35 (d, J=4.5 Hz, 1H), 4.54 (dt, J=4.9, 7.4 Hz, 1H), 3.15-3.27 (m, 2H), 2.39 (t, J=7.2 Hz, 2H), 1.53-1.84 (m, 7H), 1.30-1.50 (m, 3H), 1.05-1.30 (m, 3H), 0.78-0.92 (m, 2H).

Step 2. Deprotection of (R)—N-(3-(3-(4-cyclohexylbut-1-ynyl)phenyl)-3-hydroxypropyl)-2,2,2-trifluoroacetamide following the method used in Example 153 gave Example 161 as a colorless oil. Yield (0.377 g, 75%); $^1$H NMR (400 MHz, CD$_3$OD) δ 7.33-7.35 (m, 1H), 7.19-7.28 (m, 3H), 4.68 (dd, J=5.3, 8.0 Hz, 1H), 2.65-2.77 (m, 2H), 2.40 (t, J=7.2 Hz, 2H), 1.62-1.90 (m, 7H), 1.40-1.51 (m, 3H), 1.13-1.33 (m, 3H), 0.85-0.95 (m, 2H); $^{13}$C NMR (100 MHz, CD$_3$OD) δ 145.6, 130.1, 128.8, 128.1, 125.0, 124.3, 89.8, 80.4, 72.0, 41.6, 38.4, 36.9, 36.3, 32.9, 26.6, 26.2, 16.3; RP-HPLC $t_R$=7.65 min, 92.0% (AUC); LC-MS m/z=286.4 [M+H]$^+$.

Example 162

PREPARATION OF 4-((5-(3-AMINO-1-HYDROXYPROPYL)-2-METHOXY-PHENYL)ETHYNYL) HEPTAN-4-OL

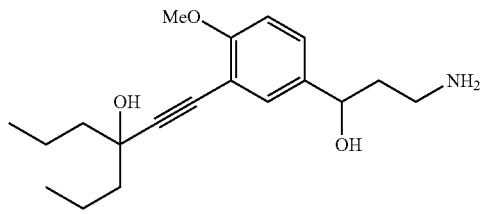 [SMILES: CCCC(O)(C#Cc1cc(C(O)CCN)ccc1OC)CCC]

4-((5-(3-Amino-1-hydroxypropyl)-2-methoxyphenyl)ethynyl)heptan-4-ol was prepared following the method used in Example 107.

Step 1: Addition of 3-bromo-4-methoxybenzaldehyde to acetonitrile gave 3-(3-bromo-4-methoxyphenyl)-3-hydroxypropanenitrile as a pale orange oil. Yield (10.32 g, 96%): $^1$H NMR (400 MHz, DMSO-$d_6$) δ 7.58 (d, J=2.0 Hz, 1H), 7.35 (dd, J=8.8, 2.0 Hz, 1H), 7.07 (d, J=8.8 Hz, 1H), 5.93 (d, J=4.4 Hz, 1H), 4.85-4.81 (m, 1H). 3.81 (s, 3H), 2.86 (ABd, J=16.4, 4.8 Hz, 1H), 2.79 (ABd, J=16.8, 6.8 Hz, 1H).

Step 2: Reduction of 3-(3-bromo-4-methoxyphenyl)-3-hydroxypropanenitrile with BH$_3$-THF followed by protection of the amine gave N-(3-(3-bromo-4-methoxyphenyl)-3-hydroxypropyl)-2,2,2-trifluoroacetamide as an orange oil. Yield (5.76 g, 40%): $^1$H NMR (400 MHz, DMSO-$d_6$) δ 9.31 (bs, 1H), 7.49 (d, J=2.0 Hz, 1H), 7.26 (dd, J=8.8, 2.0 Hz, 1H), 7.03 (d, J=8.8 Hz, 1H), 5.32 (d, J=4.8 Hz, 1H), 4.53-4.49 (m, 1H), 3.80 (s, 3H), 3.24-3.15 (m, 2H), 1.79-1.72 (m, 2H).

Step 3: N-(3-(3-bromo-4-methoxyphenyl)-3-hydroxypropyl)-2,2,2-trifluoroacetamide was coupled with alkynol 20 following the procedure described in Example 10 to give 2,2,2-trifluoro-N-(3-hydroxy-3-(3-hydroxy-3-propylhex-1-ynyl)-4-methoxyphenyl)propyl)acetamide as a yellow oil. Yield (0.92 g, 55%): $^1$H NMR (400 MHz, DMSO-$d_6$) δ 9.31 (t, J=5.0 Hz, 1H), 7.24-7.21 (m, 2H), 6.95 (d, J=9.2 Hz, 1H), 5.25 (d, J=4.8 Hz, 1H), 5.05 (s, 1H), 4.51-4.47 (m, 1H), 3.75

(s, 3H), 3.24-3.17 (m, 2H), 1.77-1.72 (m, 2H), 1.61-1.42 (m, 8H), 0.89 (t, J=7.0 Hz, 6H).

Step 4: 2,2,2-trifluoro-N-(3-hydroxy-3-(3-(3-hydroxy-3-propylhex-1-ynyl)-4-methoxyphenyl)propyl)acetamide was deprotected following the procedure in Example 1 to give Example 162 as a pale yellow oil. Yield (0.53 g, 76%): $^1$H NMR (400 MHz, DMSO-$d_6$) δ 7.22-7.19 (m, 2H), 6.92 (d, J=8.4 Hz, 1H), 5.06 (bs, 1H), 4.58-4.55 (m, 1H), 3.74 (s, 3H), 2.63-2.51 (m, 2H), 1.64-1.42 (m, 10H), 0.89 (t, J=7.0 Hz, 6H).

Example 163

PREPARATION OF 4-((3-(3-AMINO-1-HYDROXYPROPYL)-4-METHYLPHENYL)ETHYNYL)HEPTAN-4-OL

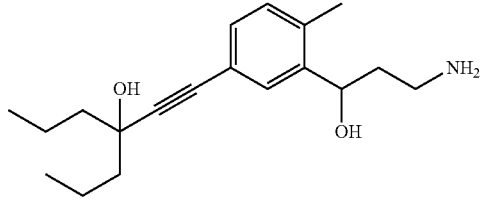 [SMILES: CCCC(O)(C#Cc1ccc(C)c(C(O)CCN)c1)CCC]

4-((3-(3-Amino-1-hydroxypropyl)-4-methylphenyl)ethynyl)heptan-4-ol was prepared following the method used in Example 154.

Step 1: Addition of 5-bromo-2-methylbenzaldehyde to acetonitrile gave 3-(5-bromo-2-methylphenyl)-3-hydroxypropanenitrile as a pale yellow oil. Yield (3.33 g, 86%): $^1$H NMR (400 MHz, DMSO-$d_6$) δ 7.61 (d, J=2.0 Hz, 1H), 7.35 (dd, J=8.0, 2.0 Hz, 1H), 7.09 (d, J=8.0 Hz, 1H), 5.96 (d, J=4.4 Hz, 1H), 5.04-5.00 (m, 1H), 2.88 (ABd, J=16.8, 4.4 Hz, 1H), 2.77 (ABd, J=16.8, 6.4 Hz, 1H), 2.23 (s, 3H).

Step 2: Reduction of 3-(3-bromo-2-methylphenyl)-3-hydroxypropanenitrile with BH$_3$-THF followed by protection of the amine gave N-(3-(3-bromo-2-methylphenyl)-3-hydroxypropyl)-2,2,2-trifluoroacetamide as a pale yellow oil. Yield (3.25 g, 69%): $^1$H NMR (400 MHz, DMSO-$d_6$) δ 9.38 (bs, 1H), 7.53 (d, J=2.4 Hz, 1H), 7.28 (dd, J=8.0, 2.4 Hz, 1H), 7.05 (d, J=8.0 Hz, 1H), 4.73-4.70 (m, 1H), 3.36-3.26 (m, 2H), 2.17 (s, 3H), 1.79-1.71 (m, 1H), 1.68-1.59 (m, 1H).

Step 3: N-(3-(3-bromo-2-methylphenyl)-3-hydroxypropyl)-2,2,2-trifluoroacetamide was coupled with alkynol 20 to give 2,2,2-trifluoro-N-(3-hydroxy-3-(5-(3-hydroxy-3-propylhex-1-ynyl)-2-methylphenyl)propyl)acetamide as a yellow oil. Yield (1.11 g, 62%): $^1$H NMR (400 MHz, DMSO-$d_6$) δ 9.38 (t, J=5.2 Hz, 1H), 7.41 (d, J=1.6 Hz, 1H), 7.11 (dd, J=8.0, 1.6 Hz, 1H), 7.07 (d, J=8.0 Hz, 1H), 5.26 (d, J=4.4 Hz, 1H), 5.08 (s, 1H), 4.74-4.70 (m, 1H), 3.35-3.25 (m, 2H), 2.21 (s, 3H), 1.78-1.70 (m, 2H), 1.68-1.40 (m, 8H), 0.89 (t, J=7.2 Hz, 6H)

Step 4: 2,2,2-trifluoro-N-(3-hydroxy-3-(5-(3-hydroxy-3-propylhex-1-ynyl)-2-methylphenyl)propyl)acetamide was deprotected to give Example 163 as a pale yellow oil. Yield (0.71 g, 85%): $^1$H NMR (400 MHz, DMSO-$d_6$) δ 7.41 (d, J=1.6 Hz, 1H), 7.08 (dd, J=7.6, 1.4 Hz, 1H), 7.05 (d, J=7.6 Hz, 1H), 5.09 (bs, 1H), 4.83-4.80 (m, 1H), 2.72-2.61 (m, 2H), 2.23 (s, 3H), 1.61-1.41 (m, 10H), 0.89 (t, J=7.0 Hz, 6H).

Example 164

PREPARATION OF (E)-4-((3-(3-AMINOPROP-1-ENYL)PHENYL)ETHYNYL)HEPTAN-4-OL

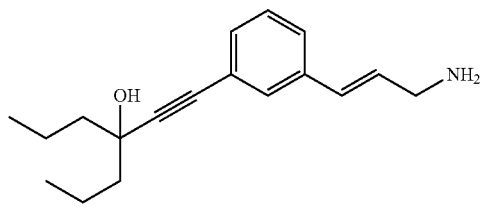 [SMILES: CCCC(O)(C#Cc1cccc(/C=C/CN)c1)CCC]

(E)-4-(3-(3-Aminoprop-1-enyl)phenyl)ethynyl)heptan-4-ol was prepared following the methods used in Example 1 and 123.

Step 1: 4-((3-bromophenyl)ethynyl)heptan-4-ol was coupled with N-allyl-2,2,2-trifluoroacetamide following the procedure described in Example 123 to give (E)-2,2,2-trifluoro-N-(3-(3-(3-hydroxy-3-propylhex-1-ynyl)phenyl)allyl)acetamide as a pale yellow oil. Yield (0.082 g, 10%): $^1$H NMR (400 MHz, DMSO-$d_6$) δ 9.68 (t, J=5.4 Hz, 1H), 7.42-7.39 (m, 2H), 7.30 (t, J=8.0 Hz, 1H), 7.23 (dt, J=7.6, 1.4 Hz, 1H), 6.51 (d, J=16.0 Hz, 1H), 6.29 (dt, J=16.0, 6.0 Hz, 1H), 5.13 (s, 1H), 3.95 (t, J=5.4 Hz, 2H), 1.60-1.40 (m, 8H), 0.89 (t, J=7.2 Hz, 6H).

Step 2: (E)-2,2,2-trifluoro-N-(3-(3-(3-hydroxy-3-propylhex-1-ynyl)phenyl)allyl)acetamide was deprotected following the procedure in Example 1 to give Example 164 as a pale yellow oil. Yield (0.038 g, 64%): $^1$H NMR (400 MHz, DMSO-$d_6$) δ 7.36 (dd, J=8.0, 1.2 Hz, 1H), 7.27 (t, J=7.8 Hz, 1H), 7.17 (dt, J=7.8 Hz, 1.4, 1H), 6.45 (d, J=16.0 Hz, 1H), 6.36 (dt, J=16.0, 5.2 Hz, 1H), 5.13 (bs, 1H), 3.28 (dd, J=4.0, 1.0 Hz, 2H), 1.62-1.42 (m, 10H), 0.89 (t, J=7.0 Hz, 6H).

Example 165

PREPARATION OF 4-((3-(3-AMINOPROP-1-YNYL)PHENYL)ETHYNYL)HEPTAN-4-OL

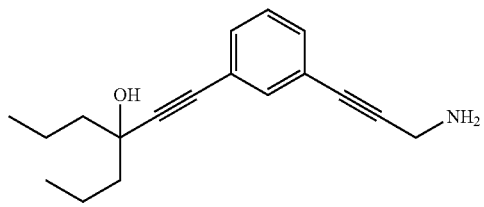 [SMILES: CCCC(O)(C#Cc1cccc(C#CCN)c1)CCC]

4-((3-(3-Aminoprop-1-ynyl)phenyl)ethynyl)heptan-4-ol was prepared following the methods used in Examples 1 and 10.

Step 1: 1,3-Dibromobenzene was coupled with alkynol 20 following the procedure described in Example 10 to give 4-((3-bromophenyl)ethynyl)heptan-4-ol as a yellow liquid. Yield (4.2 g, 65%): $^1$H NMR (400 MHz, DMSO-$d_6$) δ 7.56-7.52 (m, 2H), 7.36 (dt, J=8.0, 1.2 Hz, 1H), 7.30 (t, J=8.0 Hz, 1H), 5.18 (s, 1H), 1.60-1.40 (m, 8H), 0.89 (t, J=7.2 Hz, 6H).

Step 2: 4-((3-bromophenyl)ethynyl)heptan-4-ol was coupled with 2,2,2-trifluoro-N-(prop-2-ynyl)acetamide following the procedure described in Example 10 to give 2,2,2-trifluoro-N-(3-(3-(3-hydroxy-3-propylhex-1-ynyl)phenyl)prop-2-ynyl)acetamide as a pale yellow oil. Yield (0.083 g, 6%): $^1$H NMR (400 MHz, DMSO-$d_6$) δ 10.03 (t, J=5.2 Hz, 1H), 7.40-7.33 (m, 4H), 5.16 (bs, 1H), 4.25 (d, J=5.6 Hz, 2H), 1.61-1.39 (m, 8H), 0.89 (t, J=7.2 Hz, 6H).

Step 3: 2,2,2-trifluoro-N-(3-(3-(3-hydroxy-3-propylhex-1-ynyl)phenyl)prop-2-ynyl)acetamide was deprotected following the procedure in Example 1 to give Example 165 as a pale yellow oil. Yield (0.041 g, 75%): $^1$H NMR (400 MHz, DMSO-$d_6$) δ 7.34-7.31 (m, 4H), 5.16 (s, 1H), 3.47 (s, 2H), 1.77 (bs, 2H), 1.61-1.41 (m, 8H), 0.89 (t, J=7.2 Hz, 6H).

Example 166

PREPARATION OF
4-((3-(AMINOMETHYL)PHENYL)ETHYNYL)HEPTAN-4-OL

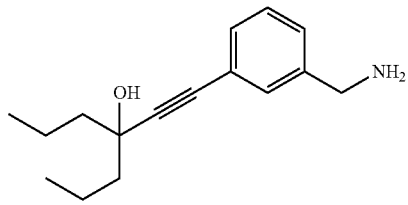 [SMILES: CCCC(O)(C#Cc1cccc(CN)c1)CCC]

4-((3-(Aminomethyl)phenyl)ethynyl)heptan-4-ol was prepared following the methods used in Examples 1 and 10.

Step 1: N-(3-bromobenzyl)-2,2,2-trifluoroacetamide was coupled with alkynol 20 following the procedure described in Example 10 to give 2,2,2-trifluoro-N-(3-(3-hydroxy-3-propylhex-1-ynyl)benzyl)acetamide as a yellow oil. Yield (0.462 g, 38%): $^1$H NMR (400 MHz, DMSO-$d_6$) δ 9.97 (t, J=5.6 Hz, 1H), 7.32 (t, J=7.8 Hz, 1H), 7.27-7.22 (m, 3H), 5.15 (bs, 1H), 4.35 (d, J=6.0 Hz, 2H), 1.60-1.41 (m, 8H), 0.89 (t, J=7.2 Hz, 6H).

Step 2: 2,2,2-trifluoro-N-(3-(3-hydroxy-3-propylhex-1-ynyl)benzyl)acetamide was deprotected following the procedure in Example 1 to give Example 166 as a pale yellow oil. Yield (0.254 g, 78%): $^1$H NMR (400 MHz, DMSO-$d_6$) δ 7.33 (s, 1H), 7.27-7.22 (m, 2H), 7.18-7.16 (m, 1H), 5.11 (bs, 1H), 3.66 (s, 2H), 1.97 (bs, 2H), 1.60-1.42 (m, 8H), 0.89 (t, J=7.0 Hz, 6H).

Example 167

PREPARATION OF 4-((3-(2-AMINOETHYL)PHENYL)ETHYNYL)HEPTAN-4-OL

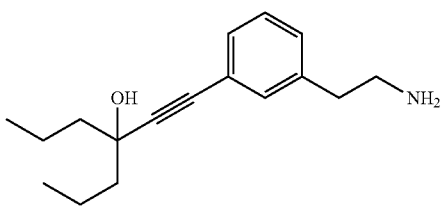 [SMILES: CCCC(O)(C#Cc1cccc(CCN)c1)CCC]

Example 167 is an alternative synthesis of 4-((3-(2-Aminoethyl)phenyl)ethynyl)heptan-4-ol which was also prepared in Example 141. 4-((3-(2-Aminoethyl)phenyl)ethynyl)heptan-4-ol was prepared following the methods used in Examples 1 and 10.

Step 1: N-(3-bromobenzyl)-2,2,2-trifluoroacetamide was coupled with alkynol 20 following the procedure described in Example 10 to give 2,2,2-trifluoro-N-(3-(3-hydroxy-3-propylhex-1-ynyl)phenethyl)acetamide as a yellow oil. Yield (0.902 g, 65%): $^1$H NMR (400 MHz, DMSO-$d_6$) δ 9.43 (t, J=5.2 Hz, 1H), 7.25 (t, J=7.8 Hz, 1H), 7.20-7.15 (m, 3H), 5.11 (s, 1H), 3.41-3.36 (m, 2H), 2.76 (t, J=7.0 Hz, 2H), 1.61-1.40 (m, 8H), 0.89 (t, J=7.2 Hz, 6H)

Step 2: 2,2,2-trifluoro-N-(3-(3-hydroxy-3-propylhex-1-ynyl)phenethyl)acetamide was deprotected following the procedure in Example 1 to give Example 167 as a pale yellow oil. Yield (0.504 g, 78%): $^1$H NMR (400 MHz, DMSO-$d_6$) δ 7.25-7.21 (m, 1H), 7.17-7.14 (m, 3H), 5.12 (bs, 1H), 2.74-2.70 (m, 2H), 2.58 (t, J=7.2 Hz, 2H), 1.60-1.41 (m, 8H), 1.34 (bs, 2H), 0.89 (t, J=7.2 Hz, 6H).

Example 168

PREPARATION OF
2-(3-(CYCLOOCTYLETHYNYL)-PHENOXY)ETHANAMINE

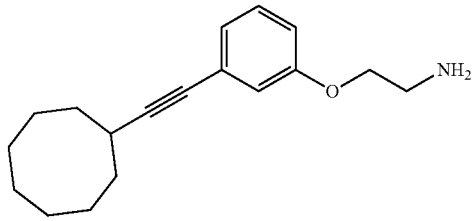 [SMILES: NCCOc1cccc(C#CC2CCCCCCC2)c1]

2-(3-(Cyclooctylethynyl)-phenoxy)ethanamine was prepared following the method used in Example 18.

Step 1: Sonogashira reaction of bromide 19 with ethynylcyclooctane gave N-(2-(3-(cyclooctylethynyl)phenoxy)ethyl)-2,2,2-trifluoroacetamide as a brown oil. Yield (0.505 g, 50%): $^1$H NMR (400 MHz, DMSO-$d_6$) δ 7.21-7.27 (m, 1H), 6.94 (d, J=7.2 Hz, 1H), 6.88-6.92 (m, 2H), 4.09 (t, J=5.4 Hz, 2H), 3.52-3.57 (m, 2H), 2.79-2.84 (m, 1H), 1.86-1.92 (m, 2H), 1.67-1.76 (m, 4H), 1.47-1.58 (m, 8H).

Step 2: Deprotection of N-(2-(3-(cyclooctylethynyl)phenoxy)ethyl)-2,2,2-trifluoroacetamide gave Example 168 as brown oil. Yield (0.071 g, 48%): $^1$H NMR (400 MHz, DMSO-$d_6$) δ 7.24-7.29 (m, 1H), 6.93-6.98 (m, 3H), 4.13 (t, J=5.0 Hz, 2H), 3.18 (t, J=5.0 Hz, 2H), 2.77-2.81 (m, 1H), 1.81-1.89 (m, 2H), 1.60-1.72 (m, 4H), 1.42-1.56 (m, 8H). $^{13}$C NMR (100 MHz, DMSO-$d_6$) δ 157.6, 129.7, 124.4, 124.2, 117.0, 114.8, 95.3, 80.2, 64.3, 38.1, 30.9, 29.8, 26.8, 24.7, 23.8. ESI MS m/z 286 [M+1]$^+$.

Example 169

PREPARATION OF (S)-4-(3-(2-AMINO-1-HYDROXYETHYL)PHENYL)-ETHYNYL)HEPTAN-4-OL

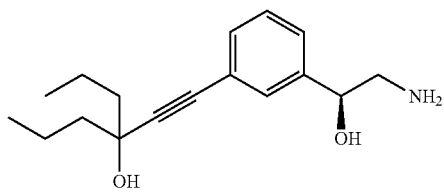 [SMILES: CCCC(O)(C#Cc1cccc([C@H](O)CN)c1)CCC]

(S)-4-((3-(2-amino-1-hydroxyethyl)phenyl)-ethynyl)heptan-4-ol was prepared following the method shown in Scheme 25.

SCHEME 25

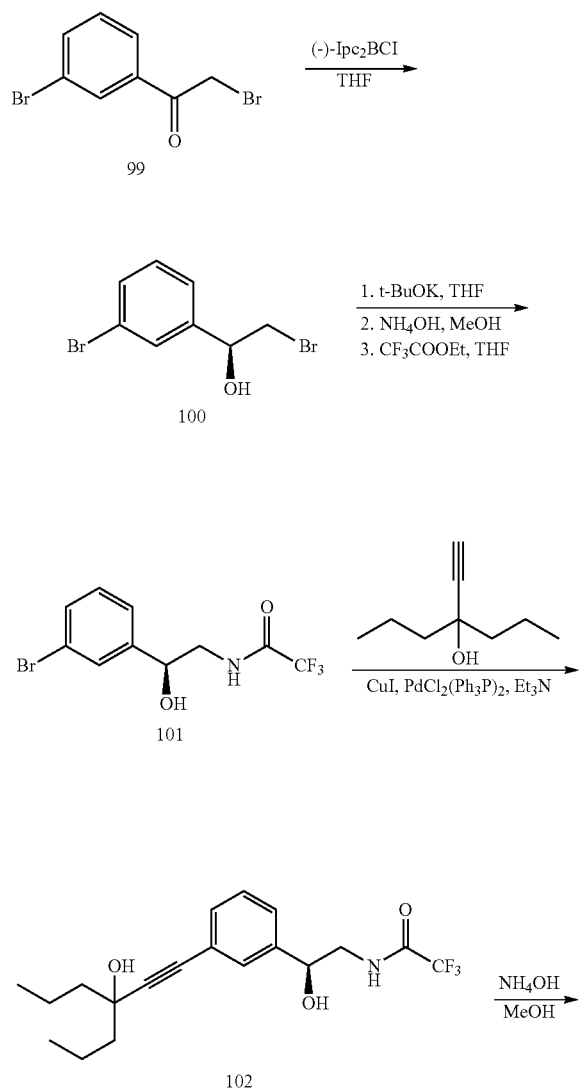

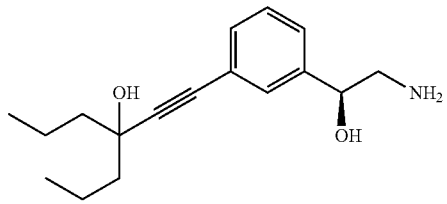

Step 1. Preparation of (−)-diisopinocampheylchloroborane solution ((+)-Ipc$_2$B—Cl): (+)-Ipc$_2$BCl solution was prepared following the method used in Example 100. The resulting solution was approximately 1.66 M. Ketone 99 was reduced following the method used in Example 100 to give hydroxybromide 100 as a colorless oil. Yield (0.818 g, 80%): $^1$H NMR (400 MHz, DMSO-d$_6$) δ 7.57 (t, J=1.8 Hz, 1H), 7.44 (ddd, J=1.0, 2.0, 7.8 Hz, 1H), 7.35-7.39 (m, 1H), 7.28 (t, J=7.8 Hz, 1H), 5.90 (d, J=4.9 Hz, 1H), 4.80 (dd, J=4.7, 6.5 Hz, 1H), 3.66 (ABd, J=4.5, 6.5 Hz, 1H), 3.57 (ABd, J=4.5, 6.5 Hz, 1H).

Step 2. To a solution of bromide 100 (0.818 g, 2.92 mmol) in anhydrous THF (10 mL) was added a solution of potassium tert-butoxide (1M, 3.5 mL), the reaction mixture was stirred at room temperature for 15 min. concentrated under reduced pressure, and the residue was treated with water. The product was extracted twice with EtOAc, organic layers were pooled, washed with brine, aq. NH$_4$Cl solution, dried over anhydrous dried over anhydrous MgSO$_4$, filtered and filtrated was concentrated under reduced pressure to give the epoxide (0.486 g) which was used in the next step without purification.

The epoxide was dissolved in 7N NH$_3$/MeOH solution (5 mL) and aqueous NH$_4$OH (25%, 5 mL) was added to the reaction mixture which was stirred at room temperature for 18 hrs. The reaction mixture was concentrated under reduced pressure to give the amine (0.801 g) which was used in the next step without purification.

The amine was dissolved in anhydrous THF (5 mL) and ethyl trifluoroacetate (1 mL) was added. The reaction mixture was stirred at room temperature for 20 min, concentrated under reduced pressure and the residue was purified by flash chromatography to give trifluoroacetamide 101 as a colorless oil. Yield (0.608 g, 67% for 3 steps): $^1$H NMR (400 MHz, DMSO-d$_6$) δ 9.45 (br. t, 1H), 7.46-7.49 (m, 1H), 7.40-7.45 (m, 1H), 7.25-7.30 (m, 2H), 5.73 (d, J=4.7 Hz, 1H), 4.68 (dd, J=6.7, 11.3 Hz, 1H), 3.47-3.52 (m, 2H).

Step 3. Sonogashira coupling of 101 with 4-ethynylheptan-4-ol following the method given in Example 17 afforded alkynol 102 as a tan oil. Yield (0.59 g, 82%): $^1$H NMR (400 MHz, DMSO-d$_6$) δ 9.44 (br t, J=5.5 Hz, 1H), 7.22-7.32 (m, 4H), 5.65 (d, J=4.7 Hz, 1H), 4.67 (dd, J=11.7, 6.8 Hz, 1H), 3.25-3.31 (m, 2H), 1.40-1.62 (m, 8H), 0.89 (t, J=7.0 Hz, 6H).

Step 4. A solution of alkynol 102 (0.59 g, 1.59 mmol) in NH$_3$/MeOH (7N, 10 mL) and aqueous NH$_4$OH (25%, 10 mL) was stirred at room temperature for 70 hrs and the concentrated under reduced pressure. Purification by flash chromatography (0% to 100% of 10% 7N NH$_3$/MeOH/CH$_2$Cl$_2$ in CH$_2$Cl$_2$) gave Example 169 as a colorless oil. Yield (0.35 g, 80%); $^1$H NMR (400 MHz, CD$_3$OD) δ 7.39-7.41 (m, 1H), 7.26-7.32 (m, 3H), 4.58 (dd, J=4.7, 7.6 Hz, 1H), 2.65-2.81 (m, 2H), 1.51-1.73 9m, 8H), 0.97 (t, J=7.0 Hz, 6H); 143.7, 130.3, 128.9, 128.3, 125.8, 123.4, 92.4, 83.7, 74.5, 70.9, 49.0, 44.5, 17.6, 13.6; LC-MS: 276.38 [M+H]$^+$; RP-HPLC t$_R$=6.21 min, 98% AUC.

Example 170

PREPARATION OF 1-(3-(3-AMINO-1-HYDROXYPROPYL)PHENYL)-3-METHYLHEX-1-YN-3-OL

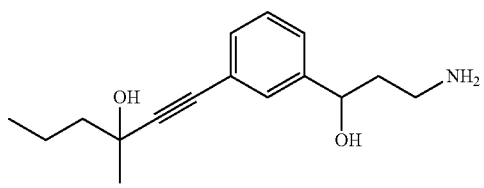 [SMILES: CCCC(C)(O)C#Cc1cccc(C(O)CCN)c1]

1-(3-(3-Amino-1-hydroxypropyl)phenyl)-3-methylhex-1-yn-3-ol was prepared following the method method used in Example 132.

Step 1: Sonogashira reaction of 25 with 3-methylhex-1-yn-3-ol yielded 2,2,2-trifluoro-N-(3-hydroxy-3-(3-(3-hydroxy-3-methylhex-1-ynyl)phenyl) propyl)acetamide as dark brown oil. Yield (0.611 g, 55%): $^1$H NMR (400 MHz, CDCl$_3$) δ 7.41 (s, 1H), 7.24-7.37 (m, 3H), 4.86 (m, 1H), 3.67-3.72 (m, 1H), 3.38-3.44 (m, 1H), 2.32 (bs, 1H), 1.94-2.01 (m, 3H), 1.71-1.76 (m, 2H), 1.59-1.62 (m, 1H), 1.53 (s, 3H), 0.99 (t, J=7.2, 3H).

Step 5: Deprotection of 2,2,2-trifluoro-N-(3-hydroxy-3-(3-(3-hydroxy-3-methylhex-1-ynyl)phenyl)propyl)acetamide gave Example 170 as yellow oil. Yield (0.269 g, 61%): $^1$H NMR (400 MHz, DMSO-d$_6$) δ 7.61 (bs, 2H), 7.25-7.36 (m, 4H), 5.60 (bs, 1H), 4.66-4.69 (m, 1H), 2.81-2.85 (m, 2H), 1.82-1.86 (m, 2H), 1.59-1.63 (m, 2H), 1.44-1.58 (m, 2H), 1.42 (s, 3H), 0.92 (t, J=7.2, 3H). $^{13}$C NMR (100 MHz, DMSO-d$_6$) δ 146.6, 130.0, 128.9, 126.0, 122.9, 95.4, 82.1, 70.2, 67.1, 46.4, 37.6, 30.4, 18.2, 14.7. ESI MS m/z 262 [M+1]$^+$.

Example 171

PREPARATION OF 3-AMINO-1-(3-((TETRAHYDRO-2H-PYRAN-2-YL)ETHYNYL)-PHENYL-PROPAN-1-OL

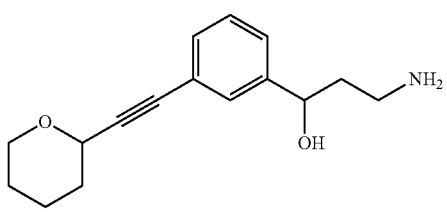 [SMILES: NCCC(O)c1cccc(C#CC2CCCCO2)c1]

3-Amino-1-(3-((tetrahydro-2H-pyran-2-yl)ethynyl)-phenyl)propan-1-ol was prepared following the method shown in Scheme 26.

SCHEME 26

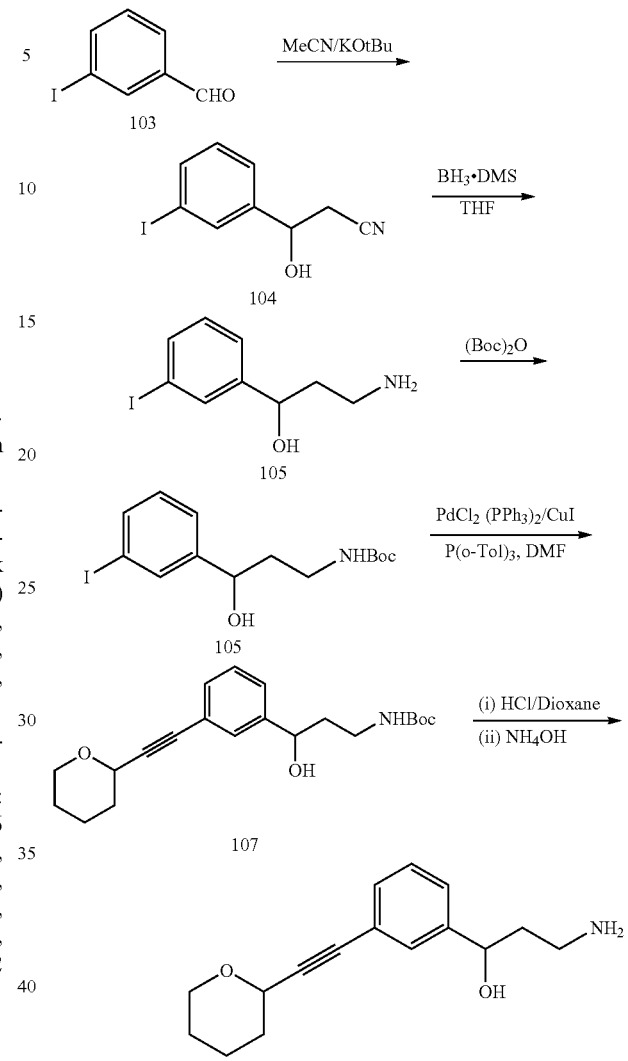

Step 1: Acetonitrile addition to 3-iodobenzaldehyde (103) yielded 3-hydroxy-3-(3-iodophenyl)propanenitrile (104) as yellow oil. Yield (2.58 g, 55%): $^1$H NMR (400 MHz, CDCl$_3$) δ 7.82 (s, 1H), 7.70 (d, J=8.0 Hz, 1H), 7.38 (d, J=8.0 Hz, 1H), 7.14 (t, J=8.0 Hz, 1H), 5.01 (m, 1H), 2.80 (d, J=6.4, 2H), 2.40 (bs, 1H).

Step 2: Nitrile reduction of 3-hydroxy-3-(3-iodophenyl) propanenitrile yielded 3-amino-1-(3-iodophenyl)propan-1-ol (105) as pale yellow oil. Yield (2.63 g, quantitative yield). This compound was utilized as such for the next transformation. $^1$H NMR (400 MHz, CDCl$_3$) δ 7.76 (s, 1H), 7.58 (d, J=7.6, 1H), 7.33 (d, J=7.6, 1H), 7.06 (t, J=8.0, 1H), 4.92 (dd, J=8.8, 2.8 Hz, 1H), 3.09-3.14 (m, 1H), 2.93-2.99 (m, 1H), 1.81-1.85 (m, 1H), 1.64-1.73 (m, 1H).

Step 3: Boc protection of amine 105 gave tert-butyl 3-hydroxy-3-(3-iodophenyl)propylcarbamate (106) as yellow oil. Yield (1.39 g, 40%). This compound was utilized as such for the next transformation. $^1$H NMR (400 MHz, CDCl$_3$) δ 7.73 (s, 1H), 7.58 (d, J=7.6, 1H), 7.33 (d, J=7.6, 1H), 7.07 (t, J=8.0, 1H), 4.86 (bs, 1H), 4.67 (m, 1H), 3.45-3.51 (m, 2H), 3.11-3.18 (m, 1H), 1.76-1.83 (m, 2H), 1.51 (s, 9H).

Step 4: Sonogashira reaction of 106 with 2-ethynyltetrahydro-2H-pyran yielded tert-butyl 3-hydroxy-3-(3-((tetrahydro-2H-pyran-2-yl)ethynyl)phenyl)propylcarbamate (107) as dark brown oil. Yield (1.21 g, 83%): $^1$H NMR (400 MHz, CDCl$_3$) δ 7.45 (s, 1H), 7.27-7.35 (m, 3H), 4.87 (bs, 1H), 4.69-4.71 (m, 1H), 4.49-4.51 (m, 1H), 4.02-4.07 (m, 1H), 3.50-3.52 (m, 1H), 3.56-3.61 (m, 1H), 3.13-3.18 (m, 1H), 1.91-1.93 (m, 2H), 1.74-1.86 (m, 4H), 1.51 (m, 2H), 1.43 (s, 9H).

Step 5: Deprotection of 107 resulted in yellow semi-solid hydrochloride salt, which was basified and purified by flash chromatography (0-10% ((9:1)MeOH—NH$_3$): DCM) to obtain Example 171 as pale yellow oil. Yield (0.273 g, 85%): $^1$H NMR (400 MHz, DMSO-d$_6$) δ 7.68 (bs, 2H), 7.40 (s, 1H), 7.31-7.39 (m, 3H), 4.67-4.70 (m, 1H), 4.51-4.54 (m, 1H), 3.84-3.88 (m, 1H), 3.48-3.53 (m, 1H), 2.80-2.85 (m, 2H), 1.79-1.88 (m, 4H), 1.60-1.64 (m, 2H), 1.47-1.52 (m, 2H). $^{13}$C NMR (100 MHz, DMSO-d$_6$) δ 146.6, 130.2, 129.0, 128.9, 126.5, 122.2, 89.2, 85.2, 69.8, 66.8, 65.9, 37.9, 37.0, 32.3, 25.7, 21.7. ESI MS m/z 260 [M+1]$^+$.

Example 172

PREPARATION OF 5-(3-(3-AMINOPROPYL)-PHENYL)-N-METHYLPENT-4-YNAMIDE

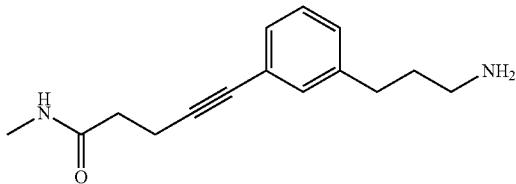 [SMILES: CNC(=O)CCC#Cc1cccc(CCCN)c1]

5-(3-(3-Aminopropyl)-phenyl)-N-methylpent-4-ynamide was prepared following the method used in Example 127.

Step 1: Sonogashira coupling of bromide 87 with N-methylpent-4-ynamide gave tert-butyl 3-(3-(5-(methylamino)-5-oxopent-1-ynyl)phenyl)propyl carbamate. Yield (1.03 g, crude). $^1$H NMR (400 MHz, CDCl$_3$) δ 7.64-7.70 (m, 1H), 7.48 (d, J=6.6 Hz, 1H), 7.21 (s, 1H), 7.10 (d, J=6.4 Hz, 1H), 5.68 (bs, 1H), 4.52 (bs, 1H), 3.10-3.18 (m, 2H), 2.85 (d, J=6.8 Hz, 3H), 2.75 (t, J=7.2 Hz, 2H), 2.60 (t, J=7.6 Hz, 2H), 2.47 (t, J=7.2 Hz, 2H), 1.75-1.82 (m, 2H), 1.44 (s, 9H).

Step 2: Deprotection of tert-butyl 3-(3-(5-(methylamino)-5-oxopent-1-ynyl)phenyl)propyl carbamate with HCl in dioxane (4M) using THF as solvent, followed by neutralization with conc. ammonia and subsequent column chromatography gave Example 172 as yellow oil. Yield (0.16 g, 75%): $^1$H NMR (400 MHz, DMSO-d$_6$) δ 7.22-7.27 (m, 1H), 7.14-7.19 (m, 3H), 2.52-2.63 (m, 9H), 2.34 (t, J=7.2 Hz, 2H), 1.58-1.66 (m, 2H). $^{13}$C NMR (100 MHz, DMSO-d$_6$): 171.1, 143.0, 131.6, 129.0, 128.9, 128.6, 123.4, 90.0, 81.1, 41.0, 34.8, 34.4, 32.5, 25.8, 15.7. ESI MS m/z 245 [M+1]$^+$.

Example 173

PREPARATION OF 5-(3-(3-AMINOPROPYL)-PHENYL)PENT-4-YNAMIDE

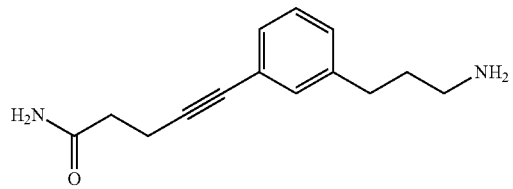 [SMILES: NCCCc1cccc(C#CCCC(N)=O)c1]

5-(3-(3-Aminopropyl)-phenyl)pent-4-ynamide was prepared following the method used in Example 127.

Step 1: Sonogashira coupling of bromide 87 with pent-4-ynamide gave tert-butyl 3-(3-(5-amino-5-oxopent-1-ynyl)phenyl)propylcarbamate. Yield (0.967 g, crude). $^1$H NMR (400 MHz, CDCl$_3$) δ 7.64-7.70 (m, 1H), 7.47 (d, J=6.4 Hz, 1H), 7.18 (s, 1H), 7.10 (d, J=6.4 Hz, 1H), 5.60-5.80 (m, 2H), 4.53 (bs, 1H), 3.10-3.18 (m, 2H), 2.75 (d, J=7.2 Hz, 2H), 2.60 (t, J=7.6 Hz, 2H), 2.54 (t, J=7.2 Hz, 2H), 1.76-1.80 (m, 2H), 1.44 (s, 9H).

Step 2: Deprotection of tert-butyl 3-(3-(5-amino-5-oxopent-1-ynyl)phenyl)propylcarbamate with HCl in dioxane (4M) using THF as solvent, followed by neutralization with conc. ammonia and subsequent column chromatography gave Example 173 as yellow oil. Yield (0.13 g, 48%): $^1$H NMR (400 MHz, DMSO-d$_6$) δ 7.23-7.27 (m, 1H), 7.15-7.20 (m, 3H), 2.52-2.62 (m, 6H), 2.33 (t, J=7.4 Hz, 2H), 1.58-1.66 (m, 2H). $^{13}$C NMR (100 MHz, DMSO-d$_6$): 172.9, 143.1, 131.6, 129.0, 128.9, 128.6, 123.4, 90.1, 81.0, 41.2, 34.8, 34.6, 32.5, 15.5. ESI MS m/z 231 [M+1]$^+$.

Example 174

PREPARATION OF 1-(3-(3-AMINO-1-HYDROXYPROPYL)PHENYL)-3-ETHYLPENT-1-YN-3-OL

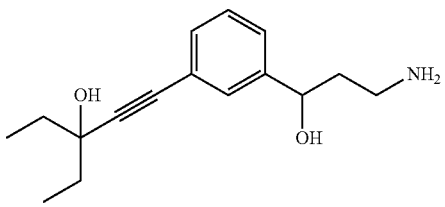 [SMILES: CCC(O)(C#Cc1cccc(C(O)CCN)c1)CC]

1-(3-(3-amino-1-hydroxypropyl)phenyl)-3-ethylpent-1-yn-3-ol was prepared following the method used in Example 132:

Step 1: Sonogashira coupling of bromide 25 with 3-ethylpent-1-yn-3-ol gave N-(3-(3-(3-ethyl-3-hydroxypent-1-ynyl)phenyl)-3-hydroxypropyl)-2,2,2-trifluoroacetamide. Yield (0.825 g, 77%). $^1$H NMR (400 MHz, CDCl$_3$) δ 7.41 (s, 1H), 7.28-7.39 (m, 3H), 4.83-4.87 (m, 1H), 3.66-3.73 (m, 1H), 3.37-3.44 (m, 1H), 1.90-2.02 (m, 2H), 1.70-1.81 (m, 4H), 1.10 (t, J=7.4 Hz, 6H).

Step 2: Deprotection of N-(3-(3-(3-ethyl-3-hydroxypent-1-ynyl)phenyl)-3-hydroxypropyl)-2,2,2-trifluoroacetamide gave Example 174 as yellow oil. Yield (0.52 g, 91%): ¹H NMR (400 MHz, DMSO-d₆) δ 7.36 (s, 1H), 7.29-7.33 (m, 2H), 7.26 (d, J=6.4 Hz, 1H), 4.68 (t, J=4.8 Hz, 1H), 2.74-2.82 (m, 2H), 1.76-1.82 (m, 2H), 1.60-1.69 (m, 4H), 0.99 (t, J=7.4 Hz, 6H). ¹³C NMR (100 MHz, DMSO-d₆): 146.5, 130.1, 128.9, 126.0, 125.0, 123.0, 100.0, 94.0, 83.3, 75.0, 71.0, 70.2, 34.5, 9.2. ESI MS m/z 262 [M+1]⁺.

Example 175

PREPARATION OF 3-AMINO-1-(3-(4-CYCLOHEXYLBUT-1-YNYL)PHENYL)PROPAN-1-OL

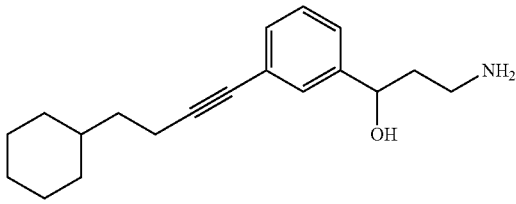 [SMILES: NCCC(O)c1cccc(C#CCCC2CCCCC2)c1]

3-Amino-1-(3-(4-cyclohexylbut-1-ynyl)phenyl)propan-1-ol was prepared following the method used in Example 132:

Step 1: Sonogashira coupling of bromide 25 with but-3-ynyl cyclohexane gave N-(3-(3-(4-cyclohexylbut-1-ynyl)phenyl)-3-hydroxypropyl)-2,2,2-trifluoroacetamide. Yield (1.1 g, 94%). ¹H NMR (400 MHz, CDCl₃) δ 7.38 (s, 1H), 7.21-7.36 (m, 3H), 4.84-4.88 (m, 1H), 3.64-3.72 (m, 1H), 3.37-3.45 (m, 1H), 2.41 (t, J=7.4 Hz, 2H), 1.96-2.0 (m, 2H), 1.64-1.78 (m, 5H), 1.48-1.54 (m, 2H), 1.36-1.46 (m, 1H), 1.14-1.30 (m, 3H), 0.88-1.0 (m, 2H).

Step 2: Deprotection of N-(3-(3-(4-cyclohexylbut-1-ynyl)phenyl)-3-hydroxypropyl)-2,2,2-trifluoroacetamide gave Example 175 as yellow oil. Yield (0.503 g, 61%): ¹H NMR (400 MHz, DMSO-d₆) δ 7.22-7.29 (m, 3H), 7.18 (d, J=6.8 Hz, 1H), 4.57 (t, J=6.4 Hz, 1H), 2.50-2.55 (m, 2H), 2.37 (t, J=7.2 Hz, 2H), 1.54-1.70 (m, 7H), 1.39-1.43 (m, 2H), 1.29-1.38 (m, 1H), 1.06-1.20 (m, 3H), 0.80-0.90 (m, 2H). ¹³C NMR (100 MHz, DMSO-d₆): 147.3, 129.7, 128.9, 128.6, 125.7, 123.4, 90.8, 81.1, 71.3, 42.6, 39.2, 36.8, 36.2, 32.8, 32.8, 26.6, 26.2. ESI MS m/z 286 [M+1]⁺.

Example 176

PREPARATION OF 3-AMINO-1-(3-(CYCLOHEPTYLETHYNYL)PHENYL)PROPAN-1-OL

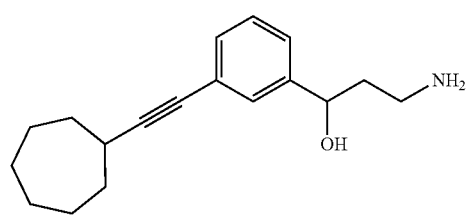 [SMILES: NCCC(O)c1cccc(C#CC2CCCCCC2)c1]

3-Amino-1-(3-(cycloheptylethynyl)phenyl)propan-1-ol was prepared following the method used in Example 19.

Step 1: Sonogashira coupling of bromide 25 with ethynylcycloheptanede by the method used in Example 1 followed by flash chromatography (5-40% EtOAc/hexanes gradient), gave N-(3-(3-(cycloheptylethynyl)phenyl)-3-hydroxypropyl)-2,2,2-trifluoroacetamide as an amber oil.

Yield (0.507 g, 51%): ¹H NMR (400 MHz, CDCl₃) δ 7.42 (br s, 1H), 7.34-7.36 (m, 1H), 7.19-7.33 (m, 3H), 4.81 (q, J=4.0 Hz, 1H), 3.48-3.68 (m, 1H), 3.32-3.42 (m, 1H), 2.74-2.82 (m, 1H), 2.48 (br s, 1H), 1.85-2.00 (m, 4H), 1.70-1.80 (m, 4H), 2.46-1.64 (m, 6H).

Step 2: Deprotection of N-(3-(3-(cycloheptylethynyl)phenyl)-3-hydroxypropyl)-2,2,2-trifluoroacetamide followed by flash chromatography (5% (7N NH3/MeOH)/dichloromethane) gave Example 176 as a yellow oil. Yield (0.173 g, 46%): ¹H NMR (400 MHz, CDCl₃) δ 7.40 (s, 1H), 7.18-7.30 (m, 3H), 4.91 (d, J=6.8 Hz, 1H), 3.00 (br s, 5H), 2.74-2.82 (m, 1H), 1.80-1.94 (m, 3H), 1.68-1.80 (m, 5H), 1.44-1.64 (m, 6H).

Example 177

PREPARATION OF 4-((3-(3-(METHYLAMINO)PROPYL)PHENYL)ETHYNYL)HEPTAN-4-OL

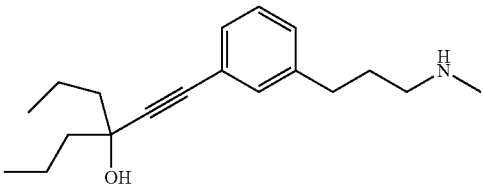 [SMILES: CCCC(O)(C#Cc1cccc(CCCNC)c1)CCC]

4-((3-(3-(Methylamino)propyl)phenyl)ethynyl)heptan-4-ol was prepared following the method shown in shown in Scheme 27.

SCHEME 27

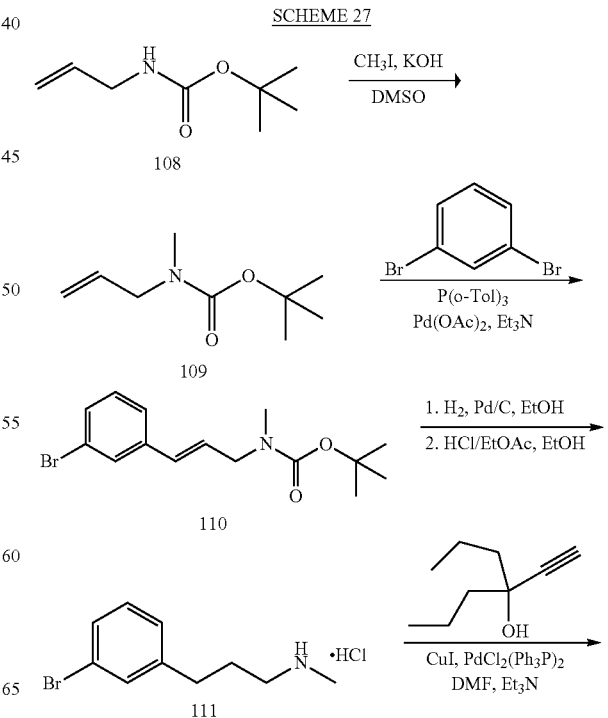

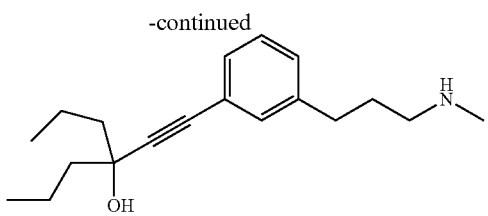

Step 1: A mixture of allylamine carbamate 108 (1.926 g, 12.2 mmol), powdered KOH (0.734 g, 13.1 mmol) in anhydrous DMSO (10 mL) was stirred at room temperature for 5 min. Then a solution of methyl iodide (2.276 g, 16.03 mmol) in DMSO (2 mL) was added and the reaction mixture was stirred at room temperature for 66 hr. Aqueous $NH_4Cl$ (25%, 100 mL) was added and the product was extracted with EtOAc (3×70 mL). Combined organic layers were washed with brine, dried over anhydrous $MgSO_4$, filtered and the filtrate was concentrated under reduced pressure to give N-methylcarbamate 109 as a light yellowish liquid with a low boiling point. Yield (1.595 g, 76%); $^1H$ NMR (400 MHz, $CDCl_3$) δ 5.74 (ddt, J=16.8, 10.6, 5.7 Hz, 1H), 5.06-5.13 (m, 2H), 3.79 (d, J=5.5 Hz, 2H), 2.80 (s, 3H), 1.43 (s, 9H).

Step 2. A solution of 1,3-dibromobenzene (4.22 g, 17.9 mmol) and N-methylcarbamate 109 (1.555 g, 9.04 mmol) in triethylamine (15 mL) was degassed by bubbling argon from 3 min. Then tri-o-tolylphosphine (0.140 g, 0.46 mmol) followed by $Pd(OAc)_2$ (0.11 g, 0.49 mmol) was added, argon was bubbled again for 1 min, then vacuum/argon was applied 3×. The reaction mixture was stirred under argon at 90° C. for 19 hr and concentrated under reduced pressure. The precipitate was filtered off, filtrate was concentrated under reduced pressure and purified by flash chromatography (5% to 20% EtOAc-hexanes gradient) to give alkene 110 as a yellow oil. Yield (0.513 g, 17%); $^1H$ NMR (400 MHz, $CDCl_3$) δ 7.50 (t, J=1.8 Hz, 1H), 7.32-7.36 (m, 1H), 7.24-7.27 (m, 1H), 7.16 (t, J=7.8 Hz, 1H), 6.36 (d, J=15.8 Hz, 1H), 6.14 (dt, J=15.8, 5.9 Hz, 1H), 3.9-4.8 (m, 2H), 2.85 (s, 3H), 1.46 (s, 9H).

Step 3. A solution of alkene 110 (0.513 g, 1.57 mmol) in absolute EtOH (10 mL) was degassed by vacuum/argon 3×, Pd/C was added (10%, 0.0577 g) and left vigorously stirring at room temperature for 1.5 hrs. The reaction mixture was filtered, filtrate concentrated under reduced pressure and purified by flash chromatography (2% to 20% EtOAc-hexanes gradient) to give the alkane as a mixture with des-bromo alkane as a white semi-solid, which was used in the next step without additional purification. Yield (0.24 g, 46%).

To a solution of the alkane mixture (0.24 g, 0.73 mmol) in EtOAc (5 mL) was added a solution of HCl in EtOH (7.4 M, 1.5 mL, 11.1 mmol) and the reaction was stirred at room temperature for 2 hours. Solvent were removed under reduced pressure and the residue was dried in vacuum overnight to give amine 111 as a mixture with des-bromoalkane as semi-solid, which was used in the next step without additional purification. Yield (0.19 g, 93%); $^1H$ NMR (400 MHz, DMSO-$d_6$) δ 8.79 (br s, 2H), 7.43 (t, J=1.6 Hz, 1H), 7.38 (dt, J=1.8, 7.2 Hz, 1H), 7.15-7.30 (m, 2H), 2.76-2.86 (m, 2H), 2.58-2.66 (m, 2H), 2.46-2.51 (m, 3H), 1.82-1.92 (m, 2H).

Step 4. Sonogashira coupling of crude arylbromide 111 and 4-ethynylheptan-4-ol following the method used in Example 17 except that DMF was additionally used and the reaction mixture was heated at 90° C. for 21 hr to give Example 177 as a colorless oil after double flash chromatography (0% to 100% of 10% 7N $NH_3$/MeOH—$CH_2Cl_2$ gradient, and then 30% to 100% of 10% 7N $NH_3$/MeOH—$CH_2Cl_2$ gradient) as a light-yellow oil. Yield (0.053 g, 26%); $^1H$ NMR (400 MHz, $CD_3OD$) δ 7.13-7.24 (m, 4H), 2.61 (t, J=7.6 Hz, 2H), 2.53 (t, J=7.2 Hz, 2H), 2.34 (d, J=0.8 Hz, 3H), 1.73-1.83 (m, 2H), 1.51-1.73 (m, 8H), 0.97 (t, J=7.0 Hz, 6H); $^{13}C$ NMR (100 MHz, $CD_3OD$) δ 142.4, 131.2, 128.9, 128.3, 128.2, 123.3, 92.0, 83.8, 70.9, 50.9, 44.5, 34.8, 33.0, 30.8, 17.6, 13.5; RP-HPLC $t_R$=6.95 min, 95.1% (AUC); LC-MS m/z=288.47 $[M+H]^+$.

Example 178

PREPARATION OF 2-(3-((TETRAHYDRO-2H-PYRAN-2-YL)ETHYNYLPHENOXY)ETHA-NAMINE

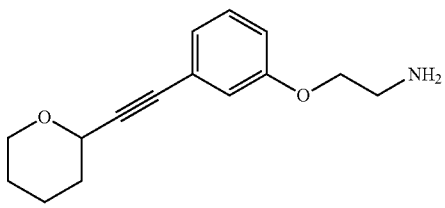 [SMILES: NCCOc1cccc(C#CC2CCCCO2)c1]

2-(3-((Tetrahydro-2H-pyran-2-yl)ethynyl)phenoxy)ethanamine was prepared following the method used in Example 18.

Step 1: Sonogashira reaction of bromide 19 with 2-ethynyltetrahydro-2H-pyran gave 2,2,2-trifluoro-N-(2-(3-((tetrahydro-2H-pyran-2-yl)ethynyl)phenoxy)ethyl)acetamide as a brown oil. Yield (0.753 g, 79%): $^1H$ NMR (400 MHz, DMSO-$d_6$) δ 7.26-7.32 (m, 1H), 7.05 (d, J=7.6 Hz, 1H), 6.95-6.98 (m, 2H), 4.50-4.53 (m, 1H), 4.11 (t, J=5.4 Hz, 2H), 3.83-3.90 (m, 1H), 3.54-3.58 (m, 2H), 3.46-3.53 (m, 1H), 1.78-1.86 (m, 2H). 1.46-1.66 (m, 4H).

Step 2: Deprotection of 2,2,2-trifluoro-N-(2-(3-((tetrahydro-2H-pyran-2-yl)ethynyl)phenoxy)ethyl)acetamide gave Example 178 as brown oil. Yield (0.125 g, 50%): $^1H$ NMR (400 MHz, DMSO-$d_6$) δ 7.26-7.31 (m, 1H), 7.02 (s, 1H), 6.97-7.01 (m, 2H), 4.50-4.53 (m, 1H), 3.99 (t, J=5.6 Hz, 2H), 3.84-3.90 (m, 1H), 3.46-3.53 (m, 1H), 2.95 (t, J=5.6 Hz, 2H), 1.75-1.87 (m, 2H), 1.54-1.68 (m, 2H), 1.46-1.53 (m, 2H). $^{13}C$ NMR (100 MHz, DMSO-$d_6$) δ 158.8, 130.3, 124.4, 123.5, 117.3, 116.7, 89.3, 84.9, 69.0, 66.8, 66.0, 40.5, 32.2, 25.7, 21.7. ESI MS m/z 246 $[M+1]^+$.

Example 179

PREPARATION OF 3-AMINO-1-(3-(4-P-TOLYL-BUT-1-YNYL)PHENYL)PROPAN-1-OL

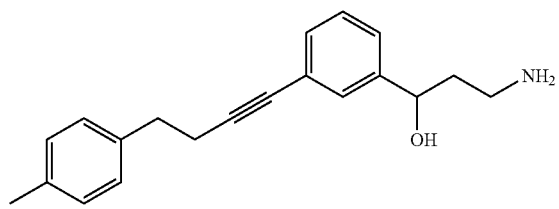 [SMILES: Cc1ccc(CCC#Cc2cccc(C(O)CCN)c2)cc1]

3-Amino-1-(3-(4-p-tolylbut-1-ynyl)phenyl)propan-1-ol was prepared following the method used in Example 132 with the excepting that the iodide of compound 25 was prepared instead of the bromide.

Step 1: To a solution of 3-amino-1-(3-iodophenyl)propan-1-ol (105) (3.9 g, 14 mmol) in DCM (50 mL) were added ethyl trifluoroacetate (2 mL, 17 mmol) and triethylamine (2.95 mL, 21 mmol) and the mixture was stirred at RT for 4 h during which the reaction was found to be complete. Concentration under reduce pressure gave (2,2,2-trifluoro-N-(3-hydroxy-3-(3-iodophenyl)propyl)acetamide) as a yellow oil. The product was pure enough to be used as such for the next transformation. Yield (4.9 g, 93%): $^1$H NMR (400 MHz, CDCl$_3$) δ 7.71 (s, 1H), 7.59 (d, J=7.6 Hz, 1H), 7.31 (d, J=7.6 Hz, 1H), 7.11 (t, J=7.6 Hz, 1H), 4.79-4.82 (m, 1H), 3.67-3.72 (m, 1H), 3.37-3.42 (m, 1H), 2.96 (bs, 1H), 1.87-1.99 (m, 2H).

Step 2: Sonogashira reaction of (2,2,2-trifluoro-N-(3-hydroxy-3-(3-iodophenyl)propyl)acetamide) with 1-(but-3-ynyl)-4-methylbenzene yielded 2,2,2-trifluoro-N-(3-hydroxy-3-(3-(4-p-tolylbut-1-ynyl)phenyl)propyl)acetamide as yellow oil. Yield (0.310 g, 60%): $^1$H NMR (400 MHz, CDCl$_3$) δ 7.29-7.51 (m, 4H), 7.17 (d, J=8.0 Hz, 2H), 7.13 (d, J=8.0 Hz, 2H), 4.84-4.86 (m, 1H), 3.66-3.70 (m, 1H), 3.38-3.43 (m, 1H), 2.89 (t, J=7.6 Hz, 2H), 2.67 (t, J=7.6 Hz, 2H), 2.33 (s, 3H), 2.25 (bs, 1H), 1.92-1.97 (m, 2H).

Step 3: Deprotection of 2,2,2-trifluoro-N-(3-hydroxy-3-(3-(4-p-tolylbut-1-ynyl)phenyl)propyl)acetamide at RT gave Example 179 as off white solid. Yield (0.189 g, 84%): $^1$H NMR (400 MHz, DMSO-d$_6$) δ 7.24-7.31 (m, 3H), 7.18-7.20 (m, 1H), 7.16 (d, J=8.0 Hz, 2H), 7.10 (d, J=8.0 Hz, 2H), 4.60-4.64 (m, 1H), 2.74-2.85 (m, 4H), 2.63 (t, J=6.8 Hz, 2H), 2.23 (s, 3H), 1.78-1.85 (m, 2H). $^{13}$C NMR (100 MHz, DMSO-d$_6$) δ 145.8, 137.4, 135.2, 129.7, 128.8, 128.5, 128.4, 125.3, 123.0, 90.1, 81.1, 69.4, 36.9, 36.5, 34.0, 21.0, 20.7. ESI MS m/z 294 [M+1]$^+$.

Example 180

PREPARATION OF 3-AMINO-1-(3-(2-O-TOLYL-BUT-1-YNYL)PHENYL)PROPAN-1-OL

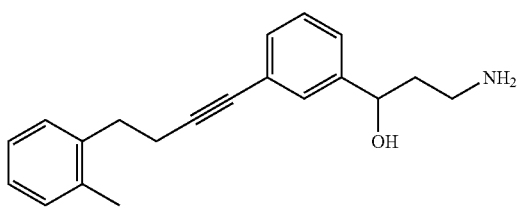 [SMILES: Cc1ccccc1CCC#Cc1cccc(C(O)CCN)c1]

3-Amino-1-(3-(2-o-tolylbut-1-ynyl)phenyl)propan-1-ol was prepared following the method used in Example 180.

Step 1: Sonogashira reaction of (2,2,2-trifluoro-N-(3-hydroxy-3-(3-iodophenyl)propyl)acetamide) with 1-(but-3-ynyl)-2-methylbenzene yielded 2,2,2-trifluoro-N-(3-hydroxy-3-(3-(2-o-tolylbut-1-ynyl)phenyl)propyl)acetamide as yellow oil. Yield (0.391 g, 75%): $^1$H NMR (400 MHz, CDCl$_3$) δ 7.15-7.37 (m, 8H), 4.84-4.86 (m, 1H), 3.66-3.70 (m, 1H), 3.38-3.44 (m, 1H), 2.94 (t, J=7.6 Hz, 2H), 2.66 (t, J=7.6 Hz, 2H), 2.36 (s, 3H), 2.32 (bs, 1H), 1.93-1.98 (m, 2H).

Step 2: Deprotection of 2,2,2-trifluoro-N-(3-hydroxy-3-(3-(2-p-tolylbut-1-ynyl)phenyl)propyl)acetamide at RT gave Example 180 as pale yellow oil. Yield (0.194 g, 66%): $^1$H NMR (400 MHz, DMSO-d$_6$) δ 7.08-7.28 (m, 8H), 4.58-4.61 (t, J=6.0 Hz, 1H), 2.83 (t, J=7.2 Hz, 2H), 2.65 (t, J=7.2 Hz, 2H), 2.55 (m, 2H), 2.30 (s, 3H), 1.61-1.64 (m, 2H). $^{13}$C NMR (100 MHz, DMSO-d$_6$) δ 146.9, 138.6, 135.7, 130.0, 129.2, 129.0, 128.5, 128.2, 126.3, 125.8, 125.4, 122.7, 89.8, 81.2, 70.9, 42.4, 31.6, 19.7, 19.0. ESI MS m/z 294 [M+1]$^+$.

Example 181

PREPARATION OF 3-AMINO-1-(3-(3-M-TOLYL-BUT-1-YNYL)PHENYL)PROPAN-1-OL

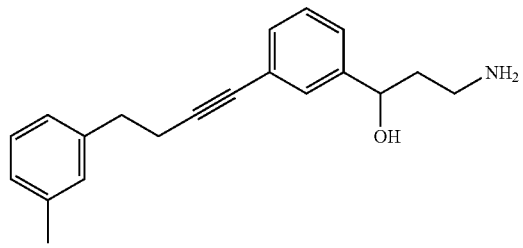 [SMILES: Cc1cccc(CCC#Cc2cccc(C(O)CCN)c2)c1]

3-Amino-1-(3-(3-m-tolylbut-1-ynyl)phenyl)propan-1-ol was prepared following the method used in Example 179.

Step 1: Sonogashira reaction of the iodide (2,2,2-trifluoro-N-(3-hydroxy-3-(3-iodophenyl)propyl)acetamide) with 1-(but-3-ynyl)-3-methylbenzene yielded 2,2,2-trifluoro-N-(3-hydroxy-3-(3-(3-m-tolylbut-1-ynyl)phenyl)propyl)acetamide as brown oil. Yield (0.410 g, 79%): $^1$H NMR (400 MHz, DMSO-d$_6$) δ 9.36 (bs, 1H), 7.22-7.33 (m, 3H), 7.19-7.22 (m, 2H), 7.18 (s, 1H), 7.16 (d, J=7.6 Hz, 1H), 7.08 (d, J=7.6 Hz, 1H), 5.39 (d, J=4.4 Hz, 1H), 4.53-4.58 (m, 1H), 3.20-3.28 (m, 2H), 2.80 (t, J=7.6 Hz, 2H), 2.67 (t, J=7.6 Hz, 2H), 2.28 (s, 3H), 1.75-1.83 (m, 2H).

Step 5: Deprotection of 2,2,2-trifluoro-N-(3-hydroxy-3-(3-(3-m-tolylbut-1-ynyl)phenyl)propyl)acetamide at RT gave Example 181 as pale yellow oil. Yield (0.190 g, 63%): $^1$H NMR (400 MHz, DMSO-d$_6$) δ 7.25-7.31 (m, 3H), 7.19-7.22 (m, 2H), 7.10 (s, 1H), 7.05 (d, J=7.6 Hz, 1H), 7.0 (d, J=7.6 Hz, 1H), 4.60-4.64 (m, 1H), 2.72-2.80 (m, 4H), 2.65 (t, J=6.8 Hz, 2H), 2.27 (s, 3H), 1.71-1.80 (m, 2H). $^{13}$C NMR (100 MHz, DMSO-d$_6$) δ 146.5, 140.8, 137.7, 130.0, 129.7, 128.8, 128.6, 127.3, 126.0, 125.7, 123.4, 90.5, 81.7, 70.2, 38.5, 37.4, 34.7, 21.5, 21.3. ESI MS m/z 294 [M+1]$^+$.

Example 182

PREPARATION OF 1-((3-(3-AMINO-1-HYDROXYPROPYL)PHENYL)ETHYNYL)CYCLOPENTANOL

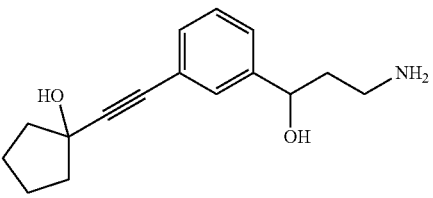 [SMILES: NCCC(O)c1cccc(C#CC2(O)CCCC2)c1]

1-((3-(3-Amino-1-hydroxypropyl)phenyl)ethynyl)cyclopentanol was prepared following the method used in Example 132.

Step 1: Sonogashira reaction of bromide 25 with 1-ethynylcyclopentanol yielded 2,2,2-trifluoro-N-(3-hydroxy-3-(3-((1-hydroxycyclopentyl)ethynyl)phenyl)propyl)-acetamide as brown oil. Yield (0.55 g, 55%): $^1$H NMR (400 MHz, CDCl$_3$) δ 7.41 (s, 1H), 7.28-7.35 (m, 3H), 4.85-4.87 (m, 1H), 3.66-3.70 (m, 1H), 3.38-3.44 (m, 1H), 2.41 (bs, 1H), 1.76-2.08 (m, 10H).

Step 2: Deprotection of 2,2,2-trifluoro-N-(3-hydroxy-3-(3-((1-hydroxy cyclopentyl)ethynyl)phenyl)propyl)acetamide at RT gave Example 182 as pale yellow oil. Yield (0.126 g, 31%): $^1$H NMR (400 MHz, DMSO-d$_6$) δ 7.24-7.33 (m, 4H), 4.63-4.66 (m, 1H), 2.71-2.83 (m, 2H), 1.76-1.80 (m, 4H), 1.44-1.78 (m, 6H). $^{13}$C NMR (100 MHz, D$_2$O) δ 143.3, 131.0, 128.9, 128.7, 126.1, 122.4, 117.7, 92.9, 82.9, 74.7, 71.1, 41.4, 36.9, 35.8, 22.8. ESI MS m/z 260 [M+1]$^+$.

Example 183

PREPARATION OF 2-(4-(3-(3-AMINO-1-HYDROXYPROPYL)PHENYL)BUT-3-YNYL)PHENOL

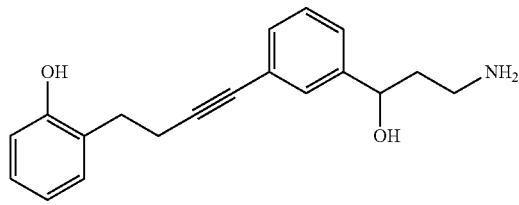 [SMILES: NCCC(O)c1cccc(C#CCCc2ccccc2O)c1]

2-(4-(3-(3-Amino-1-hydroxypropyl)phenyl)but-3-ynyl)phenol was prepared following the method used in Example 179.

Step 1: Sonogashira reaction of the iodide (2,2,2-trifluoro-N-(3-hydroxy-3-(3-iodophenyl)propyl)acetamide) with (2-(but-3-ynyl)phenoxy)(tert-butyl)dimethylsilane yielded N-(3-(3-(4-(2-(tert-butyldimethylsilyloxy)phenyl)but-1-ynyl)phenyl)-3-hydroxypropyl)-2,2,2-trifluoroacetamide as brown oil. Yield (0.220 g, 41%): $^1$H NMR (400 MHz, DMSO-d$_6$) δ 9.36 (bs, 1H), 7.26-7.31 (m, 4H), 7.19-7.21 (m, 1H), 7.11 (t, J=6.0 Hz, 1H), 6.96 (t, J=6.0 Hz, 1H), 6.88 (d, J=8.0 Hz, 1H), 5.39 (d, J=4.4 Hz, 1H), 4.53-4.56 (m, 1H), 3.22-3.24 (m, 2H), 2.85 (t, J=7.6 Hz, 2H), 2.65 (t, J=7.6 Hz, 2H), 1.75-1.81 (m, 2H), 1.0 (s, 9H), 0.23 (s, 6H).

Step 2: Deprotection of N-(3-(3-(4-(2-(tert-butyldimethylsilyloxy)phenyl)but-1-ynyl)phenyl)-3-hydroxypropyl)-2,2,2-trifluoroacetamide at RT gave Example 183 as off-white solid. Both the protecting groups were removed in one step. Yield (0.087 g, 72%): $^1$H NMR (400 MHz, DMSO-d$_6$) δ 7.23-7.30 (m, 3H), 7.19 (bd, J=7.2 Hz, 1H), 6.96 (bd, J=6.0 Hz, 1H), 6.88 (bt, J=8.0 Hz, 1H), 6.71-6.76 (m, 2H), 4.60-4.63 (m, 1H), 2.81-2.87 (m, 2H), 2.76 (t, J=7.2 Hz, 2H), 2.60 (t, J=7.2 Hz, 2H), 1.78-1.84 (m, 2H).

Example 184

PREPARATION OF 3-AMINO-1-(3-(4-CYCLOPENTYLBUT-1-YNYL)PHENYL)PROPAN-1-OL

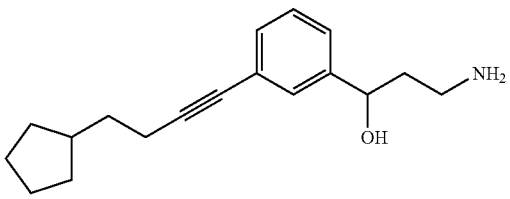 [SMILES: NCCC(O)c1cccc(C#CCCC2CCCC2)c1]

Example 184 is an alternative synthesis of 3-amino-1-(3-(4-cyclopentylbut-1-ynyl)phenyl)propan-1-ol which was also prepared in Example 71. 3-Amino-1-(3-(4-cyclopentylbut-1-ynyl)phenyl)propan-1-ol was prepared following the method used in Example 108.

Step 1: Sonogashira reaction of 25 with but-3-ynyl-cyclopentane yielded N-(3-(3-(4-cyclopentylbut-1-ynyl)phenyl)-3-hydroxypropyl)-2,2,2-trifluoroacetamide as a dark brown oil. Yield (690 mg, 69%): $^1$H NMR (400 MHz, CDCl$_3$) δ 7.22-7.57 (m, 4H), (m, 1H), 3.65-3.72 (m, 1H), 3.36-3.45 (m, 1H), 2.41 (t, J=8.0 Hz, 2H), 2.37 (bs, 1H), 1.90-1.97 (m, 3H), 1.80-1.82 (m, 2H), 1.54-1.59 (m, 4H), 1.51-1.53 (m, 2H), 1.12-1.15 (m, 2H).

Step 2: Deprotection of N-(3-(3-(4-cyclopentylbut-1-ynyl)phenyl)-3-hydroxypropyl)-2,2,2-trifluoroacetamide gave Example 184 hydrochloride as a white semi-solid (the solvent used in salt formation was DCM instead of methanol). Yield (341 mg, 68%): $^1$H NMR (400 MHz, DMSO-d$_6$) δ 7.22-7.29 (m, 4H), 4.63-4.66 (m, 1H), 2.77-2.89 (m, 2H), 2.37 (t, J=7.2 Hz, 2H), 1.76-1.89 (m, 3H), 1.68-1.73 (m, 2H), 1.44-1.58 (m, 6H), 0.93-1.11 (m, 2H). $^{13}$C NMR (100 MHz, DMSO-d$_6$) δ 146.2, 131.1, 130.1, 128.9, 125.9, 123.5, 91.1, 85.9, 80.9, 69.5, 36.9, 36.6, 35.0, 32.3, 25.1, 18.4. ESI MS m/z 272 [M+1]$^+$.

Example 185

PREPARATION OF (R)-3-AMINO-1-(3-(3-PHENOXYPROP-1-YNYL)PHENYL)PROPAN-1-OL

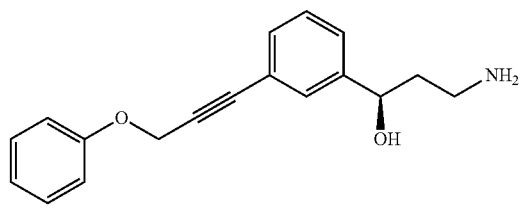 [SMILES: NCC[C@@H](O)c1cccc(C#CCOc2ccccc2)c1]

(R)-3-Amino-1-(3-(3-phenoxyprop-1-ynyl)phenyl)propan-1-ol was prepared following the method shown in shown in Scheme 28.

SCHEME 28
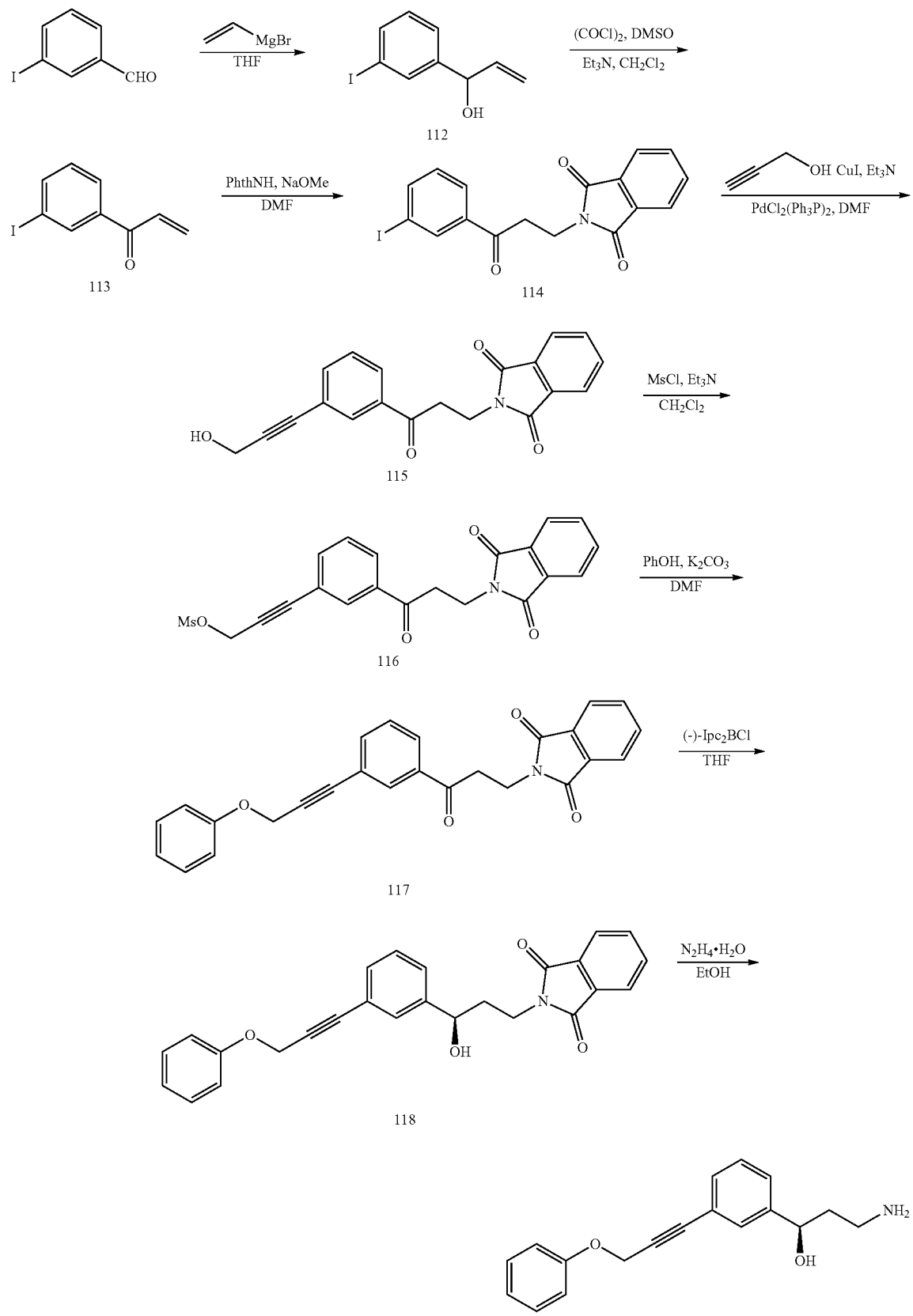

Step 1: To a cold (0° C.) solution of vinyl magnesium bromide (1M/THF, 17 mL) was added anhydrous THF (10 mL) followed by a solution of 3-iodobenzaldehyde (3.846 g, 16.6 mmol) in anhydrous THF (12 mL). The reaction mixture was stirred at 0° C. for 1.5 hr and aqueous NH$_4$Cl (25%, 25 mL) was added, stirred at room temperature, layers were separated, and aqueous layer was extracted with EtOAc. Combined organic layers were washed with aqueous NH$_4$Cl, brine, dried over anhydrous MgSO$_4$, filtered and concentrated under reduced pressure to give allyl alcohol 112 as a light-yellow oil. Yield (4.39 g, quant.); $^1$H NMR (400 MHz, CDCl$_3$) δ 7.73 (t, J=1.8 Hz, 1H), 7.61 (dt, J=1.2, 7.8 Hz, 1H), 7.30-7.34 (m, 1H), 7.08 (t, J=7.8 Hz, 1H), 5.99 (ddd, J=17.0, 10.4, 6.1 Hz, 1H), 5.37 (dt, J=17.0, 1.2 Hz, 1H), 5.22 (dt, J=10.2, 1.2 Hz, 1H), 5.14 (d, J=6.1 Hz), 1.9 (br.s, 1H).

Step 2: A solution of oxalyl chloride (1.8 mL, 20.6 mmol) in anhydrous CH$_2$Cl$_2$ (15 mL) was cooled under argon to −78° C. and a solution of anhydrous DMSO (3.0 mL, 42.2 mmol) in CH$_2$Cl$_2$ was added dropwise via an addition funnel. First half of DMSO solution was added over a period of 13 min, second half added over 1 min. Reaction mixture was stirred at −78° C. for 6 min and then a solution of allyl alcohol 112 (4.39 g, 16.6 mmol) in CH$_2$Cl$_2$ (15 mL) was added dropwise over a period of 30 min. The reaction mixture was stirred at −78° C. for 35 min after which triethylamine (9 mL, 64.6 mmol) was added dropwise over 2 min and the reaction mixture was allowed to warm to room temperature. Water (100 mL) was added and after vigorous shaking layers were separated. Aqueous layer was extracted with CH$_2$Cl$_2$, combined organic layers were consequently washed with aqueous HCl (1%, 100 mL), aq. NaHCO$_3$ (5%, 100 mL), brine (30%, 100 mL), dried over anhydrous MgSO$_4$, filtered and concentrated under reduced pressure to give crude vinyl ketone 113 (ca 75% molar) as a yellow oil which was used in the next step without purification. Yield (4.40 g, quant); $^1$H NMR (400 MHz, CDCl$_3$) δ 8.26 (t, J=1.8 Hz, 1H), 7.87-7.92 (m, 2H), 7.23 (t, J=7.8 Hz, 1H), 7.09 (dd, J=17.0, 10.7 Hz, 1H), 6.44 (dd, J=17.2, 1.6 Hz, 1H), 5.97 (dd, J=10.6, 1.6 Hz, 1H).

Step 3. To a solution of vinyl ketone 113 (3.30 g, 12.8 mmol) and phthalimide (2.38 g, 16.18 mmol) in anhydrous DMF (15 mL) was added a solution of NaOMe (30% wt in MeOH, 0.1 mL) and the reaction mixture was stirred at room temperature for 2 hr. The reaction mixture was concentrated under reduced pressure and purification by flash chromatography (10% to 70% EtOAc-hexanes gradient) afforded crude product, which was dissolved in CH$_2$Cl$_2$, white precipitate was filtered off, and the filtrate was concentrated under reduced pressure. After trituration with hexane and a small amount of EtOAc a white precipitate formed and was filtered off and dried to give phthalimidoketone 114. Yield (2.725 g, 53%); $^1$H NMR (400 MHz, DMSO-d$_6$) δ 8.19 (t, J=1.8 Hz, 1H), 7.96 (ddd, J=1.0, 1.8, 7.8 Hz, 1H), 7.91 (ddd, J=1.2, 1.6, 7.8 Hz, 1H), 7.78-7.86 (m, 4H), 7.30 (t, J=7.8 Hz, 1H), 3.89 (t, J=7.0 Hz, 2H), 3.39 (t, J=7.0 Hz, 2H).

Step 4. Sonogashira coupling of aryliodide 114 and propargyl alcohol following the method used in Example 17 gave alkynol 115 as a yellow solid. Yield (1.86 g, 83%); $^1$H NMR (400 MHz, CDCl$_3$) δ 7.98 (t, J=1.6 Hz, 1H), 7.86-7.90 (m, 1H), 7.81-7.86 (m, 2H), 7.68-6.73 (m, 2H), 7.59 (dt, J=7.8, 1.2 Hz, 1H), 7.40 (dt, J=7.8, 0.4 Hz, 1H), 4.45 (s, 2H), 4.13 (t, J=7.2 Hz, 2H), 3.40 (t, J=7.2 Hz, 2H), 1.70 (br.s, 1H).

Step 5. Mesylation of alkynol 115 with methanesulfonyl chloride following the method used in Example 18 gave sulfonate 116 as a brownish solid. Yield (1.60 g, 70%); $^1$H NMR (400 MHz, CDCl$_3$) δ 8.01 (t, J=1.6 Hz, 1H), 7.94 (dd, J=1.2, 8.0 Hz, 1H), 7.81-7.87 (m, 2H), 7.69-7.74 (m, 2H), 7.63 (dt, J=1.4, 7.6 Hz, 1H), 7.44 (t, J=7.6 Hz, 1H), 5.07 (s, 2H), 4.13 (t, J=7.2 Hz, 2H), 3.40 (t, J=7.2 Hz, 2H), 3.15 (s, 3H).

Step 6. A mixture of phenol (0.934 g, 1.0 mmol), mesylate 116 (0.316 g, 0.767 mmol) and K$_2$CO$_3$ (0.136 g, 0.984 mmol) in anhydrous DMF (5 mL) was stirred at room temperature under argon for 1 h, then at 60° C. for 20 h. The reaction mixture was concentrated under reduced pressure, the residue suspended in EtOAc, filtered through a thin layer of a silica gel, and additionally washed with EtOAc. The filtrate was concentrated under reduced pressure and purification by flash chromatography (5% to 40% EtOAc-hexanes gradient) afforded phenoxypropyne 117 as a colorless oil. Yield (0.0695 g, 22.1%); $^1$H NMR (400 MHz, CDCl$_3$) δ 7.97 (t, J=1.6 Hz, 1H), 7.88 (dt, J=7.8, 1.4 Hz, 1H), 7.68-7.73 (m, 2H), 7.59 (dt, J=7.8, 1.2 Hz, 1H), 7.39 (t, J=7.4 Hz, 1H), 7.27-7.33 (m, 2H), 6.95-7.04 (m, 3H), 4.90 (s, 2H), 4.12 (t, J=7.2 Hz, 2H), 3.38 (t, J=7.2 Hz, 2H).

Step 7. Ketone 117 was reduced with (−)-Ipc$_2$B—Cl following the method used in Example 100 to afford (R)-hydroxyphthalimide 118 as a colorless oil after purification by flash chromatography (5% to 30% EtOAc-hexanes gradient). Yield (0.0511 g, 73%); $^1$H NMR (400 MHz, CDCl$_3$) δ 7.78-7.85 (m, 2H), 7.65-7.73 (m, 2H), 7.40-4.42 (m, 1H), 7.19-7.34 (m, 5H), 6.95-7.05 (m, 3H), 4.88 (s, 2H), 4.63 (dd, J=9.0, 4.5 Hz, 1H), 3.85-3.93 (m, 2H), 1.98-2.10 (m, 2H).

Step 8. Deprotection of phthalimide 118 following the method used in Example 17 except that two molar excess hydrazine was used and the reaction mixture was stirred at room temperature for 70 hr gave Example 185 as a colorless oil after flash chromatography (0% to 100% of 10% 7N NH$_3$/MeOH—CH$_2$Cl$_2$ gradient). Yield (0.033 g, 94%); $^1$H NMR (400 MHz, CDCl$_3$) δ 7.39-7.42 (m, 1H), 7.24-7.36 (m, 5H), 6.99-7.04 (m, 2H), 6.92-6.98 (m, 1H), 4.92 (s, 2H), 4.70 (dd, J=7.8, 5.3 Hz, 1H), 2.66-2.78 (m, 2H), 1.74-1.89 (m, 2H); RP-HPLC t$_R$=6.38 min, 97.5% (AUC); LC-MS m/z=282.52 [M+H]$^+$.

Example 186

PREPARATION OF (R)-3-AMINO-1-(3-(3-(2,6-DIMETHYLPHENOXY)PROP-1-YNYL)PHENYL)PROPAN-1-OL

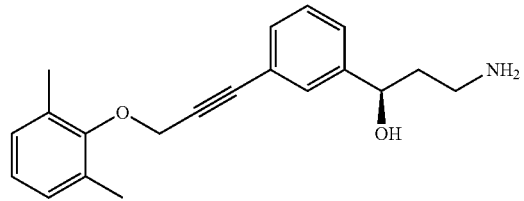

(R)-3-Amino-1-(3-(3-(2,6-dimethylphenoxy)prop-1-ynyl)phenyl)propan-1-ol was prepared following the method used in Example 185.

Step 1. Alkylation of 2,6-dimethylphenol with mesylate 116 afforded 2-(3-(3-(3-(2,6-dimethylphenoxy)prop-1-ynyl)phenyl)-3-oxopropyl)isoindoline-1,3-dione as a colorless oil. Yield (0.12 g, 42%); $^1$H NMR (400 MHz, CDCl$_3$) δ 7.96 (t, J=1.6 Hz, 1H), 7.88 (dt, J=8.0, 1.2 Hz, 1H), 7.82-7.86 (m, 2H), 7.67-7.75 (m, 2H), 7.58 (dt, J=7.8, 1.4 Hz, 1H), 7.40 (t, J=7.8 Hz, 1H), 6.99-7.04 (m, 2H), 6.90-6.96 (m, 1H), 4.71 (s, 2H), 4.13 (t, J=7.4 Hz, 2H), 3.40 (t, J=7.4 Hz, 2H), 2.35 (s, 6H).

Step 2. Chiral reduction of 2-(3-(3-(3-(2,6-dimethylphenoxy)prop-1-ynyl)phenyl)-3-oxopropyl)isoindoline-1,3-dione gave (R)-2-(3-(3-(3-(2,6-dimethylphenoxy)prop-1-ynyl)phenyl)-3-hydroxypropyl)isoindoline-1,3-dione as a colorless oil after purification by flash chromatography (5% to 30% EtOAc-hexanes gradient). Yield (0.092 g, 76%); $^1$H NMR (400 MHz, CDCl$_3$) δ 7.80-7.86 (m, 2H), 7.68-7.74 (m, 2H), 7.39-7.41 (m, 1H), 7.31 (dt, J=7.0, 1.8 Hz, 1H), 7.20-7.28 (m, 2H), 6.99-7.03 (m, 2H), 6.93 (dd, J=8.2, 6.7 Hz, 1H), 4.70 (s, 2H), 4.64 (dd, J=8.8, 4.3 Hz, 1H), 3.86-3.92 (m, 2H), 2.35 (s, 6H), 1.96-2.10 (m, 2H).

Step 3. Deprotection of (R)-2-(3-(3-(3-(2,6-dimethylphenoxy)prop-1-ynyl)phenyl)-3-hydroxypropyl)isoindoline-1,3-dione gave Example 186 as a colorless oil after flash chromatography purification (0% to 100% of 10% 7N NH$_3$/MeOH—CH$_2$Cl$_2$ gradient). Yield (0.045 g, 69%); $^1$H NMR (400 MHz, CDCl$_3$) δ 7.38-7.41 (m, 1H), 7.34 (dt, J=7.4, 1.6 Hz, 1H), 7.29 (t, J=7.4 Hz, 1H), 7.26 (dt, J=7.4, 1.6 Hz, 1H), 6.98-7.03 (m, 2H), 6.91 (dd, J=8.2, 6.8 Hz, 1H), 4.75 (s, 2H), 4.70 (dd, J=8.0, 5.3 Hz, 1H), 2.67-2.80 (m, 2H), 2.32 (s, 6H), 1.74-1.90 (m, 2H); RP-HPLC $t_R$=6.88 min, 99.4% (AUC); LC-MS m/z=310.68 [M+H]$^+$.

Example 187

PREPARATION OF (R)-3-AMINO-1-(3-(3-(2,6-DIMETHYLPHENYLTHIO)PROP-1-YNYL)PHENYL)PROPAN-1-OL

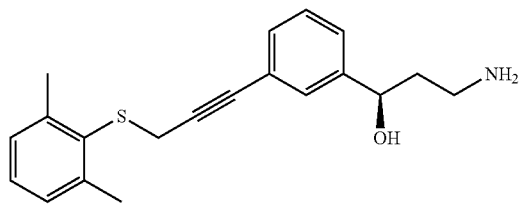

(R)-3-Amino-1-(3-(3-(2,6-dimethylphenylthio)prop-1-ynyl)phenyl)propan-1-ol was prepared following the method used in Example 18 and 185.

Step 1. Alkylation of 2,6-dimethylthiophenol with mesylate 116 according to the method used in Example 18 except that the reaction was carried out at room temperature for 18 hr, gave 2-(3-(3-(3-(2,6-dimethylphenylthio)prop-1-ynyl)phenyl)-3-oxopropyl)isoindoline-1,3-dione as a yellowish oil without purification. Yield (0.275 g, 96%); $^1$H NMR (400 MHz, CDCl$_3$) δ 7.80-7.87 (m, 3H), 7.77 (t, J=1.4 Hz, 1H), 7.68-7.73 (m, 2H), 7.41 (dt, J=1.4, 7.8 Hz, 1H), 7.33 (t, J=7.8 Hz, 1H), 7.08-7.16 (m, 3H), 4.12 (t, J=7.4 Hz, 2H), 3.60 (s, 2H), 3.37 (t, J=7.4 Hz, 2H), 2.58 (s, 6H).

Step 2. Chiral reduction of 2-(3-(3-(3-(2,6-dimethylphenylthio)prop-1-ynyl)phenyl)-3-oxopropyl)isoindoline-1,3-dione gave (R)-2-(3-(3-(3-(2,6-dimethylphenylthio)prop-1-ynyl)phenyl)-3-hydroxypropyl)isoindoline-1,3-dione as a colorless oil after purification by flash chromatography (5% to 30% EtOAc-hexanes gradient). Yield (0.178 g, 82%); $^1$H NMR (400 MHz, CDCl$_3$) δ 7.79-7.85 (m, 2H), 7.66-7.73 (m, 2H), 7.23-7.27 (m, 1H), 7.20-7.23 (m, 1H), 7.18 (t, J=7.6 Hz, 1H), 7.07-7.14 (m, 4H), 4.58-4.64 (m, 1H), 3.85-3.92 (m, 2H), 3.58 (s, 2H), 2.58 (s, 6H), 1.95-2.10 (m, 2H).

Step 3. Deprotection of (R)-2-(3-(3-(3-(2,6-dimethylphenylthio)prop-1-ynyl)phenyl)-3-hydroxypropyl)isoindoline-1,3-dione gave Example 187 as a colorless oil after flash chromatography purification (0% to 100% of 10% 7N NH$_3$/MeOH—CH$_2$Cl$_2$ gradient). Yield (0.090 g, 71%); $^1$H NMR (400 MHz, CDCl$_3$) δ 7.25-7.29 (m, 1H), 7.19-7.25 (m, 2H), 7.10-7.15 (m, 2H), 7.04-7.10 (m, 2H), 4.66 (dd, J=5.1, 7.8 Hz, 1H), 3.64 (s, 2H), 2.64-2.77 (m, 2H), 2.58 (s, 6H), 1.72-1.88 (m, 2H); RP-HPLC $t_R$=7.27 min, 94.8% (AUC); LC-MS m/z=326.93 [M+H]$^+$.

Example 188

PREPARATION OF 4-((3-(2-AMINOETHYLAMINO)—PHENYL)ETHYNYL)HEPTAN-4-OL

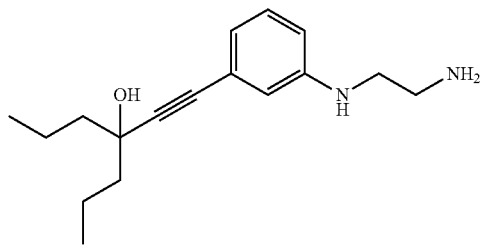 [SMILES: CCCC(O)(C#Cc1cccc(NCCN)c1)CCC]

4-((3-(2-Aminoethylamino)-phenyl)ethynyl)heptan-4-ol was prepared following the method shown in Scheme 29.

SCHEME 29

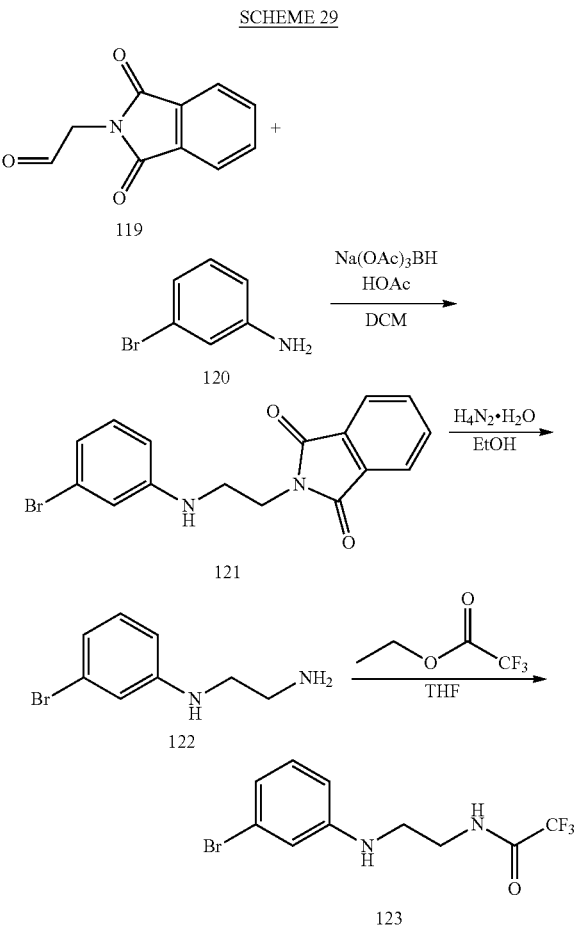

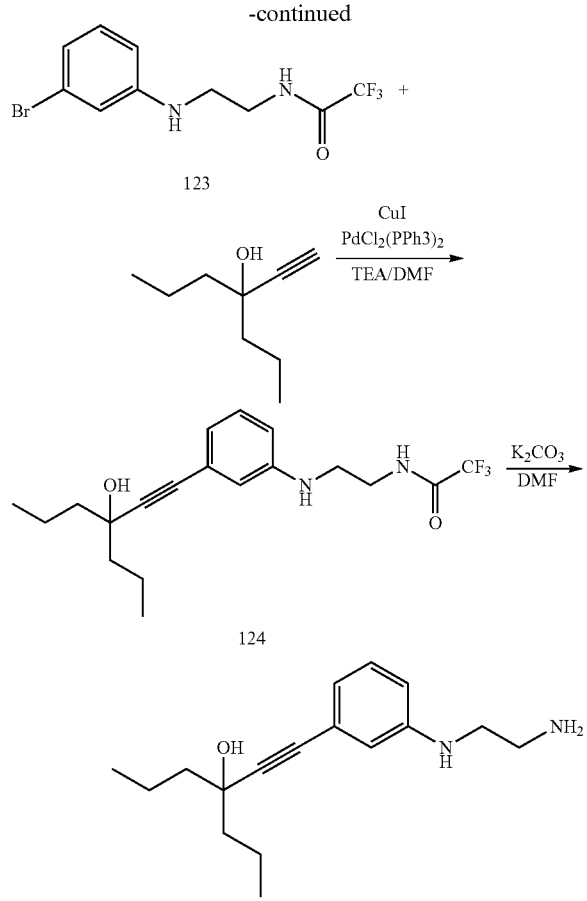

Step 1: To a stirred solution of 2-(1,3-dioxoisoindolin-2-yl)acetaldehyde (119) (3.0 g, 15.9 mmol) in CH$_2$Cl$_2$ (1000 ml) was added 3-bromoaniline (120) (2.2 g, 13.0 mmol), sodium triacetoxyborohydride (4.2 g, 20 mmol) and acetic acid (1.2 g, 20 mmol). The reaction was stirred at room temperature overnight, then washed with saturated ammonium chloride, water, and brine. The combined organics were dried over MgSO$_4$, filtered, and concentrated in-vacuo. Purification by flash chromatography (10-40% ethyl acetate/hexanes gradient) gave benzyl bromide 121 as a yellow oil. Yield (1.7 g, 38%). $^1$H NMR (400 MHz, CDCl$_3$) δ 7.80-7.88 (m, 2H), 7.68-7.78 (m, 2H), 6.93-6.99 (m, 1H), 6.72-6.77 (m, 2H), 6.49-6.54 (m, 1H), 4.23 (brs, 1H), 3.95 (t, J=6.0 Hz, 2H), 3.39 (t, J=6.0 Hz, 2H).

Step 2: Benzyl bromide 121 was deprotected according to the method used in Example 17. Purification by flash chromatography (0-10% (7N NH$_3$/MeOH)/dichloromethane) gradient) gave diamine 122 as a yellow oil. Yield (0.286 g, 57%). $^1$H NMR (400 MHz, CDCl$_3$) δ 6.99 (t, J=8.0 Hz, 1H), 6.76-6.81 (m, 1H), 6.74 (t, J=2.0 Hz, 1H), 6.49-6.54 (m, 1H), 4.19 (brs, 1H), 3.13 (t, J=6.0 Hz, 2H), 2.92 (t, J=6.0 Hz, 2H), 1.20 (brs, 2H).

Step 3: Trifluoroamide 123 was formed by addition of ethyltrifluoroacetate to diamine 122 according to the method used in Example 18. Yield (0.462 g, quantitative). $^1$H NMR (400 MHz, CDCl$_3$) δ 7.01 (t, J=8.0 Hz, 1H), 6.99 (brs, 1H), 6.82-6.86 (m, 1H), 6.74 (t, J=2.4 Hz, 1H), 6.50-6.55 (m, 1H), 4.03 (brs, 1H), 3.55 (q, J=6.0, Hz, 2H), 3.33 (t, J=6.0 Hz, 2H).

Step 4: Sonogashira coupling of trifluoroamide 123 with 4-ethynylheptan-4-ol (20) was carried out according to the method used in Example 17. Purification by flash chromatography (5-30% ethyl acetate/hexanes gradient) gave alkynol 124 as an orange oil. Yield (0.30 g, 60%). $^1$H NMR (400 MHz, CDCl$_3$) δ 7.54 (brs, 1H), 7.07 (t, J=8.0 Hz, 1H), 6.75-6.78 (m, 1H), 6.61-6.64 (m, 1H), 6.52-6.56 (m, 1H), 3.51 (q, J=5.6 Hz, 2H), 3.32 (t, J=6.0 Hz, 2H), 1.63-1.71 (m, 4H), 1.50-1.63 (m, 4H), 0.95 (t, J=7.2 Hz, 6H).

Step 5: Deprotection of alkynol 124 was carried out according to the method used in Example 1. Purification by flash chromatography (0-10% (7N NH$_3$/MeOH)/dichloromethane) gradient) gave Example 188 as a yellow waxy solid. Yield (0.14 g, 63%). $^1$H NMR (400 MHz, DMSO) δ 6.97-7.03 (m, 1H), 6.46-6.54 (m, 3H), 5.66 (t, J=5.2 Hz, 1H), 5.07 (s, 1H), 2.94 (q, J=6.4 Hz, 2H), 2.66 (t, J=6.4 Hz, 2H), 1.38-1.62 (m, 10H), 0.88 (t, J=7.8 Hz, 6H).

Example 189

PREPARATION OF 4-((3-(2-AMINOETHYLTHIO)PHENYL)ETHYNYL)HEPTAN-4-OL

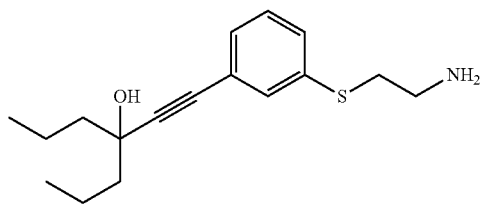 [SMILES: CCCC(O)(C#Cc1cccc(SCCN)c1)CCC]

4-((3-(2-Aminoethylthio)phenyl)ethynyl)heptan-4-ol was prepared following the method method shown in Scheme 30.

SCHEME 30

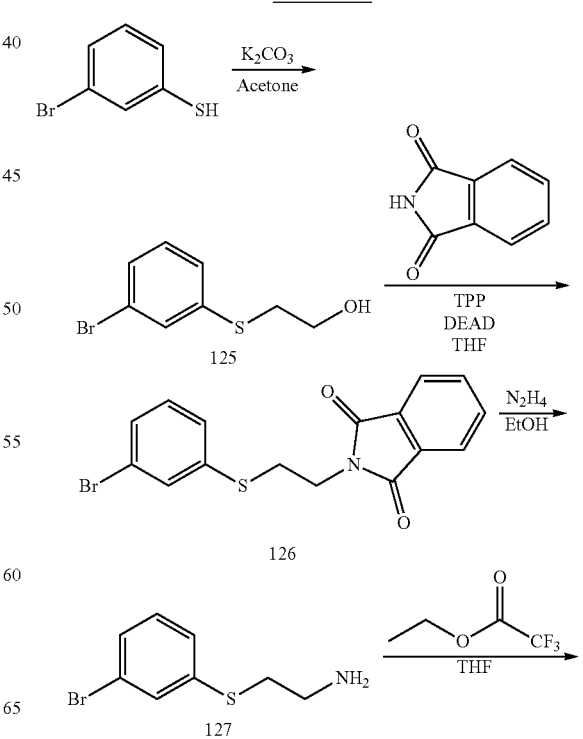

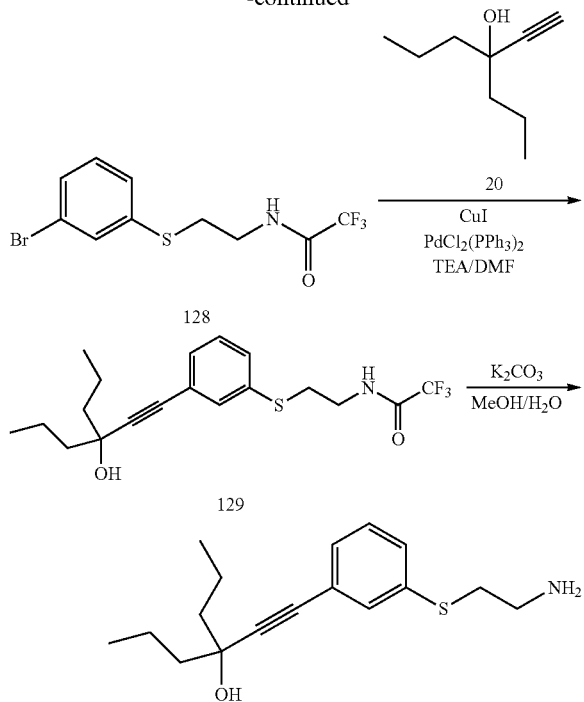

ynyl)phenylthio)ethyl)acetamide (129) as an orange. Yield (0.22 g, 52%): $^1$H NMR (400 MHz, DMSO) δ 9.52-9.60 (m, 1H), 7.26-7.36 (m, 3H), 7.16-7.20 (m, 1H), 5.11 (s, 1H), 3.60 (ddd, J=6.4 Hz, 2H), 3.11 (t, J=7.2 Hz, 2H), 1.52-1.62 (m, 4H), 1.38-1.52 (m, 4H), 0.89 (t, J=7.2 Hz, 6H).

Step 6: Deprotection of 2,2,2-trifluoro-N-(2-(3-(3-hydroxy-3-propylhex-1-ynyl)phenylthio)ethyl)acetamide (129) according to the method used in Example 1 followed by flash chromatography (0-10% (7N NH$_3$/MeOH)/dichloromethane gradient) gave Example 189 as a yellow oil. Yield (0.89 g, 68%): $^1$H NMR (400 MHz, MeOD) δ 7.36-7.38 (m, 1H), 7.32 (dt, J=1.6, 7.6 Hz, 1H), 7.25 (t, J=7.6 Hz, 1H), 7.20 (dt, J=1.6, 7.6 Hz, 1H), 3.01 (t, J=6.4 Hz, 2H), 2.78 (brs, 2H), 1.62-1.74 (m, 4H), 1.50-1.62 (m, 4H), 0.97 (t, J=7.2 Hz, 6H).

Example 190

PREPARATION OF 4-((3-(2-AMINOETHYL-SULFINYL)PHENYL)ETHYNYL)HEPTAN-4-OL

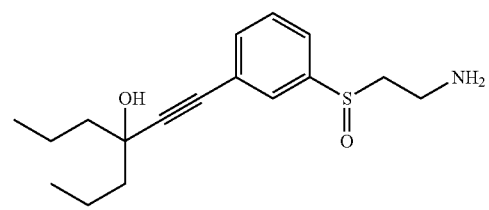 [SMILES: CCCC(O)(C#Cc1cccc(S(=O)CCN)c1)CCC]

4-(3-(2-Aminoethylsulfinyl)phenyl)ethynyl)heptan-4-ol was prepared following the method shown in Scheme 31.

Step 1: Alkylation of 3-bromobenzenethiol with 2-bromoethanol according to the method used in Example 18, gave 2-(3-bromophenylthio)ethanol (125) as a yellow oil without purification. Yield (3.6 g, 97%): $^1$H NMR (400 MHz, CDCl$_3$) δ 7.49 (t, J=2.0 Hz, 1H), 7.31 (ddd, J=0.8, 1.6, 8.0 Hz, 1H), 7.27 (ddd, J=0.8, 1.6, 8.0 Hz, 1H), 7.13 (t, J=7.6 Hz, 1H), 3.75 (t, J=6.4 Hz, 2H), 3.10 (t, J=6.4 Hz, 2H), 2.18 (brs, 1H).

Step 2: Mitsunobu coupling of 2-(3-bromophenylthio)ethanol (125) with phthalimide according to the method used in Example 17, followed by flash chromatography (5-20% ethyl acetate/hexanes gradient) gave 2-(2-(3-bromophenylthio)ethyl)isoindoline-1,3-dione (126) as a white solid. Yield (4.04 g, 72%): $^1$H NMR (400 MHz, CDCl$_3$) δ 7.77-7.84 (m, 2H), 7.66-7.72 (m, 2H), 7.50 (t, J=2.0 Hz, 1H), 7.30 (ddd, J=0.8, 1.6, 7.6 Hz, 1H), 7.19 (ddd, J=0.8, 1.6, 7.6 Hz, 1H), 7.07 (t, J=7.6 Hz, 1H), 3.93 (t, J=7.2 Hz, 2H), 3.22 (J=7.2 Hz, 2H).

Step 3: Deprotection of 2-(2-(3-bromophenylthio)ethyl)isoindoline-1,3-dione (126) according to the procedure used in Example 18 gave 2-(3-bromophenylthio)ethanamine (127) as a yellow oil. Yield (1.56 g, 98%): $^1$H NMR (400 MHz, CDCl$_3$) δ 7.44 (t, J=2.0 Hz, 1H), 7.26 (ddd, J=0.8, 1.6, 7.6 Hz, 1H), 7.21 (ddd, J=0.8, 1.6, 7.6 Hz, 1H), 7.09 (t, J=8.0 Hz, 1H), 2.87-3.0 (m, 2H), 2.82-2.86 (m, 2H), 1.7-2.4 (brs, 2H).

Step 4: Amidation of 2-(3-bromophenylthio)ethanamine (127) according to the method used in Example 18, followed by flash chromatography (5-20% ethyl acetate/hexanes gradient) gave N-(2-(3-bromophenylthio)ethyl)-2,2,2-trifluoroacetamide (128) as a colorless oil. Yield (1.75 g, 80%): $^1$H NMR (400 MHz, CDCl$_3$) δ 7.50 (t, J=2.0 Hz, 1H), 7.35 (ddd, J=0.8, 1.6, 7.6 Hz, 1H), 7.29 (ddd, J=0.8, 1.6, 7.6 Hz, 1H), 7.16 (t, J=8.0 Hz, 1H), 6.81 (brs, 1H), 3.55 (app q, J=6.4 Hz, 2H), 3.10 (t, J=6.4 Hz, 2H).

Step 5: Sonogashira coupling of alkynol 20 with N-(2-(3-bromophenylthio)ethyl)-2,2,2-trifluoroacetamide (128) according to the method used in Example 1 followed by flash chromatography (5-50% ethyl acetate/hexanes gradient) gave 2,2,2-trifluoro-N-(2-(3-(3-hydroxy-3-propylhex-1-

SCHEME 31

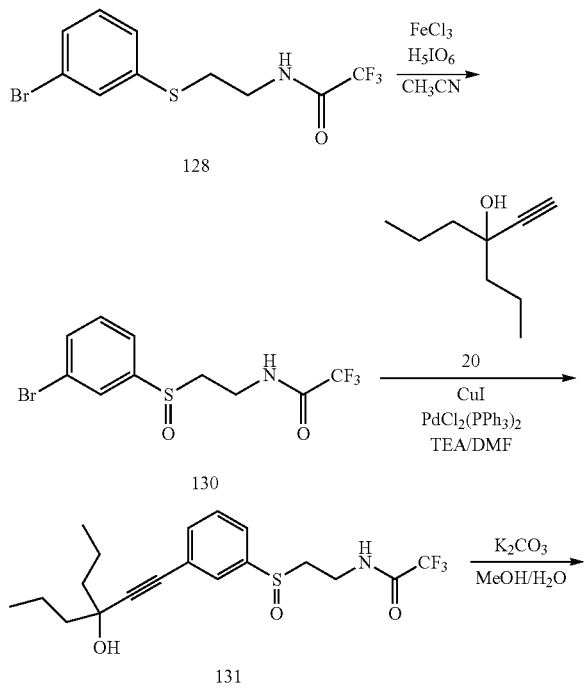

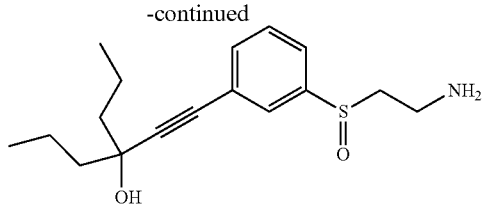

Step 1: To a solution of the bromide 128 (0.6 g, 1.83 mmol) in acetonitrile (10 mL) at room temperature was added iron III chloride (0.015 g, 0.092 mmol (5%)), and periodic acid (0.46 g, 2.0 mmol). The reaction was stirred overnight then quenched with saturated aqueous $Na_2S_2O_3$ (4 mL). Acetonitrile was removed in-vacuo and the residue was extracted from water with ethyl acetate. The combined organics was washed with brine, dried over $MgSO_4$, filtered, concentrated in-vacuo, and purified by flash chromatography (5-50% ethyl acetate/hexanes gradient), giving the sulfoxide 130 as a yellow oil. Yield (0.196 g, 31%): $^1$H NMR (400 MHz, $CDCl_3$) δ 8.37 (m, 1H), 7.74 (t, J=0.8, Hz, 1H), 7.61-7.65 (m, 1H), 7.46-7.50 (m, 1H), 7.39 (t, J=8.0 Hz, 1H), 3.78-3.89 (m, 1H), 3.63-3.73 (m, 1H), 3.20-3.29 (m, 1H), 2.87-2.95 (m, 1H).

Step 2: Sonogashira coupling of alkynol 20 with sulfoxide 130 according to the method used in Example 1 followed by flash chromatography (5-50% ethyl acetate/hexanes gradient) gave trifluoroamide-protected alkynol 131 as a yellow oil. Yield (0.15 g, 67%): $^1$H NMR (400 MHz, DMSO) δ 8.38 (brt, J=5.2 Hz, 1H), 7.57-7.60 (m, 1H), 7.40-7.52 (m, 3H), 3.76-3.86 (m, 1H), 3.62-3.72 (m, 1H), 3.18-3.27 (m, 1H), 2.85-2.94 (m, 1H), 2.77 (s, 1H), 1.62-1.74 (m, 4H), 1.48-1.62 (m, 4H), 0.93 (t, J=7.2 Hz, 6H).

Step 3: Deprotection of trifluoroamide-protected alkynol 131 according to the method used in Example 1 followed by flash chromatography (0-10% (7N $NH_3$/MeOH)/dichloromethane gradient) gave Example 190 as a yellow oil. Yield (0.06 g, 52%): $^1$H NMR (400 MHz, MeOD) δ 7.60-7.62 (m, 1H), 7.43-7.51 (m, 2H), 7.39 (t, J=8.0 Hz, 1H), 3.12-3.28 (m, 1H), 2.98-3.12 (m, 1H), 2.80-2.92 (m, 2H), 1.95 (brs, 3H), 1.60-1.72 (m, 4H), 1.47-1.60 (m, 4H), 0.93 (t, J=7.2 Hz, 6H).

Example 191

PREPARATION OF 4-((3-(2-AMINOETHYLSULFONYL)PHENYL)ETHYNYL)HEPTAN-4-OL

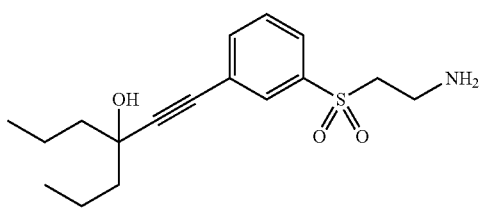 [SMILES: CCCC(O)(C#Cc1cccc(S(=O)(=O)CCN)c1)CCC]

4-(3-(2-Aminoethylsulfonyl)phenyl)ethynyl)heptan-4-ol was prepared following the method shown in Scheme 32.

SCHEME 32

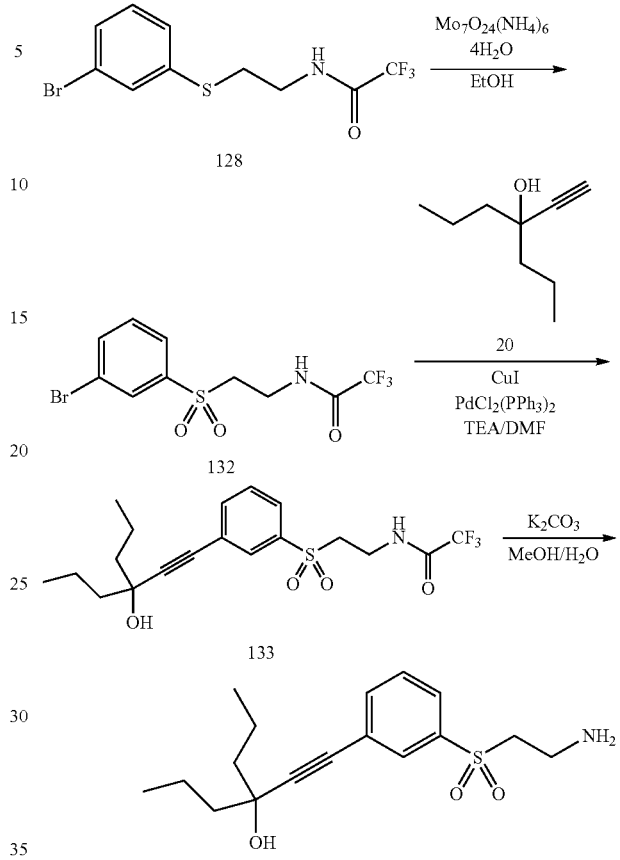

Step 1: To a solution of the bromide 128 (0.6 g, 1.83 mmol) in ethanol (10 mL) at room temperature was added ammonium molybdate tetrahydrate (0.68 g, 0.55 mmol (30%)), and hydrogen peroxide (1.9 mL of a 30% aq solution, 18.3 mmol). The reaction was stirred overnight then quenched with saturated aqueous $Na_2S_2O_3$ (4 mL). Ethanol was removed in-vacuo and the residue was extracted from water with ethyl acetate. The combined organics was washed with brine, dried over $MgSO_4$, filtered, concentrated in-vacuo, and purified by flash chromatography (5-50% ethyl acetate/hexanes gradient), giving the sulfone 132 as a white waxy solid. Yield (0.615 g, 93%): $^1$H NMR (400 MHz, $CDCl_3$) δ 8.05 (t, J=2.0 Hz, 1H), 7.81-7.87 (m, 2H), 7.49 (t, J=8.0 Hz, 1H), 7.25 (brs, 1H), 3.81-3.88 (m, 2H), 3.33-3.38 (m, 2H).

Step 2: Sonogashira coupling of alkynol 20 with sulfone 132 according to the method used in Example 1 followed by flash chromatography (5-50% ethyl acetate/hexanes gradient) gave trifluoroamide-protected alkynol 133 as a yellow oil. Yield (0.515 g, 72%): $^1$H NMR (400 MHz, DMSO) δ 7.93 (m, 1H), 7.80-7.84 (m, 1H), 7.69-7.73 (m, 1H), 7.55 (t, J=8.0 Hz, 1H), 7.27 (brs, 1H), 3.79-3.86 (m, 2H), 3.31-3.36 (m, 2H), 1.93 (brs, 1H), 1.64-1.78 (m, 4H), 1.51-1.64 (m, 4H), 0.98 (t, J=7.2 Hz, 6H).

Step 3: Deprotection of trifluoroamide-protected alkynol 133 according to the method used in Example 1 followed by flash chromatography (0-10% (7N $NH_3$/MeOH)/dichloromethane gradient) gave Example 191 as a yellow oil. Yield (0.21 g, 52%): $^1$H NMR (400 MHz, MeOD) δ 7.90-7.92 (m, 1H), 7.78-7.82 (m, 1H), 7.62-7.64 (m, 1H), 7.48 (t, J=8.0 Hz, 1H), 3.20-3.25 (m, 2H), 3.07-3.15 (m, 2H), 1.81 (brs, 3H), 1.62-1.75 (m, 4H), 1.50-1.62 (m, 4H), 0.96 (t, J=7.2 Hz, 6H).

Example 192

PREPARATION OF 4-((3-(4-AMINOBUTYL)PHENYL)ETHYNYL)HEPTAN-4-OL

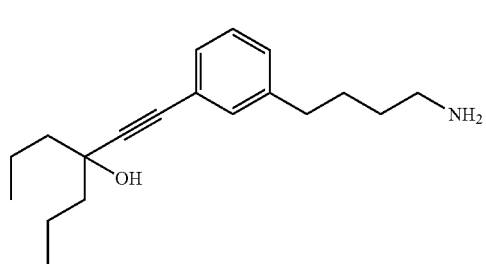 [SMILES: CCCC(O)(C#Cc1cccc(CCCCN)c1)CCC]

4-((3-(4-Aminobutyl)phenyl)ethynyl)heptan-4-ol was prepared following the method shown in shown in Scheme 33.

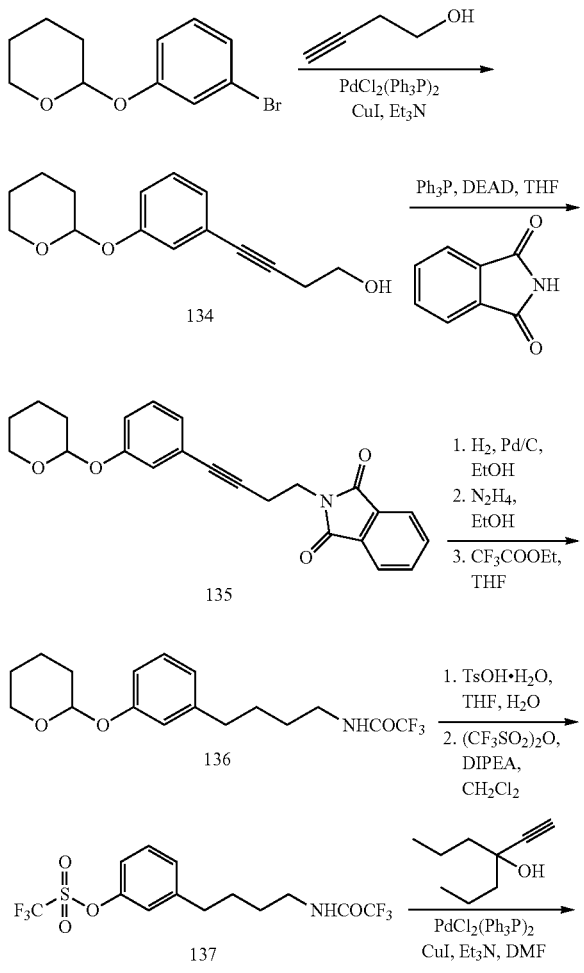

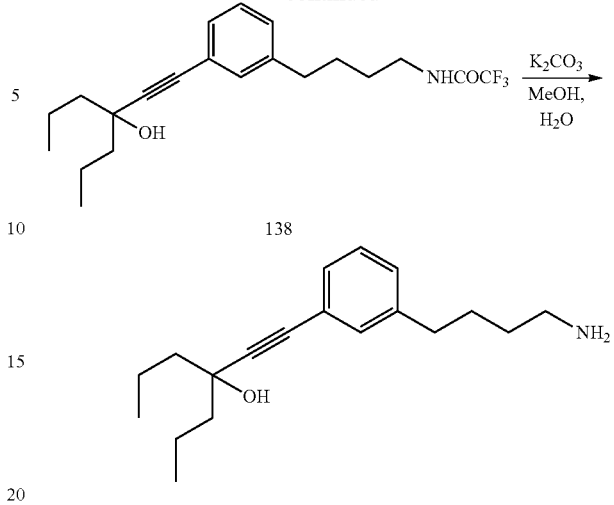

Step 1: Sonogashira coupling of tetrahydropyranylbromophenol and 3-butyn-1-ol following the method used in Example 17 except that the reaction mixture was heated at 90° C. for 18 hr to give alcohol 134 as an orange oil after flash chromatography purification (30 to 100% EtOAc-hexanes gradient). Yield (2.46 g, 85%); $^1$H NMR (400 MHz, DMSO-d$_6$) δ 7.22 (t, J=8.0 Hz, 1H), 6.93-7.01 (m, 3H), 5.45 (t, J=3.2 Hz, 1H), 4.86 (t, J=5.6 Hz, 1H), 3.66-3.75 (m, 1H), 3.48-3.58 (m, 3H), 2.51 (t, J=6.4 Hz, 2H), 1.64-1.90 (m, 3H), 1.44-1.64 (m, 3H).

Step 2: Mitsunobu coupling of alcohol 134 with phthalimide according to the method used in Example 17, followed by flash chromatography (10-40% ethyl acetate/hexanes gradient) gave phthalimide 135 as a colorless oil. Yield (1.77 g, 84%); $^1$H NMR (400 MHz, CDCl$_3$) δ 7.82-7.88 (m, 2H), 7.68-7.73 (m, 2H), 7.14 (t, J=8.0 Hz, 1H), 7.02-7.04 (m, 1H), 6.92-6.97 (m, 2H), 5.36 (t, J=3.1 Hz, 1H), 3.95 (t, J=7.2 Hz, 2H), 3.87 (ddd, J=3.13, 9.6, 14.5 Hz, 1H), 3.58 (dtd, J=1.2, 4.1, 11.2 Hz, 1H), 2.80 (t, J=7.2 Hz, 2H), 1.92-2.05 (m, 1H), 1.78-1.85 (m, 2H), 1.52-1.73 (m, 3H)

Step 3. A solution of butynephthalimide 135 (1.00 g, 2.66 mmol) in EtOH (absolute, 50 mL) was degassed by bubbling argon for 3 min. Then palladium on carbon (10%, 0.102 g) was added, the mixture was degassed by bubbling argon for 30 sec, and then by applying vacuum/H$_2$ three times. The reaction mixture was stirred under hydrogen atmosphere for 45 min. The mixture was filtered through a filter paper to remove the catalyst and the resultant solution of 2-(4-(3-(tetrahydro-2H-pyran-2-yloxy)phenyl)butyl)isoindoline-1,3-dione was used directly in the step.

Deprotection of 2-(4-(3-(tetrahydro-2H-pyran-2-yloxy)phenyl)butyl)isoindoline-1,3-dione with hydrazine monohydrate following the method used in Example 17 except that the reaction mixture was heated at +50° C. for 16 hrs afforded 4-(3-(tetrahydro-2H-pyran-2-yloxy)phenyl)butan-1-amine as a colorless oil, which was used in the next step without purification.

Protection of 4-(3-(tetrahydro-2H-pyran-2-yloxy)phenyl)butan-1-amine with ethyl trifluoroacetate following the method used in Example 18 gave trifluoroacetamide 136 as a colorless oil. Yield (0.72 g, 78% after three steps); $^1$H NMR (400 MHz, DMSO-d$_6$) δ 9.37 (br.t, 1H), 7.12-7.18 (m, 1H), 6.75-6.83 (m 3H), 5.40 (t, J=3.2 Hz, 1H), 3.69-3.77 (m, 1H), 3.47-3.54 (m, 1H), 3.17 (q, J=6.4 Hz, 2H), 2.52 (t, J=7.2 Hz, 2H), 1.63-1.90 (m, 3H), 1.40-1.62 (m, 7H).

Step 4. A mixture of THP-phenol 136 (0.72 g, 2.08 mmol), p-toluenesulfonic acid monohydrate (0.366 g) in THF:H$_2$O (3:1, 20 mL) was stirred at room temperature for 3.5 hr. The reaction mixture was treated with aqueous NaHCO$_3$-brine solution, layers were separated and aqueous layer extracted with EtOAc. Combined organic layers were washed with brine and concentrated under reduced pressure. Purification by flash chromatography (10%-50% EtOAc-hexanes gradient) gave 2,2,2-trifluoro-N-(4-(3-hydroxyphenyl)butyl)acetamide as a colorless oil, which was taken into the next step. Yield (0.438 g, 96%).

To a solution of 2,2,2-trifluoro-N-(4-(3-hydroxyphenyl) butyl)acetamide (0.438 g, 1.68 mmol) and diisopropylethylamine (0.5 mL, 2.87 mmol) in anhydrous CH$_2$Cl$_2$ (10 mL) a solution of trifluoromethanesulfonic anhydride (0.32 mL, 1.90 mmol) was added at 0° C. under argon. The reaction mixture was stirred at 0° C. for 15 min and concentrated under reduced pressure. EtOAc was added to the residue and the solution was washed with brine, dried over anhydrous MgSO$_4$, filtered and the filtrate was concentrated under reduced pressure to give crude triflate 137 as a light brown oil which was used in the next step without additional purification. Yield (0.683 g, quant.); $^1$H NMR (400 MHz, DMSO-d$_6$) δ 9.38 (brt, 1H), 7.45 (t, J=8.0 Hz, 1H), 7.24-7.34 (m, 3H), 3.17 (q, 6.4 Hz, 2H), 2.64 (t, J=7.2 Hz, 2H), 1.40-1.60 (m, 4H).

Step 5. Sonogashira coupling of triflate 137 and 4-ethynyl-heptan-4-ol following the method used in Example 177 gave alkynol 138 as a brownish oil after flash chromatography purification (5%-40% EtOAc-hexanes gradient). Yield (0.327 g, 51%); $^1$H NMR (400 MHz, DMSO-d$_6$) δ 9.38 (brt, 1H), 7.20-7.34 (m, 1H), 7.13-7.18 (m, 2H), 5.10 (s, 1H), 3.17 (q, J=6.4 Hz, 1H), 2.54 (t, J=7.2 Hz, 2H), 1.38-1.62 (m, 12H), 0.88 (t, J=7.6 Hz, 6H).

Step 6. Deprotection of trifluoroacetamide 138 following the method used in Example 1 except that the reaction mixture was stirred at 50° C. for 3.5 hr. Purification by flash chromatography (10%-100% 7N NH$_3$/MeOH/CH$_2$Cl$_2$—CH$_2$Cl$_2$) gave Example 192 as a white solid. Yield (0.175 g, 71%); $^1$H NMR (400 MHz, CD$_3$OD) δ 7.12-7.24 (m, 4H), 2.46-2.66 (m, 4H), 1.42-1.73 (m, 10H), 1.43-1.42 (m, 2H), 0.97 (t, J=7.2 Hz, 6H); $^{13}$C NMR (100 MHZ, CD$_3$OD), δ 142.8, 131.3, 128.8, 128.3, 128.2, 123.6, 91.9, 83.9, 70.9, 44.5, 41.2, 35.2, 32.2, 28.6, 17.6, 13.6; RP-HPLC t$_R$=7.06 min, 92.5% (AUC); LC-MS m/z=288.25 [M+H]$^+$.

Example 193

IN VITRO ISOMERASE INHIBITION ASSAY

The capability of alkynyl phenyl-linked amine derivative compounds to inhibit the activity of a visual cycle isomerase was determined.

Isomerase inhibition reactions were performed essentially as described (Stecher et al., *J. Biol. Chem.* 274:8577-85 (1999); see also Golczak et al., *Proc. Natl. Acad. Sci. USA* 102:8162-67 (2005)). Bovine Retinal Pigment Epithelium (RPE) microsome membranes were the source of a visual cycle isomerase.

RPE Microsome Membrane Preparation

Bovine RPE microsome membrane extracts were prepared according to methods described (Golczak et al., *Proc. Natl. Acad. Sci. USA* 102:8162-67 (2005)) and stored at −80° C. Crude RPE microsome extracts were thawed in a 37° C. water bath, and then immediately placed on ice. 50 ml crude RPE microsomes were placed into a 50 ml Teflon-glass homogenizer (Fisher Scientific, catalog no. 0841416M) on ice, powered by a hand-held DeWalt drill, and homogenized ten times up and down on ice under maximum speed. This process was repeated until the crude RPE microsome solution was homogenized. The homogenate was then subjected to centrifugation (50.2 Ti rotor (Beckman, Fullerton, Calif.), 13,000 RPM; 15360 Rcf) for 15 minutes at 4° C. The supernatant was collected and subjected to centrifugation at 42,000 RPM (160,000 Rcf; 50.2 Ti rotor) for 1 hour at 4° C. The supernatant was removed, and the pellets were suspended in 12 ml (final volume) cold 10 mM MOPS buffer, pH 7.0. The resuspended RPE membranes in 5 ml aliquots were homogenized in a glass-to-glass homogenizer (Fisher Scientific, catalog no.K885500-0021) to high homogeneity. Protein concentration was quantified using the BCA protein assay according to the manufacturer's protocol (Pierce, Rockford, Ill.). The homogenized RPE preparations were stored at −80° C.

Isolation of Human Apo Cellular Retinaldehyde-Binding Protein (CRALBP)

Recombinant human apo cellular retinaldehyde-binding protein (CRALBP) was cloned and expressed according to standard methods in the molecular biology art (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6×His-tagged human CRALBP was expressed in One Shot TOP 10 chemically competent *E. coli* cells (Invitrogen), and the recombinant polypeptide was isolated from *E. coli* cell lysates by nickel affinity chromatography using nickel (Ni) Sepharose XK16-20 columns for HPLC (Amersham Bioscience, Pittsburgh, Pa.; catalog no. 17-5268-02). The purified 6×His-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Alkkynyl phenyl-linked amine derivative compounds and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

The isomerase assay was performed in 10 mM bis-tris-propane (BTP) buffer, pH 7.5, 0.5% BSA (diluted in BTP buffer), 1 mM sodium pyrophosphate, 20 μM all-trans retinol (in ethanol), and 6 μM apo-CRALBP. The test compounds (2 μl) (final 1/15 dilution of serial dilution stocks) were added to the above reaction mixture to which RPE microsomes were added. The same volume of ethanol was added to the control reaction (absence of test compound). Bovine RPE microsomes (9 μl) (see above) were then added, and the mixtures transferred to 37° C. to initiate the reaction (total volume=150 μl). The reactions were stopped after 30 minutes by adding methanol (300 μl). Heptane was added (300 μl) and mixed into the reaction mixture by pipetting. Retinoid was extracted by agitating the reaction mixtures, followed by centrifugation in a microcentrifuge. The upper organic phase was transferred to HPLC vials and then analyzed by HPLC using an Agilent 1100 HPLC system with normal phase column: SILICA (Agilent Technologies, dp 5µ, 4.6 mm×, 25 CM; running method had flow rate of 1.5 ml/min; injection volume 100 µl). The solvent components were 20% of 2% isopropanol in EtOAc and 80% of 100% hexane.

The area under the $A_{318}$ nm curve represents the 11-cis retinol peak, which is calculated by Agilent Chemstation software and recorded manually. The $IC_{50}$ values (concentration of compound that gives 50% inhibition of 11-cis retinol formation in vitro) are calculated using GraphPad Prism® 4 Software (Irvine, Calif.). All tests are performed in duplicate.

The concentration dependent effect of the compounds disclosed herein on the retinol isomerization reaction can also be evaluated with a recombinant human enzyme system. In particular, the in vitro isomerase assay was performed essentially as in Golczak et al. 2005, PNAS 102: 8162-8167, ref. 3). A homogenate of HEK293 cell clone expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11 cis-retinol in the HPLC chromatograms were recorded and concentration dependent curves analyzed by GraphPad Prism for $IC_{50}$ values. The ability of the numerous compounds disclosed herein to inhibit isomerization reaction is quantified and the respective $IC_{50}$ value is determined. The tables below summarises the $IC_{50}$ values of various compounds of the present invention determined by either of the above two methods. FIG. 1 is a representative figure of the IC50 determination of the compound of Example 2. Other $IC_{50}$s for human and bovine in vitor data are provided in Tables 14A and 14B.

TABLE 14A

Human in vitro Inhibition Data

| $IC_{50}$ (µM) | Compound/Example Number |
|---|---|
| ≦0.01 µM | 18, 47, 100, 101, 159, 160, 164, 165 |
| ≦0.1 µM | 1, 2, 3, 4, 5, 6, 11, 19, 21, 22, 24, 25, 27, 31, 32, 36, 37, 38, 39, 52, 57, 59, 69, 78, 80, 99, 107, 108, 109, 110, 111, 112, 116, 119, 120, 121, 122, 124, 125, 132, 144, 145, 146, 147, 148, 149, 150, 151, 152, 153, 155, 161, 162, 167, 170, 174, 176, 177, 179, 180, 181, 182, 184, 185, 186, 187, 188, 189, 190, 191, 192 |
| ≦1 µM | 12, 26, 33, 41, 58, 79, 89, 105, 106, 113, 114, 115, 117, 118, 126, 128, 129, 149, 150, 154, 156, 157, 158, 166, 168, 169, 178 |
| ≦10 µM | 81, 123, 142, 163, 172, 173, |

TABLE 14

Bovine in vitro Inhibition data

| $IC_{50}$ (µM) | Compound/Example Number |
|---|---|
| ≦1 µM | 1, 2, 3, 4, 5, 6, 7, 8, 11, 15, 16, 18, 19, 21, 22, 23, 24, 25, 27, 28, 29, 30, 31, 32, 36, 37, 38, 39, 41, 42, 43, 44, 47, 48, 49, 50, 51, 52, 53, 54, 55, 57, 58, 59, 61, 67, 68, 69, 70, 72, 73, 74, 75, 77, 78, 79, 80, 85, 86, 91, 95, 99, 100, 101, 102, 141 |

TABLE 14-continued

Bovine in vitro Inhibition data

| $IC_{50}$ (µM) | Compound/Example Number |
|---|---|
| ≦10 µM | 9, 12, 13, 14, 17, 26, 33, 35, 40, 56, 60, 62, 63, 64,, 65, 66, 81, 83, 88, 89, 90, 96, 97, 98, |
| ≦100 µM | 10, 20, 34, 46, 76, 82, 84, 87, 92, 94 |
| ≦1000 µM | 45, 93 |

Example 194

IN VIVO MURINE ISOMERASE ASSAY

The capability of alkynyl phenyl-linked amine derivatives to inhibit isomerase is determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Delayed recovery, as represented by lower 11-cis-retinal oxime levels, indicates inhibition of isomerization reaction. Procedures were performed essentially as described by Golczak et al., Proc. Natl. Acad. Sci. USA 102:8162-67 (2005). See also Deigner et al., Science, 244: 968-71 (1989); Gollapalli et al., Biochim Biophys Acta. 1651: 93-101 (2003); Parish, et al., Proc. Natl. Acad. Sci. USA, 14609-13 (1998); Radu, et al., Proc Natl Acad Sci USA 101: 5928-33 (2004).

Six-week old dark-adapted CD-1 (albino) male mice were orally gavaged with compound (0.03-3 mg/kg) dissolved in 100 µl corn oil containing 10% ethanol (five animals per group). Mice were gavaged with the alkynyl phenyl derivative compounds described Examples 2, 18, 19, 100 and 101. After 2-24 hours in the dark, the mice were exposed to photobleaching of 5,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and redfiltered flashlights for spot illumination as needed) (see, e.g., Maeda et al., J. Neurochem 85:944-956, 2003; Van Hooser et al., J Biol Chem 277:19173-82, 2002). After the mice were sacrificed, the eyes were immediately removed and placed in liquid nitrogen for storage.

The eyes were placed in 500 µL of bis-tris propane buffer (10 mM, pH ~7.3) and 20 µL of 0.8M hydroxile amine (pH ~7.3). The eyes were cut up into small pieces with small iris scissors and then thoroughly homogenized at 30000 rpm with a mechanical homogenizer (Polytron PT 1300 D) in the tube until no visible tissue remained. 500 µL of methanol and 500 µL of heptane were added to each tube. The tubes were attached to a vortexer so that the contents were mixed thoroughly for 15 minutes in room temperature. The organic phase was separated from the aqueous phase by centrifugation for 10 min at 13K rpm, 4° C. 240 µL of the solution from the top layer (organic phase) was removed and transferred to clean 300 µl glass inserts in HPLC vials using glass pipette and the vials were crimped shut tightly.

The samples were analyzed on an Agilent 1100 HPLC system with normal phase column: SILICA (Beckman Coutlier, dp 5 µm, 4.6 mM×250 mM). The running method has a flow rate of 1.5 ml/min; solvent components are 15% solvent 1 (1% isopropanol in ethyl acetate), and 85% solvent 2 (100% hexanes). Loading volume for each sample is 100 μl; detection wavelength is 360 nm. The area under the curve for 11-cis retinal oxime was calculated by Agilent Chemstation software and was recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment.

Figure 2:
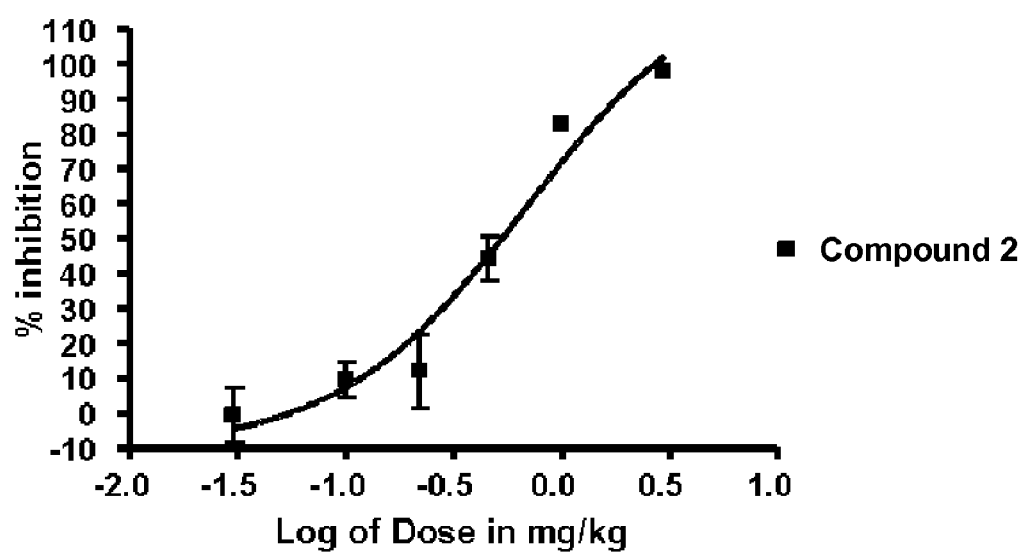
FIG. 2 depicts concentration-dependent inhibition of isomerase activity by Compound 2 in vivo.
Figure 3:
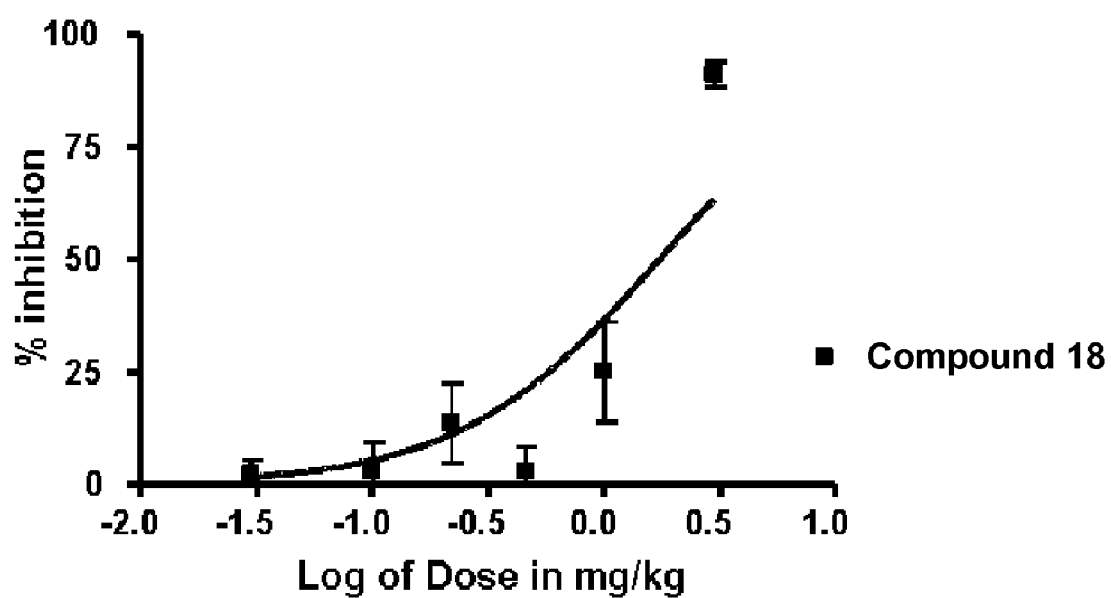
FIG. 3 depicts concentration-dependent inhibition of isomerase activity by Compound 18 in vivo.
Figure 4:
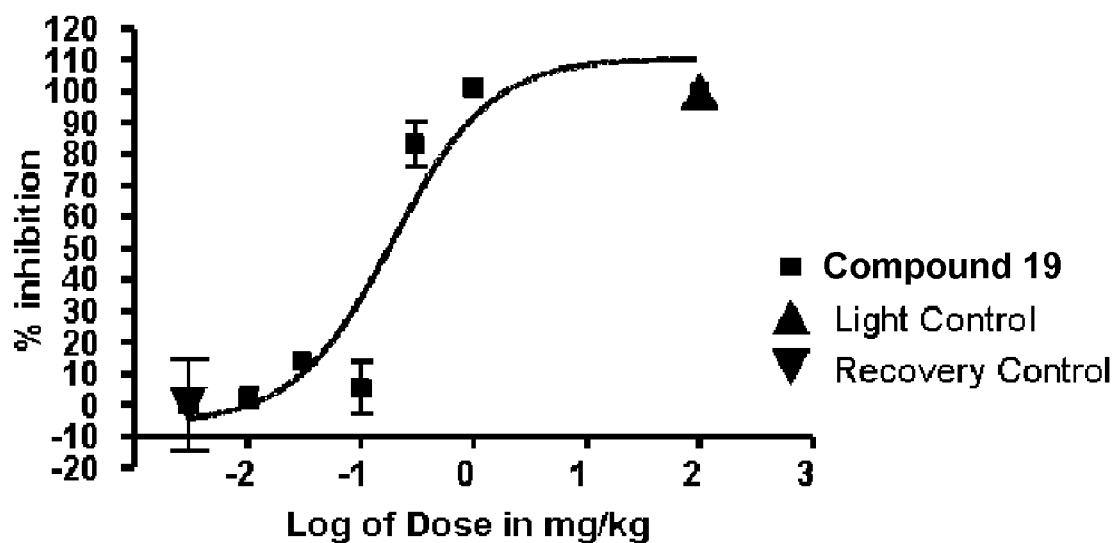
FIG. 4 depicts concentration-dependent inhibition of isomerase activity by Compound 19 in vivo.
Figure 5:
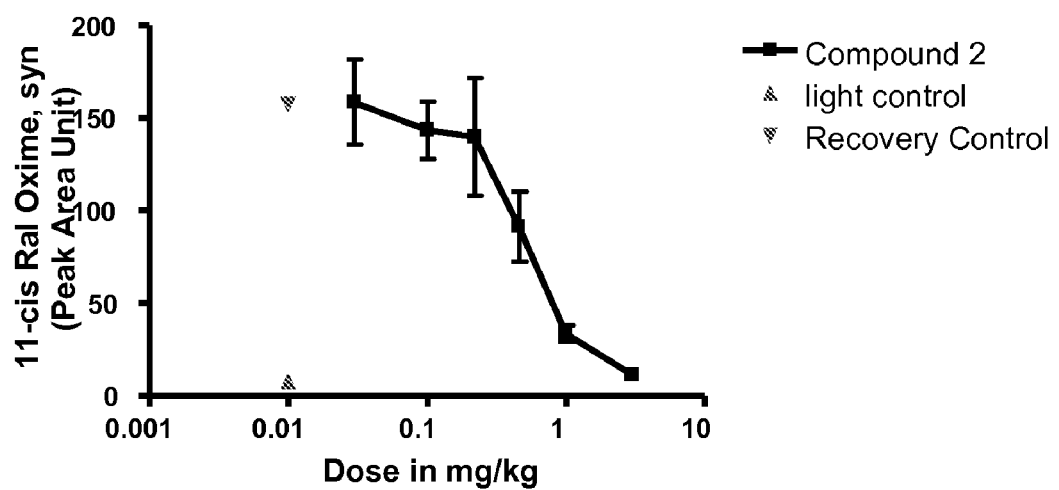
FIG. 5 depicts a concentration-dependent inhibition of isomerase activity by Compound 2 in vivo.
Figure 6:
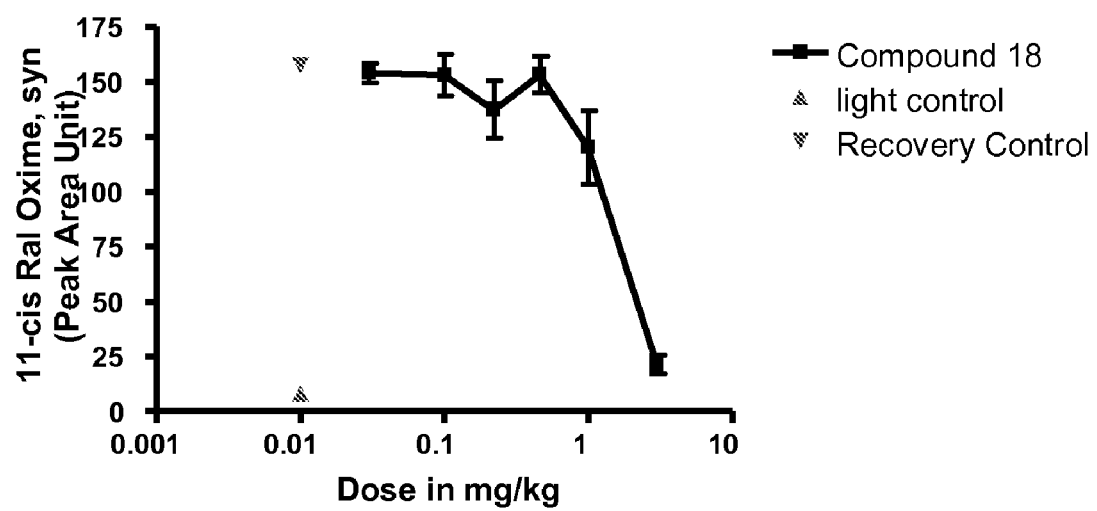
FIG. 6 depicts concentration-dependent inhibition of isomerase activity by Compound 18 in vivo.
Figure 7:
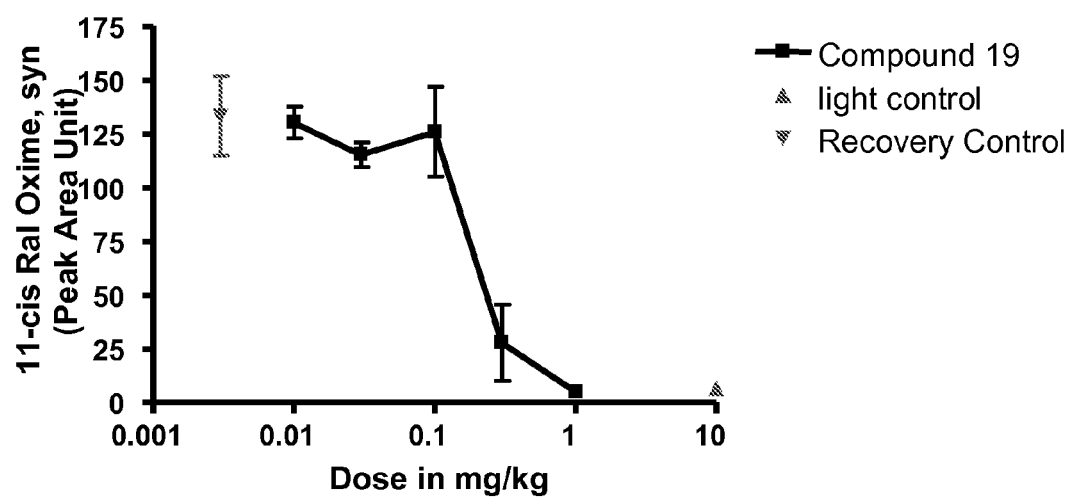
FIG. 7 depicts concentration-dependent inhibition of isomerase activity by Compound 19 in vivo.
Figure 8:
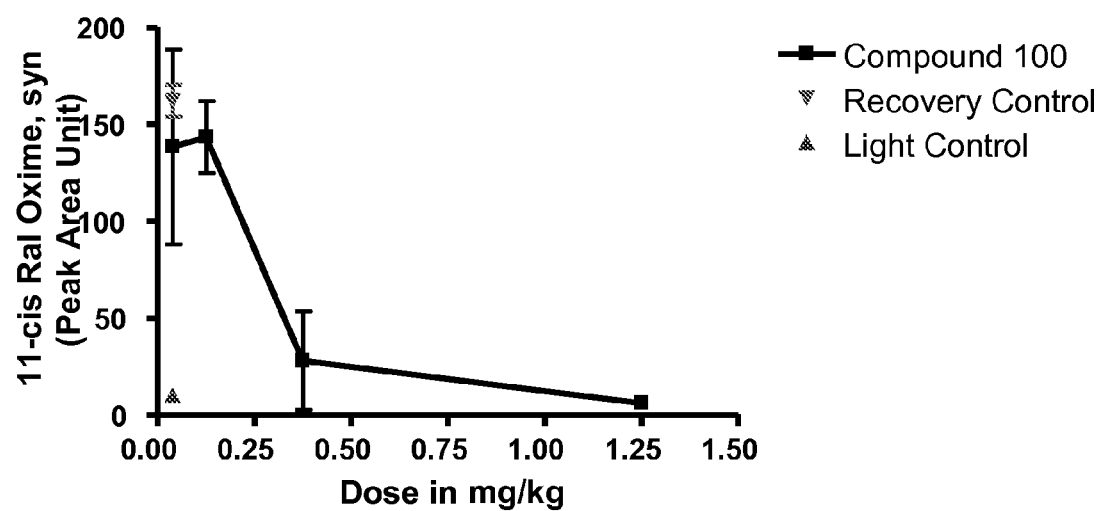
FIG. 8 depicts concentration-dependent inhibition of isomerase activity by Compound 100 in vivo.
Figure 9:
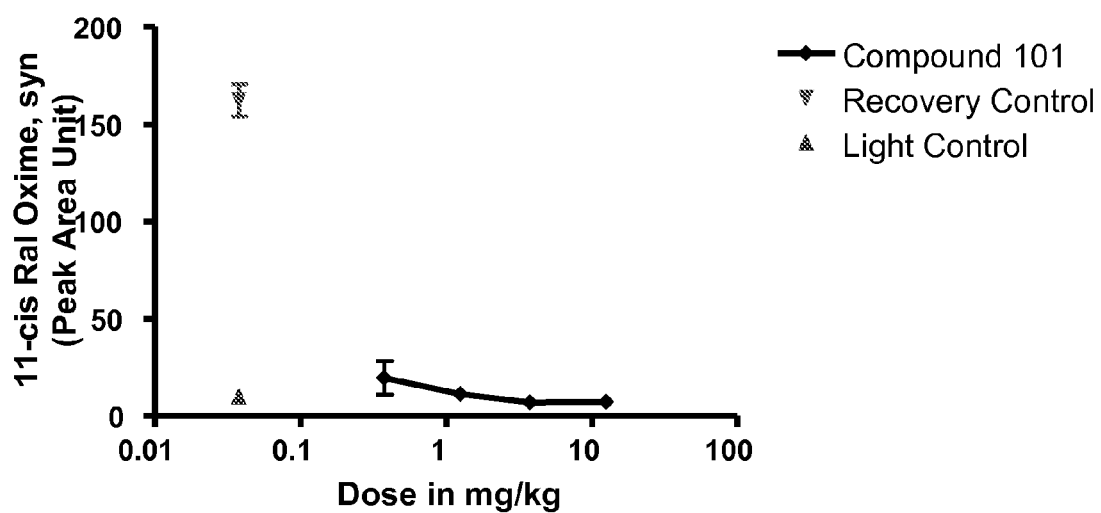
FIG. 9 depicts concentration-dependent inhibition of isomerase activity by Compound 101 in vivo.

A dose response in vivo isomerase inhibition study was performed with the compounds of Examples 2, 18, 19, 100, and 101 (Compounds 2, 18, 19, 100 and 101). Male Balb/c mice (8/group) were dosed orally with 0.03, 0.1, 0.3, 1 and 3 mg/kg of Compound 2-HCl, Compound 18-HCl, Compound 100-HCl, or Compound 101-HCl in sterile water as solution, and photobleached 4 hours after dosing. Animals that received Compound 19HCl were orally dosed with 0.01 and 1 mg/kg of compound in sterile water as solution, and photobleached 4 hours after dosing. Recovery and retinoid analysis were performed as described above. Dark control mice were vehicle-only treated, sacrificed fully dark adapted without light treatment, and analyzed. The concentration-dependent inhibition of isomerase activity at 4 hours post dosing of the Compounds 2, 18, and 19 are presented in FIGS. 2-4. Inhibition of 11-cis retinal (oxime) recovery for Compounds 2, 18, 19, 100 and 101 are presented in FIGS. 5-9 respectively. The estimated $ED_{50}$ (dose of compound that gives 50% inhibition of 11-cis retinal (oxime) recovery) are presented in Table 15B.

Figure 10:
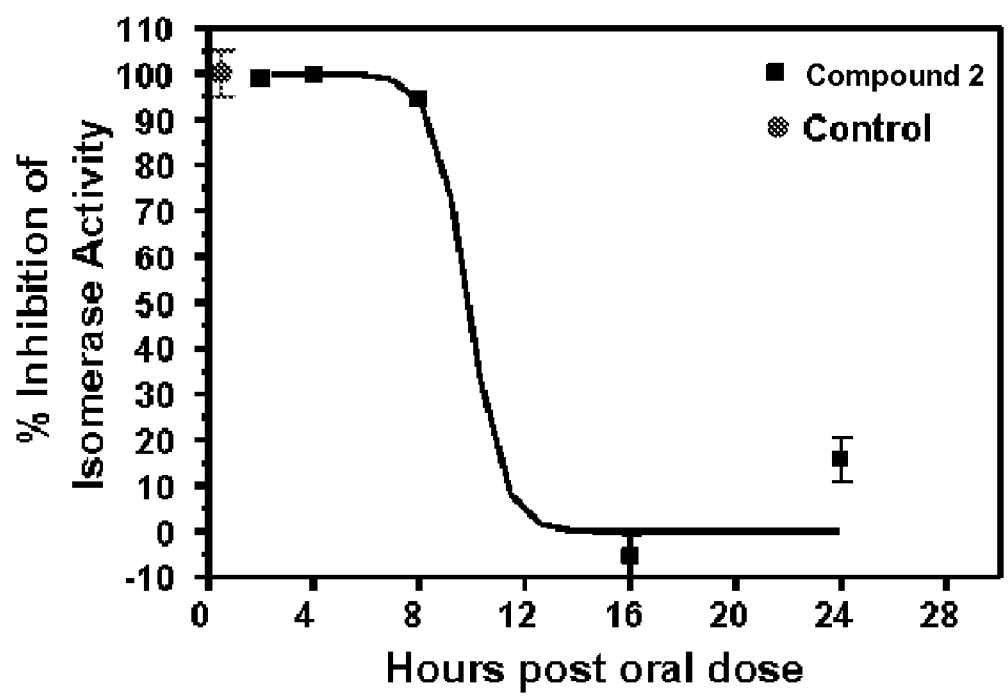
FIG. 10 depicts a time course for % inhibition of isomerase activity for Compound 2 in vivo.
Figure 11:
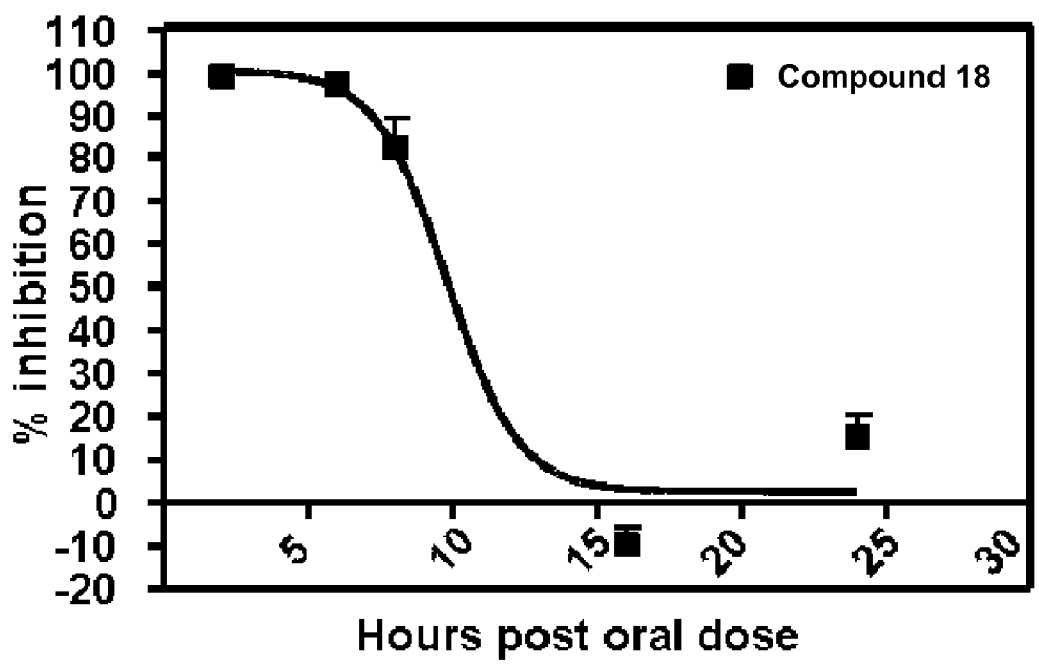
FIG. 11 depicts a time course for % inhibition of isomerase activity for Compound 18 in vivo.
Figure 12:
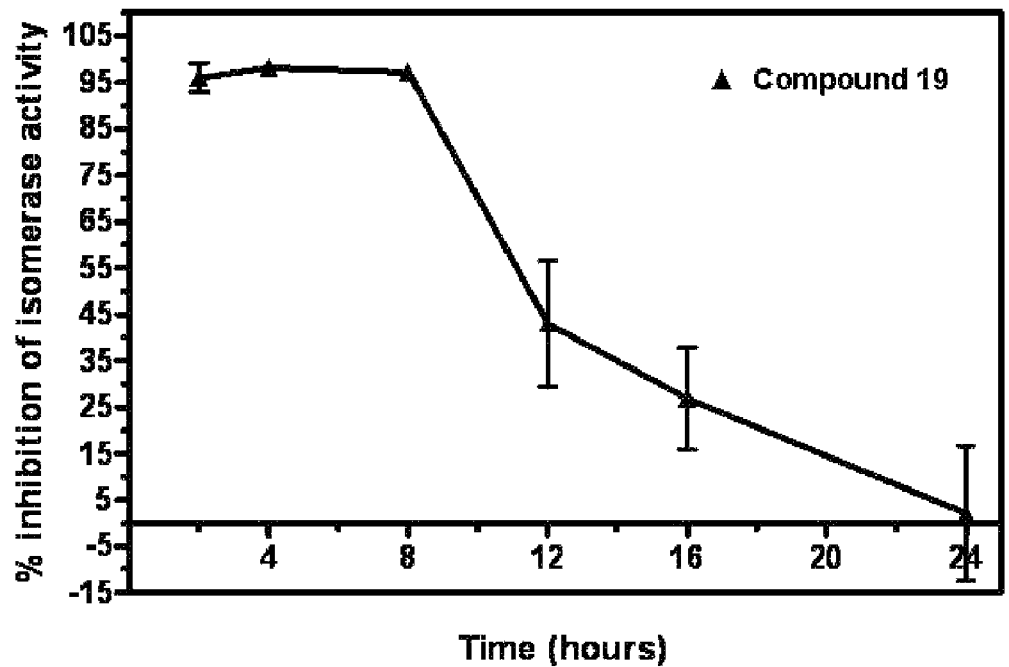
FIG. 12 depicts a time course for % inhibition of isomerase activity for Compound 19 in vivo.

A time course study was performed to determine the isomerase inhibitory activity of Compounds 2, 18 and 19. Male Balb/c mice (4/group) received 3 mg Compound 2-HCl, Compound 18-HCl or Compound 19-HCl (in water) per kg bodyweight orally, by gavage. The animals were then "photobleached" (5000 Lux white light for 10 minutes) at 2, 4, 8, 16 and 24 hours after dosing, and returned to darkness to allow recovery of the 11-cis-retinal content of the eyes. Mice were sacrificed 2 hours after bleaching, eyes were enucleated, and retinoid content was analyzed by HPLC. Results are presented in FIGS. 10-12.

Figure 13:
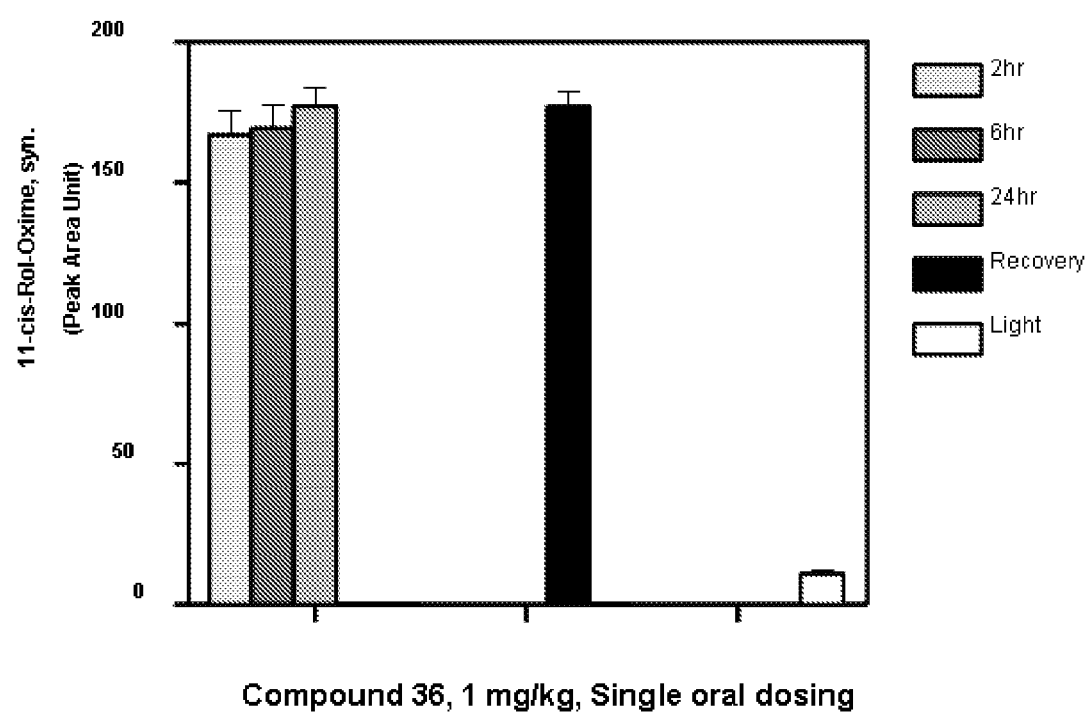
FIG. 13 depicts a single oral dosing of Compound 36, at 1 mg/kg.
Figure 14:
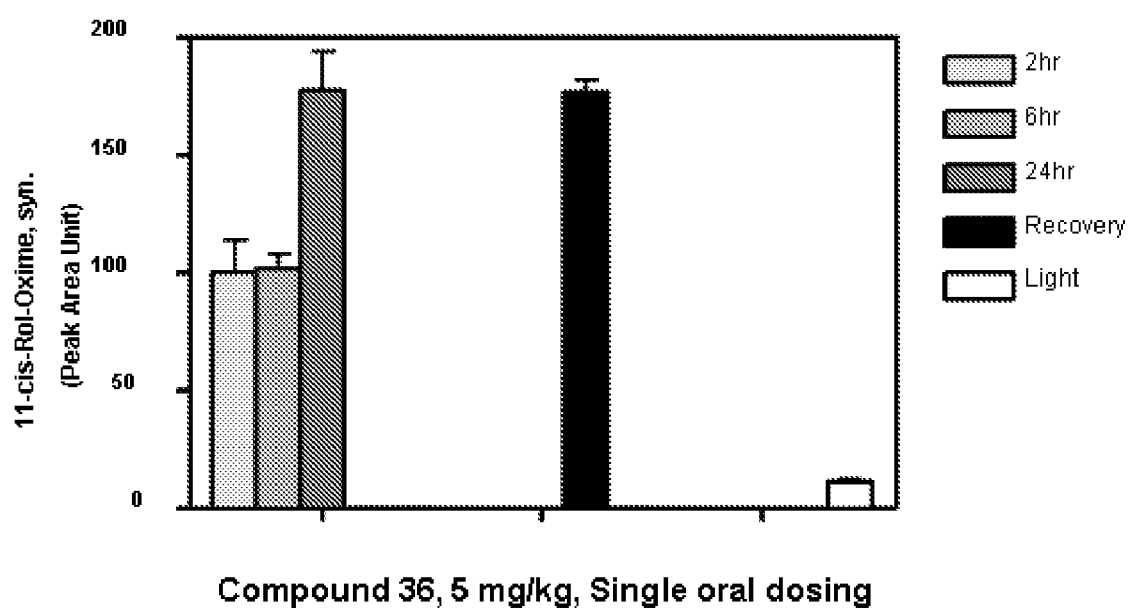
FIG. 14 depicts a single oral dosing of Compound 36, at 5 mg/kg.

A single dose study of the compound of Example 36 (Compound 36) was performed, at 1 mg/kg and 5 mg/kg oral dosing, 2, 4, 6, and 24 hours post bleaching. The experiments were carried out in CD1 male mice. Results were analyzed by HPLC. Results are presented in FIG. 13 (1 mg/kg) and 14 (5 mg/kg data) and in Table 15C. Example 36 was inactive at 1 mg/kg (FIG. 13) and at 5 mg/kg was ~50% active at 2 and 6 h with full recovery at 24 h (FIG. 14).

TABLE 15A

IN VIVO INHIBITION DATA

| Example No. | % Inhibition 1 mg/kg | | % Inhibition 5 mg/kg | |
|---|---|---|---|---|
| | 4 h | 24 h | 4 h | 24 h |
| 2 | | | | |
| 18 | | | | |
| 11 | 0 | 0 | 17 | 0 |
| 8 | | | 0 | 0 |
| 7 | | | 49 | 0 |
| 19 | | | | |
| 38 | 0 | 0 | 8 | 1 |
| 37 | 23 | 9 | 73 | 0 |
| 4 | 21 | 0 | 95 | 0 |

TABLE 15A-continued

IN VIVO INHIBITION DATA

| Example No. | % Inhibition 1 mg/kg | | % Inhibition 5 mg/kg | |
|---|---|---|---|---|
| | 4 h | 24 h | 4 h | 24 h |
| 24 | 0 | 0 | 27 | 0 |
| 32 | 75 | 14 | | |
| 27 | 7 | 6 | 65 | 0 |
| 28 | 27 | 0 | | |
| 31 | 18 | 0 | | |
| 1 | 3 | 0 | | |
| 25 | 1 | 0 | | |
| 26 | 18 | 0 | | |
| 47 | 100 | 2 | | |
| 54 | 67 | 58 | | |
| 50 | 13 | 31 | | |
| 51 | 0 | 0 | | |
| 52 | 72 | 2 | | |
| 55 | 16 | 7 | | |
| 79 | 7 | 1 | | |
| 81 | 8 | 3 | | |
| 57 | 8 | 21 | | |
| 59 | 31 | 0 | | |
| 74 | 8 | 0 | | |
| 80 | 22 | 0 | | |
| 69 | 81 | 10 | | |
| 60 | 10 | 9 | | |
| 78 | 0 | 0 | | |
| 61 | 0 | 0 | | |
| 62 | 0 | 0 | | |
| 63 | 11 | 0 | | |
| 99 | 31 | 0 | | |

TABLE 15B

IN VIVO INHIBITION DATA

| Example # | ED50 |
|---|---|
| 2 | .69 |
| 18 | 1.73 |
| 19 | .33 |
| 100 | .2 |
| 101 | .38 |

TABLE 15C

IN VIVO INHIBITION DATA

| Example # | 1 mg/kg % Inhibition | | | 5 mg/kg % Inhibition | | |
|---|---|---|---|---|---|---|
| | 2 h | 6 h | 24 h | 2 h | 6 h | 24 h |
| 36 | 6 | 5 | 0 | 46 | 45 | 0 |

Example 195

PREPARATION OF RETINAL NEURONAL CELL CULTURE SYSTEM

This Example describes methods for preparing a long-term culture of retinal neuronal cells.

All compounds and reagents are obtained from Sigma Aldrich Chemical Corporation (St. Louis, Mo.) except as noted.
Retinal Neuronal Cell Culture Porcine eyes are obtained from Kapowsin Meats, Inc. (Graham, Wash.). Eyes are enucleated, and muscle and tissue are cleaned away from the orbit. Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagles medium (DMEM)/F12 medium (Gibco BRL, Invitrogen Life Technologies, Carlsbad, Calif.) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 10% FBS. Dissociated primary retinal cells are plated onto Poly-D-lysine- and Matrigel-(BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis

The retinal neuronal cells are cultured for 1, 3, 6, and 8 weeks, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted 1:500; Chemicon, Temecula, Calif.). An antibody to mid-weight neurofilament (NFM rabbit polyclonal, diluted 1:10,000, Chemicon) is used to identify ganglion cells; an antibody to β3-tubulin (G7121 mouse monoclonal, diluted 1:1000, Promega, Madison, Wis.) is used to generally identify interneurons and ganglion cells, and antibodies to calbindin (AB1778 rabbit polyclonal, diluted 1:250, Chemicon) and calretinin (AB5054 rabbit polyclonal, diluted 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Survival of mature retinal neurons after varying times in culture is indicated by the histochemical analyses. Photoreceptor cells are identified using a rhodopsin antibody; ganglion cells are identified using an NFM antibody; and amacrine and horizontal cells are identified by staining with an antibody specific for calretinin.

Cultures are analyzed by counting rhodopsin-labeled photoreceptors and NFM-labeled ganglion cells using an Olympus IX81 or CZX41 microscope (Olympus, Tokyo, Japan). Twenty fields of view are counted per coverslip with a 20× objective lens. Six coverslips are analyzed by this method for each condition in each experiment. Cells that are not exposed to any stressor are counted, and cells exposed to a stressor are normalized to the number of cells in the control.

Example 196

EFFECT OF ALKYNYL PHENYL DERIVATIVE COMPOUNDS ON RETINAL CELL SURVIVAL

This Example describes the use of the mature retinal cell culture system that comprises a cell stressor for determining the effects of an alkynyl phenyl derivative compound on the viability of the retinal cells.

Retinal cell cultures are prepared as described in Example 195. A2E is added as a retinal cell stressor. After culturing the cells for 1 week, a chemical stress, A2E, is applied. A2E is diluted in ethanol and added to the retinal cell cultures at concentration of 0, 10 µM, 20 µM, and 40 µM. Cultures are treated for 24 and 48 hours. A2E is obtained from Dr. Koji Nakanishi (Columbia University, New York City, N.Y.) or is synthesized according to the method of Parish et al. (*Proc. Natl. Acad. Sci. USA* 95:14602-13 (1998)). An alkynyl phenyl derivative compound is then added to the culture. To other retinal cell cultures, an alkynyl phenyl derivative compound is added before application of the stressor or is added at the same time that A2E is added to the retinal cell culture. The cultures are maintained in tissue culture incubators for the duration of the stress at 37° C. and 5% $CO_2$. The cells are then analyzed by immunocytochemistry as described in Example 133.

Apoptosis Analysis

Retinal cell cultures are prepared as described in Example 195 and cultured for 2 weeks and then exposed to white light stress at 6000 lux for 24 hours followed by a 13-hour rest period. A device was built to uniformly deliver light of specified wavelengths to specified wells of the 24-well plates. The device contained a fluorescent cool white bulb (GE P/N FC12T9/CW) wired to an AC power supply. The bulb is mounted inside a standard tissue culture incubator. White light stress is applied by placing plates of cells directly underneath the fluorescent bulb. The $CO_2$ levels are maintained at 5%, and the temperature at the cell plate is maintained at 37° C. The temperature was monitored by using thin thermocouples. The light intensities for all devices were measured and adjusted using a light meter from Extech Instruments Corporation (P/N 401025; Waltham, Mass.). An alkynyl phenyl-linked amine derivative compound is added to wells of the culture plates prior to exposure of the cells to white light and is added to other wells of the cultures after exposure to white light. To assess apoptosis, TUNEL is performed as described herein.

Apoptosis analysis is also performed after exposing retinal cells to blue light. Retinal cell cultures are cultured as described in Example 195, After culturing the cells for 1 week, a blue light stress is applied. Blue light is delivered by a custom-built light-source, which consists of two arrays of 24 (4×6) blue light-emitting diodes (Sunbrite LED P/N SSP-01TWB7UWB12), designed such that each LED is registered to a single well of a 24 well disposable plate. The first array is placed on top of a 24 well plate full of cells, while the second one is placed underneath the plate of cells, allowing both arrays to provide a light stress to the plate of cells simultaneously. The entire apparatus is placed inside a standard tissue culture incubator. The $CO_2$ levels are maintained at 5%, and the temperature at the cell plate is maintained at 37° C. The temperature is monitored with thin thermocouples. Current to each LED is controlled individually by a separate potentiometer, allowing a uniform light output for all LEDs. Cell plates are exposed to 2000 lux of blue light stress for either 2 hours or 48 hours, followed by a 14-hour rest period. An alkynyl phenyl-linked amine derivative compound is added to wells of the culture plates prior to exposure of the cells to blue light and is added to other wells of the cultures after exposure to blue light. To assess apoptosis, TUNEL is performed as described herein.

To assess apoptosis, TUNEL is performed according to standard techniques practiced in the art and according to the manufacturer's instructions. Briefly, the retinal cell cultures are first fixed with 4% paraformaldehyde and then ethanol, and then rinsed in DPBS. The fixed cells are incubated with TdT enzyme (0.2 units/μl final concentration) in reaction buffer (Fermentas, Hanover, Md.) combined with Chroma-Tide Alexa568-5-dUTP (0.1 μM final concentration) (Molecular Probes) for 1 hour at 37° C. Cultures are rinsed with DPBS and incubated with primary antibody either overnight at 4° C. or for 1 hour at 37° C. The cells are then rinsed with DPBS, incubated with Alexa 488-conjugated secondary antibodies, and rinsed with DPBS. Nuclei are stained with DAPI, and the cultures are rinsed with DPBS before removing the glass coverslips and mounting them with Fluoromount-G on glass slides for viewing and analysis.

Cultures are analyzed by counting TUNEL-labeled nuclei using an Olympus IX81 or CZX41 microscope (Olympus, Tokyo, Japan). Twenty fields of view are counted per coverslip with a 20× objective lens. Six coverslips are analyzed by this method for each condition. Cells that are not exposed to an alkynyl phenyl derivative compound are counted, and cells exposed to the antibody are normalized to the number of cells in the control. Data are analyzed using the unpaired Student's t-test.

Example 197

IN VIVO LIGHT MOUSE MODEL

This Example describes the effect of an alkynyl phenyl-linked amine derivative in an in vivo light damage mouse model.

Exposure of the eye to intense white light can cause photodamage to the retina. The extent of damage after light treatment can be evaluated by measuring cytoplasmic histone-associated-DNA-fragment (mono- and oligonucleosomes) content in the eye (see, e.g., Wenzel et al., Prog. Retin. Eye Res. 24:275-306 (2005)).

Dark adapted male Balb/c (albino, 10/group) mice are gavaged with the Compounds of at various doses (0.03, 0.1, 0.3, 1, and 3 mg/kg) or vehicle only is administered. Six hours after dosing, the animals are subjected to light treatment (8,000 lux of white light for 1 hour). Mice are sacrificed after 40 hours of recovery in dark, and retinas are dissected. A cell death detection ELISA assay is performed according to the manufacturer's instructions (ROCHE APPLIED SCIENCE, Cell Death Detection ELISA plus Kit). Contents of fragmented DNA in the retinas are measured to estimate the retinal-protective activity of the compounds.

Example 198

ELECTRORETINOGRAPHIC (ERG) STUDY

This example describes determining the effect of an alkyne derivative compound that is a visual cycle modulator on the magnitude of the ERG response in the eyes of mice after oral dosing of the animals with the compound. The level of ERG response in the eyes is determined 18 and 66 hours after administering the compound to the animals.

Three groups of nine-week old mice (19-25 grams), both genders (strain C5 7BL/6, Charles River Laboratories, Wilmington, Mass.) are housed at room temperature, 72±4° F., and relative humidity of approximately 25%. Animals are housed in a 12-hour light/dark cycle environment, have free access to feed and drinking water and are checked for general health and well-being prior to use and during the study. Body weights are determined for a representative sample of mice prior to initiation of dosing. The average weight determined from this sampling is used to establish the dose for all mice in the study.

Each test compound is dissolved in the control solvent (EtOH), and diluted 1:10 (90 ml/900 ml) in corn oil (Crisco Pure Corn Oil, J.M. Smucker Company, Orrville, Ohio) to the desired dose (mg/kg) in the desired volume (~0.1 mL/animal). The control vehicle is ethanol: corn oil (1:10 (0.9 ml/9 ml)). The treatment designations and animal assignments are described in Table 16.

TABLE 16

| Group | Route | Treatment | Dose (mg/kg) | Animals |
| --- | --- | --- | --- | --- |
| 1 | oral | Example 2 | 0.5 | 4 |
| 2 | oral | Example 2 | 1 | 7* |
| Control | oral | Vehicle | None | 4 |

*aggregated result from 2 studies (n = 4, n = 3, respectively)

Animals are dosed once orally by gavage, with the assigned vehicle control or test compounds during the light cycle (between 30 min and 3 hours 30 min after the beginning of the light cycle). The volume of the administered dose does not exceed 10 mL/kg.

ERG recordings are made on dark-adapted and, subsequently (during the course of the same experiment), on light-adapted states. For the dark-adapted response, animals are housed in a dark-adapted environment for at least 1 hour prior to the recording, commencing at least 30 minutes after the start of the light cycle.

At eighteen and sixty six hours after dosing, the mice were anesthetized with a mixture of Ketamine and Xylazine (100 mg/kg and 20 mg/kg, respectively) and placed on a heating pad to maintain stable core body temperature during the course of the experiment. Pupils were dilated by placing a 5 microliter drop of mydriatic solution (tropicamide 0.5%) in the recorded eye. A mouse corneal monopolar contact lens electrode (Mayo Corporation, Inazawa, Aichi, Japan) was placed on the cornea, and a subcutaneous reference low profile needle 12 mm electrode (Grass Telefactor, W Warwick, R.I.) was placed medial from the eye. A ground needle electrode was placed in the tail. Data collection was obtained using an Espion $E^2$ (Diagnosys LLC, Littleton, Mass.) ERG recording system with Color Dome Ganzfeld stimulator. Full dark-adapted intensity-response function was determined following a brief white flash stimuli of 14 intensities ranging from 0.0001 cd·s/$m^2$ to 333 cd·s/$m^2$. Subsequently, full light-adapted intensity-response function was determined following a brief white flash stimuli of 9 intensities ranging from 0.33 cd·s/$m^2$ to 333 cd·s/$m^2$. Analysis of the obtained responses was done off-line. Intensity-response function determination was done by fitting a sigmoid function to the data (Naka K I, Rushton W A., 1966; Naka K I, Rushton W A, 1967). ERG responses are summarized in Tables 17 and 18 below.

TABLE 17

DARK-ADAPTED ERG RESPONSE

| Example Number | Dose | 4 h b-wave ampl. 0.01 cd·s/m² | Change vs. control (%) | 25 h b-wave ampl. 0.01 cd·s/m² | Change vs. control (%) |
|---|---|---|---|---|---|
| | Vehicle | 537* | | | |
| Example 2 | 0.5 | 265 | −50.65% | | |
| Example 2 | 1 | 32* | −94.04% | 430 | −19.93%** |

*aggregated average;
**compared to 4 hours vehicle

TABLE 18

LIGHT-ADAPTED ERG RESPONSE DATA

| Example Number | Dose | 4 h $V_{max}$ average* | Change vs. control (%) | 25 h $V_{max}$ average* | Change vs. control (%) |
|---|---|---|---|---|---|
| | Vehicle | 148 | | | |
| Example 2 | 0.5 | 202 | 36.49% | | |
| Example 2 | 1 | 262* | 77.03% | 284 | 91.89%** |

*aggregated average;
**compared to 4 hours vehicle

At 4 hours post-dose, dark-adapted ERG was suppressed in a dose-proportional manner by 2 doses (0.5 and 1 mg/kg) of the compound. Both doses enhanced the maximal light-adapted ERG response. At 25 hours post dose, dark-adapted ERG increased significantly at 25 hours, remaining within <20% of the vehicle-treated animals. The light-adapted ERG response remained enhanced.

A related example describes determining the effect of an alkyne derivative compound that is a visual cycle modulator on the level of ERG response in the eyes of mice after oral dosing of the animals with the compound. The experimental procedure is the same as that described in the previous example with the following exceptions: 12 to 16-week old BALB/c mice were used (body weights 16-25 g). ERG responses are summarized in Tables 19 and 20 below.

TABLE 18

DARK-ADAPTED ERG RESPONSE DATA

| Example Number | Dose | 4 h b-wave ampl. 0.01 cd·s/m² | Change vs. control (%) | 25 h b-wave ampl. 0.01 cd·s/m² | Change vs. Control (%) |
|---|---|---|---|---|---|
| | Vehicle | 558* | | | |
| Example 19 | 0.2 | 263 | −52.89% | | |
| Example 19 | 0.3 | 107* | −80.77% | 247 | −55.75%** |
| Example 19 | 0.6 | 23 | −95.92% | | |

*aggregated average;
**compared to 4 hours vehicle

TABLE 20

LIGHT-ADAPTED ERG RESPONSE DATA

| Example Number | Dose | 4 h $V_{max}$ average* | Change vs. control (%) | 25 h $V_{max}$ average* | Change vs. control (%) |
|---|---|---|---|---|---|
| | Vehicle | 163 | | | |
| Example 19 | 0.2 | 163 | −0.13% | | |
| Example 19 | 0.3 | 181 | 11.33% | 180 | 10.66% |
| Example 19 | 0.6 | 173 | 6.34% | | |

*aggregated average;
**compared to 4 hours vehicle

The dosing resulted in a significant and dose-dependent (53%-96%) suppression of ERG dark-adapted intensity-response function for the 3 doses. This was accompanied by a relatively small (<15%) increase in photopic $V_{max}$.

Example 199

EFFECT OF AN ALKYNYL PHENYL DERIVATIVE COMPOUND ON REDUCTION OF LIPOFUSCIN FLUOROPHORES

This Example describes the capability of an alkynyl phenyl derivative compound to reduce the level of existing A2E in the retina of mice as well as prevention of the formation of A2E.

The eyes of abca-4-null (abca4−/−) mutant mice (see, e.g., Weng et al., Cell 98:13-23 (1999) have an increased accumulation of lipofuscin fluorophores, such as A2E (see, e.g., Karan et al., Proc. Natl. Acad. Sci. USA 102:4164-69 (2005)). Compounds (1 mg/kg) or vehicle are administered daily for three months by oral gavage to abca4$^{-/-}$ mice that are about 2 months old. Mice are sacrificed after three months of treatment. Retinas and RPE are extracted for A2E analysis.

A similar experiment is performed with aged balb/c mice (10 months old). The test mice are treated with 1 mg/kg/day of compounds for three months and the control mice are treated with vehicle Example 200

EFFECT OF AN ALKYNYL PHENYL DERIVATIVE COMPOUND ON RETINOID NUCLEAR RECEPTOR ACTIVITY

Retinoid nuclear receptor activity is associated with transduction of the non-visual physiologic, pharmacologic, and toxicologic retinoid signals that affect tissue and organ growth, development, differentiation, and homeostasis.

The effect of the Compound 4, Compound 28, and Compound 29 and the effect of a retinoic acid receptor (RAR) agonist (E-4-[2-(5,6,7,8-tetrahydro-5,5,8,8-tetramethyl-2-naphthylenyl)-1-propenyl]benzoic acid) (TTNPB), and of all-trans-retinoic acid (at-RA), which is an RAR and retinoid X receptor (RXR) agonist, were studied on RAR and RXR receptors essentially as described by Achkar et al. (Proc. Natl. Acad. Sci. USA 93:4879-84 (1996)). Results of these assays are presented in Table 6. Amounts as great as 10 µM of each of Compound 4-HCl, Compound 28-HCl, and Compound 29-HCl did not show any significant effects on retinoid nuclear receptors (RAR and RXR). By comparison, TTNPB and at-RA activated the $RXR_\alpha$, $RAR_\alpha$, $RAR_\beta$ and $RAR_\gamma$ receptors as expected (Table 21).

TABLE 21

| Compound | RARα EC$_{50}$ (nM) | RARβ EC$_{50}$ (nM) | RARγ EC$_{50}$ (nM) | RXRα EC$_{50}$ (nM) |
|---|---|---|---|---|
| TTNPB | 5.5 +/− 4.5 | 0.3 +/− 0.1 | 0.065 +/− 0.005 | N/A |
| at-RA | N/A | N/A | N/A | 316 +/− 57 |
| Cmpd 4 | N/D | N/D | N/D | N/D |
| Cmpd 28 | N/D | N/D | N/D | N/D |
| Cmpd 29 | N/D | N/D | N/D | N/D |

N/D = No activity detected; N/A = Not applicable

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method for treating an ophthalmic disease or disorder resulting at least in part from lipofuscin pigment accumulation in an eye of a subject, comprising administering to the subject a pharmaceutical composition comprising a compound having a structure of Formula (A):

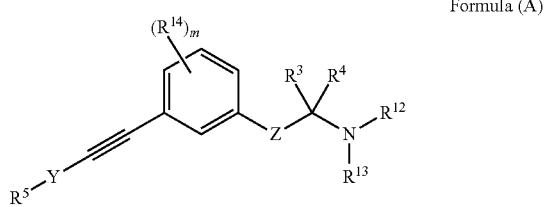

Formula (A)

as a tautomer or a mixture of tautomers, or as a pharmaceutically acceptable salt, stereoisomer, or geometric isomer thereof, wherein:

m is 0, 1, 2 or 3;

Z is —C(R$^{23}$)(R$^{24}$)—C(R$^1$)(R$^2$)—;

Y is a bond, —C(R$^{27}$)(R$^{28}$)—, or —C(R$^{27}$)(R$^{28}$)—C(R$^{29}$)(R$^{30}$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{23}$ and R$^{24}$ are each independently selected from hydrogen, halogen, C$_1$-C$_5$ alkyl, fluoroalkyl, —OR$^6$, —NR$^7$R$^8$; or R$^{23}$ and R$^{24}$ together form an oxo; or optionally, R$^{23}$ and an adjacent R$^1$ together form a direct bond to provide a double bond;

R$^3$ and R$^4$ are hydrogen; or R$^3$ and R$^4$ together form an imino;

R$^5$ is alkyl, heteroalkyl, alkenyl, heteroalkenyl, aryl, carbocyclyl, heteroaryl or heterocyclyl;

each R$^6$ is the same or different and independently hydrogen or C$_1$-C$_5$ alkyl;

each R$^7$ and each R$^8$ are each the same or different and independently hydrogen, alkyl, carbocyclyl, heteroalkyl, heterocycloalkyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or R$^7$ and R$^8$, together with the nitrogen atom to which they are attached, form an N-heterocyclyl;

each R$^9$ is the same or different and each is independently methyl, ethyl, 1-propyl, 2-propyl, 1-butyl, C$_5$-C$_8$ alkyl, alkenyl, aryl, carbocyclyl, heteroaryl or heterocyclyl;

R$^{12}$ and R$^{13}$ are the same or different and independently hydrogen, heteroalkyl, carbocyclyl, heterocyclyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$;

each R$^{14}$ is the same or different and independently alkyl, halo, fluoroalkyl or —OR$^6$;

each R$^{27}$, R$^{28}$, and R$^{29}$ are the same or different and independently hydrogen, alkyl or —OR$^6$; and R$^{30}$ is hydrogen or C$_1$-C$_5$ alkyl.

2. The method of claim 1 wherein the ophthalmic disease or disorder is age-related macular degeneration or Stargardt's macular dystrophy.

3. The method of claim 1 wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

4. The method according to claim 1 resulting in a reduction of lipofuscin pigment accumulated in an eye of the subject.

5. The method according to claim 4 wherein the lipofuscin pigment is N-retinylidene-N-retinyl-ethanolamine (A2E).

6. The method according to claim 1 wherein R$^5$ is aryl.

7. The method according to claim 6 wherein $R^5$ is phenyl, Y is a bond and the compound has a structure of Formula (B):

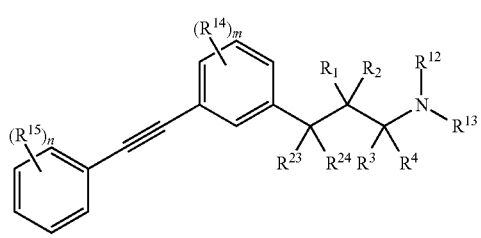

Formula (B)

as a tautomer or a mixture of tautomers, or as a pharmaceutically acceptable salt, stereoisomer, or geometric isomer thereof, wherein:

m is 0, 1, 2 or 3;
n is 0, 1, 2, 3, 4 or 5;
$R^1$ and $R^2$ are each independently selected from hydrogen, halogen, $C_1$-$C_5$ alkyl, fluoroalkyl, —$OR^6$, —$NR^7R^8$; or $R^1$ and $R^2$ together form an oxo;
$R^3$ and $R^4$ are hydrogen;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently methyl, ethyl, 1-propyl, 2-propyl, 1-butyl, $C_5$-$C_8$ alkyl, alkenyl, aryl, carbocyclyl, heteroaryl or heterocyclyl;
$R^{23}$ and $R^{24}$ are each the same or different and independently hydrogen, halogen, $C_1$-$C_5$ alkyl, fluoroalkyl, —$OR^6$, —$NR^7R^8$ or carbocyclyl; or $R^{23}$ and $R^{24}$ together form an oxo;
$R^{12}$ and $R^{13}$ are the same or different and independently hydrogen, alkyl or —C(=O)$R^9$;
each $R^{14}$ is the same or different and independently alkyl, halo, fluoroalkyl or —$OR^6$; and
each $R^{15}$ is the same or different and independently alkyl, —$OR^6$, alkenyl, alkynyl, halo, fluoroalkyl, aryl or aralkyl.

8. The method according to claim 7 wherein each of $R^{12}$ and $R^{13}$ is hydrogen.

9. The method according to claim 8 wherein $R^1$ and $R^2$, are each independently hydrogen, halogen, $C_1$-$C_5$ alkyl or —$OR^6$, wherein $R^6$ is hydrogen or $C_1$-$C_5$ alkyl;
and $R^{23}$ and $R^{24}$ are each independently hydrogen, halogen, $C_1$-$C_5$ alkyl or —$OR^6$, wherein $R^6$ is hydrogen or $C_1$-$C_5$ alkyl.

10. The method according to claim 9 wherein $R^1$ and $R^2$ are each independently hydrogen or —$OR^6$, wherein $R^6$ is hydrogen or $C_1$-$C_5$ alkyl; and $R^{23}$ and $R^{24}$ are each independently hydrogen or —$OR^6$, wherein $R^6$ is hydrogen or $C_1$-$C_5$ alkyl.

11. The method according to claim 9 wherein m is 0; n is 0, 1 or 2; and each $R^{15}$ is independently alkyl, —$OR^6$ or aryl.

12. The method according to claim 11, wherein the compound is selected from:
3-(3-((2,6-dimethylphenyl)ethynyl)phenyl)propan-1-amine;
3-(3-((2-methoxyphenyl)ethynyl)phenyl)propan-1-amine;
3-(3-(phenyl ethynyl)phenyl)propan-1-amine;
3-amino-1-(3-(biphenyl-3-ylethynyl)phenyl)propan-1-ol; and
3-amino-1-(3-((2-methoxyphenyl)ethynyl)phenyl)propan-1-ol.

13. The method according to claim 6 wherein $R^5$ is 1-naphthyl or 2-naphthyl.

14. The method according to claim 13 wherein each of $R^1$, $R^2$, $R^{23}$ and $R^{24}$ is hydrogen.

15. The method according to claim 14 wherein m is 0.

16. The method according to claim 15, wherein the compound is 3-(3-(naphthalen-2-ylethynyl)phenyl)propan-1-amine.

17. The method according to claim 1 wherein $R^5$ is C($R^{16}$)($R^{17}$)($R^{18}$), Y is a bond and the compound has a structure of Formula (C):

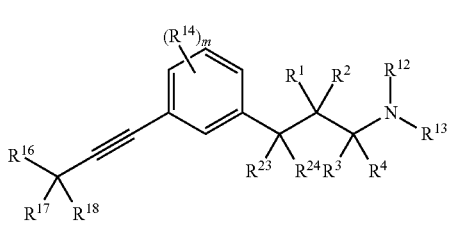

Formula (C)

as a tautomer or a mixture of tautomers, or as a pharmaceutically acceptable salt, stereoisomer, or geometric isomer thereof, wherein:

m is 0, 1, 2 or 3;
$R^1$ and $R^2$ are each the same or different and independently hydrogen, halogen, $C_1$-$C_5$ alkyl, fluoroalkyl, —$OR^6$, or —$NR^7R^8$; or $R^1$ and $R^2$ form an oxo;
$R^3$ and $R^4$ are each hydrogen;
each $R^6$ is the same or different and independently hydrogen or $C_1$-$C_5$ alkyl;
each $R^7$ and each $R^8$ are each the same or different and independently hydrogen, alkyl, carbocyclyl, or —C(=O)$R^9$; or $R^7$ and $R^8$, together with the nitrogen atom to which they are attached, form an N-heterocyclyl;
each $R^9$ is the same or different and independently methyl, ethyl, 1-propyl, 2-propyl, 1-butyl, $C_5$-$C_8$ alkyl, alkenyl, aryl, carbocyclyl, heteroaryl or heterocyclyl;
$R^{23}$ and $R^{24}$ are each independently hydrogen, halogen, $C_1$-$C_5$ alkyl, fluoroalkyl, —$OR^6$, —$NR^7R^8$; or $R^{23}$ and $R^{24}$ together form an oxo;
$R^{12}$ and $R^{13}$ are the same or different and independently hydrogen, or —C(=O)$R^9$;
each $R^{14}$ is the same or different and independently alkyl, halo, fluoroalkyl or —$OR^6$; and
each $R^{16}$, $R^{17}$ and $R^{18}$ are the same or different and independently hydrogen, alkyl, —$OR^6$, carbocyclyl or aryl.

18. The method according to claim 17 wherein each of $R^{12}$ and $R^{13}$ is hydrogen.

19. The method according to claim 18 wherein $R^1$ and $R^2$ are each independently hydrogen, halogen, $C_1$-$C_5$ alkyl or —$OR^6$, wherein $R^6$ is hydrogen or $C_1$-$C_5$ alkyl; and $R^{23}$ and $R^{24}$ are each independently hydrogen, halogen, $C_1$-$C_5$ alkyl or —$OR^6$, wherein $R^6$ is hydrogen or $C_1$-$C_5$ alkyl.

20. The method according to claim 19 wherein m is 0, and $R^1$ and $R^2$ are each independently hydrogen or —$OR^6$, wherein $R^6$ is hydrogen or $C_1$-$C_5$ alkyl; and $R^{23}$ and $R^{24}$ are each independently hydrogen or —$OR^6$, wherein $R^6$ is hydrogen or $C_1$-$C_5$ alkyl.

21. The method according to claim 20 wherein each of $R^{16}$, $R^{17}$ and $R^{18}$ is independently hydrogen, alkyl, carbocyclyl or aryl.

22. The method according to claim 21, wherein the compound is selected from:
   4-(3-(3-aminopropyl)phenyl)but-3-yn-1-ol;
   5-(3-(3-aminopropyl)phenyl)pent-4-yn-2-ol;
   3-(3-(3,3-dimethylbut-1-ynyl)phenyl)propan-1-amine;
   3-(3-(3-phenylprop-1-ynyl)phenyl)propan-1-amine;
   3-(3-(pent-1-ynyl)phenyl)propan-1-amine;
   3-(3-(hex-1-ynyl)phenyl)propan-1-amine;
   3-amino-1-(3-(3-cyclopentylprop-1-ynyl)phenyl)propan-1-ol;
   3-amino-1-(3-(3-phenylprop-1-ynyl)phenyl)propan-1-ol;
   6-(3-(3-amino-1-hydroxypropyl)phenyl)hex-5-yn-1-ol;
   4-(3-(3-amino-1-hydroxypropyl)phenyl)but-3-yn-1-ol;
   3-amino-1-(3-(hept-1-ynyl)phenyl)propan-1-ol;
   3-(3-(4-phenylbut-1-ynyl)phenyl)propan-1-amine;
   3-amino-1-(3-(4-cyclopentylbut-1-ynyl)phenyl)propan-1-ol;
   3-(3-(5-methoxypent-1-ynyl)phenyl)propan-1-amine;
   3-amino-1-(3-(4-phenylbut-1-ynyl)phenyl)propan-1-ol;
   6-(3-(3-aminopropyl)phenyl)hex-5-yn-1-ol; and
   3-(3-(6-methoxyhex-1-ynyl)phenyl)propan-1-amine.

23. The method according to claim 20 wherein $R^{16}$ is $-OR^6$, wherein $R^6$ is hydrogen or $C_1$-$C_5$ alkyl, and each of $R^{17}$ and $R^{18}$ is independently hydrogen, alkyl or aryl.

24. The method according to claim 23, wherein the compound is selected from:
   1-(3-(3-aminopropyl)phenyl)-3-ethylpent-1-yn-3-ol;
   4-((3-(3-aminopropyl)phenyl)ethynyl)heptan-4-ol;
   5-((3-(3-aminopropyl)phenyl)ethynyl)nonan-5-ol;
   3-(3-(3-methoxy-3-propylhex-1-ynyl)phenyl)propan-1-amine;
   1-(3-(3-aminopropyl)phenyl)-3-methylhex-1-yn-3-ol;
   1-(3-(3-aminopropyl)phenyl)-3,4-dimethylpent-1-yn-3-ol;
   4-(3-(3-aminopropyl)phenyl)-2-methylbut-3-yn-2-ol;
   1-(3-(3-aminopropyl)phenyl)hex-1-yn-3-ol;
   1-(3-(3-aminopropyl)phenyl)-3,4-dimethylhex-1-yn-3-ol;
   3-(3-(3-methoxyprop-1-ynyl)phenyl)propan-1-amine;
   3-(3-(3-aminopropyl)phenyl)prop-2-yn-1-ol;
   1-(3-(3-aminopropyl)phenyl)-3-tert-butyl-4,4-dimethylpent-1-yn-3-ol;
   (R)-1-(3-(3-aminopropyl)phenyl)oct-1-yn-3-ol;
   (R)-1-(3-(3-aminopropyl)phenyl)oct-1-yn-3-ol;
   (R)-3-(3-(3-aminopropyl)phenyl)-1-phenylprop-2-yn-1-ol;
   4-((3-(3-amino-1-hydroxypropyl)phenyl)ethynyl)heptan-4-ol;
   4-((3-(3-amino-2,2-dimethylpropyl)phenyl)ethynyl)heptan-4-ol;
   4-(3-(3-aminopropyl)phenyl)-2-phenylbut-3-yn-2-ol;
   1-(3-(3-aminopropyl)phenyl)-4-methylpent-1-yn-3-ol;
   1-(3-(3-aminopropyl)phenyl)-3,4,4-trimethylpent-1-yn-3-ol;
   (R)-3-(3-(3-aminopropyl)phenyl)-1-phenylprop-2-yn-1-ol;
   1-(3-(3-aminopropyl)phenyl)-3-isopropyl-4-methylpent-1-yn-3-ol;
   4-((3-(3-aminopropyl)phenyl)ethynyl)-2,6-dimethylheptan-4-ol;
   1-(3-(3-amino-1-hydroxypropyl)phenyl)-3-ethylpent-1-yn-3-ol;
   3-(3-(3-ethylpent-1-ynyl)phenyl)propan-1-amine;
   3-(3-(3-propylhex-1-ynyl)phenyl)propan-1-amine;
   3-amino-1-(3-(3-ethylpent-1-ynyl)phenyl)propan-1-ol;
   3-amino-1-(3-(3-propylhex-1-ynyl)phenyl)propan-1-ol;
   3-amino-1-(3-(3-ethylpent-1-ynyl)phenyl)-2-methylpropan-1-ol;
   1-(3-(3-amino-1-hydroxy-2-methylpropyl)phenyl)-3-ethylpent-1-yn-3-ol;
   1-amino-3-(3-(3-ethylpent-1-ynyl)phenyl)propan-2-ol;
   1-(3-(3-amino-2-hydroxypropyl)phenyl)-3-ethylpent-1-yn-3-ol;
   3-amino-2-methyl-1-(3-(3-propylhex-1-ynyl)phenyl)propan-1-ol;
   4-((3-(3-amino-1-hydroxy-2-methylpropyl)phenyl)ethynyl)heptan-4-ol;
   4-((3-(3-amino-2-hydroxypropyl)phenyl)ethynyl)heptan-4-ol; and
   1-amino-3-(3-(3-propylhex-1-ynyl)phenyl)propan-2-ol.

25. The method according to claim 1 wherein $R^5$ is carbocyclyl.

26. The method according to claim 25 wherein $R^5$ is cycloalkyl, Y is a bond and the compound has a structure of Formula (D):

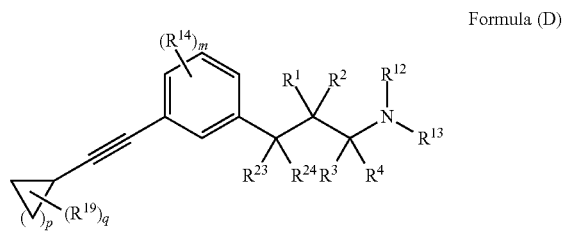

Formula (D)

as a tautomer or a mixture of tautomers, or as a pharmaceutically acceptable salt, stereoisomer, or geometric isomer thereof, wherein:
   m is 0, 1, 2 or 3;
   p is 1, 2, 3, 4, 5 or 6;
   q is 0, 1, 2, 3, 4, 5, 6, 7, 8 or 9;
   $R^1$ and $R^2$ are each the same or different and independently hydrogen, halogen, $C_1$-$C_5$ alkyl, fluoroalkyl, $-OR^6$, or $-NR^7R^8$; or $R^1$ and $R^2$ together form an oxo;
   $R^3$ and $R^4$ are each hydrogen;
   each $R^6$ is the same or different and independently hydrogen or $C_1$-$C_5$ alkyl;
   each $R^7$ and each $R^8$ are each the same or different and independently hydrogen, alkyl, carbocyclyl, heteroalkyl, heterocycloalkyl, aryl, heteroaryl, or $-C(=O)R^9$; or $R^7$ and $R^8$, together with the nitrogen atom to which they are attached, form an N-heterocyclyl;
   each $R^9$ is the same or different and independently methyl, ethyl, 1-propyl, 2-propyl, 1-butyl, $C_5$-$C_8$ alkyl, alkenyl, aryl, carbocyclyl, heteroaryl or heterocyclyl;
   $R^{23}$ and $R^{24}$ are each the same or different and independently hydrogen, halogen, $C_1$-$C_5$ alkyl, fluoroalkyl, $-OR^6$, $-NR^7R^8$ or carbocyclyl; or $R^{23}$ and $R^{24}$ together form an oxo;
   $R^{12}$ and $R^{13}$ are each the same or different and independently hydrogen, or $-C(=O)R^9$;
   each $R^{14}$ is the same or different and independently alkyl, halo, fluoroalkyl or $-OR^6$; and
   each $R^{19}$ is the same or different and independently alkyl, $-OR^6$, halo or fluoroalkyl.

27. The method according to claim 26 wherein each of $R^{12}$ and $R^{13}$ is hydrogen.

28. The method according to claim 27 wherein $R^1$ and $R^2$, are each independently hydrogen, halogen, $C_1$-$C_5$ alkyl or —$OR^6$, wherein $R^6$ is hydrogen or $C_1$-$C_5$ alkyl;

and $R^{23}$ and $R^{24}$ are each independently hydrogen, halogen, $C_1$-$C_5$ alkyl or —$OR^6$, wherein $R^6$ is hydrogen or $C_1$-$C_5$ alkyl.

29. The method according to claim 28 wherein p is 3 and $R^5$ is cyclopentyl.

30. The method according to claim 28 wherein p is 4, and $R^5$ is cyclohexyl.

31. The method according to claim 28 wherein p is 5, and $R^5$ is cycloheptyl.

32. The method according to claim 28 wherein $R^1$ and $R^2$ are each independently hydrogen or —$OR^6$, wherein $R^6$ is hydrogen or $C_1$-$C_5$ alkyl; $R^{23}$ and $R^{24}$ are each independently hydrogen or —$OR^6$, wherein $R^6$ is hydrogen or $C_1$-$C_5$ alkyl; and $R^3$ and $R^4$ are each hydrogen.

33. The method according to claim 32 wherein m is 0.

34. The method according to claim 33 wherein q is 0.

35. The method according to claim 33 wherein q is 1, 2, 3, 4 or 5, and each $R^{19}$ is independently alkyl or —$OR^6$, wherein $R^6$ is hydrogen or $C_1$-$C_5$ alkyl.

36. The method according to claim 35 wherein the compound is selected from the following:
3-(3-(cyclopentylethynyl)phenyl)propan-1-amine;
3-(3-(cyclohexylethynyl)phenyl)propan-1-amine;
3-amino-1-(3-(cyclopentylethynyl)phenyl)propan-1-ol;
3-amino-1-(3-(cyclohexylethynyl)phenyl)propan-1-ol;
1-((3-(3-aminopropyl)phenyl)ethynyl)cyclohexanol;
1-((3-(3-aminopropyl)phenyl)ethynyl)-2,2,6,6-tetramethylcyclohexanol;
1-((3-(3-aminopropyl)phenyl)ethynyl)cyclopentanol;
3-(3-(cycloheptylethynyl)phenyl)propan-1-amine;
3-amino-1-(3-(cycloheptylethynyl)phenyl)propan-1-ol;
1-amino-3-(3-(cycloheptylethynyl)phenyl)propan-2-ol;
1-amino-3-(3-(cyclohexylethynyl)phenyl)propan-2-ol;
1-amino-3-(3-(cyclopentylethynyl)phenyl)propan-2-ol;
1-((3-(3-amino-2-hydroxypropyl)phenyl)ethynyl)cyclopentanol;
1-((3-(3-amino-1-hydroxypropyl)phenyl)ethynyl)cyclopentanol;
1-((3-(3-amino-1-hydroxypropyl)phenyl)ethynyl)cyclohexanol;
1-((3-(3-amino-2-hydroxypropyl)phenyl)ethynyl)cycloheptanol;
1-((3-(3-amino-2-hydroxypropyl)phenyl)ethynyl)cyclohexanol;
1-((3-(3-amino-1-hydroxypropyl)phenyl)ethynyl)cycloheptanol; and
1-((3-(3-aminopropyl)phenyl)ethynyl)cycloheptanol.

37. The method according to claim 26 wherein $R^{12}$ is hydrogen, and $R^{13}$ is —C(=O)$R^9$, wherein $R^9$ is methyl, ethyl, 1-propyl, 2-propyl, 1-butyl, or $C_5$-$C_8$ alkyl.

38. The method according to claim 37 wherein $R^1$ and $R^2$ are each independently hydrogen or —$OR^6$, wherein $R^6$ is hydrogen or $C_1$-$C_5$ alkyl; and $R^{23}$ and $R^{24}$ are each independently hydrogen or —$OR^6$, wherein $R^6$ is hydrogen or $C_1$-$C_5$ alkyl.

39. The method according to claim 38, wherein m is 0.

40. The method according to claim 39, wherein q is 1, 2, 3, 4 or 5, and each $R^{19}$ is independently alkyl or —$OR^6$, wherein $R^6$ is hydrogen or $C_1$-$C_5$ alkyl.

41. The method according to claim 40, wherein p is 4, and $R^5$ is cyclohexyl.

42. The method according to claim 41, wherein the compound is N-(3-hydroxy-3-(3-((1-hydroxycyclohexyl)ethynyl)phenyl)propyl)acetamide.

43. The method according to claim 1 wherein $R^5$ is heterocyclyl and Y is a bond.

44. The method according to claim 43 wherein the heterocyclyl can be optionally substituted with —$OR^6$, wherein $R^6$ is hydrogen or $C_1$-$C_5$ alkyl.

45. The method according to claim 44 wherein each of $R^{12}$ and $R^{13}$ is hydrogen.

46. The method according to claim 45 wherein $R^1$ and $R^2$, are each independently hydrogen, halogen, $C_1$-$C_5$ alkyl or —$OR^6$, wherein $R^6$ is hydrogen or $C_1$-$C_5$ alkyl; and $R^{23}$ and $R^{24}$ are each independently hydrogen, halogen, $C_1$-$C_5$ alkyl or —$OR^6$, wherein $R^6$ is hydrogen or $C_1$-$C_5$ alkyl.

47. The method according to claim 45 wherein each of $R^1$, $R^2$, $R^{23}$ and $R^{24}$ is hydrogen.

48. The method according to claim 47 wherein m is 0.

49. The method according to claim 48 wherein the compound is selected from the following:
4-((3-(3-aminopropyl)phenyl)ethynyl)tetrahydro-2H-thiopyran-4-ol; and
4-((3-(3-aminopropyl)phenyl)ethynyl)tetrahydro-2H-pyran-4-ol.

50. The method according to claim 1 wherein $R^5$ is heteroaryl and Y is a bond.

51. The method according to claim 50 wherein each of $R^{12}$ and $R^{13}$ is hydrogen.

52. The method according to claim 51 wherein $R^1$ and $R^2$, are each independently hydrogen, halogen, $C_1$-$C_5$ alkyl or —$OR^6$, wherein $R^6$ is hydrogen or $C_1$-$C_5$ alkyl; and $R^{23}$ and $R^{24}$ are each independently hydrogen, halogen, $C_1$-$C_5$ alkyl or —$OR^6$, wherein $R^6$ is hydrogen or $C_1$-$C_5$ alkyl.

53. The method according to claim 52 wherein each of $R^1$, $R^2$, $R^{23}$ and $R^{24}$ is hydrogen.

54. The method according to claim 53 wherein m is 0.

55. The method according to claim 54 wherein the compound is selected from:
3-(3-(pyridin-2-ylethynyl)phenyl)propan-1-amine;
3-(3-(pyridin-3-ylethynyl)phenyl)propan-1-amine;
3-(3-(pyridin-4-ylethynyl)phenyl)propan-1-amine;
3-(3-(thiophen-2-ylethynyl)phenyl)propan-1-amine; and
3-(3-(thiophen-3-ylethynyl)phenyl)propan-1-amine.

* * * * *